US012545959B2

(12) United States Patent
McGovern et al.

(10) Patent No.: US 12,545,959 B2
(45) Date of Patent: Feb. 10, 2026

(54) DIAGNOSIS OF INFLAMMATORY BOWEL DISEASE BASED ON GENES

(71) Applicant: CEDARS-SINAI MEDICAL CENTER, Los Angeles, CA (US)

(72) Inventors: Dermot P. McGovern, Los Angeles, CA (US); Dalin Li, Walnut, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 433 days.

(21) Appl. No.: 18/063,931

(22) Filed: Dec. 9, 2022

(65) Prior Publication Data

US 2023/0366028 A1 Nov. 16, 2023

Related U.S. Application Data

(62) Division of application No. 16/303,033, filed as application No. PCT/US2017/033625 on May 19, 2017, now Pat. No. 11,549,146.

(60) Provisional application No. 62/339,357, filed on May 20, 2016.

(51) Int. Cl.
*C12Q 1/68* (2018.01)
*C12Q 1/6816* (2018.01)
*C12Q 1/6883* (2018.01)
*G16B 20/20* (2019.01)

(52) U.S. Cl.
CPC ......... *C12Q 1/6883* (2013.01); *C12Q 1/6816* (2013.01); *G16B 20/20* (2019.02); *C12Q 2600/118* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS

| | | | |
|---|---|---|---|
| 4,443,421 | A | 4/1984 | Hollifield et al. |
| 4,707,260 | A | 11/1987 | Nagayama et al. |
| 5,000,850 | A | 3/1991 | Berry |
| 7,708,996 | B2 | 5/2010 | Yu et al. |
| 8,017,122 | B2 | 9/2011 | Siadak et al. |
| 8,263,743 | B2 | 9/2012 | Smith et al. |
| 2006/0134663 | A1 | 6/2006 | Harkin et al. |
| 2009/0018031 | A1 | 1/2009 | Trinklein et al. |
| 2009/0317388 | A1 | 12/2009 | Burkly et al. |
| 2010/0240043 | A1 | 9/2010 | Rotter et al. |
| 2011/0045476 | A1 | 2/2011 | Barken et al. |
| 2011/0217310 | A1 | 9/2011 | Siegel et al. |
| 2012/0079611 | A1 | 3/2012 | Shih et al. |
| 2012/0208900 | A1 | 8/2012 | Dubinsky et al. |
| 2012/0315282 | A1 | 12/2012 | Bedinger et al. |
| 2013/0136720 | A1 | 5/2013 | McGovern et al. |
| 2014/0141983 | A1 | 5/2014 | Singh et al. |
| 2015/0008194 | A1 | 1/2015 | Davis et al. |
| 2015/0376707 | A1 | 12/2015 | Targan et al. |
| 2018/0030412 | A1 | 2/2018 | Walsh et al. |
| 2018/0110855 | A1 | 4/2018 | Bilsborough et al. |
| 2019/0194754 | A1 | 6/2019 | McGovern et al. |

FOREIGN PATENT DOCUMENTS

| | | | |
|---|---|---|---|
| CN | 104204230 | A | 12/2014 |
| CN | 104805198 | A | 7/2015 |
| JP | 2004194534 | A | 7/2004 |
| JP | 2010088432 | A | 4/2010 |
| JP | 2015502740 | A | 1/2015 |
| WO | WO-0006768 | A1 | 2/2000 |
| WO | WO-2006048291 | A2 | 5/2006 |
| WO | WO-2008106451 | A2 | 9/2008 |
| WO | WO-2008106579 | A2 | 9/2008 |
| WO | WO-2010025340 | A2 | 3/2010 |
| WO | WO-2010062960 | A2 | 6/2010 |
| WO | WO-2010075579 | A2 | 7/2010 |
| WO | WO-2011088380 | A1 | 7/2011 |
| WO | WO-2012065143 | A1 | 5/2012 |
| WO | WO-2012156515 | A1 | 11/2012 |
| WO | WO 2012161856 | A1 | 11/2012 |
| WO | WO-2013059732 | A1 | 4/2013 |
| WO | WO 2014160883 | A1 | 10/2014 |
| WO | WO-2014186750 | A2 | 11/2014 |
| WO | WO-2015054529 | A1 | 4/2015 |
| WO | WO-2015138774 | A1 | 9/2015 |
| WO | WO-2016170348 | A2 | 10/2016 |
| WO | WO-2017147468 | A1 | 8/2017 |
| WO | WO-2017201461 | A1 | 11/2017 |
| WO | WO-2018204764 | A1 | 11/2018 |
| WO | WO-2020121618 | A1 | 6/2020 |

OTHER PUBLICATIONS

NEB catalog (1998/1999), pp. 121, 284.*
Rothstein et al; PNAS, vol. 91, pp. 4155-4159; 1994.*
Anonymous: "rs918490" dbSNP pp. 1-9 (2008), NCBI, NIM.
Al et al.: Role of genetic and environmental factors in pathogenesis of inflammatory bowel disease. International Journal of Digestive Diseases 34(2):110-113 (2014) Machine English Translation of Abstract.
Barrett et al.: Constitutive TL1A Expression under Colitogenic Condition Modulates the Severity and Location of Gut Mucosal Inflammation and Induces Fibrostenosis, American Journal of Pathology, 180(2):636-649 (2012).
European Patent Application No. 17800279.6 Partial Supplemental Search Report dated Oct. 31, 2019.
European Patent Application No. 17800279.6 Extended European Search Report dated Feb. 4, 2020.

(Continued)

*Primary Examiner* — Jehanne S Sitton
(74) *Attorney, Agent, or Firm* — JONES DAY

(57) ABSTRACT

The present invention describes a method of prognosing high or low probability of developing an inflammatory bowel disease (IBD) in a subject and a method of diagnosing an inflammatory bowel disease (IBD) in a subject. The invention further provides for a method of identifying genes/genetic loci associated with a disease condition, such as IBD, CD and/or UC.

12 Claims, 27 Drawing Sheets

Specification includes a Sequence Listing.

(56) References Cited

OTHER PUBLICATIONS

Fitzpatrick, LR: Novel Pharmacological Approaches for Inflammatory Bowel Disease: Targeting Key Intracellular Pathways and the IL-23/IL-17 Axis, International Journal of Inflammation, vol. 2012, pp. 1-8.
Koga et al.: Transanal Delivery of Angiotensin Converting Enzyme Inhibitor Prevents Colonic Fibrosis in a Mouse Colitis Model: Development of a Unique Mode of Treatment, Surgery, 144(2):259-268, 2008.
Takedatsu et al.: TL1A (TNFSF15) Regulates the Development of Chronic Colitis By Modulating both T helper (TH) 1 and TH17 Activation; Gastroenterology; HHS Public Access; 135(2): 552-567 (2008).
Parente et al.: Bowel Ultrasound in Assessment of Crohn's Disease and Detection of Related Small Bowel Strictures: A Prospective Comparative Study Versus X Ray and Intraoperative Findings, Gut, 50: 490-495, 2002.
PCT/US2009/069541 International Search Report dated Mar. 4, 2010.
Pinchuk et al.: Human Colonic Myofibroblast Promote Expansion of CD4+ CD25high Foxp3+ Regulatory T Cells, Gastroenterology, 140(7):2019-2030, pp. 1-19, and p. 8, 2011.
Prometheus Biosciences, Inc. Form S-1 Registration Statement as filed with the Securities and Exchange Commission on Feb. 19, 2021 (246 pages).
Shih et al.: Constitutive TL1A (TNFSF15) Expression on Lymphoid or Myeloid Cells Leads to Mild Intestinal Inflammation and Fibrosis, PLOS One, 6(1), pp. 1-16, 2011.
Shih et al.: Reversal of murine colitis and fibrosis by neutralizing TL1A antibody: potential novel therapy to alter natural history of Crohn's disease. Gastroenterol 142(5):S84, Abstract #357, 2012.
Spinelli et al.: Intestinal Fibrosis in Crohn's Disease: Medical Treatment or Surgery?, Current Drug Targets, 11(2):242-248, 2010.
Strober et al.: Proinflammatoly Cytokines in Pathogenesis of Inflammatory Bowel Diseases, Gastroenterology, 140(6):1756-1767, 2011.
U.S. Appl. No. 16/303,033 Office Action dated Mar. 31, 2021.
U.S. Appl. No. 16/303,033 Office Action dated Sep. 30, 2021.
U.S. Appl. No. 16/303,033 Restriction Requirement dated Jun. 25, 2020.
Alonso et al., 2015, "Identification of risk loci for Crohn's disease phenotypes using a genome-wide association study," Gastroenterology, 148(4):794-805 (Epub 2014).
Barrett et al., 2008, "Genome-wide association defines more than 30 distinct susceptibility loci for Crohn's disease," Nat. Genet., 40(8):955-962.
Cleynen et al., 2016, "Inherited determinants of Crohn's disease and ulcerative colitis phenotypes: a genetic association study," Lancet, 387(10014):156-167 (Epub 2015).
DbSNP Record for ss1354380 (Ref SNP rs918490), submitted on Sep. 6, 2020 (2 pages).
Festen et al., 2011, "A meta-analysis of genome-wide association scans identifies IL18RAP, PTPN2, TAGAP, and PUS10 as shared risk loci for Crohn's disease and celiac disease," PLoS Genet., 7(1):e1001283 (6 pages).
Jacob et al., 2016, "Cytokine and anti-cytokine therapies in prevention or treatment of fibrosis in IBD," United European Gastroenterol J., 4(4):531-540.
Jostins, 2012, "Using Next-Generation Genomic Datasets In Disease Association," Contents and Chapter 4 of Ph.D Thesis, King's College University of Cambridge, Sep. 2012 (100 pages).
Kenny et al., 2012, "A genome-wide scan of Ashkenazi Jewish Crohn's disease suggests novel susceptibility loci," PLoS Genet., 8(3):e1002559 (10 pages).
Li et al., 2016, "Gene-Based Analysis Identified Multiple Novel IBD Loci," presented at Digestive Disease Week 2016, DOW 2016. San Diego, CA, United States. May 21, 2016 to May 24, 2016. Gastroenterology, 150(4):S76, Abstract 324 (3 pages).
Raelson et al., 2007, "Genome-wide association study for Crohn's disease in the Quebec Founder Population identifies multiple validated disease loci," Proc. Natl. Acad. Sci. USA, 104(37):14747-14752.
Shih et al., 2014, "Inhibition of a novel fibrogenic factor T11a reverses established colonic fibrosis," Mucosal. Immunol., 7(6):1492-1503.
Szumilas, 2010, "Explaining odds ratios," J. Can. Acad. Child Adolesc. Psychiatry, 19(3):227-229.
Van Limbergen et al., 2014, "Advances in IBD genetics," Nat. Rev. Gastroenterol. Hepatol., 11(6):372-385.
Wallace et al., 2014, "Immunopathology of inflammatory bowel disease," World J. Gastroenterol., 20(1):6-21.
Ye et al., 2016, "Genetic variation in IBD: progress, clues to pathogenesis and possible clinical utility," Expert Rev. Clin. Immunol., 12(10):1091-1107.

* cited by examiner

FIG. 4

| | | boundary | | | In IIBDGC cohort | | In Cedars Cohort | | |
|---|---|---|---|---|---|---|---|---|---|
| disease | chr | Lower | Upper | Locus/Major gene | n.snp | P.region | n.snp | p.region | p.meta |
| CD | 7 | 107255548 | 107453103 | SLC26A4 | 9 | 1.15E-09 | 8 | 0.00159 | 5.13E-11 |
| CD | 17 | 6996653 | 7077742 | DLG4 | 4 | 5.17E-05 | 4 | 0.00361 | 3.08E-06 |
| CD | 19 | 46133256 | 46346330 | GIPR | 25 | 2.73E-06 | 21 | 0.04411 | 2.04E-06 |
| CD | 20 | 39583952 | 39998520 | ZHX3 | 6 | 2.80E-09 | 5 | 0.01847 | 1.28E-09 |
| CD | 22 | 40288830 | 40797647 | TNRC6B | 10 | 1.91E-05 | 8 | 0.00048 | 1.80E-07 |
| UC | 7 | 92236164 | 92306993 | CDK6 | 4 | 1.83E-05 | 4 | 0.00721 | 2.22E-06 |
| UC | 11 | 36363575 | 36579932 | PRR5L | 35 | 5.62E-05 | 32 | 0.00044 | 4.63E-07 |
| IBD | 1 | 112869069 | 113313563 | WNT2B | 10 | 1.00E-05 | 9 | 0.00641 | 1.13E-06 |
| IBD | 6 | 25186512 | 25707171 | LRRC16A | 35 | 1.27E-09 | 31 | 0.01181 | 3.89E-10 |
| IBD | 6 | 26172219 | 27910708 | All Histone cluster1 gene | 155 | 2.94E-06 | 132 | 0.00603 | 3.34E-07 |
| IBD | 7 | 74455474 | 74509323 | GTF2IRD2B | 10 | 0.0001 | 9 | 7.78E-05 | 1.54E-07 |
| IBD | 11 | 128234772 | 128502496 | ETS1 | 449 | 1.07E-06 | 402 | 0.06996 | 1.30E-06 |
| IBD | 22 | 32339213 | 32616657 | SLC5A1 | 6 | 0.00139 | 2 | 4.12E-06 | 1.15E-07 |
| IBD | 4 | 106048291 | 106173199 | TET2 | 7 | 5.14E-08 | 6 | 0.10506 | 1.08E-07 |

FIG. 6B

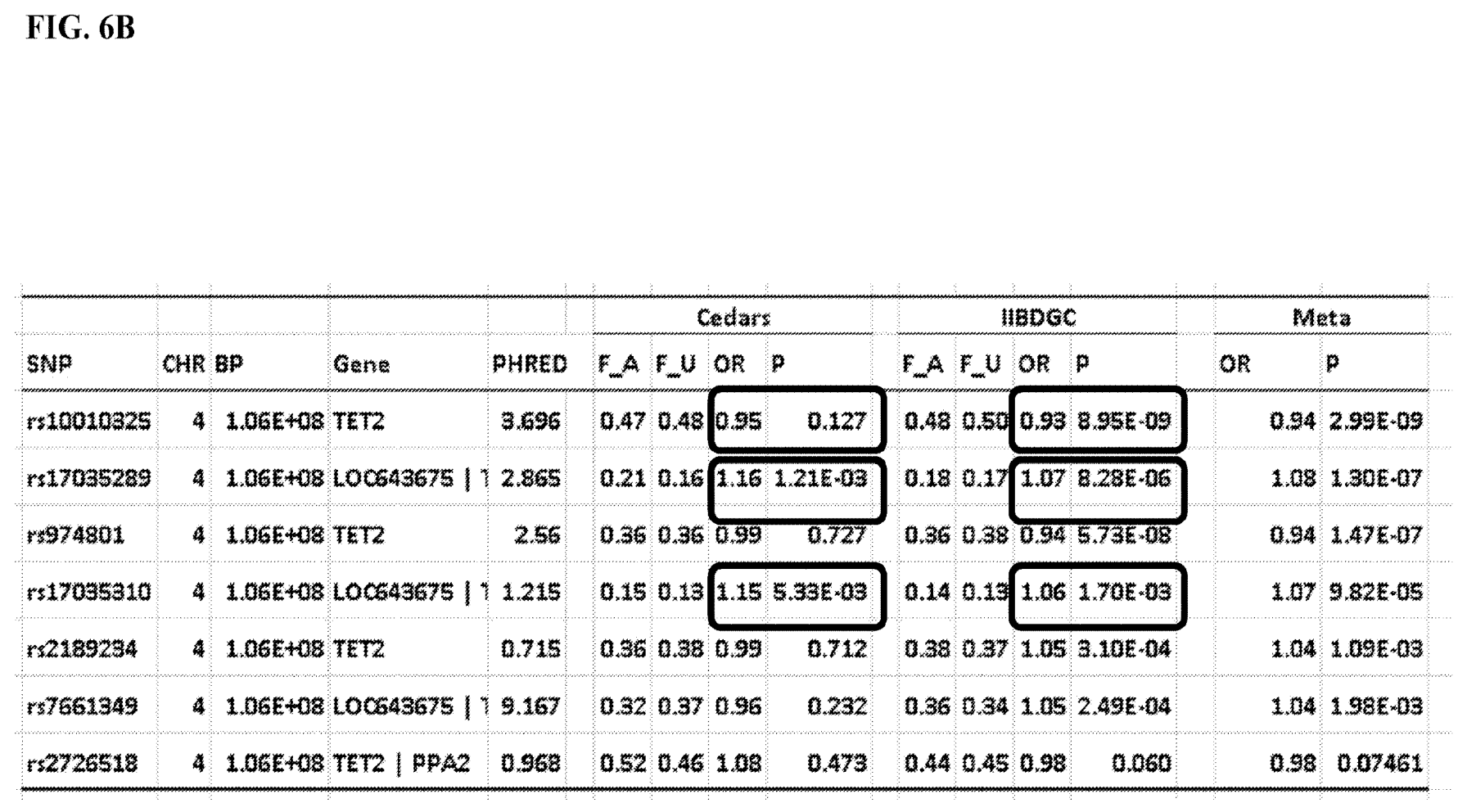

| | | | | | Cedars | | | | IIBDGC | | | | Meta | |
|---|---|---|---|---|---|---|---|---|---|---|---|---|---|---|
| SNP | CHR | BP | Gene | PHRED | F_A | F_U | OR | P | F_A | F_U | OR | P | OR | P |
| rs10010325 | 4 | 1.06E+08 | TET2 | 3.696 | 0.47 | 0.48 | 0.95 | 0.127 | 0.48 | 0.50 | 0.93 | 8.95E-09 | 0.94 | 2.99E-09 |
| rs17035289 | 4 | 1.06E+08 | LOC643675 \| T | 2.865 | 0.21 | 0.16 | 1.16 | 1.21E-03 | 0.18 | 0.17 | 1.07 | 8.28E-06 | 1.08 | 1.30E-07 |
| rs974801 | 4 | 1.06E+08 | TET2 | 2.56 | 0.36 | 0.36 | 0.99 | 0.727 | 0.36 | 0.38 | 0.94 | 5.73E-08 | 0.94 | 1.47E-07 |
| rs17035310 | 4 | 1.06E+08 | LOC643675 \| T | 1.215 | 0.15 | 0.13 | 1.15 | 5.33E-03 | 0.14 | 0.13 | 1.06 | 1.70E-03 | 1.07 | 9.82E-05 |
| rs2189234 | 4 | 1.06E+08 | TET2 | 0.715 | 0.36 | 0.38 | 0.99 | 0.712 | 0.38 | 0.37 | 1.05 | 3.10E-04 | 1.04 | 1.09E-03 |
| rs7661349 | 4 | 1.06E+08 | LOC643675 \| T | 9.167 | 0.32 | 0.37 | 0.96 | 0.232 | 0.36 | 0.34 | 1.05 | 2.49E-04 | 1.04 | 1.98E-03 |
| rs2726518 | 4 | 1.06E+08 | TET2 \| PPA2 | 0.968 | 0.52 | 0.46 | 1.08 | 0.473 | 0.44 | 0.45 | 0.98 | 0.060 | 0.98 | 0.07461 |

FIG. 6C

```
Call:
glm(formula = formu.final, family = binomial, data = dat.all)

Deviance Residuals:
    Min       1Q   Median       3Q      Max
-2.5478  -1.1799   0.4209   1.1563   2.2715

Coefficients:
            Estimate Std. Error z value Pr(>|z|)
(Intercept)  1.25452    0.16835   7.452 9.20e-14 ***
rs17035289   0.12122    0.02878   4.212 2.53e-05 ***
rs10010325  -0.06751    0.02496  -2.705  0.00683 **
rs17035310  -0.07844    0.03377  -2.323  0.02017 *
```

FIG. 7C

```
Call:
glm(formula = formu.final, family = binomial, data = dat.all)

Deviance Residuals:
    Min       1Q   Median       3Q      Max
-2.5663  -1.1808   0.4168   1.1532   2.3333

Coefficients:
            Estimate Std. Error z value Pr(>|z|)
(Intercept)  1.25350    0.16824   7.451 9.28e-14 ***
rs2690110    0.02487    0.01247   1.994 0.046101 *
rs7752195   -0.18875    0.02372  -7.957 1.76e-15 ***
rs6937918    0.04045    0.01205   3.357 0.000787 ***
rs9358858   -0.04254    0.01300  -3.273 0.001065 **
```

FIG. 8B

| rsnum | gene | feature | expression_gene_(population_and_p-value) |
|---|---|---|---|
| rs2690110 | LRRC16A | intron[NM_017640.4] | NA NA NA |
| rs7752195 | LRRC16A | intron[NM_017640.4] | BTN3A2 CEU 0.000000008<br>BTN3A2 CEU 0.0000006<br>BTN3A3 CEU 0.0000006<br>GNRHR2 YRI 0.000003<br>NEK2 YRI 0.00002<br>CACNA1E YRI 0.00004<br>TUBA1A YRI 0.00008<br>TUBA1B YRI 0.00008 |
| rs6937910 | LRRC16A | intron[NM_017640.4] | NA NA NA |
| rs9358858 | LRRC16A | intron[NM_017640.4] | OR5681 YRI 0.00002<br>KISS1 YRI 0.00002 |

FIG. 9A

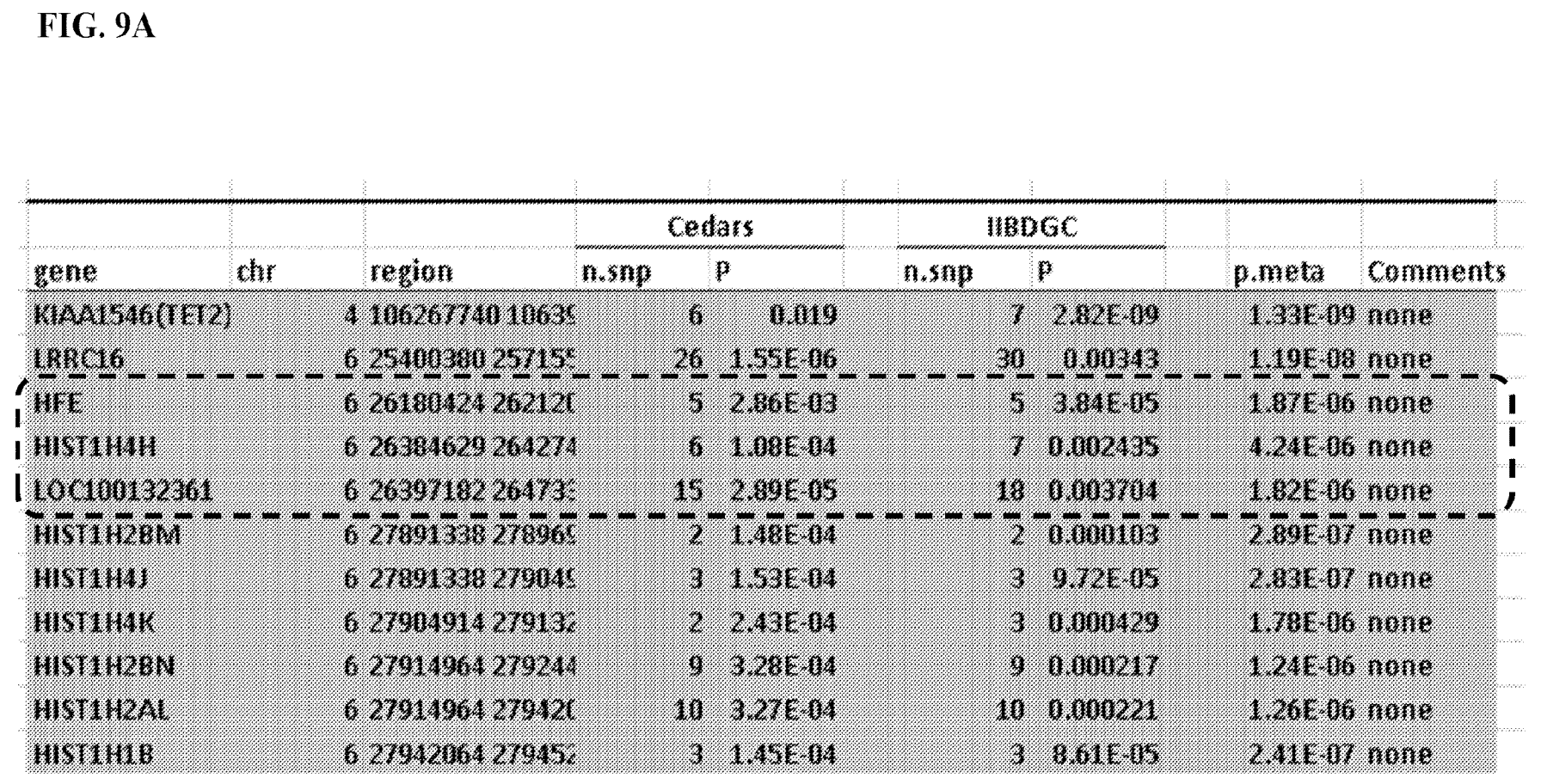

| | | | Cedars | | IIBDGC | | | |
|---|---|---|---|---|---|---|---|---|
| gene | chr | region | n.snp | P | n.snp | P | p.meta | Comments |
| KIAA1546(TET2) | 4 | 106267740 10639 | 6 | 0.019 | 7 | 2.82E-09 | 1.33E-09 | none |
| LRRC16 | 6 | 25400380 25715 | 26 | 1.55E-06 | 30 | 0.00343 | 1.19E-08 | none |
| HFE | 6 | 26180424 26212 | 5 | 2.86E-03 | 5 | 3.84E-05 | 1.87E-06 | none |
| HIST1H4H | 6 | 26384629 264274 | 6 | 1.08E-04 | 7 | 0.002435 | 4.24E-06 | none |
| LOC100132361 | 6 | 26397182 26473 | 15 | 2.89E-05 | 18 | 0.003704 | 1.82E-06 | none |
| HIST1H2BM | 6 | 27891338 27896 | 2 | 1.48E-04 | 2 | 0.000103 | 2.89E-07 | none |
| HIST1H4J | 6 | 27891338 27904 | 3 | 1.53E-04 | 3 | 9.72E-05 | 2.83E-07 | none |
| HIST1H4K | 6 | 27904914 27913 | 2 | 2.43E-04 | 3 | 0.000429 | 1.78E-06 | none |
| HIST1H2BN | 6 | 27914964 279244 | 9 | 3.28E-04 | 9 | 0.000217 | 1.24E-06 | none |
| HIST1H2AL | 6 | 27914964 27942 | 10 | 3.27E-04 | 10 | 0.000221 | 1.26E-06 | none |
| HIST1H1B | 6 | 27942064 27945 | 3 | 1.45E-04 | 3 | 8.61E-05 | 2.41E-07 | none |

FIG. 9C

```
Call:
glm(formula = IBD ~ PC1 + Source + PC2 + PC3 + PC4 + rs13198474 +
    rs198846 + rs198854 + PC1:Source + Source:PC2 + Source:PC3 +
    Source:PC4, family = binomial, data = dat.all)

Deviance Residuals:
    Min       1Q   Median       3Q      Max
-2.6098  -1.1802   0.4169   1.1534   2.3096

Coefficients:
            Estimate Std. Error z value Pr(>|z|)
(Intercept)  1.37511    0.16859   8.157 3.44e-16 ***
rs13198474  -0.25205    0.02420 -10.415  < 2e-16 ***
rs198846    -0.10895    0.01831  -5.952 2.65e-09 ***
rs198854    -0.06432    0.01362  -4.724 2.31e-06 ***
```

FIG. 10A

| rsnum | gene | feature | expression_gene_(population_and_p-value) |
|---|---|---|---|
| rs13198474 | SLC17A3 | utr-5[NM_001098486.1] | BTN3A2 CEU 0.0000000000005<br>BTN3A2 CEU 0.00000000002<br>BTN3A3 CEU 0.00000000002<br>SYT17 CEU 0.00002<br>HLA-DQA1 CEU 0.0001<br>HLA-DQA2 CEU 0.0001 |
| rs198846 | HIST1H1T | near-gene-3[NM_005323.3] | FAM20B CEU 0.000004<br>HLA-B CEU 0.000004<br>HLA-C CEU 0.000004<br>MICA CEU 0.000004<br>MICB CEU 0.000004<br>XXbac-BPG181B23.1 CEU 0.000004 |
| rs198854 | HIST1H4C | near-gene-5[NM_003542.3] | ZDHHC18 YRI 0.00005<br>PRDM15 YRI 0.00006 |

FIG. 10B

| P-value | SNP | Probe | Probe Chr. | Probe Chr. position | Gene name | FDR |
|---|---|---|---|---|---|---|
| 8.571049728721546E-6 | rs13198474 | 3890349 | 6 | 26212438 | HIST1H4C,HIST1H4A | 0.00 |
| 1.7045753691425042E-4 | rs13198474 | 3930377 | 6 | 26093147 | TRIM38 | 0.06 |

| P-value | SNP | Probe | Probe Chr. | Probe Chr. position | Gene name | FDR |
|---|---|---|---|---|---|---|
| 5.456307142692245E-21 | rs198846 | 7210333 | 6 | 26335240 | - | 0.00 |
| 4.107104411030292E-17 | rs198846 | 3930377 | 6 | 26093147 | TRIM38 | 0.00 |
| 0.00215064336881067 | rs198846 | 3890349 | 6 | 26212438 | HIST1H4C,HIST1H4A | 0.39 |
| 0.0023626413529773747 | rs198846 | 1030017 | 6 | 26265200 | HIST1H2AC,HIST1H4A,HIST1H1E | 0.41 |

| P-value | SNP | Probe | Probe Chr. | Probe Chr. position | Gene name | FDR |
|---|---|---|---|---|---|---|
| 1.935602569010773E-11 | rs198854 | 2970019 | 6 | 26393396 | HIST1H4H | 0.00 |
| 1.0360165606222519E-10 | rs198854 | 7210333 | 6 | 26335240 | - | 0.00 |
| 1.7834437343125703E-7 | rs198854 | 3930377 | 6 | 26093147 | TRIM38 | 0.00 |
| 1.4681254471856774E-4 | rs198854 | 6590594 | 6 | 26232467 | HIST1H2AC,HIST1H4A | 0.06 |
| 0.001193621305505144 | rs198854 | 1450484 | 6 | 26292370 | HIST1H2BE,HIST1H2AC,HIST1H4A | 0.27 |

FIG. 11A

| | | | Cedars | | IIBDGC | | | |
|---|---|---|---|---|---|---|---|---|
| gene | chr | region | n.snp | p | n.snp | p | p.meta | Comments |
| KIAA1546(TET2) | 4 | 106267740 10639 | 6 | 0.019 | 7 | 2.82E-09 | 1.33E-09 | none |
| LRRC16 | 6 | 25400380 25715 | 26 | 1.55E-06 | 30 | 0.00343 | 1.19E-08 | none |
| HFE | 6 | 26180424 26212 | 5 | 2.86E-03 | 5 | 3.84E-05 | 1.87E-06 | none |
| HIST1H4H | 6 | 26384629 264274 | 6 | 1.08E-04 | 7 | 0.002435 | 4.24E-06 | none |
| LOC100132361 | 6 | 26397182 26473 | 15 | 2.89E-05 | 18 | 0.003704 | 1.82E-06 | none |
| HIST1H2BM | 6 | 27891338 27896 | 2 | 1.48E-04 | 2 | 0.000103 | 2.89E-07 | none |
| HIST1H4J | 6 | 27891338 27904 | 3 | 1.53E-04 | 3 | 9.72E-05 | 2.83E-07 | none |
| HIST1H4K | 6 | 27904914 27913 | 2 | 2.43E-04 | 3 | 0.000429 | 1.78E-06 | none |
| HIST1H2BN | 6 | 27914964 279244 | 9 | 3.28E-04 | 9 | 0.000217 | 1.24E-06 | none |
| HIST1H2AL | 6 | 27914964 27942 | 10 | 3.27E-04 | 10 | 0.000221 | 1.26E-06 | none |
| HIST1H1B | 6 | 27942064 27945 | 3 | 1.45E-04 | 3 | 8.61E-05 | 2.41E-07 | none |

FIG. 11C

```
Call:
glm(formula = IBD ~ PC1 + Source + PC2 + PC3 + PC4 + rs200484 +
    rs9295740 + rs4713119 + rs9461412 + PC1:Source + Source:PC2 +
    Source:PC3 + Source:PC4, family = binomial, data = dat.all)

Deviance Residuals:
    Min       1Q   Median       3Q      Max
-2.5693  -1.1789   0.4111   1.1534   2.2937

Coefficients:
            Estimate Std. Error z value Pr(>|z|)
(Intercept)  1.26637    0.16764   7.554 4.21e-14 ***
rs200484    -0.35930    0.03202 -11.220  < 2e-16 ***
rs9295740    0.17719    0.02772   6.392 1.63e-10 ***
rs4713119   -0.08550    0.01784  -4.792 1.65e-06 ***
rs9461412   -0.14858    0.03876  -3.833 0.000126 ***
```

FIG. 12

| rsnum | gene | feature | expression_gene_(population_and_p-value) |
|---|---|---|---|
| rs200484 | HIST1H2AI<br>HIST1H2BL | near-gene-5[NM_003509.2]<br>reference[NM_003519.3] | BTN3A2 CEU 0.000000000000009<br>BTN3A2 CEU 0.0000000000002<br>BTN3A3 CEU 0.0000000000002<br>HLA-DQA1 CEU 0.0000002<br>HLA-DQA2 CEU 0.0000002<br>SYT17 CEU 0.000007<br>HIST1H4A CEU 0.00006<br>HIST1H4B CEU 0.00006<br>HIST1H4C CEU 0.00006<br>HIST1H4D CEU 0.00006<br>HIST1H4E CEU 0.00006<br>HIST1H4F CEU 0.00006<br>HIST1H4H CEU 0.00006<br>HIST1H4I CEU 0.00006<br>HIST1H4J CEU 0.00006<br>HIST1H4K CEU 0.00006<br>HIST1H4L CEU 0.00006<br>HIST2H4A CEU 0.00006<br>HIST2H4B CEU 0.00006<br>HIST4H4 CEU 0.00006 |
| rs9295740 | NA | NA | BTN3A2 CEU 0.00000000001<br>BTN3A3 CEU 0.00000000001<br>BTN3A2 CEU 0.0000000001<br>HLA-DQA1 CEU 0.000006<br>HLA-DQA2 CEU 0.000006<br>NTNG1 CEU 0.00002<br>C9orf139 CEU 0.00009 |
| rs4713119 | NA | NA | NA NA NA |
| rs9461412 | NA | NA | NA NA NA |

FIG. 13

```
Call:
glm(formula = IBD ~ PC1 + Source + PC2 + PC3 + PC4 + rs200484 +
    rs9295740 + rs4713119 + rs6937918 + rs198846 + rs7752195 +
    rs198854 + rs9358858 + rs9461412 + rs2690110 + rs13198474 +
    PC1:Source + Source:PC2 + Source:PC3 + Source:PC4, family = binomial,
    data = dat.all)

Deviance Residuals:
    Min       1Q   Median       3Q      Max
-2.6048  -1.1778   0.4082   1.1509   2.3377

Coefficients:
             Estimate Std. Error z value Pr(>|z|)
(Intercept)  1.32605    0.16916   7.839 4.54e-15 ***
rs200484    -0.29557    0.03555  -8.313  < 2e-16 ***
rs9295740    0.16562    0.02790   5.936 2.93e-09 ***
rs4713119   -0.08995    0.01796  -5.008 5.49e-07 ***
rs6937918    0.03534    0.01208   2.926  0.00343 **
rs198846    -0.10461    0.01847  -5.663 1.49e-08 ***
rs7752195   -0.08784    0.03802  -2.310  0.02087 *
rs198854    -0.06101    0.01380  -4.422 9.76e-06 ***
rs9358858   -0.03671    0.01311  -2.800  0.00511 **
rs9461412   -0.12768    0.03904  -3.271  0.00107 **
rs2690110    0.03136    0.01254   2.500  0.01241 *
rs13198474  -0.07282    0.04106  -1.774  0.07614 .
```

DIAGNOSIS OF INFLAMMATORY BOWEL DISEASE BASED ON GENES

CROSS REFERENCE

This application is a divisional of U.S. application Ser. No. 16/303,033 filed Nov. 19, 2018, now U.S. Pat. No. 11,549,146 issued on Dec. 21, 2022, which is a U.S. National Phase of International Application No. PCT/US2017/033625 filed May 19, 2017, which claims the benefit of U.S. Provisional Application Ser. No. 62/339,357 filed on May 20, 2016, each of which is incorporated herein in their entirety.

STATEMENT REGARDING FEDERALLY-SPONSORED RESEARCH

This invention was made with government support under Grant Nos. DK108140 and DK062413 awarded by the National Institutes of Health. The government has certain rights in the invention.

SEQUENCE LISTING

The instant application contains a Sequence Listing which has been submitted electronically in XML format and is hereby incorporated by reference in its entirety. Said XML copy, created on May 12, 2025, is named 56884-730.401_SL_2.xml and is 639,677 bytes in size.

FIELD OF THE INVENTION

The invention relates to genetics and medicine.

BACKGROUND

All publications cited herein are incorporated by reference in their entirety to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Crohn's disease (CD) and ulcerative colitis (UC), the two common forms of idiopathic inflammatory bowel disease (IBD), are chronic, relapsing inflammatory disorders of the gastrointestinal tract. Each has a peak age of onset in the second to fourth decades of life and prevalences in European ancestry populations that average approximately 100-150 per 100,000 (D. K. Podolsky, N Engl J Med 347, 417 (2002); E. V. Loftus, Jr., Gastroenterology 126, 1504 (2004)). Although the precise etiology of IBD remains to be elucidated, a widely accepted hypothesis is that ubiquitous, commensal intestinal bacteria trigger an inappropriate, overactive, and ongoing mucosal immune response that mediates intestinal tissue damage in genetically susceptible individuals (D. K. Podolsky, N Engl J Med 347, 417 (2002)). Genetic factors play an important role in IBD pathogenesis, as evidenced by the increased rates of IBD in Ashkenazi Jews, familial aggregation of IBD, and increased concordance for IBD in monozygotic compared to dizygotic twin pairs (S. Vermeire, P. Rutgeerts, Genes Immun 6, 637 (2005)). CD and UC are thought to be related disorders that share some genetic susceptibility loci but differ at others.

Thus, there is need in the art to determine other genes, allelic variants and/or haplotypes that may assist in explaining the genetic risk, diagnosing, and/or predicting susceptibility for or protection against inflammatory bowel disease including but not limited to CD and/or UC.

SUMMARY OF THE INVENTION

Various embodiments of the present invention provide for a method of prognosing high or low probability of developing an inflammatory bowel disease (IBD) in a subject, comprising: genotyping the subject for a risk allele at a gene/genetic locus; and upon detecting the risk allele, prognosing high probability of developing the IBD in the subject; or upon not detecting the risk allele, prognosing low probability of developing the IBD in the subject.

In various embodiments, the gene/genetic locus comprises SLC26A4, DLG4, GIPR, ZHX3, TNRC6B, CDK6, PRR5L, WNT2B, LRRC16A, HIST1 cluster (all Histone cluster 1 genes), GTF2IRD2B, ETS1, SLC5A1, or TET2, or a combination thereof. In various embodiments, the gene/genetic locus comprises ETS1, HIST1 cluster (all Histone cluster 1 genes), CDK6, LRRC16A, or a combination thereof. In various embodiments, the gene/genetic locus comprises ETS1. In various embodiments, the gene/genetic locus comprises HIST1 cluster (all Histone cluster 1 genes). In various embodiments, the gene/genetic locus comprises CDK6. In various embodiments, the gene/genetic locus comprises LRRC16A. In various embodiments, the gene/genetic locus comprise one or more of SEQ ID NO: 1-SEQ ID NO: 341.

In various other embodiments, genotyping the subject comprises: obtaining a sample from the subject; and genotyping the sample for the risk allele at the gene/genetic locus. In yet other embodiments, genotyping the sample comprises: contacting the sample with an oligonucleotide probe specific to the risk allele; generating an allele-specific hybridization complex between the oligonucleotide probe and the risk allele; and upon detecting the allele-specific hybridization complex, detecting the risk allele; or upon not detecting the allele-specific hybridization complex, not detecting the risk allele. In some embodiments, the oligonucleotide probe is labeled with a fluorescent dye, and wherein detecting the allele-specific hybridization complex comprises detecting fluorescence signal from the oligonucleotide probe. In other embodiments, the oligonucleotide probe comprises a reporter dye and a quencher dye.

In various embodiments, the method further comprises conducting PCR amplification after forming the allele-specific hybridization complex.

Various embodiments of the present invention provide for a method of diagnosing an inflammatory bowel disease (IBD) in a subject, comprising: genotyping a sample from the subject for a risk allele at a gene/genetic locus; upon detecting the risk allele, diagnosing IBD in the subject; and administering an IBD therapy to the subject diagnosed with IBD, thereby treating IBD in the subject. In various embodiments, the gene/genetic locus comprises SLC26A4, DLG4, GIPR, ZHX3, TNRC6B, CDK6, PRR5L, WNT2B, LRRC16A, HIST1 cluster (all Histone cluster 1 genes), GTF2IRD2B, ETS1, SLC5A1, or TET2, or a combination thereof. In various embodiments, the gene/genetic locus comprises ETS1, HIST1 cluster (all Histone cluster 1 genes), CDK6, LRRC16A, or a combination thereof. In various embodiments, the gene/genetic locus comprises ETS1. In various embodiments, the gene/genetic locus comprises HIST1 cluster (all Histone cluster 1 genes). In various embodiments, the gene/genetic locus comprises CDK6. In various embodiments, the gene/genetic locus comprises LRRC16A. In various embodiments, the gene/genetic locus comprise one or more of SEQ ID NO: 1-SEQ ID NO: 341. In various embodiments, the method further comprises providing an IBD therapy to the subject. In some embodiments, the IBD therapy comprises anti-TNF therapy, anti-TL1A therapy, colectomy, or a combination thereof.

Various embodiments of the present invention provide for a method, comprising: genotyping a sample from the subject for a risk allele at a gene/genetic locus; upon detecting the risk allele, diagnosing IBD in the subject; and administering the IBD therapy to the subject diagnosed with IBD, thereby treating IBD in the subject. In various embodiments, the gene/genetic locus comprises SLC26A4, DLG4, GIPR, ZHX3, TNRC6B, CDK6, PRR5L, WNT2B, LRRC16A, HIST1 cluster (all Histone cluster 1 genes), GTF2IRD2B, ETS1, SLC5A1, or TET2, or a combination thereof. In various embodiments, the gene/genetic locus comprises ETS1, HIST1 cluster (all Histone cluster 1 genes), CDK6, LRRC16A, or a combination thereof. In various embodiments, the gene/genetic locus comprises ETS1. In various embodiments, the gene/genetic locus comprises HIST1 cluster (all Histone cluster 1 genes). In various embodiments, the gene/genetic locus comprises CDK6. In various embodiments, the gene/genetic locus comprises LRRC16A. In various other embodiments, the gene/genetic locus comprise one or more of SEQ ID NO: 1-SEQ ID NO: 341. In various embodiments, the method further comprises providing an IBD therapy to the subject. In some embodiments, the IBD therapy comprises anti-TNF therapy, anti-TL1A therapy, colectomy, or a combination thereof.

Various embodiments of the present invention provide for a method of identifying genes/genetic loci associated with a condition, comprising: acquiring genetic data from samples of a cohort of the condition; performing a GLS transformation on the genetic data, thereby decorrelating the genetic data; conducting gene-based analysis on the GLS-transformed genetic data; and identifying genes/genetic loci associated with the condition. In various embodiments, the condition is IBD, CD, or UC, or a combination thereof. In some embodiments, the cohort comprises correlated subjects or family subjects. In other embodiments, the genetic data comprise SNP genotypes. In yet other embodiments, performing the GLS transformation comprises transforming the genetic data according to functions, $$G=\Sigma_o^{-1/2},$$

$$Gy=GX\beta+Ge,$$

$$\hat{\beta}_{GLS}=(X'\Sigma_o^{-1}X)^{-1}X'\Sigma_o^{-1}y,$$

$$\mathrm{var}(\hat{\beta}_{GLS})=\mathrm{var}((X'\Sigma_o^{-1}X)^{-1}X'\Sigma_o^{-1}y)=(X'\Sigma_o^{-1}X)^{-1},$$

or a combination thereof.

In various embodiments, conducting gene-based analysis comprises applying a gene-based test based on the assumption of independent or uncorrelated subjects. In various embodiments, conducting gene-based analysis comprises applying C-alpha, SKAT, SKAT-CommonRare, CMC, WSS, Variable Threshold, or Comprehensive Approach, or a combination thereof.

BRIEF DESCRIPTION OF THE DRAWINGS

Exemplary embodiments are illustrated in referenced figures. It is intended that the embodiments and figures disclosed herein are to be considered illustrative rather than restrictive.

FIG. 4 depicts, in accordance with various embodiments of the invention, a list of novel genes/regions identified in our analysis: SLC26A4, DLG4, GIPR, ZHX3, TNRC6B, CDK6, PRR5L, WNT2B, LRRC16A, HIST1 cluster (all Histone cluster 1 genes), GTF2IRD2B, ETS1, SLC5A1, and TET2.

FIGS. 6A-6D depict, in accordance with various embodiments of the invention, detailed examination of TET2 region: local plot (A), SNPs (B), fine mapping (C), and function (D). rs17035289 is SEQ ID NO: 333 and rs2726518 is SEQ ID NO: 334. All other rs numbers are found in table 1.

FIGS. 7A-7C depict, in accordance with various embodiments of the invention, detailed examination of LRRC16 region: local plot (A), local plot (B), and fine mapping with four independent signals (C).

FIGS. 8A-8C depict, in accordance with various embodiments of the invention, eQTL results: SeeQTL (A), Scandb (B), and GeneVar (C). rs9358858 is SEQ ID NO: 335. All other rs numbers are found in table 1.

FIGS. 9A-9C depict, in accordance with various embodiments of the invention, detailed examination of a first portion in the HIST1 cluster: genes (A), local signals (B), and fine mapping with three independent signals (P=2.23E-25) (C). rs2071303 is SEQ ID NO: 336, rs13198474 is SEQ ID NO: 337, rs198846 is SEQ ID NO:338 and rs198854 is SEQ ID NO: 339.

FIGS. 10A-10B depict, in accordance with various embodiments of the invention, eQTL analysis: SCANdb (A) and Blood eQTL (B). rs13198474 is SEQ ID NO: 337, rs198846 is SEQ ID NO:338 and rs198854 is SEQ ID NO:339.

FIGS. 11A-11C depict, in accordance with various embodiments of the invention, detailed examination of a second portion in the HIST1 cluster: genes (A), local signals (B), and fine mapping with four independent signals (P=3.25E-29) (C). rs9295740 is SEQ ID NO: 340 and rs9461412 is SEQ ID NO: 341.

FIG. 12 depicts, in accordance with various embodiments of the invention, eQTL analysis: SCANdb.

FIG. 13 depicts, in accordance with various embodiments of the invention, independent signals from 3 regions: LRRC16, first portion in the HIST1 cluster, and second portion in the HIST1 cluster.

DETAILED DESCRIPTION OF THE INVENTION

Figure 1B:
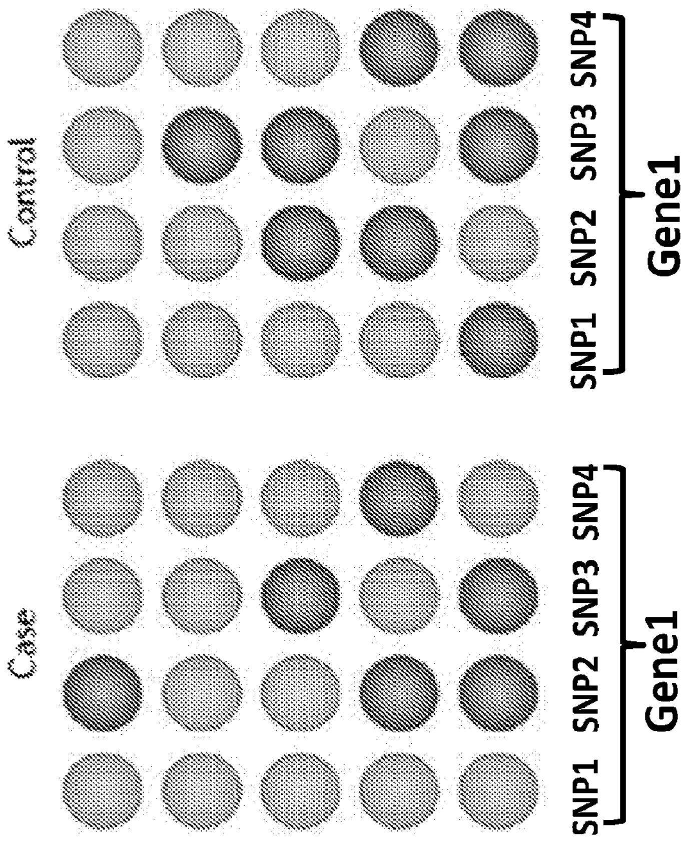
FIGS. 1A-1B depict, in accordance with various embodiments of the invention, Single-SNP based and gene-based analysis.

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* 22$^{nd}$ ed., Pharmaceutical Press (Sep. 15, 2012);

Hornyak et al., *Introduction to Nanoscience and Nanotechnology, CRC Press* (2008); Singleton and Sainsbury, *Dictionary of Microbiology and Molecular Biology* 3rd ed., revised ed., J. Wiley & Sons (New York, NY 2006); Smith, *March's Advanced Organic Chemistry* Reactions, Mechanisms and Structure 7th ed., J. Wiley & Sons (New York, NY 2013); Singleton, *Dictionary of DNA and Genome Technology* 3rd ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, NY 2012), provide one skilled in the art with a general guide to many of the terms used in the present application. For references on how to prepare antibodies, see Greenfield, Antibodies *A Laboratory Manual* 2nd ed., Cold Spring Harbor Press (Cold Spring Harbor NY, 2013); Köhler and Milstein, Derivation of specific antibody-producing tissue culture and tumor lines by cell fusion, *Eur. J. Immunol.* 1976 Jul. 6 (7): 511-9; Queen and Selick, Humanized immunoglobulins, U.S. Pat. No. 5,585,089 (1996 December); and Riechmann et al., Reshaping human antibodies for therapy, *Nature* 1988 Mar. 24, 332 (6162): 323-7.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. Unless otherwise defined, all technical and scientific terms used herein have the same meaning as commonly understood by one of ordinary skill in the art to which this invention belongs. It should be understood that this invention is not limited to the particular methodology, protocols, and reagents, etc., described herein and as such can vary. The definitions and terminology used herein are provided to aid in describing particular embodiments, and are not intended to limit the claimed invention, because the scope of the invention is limited only by the claims.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

As used herein, the terms "treat," "treatment," "treating," or "amelioration" when used in reference to a disease, disorder or medical condition, refer to both therapeutic treatment and prophylactic or preventative measures, wherein the object is to prevent, reverse, alleviate, ameliorate, inhibit, lessen, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a disease, disorder or medical condition is reduced or halted. That is, "treatment" includes not just the improvement of symptoms or markers, but also a cessation or at least slowing of progress or worsening of symptoms that would be expected in the absence of treatment. Also, "treatment" may mean to pursue or obtain beneficial results, or lower the chances of the individual developing the condition even if the treatment is ultimately unsuccessful. Those in need of treatment include those already with the condition as well as those prone to have the condition or those in whom the condition is to be prevented.

"Beneficial results" or "desired results" may include, but are in no way limited to, lessening or alleviating the severity of the disease condition, preventing the disease condition from worsening, curing the disease condition, preventing the disease condition from developing, lowering the chances of a patient developing the disease condition, decreasing morbidity and mortality, and prolonging a patient's life or life expectancy. As non-limiting examples, "beneficial results" or "desired results" may be alleviation of one or more symptom(s), diminishment of extent of the deficit, stabilized (i.e., not worsening) state of intestinal inflammation and/or fibrosis, delay or slowing of intestinal inflammation and/or fibrosis, and amelioration or palliation of symptoms associated with intestinal inflammation and/or fibrosis.

"Diseases", "conditions" and "disease conditions," as used herein may include, but are in no way limited to any form of intestinal inflammation or intestinal inflammation-related condition, disease or disorder, for example, intestinal inflammation, intestinal fibrosis, inflammatory bowel disease (IBD), Crohn's disease (CD), ulcerative colitis (UC), colitis, acute colitis, and chronic colitis.

method of prognosing high or low probability of developing an inflammatory bowel disease (IBD) in a subject, comprising: genotyping the subject for a risk allele at a gene/genetic locus; and upon detecting the risk allele, prognosing high probability of developing the IBD in the subject;

or upon not detecting the risk allele, prognosing low probability of developing the IBD in the subject.

"Risk variant" as used herein refers to an allele, whose presence is associated with an increase in susceptibility to an inflammatory bowel disease, including but not limited to Crohn's Disease and ulcerative colitis, relative to an individual who does not have the risk variant.

"High probability", as used herein refers to an increase in susceptibility to an inflammatory bowel disease, when the risk variants are present in an individual, relative to an individual who does not have the risk variants.

"Low probability", as used herein refers to a decrease in susceptibility to an inflammatory bowel disease, when the risk variants are absent in an individual, relative to an individual who has the risk variants.

As used herein, the term "administering," refers to the placement an agent as disclosed herein into a subject by a method or route which results in at least partial localization of the agents at a desired site. "Route of administration" may refer to any administration pathway known in the art, including but not limited to aerosol, nasal, oral, transmucosal, transdermal, parenteral, enteral, topical or local. "Parenteral" refers to a route of administration that is generally associated with injection, including intracranial, intraventricular, intrathecal, epidural, intradural, intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the topical route, the pharmaceutical compositions can be in the form of aerosol, lotion, cream, gel, ointment, suspensions, solutions or emulsions. In accordance with the present invention, "administering" can be self-administering. For example, it is considered as "administering" that a subject consumes a composition as disclosed herein.

The term "sample" or "biological sample" as used herein denotes a sample taken or isolated from a biological organism, e.g., a blood sample from a subject. Exemplary biological samples include, but are not limited to, cheek swab; mucus; whole blood, blood, serum; plasma; urine; saliva; semen; lymph; fecal extract; sputum; other body fluid or biofluid; cell sample; and/or tissue sample etc. The term also includes a mixture of the above-mentioned samples. The term "sample" also includes untreated or pretreated (or pre-processed) biological samples. In some embodiments, a sample can comprise one or more cells from the subject.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets.

"Mammal" as used herein refers to any member of the class Mammalia, including without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

A subject can be one who has been previously diagnosed with or identified as suffering from or having a condition in need of treatment (e.g., intestinal inflammation and/or fibrosis, IBD, CD, UC, colitis, acute colitis, and chronic colitis) or one or more complications related to the condition, and optionally, have already undergone treatment for the condition or the one or more complications related to the condition. Alternatively, a subject can also be one who has not been previously diagnosed as having a condition or one or more complications related to the condition. For example, a subject can be one who exhibits one or more risk factors for a condition or one or more complications related to the condition or a subject who does not exhibit risk factors. A "subject in need" of treatment for a particular condition can be a subject suspected of having that condition, diagnosed as having that condition, already treated or being treated for that condition, not treated for that condition, or at risk of developing that condition.

The term "statistically significant" or "significantly" refers to statistical evidence that there is a difference. It is defined as the probability of making a decision to reject the null hypothesis when the null hypothesis is actually true. The decision is often made using the p-value.

As used herein, "a disease's Odds" or "Odds of a disease" in a certain population is defined as the ratio between disease probability and non-disease probability in such a population (i.e., a disease's Odds=disease probability/non-disease probability).

As used herein, "a risk allele's Odds Ratio (OR)" or "Odds Ratio (OR) of a risk allele" with respect to a disease is defined as the ratio between the disease's Odds in the risk allele's carrier population and the disease's Odds in the risk allele's non-carrier population. (i.e., a risk allele's OR=the disease's Odds in carriers/the disease's Odds in non-carriers).

Methods of the Invention

This invention provides methods of identifying genes/genetic loci associated with a condition such as IBD. The identification of these genes/genetic loci can be used for risk stratification of a population with respect to IBD. We could use such a tool at birth to identify people at risk for IBD with the intent of impacting the population by delivering preventative interventions that could modulate environmental epigenetic factors. This invention also provides methods of diagnosing IBD and methods of individualizing IBD treatment plans as a precision medicine approach.

Prognosing

Various embodiments of the present invention provide for a method of prognosing high or low probability of developing an inflammatory bowel disease (IBD) in a subject, comprising: genotyping the subject for a risk allele at a gene/genetic locus; and upon detecting the risk allele, prognosing high probability of developing the IBD in the subject;

or upon not detecting the risk allele, prognosing low probability of developing the IBD in the subject.

In various embodiments, the gene/genetic locus comprises SLC26A4, DLG4, GIPR, ZHX3, TNRC6B, CDK6, PRR5L, WNT2B, LRRC16A, HIST1 cluster (all Histone cluster 1 genes), GTF2IRD2B, ETS1, SLC5A1, or TET2, or a combination thereof. In various embodiments, the gene/genetic locus comprises ETS1, HIST1 cluster (all Histone cluster 1 genes), CDK6, LRRC16A, or a combination thereof. In various embodiments, the gene/genetic locus comprises ETS1. In various embodiments, the gene/genetic locus comprises HIST1 cluster (all Histone cluster 1 genes). In various embodiments, the gene/genetic locus comprises CDK6. In various embodiments, the gene/genetic locus comprises LRRC16A. In various embodiments, the gene/genetic locus comprise one or more of SEQ ID NO: 1-SEQ ID NO: 341.

In various other embodiments, genotyping the subject comprises: obtaining a sample from the subject; and genotyping the sample for the risk allele at the gene/genetic locus. In yet other embodiments, genotyping the sample comprises: contacting the sample with an oligonucleotide probe specific to the risk allele; generating an allele-specific hybridization complex between the oligonucleotide probe and the risk allele; and upon detecting the allele-specific hybridization complex, detecting the risk allele; or upon not detecting the allele-specific hybridization complex, not detecting the risk allele. In some embodiments, the oligonucleotide probe is labeled with a fluorescent dye, and wherein detecting the allele-specific hybridization complex comprises detecting fluorescence signal from the oligonucleotide probe. In other embodiments, the oligonucleotide probe comprises a reporter dye and a quencher dye.

In various embodiments, the method further comprises conducting PCR amplification after forming the allele-specific hybridization complex.

Various embodiments of the present invention provide a method of prognosing high or low probability of developing an inflammatory bowel disease (IBD) in a subject. The method comprises: genotyping the subject for a risk allele at a gene/genetic locus; and upon detecting the risk allele, prognosing high probability of developing the IBD in the subject; or upon not detecting the risk allele, prognosing low probability of developing the IBD in the subject.

Various embodiments of the present invention provide a method of prognosing high probability of developing an inflammatory bowel disease (IBD) in a subject. The method comprises: genotyping the subject for a risk allele at a gene/genetic locus; and upon detecting the risk allele, prognosing high probability of developing the IBD in the subject.

Various embodiments of the present invention provide a method of prognosing low probability of developing an inflammatory bowel disease (IBD) in a subject. The method comprises: genotyping the subject for a risk allele at a gene/genetic locus; and upon not detecting the risk allele, prognosing low probability of developing the IBD in the subject.

In accordance with the present invention, high or low probability of developing IBD means that a subject has more or less likelihood of developing IBD as compared to the general population which the subject belongs to.

Diagnosing

Various embodiments of the present invention provide for a method of diagnosing an inflammatory bowel disease (IBD) in a subject, comprising: genotyping a sample from the subject for a risk allele at a gene/genetic locus; upon detecting the risk allele, diagnosing IBD in the subject; and administering an IBD therapy to the subject diagnosed with IBD, thereby treating IBD in the subject. In various embodiments, the gene/genetic locus comprises SLC26A4, DLG4, GIPR, ZHX3, TNRC6B, CDK6, PRR5L, WNT2B, LRRC16A, HIST1 cluster (all Histone cluster 1 genes), GTF2IRD2B, ETS1, SLC5A1, or TET2, or a combination thereof. In various embodiments, the gene/genetic locus comprises ETS1, HIST1 cluster (all Histone cluster 1 genes), CDK6, LRRC16A, or a combination thereof. In various embodiments, the gene/genetic locus comprises ETS1. In various embodiments, the gene/genetic locus comprises HIST1 cluster (all Histone cluster 1 genes). In various embodiments, the gene/genetic locus comprises CDK6. In various embodiments, the gene/genetic locus comprises LRRC16A. In various embodiments, the gene/genetic locus comprise one or more of SEQ ID NO: 1-SEQ ID NO: 341. In some embodiments, the IBD therapy comprises anti-TNF therapy, anti-TL1A therapy, colectomy, or a combination thereof.

Various embodiments of the present invention provide for a method, comprising: genotyping a sample from the subject for a risk allele at a gene/genetic locus; upon detecting the risk allele, diagnosing IBD in the subject; and administering an IBD therapy to the subject diagnosed with IBD, thereby treating IBD in the subject. In various embodiments, the gene/genetic locus comprises SLC26A4, DLG4, GIPR, ZHX3, TNRC6B, CDK6, PRR5L, WNT2B, LRRC16A, HIST1 cluster (all Histone cluster 1 genes), GTF2IRD2B, ETS1, SLC5A1, or TET2, or a combination thereof. In various embodiments, the gene/genetic locus comprises ETS1, HIST1 cluster (all Histone cluster 1 genes), CDK6, LRRC16A, or a combination thereof. In various embodiments, the gene/genetic locus comprises ETS1. In various embodiments, the gene/genetic locus comprises HIST1 cluster (all Histone cluster 1 genes). In various embodiments, the gene/genetic locus comprises CDK6. In various embodiments, the gene/genetic locus comprises LRRC16A. In various other embodiments, the gene/genetic locus comprise one or more of SEQ ID NO: 1-SEQ ID NO: 341. In various embodiments, the method further comprises providing an IBD therapy to the subject. In some embodiments, the IBD therapy comprises anti-TNF therapy, anti-TL1A therapy, colectomy, or a combination thereof.

Various embodiments of the present invention provide a method of identifying susceptibility to or identifying protection against an inflammatory bowel disease (IBD) in a subject. The method comprises: genotyping the subject for a risk allele at a gene/genetic locus; and upon detecting the risk allele, identifying susceptibility to the IBD in the subject; or upon not detecting the risk allele, identifying protection against the IBD in the subject.

Various embodiments of the present invention provide a method of identifying susceptibility to an inflammatory bowel disease (IBD) in a subject. The method comprises: genotyping the subject for a risk allele at a gene/genetic locus; and upon detecting the risk allele, identifying susceptibility to the IBD in the subject.

Various embodiments of the present invention provide a method of identifying protection against an inflammatory bowel disease (IBD) in a subject. The method comprises: genotyping the subject for a risk allele at a gene/genetic locus; and upon not detecting the risk allele, identifying protection against the IBD in the subject.

In accordance with the present invention, susceptibility to IBD means that a subject has more likelihood of developing IBD as compared to the general population which the subject belongs to. In accordance with the present invention, protection against IBD means that a subject has less likelihood of developing IBD as compared to the general population which the subject belongs to.

Various embodiments of the present invention provide a method of diagnosing an inflammatory bowel disease (IBD) in a subject. The method comprises: genotyping the subject for a risk allele at a gene/genetic locus; and upon detecting the risk allele, diagnosing the IBD in the subject; or upon not detecting the risk allele, not diagnosing the IBD in the subject.

Various embodiments of the present invention provide a method of diagnosing an inflammatory bowel disease (IBD) in a subject. The method comprises: genotyping the subject for a risk allele at a gene/genetic locus; detecting the risk allele; and diagnosing the IBD in the subject.

Various embodiments of the present invention provide a method of treating an inflammatory bowel disease (IBD) in a subject. The method comprises: administering the IBD therapy to the subject, wherein the subject is diagnosed with the IBD according to a method as described herein, thereby treating the IBD in the subject. In various embodiments, the method further comprises providing an IBD therapy to the subject.

Various embodiments of the present invention provide a method of treating an inflammatory bowel disease (IBD) in a subject. The method comprises: genotyping the subject for a risk allele at a gene/genetic locus; and upon detecting the risk allele, administering the IBD therapy to the subject; or upon not detecting the risk allele, not administering the IBD therapy to the subject. In various embodiments, the method further comprises providing an IBD therapy to the subject.

Various embodiments of the present invention provide a method of treating an inflammatory bowel disease (IBD) in a subject. The method comprises: genotyping the subject for a risk allele at a gene/genetic locus; detecting the risk allele; and administering the IBD therapy to the subject, thereby treating the IBD in the subject. In various embodiments, the method further comprises providing an IBD therapy to the subject.

Various embodiments of the present invention provide a method of administering an inflammatory bowel disease (IBD) therapy to a subject. The method comprises: genotyping the subject for a risk allele at a gene/genetic locus; and upon detecting the risk allele, administering the IBD therapy to the subject; or upon not detecting the risk allele, not administering the IBD therapy to the subject.

Various embodiments of the present invention provide a method of administering an inflammatory bowel disease (IBD) therapy to a subject. The method comprises: genotyping the subject for a risk allele at a gene/genetic locus; detecting the risk allele; and administering the IBD therapy to the subject.

In various embodiments, the IBD therapy comprises anti-TNF therapy, anti-TL1A therapy, or colectomy, or a combination thereof. In some embodiments, the IBD therapy is an anti-TNF antibody. In some embodiments, the IBD therapy is an anti-TL1A antibody. In some embodiments, the IBD therapy is colectomy.

In various embodiments, the subject is a human. In some embodiments, the subject is a child. In some embodiments, the subject is a teenager. In other embodiments, the subject is an adult. In various embodiments, the IBD is Crohn's disease (CD) or ulcerative colitis (UC).

In various embodiments, the sample is cheek swab; mucus; whole blood; blood; serum; plasma; urine; saliva; semen; lymph; fecal extract; sputum; other body fluid or biofluid; cell sample; or tissue sample; or a combination thereof. In various embodiments, the sample comprises a nucleic acid from the individual. In some embodiments, the nucleic acid comprises genomic DNA. In various embodiments, the sample is a body fluid. In some embodiments, the body fluid is whole blood, plasma, saliva, mucus, or cheek swab. In various embodiments, the sample is a cell or tissue. In some embodiments, the cell is a blood cell. In some embodiments, the cell is a blood cell line (e.g., a lymphoblastoid cell line) obtained from the subject and transformed with an Epstein Barr virus.

In various embodiments, the gene/genetic locus comprises 1, 2, 3, 4, 5, 6, 7, 8, 9, 10, 11, 12, 13, 14, or more, or all of the genes/genetic loci listed in Table 1 as SEQ ID NOs: 1-341. In various embodiments, the gene/genetic locus comprises SLC26A4, DLG4, GIPR, ZHX3, TNRC6B, CDK6, PRR5L, WNT2B, LRRC16A, HIST1 cluster (all Histone cluster 1 genes), GTF2IRD2B, ETS1, SLC5A1, or TET2, or a combination thereof. In various embodiments, the gene/genetic locus comprises ETS1, HIST1 cluster (all Histone cluster 1 genes), CDK6, LRRC16A, or a combination thereof. In various embodiments, the gene/genetic locus comprises ETS1. In various embodiments, the gene/genetic locus comprises HIST1 cluster (all Histone cluster 1 genes). In various embodiments, the gene/genetic locus comprises CDK6. In various embodiments, the gene/genetic locus comprises LRRC16A. Each gene can comprise the following sequences: SLC26A4 (SEQ ID NOs: 1-6); DLG4 (SEQ ID NO: 7); GIPR (SEQ ID NOs: 8-27); ZHX3 (SEQ ID NOs: 28-30); TNRC6B (SEQ ID NOs: 31-38); CDK6 (SEQ ID NOs: 39-40); PRR5L (SEQ ID NOS: 41-54); WNT2B (SEQ ID NOs: 55-58); LRRC16A (SEQ ID NOs: 59-75, 335); HIST1 cluster (all Histone cluster 1 genes-SEQ ID NOs: 76-173, 338, 339); GTF2IRD2B (SEQ ID NOs: 174-180); ETS1 (SEQ ID NOs: 181-325); SLC5A1 (SEQ ID NOs: 326-327); and TET2 (SEQ ID NOs: 328-332, 334).

In various embodiments, the risk allele comprises 1, 2, 3, 4, 5, 6, 7, 8, 9, 10, or more, or all of the risk alleles listed in Table 1 as SEQ ID NOs: 1-341. In various embodiments, the risk allele comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 99, or 100, or more, or all of the risk alleles listed in Table 1 as SEQ ID NOs: 1-341. In various embodiments, the risk allele comprises N of the risk alleles listed in Table 1 as SEQ ID NOs: 1-341, and wherein Nis a positive integer not more than 341 (i.e., $1 \leq N \leq 341$). In various embodiments, the risk allele comprises 1-5, 5-10, 10-15, 15-20, 20-25, 25-30, 30-35, 35-40, 40-45, 45-50, 50-55, 55-60, 60-65, 65-70, 70-75, 75-80, 80-85, 85-90, 90-95, or 95-100 of the risk alleles listed in Table 1 as SEQ ID NOs: 1-341. In various embodiments, the risk allele comprises 100-105, 105-110, 110-115, 115-120, 120-125, 125-130, 130-135, 135-140, 140-145, 145-150, 150-155, 155-160, 160-165, 165-170, 170-175, 175-180, 180-185, 185-190, 190-195, or 195-200 of the risk alleles listed in Table 1 as SEQ ID NOs: 1-341. In various embodiments, the risk allele comprises 200-205, 205-210, 210-215, 215-220, 220-225, 325-230, 230-235, 235-240, 240-245, 245-250, 250-255, 255-260, 260-265, 265-270, 270-275, 275-280, 280-285, 285-290, 290-295, or 295-300 of the risk alleles listed in Table 1 as SEQ ID NOs: 1-341. In various embodiments, the risk allele comprises 300-305, 305-310, 310-315, 315-320, 320-325, 325-330, or 330-341 of the risk alleles listed in Table 1 as SEQ ID NOs: 1-341.

In some embodiments, the subject's genotypes can be obtained from previous genetic or genomic tests performed on the subject and those previous tests were not performed with particular respect to IBD or any condition. For example, the subject's genotypes can be obtained from analyzing the subject's genome sequencing results, or obtained from a database storing the subject's personal genetic or genomic information. In these embodiments, genotyping the subject does not require conducting laboratory tests on the subject, as it involves acquiring and analyzing data already available. In other embodiments, for example, when personal genetic or genomic information is not available or when subject or physician desire new laboratory tests, genotyping the subject requires conducting laboratory tests on the subject.

In various embodiments of the present invention, genotyping the subject comprises: obtaining a sample from the subject; and genotyping the sample for the risk allele at the gene/genetic locus.

In some embodiments, genotyping the sample comprises: contacting the sample with an oligonucleotide probe specific to the risk allele; generating an allele-specific hybridization complex between the oligonucleotide probe and the risk allele; and upon detecting the allele-specific hybridization complex, detecting the risk allele; or upon not detecting the allele-specific hybridization complex, not detecting the risk allele. In various embodiments, the oligonucleotide probe is labeled with a fluorescent dye, and wherein detecting the allele-specific hybridization complex comprises detecting fluorescence signal from the oligonucleotide probe. In various embodiments, the oligonucleotide probe comprises a reporter dye and a quencher dye. In certain embodiments, the method further comprises conducting PCR amplification after forming the allele-specific hybridization complex. In various embodiments, detecting the allele-specific hybridization complex comprises detecting the electrophoretic mobility of the allele-specific hybridization complex.

In various embodiments, genotyping the sample comprises detecting a SNP's alleles in the sample by: contacting the sample with detection agents that specifically bind to the SNP's alleles; and detecting the binding levels between the detection agents and the SNP's alleles. Alleles can be detected by genotyping assays, PCR, Reverse transcription PCR, real-time PCR, microarray, DNA sequencing, and RNA sequencing techniques.

Various embodiments of the present invention provide a composition. In various embodiments, the composition comprises one or more detection agents that specifically bind to one or more alleles at one or more genes/genetic loci. This composition may be used to identify genes/genetic loci associated with a condition, and/or to prognose low or high probability of developing IBD, and/or to prognose susceptibility to or protection against IBD, and/or to diagnose IBD, and/or to treat IBD, and/or to direct administering an IBD therapy.

In various embodiments, the detection agents are oligonucleotide probes, nucleic acids, DNAs, RNAs, aptamers, peptides, proteins, antibodies, avimers, or small molecules, or a combination thereof. In some embodiments, the detection agents are allele-specific oligonucleotide probes targeting the SNP's alleles. In various embodiments, a SNP's alleles are detected by using a microarray. In some embodiments, the microarray is an oligonucleotide microarray, DNA microarray, cDNA microarrays, RNA microarray, peptide microarray, protein microarray, or antibody microarray, or a combination thereof.

In various embodiments, detecting a SNP's alleles comprises: contacting the sample with one or more allele-specific oligonucleotide probes targeting the SNP's alleles; generating double-stranded hybridization complex through allele-specific binding between the SNP's alleles and said allele-specific oligonucleotide probes; and detecting the double-stranded hybridization complex newly generated through allele-specific binding between the SNP's alleles and said allele-specific oligonucleotide probes. In some embodiments, the method further comprises conducting PCR amplification of the double-stranded hybridization complex.

In various embodiments, the present invention provides allele-specific oligonucleotide probes for each of the alleles (e.g., major alleles, minor alleles, risk alleles, and non-risk alleles listed Table 1. In accordance with the present invention, said allele-specific oligonucleotide probes may comprise about 10-15, 15-20, 20-25, 25-30, 30-35, 35-40, 40-45, or 45-50 nucleotides; they are either identical or complementary to a sequence segment encompassing the polymorphic position of a SNP as disclosed herein; and they are specific to one or the other allele at the polymorphic position. For a non-limiting example, rs10247487 has either T or C allele (in the context of forward strand) at its polymorphic position (e.g., "Y" at nucleotide 501 of the following exemplar sequence (SEQ ID NO: 1).

```
 60 CCTAAGGAAG TTCTAGACTA GTGTTTCATG GAGCCCATTC TTTTAAATTA AAAGTAGCCA
120 TTTAAAAAAA TTAAAGTCCC AGAAAATGAC CATTAGAATA TGCAATTTAA AAATAGCAAA
180 TAAAACAAAC TAAGGTTTTT TTGAACAGAT ATATAGAAAC AAAATTTCAC TTAGTTTACA
240 ATATAAACAT GCATTTCACA TTAGCATTAA AATGCTATTG TGATTTATCT CTCTTTCAAA
300 TACTATTGCC TCTACTTACA CAATCATATT TGTCCTTTCG CCACAATCTG CCTATTTCAG
360 CAAACTGCAT CAGCATTCCC TTTAAGTTTC CCAATGCTAA AGCTGCCAGG ACGGACTGTG
420 AAAAACACAA ACATCAGATG TACTTTAAGT TAATGAAATA AACCACAGGG AAGCAAAGGT
480 GAAGGCTATA GATAAGTGTG TGCTTTAAAG GGCCTCAAAG CAAATCAAAG CATTACACCC
540 TTTTCCGGTG TGCGATGCCA YGCAAGACAC ACCAGAACTG GGACTCTGAC CTGTTCCTAT
600 GAATGACTTT GTCCCCACAA CAGTGACAAG GCCTAGGCTG CTCTTGTGAT TATGAGATAG
660 ATGATCTGAT GGCGTTTAGT AGCCTGCACC TTGGGACAGA GAAAGGCAGA CCTTCAGACC
720 TATGACAGAC TAACATTTGG AATAAATTCC TCCCAAGCAG AGACAGTCTA ATGTGTGTTT
```

-continued

```
780 GTTTATTGGA GTCAAGGAGA TGGGGGTTGC TCTTTGTTAA AAAAAAAAAT AGCTTGGGAA

840 GCTTGAGGTC CTGGAATGAG ATGACTTGAG GCGGGCTTTC TGGGACAGCA TGAAACATAT

900 CTATCTAGTT CCTGCTATAT CCCCAGAACC TACTATGTTA AATGCATACA GGAGGGGCTT

960 TAAAATTAGT CAGTGAATGA GTGGCTGAGC CAATGAATGA ATATTTCCCA GGCCAGTACT

1001 AATCCCTACA GCCAAGCTTC AGACTTCCAA TTCTTCCACA G
```

Hence, an allele-specific oligonucleotide probe for the T allele at rs10247487 may comprise, for a non-limiting example, 21 nucleotides; and these 21 nucleotides are either identical or complementary to the sequence segment 481-501, 482-502, 483-503, 484-504, 485-505, 486-506, 487-507, 488-508, 489-509, 490-511, 491-511, 492-512, 493-513, 494-514, 495-515, 496-516, 497-517, 498-518, 499-519, 500-520, or 501-521 of the above exemplar sequence where nucleotide 501 is set as the T allele. Vice versa, an allele-specific oligonucleotide probe for the C allele at rs10247487 may comprise, for a non-limiting example, 21 nucleotides; and these 21 nucleotides are either identical or complementary to the sequence segment 481-501, 482-502, 483-503, 484-504, 485-505, 486-506, 487-507, 488-508, 489-509, 490-511, 491-511, 492-512, 493-513, 494-514, 495-515, 496-516, 497-517, 498-518, 499-519, 500-520, or 501-521 of the above exemplar sequence where nucleotide 501 is set as the C allele.

In various embodiments, said allele-specific oligonucleotide probes are labeled with one or more fluorescent dyes, and wherein detecting the double-stranded hybridization complex comprises detecting fluorescence signals from the fluorescent dyes. In some embodiments, said allele-specific oligonucleotide probes are labeled with a reporter dye and a quencher dye. In some embodiments, detecting the double-stranded hybridization complex comprises detecting the electrophoretic mobility of the double-stranded hybridization complex.

A variety of methods can be used to detect the presence or absence of a variant allele or haplotype. As an example, enzymatic amplification of nucleic acid from an individual may be used to obtain nucleic acid for subsequent analysis. The presence or absence of a variant allele or haplotype may also be determined directly from the individual's nucleic acid without enzymatic amplification.

Detecting the presence or absence of a variant allele or haplotype may involve amplification of an individual's nucleic acid by the polymerase chain reaction. Use of the polymerase chain reaction for the amplification of nucleic acids is well known in the art (see, for example, Mullis et al. (Eds.), The Polymerase Chain Reaction, Birkhauser, Boston, (1994)).

Analysis of the nucleic acid from an individual, whether amplified or not, may be performed using any of various techniques. Useful techniques include, without limitation, polymerase chain reaction based analysis, sequence analysis and electrophoretic analysis. As used herein, the term "nucleic acid" means a polynucleotide such as a single or double-stranded DNA or RNA molecule including, for example, genomic DNA, cDNA and mRNA. The term nucleic acid encompasses nucleic acid molecules of both natural and synthetic origin as well as molecules of linear, circular or branched configuration representing either the sense or antisense strand, or both, of a native nucleic acid molecule.

A TaqmanB allelic discrimination assay available from Applied Biosystems may be useful for determining the presence or absence of a variant allele. In a TaqmanB allelic discrimination assay, a specific, fluorescent, dye-labeled probe for each allele is constructed. The probes contain different fluorescent reporter dyes such as FAM and VICTM to differentiate the amplification of each allele. In addition, each probe has a quencher dye at one end which quenches fluorescence by fluorescence resonant energy transfer (FRET). During PCR, each probe anneals specifically to complementary sequences in the nucleic acid from the individual. The 5' nuclease activity of Taq polymerase is used to cleave only probe that hybridize to the allele. Cleavage separates the reporter dye from the quencher dye, resulting in increased fluorescence by the reporter dye. Thus, the fluorescence signal generated by PCR amplification indicates which alleles are present in the sample. Mismatches between a probe and allele reduce the efficiency of both probe hybridization and cleavage by Taq polymerase, resulting in little to no fluorescent signal. Improved specificity in allelic discrimination assays can be achieved by conjugating a DNA minor grove binder (MGB) group to a DNA probe as described, for example, in Kutyavin et al., "3'-minor groove binder-DNA probes increase sequence specificity at PCR extension temperature, "Nucleic Acids Research 28:655-661 (2000)). Minor grove binders include, but are not limited to, compounds such as dihydrocyclopyrroloindole tripeptide (DPI,).

Sequence analysis also may also be useful for determining the presence or absence of a variant allele or haplotype.

Restriction fragment length polymorphism (RFLP) analysis may also be useful for determining the presence or absence of a particular allele (Jarcho et al. in Dracopoli et al., Current Protocols in Human Genetics pages 2.7.1-2.7.5, John Wiley & Sons, New York; Innis et al., (Ed.), PCR Protocols, San Diego: Academic Press, Inc. (1990)). As used herein, restriction fragment length polymorphism analysis is any method for distinguishing genetic polymorphisms using a restriction enzyme, which is an endonuclease that catalyzes the degradation of nucleic acid and recognizes a specific base sequence, generally a palindrome or inverted repeat. One skilled in the art understands that the use of RFLP analysis depends upon an enzyme that can differentiate two alleles at a polymorphic site.

Allele-specific oligonucleotide hybridization may also be used to detect a variant allele or haplotype. Allele-specific oligonucleotide hybridization is based on the use of a labeled oligonucleotide probe having a sequence perfectly complementary, for example, to the sequence encompassing a variant allele or haplotype. Under appropriate conditions, the allele-specific probe hybridizes to a nucleic acid containing the variant allele or haplotype but does not hybridize to the other alleles or haplotypes, which have one or more nucleotide mismatches as compared to the probe. If desired, a second allele-specific oligonucleotide probe that matches an alternate allele also can be used. Similarly, the technique of allele-specific oligonucleotide amplification can be used to selectively amplify, for example, a variant allele or haplotype by using an allele-specific oligonucleotide primer that is perfectly complementary to the nucleotide sequence of the variant allele or haplotype but which has one or more mismatches as compared to other alleles or haplotypes (Mullis et al., supra, (1994)). One skilled in the art understands that the one or more nucleotide mismatches that distinguish between the variant allele or haplotype and the other alleles or haplotypes are preferably located in the center of an allele-specific oligonucleotide primer to be used in allele-specific oligonucleotide hybridization. In contrast, an allele-specific oligonucleotide primer to be used in PCR amplification preferably contains the one or more nucleotide mismatches that distinguish between the variant allele or haplotype and the other alleles at the 3' end of the primer.

A heteroduplex mobility assay (HMA) is another well-known assay that may be used to detect a variant allele or haplotype. HMA is useful for detecting the presence of a polymorphic sequence since a DNA duplex carrying a mismatch has reduced mobility in a polyacrylamide gel compared to the mobility of a perfectly base-paired duplex (Delwart et al., Science 262:1257-1261 (1993); White et al., Genomics 12:301-306 (1992)).

The technique of single strand conformational, polymorphism (SSCP) also may be used to detect the presence or absence of a variant allele or haplotype (see Hayashi, K., Methods Applic. 1:34-38 (1991)). This technique can be used to detect mutations based on differences in the secondary structure of single-strand DNA that produce an altered electrophoretic mobility upon non-denaturing gel electrophoresis. Polymorphic fragments are detected by comparison of the electrophoretic pattern of the test fragment to corresponding standard fragments containing known alleles.

Denaturing gradient gel electrophoresis (DGGE) also may be used to detect a variant allele or haplotype. In DGGE, double-stranded DNA is electrophoresed in a gel containing an increasing concentration of denaturant; double-stranded fragments made up of mismatched alleles have segments that melt more rapidly, causing such fragments to migrate differently as compared to perfectly complementary sequences (Sheffield et al., "Identifying DNA Polymorphisms by Denaturing Gradient Gel Electrophoresis" in Innis et al., supra, 1990).

Other molecular methods useful for determining the presence or absence of a variant allele or haplotype are known in the art and useful in the methods of the invention. Other well-known approaches for determining the presence or absence of a variant allele or haplotype include automated sequencing and RNAase mismatch techniques (Winter et al., Proc. Natl. Acad. Sci. 82:7575-7579 (1985)). Furthermore, one skilled in the art understands that, where the presence or absence of multiple alleles or haplotypes is to be determined, individual alleles or haplotypes can be detected by any combination of molecular methods. See, in general, Birren et al. (Eds.) Genome Analysis: A Laboratory Manual Volume 1 (Analyzing DNA) New York, Cold Spring Harbor Laboratory Press (1997). In addition, one skilled in the art understands that multiple alleles can be detected in individual reactions or in a single reaction (a "multiplex" assay). In view of the above, one skilled in the art realizes that the methods of the present invention may be practiced using one or any combination of the well-known assays described above or another art-recognized genetic assay. Gene Identification Various embodiments of the present invention provide for a method of identifying genes/genetic loci associated with a condition, comprising: acquiring genetic data from samples of a cohort of the condition; performing a GLS transformation on the genetic data, thereby decorrelating the genetic data; conducting gene-based analysis on the GLS-transformed genetic data; and identifying genes/genetic loci associated with the condition. In various embodiments, the condition is IBD, CD, or UC, or a combination thereof. In some embodiments, the cohort comprises correlated subjects or family subjects. In other embodiments, the genetic data comprise SNP genotypes. In yet other embodiments, performing the GLS transformation comprises transforming the genetic data according to functions $$G=\Sigma_o^{-1/2},$$

$$Gy=GX\beta+Ge,$$

$$\hat{\beta}_{GLS}=(X'\Sigma_o^{-1}X)^{-1}X'\Sigma_o^{-1}y,$$

$$\mathrm{var}(\hat{\beta}_{GLS})=\mathrm{var}((X'\Sigma_o^{-1}X)^{-1}X'\Sigma_o^{-1}y)=(X'\Sigma_o^{-1}X)^{-1},$$

or a combination thereof.

In various embodiments, conducting gene-based analysis comprises applying a gene-based test based on the assumption of independent or uncorrelated subjects. In various embodiments, conducting gene-based analysis comprises applying C-alpha, SKAT, SKAT-CommonRare, CMC, WSS, Variable Threshold, or Comprehensive Approach, or a combination thereof.

Various embodiments of the present invention provide a method of identifying genes/genetic loci associated with a condition. The method comprises: acquiring genetic data from samples of a cohort of the condition; performing a GLS transformation on the genetic data, thereby decorrelating the genetic data; conducting gene-based analysis on the GLS-transformed genetic data; and identifying genes/genetic loci associated with the condition. In various embodiments, the condition is IBD, CD, or UC, or a combination thereof.

In various embodiments, the cohort comprises correlated subjects or family subjects. In some embodiments, the cohort comprises cases subjects diagnosed with the condition. In some embodiments, the cohort comprises controls subjects who are healthy or not diagnosed with the condition. In various embodiments, the genetic data comprise SNP genotypes.

In various embodiments, performing the GLS transformation comprises transforming the genetic data according to functions (5)-(8), described above. In various embodiments, conducting gene-based analysis comprises applying a gene-based test based on the assumption of independent or uncorrelated subjects. In various embodiments, conducting gene-based analysis comprises applying C-alpha, SKAT, SKAT-CommonRare, CMC, WSS, Variable Threshold, or Comprehensive Approach, or a combination thereof.

Kits of the Invention

Various embodiments of the present invention also provide a kit. The kit may consist of or may consist essentially of or may comprise: one or more detection agents for detecting one or more alleles at one or more genes/genetic loci; instructions of using the agent to identify genes/genetic loci associated with a condition, and/or to prognose low or high probability of developing IBD, and/or to prognose susceptibility to or protection against IBD, and/or to diagnose IBD, and/or to treat IBD, and/or to direct administering an IBD therapy. In some embodiments, the one or more alleles are risk alleles associated with IBD.

Various embodiments of the present invention also provide a kit. The kit may consist of or may consist essentially of or may comprise: one or more detection agents for detecting one or more alleles at one or more genes/genetic loci; instructions of using the agent to identify genes/genetic loci associated with a condition. In various embodiments, the kit further comprises samples obtained from a cohort of the condition. In various embodiments, the condition is IBD, Crohn's disease (CD), or ulcerative colitis (UC).

Various embodiments of the present invention also provide a kit. The kit may consist of or may consist essentially of or may comprise: one or more detection agents for detecting one or more risk alleles at one or more genes/genetic loci; instructions of using the agent to prognose low or high probability of developing IBD, and/or to prognose susceptibility to or protection against IBD, and/or to diagnose IBD, and/or to treat IBD, and/or to direct administering an IBD therapy. In various embodiments, the risk alleles are associated with IBD. In various embodiments, the kit further comprises a sample obtained from a subject who desires prognosis, and/or diagnosis, and/or treatment of IBD. In various embodiments, the IBD is Crohn's disease (CD) or ulcerative colitis (UC).

In various embodiments, the one or more genes/genetic loci comprise 1, 2, 3, 4, 5, 6, 7, 8, 9, 10, 11, 12, 13, 14, or more, or all of the genes/genetic loci listed in Table 1 as SEQ ID NOs: 1-341. In various embodiments, the one or more genes/genetic loci comprise SLC26A4, DLG4, GIPR, ZHX3, TNRC6B, CDK6, PRR5L, WNT2B, LRRC16A, HIST1 cluster (all Histone cluster 1 genes), GTF2IRD2B, ETS1, SLC5A1, or TET2, or a combination thereof. In various embodiments, the one or more genes/genetic loci comprises ETS1, HIST1 cluster (all Histone cluster 1 genes), CDK6, LRRC16A, or a combination thereof. In various embodiments, the gene/genetic locus comprises ETS1. In various embodiments, the gene/genetic locus comprises HIST1 cluster (all Histone cluster 1 genes). In various embodiments, the gene/genetic locus comprises CDK6. In various embodiments, the gene/genetic locus comprises LRRC16A.

In various embodiments, the kit further comprises an IBD therapy. Examples of the IBD therapy including but are not limited to anti-TNF therapy and anti-TL1A therapy. In some embodiments, the IBD therapy is an anti-TNF antibody. In some embodiments, the IBD therapy is an anti-TL1A antibody.

The kit is an assemblage of materials or components, including at least one of the inventive elements or modules. In various embodiments, the one or more detection agents specifically bind to one or more SNP's alleles. In some embodiments, the one or more SNP's alleles can be major alleles, minor alleles, or both. In some embodiments, the one or more SNP's alleles can be risk alleles, non-risk alleles, or protection alleles, or a combination thereof.

In some embodiments, the one or more detection agents specifically bind to one or more risk alleles listed in Table 1 as SEQ ID NOs: 1-341. In some embodiments, the one or more detection agents specifically bind to 1, 2, 3, 4, 5, 6, 7, 8, 9, 10, or more, or all of the risk alleles listed in Table 1 as SEQ ID NOs: 1-341. In various embodiments, the one or more detection agents specifically bind to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 99, or 100, or more, or all of the risk alleles listed in Table 1 as SEQ ID NOs: 1-341. In some embodiments, the one or more detection agents specifically bind to N of the risk alleles listed in Table 1, and wherein N is a positive integer not more than 341 (i.e., $1 \leq N \leq 341$). In various embodiments, the one or more detection agents specifically bind to 1-5, 5-10, 10-15, 15-20, 20-25, 25-30, 30-35, 35-40, 40-45, 45-50, 50-55, 55-60, 60-65, 65-70, 70-75, 75-80, 80-85, 85-90, 90-95, or 95-100 of the risk alleles listed in Table 1 as SEQ ID NOs: 1-341. In various embodiments, the one or more detection agents specifically bind to 100-105, 105-110, 110-115, 115-120, 120-125, 125-130, 130-135, 135-140, 140-145, 145-150, 150-155, 155-160, 160-165, 165-170, 170-175, 175-180, 180-185, 185-190, 190-195, or 195-200 of the risk alleles listed in Table 1 as SEQ ID NOs: 1-341. In various embodiments, the one or more detection agents specifically bind to 200-205, 205-210, 210-215, 215-220, 220-225, 325-230, 230-235, 235-240, 240-245, 245-250, 250-255, 255-260, 260-265, 265-270, 270-275, 275-280, 280-285, 285-290, 290-295, or 295-300 of the risk alleles listed in Table 1 as SEQ ID NOs: 1-341. In various embodiments, the one or more detection agents specifically bind to 300-305, 305-310, 310-315, 315-320, 320-325, 325-330, 330-335, 335-340, 340-341 of the risk alleles listed in Table 1 as SEQ ID NOs: 1-341.

In various embodiments, the one or more detection agents are applied to contact a biological sample obtained from the subject; and the level of binding between the one or more detection agents and the one or more alleles is detected. In some embodiments, the one or more detection agents are oligonucleotide probes, nucleic acids, DNAs, RNAs, peptides, proteins, antibodies, aptamers, or small molecules, or a combination thereof. In various embodiments, the level of binding is detected using a microarray. In some embodiments, the microarray is an oligonucleotide microarray, DNA microarray, cDNA microarrays, RNA microarray, peptide microarray, protein microarray, or antibody microarray, or a combination thereof.

In various embodiments, the one or detection agents are oligonucleotide probes specific to the one or more alleles. In various embodiments, the oligonucleotide probes are labeled with a fluorescent dye. In various embodiments, the oligonucleotide probes comprise reporter dyes and quencher dyes. In various embodiments, the kit further comprises a module configured to detecting fluorescence signal from the one or more detection agents. In various embodiments, the kit further comprises a module configured for conducting PCR amplification.

The exact nature of the components configured in the inventive kit depends on its intended purpose. Instructions for use may be included in the kit. "Instructions for use" typically include a tangible expression describing the technique to be employed in using the components of the kit to affect a desired outcome. Optionally, the kit also contains other useful components, such as, spray bottles or cans, diluents, buffers, pharmaceutically acceptable carriers, syringes, catheters, applicators (for example, applicators of cream, gel or lotion etc.), pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example, the detection agents can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. The packaging materials employed in the kit are those customarily utilized in assays and therapies. As used herein, the term "package" refers to a suitable solid matrix or material such as glass, plastic, paper, foil, and the like, capable of holding the individual kit components. Thus, for example, a package can be a glass vial used to contain suitable quantities of a composition as described herein. The packaging material generally has an external label which indicates the contents and/or purpose of the kit and/or its components.

Novel Genes/Regions, SNPs and Risk Alleles

Table 1 provides information of genes/regions, SNPs, SEQ ID NOs (SEQ ID NO: 1-341) and risk alleles in accordance with various embodiments of the present invention. "Dis" stands for disease; "gene.i" stands for gene ID; "SNP" stands for single nucleotide polymorphism; "rsID" stands for Reference SNP cluster ID (rs number); "chr" stands for chromosome; "pos_hg19" stands for position in human genome version 19; "pos_hg18" stands for position in human genome version 18; "A1" stands for minor allele; "A2" stands for major allele; "risk.allele" stands for the allele that leads to increased disease risk; "OR.risk.allele" stands for Odds Ratio in meta-analysis for the risk allele; "F_A_cedars" stands for minor allele frequency in Cedars affected cases; "F_U_cedars" stands for minor allele frequency in Cedars unaffected controls; "OR_cedars" stands for Odds Ratio in Cedars cohort; "SE_cedars" stands for Standard Error for log (OR) in Cedars cohort; "L95_cedars" stands for lower boundary of 95% Confidence Interval of OR in Cedars cohort; "U95_cedars" stands for upper boundary of 95% Confidence Interval of OR in Cedars cohort; "STAT_cedars" stands for test statistics (Z-value) in Cedars cohort; "P_cedars" stands for P-value in Cedars cohort; "F_A_iibdgc" stands for minor allele frequency in IIBDGC affected cases; "F_U_iibdgc" stands for minor allele frequency in IIBDGC unaffected controls; "OR_iibdgc" stands for Odds Ratio in IIBDGC cohort; "SE_iibdgc" stands for Standard Error for log (OR) in IIBDGC cohort; "L95_iibdgc" stands for lower boundary of 95% Confidence Interval of OR in IIBDGC cohort; "U95_iibdgc" stands for upper boundary of 95% Confidence Interval of OR in IIBDGC cohort; "STAT_iibdgc" stands for test statistics (Z statistics) in IIBDGC cohort; "P_iibdgc" stands for P-value in IIBBDGC cohort; "beta_meta_fixed" stands for log (OR) in meta-analysis; "se_meta_fixed" stands for Standard Error of log (OR) in meta-analysis; and "P_meta_fixed" stands for P-value in meta-analysis.

TABLE 1

(part 1)

| dis | gene.i | SNP | rsID | SEQ ID NO | chr | pos_hg19 | pos_hg18 | A 1 | A 2 | risk allele | OR.risk. allele |
|---|---|---|---|---|---|---|---|---|---|---|---|
| CD | SLC26A4 | rs10247487 | rs10247487 | 1 | 7 | 107420354 | 107207590 | A | G | G | 1.060282 |
| CD | SLC26A4 | rs10263826 | rs10263826 | 2 | 7 | 107421072 | 107208308 | G | A | A | 1.065343 |
| CD | SLC26A4 | rs10273733 | rs10273733 | 3 | 7 | 107258121 | 107045357 | A | G | A | 1.064739 |
| CD | SLC26A4 | rs12539555 | rs12539555 | 4 | 7 | 107404473 | 107191709 | G | A | G | 1.03454 |
| CD | SLC26A4 | rs2248465 | rs2248465 | 5 | 7 | 107303628 | 107090864 | G | A | G | 1.06059 |
| CD | SLC26A4 | rs2808 | rs2808 | 6 | 7 | 107260856 | 107048092 | A | G | A | 1.074763 |
| CD | DLG4 | rs3785794 | rs3785794 | 7 | 17 | 7005915 | 6946639 | A | G | G | 1.11467 |
| CD | GIPR | chr19:50983512 | rs55681266 | 8 | 19 | 46291672 | 50983512 | A | C | C | 1.065155 |
| CD | GIPR | chr19:51014231 | rs56243424 | 9 | 19 | 46322391 | 51014231 | A | G | G | 1.069862 |
| CD | GIPR | chr19:51026971 | rs73047896 | 10 | 19 | 46335131 | 51026971 | G | A | A | 1.073444 |
| CD | GIPR | rs10401439 | rs10401439 | 11 | 19 | 46320780 | 51012620 | A | G | G | 1.077122 |
| CD | GIPR | rs10402263 | rs10402263 | 12 | 19 | 46313758 | 51005598 | C | G | G | 1.062002 |
| CD | GIPR | rs10421891 | rs10421891 | 13 | 19 | 46315809 | 51007649 | G | A | A | 1.067512 |
| CD | GIPR | rs10500292 | rs10500292 | 14 | 19 | 46327933 | 51019773 | A | G | G | 1.065373 |
| CD | GIPR | rs11883351 | rs11883351 | 15 | 19 | 46304400 | 50996240 | A | G | G | 1.068662 |
| CD | GIPR | rs12463359 | rs12463359 | 16 | 19 | 46304585 | 50996425 | A | C | C | 1.063059 |
| CD | GIPR | rs16980013 | rs16980013 | 17 | 19 | 46267453 | 50959293 | A | C | C | 1.066731 |
| CD | GIPR | rs16980051 | rs16980051 | 18 | 19 | 46345886 | 51037726 | A | G | G | 1.063307 |
| CD | GIPR | rs17878252 | rs17878252 | 19 | 19 | 46234155 | 50925995 | A | G | G | 1.066875 |
| CD | GIPR | rs2070736 | rs2070736 | 20 | 19 | 46286714 | 50978554 | C | A | A | 1.068257 |
| CD | GIPR | rs2334255 | rs2334255 | 21 | 19 | 46186150 | 50877990 | A | C | A | 1.051486 |
| CD | GIPR | rs4514788 | rs4514788 | 22 | 19 | 46317593 | 51009433 | C | A | A | 1.060853 |
| CD | GIPR | rs4802273 | rs4802273 | 23 | 19 | 46244060 | 50935900 | G | A | A | 1.068602 |
| CD | GIPR | rs4802274 | rs4802274 | 24 | 19 | 46251768 | 50943608 | G | A | A | 1.069354 |
| CD | GIPR | rs4803861 | rs4803861 | 25 | 19 | 46328179 | 51020019 | A | G | G | 1.071572 |
| CD | GIPR | rs8111071 | rs8111071 | 26 | 19 | 46307406 | 50999246 | G | A | G | 1.075838 |
| CD | GIPR | rs918490 | rs918490 | 27 | 19 | 46338729 | 51030569 | A | G | G | 1.073866 |
| CD | ZHX3 | rs6072275 | rs6072275 | 28 | 20 | 39743905 | 39177319 | A | G | A | 1.086747 |
| CD | ZHX3 | rs6072343 | rs6072343 | 29 | 20 | 39968188 | 39401602 | A | G | A | 1.100691 |
| CD | ZHX3 | rs6093462 | rs6093462 | 30 | 20 | 39908689 | 39342103 | A | G | G | 1.075153 |
| CD | TNRC6B | rs114607 | rs114607 | 31 | 22 | 40376383 | 38706329 | A | G | G | 1.04635 |
| CD | TNRC6B | rs137955 | rs137955 | 32 | 22 | 40291807 | 38621753 | A | G | A | 1.049438 |
| CD | TNRC6B | rs137956 | rs137956 | 33 | 22 | 40293463 | 38623409 | G | A | G | 1.053575 |
| CD | TNRC6B | rs137977 | rs137977 | 34 | 22 | 40320361 | 38650307 | A | C | C | 1.032278 |
| CD | TNRC6B | rs137981 | rs137981 | 35 | 22 | 40327206 | 38657152 | G | A | A | 1.055186 |
| CD | TNRC6B | rs138027 | rs138027 | 36 | 22 | 40616112 | 38946058 | G | A | A | 1.049378 |
| CD | TNRC6B | rs2958647 | rs2958647 | 37 | 22 | 40291139 | 38621085 | C | A | C | 1.050825 |
| CD | TNRC6B | rs713925 | rs713925 | 38 | 22 | 40299158 | 38629104 | C | A | A | 1.035056 |
| UC | CDK6 | rs2282978 | rs2282978 | 39 | 7 | 92264410 | 92102346 | G | A | A | 1.080458 |
| UC | CDK6 | rs4272 | rs4272 | 40 | 7 | 92236829 | 92074765 | G | A | A | 1.068931 |
| UC | PRR5L | rs11033597 | rs11033597 | 41 | 11 | 36429876 | 36386452 | A | G | A | 1.068317 |
| UC | PRR5L | rs11600757 | rs11600757 | 42 | 11 | 36473784 | 36430360 | A | G | A | 1.082739 |
| UC | PRR5L | rs11601211 | rs11601211 | 43 | 11 | 36465159 | 36421735 | G | A | G | 1.063202 |

TABLE 1-continued

| | | | | | | | | | | | |
|---|---|---|---|---|---|---|---|---|---|---|---|
| UC | PRR5L | rs12281565 | rs12281565 | 44 | 11 | 36471571 | 36428147 | G | A | G | 1.079272 |
| UC | PRR5L | rs1365120 | rs1365120 | 45 | 11 | 36438075 | 36394651 | G | A | G | 1.179 |
| UC | PRR5L | rs1895840 | rs1895840 | 46 | 11 | 36424277 | 36380853 | G | A | G | 1.061208 |
| UC | PRR5L | rs2303439 | rs2303439 | 47 | 11 | 36514290 | 36470866 | A | G | A | 1.071103 |
| UC | PRR5L | rs330260 | rs330260 | 48 | 11 | 36422172 | 36378748 | G | A | G | 1.054865 |
| UC | PRR5L | rs331485 | rs331485 | 49 | 11 | 36454231 | 36410807 | A | G | G | 1.064878 |
| UC | PRR5L | rs4077044 | rs4077044 | 50 | 11 | 36412655 | 36369231 | C | A | C | 1.038306 |
| UC | PRR5L | rs5030437 | rs5030437 | 51 | 11 | 36524755 | 36481331 | A | G | A | 1.066163 |
| UC | PRR5L | rs5030445 | rs5030445 | 52 | 11 | 36522260 | 36478836 | A | G | A | 1.064399 |
| UC | PRR5L | rs5030472 | rs5030472 | 53 | 11 | 36513786 | 36470362 | A | G | A | 1.081762 |
| UC | PRR5L | rs7929195 | rs35403761 | 54 | 11 | 36458586 | 36415162 | A | C | C | 1.051966 |
| IBD | WNT2B | rs10745330 | rs10745330 | 55 | 1 | 113083439 | 112884962 | A | G | A | 1.047821 |
| IBD | WNT2B | rs2999155 | rs2999155 | 56 | 1 | 113221658 | 113023181 | G | A | G | 1.045707 |
| IBD | WNT2B | rs3790609 | rs3790609 | 57 | 1 | 113056990 | 112858513 | A | G | A | 1.059618 |
| IBD | WNT2B | rs6682737 | rs6682737 | 58 | 1 | 113136229 | 112937752 | G | A | G | 1.046411 |
| IBD | LRRC16A | rs10456320 | rs10456320 | 59 | 6 | 25292401 | 25400380 | A | G | A | 1.071532 |
| IBD | LRRC16A | rs11755567 | rs11755567 | 60 | 6 | 25237288 | 25345267 | A | G | G | 1.049589 |
| IBD | LRRC16A | rs13191296 | rs13191296 | 61 | 6 | 25684606 | 25792585 | A | G | G | 1.094237 |
| IBD | LRRC16A | rs2690110 | rs2690110 | 62 | 6 | 25328567 | 25436546 | G | A | G | 1.060658 |
| IBD | LRRC16A | rs4712908 | rs4712908 | 63 | 6 | 25320920 | 25428899 | A | G | G | 1.038597 |
| IBD | LRRC16A | rs6921589 | rs6921589 | 64 | 6 | 25422369 | 25530348 | A | C | C | 1.06713 |
| IBD | LRRC16A | rs6937918 | rs6937918 | 65 | 6 | 25407295 | 25515274 | A | G | A | 1.035383 |
| IBD | LRRC16A | rs742132 | rs742132 | 66 | 6 | 25607571 | 25715550 | G | A | G | 1.03153 |
| IBD | LRRC16A | rs7752195 | rs7752195 | 67 | 6 | 25419094 | 25527073 | A | G | G | 1.106969 |
| IBD | LRRC16A | rs7752524 | rs7752524 | 68 | 6 | 25310585 | 25418564 | G | A | G | 1.088791 |
| IBD | LRRC16A | rs7762757 | rs7762757 | 69 | 6 | 25420992 | 25528971 | T | A | T | 1.032075 |
| IBD | LRRC16A | rs880226 | rs880226 | 70 | 6 | 25402303 | 25510282 | G | A | G | 1.033746 |
| IBD | LRRC16A | rs9295661 | rs9295661 | 71 | 6 | 25450026 | 25558005 | C | A | A | 1.105753 |
| IBD | LRRC16A | rs9358854 | rs9358854 | 72 | 6 | 25411464 | 25519443 | A | G | G | 1.038355 |
| IBD | LRRC16A | rs9461157 | rs9461157 | 73 | 6 | 25400323 | 25508302 | A | G | A | 1.035385 |
| IBD | LRRC16A | rs9461165 | rs9461165 | 74 | 6 | 25406932 | 25514911 | G | A | G | 1.036141 |
| IBD | LRRC16A | rs9467445 | rs9467445 | 75 | 6 | 25234884 | 25342863 | G | A | A | 1.054554 |
| IBD | All Histone cluster1 gene | rs10484399 | rs10484399 | 76 | 6 | 27534528 | 27642507 | G | A | A | 1.081187 |
| IBD | All Histone cluster1 gene | rs10484439 | rs10484439 | 77 | 6 | 26309908 | 26417887 | A | G | G | 1.077614 |
| IBD | All Histone cluster1 gene | rs12176317 | rs12176317 | 78 | 6 | 26372786 | 26480765 | G | A | A | 1.065838 |
| IBD | All Histone cluster1 gene | rs13194053 | rs13194053 | 79 | 6 | 27143883 | 27251862 | G | A | A | 1.055137 |
| IBD | All Histone cluster1 gene | rs13194491 | rs13194491 | 80 | 6 | 27037080 | 27145059 | A | G | A | 1.050167 |
| IBD | All Histone cluster1 gene | rs13194781 | rs13194781 | 81 | 6 | 27815639 | 27923618 | G | A | A | 1.080774 |
| IBD | All Histone cluster1 gene | rs13195040 | rs13195040 | 82 | 6 | 27413924 | 27521903 | G | A | A | 1.086088 |
| IBD | All Histone cluster1 gene | rs13199772 | rs13199772 | 83 | 6 | 27834085 | 27942064 | G | A | A | 1.080476 |
| IBD | All Histone cluster1 gene | rs13212651 | rs13212651 | 84 | 6 | 27806985 | 27914964 | G | A | A | 1.081515 |
| IBD | All Histone cluster1 gene | rs1321578 | rs1321578 | 85 | 6 | 27104783 | 27212762 | C | A | A | 1.073664 |
| IBD | All Histone cluster1 gene | rs13217599 | rs13217599 | 86 | 6 | 27586230 | 27694209 | G | A | G | 1.058743 |
| IBD | All Histone cluster1 gene | rs13218875 | rs13218875 | 87 | 6 | 27884012 | 27991991 | A | G | G | 1.081223 |
| IBD | All Histone cluster1 gene | rs13219354 | rs13219354 | 88 | 6 | 27185664 | 27293643 | G | A | A | 1.062354 |
| IBD | All Histone cluster1 gene | rs16867901 | rs16867901 | 89 | 6 | 27656076 | 27764055 | A | G | G | 1.199385 |
| IBD | All Histone cluster1 gene | rs16867911 | rs16867911 | 90 | 6 | 27662204 | 27770183 | A | C | C | 1.182881 |
| IBD | All Histone cluster1 gene | rs16891725 | rs16891725 | 91 | 6 | 26479150 | 26587129 | A | G | G | 1.064118 |
| IBD | All Histone cluster1 gene | rs175597 | rs175597 | 92 | 6 | 27810626 | 27918605 | G | A | A | 1.088234 |
| IBD | All Histone cluster1 gene | rs17693963 | rs17693963 | 93 | 6 | 27710165 | 27818144 | C | A | A | 1.06249 |
| IBD | All Histone cluster1 gene | rs17739310 | rs17739310 | 94 | 6 | 27296775 | 27404754 | A | G | A | 1.045616 |
| IBD | All Histone cluster1 gene | rs17750424 | rs17750424 | 95 | 6 | 27701122 | 27809101 | G | A | A | 1.10485 |
| IBD | All Histone cluster1 gene | rs1977 | rs1977 | 96 | 6 | 26377546 | 26485525 | G | A | A | 1.066601 |
| IBD | All Histone cluster1 gene | rs1985732 | rs1985732 | 97 | 6 | 26376161 | 26484140 | G | A | A | 1.028229 |
| IBD | All Histone cluster1 gene | rs200483 | rs200483 | 98 | 6 | 27774824 | 27882803 | A | G | G | 1.085554 |
| IBD | All Histone cluster1 gene | rs200484 | rs200484 | 99 | 6 | 27775674 | 27883653 | G | A | A | 1.085885 |

TABLE 1-continued

| | | | | | | | | | | | |
|---|---|---|---|---|---|---|---|---|---|---|---|
| IBD | All Histone cluster1 gene | rs200490 | rs200490 | 100 | 6 | 27796935 | 27904914 | A | C | C | 1.086946 |
| IBD | All Histone cluster1 gene | rs200501 | rs200501 | 101 | 6 | 27788942 | 27896921 | A | G | G | 1.082685 |
| IBD | All Histone cluster1 gene | rs200948 | rs200948 | 102 | 6 | 27835272 | 27943251 | G | A | A | 1.089064 |
| IBD | All Histone cluster1 gene | rs200953 | rs200953 | 103 | 6 | 27837267 | 27945246 | G | A | A | 1.08938 |
| IBD | All Histone cluster1 gene | rs200989 | rs200989 | 104 | 6 | 27816442 | 27924421 | G | A | A | 1.088773 |
| IBD | All Histone cluster1 gene | rs200990 | rs200990 | 105 | 6 | 27815823 | 27923802 | C | A | A | 1.090237 |
| IBD | All Histone cluster1 gene | rs200991 | rs200991 | 106 | 6 | 27815494 | 27923473 | A | C | C | 1.037049 |
| IBD | All Histone cluster1 gene | rs200995 | rs200995 | 107 | 6 | 27813694 | 27921673 | G | A | A | 1.088144 |
| IBD | All Histone cluster1 gene | rs201002 | rs201002 | 108 | 6 | 27808192 | 27916171 | G | A | A | 1.08662 |
| IBD | All Histone cluster1 gene | rs201004 | rs201004 | 109 | 6 | 27804934 | 27912913 | G | A | A | 1.032214 |
| IBD | All Histone cluster1 gene | rs2064092 | rs2064092 | 110 | 6 | 27511371 | 27619350 | A | C | A | 1.051684 |
| IBD | All Histone cluster1 gene | rs2072806 | rs2072806 | 111 | 6 | 26385093 | 26493072 | G | C | C | 1.051691 |
| IBD | All Histone cluster1 gene | rs2073529 | rs2073529 | 112 | 6 | 26375159 | 26483138 | G | A | A | 1.05463 |
| IBD | All Histone cluster1 gene | rs2093169 | rs2093169 | 113 | 6 | 26495099 | 26603078 | A | G | G | 1.040318 |
| IBD | All Histone cluster1 gene | rs2393997 | rs2393997 | 114 | 6 | 27670697 | 27778676 | A | C | C | 1.036294 |
| IBD | All Histone cluster1 gene | rs2494711 | rs2494711 | 115 | 6 | 26649421 | 26757400 | A | G | A | 1.031221 |
| IBD | All Histone cluster1 gene | rs2747054 | rs2747054 | 116 | 6 | 27783359 | 27891338 | G | A | A | 1.087876 |
| IBD | All Histone cluster1 gene | rs2893910 | rs2893910 | 117 | 6 | 27283254 | 27391233 | A | T | T | 1.043311 |
| IBD | All Histone cluster1 gene | rs34706883 | rs34706883 | 118 | 6 | 27805255 | 27913234 | C | A | A | 1.080478 |
| IBD | All Histone cluster1 gene | rs370155 | rs370155 | 119 | 6 | 27782031 | 27890010 | C | A | A | 1.086886 |
| IBD | All Histone cluster1 gene | rs3799378 | rs3799378 | 120 | 6 | 26404374 | 26512353 | G | A | A | 1.043914 |
| IBD | All Histone cluster1 gene | rs3799380 | rs3799380 | 121 | 6 | 26467182 | 26575161 | G | A | A | 1.038428 |
| IBD | All Histone cluster1 gene | rs3799383 | rs3799383 | 122 | 6 | 26510748 | 26618727 | A | G | G | 1.056523 |
| IBD | All Histone cluster1 gene | rs3800307 | rs3800307 | 123 | 6 | 27185792 | 27293771 | T | A | A | 1.048767 |
| IBD | All Histone cluster1 gene | rs3800316 | rs3800316 | 124 | 6 | 27256102 | 27364081 | C | A | A | 1.042094 |
| IBD | All Histone cluster1 gene | rs4452638 | rs4452638 | 125 | 6 | 27229265 | 27337244 | A | G | G | 1.059797 |
| IBD | All Histone cluster1 gene | rs4634439 | rs4634439 | 126 | 6 | 26598004 | 26705983 | G | A | A | 1.064038 |
| IBD | All Histone cluster1 gene | rs4712981 | rs4712981 | 127 | 6 | 26361430 | 26469409 | A | G | G | 1.030139 |
| IBD | All Histone cluster1 gene | rs4713119 | rs4713119 | 128 | 6 | 27712825 | 27820804 | G | A | A | 1.035871 |
| IBD | All Histone cluster1 gene | rs6456728 | rs6456728 | 129 | 6 | 26477779 | 26585758 | A | G | G | 1.038342 |
| IBD | All Histone cluster1 gene | rs6904071 | rs6904071 | 130 | 6 | 27047256 | 27155235 | A | G | G | 1.053969 |
| IBD | All Histone cluster1 gene | rs6904596 | rs6904596 | 131 | 6 | 27491299 | 27599278 | A | G | G | 1.092306 |
| IBD | All Histone cluster1 gene | rs6913660 | rs6913660 | 132 | 6 | 27091425 | 27199404 | A | C | C | 1.053669 |
| IBD | All Histone cluster1 gene | rs6915101 | rs6915101 | 133 | 6 | 27741682 | 27849661 | A | G | G | 1.107933 |
| IBD | All Histone cluster1 gene | rs6920256 | rs6920256 | 134 | 6 | 26537801 | 26645780 | A | G | G | 1.06397 |
| IBD | All Histone cluster1 gene | rs6923139 | rs6923139 | 135 | 6 | 26313348 | 26421327 | A | G | G | 1.082433 |
| IBD | All Histone cluster1 gene | rs6932590 | rs6932590 | 136 | 6 | 27248931 | 27356910 | G | A | A | 1.054939 |
| IBD | All Histone cluster1 gene | rs6933583 | rs6933583 | 137 | 6 | 26355283 | 26463262 | C | A | A | 1.029881 |
| IBD | All Histone cluster1 gene | rs6934794 | rs6934794 | 138 | 6 | 27519345 | 27627324 | A | G | A | 1.039168 |
| IBD | All Histone cluster1 gene | rs6938200 | rs6938200 | 139 | 6 | 27231150 | 27339129 | G | A | A | 1.055915 |

TABLE 1-continued

| | | | | | | | | | | | |
|---|---|---|---|---|---|---|---|---|---|---|---|
| IBD | All Histone cluster1 gene | rs721600 | rs721600 | 140 | 6 | 27298905 | 27406884 | A | G | A | 1.052598 |
| IBD | All Histone cluster1 gene | rs7745603 | rs7745603 | 141 | 6 | 27090404 | 27198383 | A | G | G | 1.03892 |
| IBD | All Histone cluster1 gene | rs7746199 | rs7746199 | 142 | 6 | 27261324 | 27369303 | A | G | G | 1.033691 |
| IBD | All Histone cluster1 gene | rs7749305 | rs7749305 | 143 | 6 | 27446566 | 27554545 | G | A | A | 1.091115 |
| IBD | All Histone cluster1 gene | rs7749319 | rs7749319 | 144 | 6 | 27126460 | 27234439 | A | G | G | 1.070772 |
| IBD | All Histone cluster1 gene | rs7756567 | rs7756567 | 145 | 6 | 26481642 | 26589621 | C | A | A | 1.039822 |
| IBD | All Histone cluster1 gene | rs7773938 | rs7773938 | 146 | 6 | 26474044 | 26582023 | A | G | G | 1.039994 |
| IBD | All Histone cluster1 gene | rs911186 | rs911186 | 147 | 6 | 27150599 | 27258578 | G | A | A | 1.07032 |
| IBD | All Histone cluster1 gene | rs9295739 | rs9295739 | 148 | 6 | 27662395 | 27770374 | A | G | G | 1.187594 |
| IBD | All Histone cluster1 gene | rs9295749 | rs9295749 | 149 | 6 | 27767395 | 27875374 | A | G | A | 1.051982 |
| IBD | All Histone cluster1 gene | rs9358944 | rs9358944 | 150 | 6 | 26469875 | 26577854 | C | A | A | 1.040086 |
| IBD | All Histone cluster1 gene | rs9358945 | rs9358945 | 151 | 6 | 26472114 | 26580093 | G | A | A | 1.040079 |
| IBD | All Histone cluster1 gene | rs9358946 | rs9358946 | 152 | 6 | 26478927 | 26586906 | A | G | G | 1.044383 |
| IBD | All Histone cluster1 gene | rs9366653 | rs9366653 | 153 | 6 | 26354247 | 26462226 | A | G | G | 1.062054 |
| IBD | All Histone cluster1 gene | rs9366658 | rs9366658 | 154 | 6 | 26469866 | 26577845 | A | G | G | 1.040086 |
| IBD | All Histone cluster1 gene | rs9379844 | rs9379844 | 155 | 6 | 26291527 | 26399506 | A | G | A | 1.023444 |
| IBD | All Histone cluster1 gene | rs9379851 | rs9379851 | 156 | 6 | 26354780 | 26462759 | C | A | A | 1.062436 |
| IBD | All Histone cluster1 gene | rs9379856 | rs9379856 | 157 | 6 | 26366836 | 26474815 | C | A | A | 1.058985 |
| IBD | All Histone cluster1 gene | rs9379858 | rs9379858 | 158 | 6 | 26367689 | 26475668 | G | A | A | 1.06275 |
| IBD | All Histone cluster1 gene | rs9379859 | rs9379859 | 159 | 6 | 26369549 | 26477528 | A | G | G | 1.06306 |
| IBD | All Histone cluster1 gene | rs9379870 | rs72402459 | 160 | 6 | 26374410 | 26482389 | G | A | A | 1.030307 |
| IBD | All Histone cluster1 gene | rs9379897 | rs9379897 | 161 | 6 | 26601526 | 26709505 | G | A | A | 1.064283 |
| IBD | All Histone cluster1 gene | rs9393691 | rs9393691 | 162 | 6 | 26272829 | 26380808 | G | A | G | 1.024334 |
| IBD | All Histone cluster1 gene | rs9393705 | rs9393705 | 163 | 6 | 26361011 | 26468990 | A | G | G | 1.06191 |
| IBD | All Histone cluster1 gene | rs9393708 | rs9393708 | 164 | 6 | 26362643 | 26470622 | G | A | A | 1.06285 |
| IBD | All Histone cluster1 gene | rs9393713 | rs9393713 | 165 | 6 | 26373678 | 26481657 | A | G | G | 1.065096 |
| IBD | All Histone cluster1 gene | rs9393714 | rs9393714 | 166 | 6 | 26373740 | 26481719 | A | C | C | 1.072207 |
| IBD | All Histone cluster1 gene | rs9393777 | rs9393777 | 167 | 6 | 26942027 | 27050006 | G | A | A | 1.053641 |
| IBD | All Histone cluster1 gene | rs9461362 | rs9461362 | 168 | 6 | 27303927 | 27411906 | A | G | A | 1.044123 |
| IBD | All Histone cluster1 gene | rs9467704 | rs9467704 | 169 | 6 | 26319486 | 26427465 | A | G | G | 1.078175 |
| IBD | All Histone cluster1 gene | rs9468152 | rs9468152 | 170 | 6 | 27492906 | 27600885 | C | A | C | 1.054429 |
| IBD | All Histone cluster1 gene | rs9468159 | rs9468159 | 171 | 6 | 27522374 | 27630353 | A | G | A | 1.054638 |
| IBD | All Histone cluster1 gene | rs9468202 | rs9468202 | 172 | 6 | 27688630 | 27796609 | G | A | A | 1.205805 |
| IBD | All Histone cluster1 gene | rs9468227 | rs9468227 | 173 | 6 | 27746342 | 27854321 | G | A | A | 1.12639 |
| IBD | GTF2IRD2B | imm_7_74094413 | rs138546574 | 174 | 7 | 74456477 | 74094413 | G | A | A | 1.152605 |
| IBD | GTF2IRD2B | imm_7_74108242 | rs200682695 | 175 | 7 | 74470306 | 74108242 | A | G | G | 1.046913 |
| IBD | GTF2IRD2B | imm_7_74117236 | rs111889192 | 176 | 7 | 74479300 | 74117236 | A | C | C | 1.139471 |
| IBD | GTF2IRD2B | imm_7_74118166 | rs4731019 | 177 | 7 | 74480230 | 74118166 | G | A | A | 1.040123 |
| IBD | GTF2IRD2B | imm_7_74120730 | rs111457769 | 178 | 7 | 74482794 | 74120730 | G | A | A | 1.07638 |
| IBD | GTF2IRD2B | imm_7_74133859 | rs801068 | 179 | 7 | 74495923 | 74133859 | G | A | A | 1.0382 |
| IBD | GTF2IRD2B | imm_7_74145400 | rs113516730 | 180 | 7 | 74507464 | 74145400 | A | T | T | 1.037022 |
| IBD | ETS1 | imm_11_127760024 | rs34271980 | 181 | 11 | 128254814 | 127760024 | T | A | T | 1.043861 |
| IBD | ETS1 | imm_11_127761269 | rs7118804 | 182 | 11 | 128256059 | 127761269 | G | A | G | 1.046577 |
| IBD | ETS1 | imm_11_127765567 | rs11600923 | 183 | 11 | 128260357 | 127765567 | A | G | A | 1.050849 |
| IBD | ETS1 | imm_11_127767721 | rs73025060 | 184 | 11 | 128262511 | 127767721 | G | A | A | 1.082772 |
| IBD | ETS1 | imm_11_127770666 | rs11824169 | 185 | 11 | 128265456 | 127770666 | A | C | A | 1.028063 |

TABLE 1-continued

| | | | | | | | | | | | | |
|---|---|---|---|---|---|---|---|---|---|---|---|---|
| IBD | ETS1 | imm_11_127770668 | rs11824170 | 186 | 11 | 128265458 | 127770668 | A | G | A | 1.027116 |
| IBD | ETS1 | imm_11_127774308 | rs76299412 | 187 | 11 | 128269098 | 127774308 | A | G | A | 1.048341 |
| IBD | ETS1 | imm_11_127775128 | rs11605437 | 188 | 11 | 128269918 | 127775128 | G | A | G | 1.046927 |
| IBD | ETS1 | imm_11_127776527 | rs75500046 | 189 | 11 | 128271317 | 127776527 | A | G | G | 1.085488 |
| IBD | ETS1 | imm_11_127776913 | rs118033474 | 190 | 11 | 128271703 | 127776913 | A | G | G | 1.084318 |
| IBD | ETS1 | imm_11_127777217 | rs4937327 | 191 | 11 | 128272007 | 127777217 | C | G | G | 1.03851 |
| IBD | ETS1 | imm_11_127778327 | rs55781388 | 192 | 11 | 128273117 | 127778327 | G | C | G | 1.028 |
| IBD | ETS1 | imm_11_127778329 | rs201456100 | 193 | 11 | 128273119 | 127778329 | C | G | C | 1.032237 |
| IBD | ETS1 | imm_11_127779030 | rs74563193 | 194 | 11 | 128273820 | 127779030 | A | G | G | 1.078295 |
| IBD | ETS1 | imm_11_127780425 | rs74349003 | 195 | 11 | 128275215 | 127780425 | G | C | G | 1.07275 |
| IBD | ETS1 | imm_11_127780902 | rs9943540 | 196 | 11 | 128275692 | 127780902 | G | A | A | 1.077284 |
| IBD | ETS1 | imm_11_127781839 | rs73025076 | 197 | 11 | 128276629 | 127781839 | G | A | G | 1.033321 |
| IBD | ETS1 | imm_11_127785739 | rs10893865 | 198 | 11 | 128280529 | 127785739 | A | C | C | 1.035632 |
| IBD | ETS1 | imm_11_127785963 | rs11606595 | 199 | 11 | 128280753 | 127785963 | A | G | A | 1.053418 |
| IBD | ETS1 | imm_11_127786010 | rs7106191 | 200 | 11 | 128280800 | 127786010 | A | G | A | 1.038393 |
| IBD | ETS1 | imm_11_127786836 | rs7123188 | 201 | 11 | 128281626 | 127786836 | G | A | G | 1.037267 |
| IBD | ETS1 | imm_11_127787128 | rs11221287 | 202 | 11 | 128281918 | 127787128 | A | C | A | 1.040202 |
| IBD | ETS1 | imm_11_127788828 | rs10893866 | 203 | 11 | 128283618 | 127788828 | A | C | C | 1.034095 |
| IBD | ETS1 | imm_11_127789306 | rs34431347 | 204 | 11 | 128284096 | 127789306 | G | A | G | 1.037423 |
| IBD | ETS1 | imm_11_127789441 | rs34666372 | 205 | 11 | 128284231 | 127789441 | G | A | G | 1.037304 |
| IBD | ETS1 | imm_11_127791651 | rs11602703 | 206 | 11 | 128286441 | 127791651 | G | A | G | 1.055438 |
| IBD | ETS1 | imm_11_127792287 | rs11221290 | 207 | 11 | 128287077 | 127792287 | A | G | A | 1.036389 |
| IBD | ETS1 | imm_11_127792800 | rs55977286 | 208 | 11 | 128287590 | 127792800 | T | A | T | 1.068345 |
| IBD | ETS1 | imm_11_127793060 | rs12274537 | 209 | 11 | 128287850 | 127793060 | G | A | G | 1.034643 |
| IBD | ETS1 | imm_11_127794685 | rs11604454 | 210 | 11 | 128289475 | 127794685 | G | A | G | 1.05281 |
| IBD | ETS1 | imm_11_127795453 | rs10893867 | 211 | 11 | 128290243 | 127795453 | G | A | G | 1.034646 |
| IBD | ETS1 | imm_11_127796816 | rs117812848 | 212 | 11 | 128291606 | 127796816 | G | A | A | 5.285412 |
| IBD | ETS1 | imm_11_127797523 | rs34747435 | 213 | 11 | 128292313 | 127797523 | A | T | A | 1.034896 |
| IBD | ETS1 | imm_11_127798230 | rs10790952 | 214 | 11 | 128293020 | 127798230 | G | A | A | 1.028462 |
| IBD | ETS1 | imm_11_127799892 | rs2276445 | 215 | 11 | 128294682 | 127799892 | C | G | C | 1.025932 |
| IBD | ETS1 | imm_11_127804916 | rs7108537 | 216 | 11 | 128299706 | 127804916 | C | A | A | 1.033856 |
| IBD | ETS1 | imm_11_127805367 | rs80111275 | 217 | 11 | 128300157 | 127805367 | C | A | A | 1.077566 |
| IBD | ETS1 | imm_11_127806163 | rs10893870 | 218 | 11 | 128300953 | 127806163 | G | A | G | 1.027263 |
| IBD | ETS1 | imm_11_127806304 | rs76647218 | 219 | 11 | 128301094 | 127806304 | A | G | G | 1.082183 |
| IBD | ETS1 | imm_11_127807384 | rs10750399 | 220 | 11 | 128302174 | 127807384 | A | G | A | 1.030051 |
| IBD | ETS1 | imm_11_127808758 | rs11826011 | 221 | 11 | 128303548 | 127808758 | A | G | G | 1.075004 |
| IBD | ETS1 | imm_11_127809308 | rs116927266 | 222 | 11 | 128304098 | 127809308 | A | G | G | 1.1969 |
| IBD | ETS1 | imm_11_127812329 | rs55850544 | 223 | 11 | 128307119 | 127812329 | G | A | G | 1.059518 |
| IBD | ETS1 | imm_11_127812420 | rs7119657 | 224 | 11 | 128307210 | 127812420 | A | C | A | 2.813 |
| IBD | ETS1 | imm_11_127813024 | rs12794572 | 225 | 11 | 128307814 | 127813024 | G | A | G | 1.027018 |
| IBD | ETS1 | imm_11_127819226 | rs9665767 | 226 | 11 | 128314016 | 127819226 | G | A | G | 1.029511 |
| IBD | ETS1 | imm_11_127822686 | rs58847936 | 227 | 11 | 128317476 | 127822686 | A | G | G | 1.079299 |
| IBD | ETS1 | imm_11_127823420 | rs117607284 | 228 | 11 | 128318210 | 127823420 | G | A | A | 1.196872 |
| IBD | ETS1 | imm_11_127824356 | rs4285885 | 229 | 11 | 128319146 | 127824356 | A | G | A | 1.03201 |
| IBD | ETS1 | imm_11_127825016 | rs73581085 | 230 | 11 | 128319806 | 127825016 | G | C | C | 1.076388 |
| IBD | ETS1 | imm_11_127825282 | rs4612820 | 231 | 11 | 128320072 | 127825282 | A | G | A | 1.026511 |
| IBD | ETS1 | imm_11_127825669 | rs11600936 | 232 | 11 | 128320459 | 127825669 | A | G | A | 1.026633 |
| IBD | ETS1 | imm_11_127826087 | rs114534998 | 233 | 11 | 128320877 | 127826087 | T | A | A | 1.037348 |
| IBD | ETS1 | imm_11_127826464 | rs4936050 | 234 | 11 | 128321254 | 127826464 | A | G | A | 1.03236 |
| IBD | ETS1 | imm_11_127827422 | rs6590332 | 235 | 11 | 128322212 | 127827422 | A | G | A | 1.032349 |
| IBD | ETS1 | imm_11_127828334 | rs73581091 | 236 | 11 | 128323124 | 127828334 | G | A | A | 1.074437 |
| IBD | ETS1 | imm_11_127831280 | rs117676130 | 237 | 11 | 128326070 | 127831280 | A | G | G | 1.079965 |
| IBD | ETS1 | imm_11_127831611 | rs4328228 | 238 | 11 | 128326401 | 127831611 | A | G | A | 1.031281 |
| IBD | ETS1 | imm_11_127831673 | rs4369416 | 239 | 11 | 128326463 | 127831673 | A | G | G | 1.026652 |
| IBD | ETS1 | imm_11_127834123 | rs8705 | 240 | 11 | 128328913 | 127834123 | A | G | A | 1.031641 |
| IBD | ETS1 | imm_11_127834484 | rs80112582 | 241 | 11 | 128329274 | 127834484 | G | A | A | 1.086814 |
| IBD | ETS1 | imm_11_127837472 | rs34846069 | 242 | 11 | 128332262 | 127837472 | A | G | G | 1.090197 |
| IBD | ETS1 | imm_11_127838265 | rs76404385 | 243 | 11 | 128333055 | 127838265 | A | G | G | 1.047813 |
| IBD | ETS1 | imm_11_127838713 | rs2230004 | 244 | 11 | 128333503 | 127838713 | G | A | G | 1.030912 |
| IBD | ETS1 | imm_11_127839719 | rs78844317 | 245 | 11 | 128334509 | 127839719 | A | G | G | 1.107269 |
| IBD | ETS1 | imm_11_127840459 | rs11606640 | 246 | 11 | 128335249 | 127840459 | A | G | A | 1.069059 |
| IBD | ETS1 | imm_11_127840867 | rs7926975 | 247 | 11 | 128335657 | 127840867 | A | G | G | 1.059212 |
| IBD | ETS1 | imm_11_127841724 | rs10893875 | 248 | 11 | 128336514 | 127841724 | A | G | G | 1.056335 |
| IBD | ETS1 | imm_11_127841864 | rs55661779 | 249 | 11 | 128336654 | 127841864 | A | G | G | 1.029195 |
| IBD | ETS1 | imm_11_127843207 | rs4520612 | 250 | 11 | 128337997 | 127843207 | A | G | G | 1.05811 |
| IBD | ETS1 | imm_11_127843341 | rs4523710 | 251 | 11 | 128338131 | 127843341 | A | C | C | 1.056451 |
| IBD | ETS1 | imm_11_127844385 | rs73029052 | 252 | 11 | 128339175 | 127844385 | A | C | A | 1.066578 |
| IBD | ETS1 | imm_11_127844729 | rs116842927 | 253 | 11 | 128339519 | 127844729 | A | G | A | 1.087129 |
| IBD | ETS1 | imm_11_127845557 | rs6590333 | 254 | 11 | 128340347 | 127845557 | A | G | G | 1.058241 |
| IBD | ETS1 | imm_11_127846698 | rs11600915 | 255 | 11 | 128341488 | 127846698 | G | A | G | 1.065067 |
| IBD | ETS1 | imm_11_127848167 | rs61909068 | 256 | 11 | 128342957 | 127848167 | G | A | G | 1.06541 |
| IBD | ETS1 | imm_11_127848372 | rs12294634 | 257 | 11 | 128343162 | 127848372 | A | G | A | 1.065797 |
| IBD | ETS1 | imm_11_127849992 | rs73029062 | 258 | 11 | 128344782 | 127849992 | G | A | G | 1.065176 |
| IBD | ETS1 | imm_11_127851599 | rs11600746 | 259 | 11 | 128346389 | 127851599 | G | A | G | 1.067929 |
| IBD | ETS1 | imm_11_127852250 | rs4937336 | 260 | 11 | 128347040 | 127852250 | G | A | A | 1.058017 |
| IBD | ETS1 | imm_11_127853705 | rs12276127 | 261 | 11 | 128348495 | 127853705 | A | G | G | 1.057926 |
| IBD | ETS1 | imm_11_127855281 | rs61909072 | 262 | 11 | 128350071 | 127855281 | A | G | A | 1.06503 |
| IBD | ETS1 | imm_11_127855956 | rs4937338 | 263 | 11 | 128350746 | 127855956 | A | G | G | 1.053906 |
| IBD | ETS1 | imm_11_127857027 | rs7130469 | 264 | 11 | 128351817 | 127857027 | G | A | A | 1.060292 |
| IBD | ETS1 | imm_11_127861069 | rs1122832 | 265 | 11 | 128355859 | 127861069 | G | A | G | 1.034187 |

TABLE 1-continued

| | | | | | | | | | | | |
|---|---|---|---|---|---|---|---|---|---|---|---|
| IBD | ETS1 | imm_11_127863304 | rs35394161 | 266 | 11 | 128358094 | 127863304 | A | G | A | 1.034741 |
| IBD | ETS1 | imm_11_127863391 | rs11221327 | 267 | 11 | 128358181 | 127863391 | G | A | G | 1.03498 |
| IBD | ETS1 | imm_11_127866379 | rs4937339 | 268 | 11 | 128361169 | 127866379 | A | C | A | 1.028356 |
| IBD | ETS1 | imm_11_127868447 | rs7926631 | 269 | 11 | 128363237 | 127868447 | A | G | A | 1.352044 |
| IBD | ETS1 | imm_11_127868927 | rs11604768 | 270 | 11 | 128363717 | 127868927 | G | A | A | 1.031257 |
| IBD | ETS1 | imm_11_127869177 | rs10893881 | 271 | 11 | 128363967 | 127869177 | G | A | G | 1.043651 |
| IBD | ETS1 | imm_11_127870403 | rs3924513 | 272 | 11 | 128365193 | 127870403 | C | A | C | 1.040944 |
| IBD | ETS1 | imm_11_127870895 | rs12805120 | 273 | 11 | 128365685 | 127870895 | A | T | A | 1.040738 |
| IBD | ETS1 | imm_11_127871431 | rs4254089 | 274 | 11 | 128366221 | 127871431 | G | A | G | 1.039764 |
| IBD | ETS1 | imm_11_127872972 | rs3924289 | 275 | 11 | 128367762 | 127872972 | A | G | G | 1.03512 |
| IBD | ETS1 | imm_11_127874486 | rs4937340 | 276 | 11 | 128369276 | 127874486 | G | A | G | 1.039926 |
| IBD | ETS1 | imm_11_127874807 | rs7929911 | 277 | 11 | 128369597 | 127874807 | A | G | A | 1.038031 |
| IBD | ETS1 | imm_11_127877378 | rs7941606 | 278 | 11 | 128372168 | 127877378 | A | G | A | 1.04088 |
| IBD | ETS1 | imm_11_127879923 | rs10893883 | 279 | 11 | 128374713 | 127879923 | A | G | G | 1.032625 |
| IBD | ETS1 | imm_11_127881686 | rs56086356 | 280 | 11 | 128376476 | 127881686 | C | G | C | 1.078091 |
| IBD | ETS1 | imm_11_127882690 | rs7118744 | 281 | 11 | 128377480 | 127882690 | A | G | A | 1.028394 |
| IBD | ETS1 | imm_11_127884689 | rs4937341 | 282 | 11 | 128379479 | 127884689 | A | G | G | 1.055059 |
| IBD | ETS1 | imm_11_127885952 | rs7924522 | 283 | 11 | 128380742 | 127885952 | C | A | C | 1.050035 |
| IBD | ETS1 | imm_11_127886184 | rs11221332 | 284 | 11 | 128380974 | 127886184 | A | G | A | 1.074782 |
| IBD | ETS1 | imm_11_127887077 | rs7108992 | 285 | 11 | 128381867 | 127887077 | A | C | A | 1.050031 |
| IBD | ETS1 | imm_11_127889134 | rs7117768 | 286 | 11 | 128383924 | 127889134 | G | C | G | 1.073028 |
| IBD | ETS1 | imm_11_127891116 | rs11221335 | 287 | 11 | 128385906 | 127891116 | G | A | G | 1.072272 |
| IBD | ETS1 | imm_11_127892632 | rs7946009 | 288 | 11 | 128387422 | 127892632 | A | G | A | 1.050157 |
| IBD | ETS1 | imm_11_127894601 | rs11819995 | 289 | 11 | 128389391 | 127894601 | A | G | G | 1.027193 |
| IBD | ETS1 | imm_11_127894638 | rs78111939 | 290 | 11 | 128389428 | 127894638 | G | A | A | 1.207021 |
| IBD | ETS1 | imm_11_127895279 | rs7120822 | 291 | 11 | 128390069 | 127895279 | A | T | A | 1.075029 |
| IBD | ETS1 | imm_11_127897147 | rs61907765 | 292 | 11 | 128391937 | 127897147 | A | G | A | 1.07393 |
| IBD | ETS1 | imm_11_127898835 | rs118087633 | 293 | 11 | 128393625 | 127898835 | G | A | A | 1.109805 |
| IBD | ETS1 | imm_11_127901157 | rs12805524 | 294 | 11 | 128395947 | 127901157 | G | A | G | 1.049678 |
| IBD | ETS1 | imm_11_127901948 | rs7117118 | 295 | 11 | 128396738 | 127901948 | G | A | G | 1.069811 |
| IBD | ETS1 | imm_11_127905841 | rs35656079 | 296 | 11 | 128400631 | 127905841 | G | A | A | 1.065081 |
| IBD | ETS1 | imm_11_127906568 | rs73030729 | 297 | 11 | 128401358 | 127906568 | A | G | A | 1.037954 |
| IBD | ETS1 | imm_11_127908214 | rs11825217 | 298 | 11 | 128403004 | 127908214 | A | G | A | 1.038876 |
| IBD | ETS1 | imm_11_127911648 | rs3802826 | 299 | 11 | 128406438 | 127911648 | G | A | A | 1.039032 |
| IBD | ETS1 | imm_11_127911985 | rs4520607 | 300 | 11 | 128406775 | 127911985 | A | G | A | 1.033773 |
| IBD | ETS1 | imm_11_127914294 | rs10750400 | 301 | 11 | 128409084 | 127914294 | A | G | A | 1.033742 |
| IBD | ETS1 | imm_11_127915474 | rs10893884 | 302 | 11 | 128410264 | 127915474 | G | A | A | 1.033532 |
| IBD | ETS1 | imm_11_127915554 | rs10893885 | 303 | 11 | 128410344 | 127915554 | G | A | A | 1.036858 |
| IBD | ETS1 | imm_11_127916046 | rs3809006 | 304 | 11 | 128410836 | 127916046 | G | A | G | 1.032452 |
| IBD | ETS1 | imm_11_127929821 | rs78814353 | 305 | 11 | 128424611 | 127929821 | A | G | G | 1.97122 |
| IBD | ETS1 | imm_11_127931099 | rs115308851 | 306 | 11 | 128425889 | 127931099 | A | G | G | 2.369107 |
| IBD | ETS1 | imm_11_127940676 | rs12788788 | 307 | 11 | 128435466 | 127940676 | G | C | C | 1.064003 |
| IBD | ETS1 | imm_11_127943244 | rs12284728 | 308 | 11 | 128438034 | 127943244 | A | G | G | 2.2531 |
| IBD | ETS1 | imm_11_127945727 | rs10893887 | 309 | 11 | 128440517 | 127945727 | A | G | A | 1.093 |
| IBD | ETS1 | imm_11_127945953 | rs10893888 | 310 | 11 | 128440743 | 127945953 | G | A | A | 1.051642 |
| IBD | ETS1 | imm_11_127948912 | rs117334295 | 311 | 11 | 128443702 | 127948912 | A | G | G | 1.14044 |
| IBD | ETS1 | imm_11_127956842 | rs55781052 | 312 | 11 | 128451632 | 127956842 | A | G | A | 1.030903 |
| IBD | ETS1 | imm_11_127957543 | rs78704287 | 313 | 11 | 128452333 | 127957543 | C | A | C | 1.123815 |
| IBD | ETS1 | imm_11_127957904 | rs73030764 | 314 | 11 | 128452694 | 127957904 | C | A | C | 1.122206 |
| IBD | ETS1 | imm_11_127974263 | rs12364915 | 315 | 11 | 128469053 | 127974263 | A | C | C | 1.049778 |
| IBD | ETS1 | imm_11_127979301 | rs11221386 | 316 | 11 | 128474091 | 127979301 | A | G | G | 1.035064 |
| IBD | ETS1 | imm_11_127979905 | rs117333396 | 317 | 11 | 128474695 | 127979905 | A | G | G | 1.120199 |
| IBD | ETS1 | imm_11_127981559 | rs56244679 | 318 | 11 | 128476349 | 127981559 | C | G | G | 1.029851 |
| IBD | ETS1 | imm_11_127982379 | rs11221390 | 319 | 11 | 128477169 | 127982379 | A | G | G | 1.029943 |
| IBD | ETS1 | imm_11_127982748 | rs11221391 | 320 | 11 | 128477538 | 127982748 | C | A | A | 1.033682 |
| IBD | ETS1 | imm_11_127983590 | rs73569213 | 321 | 11 | 128478380 | 127983590 | A | G | G | 1.030825 |
| IBD | ETS1 | imm_11_127983743 | rs73569215 | 322 | 11 | 128478533 | 127983743 | A | C | C | 1.029943 |
| IBD | ETS1 | imm_11_127984265 | rs73569219 | 323 | 11 | 128479055 | 127984265 | A | G | G | 1.030692 |
| IBD | ETS1 | imm_11_127984721 | rs10893894 | 324 | 11 | 128479511 | 127984721 | G | A | A | 1.033407 |
| IBD | ETS1 | rs7935286 | rs7935286 | 325 | 11 | 128501572 | 128006782 | G | A | G | 1.048707 |
| IBD | SLC5A1 | rs738203 | rs738203 | 326 | 22 | 32607074 | 30937074 | G | A | G | 1.029285 |
| IBD | SLC5A1 | rs9609429 | rs9609429 | 327 | 22 | 32517431 | 30847431 | G | A | A | 1.041716 |
| IBD | TET2 | rs10010325 | rs10010325 | 328 | 4 | 106106353 | 106325802 | A | C | C | 1.064877 |
| IBD | TET2 | rs17035310 | rs17035310 | 329 | 4 | 106064754 | 106284203 | A | G | A | 1.061851 |
| IBD | TET2 | rs2189234 | rs2189234 | 330 | 4 | 106075498 | 106294947 | A | C | A | 1.03441 |
| IBD | TET2 | rs7661349 | rs7661349 | 331 | 4 | 106066982 | 106286431 | A | G | A | 1.035217 |
| IBD | TET2 | rs974801 | rs974801 | 332 | 4 | 106071064 | 106290513 | G | A | A | 1.056745 |

(Continued, part 2)

| gene.i | SNP | F_A_cedars | F_U_cedars | OR_cedars | SE_cedars | L95_cedars | U95_cedars | STAT_cedars | P_cedars |
|---|---|---|---|---|---|---|---|---|---|
| SLC26A4 | rs10247487 | 0.2877 | 0.2731 | 0.8841 | 0.04188 | 0.8144 | 0.9597 | −2.942 | 0.003263 |
| SLC26A4 | rs10263826 | 0.3131 | 0.2921 | 0.8917 | 0.0408 | 0.8232 | 0.9659 | −2.81 | 0.004955 |
| SLC26A4 | rs10273733 | 0.3147 | 0.315 | 1.027 | 0.05335 | 0.9252 | 1.14 | 0.5027 | 0.6152 |
| SLC26A4 | rs12539555 | 0.2629 | 0.2472 | 1.074 | 0.04243 | 0.988 | 1.167 | 1.676 | 0.09383 |
| SLC26A4 | rs2248465 | 0.3052 | 0.2718 | 1.085 | 0.04075 | 1.002 | 1.175 | 2.008 | 0.04465 |
| SLC26A4 | rs2808 | 0.3165 | 0.2907 | 1.108 | 0.04051 | 1.023 | 1.2 | 2.532 | 0.01134 |
| DLG4 | rs3785794 | 0.07404 | 0.08212 | 0.7731 | 0.07098 | 0.6727 | 0.8885 | −3.625 | 0.000289 |

TABLE 1-continued

| | | | | | | | | | |
|---|---|---|---|---|---|---|---|---|---|
| GIPR | chr19:50983512 | 0.2676 | 0.2762 | 0.9193 | 0.05478 | 0.8257 | 1.023 | −1.536 | 0.1244 |
| GIPR | chr19:51014231 | NA | NA | NA | NA | NA | NA | NA | NA |
| GIPR | chr19:51026971 | 0.2793 | 0.3171 | 0.9117 | 0.04067 | 0.8419 | 0.9874 | −2.273 | 0.02303 |
| GIPR | rs10401439 | NA | NA | NA | NA | NA | NA | NA | NA |
| GIPR | rs10402263 | 0.3052 | 0.3394 | 0.9243 | 0.03954 | 0.8554 | 0.9988 | −1.99 | 0.04658 |
| GIPR | rs10421891 | 0.3172 | 0.3509 | 0.9207 | 0.03857 | 0.8537 | 0.993 | −2.141 | 0.03229 |
| GIPR | rs10500292 | 0.3716 | 0.3949 | 0.932 | 0.03805 | 0.865 | 1.004 | −1.852 | 0.06402 |
| GIPR | rs11883351 | 0.3054 | 0.3395 | 0.914 | 0.03949 | 0.8459 | 0.9875 | −2.278 | 0.02273 |
| GIPR | rs12463359 | 0.3664 | 0.3886 | 0.9227 | 0.03818 | 0.8561 | 0.9944 | −2.108 | 0.035 |
| GIPR | rs16980013 | 0.2662 | 0.3005 | 0.9146 | 0.04129 | 0.8435 | 0.9917 | −2.163 | 0.03056 |
| GIPR | rs16980051 | 0.469 | 0.4875 | 0.9272 | 0.03698 | 0.8624 | 0.9969 | −2.043 | 0.04106 |
| GIPR | rs17878252 | 0.2515 | 0.2783 | 0.9247 | 0.04211 | 0.8514 | 1.004 | −1.859 | 0.06298 |
| GIPR | rs2070736 | 0.2674 | 0.3031 | 0.9115 | 0.04125 | 0.8407 | 0.9883 | −2.245 | 0.02474 |
| GIPR | rs2334255 | 0.2628 | 0.2417 | 1.098 | 0.0424 | 1.011 | 1.193 | 2.211 | 0.02703 |
| GIPR | rs4514788 | 0.2802 | 0.2773 | 0.9195 | 0.09025 | 0.7704 | 1.097 | −0.9301 | 0.3523 |
| GIPR | rs4802273 | 0.26 | 0.2896 | 0.9181 | 0.04178 | 0.8459 | 0.9964 | −2.045 | 0.04083 |
| GIPR | rs4802274 | 0.2681 | 0.3032 | 0.915 | 0.04121 | 0.844 | 0.992 | −2.156 | 0.03109 |
| GIPR | rs4803861 | 0.2789 | 0.3162 | 0.9142 | 0.04071 | 0.8441 | 0.9901 | −2.205 | 0.02746 |
| GIPR | rs8111071 | 0.1183 | 0.08879 | 1.139 | 0.05996 | 1.013 | 1.281 | 2.174 | 0.02971 |
| GIPR | rs918490 | 0.2789 | 0.316 | 0.9158 | 0.04067 | 0.8456 | 0.9918 | −2.164 | 0.0305 |
| ZHX3 | rs6072275 | 0.1551 | 0.1448 | 1.143 | 0.05126 | 1.034 | 1.264 | 2.609 | 0.009076 |
| ZHX3 | rs6072343 | 0.1334 | 0.1342 | 1.128 | 0.05394 | 1.015 | 1.254 | 2.239 | 0.02513 |
| ZHX3 | rs6093462 | NA | NA | NA | NA | NA | NA | NA | NA |
| TNRC6B | rs114607 | 0.397 | 0.3784 | 1.083 | 0.2487 | 0.6649 | 1.763 | 0.3192 | 0.7496 |
| TNRC6B | rs137955 | 0.4479 | 0.4323 | 1.11 | 0.03725 | 1.032 | 1.194 | 2.807 | 0.004997 |
| TNRC6B | rs137956 | 0.4584 | 0.4381 | 1.115 | 0.03718 | 1.037 | 1.2 | 2.937 | 0.003312 |
| TNRC6B | rs137977 | 0.3734 | 0.3967 | 0.9134 | 0.03819 | 0.8475 | 0.9843 | −2.373 | 0.01764 |
| TNRC6B | rs137981 | 0.1026 | 0.1205 | 0.8424 | 0.05943 | 0.7497 | 0.9464 | −2.887 | 0.003892 |
| TNRC6B | rs138027 | 0.2471 | 0.264 | 0.8709 | 0.04296 | 0.8005 | 0.9474 | −3.218 | 0.001289 |
| TNRC6B | rs2958647 | 0.4584 | 0.4376 | 1.114 | 0.03715 | 1.036 | 1.198 | 2.903 | 0.003698 |
| TNRC6B | rs713925 | 0.3773 | 0.3875 | 0.9268 | 0.03813 | 0.8601 | 0.9987 | −1.993 | 0.04622 |
| CDK6 | rs2282978 | 0.358 | 0.3463 | 0.9286 | 0.04835 | 0.8447 | 1.021 | −1.532 | 0.1255 |
| CDK6 | rs4272 | 0.2059 | 0.2185 | 0.9167 | 0.05615 | 0.8211 | 1.023 | −1.55 | 0.1212 |
| PRR5L | rs11033597 | 0.1402 | 0.1309 | 1.226 | 0.06517 | 1.079 | 1.393 | 3.128 | 0.001761 |
| PRR5L | rs11600757 | 0.1637 | 0.1433 | 1.213 | 0.06156 | 1.075 | 1.368 | 3.134 | 0.001723 |
| PRR5L | rs11601211 | 0.07153 | 0.07066 | 1.13 | 0.08584 | 0.9549 | 1.337 | 1.423 | 0.1548 |
| PRR5L | rs12281565 | 0.1669 | 0.1468 | 1.214 | 0.06094 | 1.077 | 1.368 | 3.185 | 0.001449 |
| PRR5L | rs1365120 | 0.09551 | 0.09455 | 1.179 | 0.07526 | 1.018 | 1.367 | 2.191 | 0.02843 |
| PRR5L | rs1895840 | 0.1022 | 0.09673 | 1.172 | 0.07468 | 1.012 | 1.357 | 2.125 | 0.03357 |
| PRR5L | rs2303439 | 0.1673 | 0.1518 | 1.072 | 0.0615 | 0.9501 | 1.209 | 1.127 | 0.2596 |
| PRR5L | rs330260 | 0.1842 | 0.1711 | 1.192 | 0.05831 | 1.064 | 1.337 | 3.017 | 0.002556 |
| PRR5L | rs331485 | 0.1142 | 0.1079 | 0.9739 | 0.07277 | 0.8445 | 1.123 | −0.363 | 0.7166 |
| PRR5L | rs4077044 | 0.4605 | 0.4096 | 1.2 | 0.07443 | 1.037 | 1.389 | 2.452 | 0.01422 |
| PRR5L | rs5030437 | 0.1636 | 0.1698 | 1.016 | 0.1083 | 0.8216 | 1.256 | 0.1458 | 0.8841 |
| PRR5L | rs5030445 | 0.1673 | 0.152 | 1.068 | 0.06145 | 0.9469 | 1.205 | 1.072 | 0.2839 |
| PRR5L | rs5030472 | 0.1192 | 0.1064 | 1.163 | 0.07051 | 1.013 | 1.336 | 2.145 | 0.03195 |
| PRR5L | rs7929195 | 0.1381 | 0.1195 | 0.9793 | 0.0679 | 0.8573 | 1.119 | −0.3081 | 0.758 |
| WNT2B | rs10745330 | 0.4958 | 0.471 | 1.076 | 0.03194 | 1.011 | 1.146 | 2.294 | 0.02178 |
| WNT2B | rs2999155 | 0.4903 | 0.4663 | 1.073 | 0.03192 | 1.008 | 1.142 | 2.203 | 0.0276 |
| WNT2B | rs3790609 | 0.2092 | 0.1771 | 1.098 | 0.04041 | 1.014 | 1.188 | 2.313 | 0.02074 |
| WNT2B | rs6682737 | 0.4926 | 0.4667 | 1.079 | 0.03193 | 1.013 | 1.148 | 2.376 | 0.01749 |
| LRRC16A | rs10456320 | 0.1262 | 0.1178 | 1.005 | 0.04921 | 0.9127 | 1.107 | 0.1028 | 0.9181 |
| LRRC16A | rs11755567 | 0.205 | 0.189 | 0.9618 | 0.04071 | 0.888 | 1.042 | −0.9579 | 0.3381 |
| LRRC16A | rs13191296 | 0.04082 | 0.08105 | 0.8496 | 0.08258 | 0.7227 | 0.9989 | −1.973 | 0.04846 |
| LRRC16A | rs2690110 | 0.3664 | 0.3425 | 1.08 | 0.03325 | 1.012 | 1.153 | 2.309 | 0.02094 |
| LRRC16A | rs4712908 | 0.3535 | 0.3505 | 0.976 | 0.05691 | 0.873 | 1.091 | −0.4274 | 0.6691 |
| LRRC16A | rs6921589 | 0.1162 | 0.1293 | 1.007 | 0.05161 | 0.9102 | 1.114 | 0.1376 | 0.8906 |
| LRRC16A | rs6937918 | 0.4464 | 0.4014 | 1.067 | 0.0323 | 1.002 | 1.137 | 2.007 | 0.04479 |
| LRRC16A | rs742132 | 0.2809 | 0.2888 | 1.005 | 0.03593 | 0.9367 | 1.078 | 0.1397 | 0.8889 |
| LRRC16A | rs7752195 | 0.0457 | 0.07408 | 0.9385 | 0.07684 | 0.8073 | 1.091 | −0.8261 | 0.4087 |
| LRRC16A | rs7752524 | 0.09413 | 0.09466 | 1.017 | 0.05426 | 0.9148 | 1.132 | 0.3179 | 0.7505 |
| LRRC16A | rs7762757 | 0.4002 | 0.3824 | 1.013 | 0.03876 | 0.939 | 1.093 | 0.3349 | 0.7377 |
| LRRC16A | rs880226 | 0.4469 | 0.4016 | 1.068 | 0.03231 | 1.002 | 1.138 | 2.035 | 0.04185 |
| LRRC16A | rs9295661 | 0.03926 | 0.07291 | 0.8785 | 0.08061 | 0.7501 | 1.029 | −1.607 | 0.1081 |
| LRRC16A | rs9358854 | 0.3764 | 0.3399 | 0.9563 | 0.03384 | 0.895 | 1.022 | −1.319 | 0.1872 |
| LRRC16A | rs9461157 | 0.4459 | 0.4009 | 1.067 | 0.03232 | 1.001 | 1.136 | 1.996 | 0.04589 |
| LRRC16A | rs9461165 | 0.4459 | 0.4011 | 1.066 | 0.03231 | 1.001 | 1.136 | 1.98 | 0.04766 |
| LRRC16A | rs9467445 | 0.2258 | 0.2055 | 0.9524 | 0.03955 | 0.8814 | 1.029 | −1.232 | 0.2179 |
| All Histone cluster1 gene | rs10484399 | 0.05103 | 0.09845 | 0.8471 | 0.08727 | 0.7139 | 1.005 | −1.901 | 0.05726 |
| All Histone cluster1 gene | rs10484439 | 0.05239 | 0.09177 | 0.8574 | 0.07884 | 0.7346 | 1.001 | −1.952 | 0.05098 |
| All Histone cluster1 gene | rs12176317 | 0.06961 | 0.1171 | 0.8307 | 0.06794 | 0.7271 | 0.949 | −2.73 | 0.00634 |
| All Histone cluster1 gene | rs13194053 | 0.1298 | 0.1697 | 1.02 | 0.04971 | 0.9254 | 1.125 | 0.4008 | 0.6885 |
| All Histone cluster1 gene | rs13194491 | 0.0514 | 0.08248 | 0.8723 | 0.06512 | 0.7677 | 0.991 | −2.098 | 0.03588 |
| All Histone cluster1 gene | rs13194781 | 0.05128 | 0.09881 | 0.8476 | 0.08751 | 0.714 | 1.006 | −1.889 | 0.05883 |

TABLE 1-continued

| | | | | | | | | | |
|---|---|---|---|---|---|---|---|---|---|
| All Histone cluster1 gene | rs13195040 | 0.05301 | 0.09513 | 0.8981 | 0.08556 | 0.7595 | 1.062 | −1.255 | 0.2093 |
| All Histone cluster1 gene | rs13199772 | 0.0514 | 0.09872 | 0.8551 | 0.08745 | 0.7204 | 1.015 | −1.79 | 0.0735 |
| All Histone cluster1 gene | rs13212651 | 0.05115 | 0.09848 | 0.8494 | 0.08765 | 0.7153 | 1.009 | −1.862 | 0.06256 |
| All Histone cluster1 gene | rs1321578 | 0.02515 | 0.02356 | 0.9242 | 0.1494 | 0.6896 | 1.238 | −0.528 | 0.5975 |
| All Histone cluster1 gene | rs13217599 | 0.04509 | 0.05347 | 1.092 | 0.1541 | 0.8077 | 1.478 | 0.5738 | 0.5661 |
| All Histone cluster1 gene | rs13218875 | 0.05028 | 0.09619 | 0.8697 | 0.09246 | 0.7255 | 1.042 | −1.51 | 0.131 |
| All Histone cluster1 gene | rs13219354 | 0.07828 | 0.1193 | 0.9521 | 0.0649 | 0.8384 | 1.081 | −0.7568 | 0.4492 |
| All Histone cluster1 gene | rs16867901 | 0.01178 | 0.009631 | 0.8439 | 0.1903 | 0.5812 | 1.225 | −0.8918 | 0.3725 |
| All Histone cluster1 gene | rs16867911 | 0.01164 | 0.01047 | 0.8883 | 0.1547 | 0.656 | 1.203 | −0.7655 | 0.444 |
| All Histone cluster1 gene | rs16891725 | 0.07382 | 0.1186 | 0.8387 | 0.06792 | 0.7341 | 0.9581 | −2.59 | 0.009589 |
| All Histone cluster1 gene | rs175597 | 0.06849 | 0.1182 | 0.8257 | 0.07324 | 0.7153 | 0.9532 | −2.615 | 0.008922 |
| All Histone cluster1 gene | rs17693963 | 0.05933 | 0.1038 | 0.9317 | 0.08051 | 0.7957 | 1.091 | −0.8792 | 0.3793 |
| All Histone cluster1 gene | rs17739310 | 0.1637 | 0.1606 | 1.054 | 0.06205 | 0.9333 | 1.19 | 0.8475 | 0.3967 |
| All Histone cluster1 gene | rs17750424 | NA | NA | NA | NA | NA | NA | NA | NA |
| All Histone cluster1 gene | rs1977 | 0.06961 | 0.1172 | 0.8303 | 0.06792 | 0.7268 | 0.9485 | −2.739 | 0.006165 |
| All Histone cluster1 gene | rs1985732 | 0.2535 | 0.2925 | 0.9425 | 0.0373 | 0.876 | 1.014 | −1.589 | 0.1122 |
| All Histone cluster1 gene | rs200483 | 0.06899 | 0.1182 | 0.8382 | 0.073 | 0.7265 | 0.9672 | −2.417 | 0.01563 |
| All Histone cluster1 gene | rs200484 | 0.06874 | 0.1182 | 0.8328 | 0.07321 | 0.7215 | 0.9613 | −2.499 | 0.01244 |
| All Histone cluster1 gene | rs200490 | 0.06863 | 0.1187 | 0.8227 | 0.07317 | 0.7128 | 0.9496 | −2.667 | 0.007645 |
| All Histone cluster1 gene | rs200501 | 0.06989 | 0.119 | 0.8337 | 0.07267 | 0.723 | 0.9614 | −2.502 | 0.01234 |
| All Histone cluster1 gene | rs200948 | 0.06849 | 0.1183 | 0.8248 | 0.07332 | 0.7144 | 0.9523 | −2.627 | 0.008616 |
| All Histone cluster1 gene | rs200953 | 0.06886 | 0.1188 | 0.8188 | 0.07312 | 0.7095 | 0.945 | −2.734 | 0.006253 |
| All Histone cluster1 gene | rs200989 | 0.06849 | 0.1185 | 0.8206 | 0.07325 | 0.7108 | 0.9473 | −2.7 | 0.006941 |
| All Histone cluster1 gene | rs200990 | 0.06899 | 0.119 | 0.818 | 0.07301 | 0.7089 | 0.9438 | −2.752 | 0.005918 |
| All Histone cluster1 gene | rs200991 | 0.1274 | 0.1585 | 0.9787 | 0.05359 | 0.8811 | 1.087 | −0.4021 | 0.6876 |
| All Histone cluster1 gene | rs200995 | 0.06862 | 0.1186 | 0.8242 | 0.07316 | 0.7141 | 0.9513 | −2.642 | 0.00823 |
| All Histone cluster1 gene | rs201002 | 0.06899 | 0.1188 | 0.823 | 0.073 | 0.7133 | 0.9496 | −2.668 | 0.007631 |
| All Histone cluster1 gene | rs201004 | 0.1514 | 0.1945 | 0.9781 | 0.06811 | 0.8559 | 1.118 | −0.3246 | 0.7455 |
| All Histone cluster1 gene | rs2064092 | 0.09884 | 0.06948 | 1.161 | 0.05845 | 1.035 | 1.301 | 2.547 | 0.01086 |
| All Histone cluster1 gene | rs2072806 | 0.06616 | 0.09787 | 0.7719 | 0.1687 | 0.5546 | 1.074 | −1.534 | 0.125 |
| All Histone cluster1 gene | rs2073529 | NA | NA | NA | NA | NA | NA | NA | NA |
| All Histone cluster1 gene | rs2093169 | 0.1479 | 0.1792 | 0.9559 | 0.04838 | 0.8694 | 1.051 | −0.9323 | 0.3512 |
| All Histone cluster1 gene | rs2393997 | 0.08422 | 0.1084 | 0.9463 | 0.05424 | 0.8509 | 1.052 | −1.017 | 0.3092 |
| All Histone cluster1 gene | rs2494711 | 0.3718 | 0.3585 | 1.056 | 0.03353 | 0.9886 | 1.127 | 1.617 | 0.1059 |
| All Histone cluster1 gene | rs2747054 | 0.06874 | 0.1182 | 0.8324 | 0.07315 | 0.7212 | 0.9607 | −2.508 | 0.01213 |
| All Histone cluster1 gene | rs2893910 | 0.1734 | 0.1917 | 0.9412 | 0.04668 | 0.8589 | 1.031 | −1.299 | 0.1938 |
| All Histone cluster1 gene | rs34706883 | 0.05115 | 0.09854 | 0.8501 | 0.0876 | 0.716 | 1.009 | −1.853 | 0.06382 |
| All Histone cluster1 gene | rs370155 | 0.06911 | 0.1188 | 0.8263 | 0.07295 | 0.7162 | 0.9533 | −2.616 | 0.008905 |
| All Histone cluster1 gene | rs3799378 | 0.1841 | 0.2212 | 0.8456 | 0.2738 | 0.4944 | 1.446 | −0.6127 | 0.5401 |
| All Histone cluster1 gene | rs3799380 | 0.175 | 0.1937 | 0.9812 | 0.04545 | 0.8975 | 1.073 | −0.4185 | 0.6756 |

TABLE 1-continued

| | | | | | | | | | |
|---|---|---|---|---|---|---|---|---|---|
| All Histone cluster1 gene | rs3799383 | 0.08075 | 0.1241 | 0.8228 | 0.06529 | 0.724 | 0.9352 | −2.986 | 0.002822 |
| All Histone cluster1 gene | rs3800307 | 0.1582 | 0.1941 | 1.002 | 0.04583 | 0.9157 | 1.096 | 0.03818 | 0.9695 |
| All Histone cluster1 gene | rs3800316 | 0.2617 | 0.279 | 0.9671 | 0.03862 | 0.8966 | 1.043 | −0.8669 | 0.386 |
| All Histone cluster1 gene | rs4452638 | 0.07766 | 0.1186 | 0.9554 | 0.06539 | 0.8405 | 1.086 | −0.6977 | 0.4854 |
| All Histone cluster1 gene | rs4634439 | 0.06948 | 0.1166 | 0.8152 | 0.06928 | 0.7117 | 0.9338 | −2.948 | 0.003195 |
| All Histone cluster1 gene | rs4712981 | 0.2476 | 0.284 | 0.9437 | 0.03773 | 0.8764 | 1.016 | −1.537 | 0.1244 |
| All Histone cluster1 gene | rs4713119 | 0.08647 | 0.1099 | 0.9468 | 0.05375 | 0.8522 | 1.052 | −1.016 | 0.3095 |
| All Histone cluster1 gene | rs6456728 | 0.175 | 0.1936 | 0.9811 | 0.04546 | 0.8975 | 1.073 | −0.4187 | 0.6754 |
| All Histone cluster1 gene | rs6904071 | 0.1288 | 0.169 | 1.019 | 0.04992 | 0.9241 | 1.124 | 0.3779 | 0.7055 |
| All Histone cluster1 gene | rs6904596 | 0.0623 | 0.1092 | 0.8336 | 0.07738 | 0.7163 | 0.9701 | −2.353 | 0.01864 |
| All Histone cluster1 gene | rs6913660 | 0.1292 | 0.1692 | 1.023 | 0.04987 | 0.9275 | 1.128 | 0.451 | 0.652 |
| All Histone cluster1 gene | rs6915101 | 0.01858 | 0.01608 | 0.8718 | 0.1242 | 0.6835 | 1.112 | −1.105 | 0.2694 |
| All Histone cluster1 gene | rs6920256 | 0.0758 | 0.1216 | 0.8308 | 0.0666 | 0.7292 | 0.9467 | −2.783 | 0.00539 |
| All Histone cluster1 gene | rs6923139 | 0.09289 | 0.1142 | 0.8966 | 0.06213 | 0.7938 | 1.013 | −1.756 | 0.07912 |
| All Histone cluster1 gene | rs6932590 | 0.2221 | 0.2553 | 0.9681 | 0.04017 | 0.8948 | 1.047 | −0.8065 | 0.42 |
| All Histone cluster1 gene | rs6933583 | 0.2496 | 0.2851 | 0.9491 | 0.03764 | 0.8816 | 1.022 | −1.389 | 0.1648 |
| All Histone cluster1 gene | rs6934794 | 0.2156 | 0.1878 | 1.092 | 0.03964 | 1.01 | 1.18 | 2.209 | 0.02716 |
| All Histone cluster1 gene | rs6938200 | 0.1611 | 0.1567 | 0.9747 | 0.06571 | 0.8569 | 1.109 | −0.3893 | 0.697 |
| All Histone cluster1 gene | rs721600 | 0.2458 | 0.2271 | 1.057 | 0.03752 | 0.9821 | 1.138 | 1.478 | 0.1395 |
| All Histone cluster1 gene | rs7745603 | 0.1828 | 0.2223 | 0.9949 | 0.04314 | 0.9142 | 1.083 | −0.1189 | 0.9054 |
| All Histone cluster1 gene | rs7746199 | 0.1747 | 0.1929 | 0.9434 | 0.07528 | 0.814 | 1.093 | −0.7735 | 0.4392 |
| All Histone cluster1 gene | rs7749305 | 0.06205 | 0.1089 | 0.812 | 0.07602 | 0.6996 | 0.9424 | −2.74 | 0.006146 |
| All Histone cluster1 gene | rs7749319 | 0.02514 | 0.0407 | 0.8489 | 0.08917 | 0.7128 | 1.011 | −1.837 | 0.06618 |
| All Histone cluster1 gene | rs7756567 | 0.1479 | 0.1794 | 0.955 | 0.04837 | 0.8686 | 1.05 | −0.9523 | 0.3409 |
| All Histone cluster1 gene | rs7773938 | 0.1478 | 0.1795 | 0.9514 | 0.04837 | 0.8653 | 1.046 | −1.03 | 0.3028 |
| All Histone cluster1 gene | rs911186 | NA | NA | NA | NA | NA | NA | NA | NA |
| All Histone cluster1 gene | rs9295739 | 0.01164 | 0.01047 | 0.8903 | 0.1547 | 0.6574 | 1.206 | −0.7513 | 0.4524 |
| All Histone cluster1 gene | rs9295749 | 0.06886 | 0.05046 | 1.147 | 0.06866 | 1.003 | 1.312 | 2 | 0.04548 |
| All Histone cluster1 gene | rs9358944 | 0.148 | 0.1794 | 0.9553 | 0.04834 | 0.8689 | 1.05 | −0.9469 | 0.3437 |
| All Histone cluster1 gene | rs9358945 | 0.148 | 0.1795 | 0.9544 | 0.04834 | 0.8682 | 1.049 | −0.9646 | 0.3347 |
| All Histone cluster1 gene | rs9358946 | 0.1483 | 0.1871 | 0.9062 | 0.05661 | 0.8111 | 1.013 | −1.739 | 0.08199 |
| All Histone cluster1 gene | rs9366653 | 0.07035 | 0.1178 | 0.8326 | 0.06753 | 0.7293 | 0.9504 | −2.713 | 0.006659 |
| All Histone cluster1 gene | rs9366658 | 0.148 | 0.1794 | 0.9553 | 0.04834 | 0.8689 | 1.05 | −0.9469 | 0.3437 |
| All Histone cluster1 gene | rs9379844 | 0.421 | 0.3743 | 1.064 | 0.03304 | 0.9976 | 1.136 | 1.887 | 0.05922 |
| All Histone cluster1 gene | rs9379851 | 0.0701 | 0.1178 | 0.8314 | 0.06757 | 0.7283 | 0.9492 | −2.732 | 0.006303 |
| All Histone cluster1 gene | rs9379856 | NA | NA | NA | NA | NA | NA | NA | NA |
| All Histone cluster1 gene | rs9379858 | 0.06998 | 0.1179 | 0.8284 | 0.06762 | 0.7256 | 0.9458 | −2.784 | 0.005364 |
| All Histone cluster1 gene | rs9379859 | 0.06998 | 0.1179 | 0.8284 | 0.06762 | 0.7256 | 0.9458 | −2.784 | 0.005364 |
| All Histone cluster1 gene | rs9379870 | 0.2491 | 0.2842 | 0.9503 | 0.03768 | 0.8827 | 1.023 | −1.353 | 0.1761 |
| All Histone cluster1 gene | rs9379897 | 0.06948 | 0.1166 | 0.8148 | 0.06928 | 0.7114 | 0.9334 | −2.955 | 0.003123 |

TABLE 1-continued

| | | | | | | | | | |
|---|---|---|---|---|---|---|---|---|---|
| All Histone cluster1 gene | rs9393691 | 0.4209 | 0.3741 | 1.064 | 0.03302 | 0.9976 | 1.135 | 1.888 | 0.05902 |
| All Histone cluster1 gene | rs9393705 | 0.06998 | 0.1178 | 0.8305 | 0.06765 | 0.7273 | 0.9482 | −2.746 | 0.006036 |
| All Histone cluster1 gene | rs9393708 | 0.06998 | 0.1178 | 0.8305 | 0.06765 | 0.7273 | 0.9482 | −2.746 | 0.006036 |
| All Histone cluster1 gene | rs9393713 | 0.06962 | 0.1171 | 0.8318 | 0.06795 | 0.7281 | 0.9503 | −2.711 | 0.006712 |
| All Histone cluster1 gene | rs9393714 | 0.06961 | 0.1171 | 0.831 | 0.06794 | 0.7274 | 0.9493 | −2.725 | 0.006424 |
| All Histone cluster1 gene | rs9393777 | 0.09297 | 0.1022 | 0.8332 | 0.1037 | 0.68 | 1.021 | −1.759 | 0.07859 |
| All Histone cluster1 gene | rs9461362 | 0.1837 | 0.1489 | 1.045 | 0.04316 | 0.9599 | 1.137 | 1.012 | 0.3117 |
| All Histone cluster1 gene | rs9467704 | 0.0893 | 0.1131 | 0.8967 | 0.06277 | 0.7929 | 1.014 | −1.737 | 0.08239 |
| All Histone cluster1 gene | rs9468152 | 0.1702 | 0.1442 | 1.188 | 0.2952 | 0.666 | 2.119 | 0.5832 | 0.5598 |
| All Histone cluster1 gene | rs9468159 | 0.0924 | 0.06363 | 1.194 | 0.06055 | 1.061 | 1.345 | 2.932 | 0.003371 |
| All Histone cluster1 gene | rs9468202 | 0.01189 | 0.01056 | 0.8965 | 0.1537 | 0.6634 | 1.212 | −0.7106 | 0.4773 |
| All Histone cluster1 gene | rs9468227 | 0.01808 | 0.01615 | 0.8413 | 0.125 | 0.6585 | 1.075 | −1.382 | 0.1669 |
| GTF2IRD2B | imm_7_74094413 | 0.3916 | 0.4088 | 0.8676 | 0.03268 | 0.8138 | 0.925 | −4.346 | 1.38E−05 |
| GTF2IRD2B | imm_7_74108242 | 0.4014 | 0.4193 | 0.8748 | 0.03242 | 0.8209 | 0.9322 | −4.125 | 3.71E−05 |
| GTF2IRD2B | imm_7_74117236 | 0.4035 | 0.4192 | 0.8776 | 0.03238 | 0.8237 | 0.9351 | −4.031 | 5.56E−05 |
| GTF2IRD2B | imm_7_74118166 | 0.4666 | 0.46 | 0.8855 | 0.03208 | 0.8315 | 0.9429 | −3.793 | 0.000149 |
| GTF2IRD2B | imm_7_74120730 | 0.1026 | 0.1225 | 0.8373 | 0.05057 | 0.7583 | 0.9245 | −3.513 | 0.000443 |
| GTF2IRD2B | imm_7_74133859 | 0.1929 | 0.2297 | 0.7912 | 0.2746 | 0.4619 | 1.355 | −0.8529 | 0.3937 |
| GTF2IRD2B | imm_7_74145400 | NA | NA | NA | NA | NA | NA | NA | NA |
| ETS1 | imm_11_127760024 | 0.09923 | 0.09729 | 1.057 | 0.05358 | 0.9513 | 1.174 | 1.029 | 0.3036 |
| ETS1 | imm_11_127761269 | 0.1045 | 0.08108 | 1.337 | 0.4248 | 0.5816 | 3.075 | 0.6843 | 0.4938 |
| ETS1 | imm_11_127765567 | 0.1225 | 0.1356 | 1.065 | 0.0466 | 0.9719 | 1.167 | 1.349 | 0.1775 |
| ETS1 | imm_11_127767721 | 0.0296 | 0.02617 | 0.8282 | 0.09903 | 0.6821 | 1.006 | −1.904 | 0.0569 |
| ETS1 | imm_11_127770666 | 0.2654 | 0.2634 | 0.9872 | 0.03588 | 0.9202 | 1.059 | −0.3584 | 0.72 |
| ETS1 | imm_11_127770668 | 0.2656 | 0.2638 | 0.9866 | 0.03586 | 0.9196 | 1.058 | −0.3761 | 0.7068 |
| ETS1 | imm_11_127774308 | 0.1281 | 0.1396 | 1.066 | 0.04595 | 0.9746 | 1.167 | 1.4 | 0.1614 |
| ETS1 | imm_11_127775128 | 0.1286 | 0.1396 | 1.069 | 0.04592 | 0.9772 | 1.17 | 1.458 | 0.1449 |
| ETS1 | imm_11_127776527 | 0.03517 | 0.02933 | 0.8327 | 0.09292 | 0.694 | 0.999 | −1.97 | 0.04879 |
| ETS1 | imm_11_127776913 | 0.03344 | 0.02833 | 0.8482 | 0.09417 | 0.7053 | 1.02 | −1.748 | 0.08043 |
| ETS1 | imm_11_127777217 | 0.4176 | 0.4708 | 0.9489 | 0.03186 | 0.8915 | 1.01 | −1.646 | 0.09979 |
| ETS1 | imm_11_127778327 | NA | NA | NA | NA | NA | NA | NA | NA |
| ETS1 | imm_11_127778329 | 0.2401 | 0.247 | 1.034 | 0.03684 | 0.9621 | 1.112 | 0.9124 | 0.3616 |
| ETS1 | imm_11_127779030 | 0.04471 | 0.04792 | 0.888 | 0.07615 | 0.7649 | 1.031 | −1.56 | 0.1188 |
| ETS1 | imm_11_127780425 | 0.03802 | 0.03367 | 1.122 | 0.08549 | 0.9491 | 1.327 | 1.349 | 0.1775 |
| ETS1 | imm_11_127780902 | 0.04581 | 0.0487 | 0.8837 | 0.08254 | 0.7517 | 1.039 | −1.498 | 0.1341 |
| ETS1 | imm_11_127781839 | 0.2692 | 0.2885 | 0.8392 | 0.2397 | 0.5246 | 1.343 | −0.7313 | 0.4646 |
| ETS1 | imm_11_127785739 | 0.1848 | 0.1972 | 0.9376 | 0.04033 | 0.8663 | 1.015 | −1.599 | 0.1098 |
| ETS1 | imm_11_127785963 | 0.1421 | 0.1489 | 1.064 | 0.0447 | 0.9749 | 1.162 | 1.391 | 0.1644 |
| ETS1 | imm_11_127786010 | 0.2006 | 0.1899 | 1.055 | 0.03989 | 0.9759 | 1.141 | 1.349 | 0.1772 |
| ETS1 | imm_11_127786836 | 0.2008 | 0.1903 | 1.053 | 0.03987 | 0.9737 | 1.138 | 1.291 | 0.1965 |
| ETS1 | imm_11_127787128 | 0.2003 | 0.1897 | 1.055 | 0.03992 | 0.9757 | 1.141 | 1.345 | 0.1787 |
| ETS1 | imm_11_127788828 | 0.1906 | 0.2041 | 0.9357 | 0.03986 | 0.8654 | 1.012 | −1.668 | 0.0953 |
| ETS1 | imm_11_127789306 | 0.2006 | 0.1962 | 1.087 | 0.05728 | 0.9719 | 1.217 | 1.463 | 0.1435 |
| ETS1 | imm_11_127789441 | 0.201 | 0.1971 | 1.085 | 0.05721 | 0.9697 | 1.213 | 1.422 | 0.1551 |
| ETS1 | imm_11_127791651 | 0.1622 | 0.1548 | 1.087 | 0.04321 | 0.9988 | 1.183 | 1.931 | 0.05342 |
| ETS1 | imm_11_127792287 | 0.201 | 0.1903 | 1.053 | 0.0399 | 0.9737 | 1.138 | 1.291 | 0.1967 |
| ETS1 | imm_11_127792800 | 0.05115 | 0.04665 | 1.064 | 0.07416 | 0.9201 | 1.231 | 0.8374 | 0.4024 |
| ETS1 | imm_11_127793060 | 0.2016 | 0.1912 | 1.053 | 0.03983 | 0.974 | 1.139 | 1.298 | 0.1943 |
| ETS1 | imm_11_127794685 | 0.1632 | 0.1557 | 1.087 | 0.04309 | 0.9988 | 1.183 | 1.933 | 0.05325 |
| ETS1 | imm_11_127795453 | 0.202 | 0.1916 | 1.053 | 0.03978 | 0.974 | 1.138 | 1.296 | 0.1948 |
| ETS1 | imm_11_127796816 | 0.000277 | 0 | 2.68E+08 | 17210 | 0 | Inf | 0.001128 | 0.9991 |
| ETS1 | imm_11_127797523 | 0.2018 | 0.1911 | 1.055 | 0.0398 | 0.9757 | 1.14 | 1.341 | 0.1798 |
| ETS1 | imm_11_127798230 | 0.306 | 0.2976 | 0.9407 | 0.03477 | 0.8788 | 1.007 | −1.757 | 0.07891 |
| ETS1 | imm_11_127799892 | 0.5051 | 0.4805 | 0.997 | 0.03194 | 0.9365 | 1.061 | −0.09376 | 0.9253 |
| ETS1 | imm_11_127804916 | 0.1434 | 0.1323 | 0.9649 | 0.04645 | 0.881 | 1.057 | −0.7684 | 0.4423 |
| ETS1 | imm_11_127805367 | 0.03579 | 0.0314 | 0.9317 | 0.08952 | 0.7818 | 1.11 | −0.7899 | 0.4296 |
| ETS1 | imm_11_127806163 | 0.3755 | 0.3846 | 1.022 | 0.03283 | 0.9585 | 1.09 | 0.6682 | 0.504 |
| ETS1 | imm_11_127806304 | 0.03443 | 0.03077 | 0.9126 | 0.09083 | 0.7637 | 1.09 | −1.007 | 0.3137 |
| ETS1 | imm_11_127807384 | 0.1611 | 0.1639 | 0.993 | 0.04335 | 0.9121 | 1.081 | −0.1631 | 0.8705 |
| ETS1 | imm_11_127808758 | 0.03592 | 0.03158 | 0.9304 | 0.08931 | 0.781 | 1.108 | −0.8078 | 0.4192 |
| ETS1 | imm_11_127809308 | 0.005202 | 0.008031 | 0.9228 | 0.1958 | 0.6288 | 1.354 | −0.4103 | 0.6816 |
| ETS1 | imm_11_127812329 | 0.05871 | 0.0545 | 1.083 | 0.06867 | 0.9464 | 1.239 | 1.158 | 0.2467 |
| ETS1 | imm_11_127812420 | 0 | 0.000904 | 1.25E−10 | 24380 | 0 | Inf | −0.00094 | 0.9993 |
| ETS1 | imm_11_127813024 | 0.3752 | 0.3846 | 1.02 | 0.03283 | 0.9564 | 1.088 | 0.6007 | 0.548 |
| ETS1 | imm_11_127819226 | 0.1616 | 0.164 | 0.9959 | 0.04328 | 0.9149 | 1.084 | −0.09454 | 0.9247 |
| ETS1 | imm_11_127822686 | 0.03592 | 0.03176 | 0.9255 | 0.08905 | 0.7773 | 1.102 | −0.8694 | 0.3846 |
| ETS1 | imm_11_127823420 | 0.005203 | 0.008031 | 0.9229 | 0.1957 | 0.6288 | 1.354 | −0.4101 | 0.6817 |
| ETS1 | imm_11_127824356 | 0.1587 | 0.1614 | 0.988 | 0.04363 | 0.907 | 1.076 | −0.2778 | 0.7811 |

TABLE 1-continued

| | | | | | | | | | |
|---|---|---|---|---|---|---|---|---|---|
| ETS1 | imm_11_127825016 | 0.03629 | 0.03158 | 0.9352 | 0.08918 | 0.7852 | 1.114 | −0.7514 | 0.4524 |
| ETS1 | imm_11_127825282 | 0.3776 | 0.3871 | 1.023 | 0.03279 | 0.9592 | 1.091 | 0.69 | 0.4902 |
| ETS1 | imm_11_127825669 | 0.3776 | 0.3869 | 1.024 | 0.0328 | 0.9598 | 1.092 | 0.7097 | 0.4779 |
| ETS1 | imm_11_127826087 | 0.3214 | 0.3391 | 0.9933 | 0.0338 | 0.9296 | 1.061 | −0.2003 | 0.8412 |
| ETS1 | imm_11_127826464 | 0.1491 | 0.1481 | 1.005 | 0.04514 | 0.9203 | 1.098 | 0.119 | 0.9053 |
| ETS1 | imm_11_127827422 | 0.1496 | 0.149 | 1.005 | 0.04498 | 0.9199 | 1.097 | 0.1047 | 0.9166 |
| ETS1 | imm_11_127828334 | 0.03406 | 0.03032 | 0.9041 | 0.09167 | 0.7554 | 1.082 | −1.1 | 0.2713 |
| ETS1 | imm_11_127831280 | 0.01663 | 0.0246 | 1.022 | 0.1232 | 0.8025 | 1.301 | 0.1735 | 0.8622 |
| ETS1 | imm_11_127831611 | 0.1616 | 0.152 | 1.026 | 0.04416 | 0.9407 | 1.118 | 0.5757 | 0.5648 |
| ETS1 | imm_11_127831673 | 0.2755 | 0.2923 | 0.9931 | 0.03555 | 0.9263 | 1.065 | −0.1945 | 0.8458 |
| ETS1 | imm_11_127834123 | 0.267 | 0.3026 | 1.029 | 0.03531 | 0.9599 | 1.102 | 0.7999 | 0.4238 |
| ETS1 | imm_11_127834484 | 0.02106 | 0.02681 | 0.9249 | 0.1037 | 0.7548 | 1.133 | −0.7522 | 0.4519 |
| ETS1 | imm_11_127837472 | 0.01585 | 0.01922 | 1.016 | 0.1212 | 0.8012 | 1.288 | 0.1314 | 0.8955 |
| ETS1 | imm_11_127838265 | 0.07167 | 0.08269 | 1.021 | 0.06775 | 0.8943 | 1.166 | 0.3112 | 0.7556 |
| ETS1 | imm_11_127838713 | 0.4488 | 0.4731 | 1.016 | 0.03193 | 0.9544 | 1.082 | 0.4976 | 0.6187 |
| ETS1 | imm_11_127839719 | 0.008546 | 0.01534 | 0.7867 | 0.1489 | 0.5876 | 1.053 | −1.61 | 0.1073 |
| ETS1 | imm_11_127840459 | 0.1553 | 0.1515 | 1.032 | 0.0442 | 0.9466 | 1.126 | 0.7171 | 0.4733 |
| ETS1 | imm_11_127840867 | 0.122 | 0.1295 | 1.012 | 0.06897 | 0.8843 | 1.159 | 0.1765 | 0.8599 |
| ETS1 | imm_11_127841724 | 0.1095 | 0.106 | 0.8683 | 0.05228 | 0.7837 | 0.962 | −2.701 | 0.006915 |
| ETS1 | imm_11_127841864 | 0.43 | 0.4439 | 0.9506 | 0.03218 | 0.8925 | 1.012 | −1.574 | 0.1154 |
| ETS1 | imm_11_127843207 | 0.109 | 0.1057 | 0.8676 | 0.05234 | 0.783 | 0.9614 | −2.713 | 0.006676 |
| ETS1 | imm_11_127843341 | 0.1088 | 0.1053 | 0.8728 | 0.05243 | 0.7876 | 0.9673 | −2.594 | 0.009475 |
| ETS1 | imm_11_127844385 | 0.1558 | 0.1525 | 1.026 | 0.04417 | 0.9407 | 1.119 | 0.5761 | 0.5646 |
| ETS1 | imm_11_127844729 | 0.02551 | 0.01967 | 1.13 | 0.1089 | 0.913 | 1.399 | 1.124 | 0.2609 |
| ETS1 | imm_11_127845557 | 0.1145 | 0.1088 | 0.8748 | 0.05135 | 0.7911 | 0.9674 | −2.605 | 0.009196 |
| ETS1 | imm_11_127846698 | 0.1561 | 0.1529 | 1.028 | 0.04405 | 0.9428 | 1.12 | 0.6218 | 0.534 |
| ETS1 | imm_11_127848167 | 0.1566 | 0.1529 | 1.031 | 0.04402 | 0.9454 | 1.123 | 0.6847 | 0.4935 |
| ETS1 | imm_11_127848372 | 0.156 | 0.1526 | 1.027 | 0.04407 | 0.9425 | 1.12 | 0.6151 | 0.5385 |
| ETS1 | imm_11_127849992 | 0.1561 | 0.1528 | 1.029 | 0.04405 | 0.9434 | 1.121 | 0.6383 | 0.5233 |
| ETS1 | imm_11_127851599 | 0.1577 | 0.1532 | 1.03 | 0.04393 | 0.9446 | 1.122 | 0.662 | 0.508 |
| ETS1 | imm_11_127852250 | 0.1051 | 0.104 | 0.8571 | 0.05302 | 0.7725 | 0.9509 | −2.909 | 0.003627 |
| ETS1 | imm_11_127853705 | 0.1053 | 0.1043 | 0.8574 | 0.05294 | 0.7729 | 0.9512 | −2.906 | 0.003665 |
| ETS1 | imm_11_127855281 | 0.1578 | 0.1537 | 1.028 | 0.04389 | 0.9435 | 1.121 | 0.6351 | 0.5253 |
| ETS1 | imm_11_127855956 | 0.1073 | 0.1055 | 0.8632 | 0.05254 | 0.7787 | 0.9568 | −2.8 | 0.00511 |
| ETS1 | imm_11_127857027 | 0.1036 | 0.1029 | 0.8621 | 0.05334 | 0.7766 | 0.9572 | −2.781 | 0.005423 |
| ETS1 | imm_11_127861069 | 0.2813 | 0.264 | 0.9939 | 0.03613 | 0.926 | 1.067 | −0.1688 | 0.866 |
| ETS1 | imm_11_127863304 | 0.2818 | 0.264 | 0.9915 | 0.03613 | 0.9237 | 1.064 | −0.2355 | 0.8138 |
| ETS1 | imm_11_127863391 | 0.2819 | 0.264 | 0.9934 | 0.03611 | 0.9255 | 1.066 | −0.1826 | 0.8551 |
| ETS1 | imm_11_127866379 | 0.2602 | 0.2434 | 1.01 | 0.03687 | 0.9393 | 1.085 | 0.2617 | 0.7936 |
| ETS1 | imm_11_127868447 | 0.01177 | 0.01215 | 1.459 | 0.2081 | 0.97 | 2.193 | 1.814 | 0.06974 |
| ETS1 | imm_11_127868927 | 0.2025 | 0.1913 | 0.9583 | 0.04052 | 0.8852 | 1.038 | −1.051 | 0.2933 |
| ETS1 | imm_11_127869177 | 0.2994 | 0.3094 | 1.012 | 0.05015 | 0.9171 | 1.116 | 0.2349 | 0.8143 |
| ETS1 | imm_11_127870403 | 0.2722 | 0.2563 | 0.9918 | 0.03655 | 0.9232 | 1.065 | −0.2256 | 0.8215 |
| ETS1 | imm_11_127870895 | 0.2995 | 0.2695 | 0.9909 | 0.03589 | 0.9236 | 1.063 | −0.2535 | 0.7999 |
| ETS1 | imm_11_127871431 | 0.2995 | 0.2697 | 0.9901 | 0.03589 | 0.9229 | 1.062 | −0.2762 | 0.7824 |
| ETS1 | imm_11_127872972 | 0.2003 | 0.1863 | 0.893 | 0.05916 | 0.7952 | 1.003 | −1.914 | 0.05568 |
| ETS1 | imm_11_127874486 | 0.2995 | 0.2696 | 0.9913 | 0.03588 | 0.924 | 1.064 | −0.2438 | 0.8074 |
| ETS1 | imm_11_127874807 | 0.2851 | 0.2647 | 0.983 | 0.03611 | 0.9158 | 1.055 | −0.4745 | 0.6351 |
| ETS1 | imm_11_127877378 | 0.2989 | 0.269 | 0.9921 | 0.0359 | 0.9247 | 1.064 | −0.2201 | 0.8258 |
| ETS1 | imm_11_127879923 | 0.1999 | 0.1907 | 0.9578 | 0.04065 | 0.8844 | 1.037 | −1.062 | 0.2883 |
| ETS1 | imm_11_127881686 | 0.1909 | 0.1676 | 1.043 | 0.04194 | 0.9607 | 1.132 | 1.003 | 0.3159 |
| ETS1 | imm_11_127882690 | 0.4045 | 0.3813 | 1.017 | 0.03273 | 0.9535 | 1.084 | 0.506 | 0.6128 |
| ETS1 | imm_11_127884689 | 0.05927 | 0.06757 | 0.8456 | 0.472 | 0.3353 | 2.133 | −0.3554 | 0.7223 |
| ETS1 | imm_11_127885952 | 0.3706 | 0.3524 | 1.029 | 0.03319 | 0.9646 | 1.099 | 0.8743 | 0.382 |
| ETS1 | imm_11_127886184 | 0.2435 | 0.2214 | 1.066 | 0.03763 | 0.9906 | 1.148 | 1.709 | 0.08748 |
| ETS1 | imm_11_127887077 | 0.3702 | 0.3521 | 1.029 | 0.03319 | 0.9642 | 1.098 | 0.8607 | 0.3894 |
| ETS1 | imm_11_127889134 | 0.2431 | 0.221 | 1.066 | 0.03774 | 0.9904 | 1.148 | 1.705 | 0.08811 |
| ETS1 | imm_11_127891116 | 0.2431 | 0.2211 | 1.067 | 0.03774 | 0.9907 | 1.149 | 1.714 | 0.08661 |
| ETS1 | imm_11_127892632 | 0.3704 | 0.3521 | 1.03 | 0.0332 | 0.9655 | 1.1 | 0.9013 | 0.3674 |
| ETS1 | imm_11_127894601 | 0.2506 | 0.2405 | 0.9395 | 0.03731 | 0.8733 | 1.011 | −1.672 | 0.09462 |
| ETS1 | imm_11_127894638 | 0.003716 | 0.002075 | 1.374 | 0.3097 | 0.7489 | 2.521 | 1.026 | 0.3048 |
| ETS1 | imm_11_127895279 | 0.243 | 0.2207 | 1.068 | 0.03774 | 0.9915 | 1.15 | 1.735 | 0.08275 |
| ETS1 | imm_11_127897147 | 0.2232 | 0.2121 | 1.066 | 0.03857 | 0.9886 | 1.15 | 1.662 | 0.09658 |
| ETS1 | imm_11_127898835 | 0.01239 | 0.01814 | 0.9176 | 0.1286 | 0.7133 | 1.181 | −0.6686 | 0.5037 |
| ETS1 | imm_11_127901157 | 0.3059 | 0.2861 | 1.062 | 0.03509 | 0.9912 | 1.137 | 1.709 | 0.08752 |
| ETS1 | imm_11_127901948 | 0.228 | 0.2155 | 1.061 | 0.03837 | 0.9844 | 1.144 | 1.549 | 0.1213 |
| ETS1 | imm_11_127905841 | 0.03579 | 0.04864 | 0.995 | 0.07786 | 0.8542 | 1.159 | −0.06386 | 0.9491 |
| ETS1 | imm_11_127906568 | 0.388 | 0.3836 | 0.9752 | 0.03276 | 0.9146 | 1.04 | −0.7663 | 0.4435 |
| ETS1 | imm_11_127908214 | 0.3883 | 0.384 | 0.9755 | 0.03276 | 0.9148 | 1.04 | −0.7587 | 0.448 |
| ETS1 | imm_11_127911648 | 0.4828 | 0.4715 | 1.016 | 0.04546 | 0.9295 | 1.111 | 0.3513 | 0.7253 |
| ETS1 | imm_11_127911985 | 0.4903 | 0.49 | 0.9633 | 0.03179 | 0.9051 | 1.025 | −1.177 | 0.2392 |
| ETS1 | imm_11_127914294 | 0.4918 | 0.4912 | 0.9631 | 0.03178 | 0.905 | 1.025 | −1.182 | 0.2372 |
| ETS1 | imm_11_127915474 | 0.4825 | 0.4941 | 1.033 | 0.0318 | 0.9707 | 1.1 | 1.024 | 0.306 |
| ETS1 | imm_11_127915554 | 0.4827 | 0.4941 | 1.034 | 0.0318 | 0.9712 | 1.1 | 1.04 | 0.2983 |
| ETS1 | imm_11_127916046 | 0.4921 | 0.4908 | 0.9665 | 0.03176 | 0.9081 | 1.029 | −1.074 | 0.2827 |
| ETS1 | imm_11_127929821 | 0.000832 | 0 | 2.22E+08 | 9897 | 0 | Inf | 0.001942 | 0.9985 |
| ETS1 | imm_11_127931099 | 0.000124 | 0 | 3.89E+08 | 24380 | 0 | Inf | 0.000811 | 0.9994 |
| ETS1 | imm_11_127940676 | 0.0322 | 0.04675 | 0.8901 | 0.08166 | 0.7584 | 1.045 | −1.426 | 0.1538 |
| ETS1 | imm_11_127943244 | 0.000139 | 0.000904 | 0.1276 | 1.417 | 0.007941 | 2.05 | −1.453 | 0.1461 |
| ETS1 | imm_11_127945727 | 0.3529 | 0.3654 | 1.093 | 0.03356 | 1.023 | 1.167 | 2.647 | 0.008125 |

TABLE 1-continued

| | | | | | | | | | |
|---|---|---|---|---|---|---|---|---|---|
| ETS1 | imm_11_127945953 | 0.07208 | 0.07679 | 0.9935 | 0.0607 | 0.882 | 1.119 | −0.1079 | 0.9141 |
| ETS1 | imm_11_127948912 | 0.01338 | 0.01886 | 0.8931 | 0.1262 | 0.6974 | 1.144 | −0.8959 | 0.3703 |
| ETS1 | imm_11_127956842 | 0.2394 | 0.2512 | 0.9858 | 0.03721 | 0.9165 | 1.06 | −0.3845 | 0.7006 |
| ETS1 | imm_11_127957543 | 0.01553 | 0.01099 | 1.247 | 0.1637 | 0.9046 | 1.718 | 1.348 | 0.1778 |
| ETS1 | imm_11_127957904 | 0.006936 | 0.01471 | 0.7343 | 0.1582 | 0.5386 | 1.001 | −1.952 | 0.05088 |
| ETS1 | imm_11_127974263 | 0.07146 | 0.07661 | 0.9949 | 0.06078 | 0.8832 | 1.121 | −0.08418 | 0.9329 |
| ETS1 | imm_11_127979301 | 0.1644 | 0.1768 | 0.9816 | 0.04237 | 0.9034 | 1.067 | −0.4374 | 0.6618 |
| ETS1 | imm_11_127979905 | 0.006069 | 0.01065 | 0.8416 | 0.1763 | 0.5957 | 1.189 | −0.9781 | 0.328 |
| ETS1 | imm_11_127981559 | 0.1593 | 0.1708 | 0.9882 | 0.043 | 0.9083 | 1.075 | −0.2764 | 0.7822 |
| ETS1 | imm_11_127982379 | 0.1593 | 0.1708 | 0.9882 | 0.043 | 0.9083 | 1.075 | −0.2764 | 0.7822 |
| ETS1 | imm_11_127982748 | 0.1594 | 0.1709 | 0.9878 | 0.04302 | 0.908 | 1.075 | −0.2848 | 0.7758 |
| ETS1 | imm_11_127983590 | 0.1578 | 0.1698 | 0.9895 | 0.04311 | 0.9093 | 1.077 | −0.2454 | 0.8062 |
| ETS1 | imm_11_127983743 | 0.1593 | 0.1708 | 0.9882 | 0.043 | 0.9083 | 1.075 | −0.2764 | 0.7822 |
| ETS1 | imm_11_127984265 | 0.1593 | 0.1705 | 0.9898 | 0.043 | 0.9098 | 1.077 | −0.2391 | 0.811 |
| ETS1 | imm_11_127984721 | 0.1639 | 0.1818 | 0.9766 | 0.04889 | 0.8874 | 1.075 | −0.4836 | 0.6287 |
| ETS1 | rs7935286 | 0.1731 | 0.1549 | 1.076 | 0.04318 | 0.9887 | 1.171 | 1.697 | 0.08975 |
| SLC5A1 | rs738203 | 0.2295 | 0.1081 | 2.421 | 0.3734 | 1.165 | 5.033 | 2.368 | 0.01787 |
| SLC5A1 | rs9609429 | 0.2286 | 0.2801 | 0.8632 | 0.0372 | 0.8025 | 0.9285 | −3.955 | 7.65E−05 |
| TET2 | rs10010325 | 0.4693 | 0.4772 | 0.9764 | 0.03186 | 0.9173 | 1.039 | −0.7485 | 0.4541 |
| TET2 | rs17035310 | 0.1487 | 0.1265 | 1.097 | 0.04675 | 1.001 | 1.202 | 1.972 | 0.0486 |
| TET2 | rs2189234 | 0.3562 | 0.3837 | 0.9611 | 0.03307 | 0.9008 | 1.025 | −1.2 | 0.23 |
| TET2 | rs7661349 | 0.3235 | 0.3641 | 0.9541 | 0.03359 | 0.8933 | 1.019 | −1.399 | 0.1619 |
| TET2 | rs974801 | 0.3636 | 0.355 | 1.028 | 0.03308 | 0.9633 | 1.097 | 0.8306 | 0.4062 |

(Continued, part 3)

| gene.i | SNP | F_A_iibdgc | F_U_iibdgc | OR_iibdgc | SE_iibdgc | L95_iibdgc | U95_iibdgc |
|---|---|---|---|---|---|---|---|
| SLC26A4 | rs10247487 | 0.2562 | 0.2535 | 0.9522 | 0.0161 | 0.9226 | 0.9827 |
| SLC26A4 | rs10263826 | 0.2723 | 0.2697 | 0.9459 | 0.01578 | 0.9171 | 0.9756 |
| SLC26A4 | rs10273733 | 0.2937 | 0.2773 | 1.068 | 0.01553 | 1.036 | 1.101 |
| SLC26A4 | rs12539555 | 0.2607 | 0.2621 | 1.029 | 0.01607 | 0.9967 | 1.061 |
| SLC26A4 | rs2248465 | 0.2781 | 0.2642 | 1.057 | 0.01573 | 1.025 | 1.09 |
| SLC26A4 | rs2808 | 0.2968 | 0.2799 | 1.07 | 0.01547 | 1.038 | 1.103 |
| DLG4 | rs3785794 | 0.07336 | 0.07494 | 0.9162 | 0.02669 | 0.8695 | 0.9654 |
| GIPR | chr19:50983512 | 0.2904 | 0.3095 | 0.9404 | 0.01544 | 0.9124 | 0.9693 |
| GIPR | chr19:51014231 | 0.2991 | 0.3218 | 0.9347 | 0.01531 | 0.907 | 0.9631 |
| GIPR | chr19:51026971 | 0.3022 | 0.3244 | 0.9344 | 0.01522 | 0.907 | 0.9628 |
| GIPR | rs10401439 | 0.2987 | 0.3224 | 0.9284 | 0.01566 | 0.9003 | 0.9573 |
| GIPR | rs10402263 | 0.3321 | 0.3504 | 0.9441 | 0.01489 | 0.917 | 0.9721 |
| GIPR | rs10421891 | 0.3395 | 0.3596 | 0.9391 | 0.01466 | 0.9125 | 0.9665 |
| GIPR | rs10500292 | 0.383 | 0.4041 | 0.9396 | 0.01445 | 0.9134 | 0.9666 |
| GIPR | rs11883351 | 0.3289 | 0.3486 | 0.9389 | 0.01493 | 0.9118 | 0.9668 |
| GIPR | rs12463359 | 0.3775 | 0.3969 | 0.9433 | 0.01449 | 0.9169 | 0.9705 |
| GIPR | rs16980013 | 0.2881 | 0.3073 | 0.9407 | 0.01548 | 0.9126 | 0.9697 |
| GIPR | rs16980051 | 0.4789 | 0.5034 | 0.9424 | 0.01408 | 0.9167 | 0.9687 |
| GIPR | rs17878252 | 0.2689 | 0.2873 | 0.9391 | 0.01577 | 0.9106 | 0.9686 |
| GIPR | rs2070736 | 0.2909 | 0.3101 | 0.9396 | 0.01543 | 0.9116 | 0.9685 |
| GIPR | rs2334255 | 0.2601 | 0.2473 | 1.045 | 0.01603 | 1.013 | 1.079 |
| GIPR | rs4514788 | 0.3041 | 0.3246 | 0.9433 | 0.01517 | 0.9157 | 0.9718 |
| GIPR | rs4802273 | 0.2787 | 0.2977 | 0.9383 | 0.01561 | 0.91 | 0.9675 |
| GIPR | rs4802274 | 0.2915 | 0.311 | 0.938 | 0.01542 | 0.9101 | 0.9668 |
| GIPR | rs4803861 | 0.3016 | 0.3235 | 0.9359 | 0.01523 | 0.9084 | 0.9642 |
| GIPR | rs8111071 | 0.09803 | 0.08834 | 1.066 | 0.02406 | 1.017 | 1.118 |
| GIPR | rs918490 | 0.3002 | 0.3228 | 0.9334 | 0.01524 | 0.9059 | 0.9617 |
| ZHX3 | rs6072275 | 0.1584 | 0.1541 | 1.079 | 0.0193 | 1.039 | 1.121 |
| ZHX3 | rs6072343 | 0.1469 | 0.1415 | 1.097 | 0.01997 | 1.055 | 1.141 |
| ZHX3 | rs6093462 | 0.2969 | 0.3115 | 0.9301 | 0.01516 | 0.9029 | 0.9582 |
| TNRC6B | rs114607 | 0.3738 | 0.3803 | 0.9553 | 0.01445 | 0.9286 | 0.9827 |
| TNRC6B | rs137955 | 0.4466 | 0.4379 | 1.041 | 0.01413 | 1.013 | 1.071 |
| TNRC6B | rs137956 | 0.4545 | 0.4442 | 1.045 | 0.01412 | 1.016 | 1.074 |
| TNRC6B | rs137977 | 0.383 | 0.3852 | 0.9769 | 0.01443 | 0.9497 | 1.005 |
| TNRC6B | rs137981 | 0.1172 | 0.1193 | 0.9627 | 0.0217 | 0.9226 | 1.005 |
| TNRC6B | rs138027 | 0.2464 | 0.2498 | 0.9653 | 0.01625 | 0.935 | 0.9965 |
| TNRC6B | rs2958647 | 0.4529 | 0.4434 | 1.042 | 0.01412 | 1.014 | 1.071 |
| TNRC6B | rs713925 | 0.3734 | 0.3741 | 0.9722 | 0.0148 | 0.9444 | 1.001 |
| CDK6 | rs2282978 | 0.3299 | 0.3463 | 0.9252 | 0.01595 | 0.8967 | 0.9546 |
| CDK6 | rs4272 | 0.203 | 0.2149 | 0.9376 | 0.01859 | 0.9041 | 0.9724 |
| PRR5L | rs11033597 | 0.1408 | 0.1371 | 1.052 | 0.02179 | 1.008 | 1.098 |
| PRR5L | rs11600757 | 0.1609 | 0.156 | 1.069 | 0.02064 | 1.026 | 1.113 |
| PRR5L | rs11601211 | 0.07534 | 0.07393 | 1.056 | 0.02867 | 0.9985 | 1.117 |
| PRR5L | rs12281565 | 0.1636 | 0.1588 | 1.065 | 0.0205 | 1.023 | 1.108 |
| PRR5L | rs1365120 | NA | NA | NA | NA | NA | NA |
| PRR5L | rs1895840 | 0.1078 | 0.106 | 1.05 | 0.02442 | 1.001 | 1.101 |
| PRR5L | rs2303439 | 0.1648 | 0.1563 | 1.071 | 0.02079 | 1.028 | 1.115 |
| PRR5L | rs330260 | 0.1762 | 0.1711 | 1.04 | 0.01987 | 0.9998 | 1.081 |
| PRR5L | rs331485 | 0.1044 | 0.1088 | 0.9352 | 0.02452 | 0.8913 | 0.9812 |
| PRR5L | rs4077044 | 0.4255 | 0.4166 | 1.032 | 0.01527 | 1.001 | 1.063 |
| PRR5L | rs5030437 | 0.1644 | 0.1564 | 1.068 | 0.02047 | 1.026 | 1.112 |
| PRR5L | rs5030445 | 0.1642 | 0.1565 | 1.064 | 0.02048 | 1.022 | 1.108 |

TABLE 1-continued

| | | | | | | | |
|---|---|---|---|---|---|---|---|
| PRR5L | rs5030472 | 0.1172 | 0.1119 | 1.073 | 0.02363 | 1.025 | 1.124 |
| PRR5L | rs7929195 | 0.1151 | 0.1176 | 0.9472 | 0.02357 | 0.9044 | 0.992 |
| WNT2B | rs10745330 | 0.4918 | 0.4858 | 1.044 | 0.01185 | 1.02 | 1.068 |
| WNT2B | rs2999155 | 0.4886 | 0.4837 | 1.042 | 0.01185 | 1.019 | 1.067 |
| WNT2B | rs3790609 | 0.1816 | 0.1714 | 1.054 | 0.01562 | 1.023 | 1.087 |
| WNT2B | rs6682737 | 0.4882 | 0.4826 | 1.042 | 0.01185 | 1.018 | 1.067 |
| LRRC16A | rs10456320 | 0.1246 | 0.117 | 1.081 | 0.01823 | 1.043 | 1.121 |
| LRRC16A | rs11755567 | 0.1874 | 0.1875 | 0.9515 | 0.0152 | 0.9236 | 0.9803 |
| LRRC16A | rs13191296 | 0.06723 | 0.07411 | 0.9191 | 0.02308 | 0.8784 | 0.9616 |
| LRRC16A | rs2690110 | 0.3606 | 0.3506 | 1.058 | 0.01239 | 1.032 | 1.084 |
| LRRC16A | rs4712908 | 0.3591 | 0.3703 | 0.9622 | 0.01257 | 0.9387 | 0.9862 |
| LRRC16A | rs6921589 | 0.1181 | 0.1271 | 0.9289 | 0.01803 | 0.8966 | 0.9623 |
| LRRC16A | rs6937918 | 0.4176 | 0.406 | 1.031 | 0.01213 | 1.007 | 1.056 |
| LRRC16A | rs742132 | 0.3025 | 0.2961 | 1.035 | 0.0129 | 1.009 | 1.061 |
| LRRC16A | rs7752195 | 0.0614 | 0.06885 | 0.9 | 0.02404 | 0.8585 | 0.9434 |
| LRRC16A | rs7752524 | 0.09931 | 0.09399 | 1.099 | 0.02007 | 1.057 | 1.143 |
| LRRC16A | rs7762757 | 0.3822 | 0.3714 | 1.034 | 0.01225 | 1.009 | 1.059 |
| LRRC16A | rs880226 | 0.4177 | 0.4066 | 1.029 | 0.01214 | 1.005 | 1.054 |
| LRRC16A | rs9295661 | 0.06122 | 0.06873 | 0.9067 | 0.02405 | 0.865 | 0.9505 |
| LRRC16A | rs9358854 | 0.3352 | 0.3363 | 0.964 | 0.01258 | 0.9405 | 0.9881 |
| LRRC16A | rs9461157 | 0.4165 | 0.4052 | 1.031 | 0.01214 | 1.007 | 1.056 |
| LRRC16A | rs9461165 | 0.4169 | 0.4055 | 1.032 | 0.01213 | 1.008 | 1.057 |
| LRRC16A | rs9467445 | 0.2048 | 0.2063 | 0.9477 | 0.01469 | 0.9208 | 0.9754 |
| All Histone cluster1 gene | rs10484399 | 0.08249 | 0.08954 | 0.9297 | 0.02116 | 0.8919 | 0.969 |
| All Histone cluster1 gene | rs10484439 | 0.07707 | 0.08335 | 0.9336 | 0.02179 | 0.8945 | 0.9743 |
| All Histone cluster1 gene | rs12176317 | 0.1064 | 0.1129 | 0.9475 | 0.01931 | 0.9123 | 0.984 |
| All Histone cluster1 gene | rs13194053 | 0.1646 | 0.173 | 0.9407 | 0.01584 | 0.9119 | 0.9703 |
| All Histone cluster1 gene | rs13194491 | 0.07371 | 0.06948 | 1.075 | 0.02311 | 1.028 | 1.125 |
| All Histone cluster1 gene | rs13194781 | 0.0828 | 0.08981 | 0.93 | 0.02112 | 0.8923 | 0.9693 |
| All Histone cluster1 gene | rs13195040 | 0.08117 | 0.08842 | 0.9222 | 0.02162 | 0.8839 | 0.9621 |
| All Histone cluster1 gene | rs13199772 | 0.0828 | 0.0898 | 0.9298 | 0.02112 | 0.8921 | 0.9691 |
| All Histone cluster1 gene | rs13212651 | 0.08267 | 0.08977 | 0.9292 | 0.02113 | 0.8915 | 0.9684 |
| All Histone cluster1 gene | rs1321578 | 0.03625 | 0.04163 | 0.9317 | 0.03097 | 0.8768 | 0.99 |
| All Histone cluster1 gene | rs13217599 | 0.07214 | 0.06972 | 1.058 | 0.02321 | 1.011 | 1.107 |
| All Histone cluster1 gene | rs13218875 | 0.08106 | 0.08864 | 0.9279 | 0.02129 | 0.89 | 0.9675 |
| All Histone cluster1 gene | rs13219354 | 0.1074 | 0.1155 | 0.9404 | 0.01886 | 0.9063 | 0.9758 |
| All Histone cluster1 gene | rs16867901 | 0.008384 | 0.008575 | 0.8326 | 0.06461 | 0.7336 | 0.945 |
| All Histone cluster1 gene | rs16867911 | 0.008367 | 0.008525 | 0.8381 | 0.06472 | 0.7382 | 0.9514 |
| All Histone cluster1 gene | rs16891725 | 0.1081 | 0.1149 | 0.9483 | 0.01917 | 0.9133 | 0.9846 |
| All Histone cluster1 gene | rs175597 | 0.1011 | 0.1088 | 0.9258 | 0.01934 | 0.8914 | 0.9616 |
| All Histone cluster1 gene | rs17693963 | 0.08976 | 0.09625 | 0.9418 | 0.02044 | 0.9048 | 0.9802 |
| All Histone cluster1 gene | rs17739310 | 0.1507 | 0.1418 | 1.045 | 0.01685 | 1.011 | 1.08 |
| All Histone cluster1 gene | rs17750424 | 0.07922 | 0.08769 | 0.9051 | 0.02218 | 0.8666 | 0.9453 |
| All Histone cluster1 gene | rs1977 | 0.1065 | 0.1131 | 0.9468 | 0.0193 | 0.9116 | 0.9833 |
| All Histone cluster1 gene | rs1985732 | 0.2866 | 0.2918 | 0.9763 | 0.01307 | 0.9516 | 1.002 |
| All Histone cluster1 gene | rs200483 | 0.1014 | 0.1089 | 0.9273 | 0.01932 | 0.8929 | 0.9631 |
| All Histone cluster1 gene | rs200484 | 0.1013 | 0.1087 | 0.9274 | 0.01935 | 0.8929 | 0.9633 |
| All Histone cluster1 gene | rs200490 | 0.1014 | 0.109 | 0.9272 | 0.01931 | 0.8928 | 0.963 |
| All Histone cluster1 gene | rs200501 | 0.1021 | 0.1094 | 0.9303 | 0.01926 | 0.8958 | 0.9661 |
| All Histone cluster1 gene | rs200948 | 0.1011 | 0.1088 | 0.9251 | 0.01934 | 0.8907 | 0.9608 |
| All Histone cluster1 gene | rs200953 | 0.1015 | 0.1091 | 0.9253 | 0.01931 | 0.891 | 0.961 |

TABLE 1-continued

| | | | | | | | |
|---|---|---|---|---|---|---|---|
| All Histone cluster1 gene | rs200989 | 0.1012 | 0.1089 | 0.9257 | 0.01933 | 0.8913 | 0.9614 |
| All Histone cluster1 gene | rs200990 | 0.1015 | 0.1092 | 0.9246 | 0.0193 | 0.8902 | 0.9602 |
| All Histone cluster1 gene | rs200991 | 0.1474 | 0.1511 | 0.9629 | 0.01661 | 0.9321 | 0.9948 |
| All Histone cluster1 gene | rs200995 | 0.1013 | 0.1089 | 0.926 | 0.01932 | 0.8915 | 0.9617 |
| All Histone cluster1 gene | rs201002 | 0.1015 | 0.109 | 0.9275 | 0.0193 | 0.8931 | 0.9633 |
| All Histone cluster1 gene | rs201004 | 0.1773 | 0.1813 | 0.9683 | 0.01569 | 0.939 | 0.9986 |
| All Histone cluster1 gene | rs2064092 | 0.0821 | 0.07479 | 1.037 | 0.02204 | 0.9932 | 1.083 |
| All Histone cluster1 gene | rs2072806 | 0.1088 | 0.1148 | 0.9534 | 0.01912 | 0.9184 | 0.9898 |
| All Histone cluster1 gene | rs2073529 | 0.1066 | 0.113 | 0.9482 | 0.01928 | 0.913 | 0.9847 |
| All Histone cluster1 gene | rs2093169 | 0.1742 | 0.1786 | 0.9618 | 0.01557 | 0.9329 | 0.9916 |
| All Histone cluster1 gene | rs2393997 | 0.1124 | 0.1192 | 0.9672 | 0.01861 | 0.9326 | 1.003 |
| All Histone cluster1 gene | rs2494711 | 0.3864 | 0.383 | 1.028 | 0.01217 | 1.004 | 1.053 |
| All Histone cluster1 gene | rs2747054 | 0.1014 | 0.1091 | 0.9256 | 0.01931 | 0.8913 | 0.9613 |
| All Histone cluster1 gene | rs2893910 | 0.1688 | 0.1672 | 0.9605 | 0.01585 | 0.9311 | 0.9908 |
| All Histone cluster1 gene | rs34706883 | 0.08273 | 0.08976 | 0.9301 | 0.02112 | 0.8924 | 0.9694 |
| All Histone cluster1 gene | rs370155 | 0.1017 | 0.1092 | 0.927 | 0.01929 | 0.8926 | 0.9627 |
| All Histone cluster1 gene | rs3799378 | 0.2164 | 0.225 | 0.9583 | 0.01517 | 0.9302 | 0.9872 |
| All Histone cluster1 gene | rs3799380 | 0.1884 | 0.1907 | 0.961 | 0.01512 | 0.933 | 0.9899 |
| All Histone cluster1 gene | rs3799383 | 0.1152 | 0.1206 | 0.9571 | 0.01841 | 0.9232 | 0.9923 |
| All Histone cluster1 gene | rs3800307 | 0.1926 | 0.1998 | 0.9485 | 0.01492 | 0.9212 | 0.9767 |
| All Histone cluster1 gene | rs3800316 | 0.266 | 0.2635 | 0.9587 | 0.01346 | 0.9337 | 0.9843 |
| All Histone cluster1 gene | rs4452638 | 0.1072 | 0.115 | 0.9426 | 0.01886 | 0.9084 | 0.9781 |
| All Histone cluster1 gene | rs4634439 | 0.1051 | 0.1122 | 0.95 | 0.01907 | 0.9152 | 0.9862 |
| All Histone cluster1 gene | rs4712981 | 0.2765 | 0.2812 | 0.9741 | 0.01319 | 0.9492 | 0.9996 |
| All Histone cluster1 gene | rs4713119 | 0.114 | 0.1209 | 0.9676 | 0.01852 | 0.9331 | 1.003 |
| All Histone cluster1 gene | rs6456728 | 0.1883 | 0.1906 | 0.9611 | 0.01512 | 0.9331 | 0.99 |
| All Histone cluster1 gene | rs6904071 | 0.1645 | 0.1727 | 0.942 | 0.01584 | 0.9132 | 0.9717 |
| All Histone cluster1 gene | rs6904596 | 0.09093 | 0.09787 | 0.9214 | 0.02027 | 0.8855 | 0.9587 |
| All Histone cluster1 gene | rs6913660 | 0.1644 | 0.1727 | 0.9419 | 0.01585 | 0.9131 | 0.9716 |
| All Histone cluster1 gene | rs6915101 | 0.0154 | 0.01453 | 0.9074 | 0.04865 | 0.8249 | 0.9982 |
| All Histone cluster1 gene | rs6920256 | 0.1115 | 0.1181 | 0.9493 | 0.01894 | 0.9147 | 0.9852 |
| All Histone cluster1 gene | rs6923139 | 0.09521 | 0.0993 | 0.9267 | 0.01995 | 0.8912 | 0.9637 |
| All Histone cluster1 gene | rs6932590 | 0.2445 | 0.247 | 0.9455 | 0.014 | 0.9199 | 0.9718 |
| All Histone cluster1 gene | rs6933583 | 0.2779 | 0.2825 | 0.9737 | 0.01317 | 0.9489 | 0.9991 |
| All Histone cluster1 gene | rs6934794 | 0.2054 | 0.1997 | 1.032 | 0.01481 | 1.003 | 1.063 |
| All Histone cluster1 gene | rs6938200 | 0.1935 | 0.2009 | 0.9456 | 0.01514 | 0.918 | 0.9741 |
| All Histone cluster1 gene | rs721600 | 0.244 | 0.2357 | 1.052 | 0.01385 | 1.024 | 1.081 |
| All Histone cluster1 gene | rs7745603 | 0.2233 | 0.2288 | 0.9591 | 0.01419 | 0.9328 | 0.9861 |
| All Histone cluster1 gene | rs7746199 | 0.1738 | 0.1696 | 0.9686 | 0.01667 | 0.9374 | 1.001 |
| All Histone cluster1 gene | rs7749305 | 0.09055 | 0.0974 | 0.9244 | 0.02025 | 0.8885 | 0.9619 |

TABLE 1-continued

| | | | | | | | |
|---|---|---|---|---|---|---|---|
| All Histone cluster1 gene | rs7749319 | 0.03685 | 0.04178 | 0.9446 | 0.0308 | 0.8893 | 1.003 |
| All Histone cluster1 gene | rs7756567 | 0.1742 | 0.1785 | 0.9624 | 0.01557 | 0.9335 | 0.9923 |
| All Histone cluster1 gene | rs7773938 | 0.1742 | 0.1786 | 0.9626 | 0.01556 | 0.9336 | 0.9924 |
| All Histone cluster1 gene | rs911186 | 0.2158 | 0.2223 | 0.9343 | 0.01453 | 0.9081 | 0.9613 |
| All Histone cluster1 gene | rs9295739 | 0.008401 | 0.008577 | 0.8339 | 0.06458 | 0.7348 | 0.9464 |
| All Histone cluster1 gene | rs9295749 | 0.06175 | 0.05791 | 1.04 | 0.02499 | 0.9901 | 1.092 |
| All Histone cluster1 gene | rs9358944 | 0.1741 | 0.1786 | 0.9621 | 0.01557 | 0.9332 | 0.9919 |
| All Histone cluster1 gene | rs9358945 | 0.1742 | 0.1786 | 0.9622 | 0.01556 | 0.9333 | 0.992 |
| All Histone cluster1 gene | rs9358946 | 0.1741 | 0.1785 | 0.9615 | 0.01557 | 0.9326 | 0.9913 |
| All Histone cluster1 gene | rs9366653 | 0.1075 | 0.1136 | 0.951 | 0.01922 | 0.9158 | 0.9875 |
| All Histone cluster1 gene | rs9366658 | 0.174 | 0.1784 | 0.9621 | 0.01557 | 0.9332 | 0.9919 |
| All Histone cluster1 gene | rs9379844 | 0.3814 | 0.3795 | 1.018 | 0.01224 | 0.9941 | 1.043 |
| All Histone cluster1 gene | rs9379851 | 0.1076 | 0.1138 | 0.9507 | 0.01919 | 0.9156 | 0.9871 |
| All Histone cluster1 gene | rs9379856 | 0.1062 | 0.1128 | 0.9443 | 0.01944 | 0.909 | 0.981 |
| All Histone cluster1 gene | rs9379858 | 0.1075 | 0.1136 | 0.9507 | 0.01923 | 0.9156 | 0.9872 |
| All Histone cluster1 gene | rs9379859 | 0.1074 | 0.1136 | 0.9504 | 0.01923 | 0.9152 | 0.9869 |
| All Histone cluster1 gene | rs9379870 | 0.2769 | 0.2818 | 0.9731 | 0.01319 | 0.9482 | 0.9986 |
| All Histone cluster1 gene | rs9379897 | 0.1051 | 0.1122 | 0.9498 | 0.01907 | 0.915 | 0.986 |
| All Histone cluster1 gene | rs9393691 | 0.3813 | 0.3793 | 1.019 | 0.01224 | 0.9947 | 1.044 |
| All Histone cluster1 gene | rs9393705 | 0.1075 | 0.1136 | 0.9513 | 0.01922 | 0.9161 | 0.9878 |
| All Histone cluster1 gene | rs9393708 | 0.1075 | 0.1136 | 0.9504 | 0.01923 | 0.9153 | 0.9869 |
| All Histone cluster1 gene | rs9393713 | 0.1065 | 0.1129 | 0.9481 | 0.0193 | 0.9129 | 0.9846 |
| All Histone cluster1 gene | rs9393714 | 0.1059 | 0.1129 | 0.9414 | 0.01932 | 0.9065 | 0.9778 |
| All Histone cluster1 gene | rs9393777 | 0.1291 | 0.1356 | 0.9526 | 0.01746 | 0.9206 | 0.9858 |
| All Histone cluster1 gene | rs9461362 | 0.1656 | 0.1562 | 1.044 | 0.01613 | 1.012 | 1.078 |
| All Histone cluster1 gene | rs9467704 | 0.0935 | 0.09761 | 0.9307 | 0.02007 | 0.8948 | 0.9681 |
| All Histone cluster1 gene | rs9468152 | 0.141 | 0.1351 | 1.054 | 0.01725 | 1.019 | 1.091 |
| All Histone cluster1 gene | rs9468159 | 0.07473 | 0.06852 | 1.036 | 0.02295 | 0.9901 | 1.083 |
| All Histone cluster1 gene | rs9468202 | 0.008533 | 0.008812 | 0.8182 | 0.06399 | 0.7218 | 0.9275 |
| All Histone cluster1 gene | rs9468227 | 0.01521 | 0.01454 | 0.8951 | 0.0488 | 0.8135 | 0.985 |
| GTF2IRD2B | imm_7_74094413 | NA | NA | NA | NA | NA | NA |
| GTF2IRD2B | imm_7_74108242 | 0.4115 | 0.4149 | 0.9669 | 0.01207 | 0.9443 | 0.9901 |
| GTF2IRD2B | imm_7_74117236 | NA | NA | NA | NA | NA | NA |
| GTF2IRD2B | imm_7_74118166 | 0.4481 | 0.4464 | 0.9725 | 0.01197 | 0.95 | 0.9956 |
| GTF2IRD2B | imm_7_74120730 | 0.1095 | 0.1148 | 0.9425 | 0.01881 | 0.9084 | 0.9779 |
| GTF2IRD2B | imm_7_74133859 | 0.1855 | 0.1917 | 0.9638 | 0.01538 | 0.9352 | 0.9933 |
| GTF2IRD2B | imm_7_74145400 | 0.2109 | 0.2169 | 0.9643 | 0.01458 | 0.9371 | 0.9922 |
| ETS1 | imm_11_127760024 | 0.09922 | 0.08999 | 1.042 | 0.02024 | 1.001 | 1.084 |
| ETS1 | imm_11_127761269 | 0.09956 | 0.08984 | 1.046 | 0.02016 | 1.006 | 1.088 |
| ETS1 | imm_11_127765567 | 0.1472 | 0.1416 | 1.049 | 0.01691 | 1.014 | 1.084 |
| ETS1 | imm_11_127767721 | 0.02355 | 0.02322 | 0.9396 | 0.03937 | 0.8698 | 1.015 |
| ETS1 | imm_11_127770666 | 0.2646 | 0.254 | 1.034 | 0.01352 | 1.007 | 1.062 |
| ETS1 | imm_11_127770668 | 0.2647 | 0.2543 | 1.033 | 0.01351 | 1.006 | 1.061 |
| ETS1 | imm_11_127774308 | 0.1495 | 0.1444 | 1.046 | 0.01681 | 1.012 | 1.081 |
| ETS1 | imm_11_127775128 | 0.1493 | 0.1446 | 1.044 | 0.01682 | 1.01 | 1.079 |
| ETS1 | imm_11_127776527 | 0.02585 | 0.0254 | 0.9365 | 0.03746 | 0.8702 | 1.008 |
| ETS1 | imm_11_127776913 | 0.02484 | 0.02456 | 0.935 | 0.03816 | 0.8676 | 1.008 |
| ETS1 | imm_11_127777217 | 0.4539 | 0.467 | 0.9649 | 0.01193 | 0.9426 | 0.9877 |
| ETS1 | imm_11_127778327 | 0.2567 | 0.2557 | 1.028 | 0.01368 | 1 | 1.056 |
| ETS1 | imm_11_127778329 | 0.2599 | 0.2578 | 1.032 | 0.01352 | 1.005 | 1.06 |

TABLE 1-continued

| | | | | | | | |
|---|---|---|---|---|---|---|---|
| ETS1 | imm_11_127779030 | 0.0399 | 0.04089 | 0.9337 | 0.0301 | 0.8802 | 0.9905 |
| ETS1 | imm_11_127780425 | 0.03316 | 0.02847 | 1.065 | 0.03436 | 0.9961 | 1.14 |
| ETS1 | imm_11_127780902 | 0.04105 | 0.0418 | 0.9342 | 0.02972 | 0.8814 | 0.9903 |
| ETS1 | imm_11_127781839 | 0.2721 | 0.2603 | 1.034 | 0.01347 | 1.007 | 1.062 |
| ETS1 | imm_11_127785739 | 0.1949 | 0.1969 | 0.9695 | 0.01494 | 0.9415 | 0.9983 |
| ETS1 | imm_11_127785963 | 0.1598 | 0.1524 | 1.052 | 0.01641 | 1.019 | 1.087 |
| ETS1 | imm_11_127786010 | 0.1928 | 0.1842 | 1.036 | 0.01521 | 1.006 | 1.068 |
| ETS1 | imm_11_127786836 | 0.193 | 0.1845 | 1.035 | 0.0152 | 1.005 | 1.067 |
| ETS1 | imm_11_127787128 | 0.1926 | 0.1839 | 1.038 | 0.01546 | 1.007 | 1.069 |
| ETS1 | imm_11_127788828 | 0.2023 | 0.2042 | 0.9714 | 0.01475 | 0.9438 | 0.9999 |
| ETS1 | imm_11_127789306 | 0.1917 | 0.1836 | 1.034 | 0.01524 | 1.003 | 1.065 |
| ETS1 | imm_11_127789441 | 0.1917 | 0.1835 | 1.034 | 0.01524 | 1.003 | 1.065 |
| ETS1 | imm_11_127791651 | 0.1617 | 0.1537 | 1.051 | 0.01634 | 1.018 | 1.086 |
| ETS1 | imm_11_127792287 | 0.1928 | 0.1845 | 1.034 | 0.0152 | 1.004 | 1.065 |
| ETS1 | imm_11_127792800 | 0.04818 | 0.04146 | 1.069 | 0.02876 | 1.01 | 1.131 |
| ETS1 | imm_11_127793060 | 0.1932 | 0.1851 | 1.032 | 0.01519 | 1.002 | 1.063 |
| ETS1 | imm_11_127794685 | 0.1622 | 0.1544 | 1.048 | 0.01631 | 1.015 | 1.082 |
| ETS1 | imm_11_127795453 | 0.1932 | 0.1851 | 1.032 | 0.01518 | 1.002 | 1.063 |
| ETS1 | imm_11_127796816 | 4.97E−05 | 0.0001685 | 0.1892 | 0.6633 | 0.05156 | 0.6941 |
| ETS1 | imm_11_127797523 | 0.193 | 0.1849 | 1.032 | 0.01519 | 1.002 | 1.063 |
| ETS1 | imm_11_127798230 | 0.29 | 0.2885 | 0.9769 | 0.0131 | 0.9521 | 1.002 |
| ETS1 | imm_11_127799892 | 0.4819 | 0.4679 | 1.03 | 0.01188 | 1.007 | 1.055 |
| ETS1 | imm_11_127804916 | 0.1266 | 0.127 | 0.9676 | 0.01783 | 0.9344 | 1.002 |
| ETS1 | imm_11_127805367 | 0.02671 | 0.02685 | 0.9274 | 0.03669 | 0.863 | 0.9965 |
| ETS1 | imm_11_127806163 | 0.3819 | 0.3803 | 1.028 | 0.01227 | 1.003 | 1.053 |
| ETS1 | imm_11_127806304 | 0.0259 | 0.02615 | 0.926 | 0.03726 | 0.8608 | 0.9961 |
| ETS1 | imm_11_127807384 | 0.1779 | 0.1697 | 1.035 | 0.01568 | 1.003 | 1.067 |
| ETS1 | imm_11_127808758 | 0.02694 | 0.02699 | 0.9302 | 0.03659 | 0.8659 | 0.9994 |
| ETS1 | imm_11_127809308 | 0.00681 | 0.007868 | 0.8251 | 0.06948 | 0.72 | 0.9454 |
| ETS1 | imm_11_127812329 | 0.05509 | 0.0491 | 1.056 | 0.02675 | 1.002 | 1.113 |
| ETS1 | imm_11_127812420 | 0.0003485 | 0.0001181 | 2.813 | 0.4443 | 1.178 | 6.721 |
| ETS1 | imm_11_127813024 | 0.3817 | 0.3801 | 1.028 | 0.01226 | 1.003 | 1.053 |
| ETS1 | imm_11_127819226 | 0.1782 | 0.17 | 1.034 | 0.01567 | 1.003 | 1.066 |
| ETS1 | imm_11_127822686 | 0.02694 | 0.02711 | 0.9267 | 0.0365 | 0.8627 | 0.9954 |
| ETS1 | imm_11_127823420 | 0.00681 | 0.007868 | 0.8251 | 0.06948 | 0.7201 | 0.9455 |
| ETS1 | imm_11_127824356 | 0.1728 | 0.1635 | 1.038 | 0.0159 | 1.006 | 1.07 |
| ETS1 | imm_11_127825016 | 0.02693 | 0.02704 | 0.928 | 0.03657 | 0.8638 | 0.9969 |
| ETS1 | imm_11_127825282 | 0.3867 | 0.3861 | 1.027 | 0.01223 | 1.003 | 1.052 |
| ETS1 | imm_11_127825669 | 0.3867 | 0.3861 | 1.027 | 0.01223 | 1.002 | 1.052 |
| ETS1 | imm_11_127826087 | 0.3308 | 0.3444 | 0.96 | 0.01259 | 0.9366 | 0.984 |
| ETS1 | imm_11_127826464 | 0.1616 | 0.1525 | 1.036 | 0.01634 | 1.004 | 1.07 |
| ETS1 | imm_11_127827422 | 0.1625 | 0.1534 | 1.036 | 0.01631 | 1.003 | 1.069 |
| ETS1 | imm_11_127828334 | 0.02583 | 0.02575 | 0.9352 | 0.03729 | 0.8693 | 1.006 |
| ETS1 | imm_11_127831280 | 0.02528 | 0.02935 | 0.918 | 0.03643 | 0.8548 | 0.986 |
| ETS1 | imm_11_127831611 | 0.1634 | 0.1544 | 1.032 | 0.01627 | 1 | 1.066 |
| ETS1 | imm_11_127831673 | 0.2897 | 0.3008 | 0.9715 | 0.01305 | 0.947 | 0.9967 |
| ETS1 | imm_11_127834123 | 0.3021 | 0.3039 | 1.032 | 0.01301 | 1.006 | 1.059 |
| ETS1 | imm_11_127834484 | 0.02454 | 0.027 | 0.9195 | 0.03741 | 0.8545 | 0.9894 |
| ETS1 | imm_11_127837472 | 0.01796 | 0.01939 | 0.9051 | 0.0438 | 0.8307 | 0.9863 |
| ETS1 | imm_11_127838265 | 0.08005 | 0.08871 | 0.948 | 0.02134 | 0.9092 | 0.9885 |
| ETS1 | imm_11_127838713 | 0.4807 | 0.4766 | 1.033 | 0.0119 | 1.009 | 1.057 |
| ETS1 | imm_11_127839719 | 0.01287 | 0.01496 | 0.9178 | 0.05089 | 0.8307 | 1.014 |
| ETS1 | imm_11_127840459 | 0.171 | 0.1594 | 1.074 | 0.01598 | 1.04 | 1.108 |
| ETS1 | imm_11_127840867 | 0.1083 | 0.1173 | 0.9393 | 0.01868 | 0.9056 | 0.9744 |
| ETS1 | imm_11_127841724 | 0.09519 | 0.09676 | 0.9589 | 0.02015 | 0.9217 | 0.9975 |
| ETS1 | imm_11_127841864 | 0.4192 | 0.4279 | 0.9746 | 0.01201 | 0.9519 | 0.9978 |
| ETS1 | imm_11_127843207 | 0.09459 | 0.09635 | 0.9572 | 0.0202 | 0.92 | 0.9958 |
| ETS1 | imm_11_127843341 | 0.09506 | 0.09672 | 0.958 | 0.02017 | 0.9209 | 0.9966 |
| ETS1 | imm_11_127844385 | 0.1721 | 0.1603 | 1.072 | 0.01597 | 1.039 | 1.106 |
| ETS1 | imm_11_127844729 | 0.026 | 0.02423 | 1.082 | 0.03808 | 1.004 | 1.166 |
| ETS1 | imm_11_127845557 | 0.09794 | 0.0995 | 0.956 | 0.01992 | 0.9194 | 0.9941 |
| ETS1 | imm_11_127846698 | 0.172 | 0.1606 | 1.07 | 0.01591 | 1.037 | 1.104 |
| ETS1 | imm_11_127848167 | 0.1719 | 0.1604 | 1.07 | 0.01593 | 1.037 | 1.104 |
| ETS1 | imm_11_127848372 | 0.1708 | 0.1593 | 1.071 | 0.01597 | 1.038 | 1.105 |
| ETS1 | imm_11_127849992 | 0.1718 | 0.1603 | 1.07 | 0.01593 | 1.037 | 1.104 |
| ETS1 | imm_11_127851599 | 0.1724 | 0.1605 | 1.073 | 0.0159 | 1.04 | 1.107 |
| ETS1 | imm_11_127852250 | 0.09357 | 0.09526 | 0.9588 | 0.02029 | 0.9214 | 0.9977 |
| ETS1 | imm_11_127853705 | 0.09349 | 0.0952 | 0.9589 | 0.0203 | 0.9215 | 0.9978 |
| ETS1 | imm_11_127855281 | 0.1721 | 0.1605 | 1.07 | 0.01592 | 1.038 | 1.104 |
| ETS1 | imm_11_127855956 | 0.09482 | 0.09605 | 0.9622 | 0.02019 | 0.9249 | 1.001 |
| ETS1 | imm_11_127857027 | 0.09246 | 0.09451 | 0.9556 | 0.02039 | 0.9181 | 0.9945 |
| ETS1 | imm_11_127861069 | 0.2667 | 0.2531 | 1.04 | 0.01357 | 1.013 | 1.068 |
| ETS1 | imm_11_127863304 | 0.2666 | 0.2528 | 1.041 | 0.01358 | 1.014 | 1.069 |
| ETS1 | imm_11_127863391 | 0.2668 | 0.2531 | 1.041 | 0.01358 | 1.013 | 1.069 |
| ETS1 | imm_11_127866379 | 0.247 | 0.2357 | 1.031 | 0.01392 | 1.003 | 1.06 |
| ETS1 | imm_11_127868447 | 0.001438 | 0.0007947 | 1.274 | 0.1839 | 0.8881 | 1.826 |
| ETS1 | imm_11_127868927 | 0.1886 | 0.1862 | 0.9713 | 0.01518 | 0.9428 | 1.001 |
| ETS1 | imm_11_127869177 | 0.2692 | 0.2553 | 1.046 | 0.01355 | 1.018 | 1.074 |
| ETS1 | imm_11_127870403 | 0.2604 | 0.2475 | 1.048 | 0.01366 | 1.02 | 1.076 |
| ETS1 | imm_11_127870895 | 0.2704 | 0.256 | 1.048 | 0.01351 | 1.02 | 1.076 |

TABLE 1-continued

| | | | | | | | |
|---|---|---|---|---|---|---|---|
| ETS1 | imm_11_127871431 | 0.2704 | 0.2561 | 1.047 | 0.01351 | 1.02 | 1.075 |
| ETS1 | imm_11_127872972 | 0.1881 | 0.1857 | 0.9711 | 0.0152 | 0.9426 | 1 |
| ETS1 | imm_11_127874486 | 0.2705 | 0.2561 | 1.047 | 0.0135 | 1.02 | 1.075 |
| ETS1 | imm_11_127874807 | 0.2679 | 0.2544 | 1.046 | 0.01353 | 1.019 | 1.075 |
| ETS1 | imm_11_127877378 | 0.2696 | 0.2553 | 1.048 | 0.01353 | 1.021 | 1.076 |
| ETS1 | imm_11_127879923 | 0.187 | 0.1854 | 0.9699 | 0.01521 | 0.9414 | 0.9993 |
| ETS1 | imm_11_127881686 | 0.1838 | 0.1678 | 1.083 | 0.01554 | 1.05 | 1.116 |
| ETS1 | imm_11_127882690 | 0.3868 | 0.3761 | 1.03 | 0.01225 | 1.006 | 1.055 |
| ETS1 | imm_11_127884689 | 0.06242 | 0.06577 | 0.9481 | 0.02426 | 0.9041 | 0.9943 |
| ETS1 | imm_11_127885952 | 0.3619 | 0.3492 | 1.053 | 0.01239 | 1.028 | 1.079 |
| ETS1 | imm_11_127886184 | 0.2407 | 0.2278 | 1.076 | 0.01398 | 1.047 | 1.106 |
| ETS1 | imm_11_127887077 | 0.3616 | 0.3489 | 1.053 | 0.0124 | 1.028 | 1.079 |
| ETS1 | imm_11_127889134 | 0.24 | 0.2272 | 1.074 | 0.01401 | 1.045 | 1.104 |
| ETS1 | imm_11_127891116 | 0.2401 | 0.2276 | 1.073 | 0.01401 | 1.044 | 1.103 |
| ETS1 | imm_11_127892632 | 0.3616 | 0.3489 | 1.053 | 0.0124 | 1.028 | 1.079 |
| ETS1 | imm_11_127894601 | 0.2237 | 0.2193 | 0.9786 | 0.01426 | 0.9516 | 1.006 |
| ETS1 | imm_11_127894638 | 0.003712 | 0.004179 | 0.7901 | 0.09484 | 0.6561 | 0.9515 |
| ETS1 | imm_11_127895279 | 0.2405 | 0.2275 | 1.076 | 0.014 | 1.047 | 1.106 |
| ETS1 | imm_11_127897147 | 0.233 | 0.2215 | 1.075 | 0.01414 | 1.046 | 1.106 |
| ETS1 | imm_11_127898835 | 0.01773 | 0.02054 | 0.8992 | 0.04333 | 0.826 | 0.9789 |
| ETS1 | imm_11_127901157 | 0.3033 | 0.2932 | 1.048 | 0.01299 | 1.022 | 1.075 |
| ETS1 | imm_11_127901948 | 0.2366 | 0.2253 | 1.071 | 0.01406 | 1.041 | 1.1 |
| ETS1 | imm_11_127905841 | 0.04931 | 0.05841 | 0.9326 | 0.02651 | 0.8854 | 0.9823 |
| ETS1 | imm_11_127906568 | 0.3857 | 0.3706 | 1.047 | 0.01222 | 1.022 | 1.073 |
| ETS1 | imm_11_127908214 | 0.3861 | 0.3708 | 1.048 | 0.01221 | 1.023 | 1.074 |
| ETS1 | imm_11_127911648 | 0.504 | 0.488 | 0.958773 | 0.01206 | 1.018 | 1.068 |
| ETS1 | imm_11_127911985 | 0.4904 | 0.4756 | 1.044 | 0.01187 | 1.02 | 1.068 |
| ETS1 | imm_11_127914294 | 0.4917 | 0.4766 | 1.044 | 0.01187 | 1.02 | 1.068 |
| ETS1 | imm_11_127915474 | 0.5043 | 0.4882 | 0.958773 | 0.01187 | 1.019 | 1.068 |
| ETS1 | imm_11_127915554 | 0.5053 | 0.4884 | 0.95511 | 0.01189 | 1.023 | 1.072 |
| ETS1 | imm_11_127916046 | 0.4916 | 0.4769 | 1.042 | 0.01186 | 1.018 | 1.067 |
| ETS1 | imm_11_127929821 | 0.0003317 | 0.0005059 | 0.5073 | 0.2845 | 0.2905 | 0.8861 |
| ETS1 | imm_11_127931099 | 0.0002154 | 0.0003706 | 0.4221 | 0.355 | 0.2105 | 0.8465 |
| ETS1 | imm_11_127940676 | 0.04603 | 0.05305 | 0.9457 | 0.02759 | 0.896 | 0.9983 |
| ETS1 | imm_11_127943244 | 0.0001657 | 0.0002359 | 0.4952 | 0.42 | 0.2174 | 1.128 |
| ETS1 | imm_11_127945727 | NA | NA | NA | NA | NA | NA |
| ETS1 | imm_11_127945953 | 0.07363 | 0.07921 | 0.9453 | 0.02227 | 0.905 | 0.9875 |
| ETS1 | imm_11_127948912 | 0.0179 | 0.0213 | 0.875 | 0.04286 | 0.8045 | 0.9517 |
| ETS1 | imm_11_127956842 | 0.2625 | 0.2581 | 1.037 | 0.01351 | 1.009 | 1.064 |
| ETS1 | imm_11_127957543 | 0.01694 | 0.0148 | 1.114 | 0.04754 | 1.015 | 1.223 |
| ETS1 | imm_11_127957904 | 0.01243 | 0.01016 | 1.184 | 0.05624 | 1.061 | 1.322 |
| ETS1 | imm_11_127974263 | 0.07319 | 0.07868 | 0.947 | 0.02235 | 0.9064 | 0.9894 |
| ETS1 | imm_11_127979301 | 0.1778 | 0.1862 | 0.9641 | 0.01539 | 0.9354 | 0.9936 |
| ETS1 | imm_11_127979905 | 0.01105 | 0.01341 | 0.8977 | 0.05428 | 0.8071 | 0.9985 |
| ETS1 | imm_11_127981559 | 0.1743 | 0.1821 | 0.9688 | 0.01551 | 0.9398 | 0.9987 |
| ETS1 | imm_11_127982379 | 0.1742 | 0.1821 | 0.9687 | 0.01552 | 0.9396 | 0.9986 |
| ETS1 | imm_11_127982748 | 0.1743 | 0.1828 | 0.9648 | 0.0155 | 0.9359 | 0.9946 |
| ETS1 | imm_11_127983590 | 0.173 | 0.1813 | 0.9676 | 0.01555 | 0.9385 | 0.9975 |
| ETS1 | imm_11_127983743 | 0.1742 | 0.1821 | 0.9687 | 0.01552 | 0.9397 | 0.9987 |
| ETS1 | imm_11_127984265 | 0.1741 | 0.1821 | 0.9677 | 0.01552 | 0.9387 | 0.9975 |
| ETS1 | imm_11_127984721 | 0.1797 | 0.1878 | 0.9668 | 0.01533 | 0.9382 | 0.9963 |
| ETS1 | rs7935286 | 0.168 | 0.1606 | 1.045 | 0.01603 | 1.012 | 1.078 |
| SLC5A1 | rs738203 | 0.2253 | 0.2201 | 1.028 | 0.01427 | 0.9996 | 1.057 |
| SLC5A1 | rs9609429 | 0.2575 | 0.2651 | 0.9735 | 0.01351 | 0.948 | 0.9996 |
| TET2 | rs10010325 | 0.4771 | 0.4978 | 0.934 | 0.01188 | 0.9125 | 0.956 |
| TET2 | rs17035310 | 0.1357 | 0.1276 | 1.057 | 0.01753 | 1.021 | 1.093 |
| TET2 | rs2189234 | 0.3781 | 0.3659 | 1.045 | 0.01231 | 1.02 | 1.071 |
| TET2 | rs7661349 | 0.3552 | 0.3446 | 1.047 | 0.01251 | 1.022 | 1.073 |
| TET2 | rs974801 | 0.3639 | 0.3836 | 0.9356 | 0.01226 | 0.9134 | 0.9584 |

(Continued, part 4)

| gene.i | SNP | STAT_iibdgc | P_iibdgc | beta_meta_fixed | se_meta_fixed | P_meta_fixed |
|---|---|---|---|---|---|---|
| SLC26A4 | rs10247487 | −3.044 | 0.002336 | −0.058534716 | 0.015027789 | 9.82E−05 |
| SLC26A4 | rs10263826 | −3.525 | 0.0004233 | −0.063296566 | 0.014717569 | 1.70E−05 |
| SLC26A4 | rs10273733 | 4.232 | 2.32E−05 | 0.062729759 | 0.014911083 | 2.59E−05 |
| SLC26A4 | rs12539555 | 1.753 | 0.07962 | 0.033957032 | 0.015028243 | 0.023849341 |
| SLC26A4 | rs2248465 | 3.499 | 0.0004666 | 0.058825282 | 0.014674647 | 6.11E−05 |
| SLC26A4 | rs2808 | 4.39 | 1.13E−05 | 0.072100199 | 0.014452056 | 6.07E−07 |
| DLG4 | rs3785794 | −3.279 | 0.001041 | −0.108558148 | 0.024982227 | 1.39E−05 |
| GIPR | chr19:50983512 | −3.978 | 6.96E−05 | −0.06312005 | 0.014860986 | 2.16E−05 |
| GIPR | chr19:51014231 | −4.412 | 1.02E−05 | −0.067529657 | 0.01531 | 1.03E−05 |
| GIPR | chr19:51026971 | −4.454 | 8.45E−06 | −0.070871869 | 0.014254528 | 6.63E−07 |
| GIPR | rs10401439 | −4.746 | 2.08E−06 | −0.074292605 | 0.01566 | 2.09E−06 |
| GIPR | rs10402263 | −3.859 | 0.000114 | −0.060155652 | 0.013934687 | 1.58E−05 |
| GIPR | rs10421891 | −4.286 | 1.82E−05 | −0.065331129 | 0.013703526 | 1.87E−06 |
| GIPR | rs10500292 | −4.313 | 1.61E−05 | −0.063324672 | 0.013508683 | 2.76E−06 |
| GIPR | rs11883351 | −4.223 | 2.41E−05 | −0.06640775 | 0.013965247 | 1.98E−06 |
| GIPR | rs12463359 | −4.026 | 5.67E−05 | −0.061150814 | 0.013547181 | 6.36E−06 |

TABLE 1-continued

| | | | | | | |
|---|---|---|---|---|---|---|
| GIPR | rs16980013 | −3.951 | 7.78E−05 | −0.06459853 | 0.014494808 | 8.32E−06 |
| GIPR | rs16980051 | −4.217 | 2.47E−05 | −0.061384259 | 0.013158489 | 3.09E−06 |
| GIPR | rs17878252 | −3.982 | 6.83E−05 | −0.064733932 | 0.01476836 | 1.17E−05 |
| GIPR | rs2070736 | −4.036 | 5.43E−05 | −0.066027936 | 0.014452018 | 4.91E−06 |
| GIPR | rs2334255 | 2.756 | 0.005854 | 0.050203976 | 0.014994188 | 0.000813298 |
| GIPR | rs4514788 | −3.846 | 0.0001199 | −0.059073081 | 0.014960132 | 7.86E−05 |
| GIPR | rs4802273 | −4.078 | 4.55E−05 | −0.066351462 | 0.014622704 | 5.69E−06 |
| GIPR | rs4802274 | −4.147 | 3.37E−05 | −0.067054341 | 0.014442081 | 3.43E−06 |
| GIPR | rs4803861 | −4.351 | 1.36E−05 | −0.06912685 | 0.014264465 | 1.26E−06 |
| GIPR | rs8111071 | 2.662 | 0.00776 | 0.073099463 | 0.022329376 | 0.001061529 |
| GIPR | rs918490 | −4.521 | 6.14E−06 | −0.071265294 | 0.014270954 | 5.92E−07 |
| ZHX3 | rs6072275 | 3.936 | 8.28E−05 | 0.083189003 | 0.018062159 | 4.11E−06 |
| ZHX3 | rs6072343 | 4.657 | 3.20E−06 | 0.095938396 | 0.018727722 | 3.01E−07 |
| ZHX3 | rs6093462 | −4.779 | 1.76E−06 | −0.072463172 | 0.01516 | 1.75E−06 |
| TNRC6B | rs114607 | −3.167 | 0.001542 | −0.045307725 | 0.014425671 | 0.001685039 |
| TNRC6B | rs137955 | 2.873 | 0.00406 | 0.048254792 | 0.013211434 | 0.000259697 |
| TNRC6B | rs137956 | 3.097 | 0.001955 | 0.052189562 | 0.013200134 | 7.69E−05 |
| TNRC6B | rs137977 | −1.618 | 0.1056 | −0.03176774 | 0.013498551 | 0.018601682 |
| TNRC6B | rs137981 | −1.753 | 0.07963 | −0.0537168 | 0.020383686 | 0.008406691 |
| TNRC6B | rs138027 | −2.173 | 0.02978 | −0.048197853 | 0.015199003 | 0.001518527 |
| TNRC6B | rs2958647 | 2.914 | 0.003573 | 0.049575793 | 0.01319879 | 0.000172591 |
| TNRC6B | rs713925 | −1.906 | 0.05667 | −0.034455366 | 0.013797129 | 0.012514829 |
| CDK6 | rs2282978 | −4.876 | 1.08E−06 | −0.077385341 | 0.01514709 | 3.24E−07 |
| CDK6 | rs4272 | −3.465 | 0.0005296 | −0.06665877 | 0.01764793 | 0.000158637 |
| PRR5L | rs11033597 | 2.333 | 0.01965 | 0.066084117 | 0.020665458 | 0.001384776 |
| PRR5L | rs11600757 | 3.227 | 0.001252 | 0.079494189 | 0.019569349 | 4.86E−05 |
| PRR5L | rs11601211 | 1.906 | 0.05667 | 0.061285288 | 0.02719336 | 0.024215943 |
| PRR5L | rs12281565 | 3.058 | 0.002229 | 0.076286578 | 0.019430079 | 8.63E−05 |
| PRR5L | rs1365120 | NA | NA | 0.164666622 | 0.07526 | 0.028671788 |
| PRR5L | rs1895840 | 1.992 | 0.04641 | 0.059408267 | 0.023210602 | 0.010481334 |
| PRR5L | rs2303439 | 3.289 | 0.001006 | 0.068688505 | 0.019695087 | 0.000487384 |
| PRR5L | rs330260 | 1.95 | 0.05112 | 0.053412942 | 0.018807986 | 0.00451266 |
| PRR5L | rs331485 | −2.732 | 0.006288 | −0.062860555 | 0.023236366 | 0.006824967 |
| PRR5L | rs4077044 | 2.032 | 0.04212 | 0.037590443 | 0.014958442 | 0.011971209 |
| PRR5L | rs5030437 | 3.215 | 0.001304 | 0.064066031 | 0.020113864 | 0.001446701 |
| PRR5L | rs5030445 | 3.046 | 0.002317 | 0.062410516 | 0.01942935 | 0.001317331 |
| PRR5L | rs5030472 | 2.985 | 0.00284 | 0.078591165 | 0.022405282 | 0.000451987 |
| PRR5L | rs7929195 | −2.301 | 0.02139 | −0.050660959 | 0.022266607 | 0.022894005 |
| WNT2B | rs10745330 | 3.629 | 0.0002849 | 0.046712378 | 0.011110013 | 2.62E−05 |
| WNT2B | rs2999155 | 3.507 | 0.0004534 | 0.044692937 | 0.011109171 | 5.74E−05 |
| WNT2B | rs3790609 | 3.389 | 0.0007022 | 0.057908753 | 0.014569453 | 7.05E−05 |
| WNT2B | rs6682737 | 3.484 | 0.0004939 | 0.045366037 | 0.011109592 | 4.44E−05 |
| LRRC16A | rs10456320 | 4.283 | 1.84E−05 | 0.069089475 | 0.017094699 | 5.31E−05 |
| LRRC16A | rs11755567 | −3.27 | 0.001076 | −0.048398263 | 0.014239808 | 0.000676821 |
| LRRC16A | rs13191296 | −3.657 | 0.0002549 | −0.090057293 | 0.02222817 | 5.09E−05 |
| LRRC16A | rs2690110 | 4.521 | 6.15E−06 | 0.058889627 | 0.011610134 | 3.93E−07 |
| LRRC16A | rs4712908 | −3.068 | 0.002157 | −0.037870543 | 0.012274163 | 0.002032874 |
| LRRC16A | rs6921589 | −4.091 | 4.29E−05 | −0.064973129 | 0.017021208 | 0.000134982 |
| LRRC16A | rs6937918 | 2.547 | 0.01085 | 0.034771379 | 0.011355649 | 0.002198387 |
| LRRC16A | rs742132 | 2.65 | 0.008053 | 0.031042809 | 0.012141191 | 0.010563462 |
| LRRC16A | rs7752195 | −4.384 | 1.16E−05 | −0.101626038 | 0.02294336 | 9.45E−06 |
| LRRC16A | rs7752524 | 4.709 | 2.49E−06 | 0.085068327 | 0.018823587 | 6.21E−06 |
| LRRC16A | rs7762757 | 2.712 | 0.006697 | 0.031571387 | 0.011680522 | 0.006873559 |
| LRRC16A | rs880226 | 2.361 | 0.01824 | 0.033189564 | 0.011364287 | 0.003494541 |
| LRRC16A | rs9295661 | −4.072 | 4.67E−05 | −0.100526188 | 0.023046161 | 1.29E−05 |
| LRRC16A | rs9358854 | −2.913 | 0.003579 | −0.037637711 | 0.011791575 | 0.001413326 |
| LRRC16A | rs9461157 | 2.527 | 0.01151 | 0.034772904 | 0.011364722 | 0.002215417 |
| LRRC16A | rs9461165 | 2.596 | 0.009444 | 0.035502949 | 0.011356083 | 0.001769983 |
| LRRC16A | rs9467445 | −3.659 | 0.0002536 | −0.053117524 | 0.013770777 | 0.000114663 |
| All Histone cluster1 gene | rs10484399 | −3.446 | 0.0005686 | −0.078059586 | 0.020564152 | 0.000147105 |
| All Histone cluster1 gene | rs10484439 | −3.156 | 0.001602 | −0.074749526 | 0.021002594 | 0.000372182 |
| All Histone cluster1 gene | rs12176317 | −2.796 | 0.005176 | −0.063761509 | 0.018574335 | 0.000597438 |
| All Histone cluster1 gene | rs13194053 | −3.863 | 0.0001122 | −0.053670759 | 0.015092309 | 0.000376306 |
| All Histone cluster1 gene | rs13194491 | 3.139 | 0.001698 | 0.048949414 | 0.021779199 | 0.024606145 |
| All Histone cluster1 gene | rs13194781 | −3.437 | 0.0005871 | −0.077677154 | 0.020530542 | 0.000154643 |
| All Histone cluster1 gene | rs13195040 | −3.747 | 0.0001788 | −0.082582505 | 0.020961156 | 8.16E−05 |
| All Histone cluster1 gene | rs13199772 | −3.447 | 0.0005665 | −0.077401483 | 0.020529767 | 0.000163112 |
| All Histone cluster1 gene | rs13212651 | −3.477 | 0.0005067 | −0.078363109 | 0.020541534 | 0.000136259 |
| All Histone cluster1 gene | rs1321578 | −2.286 | 0.02228 | −0.071077407 | 0.030325291 | 0.019086731 |

TABLE 1-continued

| | | | | | | |
|---|---|---|---|---|---|---|
| All Histone cluster1 gene | rs13217599 | 2.421 | 0.01546 | 0.057081966 | 0.022951133 | 0.012878599 |
| All Histone cluster1 gene | rs13218875 | −3.514 | 0.0004412 | −0.078092819 | 0.020747093 | 0.000167192 |
| All Histone cluster1 gene | rs13219354 | −3.26 | 0.001115 | −0.060487086 | 0.018110779 | 0.00083827 |
| All Histone cluster1 gene | rs16867901 | −2.835 | 0.004582 | −0.181808618 | 0.061179996 | 0.002961555 |
| All Histone cluster1 gene | rs16867911 | −2.729 | 0.006351 | −0.167952934 | 0.059705622 | 0.004907905 |
| All Histone cluster1 gene | rs16891725 | −2.769 | 0.005622 | −0.062146342 | 0.018449232 | 0.000755768 |
| All Histone cluster1 gene | rs175597 | −3.986 | 6.72E−05 | −0.084555864 | 0.018699048 | 6.13E−06 |
| All Histone cluster1 gene | rs17693963 | −2.936 | 0.003324 | −0.060615226 | 0.019811487 | 0.002216328 |
| All Histone cluster1 gene | rs17739310 | 2.613 | 0.008972 | 0.044605836 | 0.016261099 | 0.006086197 |
| All Histone cluster1 gene | rs17750424 | −4.497 | 6.88E−06 | −0.099709844 | 0.02218 | 6.94E−06 |
| All Histone cluster1 gene | rs1977 | −2.835 | 0.004583 | −0.064477268 | 0.018565026 | 0.000514579 |
| All Histone cluster1 gene | rs1985732 | −1.832 | 0.06692 | −0.027838373 | 0.012334681 | 0.024013157 |
| All Histone cluster1 gene | rs200483 | −3.905 | 9.42E−05 | −0.0820908 | 0.018676968 | 1.11E−05 |
| All Histone cluster1 gene | rs200484 | −3.894 | 9.84E−05 | −0.082395729 | 0.018707585 | 1.06E−05 |
| All Histone cluster1 gene | rs200490 | −3.912 | 9.16E−05 | −0.083371878 | 0.018670767 | 7.99E−06 |
| All Histone cluster1 gene | rs200501 | −3.751 | 0.0001759 | −0.0794437 | 0.018617232 | 1.98E−05 |
| All Histone cluster1 gene | rs200948 | −4.027 | 5.65E−05 | −0.085318783 | 0.018700377 | 5.06E−06 |
| All Histone cluster1 gene | rs200953 | −4.019 | 5.86E−05 | −0.085609176 | 0.018669936 | 4.53E−06 |
| All Histone cluster1 gene | rs200989 | −3.995 | 6.47E−05 | −0.085051111 | 0.018690175 | 5.35E−06 |
| All Histone cluster1 gene | rs200990 | −4.065 | 4.81E−05 | −0.08639512 | 0.018659065 | 3.65E−06 |
| All Histone cluster1 gene | rs200991 | −2.275 | 0.02291 | −0.036379215 | 0.015865406 | 0.02184859 |
| All Histone cluster1 gene | rs200995 | −3.981 | 6.85E−05 | −0.084473289 | 0.01867964 | 6.12E−06 |
| All Histone cluster1 gene | rs201002 | −3.897 | 9.74E−05 | −0.083072055 | 0.018658898 | 8.50E−06 |
| All Histone cluster1 gene | rs201004 | −2.05 | 0.04039 | −0.031705869 | 0.015289559 | 0.03810772 |
| All Histone cluster1 gene | rs2064092 | 1.651 | 0.09883 | 0.050392502 | 0.020622596 | 0.014543248 |
| All Histone cluster1 gene | rs2072806 | −2.495 | 0.0126 | −0.050399006 | 0.018998369 | 0.007982551 |
| All Histone cluster1 gene | rs2073529 | −2.76 | 0.005781 | −0.053189829 | 0.01928 | 0.005801251 |
| All Histone cluster1 gene | rs2093169 | −2.503 | 0.0123 | −0.039526244 | 0.014821362 | 0.007656748 |
| All Histone cluster1 gene | rs2393997 | −1.792 | 0.07312 | −0.035650813 | 0.017602717 | 0.042836389 |
| All Histone cluster1 gene | rs2494711 | 2.25 | 0.02442 | 0.030743293 | 0.011439774 | 0.007200984 |
| All Histone cluster1 gene | rs2747054 | −4.003 | 6.27E−05 | −0.084226868 | 0.018670435 | 6.44E−06 |
| All Histone cluster1 gene | rs2893910 | −2.542 | 0.01104 | −0.042399602 | 0.015008424 | 0.004727271 |
| All Histone cluster1 gene | rs34706883 | −3.429 | 0.0006061 | −0.077403838 | 0.020531703 | 0.000163269 |
| All Histone cluster1 gene | rs370155 | −3.931 | 8.47E−05 | −0.083316959 | 0.018649027 | 7.91E−06 |
| All Histone cluster1 gene | rs3799378 | −2.808 | 0.004985 | −0.042977293 | 0.015146769 | 0.0045484 |
| All Histone cluster1 gene | rs3799380 | −2.629 | 0.008566 | −0.03770809 | 0.01434693 | 0.008581185 |
| All Histone cluster1 gene | rs3799383 | −2.381 | 0.01728 | −0.054983285 | 0.017719062 | 0.001915318 |
| All Histone cluster1 gene | rs3800307 | −3.542 | 0.0003964 | −0.047615302 | 0.014187129 | 0.000790121 |
| All Histone cluster1 gene | rs3800316 | −3.133 | 0.001733 | −0.041232193 | 0.012710172 | 0.001178508 |

TABLE 1-continued

| | | | | | | |
|---|---|---|---|---|---|---|
| All Histone cluster1 gene | rs4452638 | −3.137 | 0.001709 | −0.05807739 | 0.018121317 | 0.001350996 |
| All Histone cluster1 gene | rs4634439 | −2.688 | 0.007195 | −0.062071323 | 0.018386175 | 0.000735538 |
| All Histone cluster1 gene | rs4712981 | −1.99 | 0.04664 | −0.029694159 | 0.012451086 | 0.017085387 |
| All Histone cluster1 gene | rs4713119 | −1.777 | 0.07556 | −0.035242617 | 0.017509761 | 0.044141868 |
| All Histone cluster1 gene | rs6456728 | −2.623 | 0.008717 | −0.037625374 | 0.014347244 | 0.008729217 |
| All Histone cluster1 gene | rs6904071 | −3.774 | 0.0001608 | −0.052562718 | 0.015098153 | 0.000498799 |
| All Histone cluster1 gene | rs6904596 | −4.041 | 5.33E−05 | −0.08829141 | 0.019608398 | 6.71E−06 |
| All Histone cluster1 gene | rs6913660 | −3.775 | 0.0001599 | −0.052278347 | 0.015105424 | 0.000538375 |
| All Histone cluster1 gene | rs6915101 | −1.996 | 0.04591 | −0.10249597 | 0.04529877 | 0.023656309 |
| All Histone cluster1 gene | rs6920256 | −2.749 | 0.005984 | −0.062007017 | 0.01821765 | 0.00066485 |
| All Histone cluster1 gene | rs6923139 | −3.814 | 0.0001366 | −0.07921173 | 0.018994782 | 3.04E−05 |
| All Histone cluster1 gene | rs6932590 | −4.006 | 6.19E−05 | −0.053482958 | 0.013220111 | 5.22E−05 |
| All Histone cluster1 gene | rs6933583 | −2.025 | 0.04291 | −0.029443093 | 0.012431026 | 0.017859578 |
| All Histone cluster1 gene | rs6934794 | 2.135 | 0.03275 | 0.038420767 | 0.013873353 | 0.005616085 |
| All Histone cluster1 gene | rs6938200 | −3.692 | 0.0002221 | −0.054407673 | 0.014753455 | 0.000226208 |
| All Histone cluster1 gene | rs721600 | 3.681 | 0.0002323 | 0.051261731 | 0.012993034 | 7.97E−05 |
| All Histone cluster1 gene | rs7745603 | −2.944 | 0.003236 | −0.038182055 | 0.01347952 | 0.004617148 |
| All Histone cluster1 gene | rs7746199 | −1.914 | 0.05556 | −0.033135773 | 0.01627573 | 0.041760311 |
| All Histone cluster1 gene | rs7749305 | −3.879 | 0.0001048 | −0.087200073 | 0.019567667 | 8.34E−06 |
| All Histone cluster1 gene | rs7749319 | −1.85 | 0.06438 | −0.068379642 | 0.02911228 | 0.018832771 |
| All Histone cluster1 gene | rs7756567 | −2.459 | 0.01392 | −0.039049815 | 0.014821075 | 0.008419948 |
| All Histone cluster1 gene | rs7773938 | −2.452 | 0.01422 | −0.039214842 | 0.014812449 | 0.008110743 |
| All Histone cluster1 gene | rs911186 | −4.676 | 2.93E−06 | −0.067957693 | 0.01453 | 2.91E−06 |
| All Histone cluster1 gene | rs9295739 | −2.813 | 0.004915 | −0.171929423 | 0.059595654 | 0.003914979 |
| All Histone cluster1 gene | rs9295749 | 1.562 | 0.1183 | 0.050676086 | 0.02348294 | 0.03092816 |
| All Histone cluster1 gene | rs9358944 | −2.484 | 0.01298 | −0.039303573 | 0.014820211 | 0.008001058 |
| All Histone cluster1 gene | rs9358945 | −2.478 | 0.0132 | −0.039297112 | 0.014811587 | 0.00797484 |
| All Histone cluster1 gene | rs9358946 | −2.521 | 0.01172 | −0.043426492 | 0.015012525 | 0.003819653 |
| All Histone cluster1 gene | rs9366653 | −2.616 | 0.008893 | −0.060204646 | 0.018485852 | 0.001126775 |
| All Histone cluster1 gene | rs9366658 | −2.484 | 0.01301 | −0.039303573 | 0.014820211 | 0.008001058 |
| All Histone cluster1 gene | rs9379844 | 1.473 | 0.1407 | 0.023173367 | 0.01147771 | 0.04348838 |
| All Histone cluster1 gene | rs9379851 | −2.634 | 0.008427 | −0.060564616 | 0.018459972 | 0.001034905 |
| All Histone cluster1 gene | rs9379856 | −2.948 | 0.003203 | −0.057311367 | 0.01944 | 0.003197175 |
| All Histone cluster1 gene | rs9379858 | −2.629 | 0.008567 | −0.060859987 | 0.018496594 | 0.001000683 |
| All Histone cluster1 gene | rs9379859 | −2.648 | 0.008105 | −0.061151979 | 0.018496594 | 0.000945972 |
| All Histone cluster1 gene | rs9379870 | −2.069 | 0.0385 | −0.029856537 | 0.012449286 | 0.016473483 |
| All Histone cluster1 gene | rs9379897 | −2.698 | 0.006973 | −0.06230161 | 0.018386175 | 0.000702752 |
| All Histone cluster1 gene | rs9393691 | 1.526 | 0.1271 | 0.024042273 | 0.01147687 | 0.036184711 |
| All Histone cluster1 gene | rs9393705 | −2.599 | 0.00936 | −0.060068739 | 0.018488308 | 0.001158065 |

TABLE 1-continued

| | | | | | | |
|---|---|---|---|---|---|---|
| All Histone cluster1 gene | rs9393708 | −2.644 | 0.008194 | −0.060954265 | 0.018497208 | 0.000983088 |
| All Histone cluster1 gene | rs9393713 | −2.762 | 0.00575 | −0.063064838 | 0.018565638 | 0.000681643 |
| All Histone cluster1 gene | rs9393714 | −3.124 | 0.001784 | −0.069719509 | 0.018583234 | 0.00017561 |
| All Histone cluster1 gene | rs9393777 | −2.78 | 0.005444 | −0.052252011 | 0.017217658 | 0.002407016 |
| All Histone cluster1 gene | rs9461362 | 2.679 | 0.007387 | 0.043176822 | 0.01510931 | 0.004268175 |
| All Histone cluster1 gene | rs9467704 | −3.575 | 0.0003501 | −0.075270063 | 0.019116602 | 8.24E−05 |
| All Histone cluster1 gene | rs9468152 | 3.068 | 0.002153 | 0.05299972 | 0.017220624 | 0.002086127 |
| All Histone cluster1 gene | rs9468159 | 1.528 | 0.1265 | 0.05319711 | 0.021460219 | 0.013179903 |
| All Histone cluster1 gene | rs9468202 | −3.135 | 0.001717 | −0.187147607 | 0.05907474 | 0.00153502 |
| All Histone cluster1 gene | rs9468227 | −2.27 | 0.02321 | −0.119017937 | 0.045458584 | 0.008840483 |
| GTF2IRD2B | imm_7_74094413 | NA | NA | −0.1420245 | 0.03268 | 1.39E−05 |
| GTF2IRD2B | imm_7_74108242 | −2.787 | 0.005313 | −0.045845816 | 0.011311498 | 5.06E−05 |
| GTF2IRD2B | imm_7_74117236 | NA | NA | −0.13056437 | 0.03238 | 5.52E−05 |
| GTF2IRD2B | imm_7_74118166 | −2.329 | 0.01984 | −0.039338514 | 0.011214741 | 0.000451913 |
| GTF2IRD2B | imm_7_74120730 | −3.147 | 0.001648 | −0.073603881 | 0.017629911 | 2.98E−05 |
| GTF2IRD2B | imm_7_74133859 | −2.398 | 0.01648 | −0.037488569 | 0.015355933 | 0.014634152 |
| GTF2IRD2B | imm_7_74145400 | −2.495 | 0.01261 | −0.036352829 | 0.01458 | 0.012654926 |
| ETS1 | imm_11_127760024 | 2.032 | 0.04215 | 0.042926789 | 0.018934111 | 0.023380035 |
| ETS1 | imm_11_127761269 | 2.237 | 0.02528 | 0.045524943 | 0.020137336 | 0.023776399 |
| ETS1 | imm_11_127765567 | 2.805 | 0.005028 | 0.049598679 | 0.015895787 | 0.001807035 |
| ETS1 | imm_11_127767721 | −1.582 | 0.1136 | −0.079524768 | 0.036584875 | 0.029727209 |
| ETS1 | imm_11_127770666 | 2.497 | 0.01254 | 0.027675982 | 0.012651619 | 0.028702789 |
| ETS1 | imm_11_127770668 | 2.422 | 0.01543 | 0.026754934 | 0.012642548 | 0.034322604 |
| ETS1 | imm_11_127774308 | 2.691 | 0.007129 | 0.047208966 | 0.015786763 | 0.002785991 |
| ETS1 | imm_11_127775128 | 2.544 | 0.01096 | 0.045858868 | 0.015793826 | 0.003689054 |
| ETS1 | imm_11_127776527 | −1.751 | 0.07986 | −0.08202922 | 0.034742961 | 0.018224191 |
| ETS1 | imm_11_127776913 | −1.761 | 0.0783 | −0.080950891 | 0.035366597 | 0.022084689 |
| ETS1 | imm_11_127777217 | −2.993 | 0.00276 | −0.037787017 | 0.011172423 | 0.000719161 |
| ETS1 | imm_11_127778327 | 1.993 | 0.0463 | 0.027615167 | 0.01368 | 0.043523344 |
| ETS1 | imm_11_127778329 | 2.349 | 0.01883 | 0.031728477 | 0.012692271 | 0.012425409 |
| ETS1 | imm_11_127779030 | −2.278 | 0.02271 | −0.075381275 | 0.027992548 | 0.007083243 |
| ETS1 | imm_11_127780425 | 1.845 | 0.06506 | 0.070225777 | 0.031881326 | 0.027614175 |
| ETS1 | imm_11_127780902 | −2.289 | 0.02208 | −0.074442787 | 0.027962569 | 0.007762485 |
| ETS1 | imm_11_127781839 | 2.504 | 0.0123 | 0.032777667 | 0.013448782 | 0.014800589 |
| ETS1 | imm_11_127785739 | −2.072 | 0.0383 | −0.035012045 | 0.014009631 | 0.012449473 |
| ETS1 | imm_11_127785963 | 3.101 | 0.001927 | 0.052040195 | 0.015404731 | 0.000729632 |
| ETS1 | imm_11_127786010 | 2.345 | 0.01902 | 0.037673992 | 0.014211921 | 0.008028412 |
| ETS1 | imm_11_127786836 | 2.275 | 0.0229 | 0.036589399 | 0.014202859 | 0.009989296 |
| ETS1 | imm_11_127787128 | 2.382 | 0.0172 | 0.039414469 | 0.01441664 | 0.006257827 |
| ETS1 | imm_11_127788828 | −1.965 | 0.04944 | −0.033526672 | 0.013833259 | 0.01536634 |
| ETS1 | imm_11_127789306 | 2.183 | 0.029 | 0.036739352 | 0.014727637 | 0.01261043 |
| ETS1 | imm_11_127789441 | 2.164 | 0.03043 | 0.036624882 | 0.014726445 | 0.012882018 |
| ETS1 | imm_11_127791651 | 3.062 | 0.002198 | 0.053955711 | 0.015283716 | 0.000415129 |
| ETS1 | imm_11_127792287 | 2.193 | 0.02832 | 0.035742383 | 0.014204214 | 0.011858661 |
| ETS1 | imm_11_127792800 | 2.306 | 0.02113 | 0.066110717 | 0.026814214 | 0.013681829 |
| ETS1 | imm_11_127793060 | 2.06 | 0.03942 | 0.034056541 | 0.014192892 | 0.01641528 |
| ETS1 | imm_11_127794685 | 2.898 | 0.003755 | 0.051462381 | 0.015253854 | 0.000741571 |
| ETS1 | imm_11_127795453 | 2.084 | 0.03712 | 0.034059211 | 0.014182472 | 0.016327993 |
| ETS1 | imm_11_127796816 | −2.51 | 0.01206 | −1.664950591 | 0.6633 | 0.012069633 |
| ETS1 | imm_11_127797523 | 2.077 | 0.03779 | 0.034301166 | 0.014191533 | 0.01564832 |
| ETS1 | imm_11_127798230 | −1.785 | 0.07422 | −0.028064721 | 0.012258798 | 0.022058826 |
| ETS1 | imm_11_127799892 | 2.523 | 0.01165 | 0.025601331 | 0.011134725 | 0.021491698 |
| ETS1 | imm_11_127804916 | −1.846 | 0.06484 | −0.03329535 | 0.016645797 | 0.045475907 |
| ETS1 | imm_11_127805367 | −2.056 | 0.03982 | −0.074705008 | 0.033949249 | 0.027772097 |
| ETS1 | imm_11_127806163 | 2.233 | 0.02553 | 0.026897717 | 0.0114935 | 0.019270591 |
| ETS1 | imm_11_127806304 | −2.064 | 0.03899 | −0.078980642 | 0.034472261 | 0.021955543 |
| ETS1 | imm_11_127807384 | 2.165 | 0.0304 | 0.029608627 | 0.014745076 | 0.044639585 |
| ETS1 | imm_11_127808758 | −1.977 | 0.04808 | −0.072324763 | 0.033858572 | 0.032672546 |
| ETS1 | imm_11_127809308 | −2.768 | 0.005647 | −0.179735204 | 0.065479608 | 0.006052869 |
| ETS1 | imm_11_127812329 | 2.044 | 0.04094 | 0.0578145 | 0.024925603 | 0.020368891 |
| ETS1 | imm_11_127812420 | 2.328 | 0.01991 | 1.034251522 | 0.4443 | 0.019921533 |
| ETS1 | imm_11_127813024 | 2.23 | 0.02575 | 0.026659 | 0.01148528 | 0.020279014 |
| ETS1 | imm_11_127819226 | 2.124 | 0.0337 | 0.029083683 | 0.014734003 | 0.048391311 |
| ETS1 | imm_11_127822686 | −2.085 | 0.03704 | −0.076311769 | 0.033773092 | 0.0238496 |
| ETS1 | imm_11_127823420 | −2.766 | 0.005668 | −0.179711713 | 0.065475865 | 0.006056594 |
| ETS1 | imm_11_127824356 | 2.321 | 0.02029 | 0.031507947 | 0.014938913 | 0.034934297 |
| ETS1 | imm_11_127825016 | −2.044 | 0.04092 | −0.073610998 | 0.033835636 | 0.029589194 |
| ETS1 | imm_11_127825282 | 2.168 | 0.03012 | 0.026165347 | 0.011458899 | 0.022406326 |
| ETS1 | imm_11_127825669 | 2.152 | 0.03141 | 0.026284858 | 0.011459326 | 0.021804716 |
| ETS1 | imm_11_127826087 | −3.239 | 0.001199 | −0.036667302 | 0.01179811 | 0.001884242 |

TABLE 1-continued

| | | | | | | |
|---|---|---|---|---|---|---|
| ETS1 | imm_11_127826464 | 2.179 | 0.02933 | 0.031847589 | 0.015364357 | 0.038188781 |
| ETS1 | imm_11_127827422 | 2.146 | 0.03188 | 0.031836913 | 0.0153331 | 0.037861413 |
| ETS1 | imm_11_127828334 | −1.796 | 0.07255 | −0.0717967 | 0.034541489 | 0.03765743 |
| ETS1 | imm_11_127831280 | −2.347 | 0.01891 | −0.076928682 | 0.034934703 | 0.02766032 |
| ETS1 | imm_11_127831611 | 1.965 | 0.04947 | 0.030801761 | 0.015266783 | 0.043636358 |
| ETS1 | imm_11_127831673 | −2.213 | 0.02687 | −0.026302648 | 0.012250664 | 0.03179022 |
| ETS1 | imm_11_127834123 | 2.449 | 0.01434 | 0.031150692 | 0.012207726 | 0.010719278 |
| ETS1 | imm_11_127834484 | −2.245 | 0.02479 | −0.083250933 | 0.035190155 | 0.017993833 |
| ETS1 | imm_11_127837472 | −2.276 | 0.02286 | −0.086358386 | 0.04119264 | 0.036042131 |
| ETS1 | imm_11_127838265 | −2.501 | 0.01238 | −0.0467051 | 0.020354171 | 0.021754875 |
| ETS1 | imm_11_127838713 | 2.706 | 0.0068 | 0.030443434 | 0.011150762 | 0.006330239 |
| ETS1 | imm_11_127839719 | −1.685 | 0.09208 | −0.101896739 | 0.048155183 | 0.034344151 |
| ETS1 | imm_11_127840459 | 4.443 | 8.88E−06 | 0.066778559 | 0.015027999 | 8.85E−06 |
| ETS1 | imm_11_127840867 | −3.349 | 0.0008102 | −0.057525516 | 0.018030387 | 0.001420387 |
| ETS1 | imm_11_127841724 | −2.083 | 0.03722 | −0.05480528 | 0.018801811 | 0.003558098 |
| ETS1 | imm_11_127841864 | −2.143 | 0.03209 | −0.028776523 | 0.01125191 | 0.010543391 |
| ETS1 | imm_11_127843207 | −2.168 | 0.03017 | −0.056484024 | 0.018845217 | 0.002724178 |
| ETS1 | imm_11_127843341 | −2.128 | 0.03337 | −0.054915038 | 0.018825026 | 0.00353269 |
| ETS1 | imm_11_127844385 | 4.361 | 1.29E−05 | 0.064455567 | 0.015018502 | 1.77E−05 |
| ETS1 | imm_11_127844729 | 2.063 | 0.03914 | 0.083540439 | 0.035945727 | 0.020121663 |
| ETS1 | imm_11_127845557 | −2.259 | 0.02389 | −0.056607744 | 0.018571567 | 0.002303036 |
| ETS1 | imm_11_127846698 | 4.256 | 2.08E−05 | 0.063037728 | 0.014963881 | 2.52E−05 |
| ETS1 | imm_11_127848167 | 4.248 | 2.15E−05 | 0.063359292 | 0.014979336 | 2.34E−05 |
| ETS1 | imm_11_127848372 | 4.292 | 1.77E−05 | 0.063723341 | 0.01501456 | 2.19E−05 |
| ETS1 | imm_11_127849992 | 4.259 | 2.05E−05 | 0.063139897 | 0.014980517 | 2.50E−05 |
| ETS1 | imm_11_127851599 | 4.416 | 1.00E−05 | 0.065721185 | 0.014950847 | 1.10E−05 |
| ETS1 | imm_11_127852250 | −2.074 | 0.03811 | −0.056396101 | 0.018949807 | 0.002919607 |
| ETS1 | imm_11_127853705 | −2.069 | 0.03855 | −0.056310436 | 0.018954288 | 0.002969723 |
| ETS1 | imm_11_127855281 | 4.274 | 1.92E−05 | 0.063002728 | 0.014965887 | 2.56E−05 |
| ETS1 | imm_11_127855956 | −1.906 | 0.05663 | −0.052503353 | 0.018846373 | 0.005338596 |
| ETS1 | imm_11_127857027 | −2.228 | 0.02586 | −0.058543871 | 0.019045877 | 0.002113268 |
| ETS1 | imm_11_127861069 | 2.908 | 0.003636 | 0.033615546 | 0.012703529 | 0.008141175 |
| ETS1 | imm_11_127863304 | 2.985 | 0.002833 | 0.034151141 | 0.012711732 | 0.007218671 |
| ETS1 | imm_11_127863391 | 2.936 | 0.003319 | 0.0343825 | 0.01271086 | 0.006831048 |
| ETS1 | imm_11_127866379 | 2.209 | 0.02719 | 0.027961868 | 0.013022783 | 0.031781351 |
| ETS1 | imm_11_127868447 | 1.315 | 0.1886 | 0.301617605 | 0.137802383 | 0.028613623 |
| ETS1 | imm_11_127868927 | −1.917 | 0.05524 | −0.030778263 | 0.014215206 | 0.030375071 |
| ETS1 | imm_11_127869177 | 3.291 | 0.0009998 | 0.042725144 | 0.01308094 | 0.00108996 |
| ETS1 | imm_11_127870403 | 3.406 | 0.0006589 | 0.040128462 | 0.012795572 | 0.001711985 |
| ETS1 | imm_11_127870895 | 3.461 | 0.0005381 | 0.039930201 | 0.012643861 | 0.001588174 |
| ETS1 | imm_11_127871431 | 3.409 | 0.000651 | 0.038993789 | 0.012643861 | 0.002042311 |
| ETS1 | imm_11_127872972 | −1.931 | 0.0535 | −0.034517826 | 0.014721847 | 0.019044089 |
| ETS1 | imm_11_127874486 | 3.415 | 0.0006384 | 0.039149608 | 0.012635226 | 0.001945363 |
| ETS1 | imm_11_127874807 | 3.355 | 0.0007941 | 0.037325948 | 0.012669831 | 0.00321861 |
| ETS1 | imm_11_127877378 | 3.476 | 0.0005082 | 0.040066089 | 0.01266069 | 0.001552934 |
| ETS1 | imm_11_127879923 | −2.006 | 0.04482 | −0.032104052 | 0.014245451 | 0.024219122 |
| ETS1 | imm_11_127881686 | 5.101 | 3.38E−07 | 0.07519188 | 0.014571861 | 2.47E−07 |
| ETS1 | imm_11_127882690 | 2.424 | 0.01534 | 0.027998152 | 0.011472767 | 0.014670969 |
| ETS1 | imm_11_127884689 | −2.195 | 0.02818 | −0.053596757 | 0.024228018 | 0.026954177 |
| ETS1 | imm_11_127885952 | 4.173 | 3.01E−05 | 0.04882324 | 0.011607573 | 2.60E−05 |
| ETS1 | imm_11_127886184 | 5.214 | 1.85E−07 | 0.072118037 | 0.013104848 | 3.73E−08 |
| ETS1 | imm_11_127887077 | 4.156 | 3.24E−05 | 0.048819243 | 0.011615795 | 2.64E−05 |
| ETS1 | imm_11_127889134 | 5.127 | 2.94E−07 | 0.070484447 | 0.013134204 | 8.03E−08 |
| ETS1 | imm_11_127891116 | 5.021 | 5.13E−07 | 0.069779303 | 0.013134204 | 1.08E−07 |
| ETS1 | imm_11_127892632 | 4.17 | 3.05E−05 | 0.048939649 | 0.011616223 | 2.52E−05 |
| ETS1 | imm_11_127894601 | −1.516 | 0.1296 | −0.026829502 | 0.013320245 | 0.043989602 |
| ETS1 | imm_11_127894638 | −2.484 | 0.01299 | −0.188155241 | 0.090683227 | 0.037999265 |
| ETS1 | imm_11_127895279 | 5.254 | 1.49E−07 | 0.072347736 | 0.013125964 | 3.55E−08 |
| ETS1 | imm_11_127897147 | 5.135 | 2.82E−07 | 0.071324587 | 0.013275971 | 7.77E−08 |
| ETS1 | imm_11_127898835 | −2.452 | 0.01419 | −0.104184655 | 0.041061849 | 0.011172342 |
| ETS1 | imm_11_127901157 | 3.634 | 0.0002788 | 0.048482987 | 0.012182068 | 6.90E−05 |
| ETS1 | imm_11_127901948 | 4.845 | 1.27E−06 | 0.067482299 | 0.013201602 | 3.19E−07 |
| ETS1 | imm_11_127905841 | −2.633 | 0.008471 | −0.06305062 | 0.02509525 | 0.011989528 |
| ETS1 | imm_11_127906568 | 3.779 | 0.0001574 | 0.037251522 | 0.011449394 | 0.001139605 |
| ETS1 | imm_11_127908214 | 3.85 | 0.0001181 | 0.038139717 | 0.011441168 | 0.000857449 |
| ETS1 | imm_11_127911648 | 3.474 | 0.0005128 | −0.038289326 | 0.011656784 | 0.001020821 |
| ETS1 | imm_11_127911985 | 3.592 | 0.0003287 | 0.033215696 | 0.01112011 | 0.002817358 |
| ETS1 | imm_11_127914294 | 3.612 | 0.0003037 | 0.033184837 | 0.011119682 | 0.00284197 |
| ETS1 | imm_11_127915474 | 3.587 | 0.0003349 | −0.032982076 | 0.011120538 | 0.003018275 |
| ETS1 | imm_11_127915554 | 3.886 | 0.0001018 | −0.036194682 | 0.011136979 | 0.001154232 |
| ETS1 | imm_11_127916046 | 3.497 | 0.00047 | 0.031936936 | 0.011110604 | 0.004047249 |
| ETS1 | imm_11_127929821 | −2.385 | 0.01708 | −0.678652718 | 0.2845 | 0.017059514 |
| ETS1 | imm_11_127931099 | −2.429 | 0.01513 | −0.862513022 | 0.355 | 0.015114905 |
| ETS1 | imm_11_127940676 | −2.022 | 0.04321 | −0.062037894 | 0.026138425 | 0.01762342 |
| ETS1 | imm_11_127943244 | −1.673 | 0.09426 | −0.812307098 | 0.402683738 | 0.043671159 |
| ETS1 | imm_11_127945727 | NA | NA | 0.088926209 | 0.03356 | 0.00805471 |
| ETS1 | imm_11_127945953 | −2.524 | 0.01162 | −0.050352946 | 0.020907291 | 0.016022978 |
| ETS1 | imm_11_127948912 | −3.115 | 0.001838 | −0.131414033 | 0.040583382 | 0.001203184 |
| ETS1 | imm_11_127956842 | 2.659 | 0.007839 | 0.030434638 | 0.012698899 | 0.016546358 |
| ETS1 | imm_11_127957543 | 2.276 | 0.02283 | 0.116729213 | 0.0456538 | 0.010562944 |

TABLE 1-continued

| | | | | | | |
|---|---|---|---|---|---|---|
| ETS1 | imm_11_127957904 | 3.005 | 0.002655 | 0.115296546 | 0.052991094 | 0.029572303 |
| ETS1 | imm_11_127974263 | −2.438 | 0.01479 | −0.04857884 | 0.020976737 | 0.020566818 |
| ETS1 | imm_11_127979301 | −2.378 | 0.01741 | −0.034463525 | 0.014465314 | 0.017195808 |
| ETS1 | imm_11_127979905 | −1.988 | 0.04682 | −0.113506773 | 0.051876884 | 0.028669391 |
| ETS1 | imm_11_127981559 | −2.045 | 0.04084 | −0.029414518 | 0.014589917 | 0.04379105 |
| ETS1 | imm_11_127982379 | −2.052 | 0.04018 | −0.029503242 | 0.01459824 | 0.043278356 |
| ETS1 | imm_11_127982748 | −2.311 | 0.02081 | −0.033127504 | 0.014582372 | 0.023101611 |
| ETS1 | imm_11_127983590 | −2.119 | 0.03407 | −0.0303598 | 0.014627509 | 0.037937657 |
| ETS1 | imm_11_127983743 | −2.046 | 0.04074 | −0.029503242 | 0.01459824 | 0.043278356 |
| ETS1 | imm_11_127984265 | −2.118 | 0.03414 | −0.030230583 | 0.01459824 | 0.038373979 |
| ETS1 | imm_11_127984721 | −2.201 | 0.02777 | −0.032860786 | 0.014627752 | 0.02467401 |
| ETS1 | rs7935286 | 2.73 | 0.006328 | 0.047557767 | 0.015027868 | 0.001552758 |
| SLC5A1 | rs738203 | 1.932 | 0.05333 | 0.02886435 | 0.014259591 | 0.042948954 |
| SLC5A1 | rs9609429 | −1.99 | 0.04659 | −0.040869749 | 0.012698502 | 0.001288764 |
| TET2 | rs10010325 | −5.75 | 8.95E−09 | −0.062859518 | 0.011131325 | 1.63E−08 |
| TET2 | rs17035310 | 3.138 | 0.001702 | 0.06001359 | 0.016413995 | 0.000255937 |
| TET2 | rs2189234 | 3.607 | 0.0003095 | 0.033831361 | 0.011536644 | 0.003362306 |
| TET2 | rs7661349 | 3.663 | 0.0002491 | 0.034610864 | 0.011723345 | 0.003154135 |
| TET2 | rs974801 | −5.427 | 5.73E−08 | −0.055192987 | 0.011495877 | 1.58E−06 |

Many variations and alternative elements have been disclosed in embodiments of the present invention. Still further variations and alternate elements will be apparent to one of skill in the art. Among these variations, without limitation, are the selection of constituent modules for the inventive methods, compositions, kits, and systems, and the various conditions, diseases, and disorders that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Examples

The invention will be further explained by the following Examples, which are intended to be purely exemplary of the invention, and should not be considered as limiting the invention in any way. The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1 GLS-SKAT: a Novel Approach for Gene-Based Analysis in Cohorts with Family Structure Gene-based analysis can be important in identifying novel loci for complex diseases. However most of the available approaches are based on independent assumption, aiming at population based case-control sample. Here we proposed a generalized least square (GLS) based analysis strategy to identify genes using data with complex family structures. Rational of this approach can be described as following.

Given a linear specification of the association of a set of genetic factors X and the outcome y, we have:

$$y=X\beta+e \tag{1}$$

Suppose that the variance of outcome y can be written as:

$$\mathrm{var}(y)=\Sigma_o \tag{2}$$

When the subjects in the sample are uncorrelated, the estimate of β can be written as:

$$\hat{\beta}_T=(X'X)^{-1}X'y \tag{3}$$

$$\mathrm{var}(\hat{\beta}_T)=\hat{\sigma}_T^2(X'X)^{-1}. \tag{4}$$

When the samples are correlated, e.g. in family-based samples, the ordinary least squares (OLS) estimate of β will be problematic and will lead to a biased estimate of $\mathrm{var}(\hat{\beta}_T)$. This will affect any model based on independent assumption, including most gene-based tests.

One of the solutions to the violation of independence assumption in linear model is to perform the generalized least square transformation. Let:

$$G=\Sigma_o^{-1/2} \tag{5}$$

And a GLS transformed model can be written as:

$$Gy=GX\beta+Ge \tag{6}$$

And estimate based on the transformed model can be written as: (6)

$$\hat{\beta}_{GLS}=(X'\Sigma_o^{-1}X)^{-1}X'\Sigma_o^{-1}y \tag{7}$$

$$\mathrm{var}(\hat{\beta}_{GLS})=\mathrm{var}((X'\Sigma_o^{-1}X)^{-1}X'\Sigma_o^{-1}y)=(X'\Sigma_o^{-1}X)^{-1} \tag{8}$$

Clearly this is Best Linear Unbiased Predictor (BLUP) by construction. In other words, after the GLS transformation the data is de-correlated while retaining an unbiased estimator. Thereby any model developed with independence assumption can be applied to the GLS transformed data. Here for gene-based analysis, we choose to apply SKAT-CommonRare in the GLS transformed data as it has better performance in most scenarios while the independence assumption holds. The transformation matrix G was calculated as the inverse of the decomposition of the kinship matrix. We call this approach GLS-SKAT.

Example 2 Multiple Novel Loci Identified via Gene-based Analysis

Figure 1A:
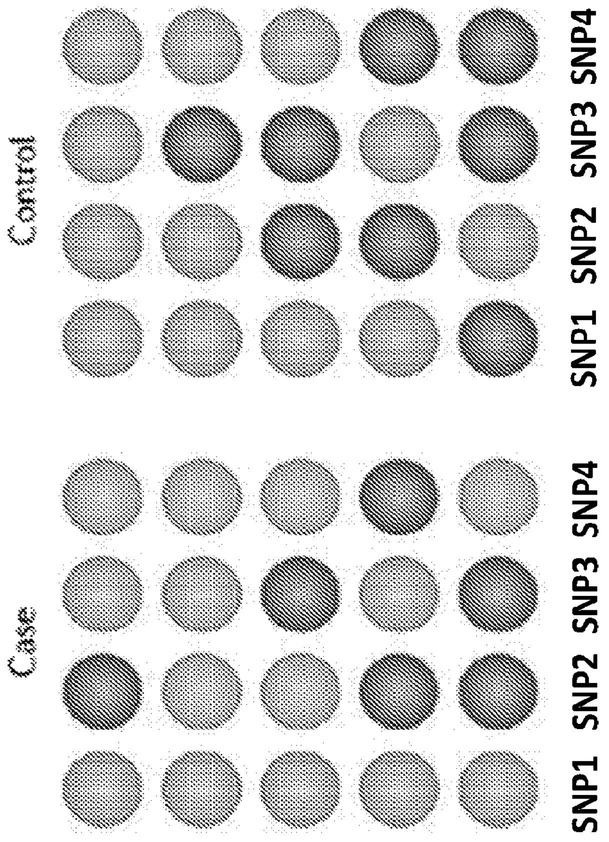
Figure 2A:
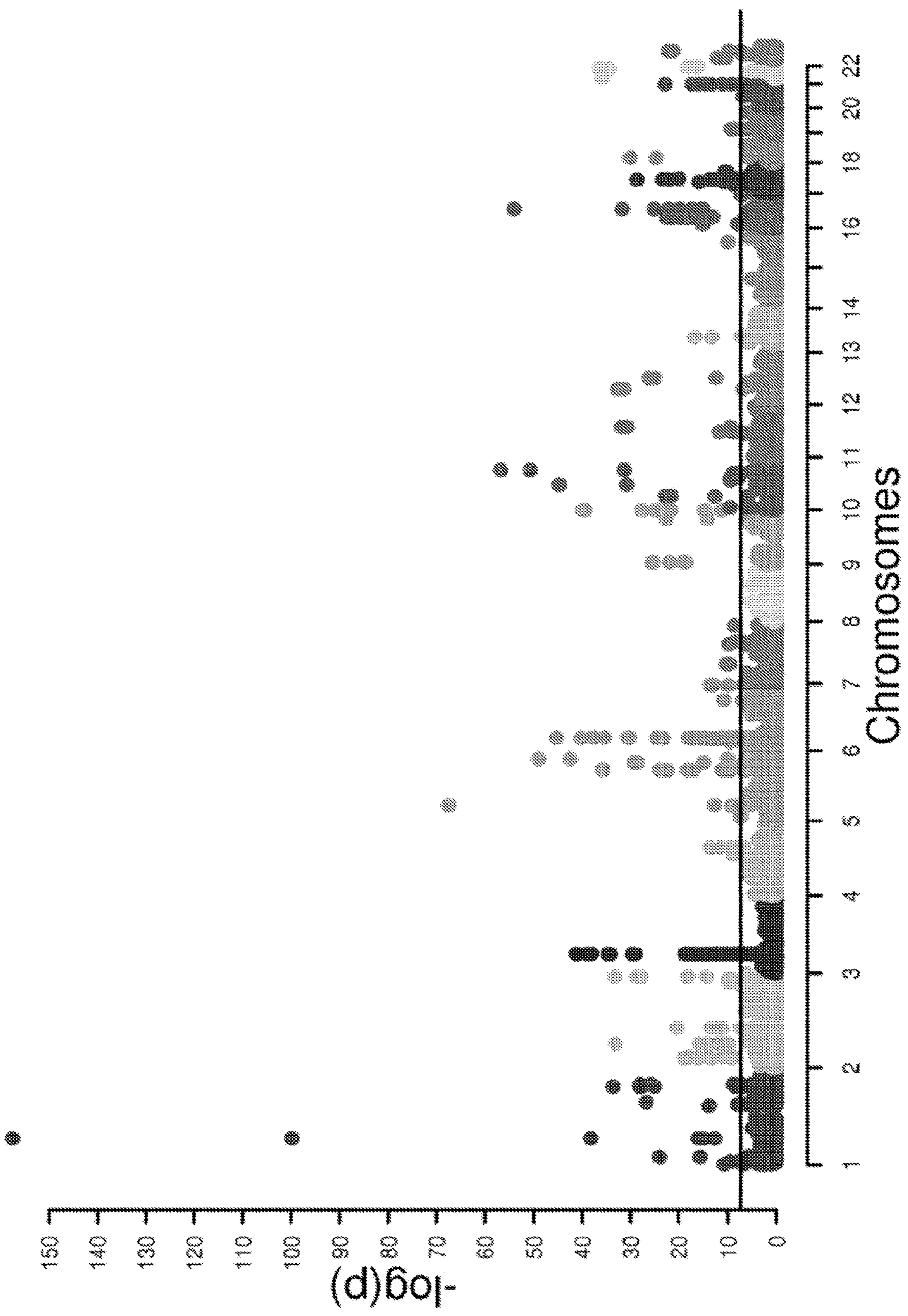
FIGS. 2A-2B depict, in accordance with various embodiments of the invention, Manhattan plots.
Figure 2B:
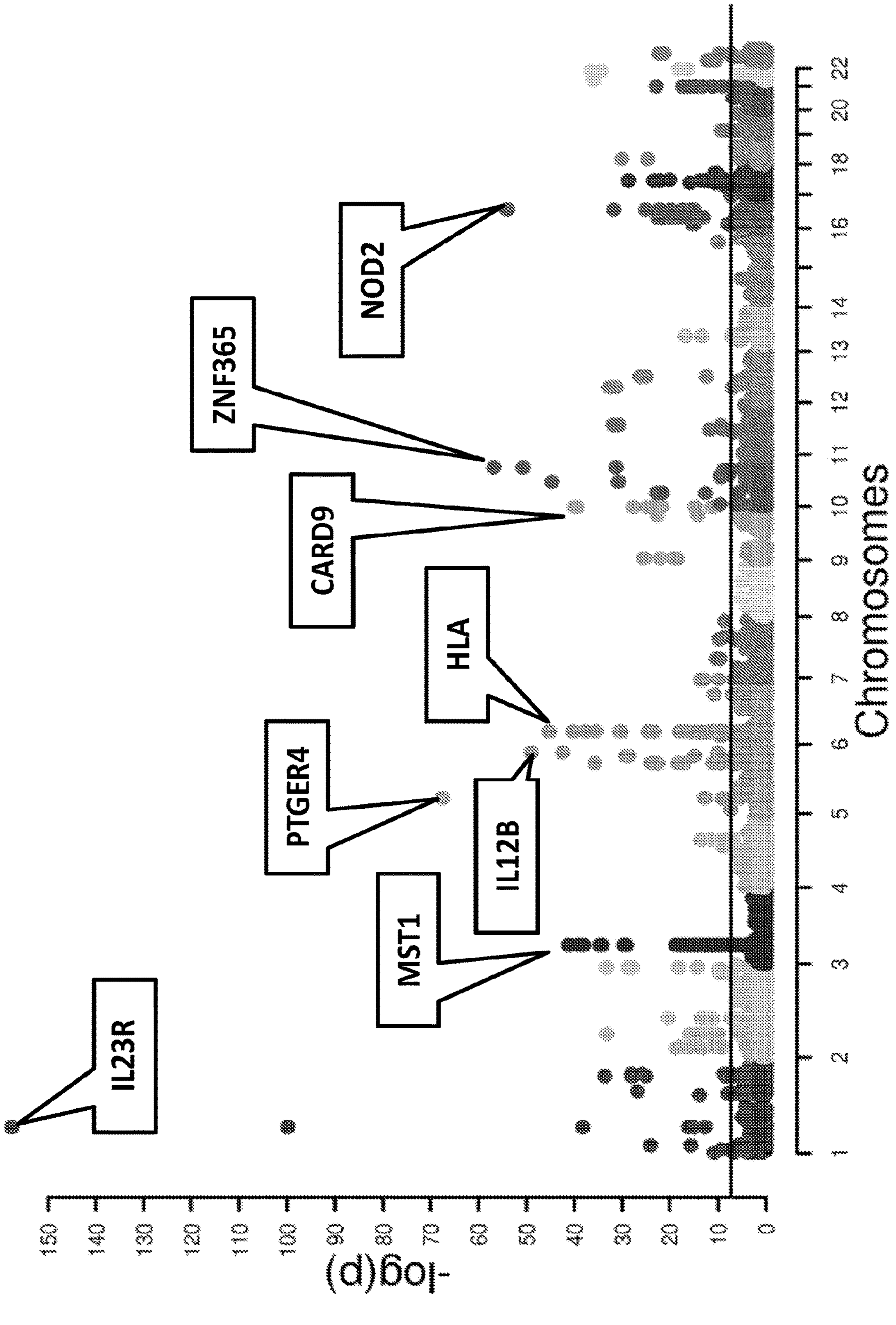
Figure 3:
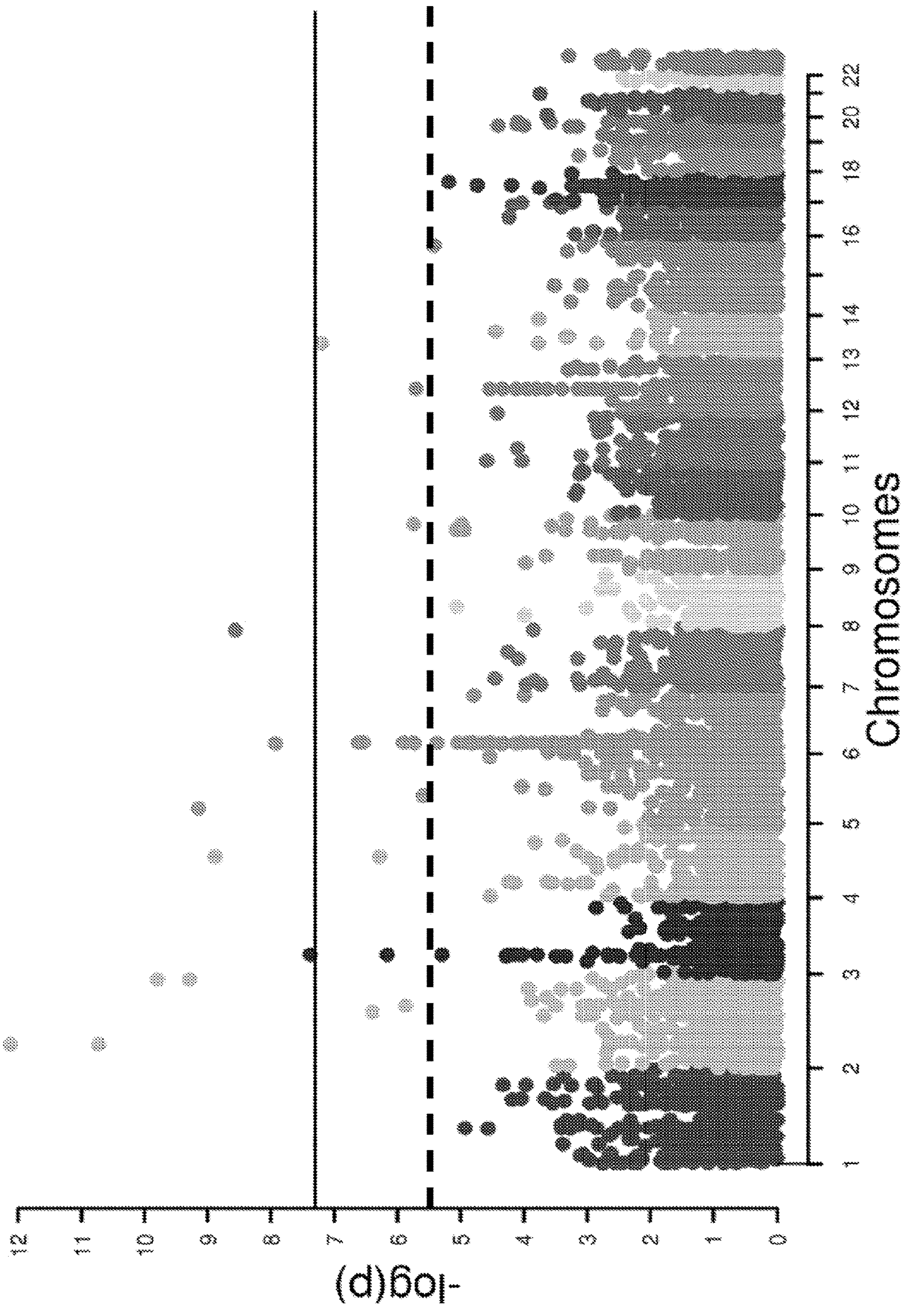
FIG. 3 depicts, in accordance with various embodiments of the invention, Manhattan plot: exclude Jostin regions
Figure 5A:
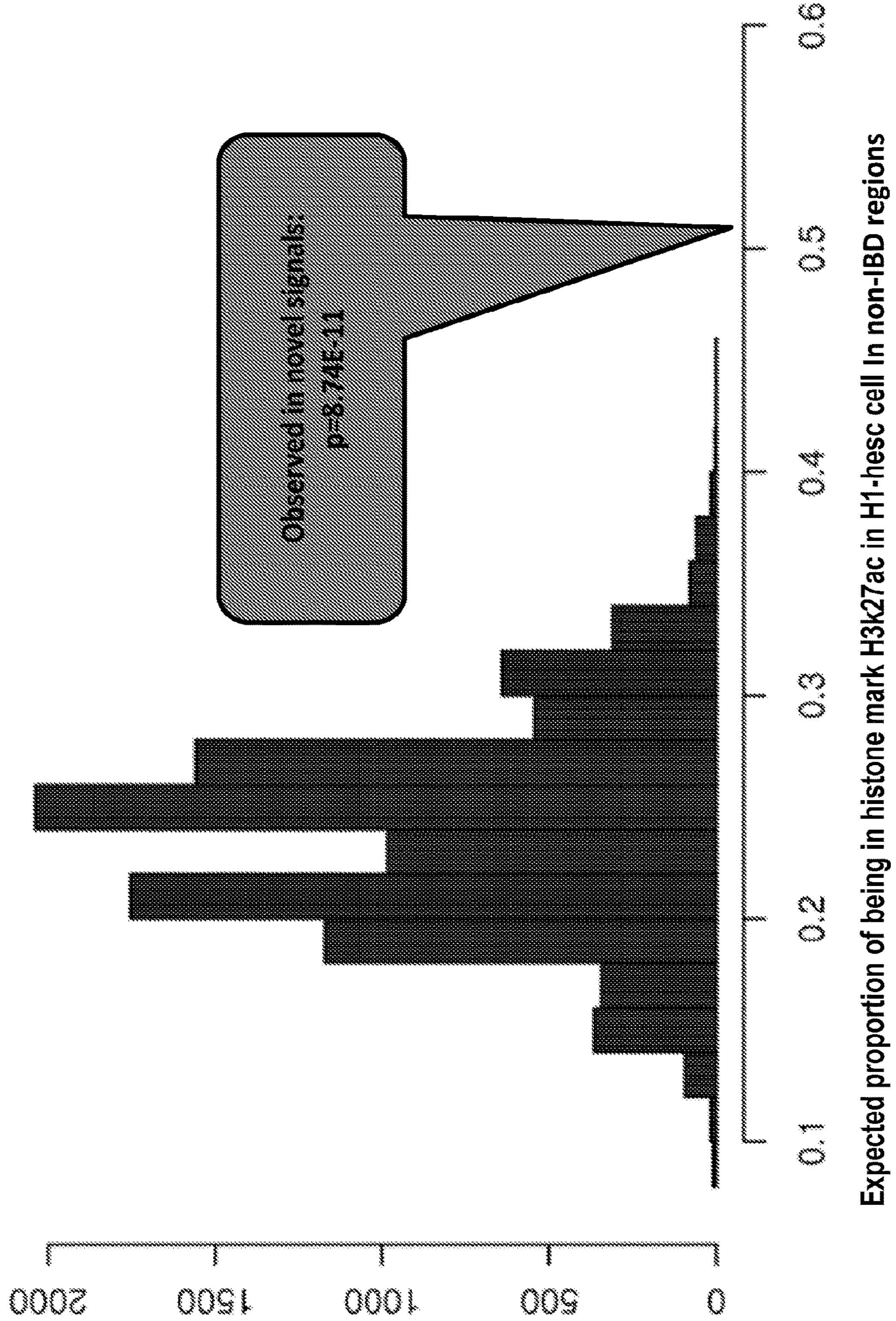
FIG. 5A-5B depicts, in accordance with various embodiments of the invention, (A) increased chance of being in histone marks compared to non-IBD regions and (B) increased chance of being in histone marks compared to known IBD SNPs.
Figure 5B:
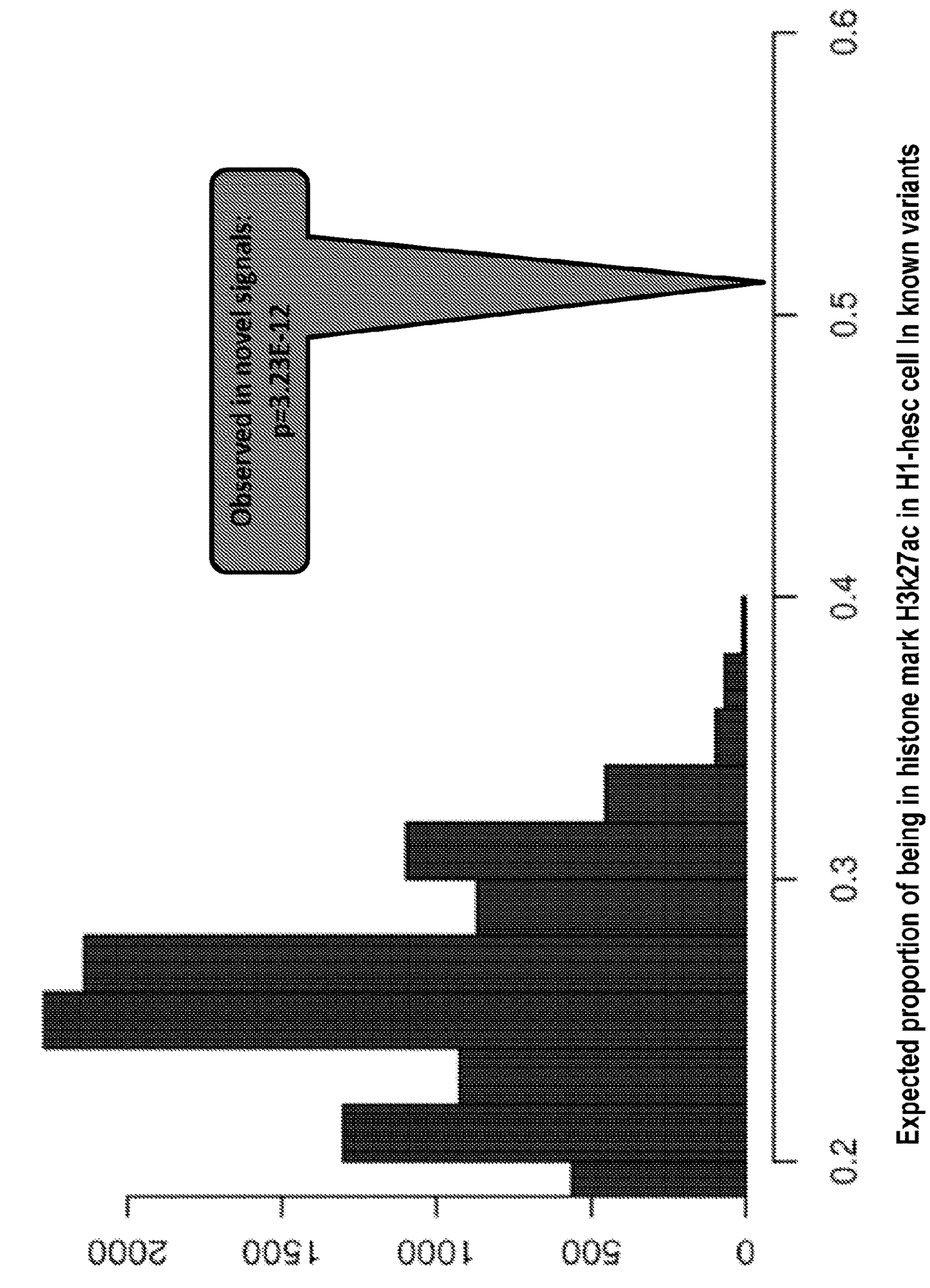
Figure 6A:
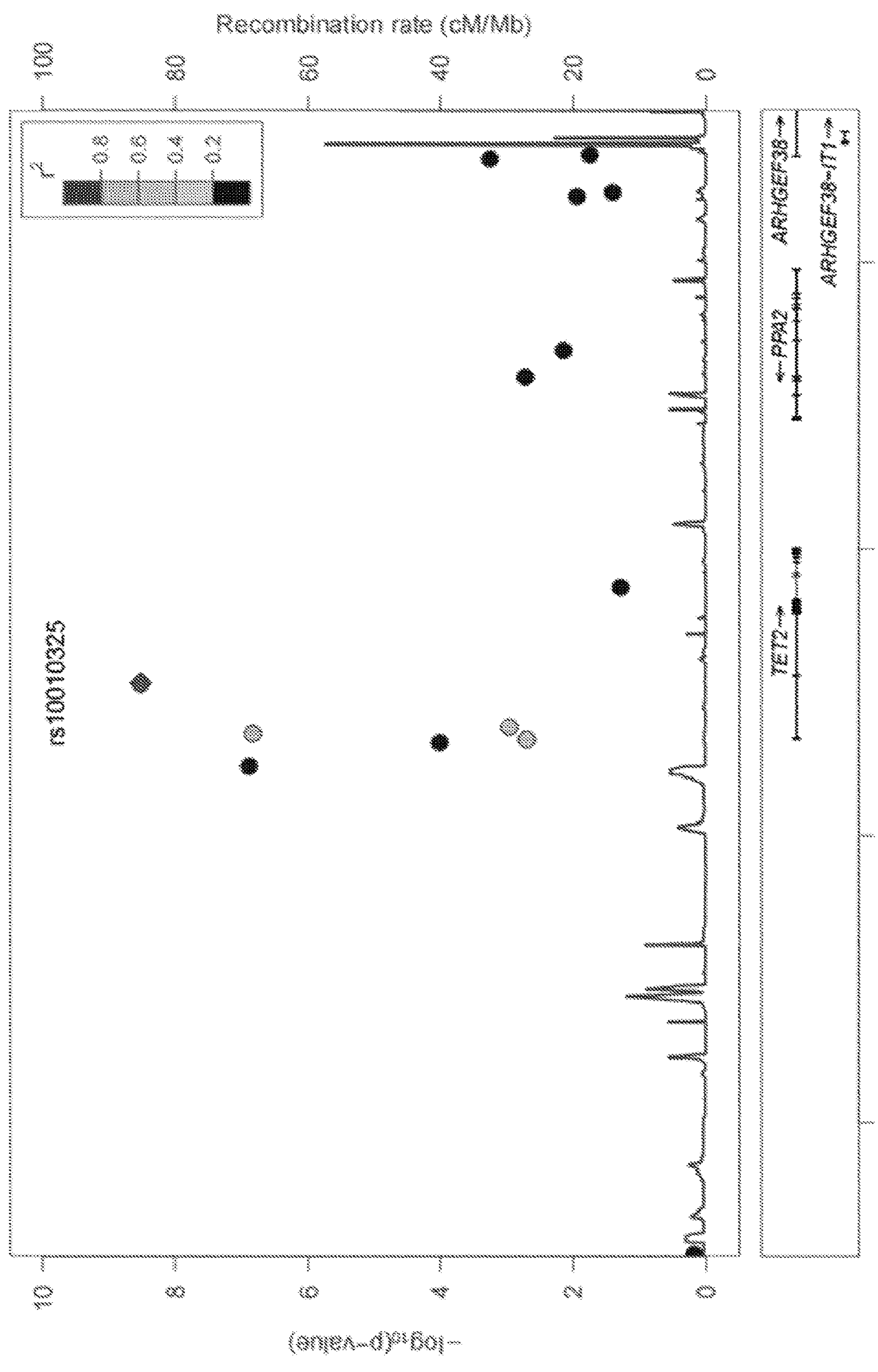
Figure 6D:
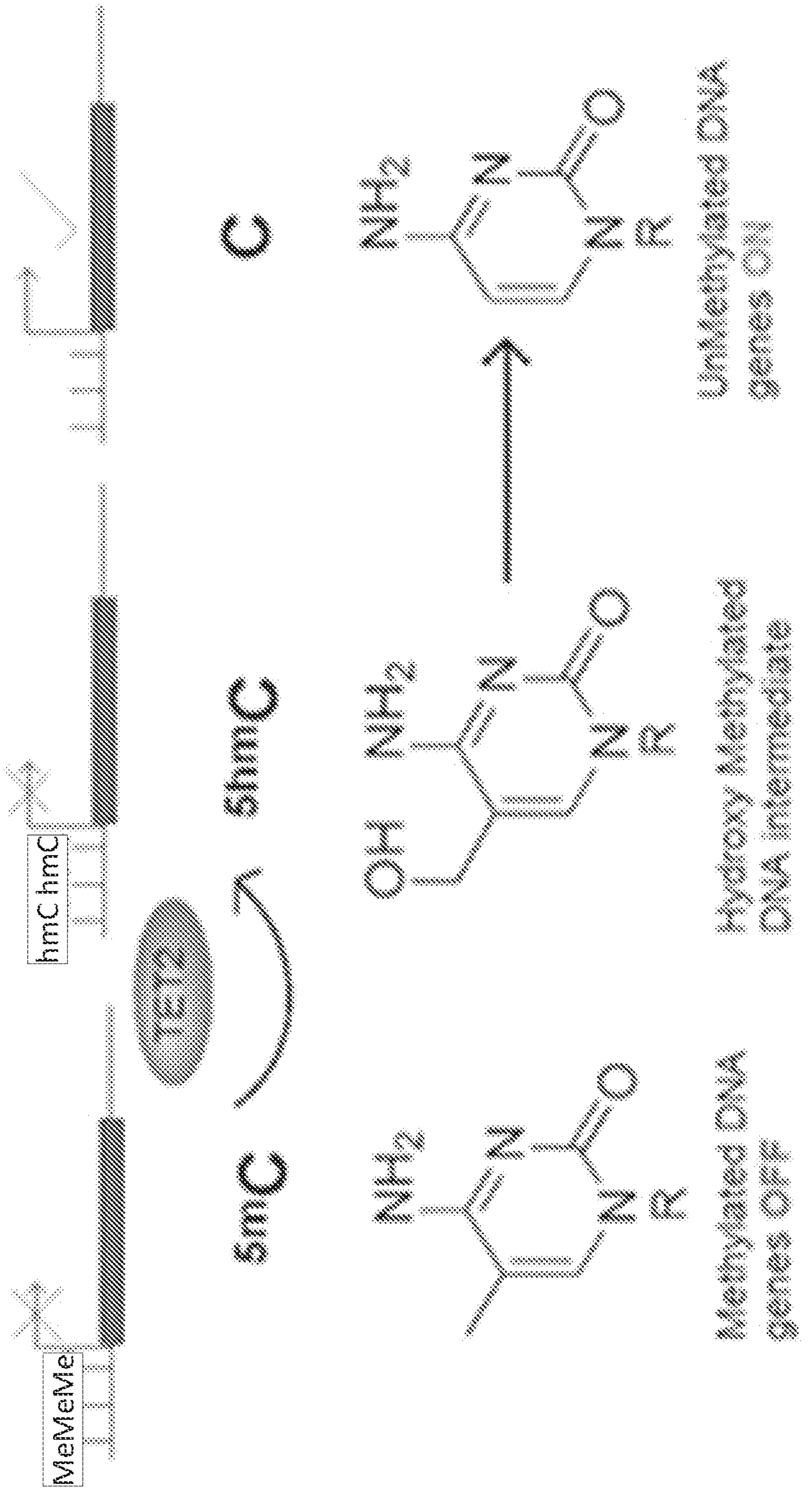
Figure 7A:
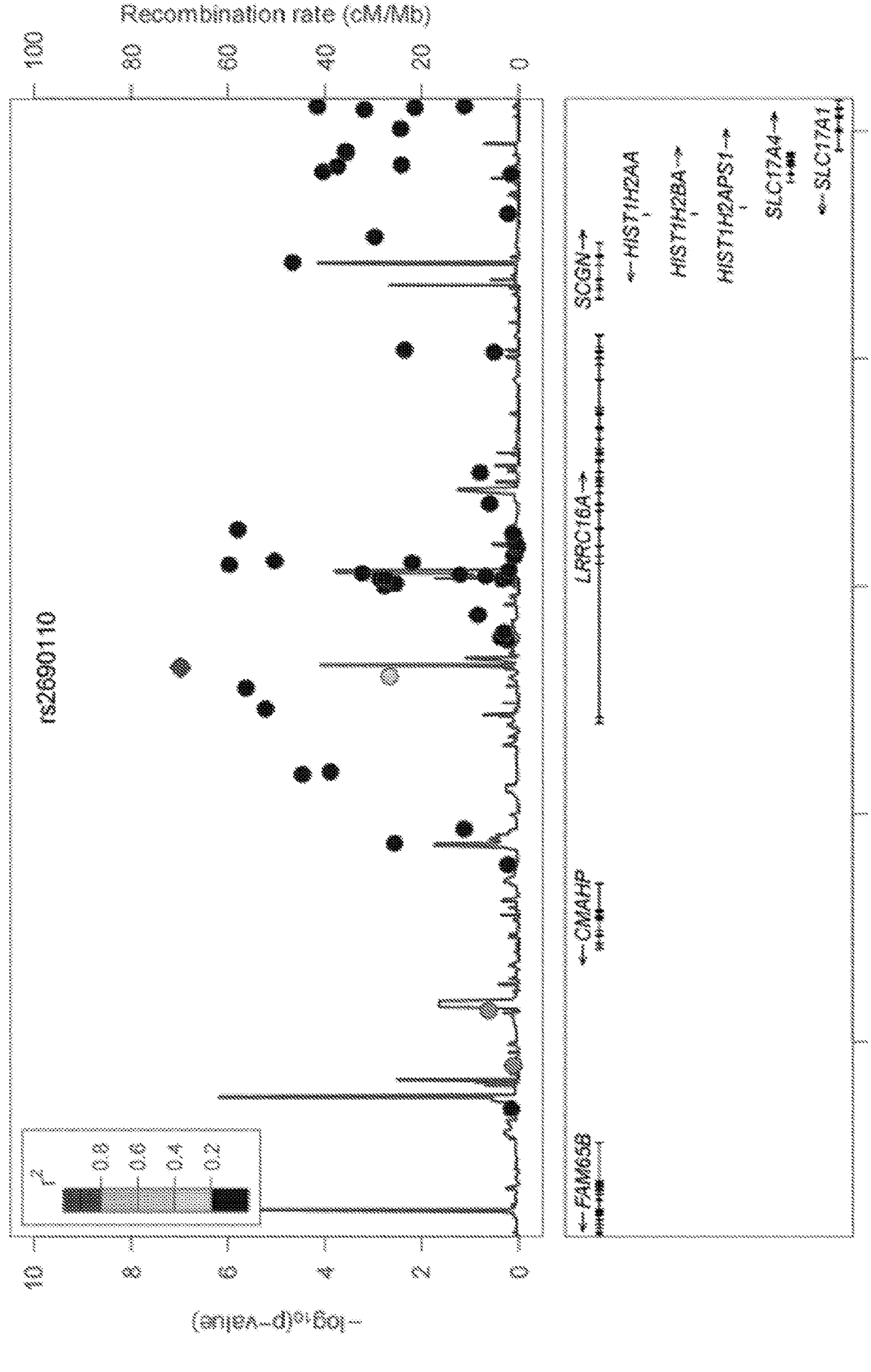
Figure 7B:
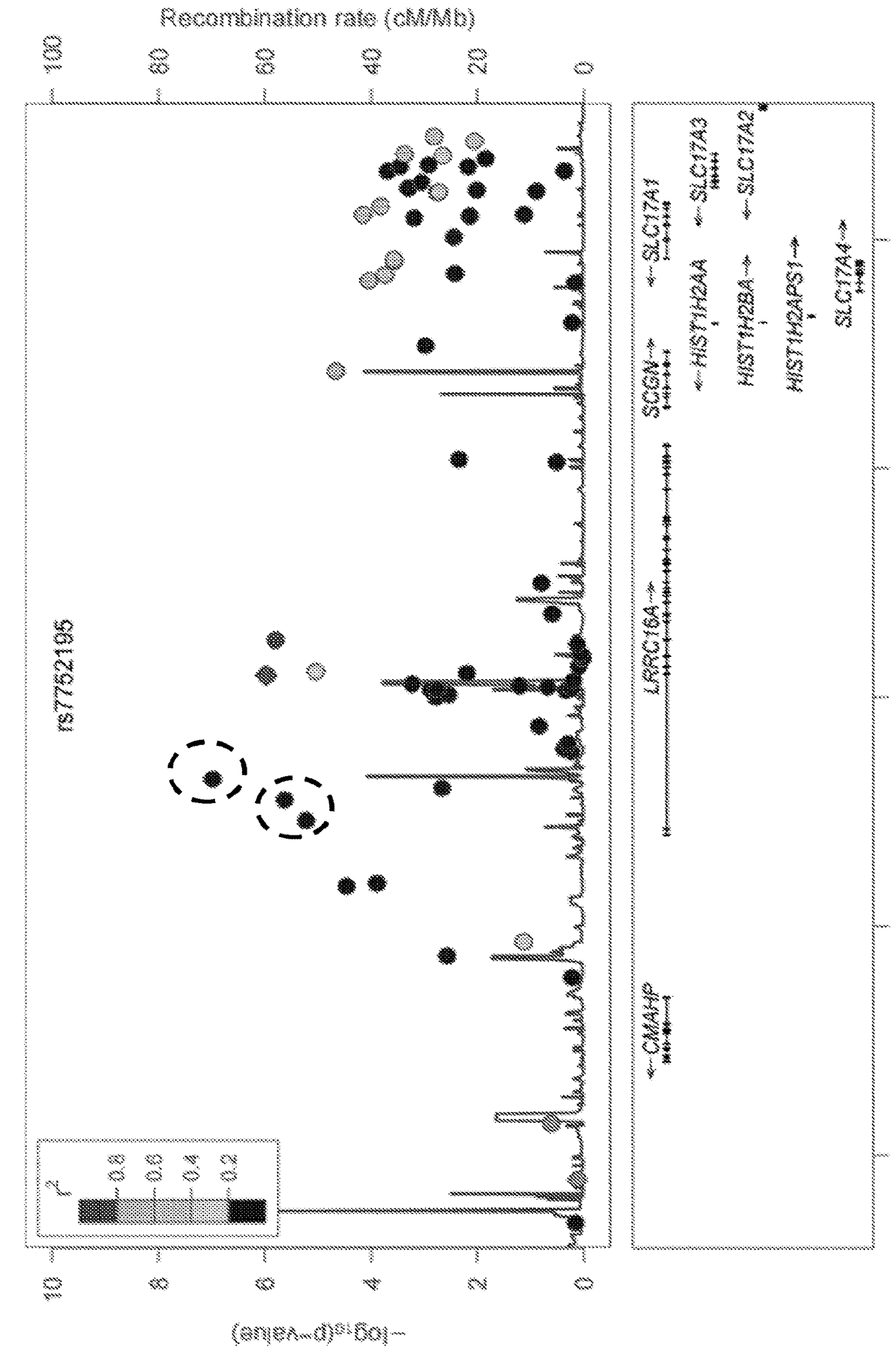
Figure 8A:
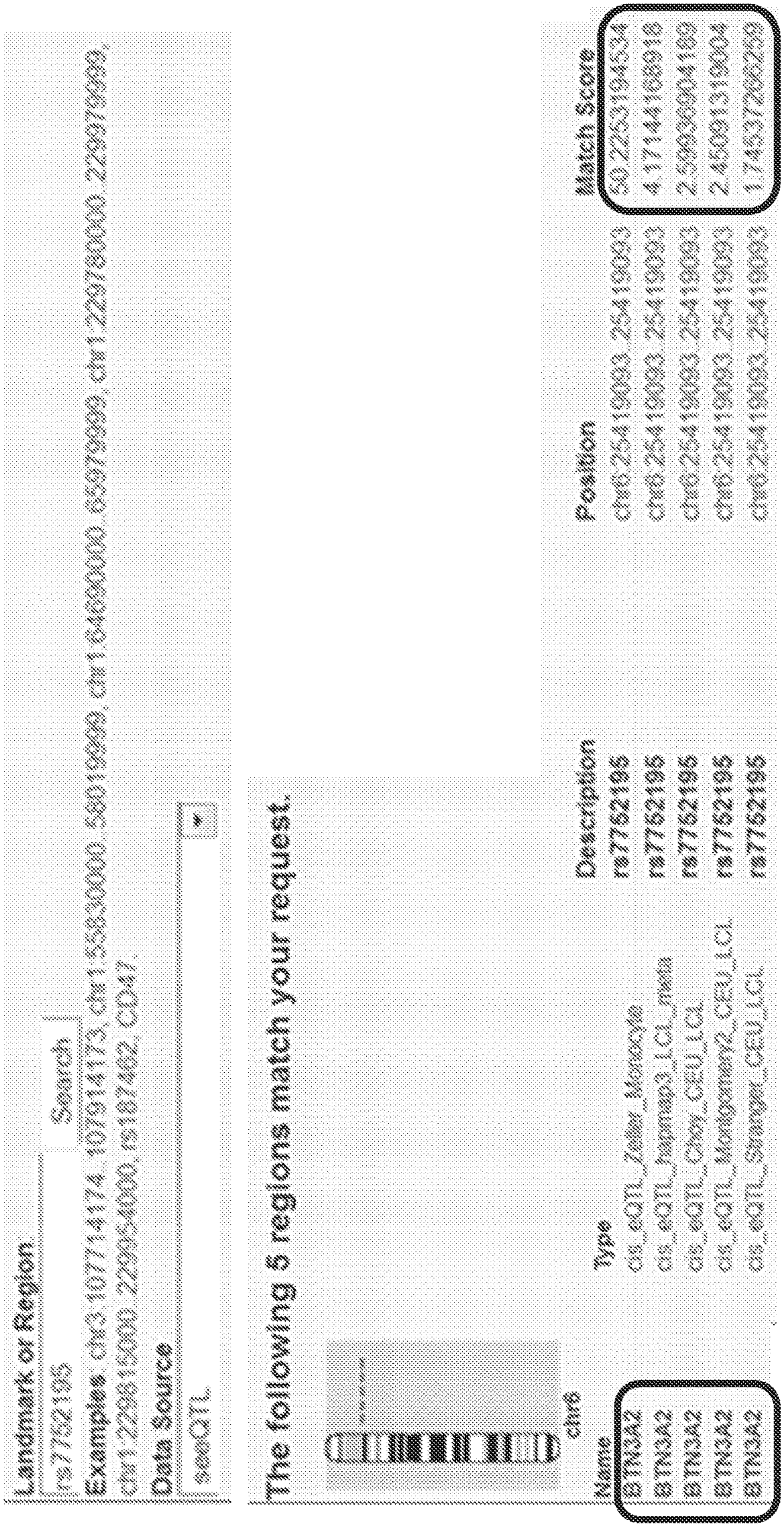
Figure 8C:
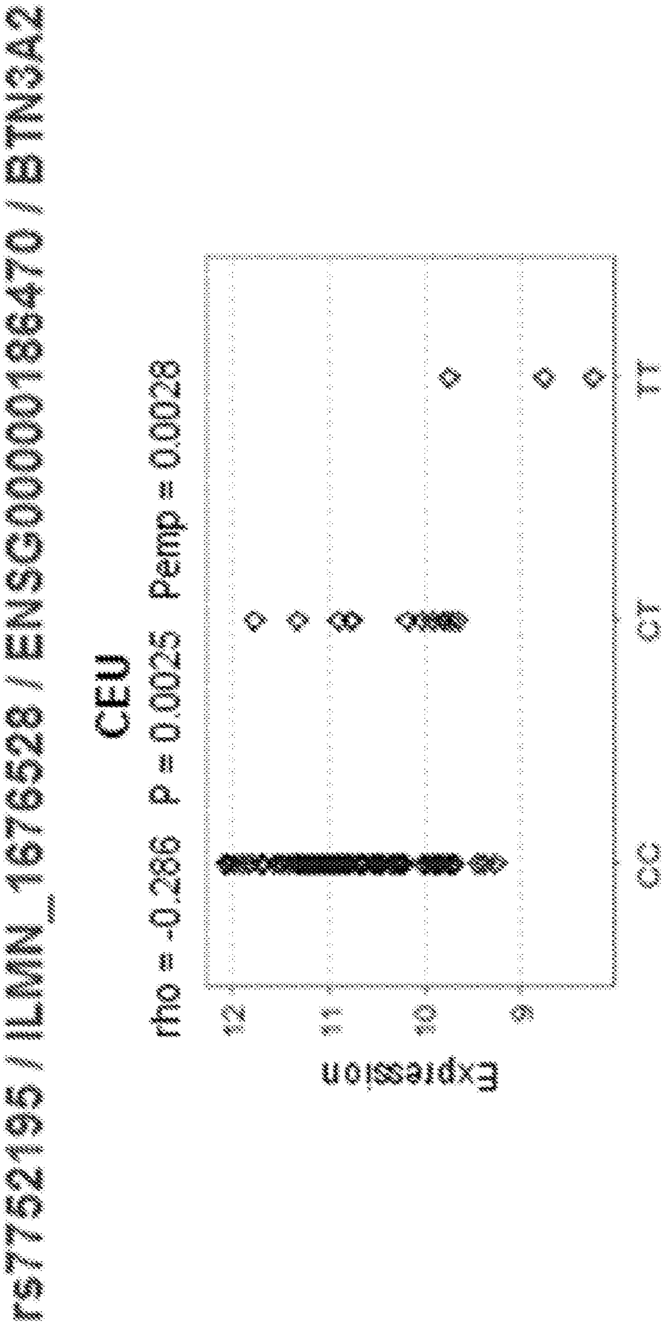
Figure 9B:
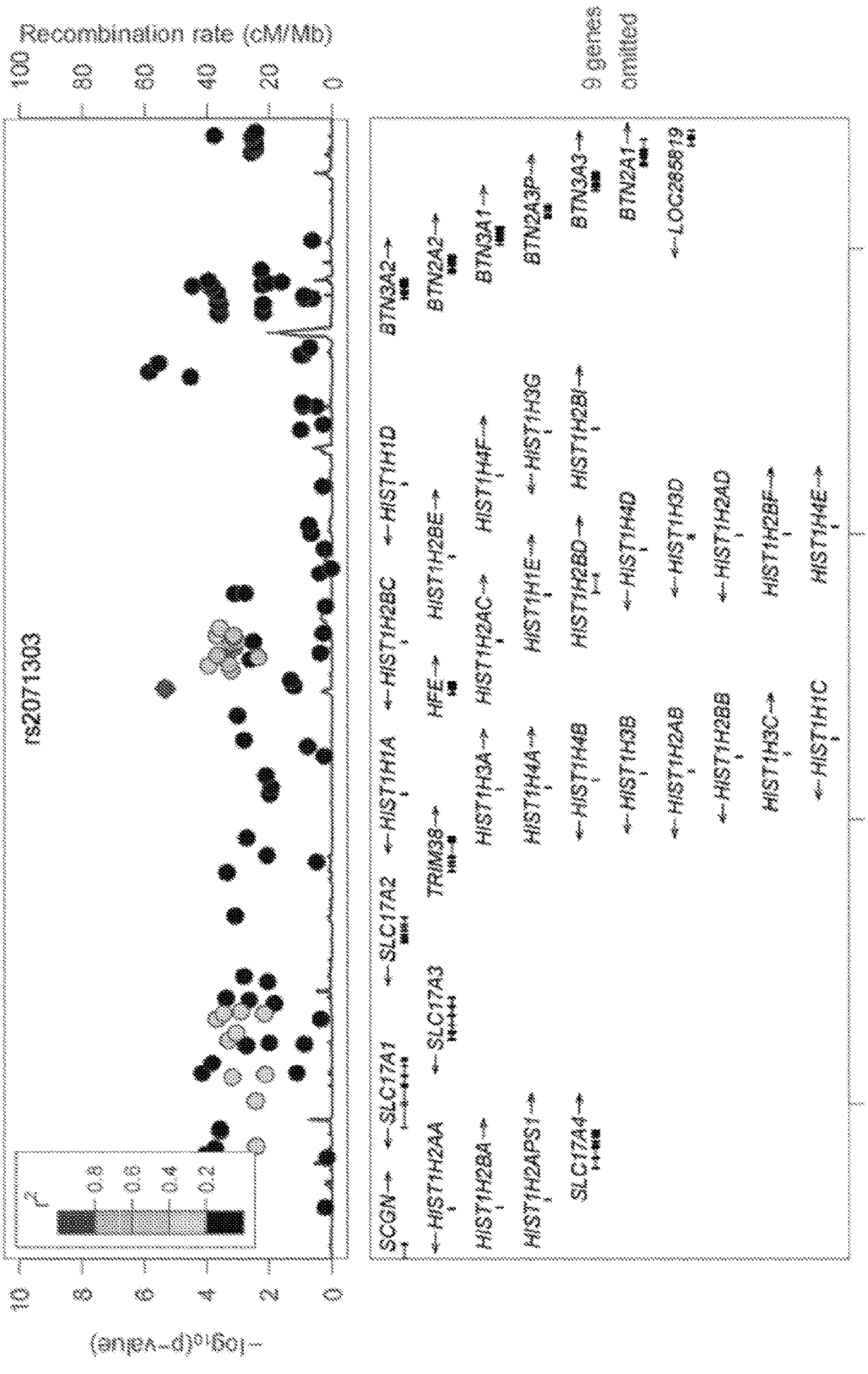
Figure 11B:
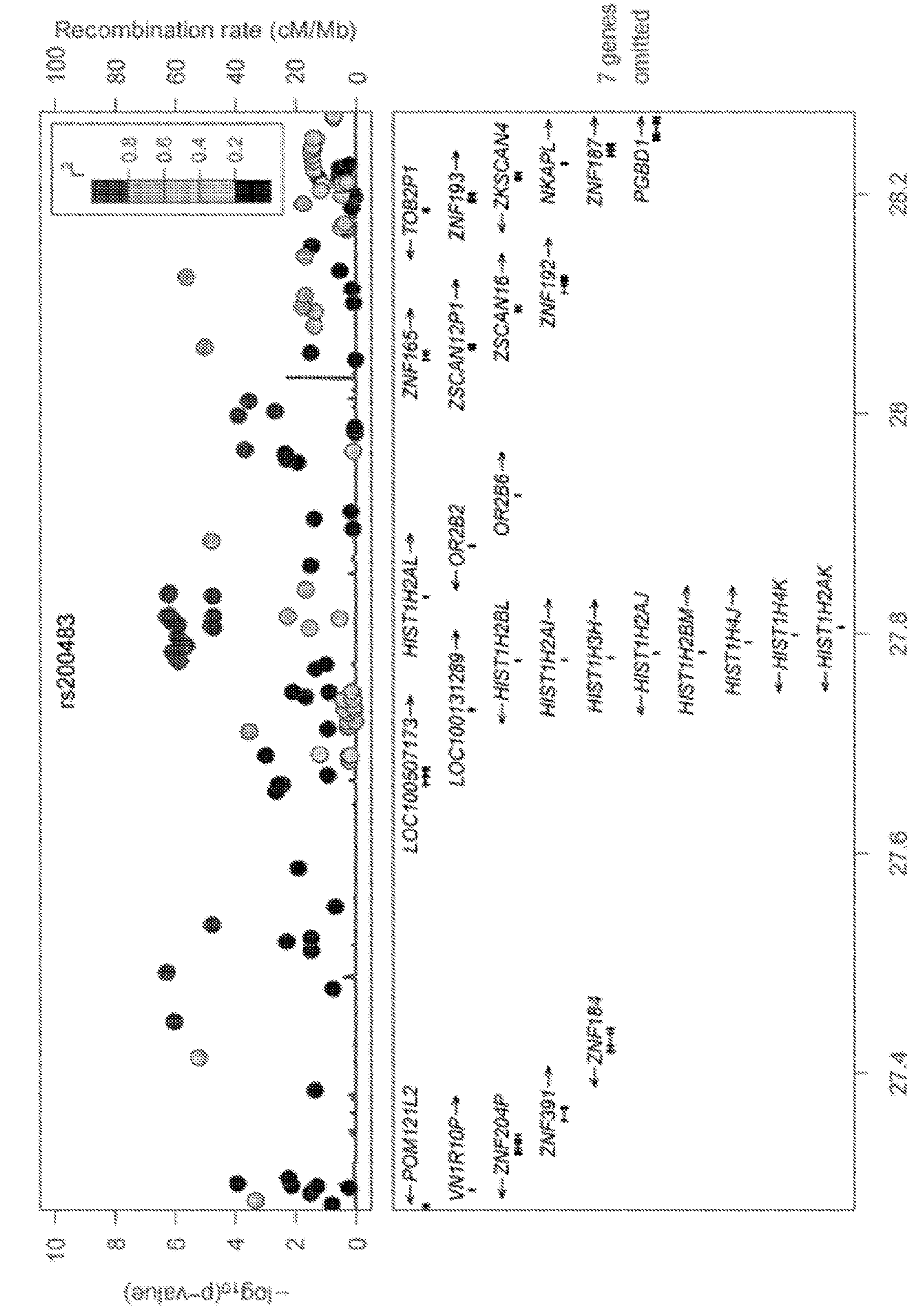

Single-SNP based association drives most GWAS findings mostly because it's simple and straightforward (FIG. 1A). It tests if frequency of a single SNP is the same in case and control. However, it suffers from some drawbacks including: multiple testing correction, forbidding as the number of variants increases, ignoring multiple weak signals; and missing some causal loci.

Gene-based analysis examines a gene as a whole instead of looking at single SNPs (FIG. 1B). It tests if distribution of all the SNPs in a given gene is the same in case and control. It is more powerful, when there are multiple causal SNPs with weak effects. It can reduce multiple-testing penalty for millions of SNPs and about 25000 known genes.

Current approaches for gene-based analysis include data collapsing approaches (e.g., Combining Multivariate and Collapsing approach (CMC), Weighted Sum Statistics (WSS), variable threshold, and comprehensive approach) and distribution based approaches (e.g., C-alpha, SNP Set Kernel Association Test (SKAT), and SKAT-CommonRare. Most of these approaches can only be applied to population-based design, assuming independence of the subjects.

The present invention provides a new approach GLS-SKAT for gene-based analysis in families. Considering the following linear model:

$$\underset{n\times 1}{Y} = \underset{n\times m}{G}\,\underset{m\times 1}{\beta} + \underset{n\times 1}{\varepsilon}$$

For independent subjects:

$$\varepsilon \sim MVN(0,\Sigma^2 I)$$

For correlated subjects:

$$\varepsilon \sim MVN(0,\Sigma^2 \Sigma)$$

To transform the correlated data to independent, we let:

$$UU'=\Sigma; T=U^{-1}$$

So we can multiply T in the linear model:

$$\underset{n\times n}{T}\,\underset{n\times 1}{Y} = \underset{n\times n}{T}\,\underset{n\times m}{G}\,\underset{m\times 1}{\beta} + \underset{n\times n}{T}\,\underset{n\times 1}{\varepsilon}$$

Then, $$\mathrm{var}(T\varepsilon)=\Sigma^2 TUU'T'=\Sigma^2 I$$

That is, the correlated data are now "de-correlated" OLS estimate with the GLS transformed data:

$$\beta_{GLS}=(G'T'TG)^{-1}G'T'TY=(G'\Sigma^{-1}G)^{-1}G'\Sigma^{-1}Y \quad \mathrm{var}(\beta_{GLS})=(G'\Sigma^{-1}G)^{-1}$$

This is exactly the maximal likelihood estimate of the true model:

$$Y \sim N(G\beta,\Sigma)$$

GLS-SKAT is applied to iChip data Cedars vs. BBC: 4600 cases and 6800 controls. SKAT-CommonRare is applied to IIBDGC (excluding Cedars and BBC samples): 30200 cases and 29700 controls. PCA is included to control for confounding factors. Gene region is defined as 100 Kb up and downstream of each gene. Analysis is focused on IBD and genes with at least 2 SNPs (about 8000 genes). Thus, the significant threshold is 0.05/8000-6.25E-6. Fisher's combined P value is used for the meta-analysis of the gene-level p-value.

TET2 codes for Tet Methylcytosine Dioxygenase 2, is involved in Foxp3 demethylation to drive regulatory T Cell differentiation and maintain immune homeostasis.

LRRC16A (leucine rich repeat containing 16A) is a protein-coding gene. Diseases associated with LRRC16A include acute urate nephropathy. An important paralog of this gene is LRRC16B. LR16A_HUMAN Q5VZK9 binds CAPZA2 with high affinity and significantly decreases CAPZA2 affinity for actin barbed ends. It increases the rate of elongation from seeds in the presence of CAPZA2; however, it seems unable to nucleate filaments. It rapidly uncaps barbed ends capped by CAPZA2 and enhances barbed-end actin polymerization b similarity. It may control actin dynamics in lamellipodia, and is required for cell migration.

The whole HIST1 region has joint association. HIST1 cluster portion 1 (~26.2M, first portion) and HIST1 cluster portion 2 (~27.8 M, second portion). After combining the ~1.6M (from 26.2 M to 27.8 M) into one big region, the overall region-based association P value is $1.64\times10^{-7}$.

BTN3 A1/A2/A3 is an interesting gene cluster. Butyrophilin, Subfamily 3; belong to the B7 family members and are expressed in various immune cells such as T and NK cells. BTN3/CD277 comprises three structurally related members, BTN3A1, BTN3A2 and BTN3 A3. It plays a role in T-cell responses in the adaptive immune response, and inhibits the release of IFNG from activated T-cells. It plays an important role in human y8 T-cell antigenic activation. It has differential role for CD277 as a co-regulator of the immune signal in T and NK cells (see e.g., Messal N, Mamessier E, et al. Eur J Immunol. 2011 December;41 (12): 3443-54). While T cells express all BTN3/CD277 transcripts, NK cells express mostly BTN3 A2, which lacks the B30.2 intracellular domain. Furthermore, NKp30-induced cytokine production is decreased by the specific engagement of BTN3A2, but not by BTN3A1 triggering.

We identified fourteen novel loci via gene-based analysis of iChip data (FIG. 4 and Table 1). All of them have multiple weak signals, while some signals are very strong in joint model. BTN3A2 is also strongly implicated in IBD pathogenesis based on the eQTL analysis of the LRRC16A region.

Example 3 Gene-Based Analysis Identified Multiple Novel IBD Loci

More than 200 genetic loci have been identified in Inflammatory Bowel Disease (IBD), mostly via single SNP analysis. In this study, we aim to utilize gene-based analysis, which combines signals from all the SNPs in a gene, to identify novel IBD loci that have been missed in single SNP analysis.

3312 IBD cases from Cedars-Sinai Medical Center and 7154 family and population-based controls with Immuno- Chip data were included as the discovery cohort. Genes with gene-level p-value <0.05 were then replicated in IIBDGC (30179 cases and 29678 controls, with samples overlapped with the discovery stage excluded). SKAT-CommonRare was performed to evaluate the gene-level association. Fisher's combined p-value was calculated to combine p-value from the discovery and replication cohorts. Bonferroni Corrected significance threshold of 6.25E-6 was used for gene-based p-value to count for 7,924 genes with at least 2 SNPs on iChip.

In addition to the known IBD genes such as IL23R and NOD2, we identified multiple novel genes associated with IBD. Those genes include: TET2 (Discovery p-value 0.019, replication p-value 2.82E-9, combined p-value 1.33E-9); LRRC16A (Discovery p-value 1.55E-6, replication p-value 3.43E-5, combined p-value 1.19E-8); and multiple genes in Histone Cluster 1 locus (e.g.: HIST1H4H, discovery p-value 2.89E-5, replication p-value 2.44E-4, combined p-value 4.24E-6; HIST1HIB. discovery p-value 1.45E-4, replication p-value 8.61E-5, combined p-value 2.41E-7). The SNPs of these genes are listed in Table 1.

Our Bioinformatics analysis indicates that top SNP (rs7752195) driving the LRRC16A signal is a strong expression quantitative trait locus (eQTL) (In seeQTL, p=5.96E-51; in SCANdb, p=8E-9; in GeneVar, p=0.0025) of BTN3A2, which plays an important role in regulating adaptive immune response. Moreover, the top gene identified in current study, TET2 which codes for translocation (Tet) methylcytosine dioxygenase 2, was reported to drive T cell differentiation via DNA demethylation of FOXP3. It has also been reported to mediate interleukin-6 (IL-6) transcription by regulation of chromatin structure.

Without being bound to any particular theory, novel loci identified via gene-based analysis in the current study strongly suggest that it is worthwhile to re-examine previous single-SNP based GWAS at gene level.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

The invention claimed is:

1. A kit comprising:

(I) a nucleic acid molecule comprising:

a) a detectable label; and b) at least 10 contiguous nucleic acids identical to at least one of:

i. nucleobases 475-525 of SEQ ID NO: 27, the nucleic acid molecule comprising an "A" at nucleoposition 501;

ii. nucleobases 475-525 of SEQ ID NO: 147, the nucleic acid molecule comprising an "A" at nucleoposition 501;

iii. nucleobases 26-76 of SEQ ID NO: 174, the nucleic acid molecule comprising an "A" at nucleoposition 51;

iv. nucleobases 475-525 of SEQ ID NO: 55, the nucleic acid molecule comprising an "A" at nucleoposition 501;

V. nucleobases 275-325 of SEQ ID NO: 42, the nucleic acid molecule comprising an "A" at nucleoposition 301; and vi. nucleobases 585-635 of SEQ ID NO: 33, the nucleic acid molecule comprising an "G" at nucleoposition 604; and (II) an inflammatory bowel disease (IBD) therapy comprising an anti-Tumor Necrosis Factor-like Cytokine IA (TL1A) therapy or an anti-Tumor Necrosis Factor-alpha (TNFa) therapy.

2. The kit of claim 1, wherein the anti-TL IA therapy is an anti-TL IA antibody or antigen-binding fragment.

3. The kit of claim 1, comprising the at least 10 contiguous nucleic acids identical to nucleobases 475-525 of SEQ ID NO: 27, the nucleic acid molecule comprising an "A" at nucleoposition 501.

4. The kit of claim 1, comprising the at least 10 contiguous nucleic acids identical to nucleobases 475-525 of SEQ ID NO: 147, the nucleic acid molecule comprising an "A" at nucleoposition 501.

5. The kit of claim 1, comprising the at least 10 contiguous nucleic acids identical to nucleobases 26-76 of SEQ ID NO: 174, the nucleic acid molecule comprising an "A" at nucleoposition 51.

6. The kit of claim 1, comprising the at least 10 contiguous nucleic acids identical to nucleobases 475-525 of SEQ ID NO: 55, the nucleic acid molecule comprising an "A" at nucleoposition 501.

7. The kit of claim 1, comprising the at least 10 contiguous nucleic acids identical to nucleobases 275-325 of SEQ ID NO: 42, the nucleic acid molecule comprising an "A" at nucleoposition 301.

8. The kit of claim 1, comprising the at least 10 contiguous nucleic acids identical to nucleobases 585-635 within SEQ ID NO: 33, the nucleic acid molecule comprising a "G" at nucleoposition 604.

9. The kit of claim 1, comprising at least 10 contiguous nucleic acids identical to at least two of (i) nucleobases 475-525 of SEQ ID NO: 27, the nucleic acid molecule comprising an "A" at nucleoposition 501; (ii) nucleobases 475-525 of SEQ ID NO: 147, the nucleic acid molecule comprising an "A" at nucleoposition 501; (iii) nucleobases 26-76 of SEQ ID NO: 174, the nucleic acid molecule comprising an "A" at nucleoposition 51; (iv) nucleobases 475-525 of SEQ ID NO: 55, the nucleic acid molecule comprising an "A" at nucleoposition 501; (v) nucleobases 275-325 of SEQ ID NO: 42, the nucleic acid molecule comprising an "A" at nucleoposition 301; and (vi) nucleobases 585-635 within SEQ ID NO: 33, the nucleic acid molecule comprising a "G" at nucleoposition 604.

10. The kit of claim 1, comprising at least 10 contiguous nucleic acids identical to at least three of (i) nucleobases 475-525 of SEQ ID NO: 27, the nucleic acid molecule comprising an "A" at nucleoposition 501; (ii) nucleobases 475-525 of SEQ ID NO: 147, the nucleic acid molecule comprising an "A" at nucleoposition 501; (iii) nucleobases 26-76 of SEQ ID NO: 174, the nucleic acid molecule comprising an "A" at nucleoposition 51; (iv) nucleobases 475-525 of SEQ ID NO: 55, the nucleic acid molecule comprising an "A" at nucleoposition 501; (v) nucleobases 275-325 of SEQ ID NO: 42, the nucleic acid molecule comprising an "A" at nucleoposition 301; and (vi) nucleobases 585-635 within SEQ ID NO: 33, the nucleic acid molecule comprising a "G" at nucleoposition 604.

11. The kit of claim 1, comprising at least 10 contiguous nucleic acids identical to at least four of (i) nucleobases 475-525 of SEQ ID NO: 27, the nucleic acid molecule comprising an "A" at nucleoposition 501; (ii) nucleobases 475-525 of SEQ ID NO: 147, the nucleic acid molecule comprising an "A" at nucleoposition 501; (iii) nucleobases 26-76 of SEQ ID NO: 174, the nucleic acid molecule comprising an "A" at nucleoposition 51; (iv) nucleobases 475-525 of SEQ ID NO: 55, the nucleic acid molecule comprising an "A" at nucleoposition 501; (v) nucleobases 275-325 of SEQ ID NO: 42, the nucleic acid molecule comprising an "A" at nucleoposition 301; and (vi) nucleobases 585-635 within SEQ ID NO: 33, the nucleic acid molecule comprising a "G" at nucleoposition 604.

12. The kit of claim 1, comprising at least 10 contiguous nucleic acids identical to at least five of (i) nucleobases 475-525 of SEQ ID NO: 27, the nucleic acid molecule comprising an "A" at nucleoposition 501; (ii) nucleobases 475-525 of SEQ ID NO: 147, the nucleic acid molecule comprising an "A" at nucleoposition 501; (iii) nucleobases 26-76 of SEQ ID NO: 174, the nucleic acid molecule comprising an "A" at nucleoposition 51; (iv) nucleobases 475-525 of SEQ ID NO: 55, the nucleic acid molecule comprising an "A" at nucleoposition 501; (v) nucleobases 275-325 of SEQ ID NO: 42, the nucleic acid molecule comprising an "A" at nucleoposition 301; and (vi) nucleobases 585-635 within SEQ ID NO: 33, the nucleic acid molecule comprising a "G" at nucleoposition 604.

* * * * *

```
                         SEQUENCE LISTING


Sequence total quantity: 341
SEQ ID NO: 1             moltype = DNA  length = 1001
FEATURE                  Location/Qualifiers
source                   1..1001
                         mol_type = genomic DNA
                         organism = Homo sapiens
SEQUENCE: 1
cctaaggaag ttctagacta gtgtttcatg gagcccattc ttttaaatta aaagtagcca  60
tttaaaaaaa ttaaagtccc agaaaatgac cattagaata tgcaatttaa aaatagcaaa  120
taaaacaaac taaggttttt ttgaacagat atatagaaac aaaatttcac ttagtttaca  180
atataaacat gcatttcaca ttagcattaa aatgctattg tgatttatct ctctttcaaa  240
tactattgcc tctacttaca caatcatatt tgtcctttcg ccacaatctg cctatttcag  300
caaactgcat cagcattccc tttaagtttc ccaatgctaa agctgccagg acggactgtg  360
aaaaacacaa acatcagatg tactttaagt taatgaaata aaccacaggg aagcaaaggt  420
gaaggctata gataagtgtg tgctttaaag ggcctcaaag caaatcaaag cattacaccc  480
ttttccggtg tgcgatgcca rgcaagacac accagaactg ggactctgac ctgttcctat  540
gaatgacttt gtccccacaa cagtgacaag gcctaggctg ctcttgtgat tatgagatag  600
atgatctgat ggcgtttagt agcctgcacc ttgggacaga gaaaggcaga ccttcagacc  660
tatgacagac taacatttgg aataaattcc tcccaagcag agacagtcta atgtgtgttt  720
gtttattgga gtcaaggaga tgggggttgc tctttgttaa aaaaaaaaat agcttgggaa  780
gcttgaggtc ctggaatgag atgacttgag gcgggctttc tgggacagca tgaaacatat  840
ctatctagtt cctgctatat ccccagaacc tactatgtta aatgcataca ggaggggctt  900
taaaattagt cagtgaatga gtggctgagc caatgaatga atatttccca ggccagtact  960
aatccctaca gccaagcttc agacttccaa ttcttccaca g                      1001

SEQ ID NO: 2             moltype = DNA  length = 1001
FEATURE                  Location/Qualifiers
source                   1..1001
                         mol_type = genomic DNA
                         organism = Homo sapiens
SEQUENCE: 2
ttgtttattg gagtcaagga gatgggggtt gctctttgtt aaaaaaaaaa atagcttggg  60
aagcttgagg tcctggaatg agatgacttg aggcgggctt tctgggacag catgaaacat  120
atctatctag ttcctgctat atccccagaa cctactatgt taaatgcata caggaggggc  180
tttaaaatta gtcagtgaat gagtggctga gccaatgaat gaatatttcc caggccagta  240
ctaatcccta cagccaagct tcagacttcc aattcttcca cagccagaat gtgatctttt  300
atcttgcagg aattgtgata gttaaggtga aaaatgctga atagctaagt atattctctt  360
cattctttgg attttatcgt aattgtagga acatgcccct caccgtcctg ttccccctgc  420
caatttattt tattctgaat ggagtatgga atttgtatac tgctatacca tgaaaacaca  480
gtgtacaaag aaaagccaaa hacagttttt atttttatat cttgaggaca gttgaactga  540
tctgcctatt tctaattttc acaggtaatc cttataatat aatatctaag caattaattt  600
tactaactgt gagaatagag gtcacagttt agaagaaata tggtcttaag tgacttttaa  660
aaaatttggc acacaagtga atgccagtta aaaaatggtg aaaattgaat aaagtctgta  720
atctacttaa catactatac taatgtatag tactgatatt gtactacagc tgtgtaagat  780
gtcaccattg tggtagctag gcaaagaagt cagaggactg tacaacgggc ctctccattt  840
tgcaggactt ttaattctct aagtataaaa tatgtcaaga gacacctgtg cgaagagact  900
ttttttttcc attgggcatt atttcccacc tagtcagtat tctacggaaa aacaatttga  960
agtaatttac gatgacatac atatacaaca gattactttt a                      1001

SEQ ID NO: 3             moltype = DNA  length = 1001
FEATURE                  Location/Qualifiers
source                   1..1001
                         mol_type = genomic DNA
                         organism = Homo sapiens
SEQUENCE: 3
tcttagatat tgaattatat gctaaggttc tttggaacta gcttcctgaa ttttacacag  60
ttgacatatt ttcattggaa caatcataaa acgaaagatc attaaaatat taaggaaaca  120
aaggttaaag agggaaacgc tgatttcttt actgtaaata gatcccaatt tgcatctttt  180
aaatcctttt ggatttcccc atctggtccc ctccctgtta taggcactaa ataaatatta  240
gaaaacagtc ccttcaaaac atgtagtcct ttccttattt gccctgcctc tcttctaaaa  300
aaaaagaaaa acagaactaa ctagagatta ttggctgcac aaacccatca gcacctgcca  360
gtttttaaat ttcattttgg aaaatcagcc atcacttaag ggacttgtcc ataatagctt  420
cattaaagct ttgtttttta tcaaaagggg gccacatatg taaacttgtg gaagtaattt  480
acctcctcta ctcttgtctt rttatttgat tgcaaaagtt aatgttatta aagttgctat  540
ggaagcatta atgttcagcc tgaacaagag cttgacgaac ttctttatac aagcaataac  600
actctgcaac cccattttat gagatatttt tcatgatgta gacatttact ttcttagcac  660
aagtgatctc ttaagattaa tttcttttcc attttccttc agttttaaat gatgtaatat  720
agtaatcttt ataacatgat cagccaagta taatttgaga agtcagttct gttggcaaat  780
atctgaagga caaaaccaaa gccaccctag ctgaggtttt tgtcccttcc ttctttcatt  840
taccaaaaac cttaattggg ttaacagtag gggaatttta gaaatcatgt tttcctaatg  900
taacctgtga aacaaaagca aaatagatta aggcaagggg aaaaatgaac ttaccaagag  960
tgttcttttt cctaagtaaa aaccacaaat tttatagttt t                      1001
```

```
SEQ ID NO: 4            moltype = DNA  length = 1001
FEATURE                 Location/Qualifiers
source                  1..1001
                        mol_type = genomic DNA
                        organism = Homo sapiens
SEQUENCE: 4
gatttcctgg tggatttttt ggcttgatca gcttaagaaa aatggagttg tcattaactg  60
aggtagaaaa aatgctggta gagcagatta ggggaagatc agcagatcag ccttgacatg  120
ttgaaatcca gaggaagatg ctagaaacat gaattaaata tccctctttt atattcttgt  180
tcatgcagtg tagggtcagc catttaaaaa atttcattta catttctaag tggtaagttc  240
ctgtgtttag acaaaaatat gtatcaagtg cttaaataac ttacaaaata attttaaaga  300
tacactgctc aacatgtatt actttcacac tttatgaatt tctgtaatgt atttgtctct  360
tcacaagttg ttctgtctcc cagttgcctc ctctcccctc caatcttgtt ctggtttata  420
tacgtttatt tttatcttcc aacatggtct cttgacttct tcctaaatta gggatcagat  480
tttggtacta ggaaatttcc ratatgtgct ctgaggcagg caagtagagg ctcagcccca  540
tgtattccca ttactagaag catacccaac cttagtggcc tacaagaaag aaaacattta  600
aggataagga taagtaaacc tctaaggtgt taaggttgaa tgtactgtga tgtgggcaca  660
agaattggag tgcttgtgct tgtttcttga gtttttgtt tttgtttggt ttggtttggt  720
ttggttggca agaagagtgc agagggcacc tttgcttggg aagatggaga cctcagcgac  780
aatcctatat ataaggcatt tgcctcaact tcaagccaaa tgattgagta aataggctcc  840
tgttttcaat ttcgacttcc tactcttttt agaggagaag ttcttaaccc aagatttgtg  900
aggcatttta tatgtaaatt gtgtgtgtgt gtgtgtgtgt gtgtgtgtgt gtgtgtgtgt  960
gtgtgtgtat tttttccccc aaagtccata gggtgtatga g                     1001

SEQ ID NO: 5            moltype = DNA  length = 1001
FEATURE                 Location/Qualifiers
source                  1..1001
                        mol_type = genomic DNA
                        organism = Homo sapiens
SEQUENCE: 5
aattgagtca ttattaaaat gtccaatcgt cccataaatg ccttaattaa aaaacaattt  60
attcaaatca ggagttatac cacctacttt tgatattttt ctttcatctg taggtcactg  120
aatttaaaaa ctaccaagta gcaaggtata aggtatacat tcctcatgct aagatttttg  180
taaaaactag ctccaggctt gtattgccaa aatatactca gtgtgtttat cttctttaaa  240
gaaaataata ataataaggc gcctggatta ggagtctgaa aagtaatctc catttagaga  300
ctccacatcc atcagtctct ggctggacca gaaaataggt ttttgtgtag gaatattttt  360
tcagaggatt aaaaatgtga gcgaggggtg ggacacttaa tcctgtgttc tctagaagag  420
tgcatttaaa aggatagata cagttcttgg caaaagcatg gtaagcactt cagggttatt  480
attttccagg aaatacttat rctttttcca aatagttata aacatcagca gaatccagtt  540
cataactttg tgatttgcaa attggttgtg actgagattg gattgaaaac ccagttttct  600
tgctttttga cagttgttca agaaagagag cctttggtgt gctaaagact cttgtgccca  660
tcttggagtg gctccccaaa taccgagtca aggaatggct gcttagtgac gtcatttcgg  720
gagttagtac tgggctagtg gccacgctgc aaggtaagat gttggcagat tgagagttct  780
ggtctccagc aggagtttaa cacttctccc cagctaccat aggtctgtga cagatggttg  840
cttacccttc aaggcctgta tctttcctgt agagcccctt agtggagaga gtcacctctc  900
ttctcccctt ccttagagtt ctcttcctgg gaaactgctg ccccactagg tgcagaggtc  960
caatttagag gcatatacta ggcagtggct tctcaatttt t                     1001

SEQ ID NO: 6            moltype = DNA  length = 1001
FEATURE                 Location/Qualifiers
source                  1..1001
                        mol_type = genomic DNA
                        organism = Homo sapiens
SEQUENCE: 6
tcaggctaat atctcagaga gtagttaaac tttaggctct tgattggggt tccagggcag  60
gactctgtca ctgaaaggga atcctagttc tcagcatact aggaaaaata gccaagagag  120
gaacttatgc cctaaagaac aaggcatgaa tctaattagc agcactgggg tccaagatag  180
agctggacaa acaacaagga taactcatcc caaattctgg agtgcttatc cagaacttgc  240
taagtgctac ttcctaaaga ccagaacctc caggcagatt tgcaagtagg gggaaagtct  300
aataaaactt taggtaattc tgatggaaaa aggcaagaat aacattcctg tgtttgaatt  360
tataatacag cctaagacat aaagaagtca ttattgacaa tgggaaggaa agtaatttaa  420
tatgcaacat aactcaatcc atgaaataaa tatttattta tgtaatacaa tttgctaaac  480
accaccatta ttaaggagag ractaggaaa aactaccaaa cacagcatgt gaaacagttg  540
ggcacggtgg taaagggcac agactctgga gccacagccg gctaatacac tgcaatattt  600
tatgtttagc aaattatagc tggtctgtgt ataaccagaa gagcggtatc tgggggatca  660
ggatatctaa attctagact tacagcctgg ccctgaatct aactatcaat gttgccttgg  720
aaaaactgct caaactttttg atgtctaaag tttcagactt gtaaacttga gagggttgag  780
gtccaaggtc ccttaaatgt aaactttaaa atgctttttt gggaatcttt caaatcttca  840
agctcttcaa agtgcaacca gactttctcc ttactataca gtctgaacaa ctttgagaat  900
cactgtatta tcttagttta tatagtaatc ctgacctaaa ttttattatt ctcattttgg  960
agacaaggaa atagaggcct aggctagcat ggctaaataa g                     1001

SEQ ID NO: 7            moltype = DNA  length = 1001
FEATURE                 Location/Qualifiers
source                  1..1001
                        mol_type = genomic DNA
                        organism = Homo sapiens
SEQUENCE: 7
```

```
actttctcca caaaaccagg tgaccacacc ttcccctcct accctaccga accacgggac  60
ctaggtcccc aggaacagct gtatgtgtaa gagaaagcca cttggagggg ctaccgtgct  120
gggagtgtgg gtgcgcgtgg gtcccgggga gctatctgca ggctcgaagt ccactttcac  180
ccaagcccct ggcaactggc tgtccgggct gcttcctcac accccggtgt cttcctattt  240
tgccccgatt gtcagactcc acgtagctag atcataatgg ggccctgggc agtgggtcca  300
agcttagaag ctcccgggcc tgacagatct caggaaatga cagctacaca tagaagcgag  360
agctaccagg ggccaatgta cttgagaggc cagtgaaact gagatcttca gtgggtctgg  420
ggtctggggg gcagtaagag cagggaccag ggtcgggatc ccaggagttc gaggctgtgg  480
gcagaagaca gggagagaac rggaacttgg gtagagccat aagctgggaa tgaaggggga  540
caccggccca gggctgtgaa caggggacag tggccactaa ctcaggtaca ggattggctc  600
tctggctctg caactccctg caaaatgtgg tcactgcagt gcccatctta gagagcttct  660
gaggattaaa tgagatcatc tttgcacaga cagcacgaag tctagcctag caaatgtgca  720
ctgaacagta gctagagtga cggaagaaaa agctaggaag cagtcttgtc gggagctggt  780
gcttcagcct gagggcagat caggctgggg aaggctgaga ggggccacag ttccatgcct  840
gcatggaggg aggagaaagg cacaagagac tagaaatttc ctgtttgcct gtgtttccag  900
aaattcattg tacaacacac gaaccccttc aatacctgga taggtctcac ggacagtgat  960
ggctcttgga aatgggtgga tggcacagac tataggcaca a                       1001

SEQ ID NO: 8            moltype = DNA  length = 1001
FEATURE                 Location/Qualifiers
source                  1..1001
                        mol_type = genomic DNA
                        organism = Homo sapiens
SEQUENCE: 8
tactaaaaat acaaaaatta gccaggcatg gtggcgggcg cctatagtcc cagctactca  60
ggaggctgag gcagaattgc ttgaacccgg gaggcggagg ttgcagtgag gggagatcat  120
gccactgtac tccagcctgg gcgacagagc gagactccac ctcaaaataa aaaaaaaaga  180
aaaaatacac ccagaatctg acctcctctc accatcccat tcaaccaccc caagcctgca  240
atgctgtgtg actggcctca ggctccaatg cctgggcctg tctgtcctct gcagccgcca  300
cagcgatgct ctgtgaagta tcagccagca cctggcactg tcctgctctg aacacttcgc  360
agcctctctc aagcagggtt ccagagcctg aggccctaat gctctcaggc agccagtgta  420
tgcaactaag gagctgctct cccaggatga ggtgcctccc atccctggga gaactgaaca  480
aataatcact ctagtcactt mtgccttcca gggctcaggt gagccccaat gagaaaggct  540
cctccacagg cttccaacta agagtaaggc aaaatctctc cgtgaccttc cagactctcc  600
atgagccagc ccctccgtta tttcttggaa ctcatctacc atcttctctc cctcagtaac  660
tgcactggcc acacggcttc tgtgcaatcc tgcatttgtc ctagctggcc ccgatactca  720
gaatgtcctt cttggctggg tgtgatggct cacgcctata atcccagcgc tttgggaggc  780
caaagcagga gaatagcttg agcccaggag ttcgagacca gcttgggcaa cacaaagaga  840
ccccgcctct acaaaaaata caaaagttag ccagttgtgg tggtgcatgc atgtagtccc  900
agctactcag gaggctgata tgggaggact gcttgagcct gggaggcgga ggttgcagtg  960
aacgaagatc gtaccactgc actccagcat ggacgacaga g                       1001

SEQ ID NO: 9            moltype = DNA  length = 1001
FEATURE                 Location/Qualifiers
source                  1..1001
                        mol_type = genomic DNA
                        organism = Homo sapiens
SEQUENCE: 9
gccaggctaa gggctgtgtt gggcatatgg gcacaatcag agtaatagcg aagggaggga  60
caagagaagg ctggggccgg ggcatacgat gaccccccga ctcaacaccc agtgccagta  120
ccagtaggac ccagagggtt ggcacagcac aagcacccat gaaggcaggc cctggggtct  180
gttccccgag tgggtggcca tgccccaatc cacagtgcta atgggaggcc ccaggagctg  240
cctttgaagc ccttccccaa acaccacttg ccatgtgagt gtcaaccagg aagtctttat  300
tgagccagaa gagcacccca accccccaaa tccttgagag gctaatggag aacaggggtg  360
gggtctctaa gggggggggc gtagacaggt ggggaggagg ctgaatgggc agagcagaca  420
gtggaggtga ggacctgcca gaaaccgagg aagcccctgc tcctcgtcag ggccaggtgg  480
tcactggtcc tgcctgctca rccaccccaa ggctccagaa tcacccctcc cctcttcctt  540
ccctgtcggc tttgccccag ccccccacct gggcctcccc cgagcctccg atccattctc  600
catatagcag cctgaagggt gttttggaaa gctcagacct gacttgcctc ccagagaccc  660
tcaagaaaca aggtcaaatt cccacctcgg cctgcgagac tcctgtgtgg gcaggcccca  720
ggggcacctt tcccaatggc gacagcctga cctcctccct tgaccaggcc ccctccttcg  780
tcccctaggt ccagaaccag ccagcaagca cctccctcgg tccctgcagt ctcctgctgc  840
tgccgcctac tcatccttcc ttggtctcag cctgagtgtc cccttttttcg ggaagtcttc  900
cctgatgtcc cacacccagg ctgggttaca tggcccctct gggctgccca gtcccaggcc  960
acccctctca gttgttactg gccagggact tcttgtctct c                       1001

SEQ ID NO: 10           moltype = DNA  length = 1001
FEATURE                 Location/Qualifiers
source                  1..1001
                        mol_type = genomic DNA
                        organism = Homo sapiens
SEQUENCE: 10
agaggactca ccggggctga gtgacaggga taatgggctc tggcctcctc ttggcctgcg  60
gtgcctcttc ctccaggggg gacatggagc tcagggaacc caccaccgag atggcttggc  120
cctgggctga caggcgccgc ttgatcagga cgctctctgt cttcaccacc ttctcctcct  180
tgggctcctc cttgcactgt ttggtctgct ctacacctga gggggaggca gcaaacagac  240
acccagtgcg tcagacccac ctgctccaac ccgaggacct cctgtgtgcc tggctctgtt  300
ctgagccctg tacacacaaa acctcgttta aatccacaca acactgtcct ggagtgggta  360
ctctttttat ccccactttt caatacaact gaggctcaaa ctagaaatgc cattcattgc  420
```

```
tggggggagc agcaaatgct acagccactt tggaaacatg atgagcagtt tttgtttttt  480
agactgggtg tcactctgtc rcccaggctg gagtacggtg gtgcaatcag ggctcactgc  540
agtcttgacc tcctgggctc aagcaatcct cctgcctcag cctctcagcc tcccaactag  600
ctgggactac aggcgcatgc caacatacct agctaatttt tgtatttttt tgtagagatg  660
aggtctccat atgttgccca gcttagtctt gaactcctgg gctcaagcga tcctcccgcc  720
ttggacttcc aaagtgctgg gattacaggt atgagccact gtgcccagcc ctcagctgtt  780
ttttttggag acggagtctc actccatcac caaggctgga gtgcagtggc ttgatcctga  840
ctcgctgcag cctccacctc ctgggtccaa gccattttcc cacctcagct tctggagtag  900
ctgggattat agacacccac tgccacaccc agctaatttt tttgttttca gtagagacgg  960
ggtttcacca cattggccag gctggtcttg aactgctgac c                        1001

SEQ ID NO: 11          moltype = DNA  length = 1001
FEATURE                Location/Qualifiers
source                 1..1001
                       mol_type = genomic DNA
                       organism = Homo sapiens
SEQUENCE: 11
ccccgagcct tgacactggg agaaagacct tgccaagacc atgcccaaat cccaccatcc  60
aagattcctc tggatgggca acaagcagcc ccgacctccc tccagaggcc tttgtcttcc  120
cgatccaggc ggctggacca cgagggcaac ttgggaaggg ggtggaagaa aactcagccg  180
ccttttacca gagctccccc tggccaggc ccaggctaag tgctgcggga gcacctctca  240
tgacattctc acggcagcct ccagggggcg aaattacccc tgctaaacag cggaggtccg  300
tgccggtgcc gggacctgtc ctgggtcaca tgtacattct caccgcagcc tccagggggc  360
gacattagtc ctgcggggtt tggttttttt gttctctttt tttttttttt tttttttttt  420
ttttgagaga tggtcttact ctgccgccca ggctagagtg cagtgagtgg cgcgtttctt  480
cctcactgca gccccaaact rctgggctca agcagtcctc ctgtctcggc ctcccaaaga  540
gttggcatta caggtgtgaa ccatcacacc tggccttatc gtggtatttc taaagcccaa  600
atttctagca cctcttaaaa aactgggcca tttttcagct ctgggatgca tcctggccgg  660
gcacacagcg gtggagggtg aggagcagcc atgcctctcc cgggtgcaca ccccttgagg  720
gttaccacag ctcctaccac ccagctgccc tccctcatca cctgggagct ggcccagtca  780
tacaccctgg agcactgcta ttttcttggc aggaggcaga gcagagcctg ctgtcctcca  840
ccgggctccc tccggggtca gacgggggaa ggggagggca agcaggctag aagctgctgt  900
ctgcagcctg gaggcggggt ggccggggat gggttacctg cttcatgatg aggcgggaca  960
ggatgttcat gacgaagccc cccaggcggg ggtacatggt c                        1001

SEQ ID NO: 12          moltype = DNA  length = 1001
FEATURE                Location/Qualifiers
source                 1..1001
                       mol_type = genomic DNA
                       organism = Homo sapiens
SEQUENCE: 12
gaccccacat taagaactcc agctcttggc tgggagtggt ggctcacgcc tgtaatccta  60
atactttggg aggccgaggc aggaggatgg cttgaggcca agagttcaag accaacccgg  120
ccaacatagc aagaccccca tctcaattat ttttatttat ttatttattt ttatttattt  180
atttttttga gacagagtct cgctctgttg cccaggctgg agtgcagtgg tgtgatctcg  240
gctcactgcc aagctccgcc tcctgggttc atgccattct cctgcctcag cctccggagt  300
agctgggact gcatgtgcct gctgccacgc ttggctaatt tcttatattt ttagtagaga  360
cggggtttca tcatgttagc aaagatggtc ttgatctcct gacctcgtga tctgcccacc  420
tcggcctccc aaagtgctga ggttacagat gtaagccacc ccatcctgcc aagactgaag  480
ttgttttgtg actggattgt scaatgctgt ctttcgcctc caggccttgg cacaggctgt  540
gccctaagta tgcttgggcc cccactgacc ctgatgccca cctctcctga ctggctcact  600
caccacctcc tcctccatct cctgttcgcc ttcagtgccg cctccactcc gggtgaacag  660
cgccttctgt ttctccgcca tcttgtaggt gggctgcatc tcggggtcgt cccgcagcgt  720
gtccagcttg gggtggaacc actcccactg cgtggtgcgg ttcagagact ccaggacaga  780
caaggggtcc tcaggccgct ggttcaggat cttggtcagc agattcacca ggtgctcgta  840
cctgcctccc gcaggaggag tgggaggaga gggacctcac tcactcagct cactgagctg  900
gctcccatgt gcctggccct gtgcctggtg ctggggacac agtagggaac tgaaaaggtc  960
cctgcccagg tgtagctgac atttatttat ttatttttat t                        1001

SEQ ID NO: 13          moltype = DNA  length = 1001
FEATURE                Location/Qualifiers
source                 1..1001
                       mol_type = genomic DNA
                       organism = Homo sapiens
SEQUENCE: 13
gttaacaggt gtgaaccacc gtgcctggcc aacatttgta ttttttgtat ttttttttttg  60
agacagggtc tcactttgtc actcaggctg gagtgcagtg gctcggtctt ggctcactgc  120
aacctctggt tcccgggttc aagtgattct cccacctcag actccccaga gctgggatta  180
cacgtgtgcc aacatgcctg gctaattttt gtactttttg tagagatggg gttttgccat  240
gttgcccagg ctggtctcaa actcctggac tcaagtgatc tgcctgcctc agcctcccca  300
actgctggga ttacaggcgt gagccaccag gcccggccac agtcagcctt tgaaaccaag  360
ttggtctgat ttccaagcat gtatgtgtca ccttttgctt tgcggaagct gttttgttgg  420
cagtcttggg tgtggtgttg ggccatcatg gaagttggga agggtaagaa gaggtgagac  480
tttggctagg gcttctcagg ragagagcct gaagctctga agagctggca cttggggaat  540
agccagaggt taattctgac tagattctag gatccgagga aggagcaggt agtgactaga  600
aatcaagttt ggtcagcggc caggggctga accacgtaag gccttttgtt tgttggtttg  660
tttgagacag agtctcgctc tgttgctcag gctggagtgc actggcacga tcttggctca  720
ctgcagcctc tgcctcccgg ttcaagtgat tctcctgcct cagcctcccg agtagctgag  780
atcacaggcg tgtgccacca cgcctggcta actttttgta tttttagtag agacagggtt  840
```

```
ttgccatgtt ggccaggctg gtcttgaact cctgacttcg agttatctgt ctgcctcagc  900
ctcccaaagt gctgggatca caggcatgag caaggcctta tatgtctcag gccaggagcc  960
ttgaaggttg tggtgaggag tctgagcttc cccctgtggg c                      1001

SEQ ID NO: 14          moltype = DNA  length = 1001
FEATURE                Location/Qualifiers
source                 1..1001
                       mol_type = genomic DNA
                       organism = Homo sapiens
SEQUENCE: 14
gttcactggt gaagatgttt ctggctccac ccacctgctt cgtgactcgg tttctcaggc  60
gcagctggct tggctgcgag cccagaccag gctccacctg ctgctgcttc ctgagcctgc  120
tctgcggtga atgccaaaca ggagccaggg ccaggctcca cctctgccca gtaacgttta  180
cgctcctgac taaaaccgac tgtctctgcc ctcgagaagc tcacagccct gccagataac  240
ttttctgcaa agtgagatca cttttccaca gctggaccac cttgagaatg gggctaaaaa  300
tctgtttcct cccaactaca agcctgttat ccccattttc caggtaaggg ccccactgaa  360
cccaaatggc agataggtgg ggattaacat acacttctct ctcccgttta tcacgaaaat  420
gttctgtaat ccaaaaatgt caggggcaga aagaaaaaaa gtggtttcaa atcctgctgc  480
aaactggaag agcagacctt rtaatctcag gtgctagtct gtcactgagc tgcttctcat  540
gtgggcagac ctgtgcctct agagagaggg gcaggaagga cttatgttta tgtaatgaca  600
gctaaagagt cccgttagca acactgggaa ggccagctca taaagtgaca gtaacacaga  660
ggtttatgtg cctgagttca tggactcctt gcatcagcgt ggagggactg gaacgtcttc  720
cccattttta ctgacgggcc caaggtcgca gtgagaaagc gagaagtgaa cgcgaaccca  780
ggtctatcag ctccaggctc ctaactgccg ggccacttga cgtttcctca ggagtgacat  840
gcggaccgcc tgcaagctac acagcctggg tcggcccggg gtgaccaccc ttcgggcttg  900
gcacactctg aggtggagca ggttggggaa gagctggagc tggggacaca gccttgcccg  960
tgggtgggca gggcctggtg ggctcagggg cctcaccggc t                      1001

SEQ ID NO: 15          moltype = DNA  length = 1001
FEATURE                Location/Qualifiers
source                 1..1001
                       mol_type = genomic DNA
                       organism = Homo sapiens
SEQUENCE: 15
aggcagcagt gagggaggcc tggaggggca tgaggggaac tatagccacc aacagctcgg  60
gctgcggtgt ttgaaccctc gctgcagacc acacacacac acacacacac acacacacac  120
acacacacac acactctctc tctctctctc gctctctttt tttttttttt ggagacagag  180
tctcgtcgct ttgtcactca ggctgcagtg cagtggtgtg agctcgactc actgcaacct  240
ctgcctccca ggttcaaacg actctccttc ctcaacctcc cgagtagctg ggattacagg  300
catgcaccac cacgcccggc taatttttgt atttttagta gagacagggt ttcaccatgt  360
tggccaagct ggtctcgaac tcctgacctc aggtgatcca cccgcctcag ccccccaaag  420
tgctgggatt acaggcgtga gccacctcgc ctggcctgga ccactctttc tctatgtggc  480
cccaggaagc cagttcacct rtctgagcct cagtggctgc acccaggaaa tggggagact  540
catctggcct ttgttgcagg gtggcagtga agcctggtga caaggtctgc agcacacctg  600
ctgcagtgcc tggcgcccag cagggcctcc agactgggaa gccactgtga ttccactccc  660
gagttggtca tcggtttgga ccagggtgca gagggaaggg cacaggctgg caggatctgg  720
cttcaaatcc aggacctgtc ccctggccca ctcctagcct ctctctccac ttccctccgg  780
gtgcctgagg ccccaacctt aaaaaattcc tgtccattca tccaaaatcc agctccaggt  840
tgggcacagt ggctcctgcc tgtaatccca gcactttggg aggccgagta aggtggatca  900
cttgaggcca ggagttcgag atcagcctgg ccaacatggt gaaaccccat ctccactaaa  960
aatacaaaag ttatctgggc gtggtggcac acgcctgcaa t                      1001

SEQ ID NO: 16          moltype = DNA  length = 1001
FEATURE                Location/Qualifiers
source                 1..1001
                       mol_type = genomic DNA
                       organism = Homo sapiens
SEQUENCE: 16
tcgctttgtc actcaggctg cagtgcagtg gtgtgagctc gactcactgc aacctctgcc  60
tcccaggttc aaacgactct ccttcctcaa cctcccgagt agctgggatt acaggcatgc  120
accaccacgc ccggctaatt tttgtatttt tagtagagac agggtttcac catgttggcc  180
aagctggtct cgaactcctg acctcaggtg atccacccgc ctcagccccc caaagtgctg  240
ggattacagg cgtgagccac ctcgcctggc ctggaccact ctttctctat gtggccccag  300
gaagccagtt cacctgtctg agcctcagtg gctgcaccca ggaaatgggg agactcatct  360
ggcctttgtt gcagggtggc agtgaagcct ggtgacaagg tctgcagcac acctgctgca  420
gtgcctggcg cccagcaggg cctccagact gggaagccac tgtgattcca ctcccgagtt  480
ggtcatcggt ttggaccagg mtgcagaggg aagggcacag gctggcagga tctggcttca  540
aatccaggac ctgtcccctg gcccactcct agcctctctc tccacttccc tccgggtgcc  600
tgaggcccca accttaaaaa attcctgtcc attcatccaa aatccagctc caggttgggc  660
acagtggctc ctgcctgtaa tcccagcact ttgggaggcc gagtaaggtg gatcacttga  720
ggccaggagt tcgagatcag cctggccaac atggtgaaac cccatctcca ctaaaaatac  780
aaaagttatc tgggcgtggt ggcacacgcc tgcaatccag ctactcagga ggctgagacg  840
ggagaattgc aggaacccga gaggttgagg ttgcagtgag ccaagattgc accactacac  900
cctagcctgg gtgacagagc tggactccat ctcaaaacaa caacaatgac aacaacacca  960
ccaccaccac acacacacac acacacatac acacacatgc a                      1001

SEQ ID NO: 17          moltype = DNA  length = 1001
FEATURE                Location/Qualifiers
source                 1..1001
```

```
                          mol_type = genomic DNA
                          organism = Homo sapiens
SEQUENCE: 17
tctgatttc ctgtcgcttg gccacctcga ctcccccgaa tcctgtcccc tccaccttca  60
aggagctgcc acctgccctg gctcctgact ttgaacacat cccagagccc ttggccgagt  120
cccatcttac tgactgggac ttggtggacc caaggctcgc ccaatagagg ctaaaacggt  180
ggcccaggcc cctgcgggga cacaggattg ggagtggtac agggatgccc gggaggcgag  240
tgaggaagcc aggccatcct gccaccgtct ccccagcacc aaggctcgca ggttcagccg  300
ccagcacaac cgcatcgtga agcaggacgg ctccagcagc gaggctgagg actgggagac  360
gccaaagccc ttctaccagc tgctggccga gaaggccttg ccgctgcccc cgcacctcca  420
gtgagagggc ggcccctcgc ctcgctcccc tcacccctca tggcaaccgc ggctcttgct  480
ggaagccagg acccatcgat maacttgtcc ctcctgggcc tccagcccct gagaatgcag  540
gtcccatggg actggggagg ggggcactga ttagccccaa ccgctgggca catttgcctg  600
gagcaccaga gtcacccaca gctgccttga ttctccccca ggcttaggaa ggaaacccaa  660
aatgaaatgc ggggtgtcgg aaggtgaagt ttacccaccc ctctcccctt cccttcccca  720
ccccagagcc actcggttgc aaccctgttc atgctcacct caccctactc ctccctctcc  780
tgttctattt ttagactatt tattgtttta aataaaataa agcaagtgga acctttgtta  840
ccagcaagag agacaagggc aggccctcct gcgtcccccct gctgccccac tggggtgctc  900
cgtccaccct catctggagg cctgtggctt gcaagaggcc tcagtgccac cccctcccca  960
gccactctgt gcatctgaat gcaaacccct cttcccctcg g                     1001

SEQ ID NO: 18             moltype = DNA  length = 1001
FEATURE                   Location/Qualifiers
source                    1..1001
                          mol_type = genomic DNA
                          organism = Homo sapiens
SEQUENCE: 18
gcctggccca cataacataa tctataatat aatcttagta aatacaaatt cagcatagtt  60
taaggtaaat aatgaaacat ttcagcatgg tctgcctgcc ccacccccacc agcccctctc  120
acccagcttc atcttcttga gtgtggagtc cgagtcatcg cggggccgct tgcgggtgtc  180
cttgctgctc ggcatgttgc gggcgatctc ggcctgaggt gtgcccaggt ccaccagcag  240
ggtggtgatc tgggcctgga actccaagga agccgggtgc ttcagcacac tcaacaggtg  300
cagcttcaga ttcttacgca cactgctcac ctgcgatttg gccagcgtcg ggggcaggtt  360
ggctgtgagg aaagtggcag gagctgtgtc ttgtggaaga tctcatggca tgctgccagt  420
cttaattctc aaccccaaac ttgggcagtg gtcttgcagg catctactag aaaagttcct  480
tcaccctcag atctaacgtg rggctttccg ccttacaagc tgatgcttca aaccctgggg  540
gtctccatca gtatcagtca atcttaaaga gaaaaactca ccctctcttt tagtaaatac  600
atacaatttc gtcctcctcc atctctggtc tggaaattca catatgcttc gcttggggag  660
ggttataatc accacttttg cctccagaaa cccccaactg aactgctgca acagctcact  720
gctagtctcc ctgacgccag gatgactttc taatggtcac cctgataagt gagcctcccc  780
tgttccacag tgaaaaagga tgcctgtaat tctgcctgcc tagcatccac tgccccttcc  840
tcagccaaca acacaaccca ctctccgtta agggagaccc cccttctcca gtctccttcc  900
gagtgggcat gagacctggg gccagtgaga ataccacatt cccttggcca ctgtaattgg  960
ctcagagact ggctcataat ctctgctcag ccaatcagaa a                     1001

SEQ ID NO: 19             moltype = DNA  length = 1001
FEATURE                   Location/Qualifiers
source                    1..1001
                          mol_type = genomic DNA
                          organism = Homo sapiens
SEQUENCE: 19
ttgcagtgag ccgaaattgc gccactgcac tccagcctgg gtgacagagc aagactccgt  60
ctcaaaaaaa aaaaaaaaaa gaaggggatg gatgggaagg agtttggaaa agcacaagga  120
gctgttagct attgtgttga tcggcacaaa tgaatcaata aatttgctct tccccaactc  180
tccacccctc accaacaccc tattgcaata ttctcaattc ccttcccaag ggcctcgggc  240
aaaaatggag ccctcctggc tagactccat ctcccagcgc gcccagcggg gaagcaccct  300
gcgcttgcgc tgccaagtcc tccccggctt tgtctcccgg gagttcgagt cgttcttttc  360
ctccgcccgc ctaatttgct tcctacccca cctccaagct tgaccgtgct gccttctggg  420
ggatgtagtc cgtggctgcc cggacttcaa ttcccagcgg gcttcgggac gagaacccgg  480
aaggggaggc tggagaggag rgagtggggg aaacccgcgt agccgaggga gatgcagcgc  540
gcggcgatgg tgagagccca ggcgcgggcc gggggcgctg gagagtcggg acgggggttc  600
gggaccgggt gacgaggggg aagaggcagg ggcgaaagaa ggggctgggt gaggggagat  660
tgcctggggg agaggactgg gaggaatggg agccggaggt agtagtagaa gaatggtggc  720
ttggggaggg gtcttggagg tggggtggga gtggagcttt ggaattgatt gtaaaggggc  780
tcagagctgg ggaagtgggc cccgagttgg agactgggct ggacatccag gtagaggccc  840
tgaaggggtc gatttcgatg ggggcttaac ctgcggcgag ggtatgagga tcagggttag  900
gatgagtgag gggtctgga agctccaagg gacaggcgaa cggtggacgc aatgggttgg  960
ggcctctgga tcggattggg ggcaggaagg caagttgagg a                     1001

SEQ ID NO: 20             moltype = DNA  length = 1001
FEATURE                   Location/Qualifiers
source                    1..1001
                          mol_type = genomic DNA
                          organism = Homo sapiens
SEQUENCE: 20
cactcctggg gagagactcc ccgcccctgc cacaagagcc ccaggtctgc agtgtgcccc  60
tcagttgagt gggcagggcc gggggtggtc cagccctcgc ccggccccca ccccagctgc  120
ccttgctatt gtctgtgctt ttgaagagtg ttaaattatg gaagcccctc aggttcctcc  180
ctgtcccgca ggacctctta tttatactaa agttccctgt tttctcagcg ggtctgtccc  240
```

-continued

```
cttcggagga gatgatgtag aggacctgtg tgtgtactct gtggttctag gcagtccgct  300
ttccccagag gaggagtgca ggcctgctcc cagcccagcg cctcccaccc cttttcatag  360
caggaaaagc cggagcccag ggagggaacg gacctgcgag tcacacaact ggtgacccac  420
accagcggct ggagcaggac cctcttgggg agaagagcat cctgcccgca gccagggccc  480
ctcatcaaag tcctcggtgt mttttaaatt atcagaactg cccaggacca cgtttcccag  540
gccctgccca gctgggactc ctcggtcctt gcctcctagt ttctcaggcc tggccctctc  600
aaggcccagg caccccaggc cggttggagg ccccgacttc cactctggag aaccgtccac  660
cctggaaaga agagctcaga ttcctcttgg ctctcggagc cgcagggagt gtgtcttccc  720
gcgccaccct ccaccccccg aaatgtttct gtttctaatc ccagcctggg caggaatgtg  780
gctccccggc caggggccaa ggagctattt tggggtctcg tttgcccagg gagggcttgg  840
ctccaccact ttcctccccc agcctttggg cagcaggtca cccctgttca ggctctgagg  900
gtgccccctc ctggtcctgt cctcaccacc ccttccccac ctcctgggaa aaaaaaaaaa  960
aaaaaaaaaa aaagctggta taaagcagag agcctgaggg c                    1001

SEQ ID NO: 21           moltype = DNA  length = 1001
FEATURE                 Location/Qualifiers
source                  1..1001
                        mol_type = genomic DNA
                        organism = Homo sapiens
SEQUENCE: 21
tcaggtgcat tggagattct taggagtgtc tcttgggggt aatattttat tttttaaaaa  60
atgaggatgt cactcttacc caggttggtc ttgaactcct gggctcaagc aatcctccca  120
ccacgggtct ctcaaagtgc tgggattaca ggcgtgagcc accgcacccg gctttttttt  180
tttttttaa acggagtctc actctgtcac ccaggctgga gtgcagtggt gcaatttcag  240
ctcactgcac cctccacctc ccgagttcaa gcctcccggg tagctgggat tacaggcacc  300
gccaccatgc ctggctaatt tttgcatttt cagtagagat agggtttctc catgttggcc  360
aggctggtct cgaactcctg acctcaagtg atccacccac ctcagcctcc caaagtgctg  420
ggattacagg cataagccac catgcccggc ccaaatgggc taatgtttta aacagatcct  480
tcttgtctgc cctgtaggag macaaattat caggggcagg ggtggaagct ggagcccaga  540
aaggagggga ctgcaggtgg gaagtgatgg tggctggacc aggatggagg ccactgaggg  600
gtatgaagca gtcggatttg aagctgttta aaaggtggag gtgagaggat ttcatgaagg  660
agcacatgag gacacagcag cagagaggac tccttggctt tggatggtgg agagactaaa  720
gatagagaga ttgggttcgg gtagggggag aaccacgtgt gctctttgga aaggttaggc  780
tggcagtgtt tgtaggacat gacaggacac tgagtgtaag ggtctggagc tctcaggaga  840
ggggcgagct ggagatagta atgtgagagg cactgggtcc tgagagggtg atttggtgtg  900
gaccggagca caggtgaggc aaggcaggcc tcgcagctga aactttatat ccagagcagc  960
cagggccact gctggctgcg gagtgaggac gcatatcccc a                    1001

SEQ ID NO: 22           moltype = DNA  length = 1001
FEATURE                 Location/Qualifiers
source                  1..1001
                        mol_type = genomic DNA
                        organism = Homo sapiens
SEQUENCE: 22
ctcaggcagg gaggtttagt tgcaggataa gagggtctca ggagggctgg gcacggtggt  60
tcatgcctgc aatcctagca ctttgggagg ctgagatggg cggatcactt gaggtcgagt  120
ttgagactag cctgggcaac atggtgaaat cttgcctcta ctaaaaatac aaaaattagc  180
tgggtgaagt ggagcgcgcc tgtaacccca actactcggg aggctgaagc agaagaatca  240
cttgaacttg ggaaggagag gttgccctaa gccaagacca cgccactgtg ctccagcctg  300
ggtgacaggg tgagactatg tctgggggaa aaaaaaagca agagggcttg gggagccaaa  360
tcacgtgttc tggaatcctg actctgccat atcctagctg tgtagttttg ggtaagcgac  420
ccaacttctc tgtgtctcgg tctcctcctc tgtaaagtag gatgagctga tgtgctcatc  480
tccggtgaga attaggtgag dgtgtgcagt gccagcacat gtctgggaag tgaatgctag  540
ctgttgttgg cattgattcc gactcagctg aattagagtc actggttttc catgagggat  600
gatcccttgt ctgactgact gaggcaggca cttcgggtgg ggcccctccc tgcctgggtc  660
ccccacccgc cccactccta gcccctgctc acaggctgag gtcgcaattg atgctggtct  720
gcagcaggta ggccttggcg ttctgcacgg ccagctccag aggctcgggc tcaggcacct  780
gggcactgta gtgtgggaag cccagctcag agggcaagaa ctgaagggca gggtcatccc  840
ttatgtaagg cccgtgctgg gcaccttcag agaactggtc tgtctggtag aggttgaact  900
ggcccaaggg gttgactggg ggctcctgga aggtggggtc cagttgctgg aacaggctgc  960
tttggccctg ctggagccgc tgcagcatta ggctggtggt g                    1001

SEQ ID NO: 23           moltype = DNA  length = 1001
FEATURE                 Location/Qualifiers
source                  1..1001
                        mol_type = genomic DNA
                        organism = Homo sapiens
SEQUENCE: 23
gtcacacagc aagcggagga actaggattt gaatcccagt ctttctgctt caaaaactgg  60
agcttatata tcaaccttta tgccacctcc tgggactgtc ccctgctttg tcccactttg  120
gggcagctct tactcttaca tccctacaca ctattaaaac aaatgaaggc cgggcacgga  180
ggctcacgcc tgtaatccca aaactttggg aggccaaggc ggatagatca cgaggtcagg  240
agattgagac catcctggcc aacatggtga aaccccgtct ctactaaaaa tacaaaaaat  300
tagccaggtg tggtggcaca tgcctgtaat ctcagctact caggaggctg aggcaggaga  360
atcgcttgaa cccaggagac ggaggttgca gtgagccgag atcgtgccac tgtactccag  420
cctgggcaac aaggcgagac tccatctcaa taataataat aataataata ataataataa  480
taataataat aataacaatg rtaataaagt aactagggta tgttcaggtt gattagctca  540
gggaaaagga aacttgagaa ttaggttcat atgccacttt agaagtctga gcagctatcc  600
caagaccttt cagtattcat taattcaata attctttatt gagcacccac taagtgttag  660
```

```
gcattattcc aggacttaag ggatataacc agcgcagcat tatggcttct gtgggcccta  720
tacaatttta ccttcttgat ccccttcttc catagaaaaa tattaacgct gggtgcggtg  780
gctcacgcct gtaatcccag cactttagga ggccaaggcg ggcagatcac gaggtcagga  840
gttcgagacc agtctggcca acatggtgaa accccgtctc tactaaaaat acaaaaattg  900
ggaggcatgg tggcgggcac ctgcaatccc agctacttgg gttgctgatg cagaagaatc  960
gcttgaatct gggaggcgga gatttcagtg agctgagatc g                     1001

SEQ ID NO: 24          moltype = DNA  length = 1001
FEATURE                Location/Qualifiers
source                 1..1001
                       mol_type = genomic DNA
                       organism = Homo sapiens
SEQUENCE: 24
ggaagtggag gttgcaatga gtcgagatca taccactgca ctccagcctg agcaacagag  60
taagaccctg tctttttttt tttttgaga cggagtcccg ctctgtaccc caggctggag  120
tgcagtggca ccatctcggc tcactgcaag ctctgcctcc tgggttcacg ccattctcct  180
gcctcagcct cctgagtggc tgggactaca ggtgcccgcc accacgcccg gccaattagt  240
ttttgtattt ttagtaaaga cagggtttca ccgtgttagc caggatgacc tcgatctcct  300
gacttcgtga tccacccgcc tcgggctctg aaagtgctgg gattacaggc gtgagccacc  360
gcgcctggcc atgagacccc atcttaaaag aaatagagtc agatgtatct cactccaaag  420
gctcttgcct tcaaccattc tgtcactcaa ggttcaatag atgtttgttg aatgactgaa  480
tgagctccct ttgttgggac rgttacagga cctgttgatc ttaccttcag aaggtctttg  540
agagtccaga ctctggtgta gcccccaagc taaccttcct gaagtttcaa ttactgaggc  600
atctgtcttg aaatctggga tgatgcccaa ttgctttcta catacaacct ttatactagt  660
aataataagt aacatttata tattacttca tggtttataa ggactttttc ttagcgagtg  720
ccaaccatat gctccaagcc tggtattaga gataataagc ttaaaaagac tgaggctggc  780
tgggtgcagt ggctcacaca tgtaatccca gcactttggg aggccgaggt gggtggatca  840
cttgaggtcg gtagttcgag accaacctgg ccaacatggt gaaaccttgt ctctactaaa  900
aatacaaaaa ttagccaagc gtggtggcac attcctgtag cccctgctac tcaggaggtt  960
gaggtgggag aatcgcttga acctgggagt cagaggctgc a                     1001

SEQ ID NO: 25          moltype = DNA  length = 1001
FEATURE                Location/Qualifiers
source                 1..1001
                       mol_type = genomic DNA
                       organism = Homo sapiens
SEQUENCE: 25
gcaaagtgag atcacttttc cacagctgga ccaccttgag aatggggcta aaaatctgtt  60
tcctcccaac tacaagcctg ttatccccat tttccaggta agggccccac tgaacccaaa  120
tggcagatag gtggggatta acatacactt ctctctcccg tttatcacga aaatgttctg  180
taatccaaaa atgtcagggg cagaaagaaa aaaagtggtt tcaaatcctg ctgcaaactg  240
gaagagcaga ccttctaatc tcaggtgcta gtctgtcact gagctgcttc tcatgtgggc  300
agacctgtgc ctctagagag aggggcagga aggacttatg tttatgtaat gacagctaaa  360
gagtcccgtt agcaacactg ggaaggccag ctcataaagt gacagtaaca cagaggttta  420
tgtgcctgag ttcatggact ccttgcatca gcgtggaggg actggaacgt cttccccatt  480
tttactgacg ggcccaaggt rgcagtgaga aagcgagaag tgaacgcgaa cccaggtcta  540
tcagctccag gctcctaact gccgggccac ttgacgtttc ctcaggagtg acatgcggac  600
cgcctgcaag ctacacagcc tgggtcggcc cggggtgacc acccttcggg cttggcacac  660
tctgaggtgg agcaggttgg ggaagagctg gagctgggga cacagccttg cccgtgggtg  720
ggcagggcct ggtgggctca ggggcctcac cggctgctca atgaccctca gcaccgtccg  780
cttgatgtcg gcgatggctt cagtgtacac ggccgccagt tcgtggatca gcttgtggtt  840
ctgaggcagg agggccaggt agaggtacag acactgcttc actgtctcct ccgtccaggg  900
tgctgccacc tctgacaggg caggagcggg catcagattg gcccacactc ttctccaacc  960
ccctcggacc ctcaggaatg tcccttcttg ggcagtggag c                     1001

SEQ ID NO: 26          moltype = DNA  length = 1943
FEATURE                Location/Qualifiers
source                 1..1943
                       mol_type = genomic DNA
                       organism = Homo sapiens
SEQUENCE: 26
gctaagggga ggtgggaaac gggctgacag aactgctgtg ttgaggtgag gactcctgac  60
tgtgcgaccc ccattcatgc attcattcac tcattgaatt tttttttttt ttttttttg  120
agatggagtt ttactctgtg gcccaggctg gagtgcagtg gcacaatctt ggctcactgc  180
aacctctgcc tcccggttta agtgattctc ctgcgtcagc ctcctgagta gctgggatta  240
caggtgcctg acaccacgcc tggctaattt ttgtattttt tagtagagac ggggtttcac  300
caagttggcc aggctggtct cgaactcctg acctcaaatg atccacccgc cttggcctcc  360
caaagtgctg ggattacagg tgcgagccat tgcacctggc ccactcattg attcttttct  420
tttttttttt tgagatggag tctggctctg tcgcccaggc tgaagtgcag tggctcactg  480
aaagctccgc ctcctgggtt cacgccattc tcctacctca gcctcccaag cagtggctta  540
cgcctgtaat cccagcactt tgggaggctg aggcgggcgg atcacgaggt caggagatag  600
agaccatcct ggctaacacg gtgaaacccc atctctacta aaactacaaa aaaaatagcc  660
gggcatggtg gcgggcgcct gtagtcccag ctactcagga ggctgaggca ggagaatggc  720
gtgaacctag gaggcagagc ttgcagtgag ccgagatcac gccactgcac tccagcctgg  780
gcaatagagc gagactccgt ctcagaaaaa aaaaaaaaaa aagccaggca tagttgtggt  840
ggtatgtgcc tgtagtccta actactcggg aggctaaggt gggaggattg cttgagccct  900
ggaggtcagg gtagcagtga gttatgatct catcactgca cgccagcctg ggcaacaaag  960
caagttgcta tgtcttaaaa gaaaaaaaaa gctgggcatg gtggctcatg cctgtaatcc  1020
cagcactttg agaggctgag gcgggcagat cacctgaggt caggagtttg agaccagcct  1080
```

```
gaccaacatg aagaaaccct gtctctccta aaagtacaaa attagttggg cgtgatggca  1140
catgcctgta atcccagcta cttgggaggc tgaggtggga gaattcgctt gaactaggga  1200
ggcggaggtt gcggtgagcc gagatcacgc cattgtactc cagcctgggc aacaagagcg  1260
aaattctgtc tcaaaaagaa aagaaaagaa aaaaaaaaaa aaccagccag ggcgcagtgg  1320
ctcatgtcta taatcctagc actttgggag gccaaggtag gcagattgtc tgagctcagg  1380
actttgagac cagcttgggc aacacagtga aacctcatct ctactaaaat acaaaaaatt  1440
agccaggtgt ggcagcgtgt gcctgtaatc ccagctactc aggaggctga ggcgggacaa  1500
tcgcttgaac ccaggaggtg gaggttgcag tgagccgaga tcgtaccact gcactccatc  1560
ctgggtgaca agagcgagac tctgtctcaa aaaaaaaaaa agaaaagaaa agaaaagaaa  1620
aagaaaaaaa agaagaaaga aagaaaagaa aaaaaaatgc ctctgtcccc aaaggtttct  1680
gatgggatta tccgctaata tctgttgaac caatgaatgg atggatgaat gaacgaatga  1740
atrttagttg cccagcagag agtaagagct tgatgtcagt attgcagggt catgcgtgag  1800
ccccctgctc ctgccgtttg tgagaggcgg gagtcccggc gctcacctgc ggcaggatgt  1860
gctgtgtgtg atgcacccag ttggccatgg agtcgaccag ctccagcacg gggatgccct  1920
cgaagtccgg gttctcctcg tag                                          1943

SEQ ID NO: 27          moltype = DNA  length = 1001
FEATURE                Location/Qualifiers
source                 1..1001
                       mol_type = genomic DNA
                       organism = Homo sapiens
SEQUENCE: 27
aacactcttc actgaacctc tttttgcttt ctttctttct ttctttcttt ctttatgaat  60
gagatggagt cttgctctgt cacccaggct ggagtgcagt agcgcgatct cggctcactg  120
caactgctgc cgcctggatt caagcaatta tcctgcctca gcctcccgag tagctgggat  180
tacaggcaca tgctgctgcg ccaggctaat ttttgtattt ttagtagaga cagggtttca  240
ccatgttggc caggctggtc ttgggctcct gacctcaagt gatctacctg ccttagcctc  300
tcaaagtgct gggattgcag gcatgaccca ctgcacctgg cctcttttgt tctctggaca  360
gggtgccagc tctgctgctt cttagccttc tcccatggtg tttctctacg gggaatacac  420
acccctccca cctcaaaacc ttgtcctgta ttatgctgac tcctgccctc ccctcagttc  480
tcagcctagg tgcttcttgc rcagggagcc cttgccttgc ctggctcctg ctgtggctca  540
cagtgccctt catgttaccc tctcaagcac tacactatat aattatttgt tttctctgtg  600
acttccagaa gaggctgggc cccaggagag caggcccaag tcggtcttag gcactgccat  660
ttccccagta ttggcatggg catggaaaga atgcttcttg agttaatgat taaggagagg  720
ctctcttcct gggcatccca caggtcctca tcagcatggt gtacctaccc gaggccatgc  780
cagcctcctt ccaggccatc tacacccccg tggagtcagc aggcacggaa gcccagatca  840
agcacctggc tcggctcatg gccacacaga tgacagctgc cggactggga ccaggtgagt  900
gtgtcctggc cctaacctgg gccagggatt ggcacttgtg gcttctgggt tctccttact  960
ggaagagcaa cttctcgtgg tgcagttgaa aatcatgtgg g                      1001

SEQ ID NO: 28          moltype = DNA  length = 1001
FEATURE                Location/Qualifiers
source                 1..1001
                       mol_type = genomic DNA
                       organism = Homo sapiens
SEQUENCE: 28
cccaacctaa tcttttccat agtattgggc ttgaaccaga gacttacagt gtgcaggatc  60
ctaataatcc agcccaccag cagtcctctt cttataaaga cacctcttct cataaggaca  120
ccataatcag taatcaggtt ttgctggctg tggaagtact ctggacagat tagataacag  180
tatgtatcaa tgtaaatttt tgaagctgat actgtgtaaa tgtaagggaa tatctatttt  240
tagaacatac acactgaaat gtttaggacc atattataag taagtactta taaatgtact  300
ttaggaccat attataagta agtacttata aatgtacttt aggaccatat tataagtaag  360
tgcttataaa tggctcagaa caaacaatta tgtatatata tctgtaaata tacacatgga  420
gagagtgagc atacatgcac actgtgcaaa tgatgaatgg ggtaaaatgt taacagtgaa  480
tctcggtgac ggatgtatgc rtgttccttg tgccttttttc tttgcaagtt tctttaagtt  540
tggggttatt tctaaagtta ggattttttt caagagtaat aattaggatt cacttatatc  600
ttttaggttt ttaagaacct acaactattt atggagaaca agcagcccga ggatgatctt  660
tttgatagac tcaatgtgag tagatgaagc acacaatgtt gaagggagtc ccagccagag  720
cctcacagta cctaaagggg agggttgctg gcagatgact tgggctctcc ctttagcctg  780
gcctgctctg tggcatccca tacactctct cttcctccct ctgagtccac ggtgaatctg  840
tagtcaagag aagacacatc tgctgcagaa caactgctaa agcactcagg gtgggggggta  900
gatgagccct accttttatc cttccctgct cctgcagagc tttcccttca ctgaatgccc  960
agccacccct gctggagacc caaaacctgt ccctgatatc t                      1001

SEQ ID NO: 29          moltype = DNA  length = 801
FEATURE                Location/Qualifiers
source                 1..801
                       mol_type = genomic DNA
                       organism = Homo sapiens
SEQUENCE: 29
acaaccttta tatcaacttt ttttcctcta acaatgaaca atgaaaacaa tttgtgctcc  60
atctttaaaa atgtgtgaca caaaaatttt ttaaataaaa ataaatatgt gataaacatt  120
cctgaatgcc tagtgtgtgc cctggcgctg tgctctgcat ttaatttgga tcagcagttc  180
tcagccttgt ttgtacatta caaccaactg gagaggtttt taaactccca gtatccgggg  240
catcagtatt cgtctagggc acagtgattc taacacacag tcaaggttga gaaccactta  300
tttaattcat cctgtaaatc ctcacaatag aatcctgcaa ggtagctttt atcaccacct  360
ttgccgatga aattgaggct caaagaggta aattgatttc rgcatctgta gccccaacct  420
gtgacctctc cttccttcct tctcgggctc ccttcaggga tttcctgatg ttacagaaaa  480
tggtatgtat gacgctgccc tcctggccac cttgacatag ctctgctccc aacagggctc  540
```

```
ttctgagata gcagccagac actacctggg atcaggactg atactaaatg acttctgcca  600
aaatgaggac aactgaggcc agtcacttcc aaacaggttc tgtcaccctg agtcagaata  660
atggcagcta cctctcctcc tcaccgccca gtcgtttcta agcctggctc gtcgccgttg  720
ctgctccgcc aagcctttcc tcggtgccct ctctctttta gaacaaatta cttcatctcc  780
aggcccttct cagggcagct t                                            801

SEQ ID NO: 30          moltype = DNA  length = 1001
FEATURE                Location/Qualifiers
source                 1..1001
                       mol_type = genomic DNA
                       organism = Homo sapiens
SEQUENCE: 30
cttcttgttc atcataaata atgattaact tagaatgtac ttctcccctc tcttaaaatg  60
accaatataa aagactactt attaaaagaa tatatattat aaaaatacaa gagtaataag  120
ttcacagcag cacaggataa acaggaaaga caccatcaga atagcatgag gacttctggg  180
ccaaagggag gggaaatgcc atcaggactg actgaatgac agcaatacta agacgtaaag  240
gaaatttcaa tttgaaccaa gcaaaagaag gaaactctaa aactgtgaat ataaccatag  300
aaccctaggg gggaacaaac tcaaattcag agataagtga agctggatgt agaagtagaa  360
gtgagcccag gactgtcagg agaataatta gaggcctatg gaacagctgc atcctccagt  420
gttctcagaa aggctaaggt gtgagaacag ctctctgtaa taaagtggag gatcagctgt  480
gggggaacca cccacacagg rgctgggact acagaatgaa gaaacagcac cacaaatgac  540
aatgcacaca cccacccaga aggcagctga ctgaatccct ggacgtatat ccctggtact  600
tagcaggacc agcactcctg tactctgaat ttacttctgg aagaataatt cccacttgtg  660
ctgagagaac ccactacagt taccactcgg atcacacaaa gagttctcaa tcctggatgc  720
acatcagaat catctgctga gctttttaga aataccaatt gcctgggccc caccgcaatg  780
caactgaatc agtatttata gagggaagag ggatctaggc atttgtattt aaatattctc  840
cagataattt aatgtgccct taagtaataa caaataaaaa cagcaaagga agcagaaaat  900
aattgtagta ttctctgaaa gatctattaa gataccattt caaagatcta tggagatact  960
aagggagagg aacaatacta aaaagttatt agtggggaat a                      1001

SEQ ID NO: 31          moltype = DNA  length = 1093
FEATURE                Location/Qualifiers
source                 1..1093
                       mol_type = genomic DNA
                       organism = Homo sapiens
SEQUENCE: 31
cagtgatgtc tctgagcatc agtggtgtct cttctcagtg gcttacagct ccagacatca  60
catgcagacg tgacaatgtc taatggagaa ggggcacatt ctctcccaat tctactcaat  120
gagaaaccct ttccttcctg gaggtccttc agcggccatt cacacagatc ccactggcaa  180
gactggatcc catgctgttc ttacaccagc catttccaag agaatgaggc caccataact  240
ggcttaggcc aattggtagg acccttcagg aggcagaacc tgggaaccta ggcagggctc  300
tgcccacagg aagaagcagg tgagcgtgtg ggggtggcgg rtggttgtca aaacccaata  360
tacagggaac attacaggaa gagtcactta ctttacaatc atgtcatttc ataaacattt  420
cttgacataa ttagggaaca agaggcagca tgaaggagca cagcttccct gccattcccc  480
ccgccacagt gagacgcctg caaggacaca gacacagcct ttccatcagc cttcctctgt  540
ggatccccca tccacactga gccagcaggt caatggggac aggttccatg ctgttcagag  600
aaaccagcac tgtacacagt ggggccctgc atccactgca ggggtggacg cctcagccag  660
cccaggactg tgccgtcatc cctgagactc actgatcctg atgtgagact ctccccgaca  720
ggggcttcca ggcatggctc tatgcagggt catttgtggc cacactatga cgtgggcgat  780
cccatttcta cacatctaaa ttccccaggg caggcagcat gtggtatctc actccctcgg  840
ctctaacctg gttatgggaa gttgctaggt aactgcttcc cacactggag gaggcttagt  900
taccatggaa agtccagatg ggtggggggg cacagaggaa gggagcactg gctggggggt  960
ctgcagctgg gattctgtcc ccactctctc ctgagcccct ggacctaagg ggagtctctc  1020
aacccctctg ggcctcagtt tcctcctagt aaaatgaagg aaaggctggg tcacttcttg  1080
ctctaaacca ctg                                                     1093

SEQ ID NO: 32          moltype = DNA  length = 1001
FEATURE                Location/Qualifiers
source                 1..1001
                       mol_type = genomic DNA
                       organism = Homo sapiens
SEQUENCE: 32
ataataataa tagcccacat tattgatact gacatgtaga taggtgaatc caatataaaa  60
tgataggagg tatgaaagaa gttggtgagt ttggaatatt atttgactgg ctataatata  120
gagtaatggg gtgggagcca gagggaaatc gaaaaggtga cctggaaaac attgttcagg  180
gccttgaatg ctatgttgag gtattttgac tttataaaat agtgggggac aaactacaag  240
tattttatac attgaggtat agtttatgaa gtttttttat atgtatagct tatgtaaatc  300
tcaaaggaat gctgagaagt aggcgttatt atcccattgt acaggtgaga aagctgagtt  360
tgtggaatat gcatacattc tacattattg agcacctgct atttgccaag cactatgctg  420
agctatgaga ctagaaggaa gttgtagttt aatactctaa tagaggaaac aggaataaat  480
cagcaattgt aagtagttgc rataataaag gcaaacaatg ttacgggagt gaaaggggga  540
cttgtctata tttgcatagt cagggaaggc ttcctggagg aggtgagctt aaactgagtt  600
tggagaaaca aatagattac agtaattgcc cagagatatt taactaggaa gcagtttacc  660
tgaaacttga acccaaatct cctgtgtcta gctctttccc ctactccaag gaccaatctt  720
tggtccttga ttttaagctc tatcagcaac tcagtcacaa gtggacttgt tatgtttgga  780
gaaggtcaga gattccaatt ttttattttt aaattcattc attttctcct tttaaaatct  840
ctgtgtgtgc tcaaagagta gattggaagc agaggaactg gaagaagaac agaatgttct  900
gatagttcag gcaataagtg atgaaggcca taactaaggc agaggtcatg ggcatagtgt  960
gaatctccac tctgttcact ctcctcacac atatactttt a                      1001
```

```
SEQ ID NO: 33           moltype = DNA  length = 2093
FEATURE                 Location/Qualifiers
source                  1..2093
                        mol_type = genomic DNA
                        organism = Homo sapiens
SEQUENCE: 33
tggttttctc ctttaatttt ttgaacttga ggttctataa aagtgaacac agtttgcttc  60
acctgacttc ccggacacca tttctccttc tcatctcctt gactcatccg ttctcaattc  120
tatgacctct caactttgaa ggagcccatt ctctaacctc ttgtcttctc tatctatatt  180
cactccacag gtagtgttat ccacttgcaa agcggtaaat actcttcgat tctgacaact  240
ctcaaggttt tctcttcagc ttctcctgac ctccaaactc gtgtatctaa ctaccttgac  300
ctctactcct ggtcttgcct tccaaacctt ctctcccacg gtctctcctg tctcagtaaa  360
tgacacatcc ttgcttctag gttctcaggc catgaacctg ggagtcacct taactcctgt  420
gtttgtctct tatagctctc atgatatcca tgagcttacc tttgaaatac aaggtggcta  480
cccagtctag ataataaatg atttattgat gctacattct aatacaagat acaataacat  540
tatctatgtt tctagacttt atgatcaccc tgtatattca aaatccaacc acttcccacc  600
actracatca tcctgtttta agccacaacc atctctggtc tggactatga aagtagcctc  660
ttttttttt ttttttttt tgagatggag ttttgctctt attgcccagg ctggagtgca  720
atggcgcaat ctcggctcac tgcaacctcc gcctcccggg ttcaagcgat tcttctgcct  780
cagcctccct agtagctggg attacaggca tgcgccacca tgcctggcta attttgtatt  840
tttagtagaa attgggtttc tccatgttga tcaggatggt ctcaaactcc cgacctcagg  900
tgatccatcc gcctcagtct cccaaagtgc tgggattaca ggcatgagcc aaccatgcct  960
ggccaacagt aggctcctaa ctggtctctc ttcttctgtt cttgctccct tgctatctaa  1020
tttcagcaca acagccagag ctaccctttt aaaacttaaa acccaagtca gatcatacta  1080
ctccccagtt caaaatcttc cattggcttc catctcactc agagtaaaat ccaaaggcct  1140
cgccatggca acaaggccct acatgttctg ctctctctct gatctccatc ccaactcctc  1200
tccacctcac tcacagtgtt aaacatgtct ccacctgaag tctttgcact tgctagtccc  1260
tatacctgca aaagctattt ccccagatgt ccatccagga agtactggct tcttcacttt  1320
gttctagact ttgctcaaat gtcctttgat ttcccaacgt aaaatcgcaa cccccatctc  1380
agccacactc cctgtggctc ttgcatcatt ttatttttct ccctaacagt aggaccatct  1440
gatgtacctt ctgtttctcc ctttaccaga atgtaagatc caggagggca gagattatgt  1500
tttgttcact gatagtttc cagcacctag aacaggacta acacagagta ggtgttcaaa  1560
ctttatttat tgaataaatg aaacgagaat gtctgaatgc acactattaa ataagaagta  1620
catattttac cataaagtta aattgagcat aattatggca agaagttcag atattggcca  1680
ggcgcagtgg ctcatgcctg taatcccagc actttggggg gccaaggtgg gcagatcacc  1740
tgaggtcagg agttcgagac cagcctgacc aacatggcga aacctcagct gtcctaaaaa  1800
tatacaaatt agctgggtgt ggtggcaggt gcctgcaatc ccagctactc gggaggctga  1860
ggcaggagaa tcatttgaac ttaggaggtg gaggttgcag tgagccaaga ttgcgtcact  1920
gtactctagc ctgggcaacc gagcgagact cagtctccaa aaaacaaaat aaaacaaaaa  1980
acaaaacaaa acagaagttc agatataaac aaatgacccc tcaaaaggaa ttgattaaaa  2040
aaattttaaa caaagtatgg tttaaaaaag aaacttctcc actgtggcta agt         2093

SEQ ID NO: 34           moltype = DNA  length = 1001
FEATURE                 Location/Qualifiers
source                  1..1001
                        mol_type = genomic DNA
                        organism = Homo sapiens
SEQUENCE: 34
ctgcacagtt gtacatattg gcagggctca gcttccttaa atgccattgg atcagtaggg  60
aaatggtgat tttccttatt gatttaatgc cagttcctct tttatgaaaa atcccacgtg  120
ctgctcactg gcgtatgtac cataaaaact gaacgtaggg ggccagaaat taagtaagtc  180
actcatgttc ttctccagcc atgtgacgtt aaaccatctc tactttcagg ctggagtgtt  240
caatcattct ccctttaaat ttagcagagt gattattcct cctggtggat tgcacatatg  300
ctcctttgat ctatgaaata ctcattctgg atgaacttta agctcccagg aaatgcatgt  360
aaaatactgt ttataaatcg cgggagaaat gtttcacatt cttattactc ccaagtaatc  420
ataccaagcc tctctctcca agattcgctt tttttcctag aagagggaaa aagaacttcg  480
ggcagtagca ctgtgacaat matcaccacg gtcgtacttt ccatgagttt tacgcagtag  540
gctcacggaa gtgacaatgc atggtcgggc gcggtggctc atgcctgtaa tcccaacact  600
tcgggaggcc gaagtgggtg gatcaactga ggtcaggagt tcaagaccac cctggccaac  660
atagtgaaac cctatctcta ctaaaaatac aaaagattag ccggacgtgg tggtgggcgc  720
ctgcaatcct agctactcgg gaggctgagg caggataatc acttcaaccc gggcggcgga  780
ggttgcagtg agccaagatt ataccactac actctagcct gggtgacaaa acgagactcc  840
gtctcaaaaa aaaaaagaag tgacaatgta ggataccat tcatcagcaa atatttaatg  900
tgagcaggac aatgtgctaa gtccatagac tgcaaagagg agtgaggctg ggttcccatc  960
ctctggggct tacaaggtag ctggagaagt aaaactcaaa c                      1001

SEQ ID NO: 35           moltype = DNA  length = 658
FEATURE                 Location/Qualifiers
source                  1..658
                        mol_type = genomic DNA
                        organism = Homo sapiens
SEQUENCE: 35
tgattaaaca ttcctgaatg caaatgtttt caaatgtcca atgacttccc atcatccttg  60
gtatgaagtc ctaagtccct ggcatgcttt caatgtcctc catgatctgc ccccagtcca  120
atcactgatc ccatctcctg ccagtccatg attgaaccag ttgggtcccc aactcctatt  180
tgcacacacc attctctctg tgtgtcatat atgagctctc tactctgcct agctacttgt  240
ctgcaagact cagttcaatt gtcacctcat ttgggaagct tccactaatc cctcctgcac  300
ctgtctccgt cctaggctag attaggagcc tgccctttgg gttcctgaac cacttgaggt  360
```

```
gtggttcctt tatcatgctg atctcactgg tttggctgac ttgtttttcc tacaagactg  420
aactgtctga ggtcttaaga tgggctgtct agtccacact ggatcttcat gctctacaca  480
gggcttgaca cagagtgggg cacaggaaat gtttgttgaa cgaatacaca aagcatatgg  540
atactcctga gagagagrag gtgggcaaga cagccttgtg aagttaagca gcagaaaatc  600
tgaaaacgaa cctggataga aatcaccaat tcctggaagt acagagagag gaaggaga    658

SEQ ID NO: 36          moltype = DNA  length = 1001
FEATURE                Location/Qualifiers
source                 1..1001
                       mol_type = genomic DNA
                       organism = Homo sapiens
SEQUENCE: 36
tggccaccca gacctccttc ctgcgcttca cactcaaaca aggctgttcc ccatgtcttg  60
ggtctgtctt tcctctacct ggatcgttct tccccatggc ctggtctcag cattgagttc  120
tcaaatgtcc cccctccct caccttatcc gaaggaccca ttccccgtcc tctctacatt  180
ctgtcctatt accctgtctg gtttattttc ttcctagtat tgattactac tggaatcctc  240
atattcatca gtctgctggt ttaatgcctg ttccctttac tggaatgtaa gcatgatttt  300
ggtctttttc tcctctgtcc tgagtaccca gaacaaagcg tggcctatgg aggacactaa  360
atgaacgcat gggggaaaaa cggtttttat tgcagaggga gaccctttgt ttcatacaga  420
tcgtttgtaa acttagatat tttattagca acaaattatg atagagctta caaactcctt  480
gagaatcgct gcggtagtag rtgggggtgg agcttctcta ggcagcattt cagtgtgtcc  540
tagcttggat gctgtggctt cccgagctct gaatctatac tgcttactct gggcttatgg  600
agtgtgtagc agggaatcct tgttgaagga tccccaaacc cttgatagcc atggacagcc  660
cacagtggtc atggagccgg agccagaatg taattcccag tgtgaccagg agctagagtt  720
taagtcaagg cagcaggtat actcaggtgc attttccatt ccctttgagg gaggggtgga  780
ggtttgagcc ccctccacat cccaccccat tggggtgcct ttgtcactct tgacagcttt  840
agagtgactt agatgggaga ttggtgggga ggaggggggg aggggcactg tttgaatcta  900
ccctgctgga ggcactgaat agttttataa gtatgtgtac actctattgt tcaagtgttt  960
gcttaaatca ctgtatcttc ttagaaattt ttgtaacctt t                    1001

SEQ ID NO: 37          moltype = DNA  length = 1001
FEATURE                Location/Qualifiers
source                 1..1001
                       mol_type = genomic DNA
                       organism = Homo sapiens
SEQUENCE: 37
gataataacg cctacttctc agcattcctt tgagatttac ataagctata catataaaaa  60
aacttcataa actatacctc aatgtataaa atacttgtag tttgtccccc actattttat  120
aaagtcaaaa tacctcaaca tagcattcaa ggccctgaac aatgttttcc aggtcacctt  180
ttcgatttcc ctctggctcc caccccatta ctctatatta tagccagtca aataatattc  240
caaactcacc aacttctttc atacctccta tcattttata ttggattcac ctatctacat  300
gtcagtatca ataatgtggg ctattattat tataattatg actgaagtag taggagatag  360
aaacaaatgt tgcttttgtc tactaagtgt tttgttatcc tctgtctttt cccctcatcc  420
tagtcaatat tccattaaaa cacaggttcg attacatttt tcaatgccta ctggataaaa  480
tcaccttgta gtatggataa mgttcttcat gatccaactt ccctctgtta tttaaccttc  540
ctctgctgct ccactaatag cctttgtgac agttgtagta actacagtac atgtagtttt  600
tccaagataa taggctggct cagctttcat gcctttacac atgatgtgtc ctttgcctct  660
tacgtcctcc tctactttgt ctatccagtg aactccctgt catcctttaa gattcaattc  720
agatgtaaac tcttctgtga aacctgccct taaatactca gtggcagaat tagatgatct  780
cttctctctt actatgccat acatatcttg ttacaatctt ctctgacggt gcctgtcacc  840
tccactagcc tgtaaacgta tccagcagag ggctgctttt tatctccgag tccttactgt  900
ctggcacaaa gtgggtgctc acggaaaatc agttgaatac atcaacaatt acccgtcagt  960
ggcacctgaa gccatcagtc actggagcta ccccatcatt g                    1001

SEQ ID NO: 38          moltype = DNA  length = 1001
FEATURE                Location/Qualifiers
source                 1..1001
                       mol_type = genomic DNA
                       organism = Homo sapiens
SEQUENCE: 38
gactttactg aagcagagga gaaggagatg atcaatctat tcaatatgaa gaaatatctc  60
tgttgctaat acaatatcct tttgaatatc tcccacatct taggccctgg tgaaaatccc  120
tttcaattgt tctgtctacc tcgtagggat gttgtaagaa taaatgagtt aacatagata  180
tgaagtgcct taggaaaaag gctctataaa aatgcaaggc gatatcatga ttagttgttt  240
ctttgactct tgatcatttt cttcccactt cttatacaaa atgtctctca cttatttcct  300
gaagccatct cttttagaac tattgcttcc tagaagagct gaaaatgatc ctagttccaa  360
catatttatt gattcccaga taataacacc cactggtgtt gatgactgac agggttcatg  420
cctaagcttg agtagaactt gcccttttt cctgggtcaa gaaaagtctg caattgttcg  480
aaaatgtgtc agtaagtgtg mttccatcac gatttcttaa ataagtaaca gttgctgctg  540
gataatcctg ggggcagatg attcattttt gtgcccctat caaacaaact caaaacttgt  600
taaagaatct ttataagttg tttgaatcaa acaataggt cgctaggtcc ccattttgtc  660
catttgaggt atttgcccag cataccttgg tctgtaaaga aatagcacag ccttggctgg  720
gcgcggtggc tcatgcttat aatcctagca ctttgggagg ccgaggtggg cagatctcca  780
aaaataaata ataataatga taataacaca gcctcatgag tcttttttt ttttttttt  840
ttgagacagg gtctcactct gtcactcagg ctggagtaca gtggcacaat cacagctcac  900
tgcagcctca actaccctgg gtttagtgat cctcccacct cagcctctca agtagctgag  960
actacaggta cacaccacca cacctggcta atattgtatt t                    1001

SEQ ID NO: 39          moltype = DNA  length = 1001
```

```
FEATURE                Location/Qualifiers
source                 1..1001
                       mol_type = genomic DNA
                       organism = Homo sapiens
SEQUENCE: 39
gaaacctttt atatccttac aactattcaa tcttcctgtt caggaaaatg gaatatttaa  60
tatctttcta ataatcaaat attctctata tctaggaaag tcatttttat gtatctcaat  120
caagttttat agttttcttg atatgggttc tacacattga cttacatcca tctacatttt  180
tgatttttat actgggaatg agatggagct gctgctaact ctggagaaac ttactgctga  240
tcttttatct ttggacatga tcctgactgt tctcctaagt gatggattat cttagatttg  300
aaaagtatag gaagtaaagg acaagaggga catgtggggg gatgtagtag agtctgtttt  360
atattcatag tgagaagact ctgaacctcc caggagggct ctaaaggtta aaaaacatgc  420
aaccaaaagc accgaggatt agtaaaaaga aataatgtgc agtaagtgct cagagggatg  480
actcattgca ttggatcatc rttgggaaac cacctactaa gcagaattta gcagctaaag  540
cgttattttt ggtgcacagt ttattgctac ttcctcttgg gaaaaaaaga ttaatcctag  600
ctccctaaaa cacttaagaa tggtcaccct ggcaaaccgg cctgtcaggt aacaatgttg  660
tttccagatc agggcagtgt taggttccct gtagggattt cttcagaaca agggagaagc  720
actttaccac atgttatgga aaggagtata gaccaggaga cagaagatcc agctcttagt  780
gctggctctg taactgatta acaaataaat cccagagtgc aggcaggcca cttaatctct  840
gctcatctgc taaaaaacag atatcacagc ttctgtcgta ctccatatca tggaagaaaa  900
taacacaaaa taataaacca tgtgaatgaa gcagttaaaa ctgctgagaa ataaaattaa  960
cctgctcagt aaaagtaagg ctaccaatca agaacaaata g                      1001

SEQ ID NO: 40          moltype = DNA  length = 1001
FEATURE                Location/Qualifiers
source                 1..1001
                       mol_type = genomic DNA
                       organism = Homo sapiens
SEQUENCE: 40
ggcaatcctt gctttttatt accacactgg attgcttctg tacacagcta agttgcctga  60
agcatggaaa cttggacttc tccatctgac acgttctgga agcctcaagg cacaagctga  120
cagttctgct tctacagaaa aactctcaca ctgctctcct ctcaacagta ctgcctgttc  180
ccactactcc acatgacacc tacgagggca ctacatcacg tgagggaagc ttcttcatga  240
gggcagacaa gaggaggcac cacccaggca ctggtctctg cctggcatct attccgaggg  300
ccacctggca cagtttctaa attaaggcat atctaaaatg cttttctacc tttagttttt  360
atttttgcta tatttttgca ctctactata tgcatattta ataaaaacaa ctacaaagtc  420
ctttacttta attcctttac ataatgataa aacacctaga tacccaaaat actacatcta  480
tatattcaaa tctactaatc rtgttacaaa tgcatgcagc ttatttgggg gcttagtcta  540
atttttattt tcttaggtcc atcaatacca tgataatgaa cattagatgc aaaatcctaa  600
cactttctgc cttcagttgt actttcacag gactagtgtg attcagaaat aaataacata  660
catgaataat aatagaaata atttatgcaa atgtagaaca acttgaaaaa aaatcccccg  720
cctgtcaggt gctgttcctg ggggtagctg atgctataaa ttccatgtac taactaatat  780
atttactaca ggtaatagga aaacaaatga ataaaaagtg aggaactatg atatacatgt  840
gtatattttt gcaaacacag gatcagaatg aaaagatata tcatgcactg tgaggtttaa  900
gaaatgtatt actgctggga tttgttttat tattcagact ttaagatcaa actgagagtt  960
gttggtgatc acagaaatat tgctagctga tacatattat t                      1001

SEQ ID NO: 41          moltype = DNA  length = 1001
FEATURE                Location/Qualifiers
source                 1..1001
                       mol_type = genomic DNA
                       organism = Homo sapiens
SEQUENCE: 41
cctttccatt taagacatgt ctttgaaaat agactctagt ttaaatgtta gcagatagac  60
tttgaagtaa ttatgaggaa gaacttggga ctgaggatgg tcaaattcta aaacacagta  120
ttggatccaa agacaggttt ctccaccctt taagaataaa tctgtcaggc caggtgcggt  180
ggctcacccc gtagtcccag aactttgaga ggccaaggca ggtggatcac ctgaggtcag  240
gagtttgaga ccagcctggc cagcatggca aaaccctgac tctactaaaa atacaaaaat  300
tagccaggtg tggtggtgtg cgcctgtaat cccagccagc tatttttggg aggctgaggc  360
aggagaatcg cttgaacctg ggagacagag gttgcagtga gccaagatcg tgccacactg  420
cactccagcc tgggggacag agagagaatt tgtctcaaaa aaaaaaaaaa tccatcagaa  480
acgtctcacc tcaatatagc rgccaatgtt gtcccatgta aaagtcaggg cacatggtct  540
attgatatga aaaccataaa tcagaatatt tcccattgaa actgccttag gcacagcttg  600
cacattgtaa tatctctcaa ggcaagaaaa tgacctttca gaatagacgt attctagcta  660
aatccccagg catcccaatc aacaattctg gcttccctaa atttccatct gccagagttc  720
gggctgattc tgggagtctt cttgttttga attctcaatg gggtgttagt gcggttttta  780
acacccctct ccagcctcac ccctgatgtg gctgcatttt ggcagcgagg aaaagtctgg  840
gttagaggtt tgggtttcat gagcccttcc aagaacaaga gcagctaagc tgacacaaga  900
gcacactctc cctaaacagt cttttctgcc acctctccca ctgattttat gtaaccgaga  960
agaattagaa aagtgtgaaa aaagcaagac tgatgtttgc t                      1001

SEQ ID NO: 42          moltype = DNA  length = 601
FEATURE                Location/Qualifiers
source                 1..601
                       mol_type = genomic DNA
                       organism = Homo sapiens
SEQUENCE: 42
gaaaatctgg agatgaatca gatctgttcc ttctctcagt gacactgcag tctagatggg  60
ttcagtacaa atatctctat aatacaaaat agctctcaga ccagtctttg tagaaatagc  120
```

```
tgtatgataa ggcttccaat aattataata ataaaaaacc cagttattgt ctgaaatata  180
aacgctcaaa atgcagaaat gttttattca ttgttctgtc cccaggaatg gtgcctggcg  240
tatagtaggc actcaaaaaa tgttagatga tggcagcaac ggtacttcag ggccagggga  300
rccagcaccc atggagagat gcagaggcag aaatggatta ctcaaattgg gaacctgatg  360
ccccctcttc tcactttaat ggagttgtag tagttgagct tcaaagaaag gagcgtcctc  420
cagtgaggtt cctgcccctt cctgggcctc tctaccacag caagagccag ggccagctgg  480
cagttttcac caccctgctc atgtttttct ggagacacca gcttaaccac agccaccaca  540
gatcggaggg tgctggcccc agcctgctgc ctgctggttc ttctccttcc tccctccctt  600
c                                                                   601

SEQ ID NO: 43           moltype = DNA  length = 1001
FEATURE                 Location/Qualifiers
source                  1..1001
                        mol_type = genomic DNA
                        organism = Homo sapiens
SEQUENCE: 43
tacagtcctg caggctgtat atgaaacaca gtaccagcat ctgctcctgg tgaggcttca  60
ggaagcttat aaccgtggca gaaaggtgat ggggagccgg tgtatcacat gatgagagaa  120
ggaagcaaga gatgggggaa gaggcaccag gctcttttaa acaactagct ctcatgtgaa  180
ttaattgaga actcacttat caccaagggg agggcaccta agccattcat gagggatccg  240
ctctcatgac ccaaacacct cctgctaggc cccacctata acactggaga aaacatttca  300
acatgagatt tggaggggac aaatatccaa accatgtcac tgacctgggt tcacattgtc  360
agtctgccac ttatcatctt gatattcttg ggaagataac tttgcttctc tgagccttgg  420
ttttcttcta gaaaataata aaacttgctt cacaggagtg ttaagaagag taagtgagat  480
aatacttgaa aagcacttaa rtttgcatat gacacacagt aagggcttaa gaattgtcgc  540
catcatcatc aatatcatta ttattctctg cacaataaaa tgtgttggaa tcacagcaga  600
taatccagtt atttggatga gtttttccca cgtcatgggc tgagcagatg agttgacaat  660
gggtgactgt tgagtgtcta ccatatactg gcactgttat ggaagtgtgg gcacagctcc  720
tgagagttgc ctaagtgggg ttatgacctg tattttccta gtcatcctac ttaggaaatc  780
atccccccag ttggtgtaag acagtaggct ctcttataca ctgttgctgg gagtacaaat  840
ggatgcaatc tttttggaga gcaacatggc agtatttttt tacgactttt taaaggcata  900
tttggattga gtaattttcc tttgcaggag aataatctgg atatgctgat aaaatatgcc  960
caacgtggca tggataaata tgtttgaaac acacacacac a                       1001

SEQ ID NO: 44           moltype = DNA  length = 1001
FEATURE                 Location/Qualifiers
source                  1..1001
                        mol_type = genomic DNA
                        organism = Homo sapiens
SEQUENCE: 44
ggagatattg accactgtga agatctgttt cctcccagct gatgcagaca ggtcctgaga  60
ccaccggaat ggtgcattct caggggcccc agccaggcag ggtgtgcagc ctgtactcag  120
aggaccctga gcttggtttt attttctccc atcagcattt gacactctta atgatttttg  180
aacacgaggc cctgcatttt cattttacgc tggaccacac aaattccata gctgtttggc  240
agccaagcca agggctgagg acagcacctt cctagagggc tgtgcacaag ccaagttctc  300
agcagcaact tttctgagag aaaaccatct agctccaaat cacgtgttca ttatccattt  360
tcttcccacc ttttgccact tctccttttt ctgtggtccc tccctgttta gcaggtatgg  420
aaggtttggg ggagaagcca ctcattttct ctgcatctct tctggccctg tttctacctc  480
caaatctgca ccatagcccc rtcctcagct tccttgtatt tcctgaagct gtgtcctctc  540
tcccccagcc cctggccgca cccatctcag tgtaatggta ccataaaggg gccaaggaag  600
agcctgtttc cttggcagct tacatctccc cctgggattg ccaacatgca ggagtcagcc  660
cttcctgcct cattacctga acagcttccc cttcaatccc tgaaacactg cactggagtg  720
gagtctactt tgaaagtgaa agtgatttag agtctactcc atttcgagaa tttgcatgtt  780
aacccccttgg gctgggcaca gccccatgga gatttgtttc tttcctggcc agtcccctct  840
cctgccaggt ggtctttgct tctttgcagc ccctcaacat gacagcatgt ttgagtcctt  900
tccagcaaga agctgaactc cccaggagtc tgccagtttt ctagaaaaca ttggttactg  960
gctcctttct ggttttgacc attctttact cagggcttag c                       1001

SEQ ID NO: 45           moltype = DNA  length = 1001
FEATURE                 Location/Qualifiers
source                  1..1001
                        mol_type = genomic DNA
                        organism = Homo sapiens
SEQUENCE: 45
ttaaggggga cttcaaaata aaaaactatg gacacactcc tggagagcag cacggaggag  60
ggatctatga tggtgtaata attgtgagtt tgggctagat atgactgaac aagtaaaggt  120
tgccccaggc atctcacagc gggatgcaga aaagcatcct gatgctaccc agttgaggaa  180
tccaagacat ctcctcccct cctatcaggg agggcacgaa ggggcttcac tctacaggga  240
gggtggaagc acagcagcct tacattgcag ctagggtgca gcaagccaca gccaaggcca  300
gaattctgca gagtgtccca ggaagagaaa agtctaggta gaaatcagcc aataacagag  360
cagaagctaa agagcagaca atgcaacttc caagacaaag acttagcaga aaggactctg  420
aagctagaag cagctgtaac aggggggatg agatggtaat ggttaggaat aaagaagtag  480
aacatgaaga ggggcctttc rccatgctga tagtgataac catttcttta ctgaggagga  540
accagacacg atgtggtaat ctgctttata tactttaaat gtaatgggcc atagccaggt  600
acagtaggag aaccacacac ttgtcctttt ataaaatcca gaatgcaaaa ccttctccac  660
taggtactgt tcatagaatt atctgaacag aaaagacctt tcttaataat ttaagtcaag  720
attctattgc tctacctggg caaatcagta agctacactg cccttatccc ttacaaaatc  780
ctgccttctg tctgggcatg ataacatggt tagacagggt cacatgttat atatatatat  840
gcagagtttt tcattgcagc aaaatataga aatcaacata aatatgcacc aataaagtgc  900
```

```
taataaaaag attatgttca tccaggcaat ggaattctat gcaactattt taaaaagggt  960
gtgaagaagt gctctaaata atatgaaaga tctaagtcat a                      1001

SEQ ID NO: 46          moltype = DNA  length = 701
FEATURE                Location/Qualifiers
source                 1..701
                       mol_type = genomic DNA
                       organism = Homo sapiens
SEQUENCE: 46
cacagccact gtcttcacag ggaagcttgg tggccttgag ctaacatgaa ccggtaagtc  60
ctttcctttt taacagcact ttccttggaa gaatttctcg caggccagcc ttacaggctc  120
ctcacatgtc cactcgtgtg aggtgtaccg gcagtagagt tagtcccttg agaggccata  180
tcagggctta ctccacagcc rctgggacga cagcccagtg tttcagcaaa ggagctgctt  240
acaatcttgt ctatattaag gcccctggcc tttcctttaa agaacaggga tccatttaac  300
accaaaacat tttggagccc cctctctcca tccctatcat cagagtcctg ctttctgtgt  360
ccattcattt aaaatatcca taatgggctg ggcacagtgg ctcacgcctg taatcccagc  420
actttgggag gcagaggcag gtggatcact tgaggtcagg agttcgagac cagtctggcc  480
aacatggtga aatcccgtct ctactaaaaa tacaaaatca gtcaggtgtg gtggcacgca  540
cttgtaaacc cagctactta ggaggctgag gcaggagaat cgcttgaacc tgggaggcag  600
agattgcagt tagccaagat tgcaccactg cactccagcc tgggtaacag agcaagattg  660
tctcaagaaa agaaaaaaga gaaaagatcc ataacgatcc a                      701

SEQ ID NO: 47          moltype = DNA  length = 1001
FEATURE                Location/Qualifiers
source                 1..1001
                       mol_type = genomic DNA
                       organism = Homo sapiens
SEQUENCE: 47
aactacttgt agttcctcaa atcaccatgc tcactctttc tcactggtct tctctccttt  60
gtcttcttgg aaaactattt cacctgtcaa gattcagccc aaagcatcat gttttgtcaa  120
gtctgtctga atgctttagg cattgctaag tatgcctttg cttctgctca cagcatccat  180
gaataactct attatatcac ttattacact gctttacaac tacatctaca ttcttgttgt  240
tattctccac tacatgatgt aaatattttt ttttacttat attcaagaat taaaagaaaa  300
aaaaacctta ccttttcatg gcaaccaaaa gtactgaatg tgcatggaat tggggctgta  360
gggcagtcta gatcataatg attaggcatc tgaaatccaa aacaaaggct gaaaaatctc  420
ttccttgcat atcattttct agtttgatgc gatcacattt aaactgtatt gtcaatggct  480
gctttgtacc acattggcag rtgaataggt gcagcataaa ccatcaccca caaaaattaa  540
aagaacatct actttcaaaa gttatagaga aaggaaatat caacatctca taatatcccc  600
tccaattatc caaaattcat ttcaagaaaa tgaatttgtt cctcttgctg ggaactggca  660
ccctctagtg gcactttaca gaaaaaacac ctaacaatag ctacaagtgc aaactggatt  720
aagactccca ctatggtcta ggccatttaa taggaaccag tcaactgcat gcactgaagc  780
cactgactac acccatactt gcctcatgac cacctctcaa aaatcatctt tgaccacctt  840
tcaacaatct tcttaacttt tgttaagctg ggcatatttt agctacaatg gggagactca  900
gatgttagaa ggtactttaa acacattaat agaagctcta aaaaaagtct cagtcctgga  960
ttttgggact ctaagacaca ttctctaagg taagatcctt t                      1001

SEQ ID NO: 48          moltype = DNA  length = 1001
FEATURE                Location/Qualifiers
source                 1..1001
                       mol_type = genomic DNA
                       organism = Homo sapiens
SEQUENCE: 48
taagtcctgg tgacagttca gcttcacctc taggaccaga aggttccgaa tgccctcgga  60
aagggcttct ccaggggctg ccttcaggcc ctcaggcttt cttaaaacca caaacgtagc  120
caacacctga aaagagaggg aagcttttat tgagaactcc tggcctgaga acacctctta  180
gaggaagttg gctgggactt tccagcctaa ctaccccgaa aacaactgcg ggacccagca  240
atagcatcta ttccctggca ggttcccatt cacaagtttg cacagggctc ttttcggttg  300
taacagtgtg gtcaccctca agtgggaaga cagtgacaat ggggccagcc taaggccagt  360
cctgcagaaa aatgatttct aagctgtgct agactctggt tccaatatgc agccatcagt  420
ttgagcactg cctgggttcc tgtggcccac gatgttgtgc agtaagagat ggatttttaa  480
aaaatgtctc aaggaggaca raagagctcc tcatcctggc attgatgacc atccatgata  540
tgcccttacc aagccagtct gcatatattg ctcagttttt ctcaaagtat cagtgactct  600
tcactcaagc acatctcacc ttcccttacc tgctgttcct tcactcattt catcaggaca  660
cactcactga gtgtttgcta tttattaacc actgtgagtt gcagaacatc caaagatttc  720
taagaccaaa tccctgctct cagggtactc agcctatgga gaagataaca gtcttttcaa  780
gtattcactc atgcaataaa tatttattga gcagctacta tgcatagcca ctcaggcact  840
gggagatata agatggctcc agaggccctg gtgccctgcc ccgtggagct cgcaaccagc  900
aggcactctt ctatgtcatg cacagtcctt cccccacact tttgctcgta ccaactactc  960
ctcttgccca gaattctctt ccttttcccc tctgcttatt t                      1001

SEQ ID NO: 49          moltype = DNA  length = 1001
FEATURE                Location/Qualifiers
source                 1..1001
                       mol_type = genomic DNA
                       organism = Homo sapiens
SEQUENCE: 49
aaatataatt aacactactg aactgtaaag tactgaaatt ataaagaggg tatattttat  60
attgtgtggg gttttgttta accacaattt aaatttttttt ttctaaaggt cttgggttat  120
tgggtattta taaggttgaa aaaaaaatgt catcgatgta ttcaagggaa gaatggctac  180
```

```
aggttcagcc aactctcaaa tgtgcaaagg ttaatttcta acctctattc ttcccaaggc  240
ttggtaagca ttaactgttt gccagacctt ggaactttcc agcgtcagtt tctcattttc  300
cttcctactt tgtctttcta ggagcccctt tcctggacac actcgtgtct ttcccaggga  360
atgggaagaa acaaaaggat gatgacatga cacctaataa gtctggatct ggaagtaagt  420
ttgatctacg gttcattagg ctggagcaga aaaaaaagaa agggtccggt atgttcgcct  480
gtgtgccagg tatggtgtta rgccactcat gtgccttata ttccctacaa cccctcaccc  540
caatttatca cttcaaaaat gataaaagct gagacttgga gaaactagta actaaccaaa  600
agtcacccaa gaaggaggtg gcaagctaag atcaagcccc actttggtgg gagctaagag  660
tagcccttgg tagagtcatg gggttggcta attcttgcct ttggaacctg tttctatctc  720
cattcagttc ctttctttcc tgtcagttgg actttaaact ctaagatcag gaaatttccc  780
tttatctatc aaatcatacc ctattgagtg agtgcctgct tagcctaatg tcctgcaaat  840
ggacaggact cctctcttct atgactcccc agaaatatta caaaggcctg taggaaatag  900
ctcgggacag accagaggaa atagcatgga ggattcacag tataacttat accttcaaag  960
gtgaccacca gcctgcatcc cattaaaaac aaaaacaaaa a                     1001

SEQ ID NO: 50          moltype = DNA  length = 1001
FEATURE                Location/Qualifiers
source                 1..1001
                       mol_type = genomic DNA
                       organism = Homo sapiens
SEQUENCE: 50
ccatttacat taagaaaaat ccccttcaaa agcaacttaa aagttttggt gctgaaaggg  60
ttaacttcag ttatctggaa agcccaggcc ctgggtccgg gaaattcggt ggcagttaca  120
gggttactgg gaggtatcac aggccttgct aacactcagc ttatatgagt ttcatcaaaa  180
acttccaaga tgtgtttcta ggagaaaaag aatgtgtcat ctcactttct cctcacagct  240
gccacgccag ggcatggaga tggggcacag ccctgcctgc tggggcagtg ggtagaggaa  300
gatgctgcac ttagtggaaa atgcaaatga attccactag ggctccaacc tttgactctg  360
aaaagggaag tagaatcatg gcccaacaac ttaaaataaa gaagtgggtg gcttataata  420
actctgaggc ttccaggaaa aagccattct gagtgtaagt aacaaagaag tcaaagaaaa  480
cagccatgcc atctgatgtg hctgcctgga aaacaaggag aaactagtta ccacggaaac  540
aagagagatg gcctctttta cacacaaccc tcggaagctt ctgcagtcag aaagcccagc  600
gtgcaaatcc ttccctggac catgaacaca ggaatgaccc aatgtccttc cacaccacca  660
ggatttagat aatgatcggt caaactcaac tgatccattc tctaattgca gtcagaatgg  720
tctttctaat gacaaccttg atgatcatga tagcaccatt tactgactgc caactgtgag  780
gcgggcactt gacatgtatt atctcagcat tttaaaaatg aacttagagg gtcttgactt  840
ttagtgaaat ggaatagaaa atatcggagt gcatcacatt tggagaaaat aaatttattc  900
atgattactg ggttaaaatg cctcatttat ttcatacctc atatggcact caaaactaca  960
tgaaagcacc tgtttggaag cacctgtgtc tgatcttaca a                     1001

SEQ ID NO: 51          moltype = DNA  length = 1001
FEATURE                Location/Qualifiers
source                 1..1001
                       mol_type = genomic DNA
                       organism = Homo sapiens
SEQUENCE: 51
tcttgccatt gtttgcttcc tttcaatctg tatgaacctt ccctaggagt ccacatcaga  60
tatagcaagg ccatgggagc tatttttaac ttcgggaata ctgtatcaaa actaaataaa  120
ccacagccgg gctcgggggt tcgtgcctta atctcaacac tttgggaggc cagggcaggt  180
ggatcgtttg aggtgaggag ttccagacca gcctggccaa catggcaaaa ccccgtctct  240
actaaacaca aaaattagtt gggcgtggtg gcgggcgcct gtaatcccag ctattgggga  300
ggctgaggcg ggagaaccca gaggcggggg ttgcagtgag tcgagatcgt gccattgcac  360
tccagcctga gcgacagagt gagactctgt ctcaaaaaaa aaaaaaaaaa cttaagtaaa  420
ccacatgcca agtttctttg cagattcttt ggaattctgt caatgtagtg tagtagtgct  480
ggacagacca tgtttaatag ragctgtggc cagcacttta gtgtaataaa ataaaggcaa  540
ataaatttta aatgcagctt catggacaaa ttggtcaaaa catggataaa agtagtgtat  600
tacaaagtgc aaagctccaa ggtcaggtag acgtgggttc tgatcccaac tctgttactt  660
attagttggg taatcttagg taagttactt aacctttttaa gctccatagt taccactttg  720
ataagtggtg acaacaaaac ttaaatacta cataaagttg ttgtaataat tcattcttac  780
tgcctggcac tgttctaagt gctttgcaca tattaacaca tttaatcttc tcagtaactc  840
aagtggattt tattgttaga accattttac agatgagaaa attgaagcac agaaaggtta  900
tataatttgc ccagctcata aatggaagaa aagagttaaa ttcgtatcat tcaattccag  960
cacctgagct catcaccact tattagcact gcgtttccag c                     1001

SEQ ID NO: 52          moltype = DNA  length = 1001
FEATURE                Location/Qualifiers
source                 1..1001
                       mol_type = genomic DNA
                       organism = Homo sapiens
SEQUENCE: 52
cataagaaaa aatggtgtcc tataacagaa ccagatgcag agaacattgt tacatagaac  60
atggaacatc ccaaaagtag tcttacacat aaaaagctac ttaggaaaaa agaacaatgg  120
acagaaaatt gagaaagtta gattcttatc ccagtttcca ctgttgtgtg aaaagtgact  180
tgaatctcct cctctcttga cccttggata aataagtaaa taatttgcta cttttactta  240
aagcaattct aatgcagact ggggagtgac tctatgcttt aaagaaaata gtatttttta  300
aatgtacctt aaattatgat gctactagat aaggataatc tcaaccacac aaagaatact  360
gactctgtaa gtgatcagtt attgtgattt taggcatgtt aaatcttgtt tattacctaa  420
agtgtatggt caactgtaaa attaccagta tttttaaaga aagtattaac tgaaggctct  480
accttcataa tatatccaaa rtccagtccc ttctcacttc ctccctctgc taccaccctg  540
ttgtgactca ccaccagctc tctaacaggc ctcctgcttt ctattcttgt cttccaggct  600
```

```
gttctcaata cagcagcggg agtggaccta gtaaaataag taagatgatg tcatctctgc  660
tcagaccatt gtagcagggt atctgggagt aaaagctaaa atccttataa gaccctgtgt  720
gataggccca tgattcattt cctgacctct tttctgctgc actctttgtc cttctaccca  780
ttcattccct ctttgctatc ccttgaacat gtcaggcatg ctcctgcctt ggtgagtggt  840
ggctttagct cttctgtttg taacactctt gccacagcta accccttaac tcttccactt  900
tggctcaaat ctcaccttct cataggtccc ctcaccaccg tatttatacc acagcgtggt  960
tccacctttc ttgccgaaca atcccaatct ctccacctgg c                      1001

SEQ ID NO: 53          moltype = DNA  length = 1001
FEATURE                Location/Qualifiers
source                 1..1001
                       mol_type = genomic DNA
                       organism = Homo sapiens
SEQUENCE: 53
ccaatgtggt acaaagcagc cattgacaat acagtttaaa tgtgatcgca tcaaactaga  60
aaatgatatg caaggaagag atttttcagc ctttgttttg gatttcagat gcctaatcat  120
tatgatctag actgccctac agccccaatt ccatgcacat tcagtacttt tggttgccat  180
gaaaaggtaa ggtttttttt tcttttaatt cttgaatata agtaaaaaaa aatatttaca  240
tcatgtagtg gagaataaca acaagaatgt agatgtagtt gtaaagcagt gtaataagtg  300
atataataga gttattcatg gatgctgtga gcagaagcaa aggcatactt agcaatgcct  360
aaagcattca gacagacttg acaaaacatg atgctttggg ctgaatcttg acaggtgaaa  420
tagttttcca agaagacaaa ggagagaaga ccagtgagaa agagtgagca tggtgatttg  480
aggaactaca agtagtttgt rttgtgctag ttcaacccaa tagcaatgta gatgatttga  540
ggtggaggtg ggggtactag tacctgagct gttggaatac ctaagtgaag acagcttgaa  600
ttatggcgat gaccgtcaag atagacctag gagccagtac atatttagga gagaagatct  660
actgcctgtg tgactaaata aatgtgatga gtgaaggaga gggaggcgtc tagaatgact  720
cttggtttct ggcctttgtc actgggtaga tggaagggcc attcggcaaa aaagagtgaa  780
cacaggaaga actgactgga ggtagagttt aaaaaaaaaa tctgttttaa tgtattgaat  840
tacagataat gacttcaccc agctagggaa caggtgggat gactgacatg cattatgtgc  900
tgtcttaagc cccaaagaga aattaggact cagagtattg atttgggaaa gtgatttgtg  960
gtaataatgg aagttgtgat tgagatcata tggcgtatgt a                      1001

SEQ ID NO: 54          moltype = DNA  length = 601
FEATURE                Location/Qualifiers
source                 1..601
                       mol_type = genomic DNA
                       organism = Homo sapiens
SEQUENCE: 54
tggaatcaca gctctgcctt cgagctgtgt gactttgggg cagttagttg gcctctctga  60
gcctgtaaag cgggggtatt agagtctagt catgagatat cttataggta agtaaactag  120
catagtgctg gataatgttg taacaattca tgtaataaca attactatgt gattttaaga  180
tgtcagctcc cttttctgga ttggaggatg gaaaggcata tttgcatatt ttcagttgag  240
ttctcccacc cagtcctaca tttactatag taaaaccttg tagatcaaat gtaagtaatg  300
nctctctttc ctcccccacac ctaatgctgc acctcccatt cagagtctta ctagtgaaga  360
ctagtaagtt tagattactt attagtaaga ccagagagtt aggatcaata cgtgcaccct  420
tgtgagatgg aatatatttc tgccctgaga atctctgttg gtcttagcct ggaattaaga  480
tcctgtagca ccacacctct gctctctggg ctttaatagc tcctggctgc aagtttttta  540
gcatgtgcag cttgacattt tatgtggaac tgtcttctgg cctctcctac aagtaatgac  600
g                                                                  601

SEQ ID NO: 55          moltype = DNA  length = 1001
FEATURE                Location/Qualifiers
source                 1..1001
                       mol_type = genomic DNA
                       organism = Homo sapiens
SEQUENCE: 55
atggatggaa ttctctttct aggccatttt tattcgatgc cagattacat agtaaggtca  60
tttcagtttg agatgcactc actcaactat tagcactact gcaaataaca gttatgagta  120
tgatcactaa gtgttcattt tacactgaaa agaaatagaa tagtcagttt ccaaaccaaa  180
tagctatact ccctgaacaa cagtggaaag tcattcttct tgaagtttga cccagaatca  240
agtgcagact cagactccta ggcctacagc cagtggcaac ttaacacatt atatggttga  300
ccttcaggga aaaagggaaa ccactgctct taccactggt gccagaaaaa agccaactaa  360
tctttaaggc acaaaataaa ctattcttaa ggcagaaaaa gaaactgtga ggaaacaagt  420
tagaatggag gcatatagag aaaaatacag aaaatacatt accaagtaag gactagtttt  480
tccatggttc tcagtgtttt ratttttggg aatataatta atcagcattt tctttttggg  540
ttttaactcc tactacctgg tagaaatgca aagatgtaca agaaagatgc atttttaaaa  600
aggcttggag acttaaaggc aattatcttt gctaatttta ctttgagcca gtgacattaa  660
taagttcata tagaaaagta aatagttgct gggcatggcg gctcatgcct gtaatcccag  720
cactttggga ggctgaggcg ggcagatcac ttgagcccag gagttcaaga ccagcctggg  780
caacatggca aaaccctgcc tctacaaaaa atacaaacat tagctgggca tggtggcatg  840
tgcctatagt cccagctact cggggggctg aggcgggagg actgttgaac ccaggaggcg  900
gaggctgcag tgagctgaga tcgtaccact gcactccagc ctgggtcaca gcgagacctt  960
gtctcagaaa aaaaaaaaaa agtaaatagt gatgggatac c                      1001

SEQ ID NO: 56          moltype = DNA  length = 1001
FEATURE                Location/Qualifiers
source                 1..1001
                       mol_type = genomic DNA
                       organism = Homo sapiens
```

SEQUENCE: 56
atttacaact ccatagtcca caaaattaag tctttaatat ggcaccttcc aagatcctcc 60
atagtaacaa cgataatgca aatacaataa catcaacaga aaacgtttcc tgaatgcatt 120
atctcattca atcctcaaaa caaccctttg aggtagtaat tattatcatc ccattttaga 180
gaaaaagaaa ttgaggtaca catcctcaac cacacttggc ctcttgtcaa tccatcctta 240
tttcagccat tcccaactac ttgtatcact gtgcccctct gcagacttct gtgctgtgga 300
catccttagc ctgcactgcc ctgccttagg ccgcccctgc tgtttgttgg gtgaacaatg 360
gctaatcttt ttagacccag ttcaggaaag gccaaaagct agaggaatgg tatttcagca 420
catatgatca gatttggaag tgatcttaaa gagacatcta gtttcacaat ctatagacta 480
tggattccaa ctcccattag rgggtcaaag ccagggtttt tataaaattg aaataaaata 540
gaataaaaaa tatcagagag cagggagtga aactatgtat tgtttcaagg gcaggcattg 600
ttttgtgaag gttgtgtatg ccaggtccca aagtaaaatg tgttttttac tgtgggtaga 660
ggtccaacca ccaagccact ctccacgcca gaagccagaa tgatctttct aaatctgatt 720
acgtcagact cttactttga aattttctgt gttttcctat ttccattaag attaaagaca 780
aaacaaaaca cctcacaatg cctacccagg gccctgctgg tctcccgttc ttctgaggtc 840
atcccaagcc tttgaaggtg ctgttcctgc ctgtacactc taccettgcc ctttacacct 900
tctaagtccc attaatcctt caagattcta ctcaaatatc actttcccca agaaacctct 960
gcctaagttt cttgatctag tctaggttgc tagactagga c 1001

SEQ ID NO: 57 moltype = DNA length = 1001
FEATURE Location/Qualifiers
source 1..1001
mol_type = genomic DNA
organism = Homo sapiens
SEQUENCE: 57
ctggaggaag tgggtgaatg ggtcagatct catttggtgg cctcttgggg aagaagggtg 60
atatactcct gttttctctc tgaaatattc ttcctgaggc ttgtggtggg atccagggtt 120
aaaactgagt gaagagaaaa tattgccttg agaaacaata atgactctgg caacccacct 180
attctttagt agcccatctc aattgacctt cttttaattg ttcatattgg acagactgga 240
gactgcagtg tggggagagt catcctctta cttatcttgg cctttggctt cccactgcag 300
acagcccttg caggtccatc caggttgggg aagatggttt taaaaggttc attagttaag 360
aaaggccctg gggcctggaa ataaagggtt tgaggaggag agtagagggt ggggtcttcc 420
tccccggacc tcacgattgg gaatgaggat ttttttagc tacacgggtc tgactagagc 480
tgtaaacgtt actcagattg rtcactatgt ctcttcccac gagcccctcc ctgtcaccac 540
ccccctgctg tcaaaccata tcttcgtgga ccagccatgc gggacatccc tcttaatggg 600
agcataagag tgttgtctca gacccttatt ttgttagttt atgtttccat gaagctctta 660
atgtttatta aataaacaga caatgagttt gtgtgacatg cccacagctt ctgtgtatgt 720
gacacatgcc tagcctgtgt tctgggagtg tatgtcactt tggcctttgg ctggggaact 780
ggtgatggtg ggaggccact caattactct ctctgcaact gtataactat taatacttct 840
tcagaactgt gggaaatggt tctactcatc agctttatgg aatgtgggtt agggagaggg 900
gacagaatct cttcaaggtc tggatgctaa acgtacccct tccttattcc ctcccaatgc 960
agaaaaaggt ctgggatgtt ctgacagggc catctctgcc t 1001

SEQ ID NO: 58 moltype = DNA length = 1001
FEATURE Location/Qualifiers
source 1..1001
mol_type = genomic DNA
organism = Homo sapiens
SEQUENCE: 58
attttcattt gtgtttttt aaatttctag tgaggtcatc taattcacct ttaaatattt 60
tatcttattc ttttgtttc aaatgctcta cctagccttt caagagtatt cttcacaacc 120
aaagcagtcc taagcctaag cagaaaggag aaataaagtt gatgggggaa aaatgtatat 180
attttttct aaaataaggc ttaggagtaa tttaaaacaa aatgctgatt tggtattcaa 240
ttgtcctctt taagggctct taatatgctg aatataatta aaacaagcaa ttagcaattc 300
actcaaattt atctattttt caagttaaat aacattctaa taagctaaca agcacaaaac 360
agatcagcag ttatcataag gtcaggggtc ataaatatgt aaatgcctac aaatgccagg 420
cattaaacat aaatgagtga actgaaagca cattcactgt ctcaaaggga gagccacaac 480
tcagttccat cttattactg rcaagtgtaa attcaagttc aattttgccc tatttttcaa 540
acttcaaaag gcataaattc agattttaat gtaaaatctc ctgattttta aatgctgaag 600
aaaaaatcc aaaaaacaat ggtgggccct tctggataag tttgttctct gccctagata 660
aattaataga ataagaacaa aatctaattt agttattact gatgacagta agtcaagaga 720
aatttgccac atcacaaaaa tacacatttg tatttctgaa aataaaacta ctgatataaa 780
tcatgacctt tatgtgaggg tctgaaaaga tcaatatgga atcaacagtc catttctgaa 840
gatcattcac agatacactc tgtcctcctt gagttcaacc tttagctggg gttagacaca 900
cctctagaga agtacataaa actttgcaag gaccaaaatg gaatacatgg ttttaagaaa 960
atcaacttct aaagcttcaa ctttatcact ctttcctata a 1001

SEQ ID NO: 59 moltype = DNA length = 501
FEATURE Location/Qualifiers
source 1..501
mol_type = genomic DNA
organism = Homo sapiens
SEQUENCE: 59
taggggaagc tttattctga gatctgcaca aaagtgggtt atcctggcag cacagtgtac 60
ctcgtagttg ttctctgatg tgtaaaactt ggtgtaacac atctgagtgt gtgtgttggt 120
gttttattcc agtagttaaa atagacataa gacaaattca tataaaatgt ttgtagactg 180
caatgtcttc tgaagaatgc tgtcagaaaa tcattattct aggtccccag gtttacatcc 240
ctctgtgaga rgctcttgta ccagttgttg ggtaatttga acagttgcct ttgtggtacc 300
attaggagtc tcaactttta aggatcactt acagttctgt gcataggtga ttttcaaagc 360

```
acctgggtga agttacatgg ctctagaaaa ttgagcttta gaaaacagca ataacactga  420
aacaatcttt gggagtgagt tatcagagaa cgtgcattgt tgccaaggat gctggcataa  480
attctgggaa cctcaaaata a                                           501

SEQ ID NO: 60          moltype = DNA  length = 807
FEATURE                Location/Qualifiers
source                 1..807
                       mol_type = genomic DNA
                       organism = Homo sapiens
SEQUENCE: 60
aagtgtatag actgcacctc cccactgtct cttcctccta ctctggccag gtgaagtatt  60
tgctctccct ttgccctcca ccatgatcat aagtttcctg aggcctcccc aaaagctgat  120
gtcaccatac ctgtacggaa tcatgggcct atggaaccgt gagccagtta gcctcttttc  180
tttataaatt acccagtctc aggtatttcc tcatagcagt gtgagaacaa actagtaaac  240
agtgtaaatg ctttgtaaat agttgttagt taaactgtac tgttttggga ataatgacaa  300
agaaaagagt ctgtatgtat tcagtacaga ggcagccatc catttttaa aaatatcttt  360
aatccacaga tgcagaaccc atgagtgtag agggctggac tgtatacatg aatacatatt  420
gacatcttta tttctatatc tatatatcca aatatatttt gaaaatcatg agtttacact  480
gatacctcta gtttgaatcc rataacacag gttcattcta gtttactccc ttttcatatt  540
tatacctttc ttctctgaca gtgagaaatc aggcttcctt tatcctcagt atattcactt  600
actggctaat ttcccctccc cattgcctat aaactactca tctcccattg gtgctgccac  660
cacaatccct caatctcata tgcatatggg tgacctcctc actccacttg gtctctgaca  720
tcctgtgtga gctccctgtc actgccctcc cccccatatg ggtgctcttc tcacccctct  780
ttggcttaaa aacccaattc tgggttg                                     807

SEQ ID NO: 61          moltype = DNA  length = 1001
FEATURE                Location/Qualifiers
source                 1..1001
                       mol_type = genomic DNA
                       organism = Homo sapiens
SEQUENCE: 61
ttatgcaaac cttgagtttt atgcaaataa gaattcagtt ccaagcacaa ataattaaaa  60
gcagggtttt tacagtcacg attgcccccct ggacatttga aattcaagtg agacatgggg  120
caattcttca ttctgcagaa atttccatgc aatgccagaa acctaatatc cctagcccta  180
tgtacaaaat gctagttgtg cccccctttat cactgtgata actaataggg ccttctgcat  240
gagtctaaac actctgtaga ggcgggtttg ctatggtcct gctggtaggg cagggactat  300
gctctaatcc cttgaataac ttctcacttg gtggagtgtt gtgtacttgg ggggattcaa  360
tgagtagttg tgaattgatg gagttacagt agcactgaac agagatgaaa ggcagcaaaa  420
tcagttagta tagtacagtc ttccctaagt atcctctggg gattggttcc agaacctccg  480
cggataccag atacccaaat rctcggatgt tcaagtccca caattggccc tgaagaaccc  540
acagataggg ggtgccaagt gtatttcaaa accagtttga tacggaattt gaaaatgtga  600
actgtggtaa gcagaataaa gatgtccacg tcttaggctg ggtgcagtgg ctcacacttg  660
taatcccagc actgtgggag gccgaggcag gtgcatcact tgaggtcaga gtttgaggcc  720
agcctggcca gcatagtgaa accctgtgtc tactaaaaat acaaaaaaata aaataaaata  780
aaattagctg ggtgtggtgg tgcatgcctg tagttccagc tcttcaagag gctcaggcag  840
gagaatcgct tgaactcagg aggcagagtt tgcagtgagc caagattgcg tcacagtact  900
ctagttaggt gactgagcaa gattctatct caaaaaaaaga aaggaaaaaa aagatatcca  960
catcctaata tccagaactg gtgactattt tatgttacat g                     1001

SEQ ID NO: 62          moltype = DNA  length = 1001
FEATURE                Location/Qualifiers
source                 1..1001
                       mol_type = genomic DNA
                       organism = Homo sapiens
SEQUENCE: 62
tctcattgca tttttttaa atttttaatt attatgacta cataatagtt atatatattc  60
ctcatatctc aatttaatta ccacaatcac tgtttttaca aggtcccagg caagaagagg  120
tgaggcaaat ggaggctctg aggaaagtgg ctccaaagcc tacatgatgg aagataactc  180
tggaagagaa agagatgacg ttcctaagct tgtatagcaa aacttgagag aaggtaacga  240
agatgtgaca tctgaactca gagaaatata acttctatag aaaagaaaca aggccttgca  300
gctctataag gaacagtaaa taaatcaagt atgcacacaa gaagtaaaaa aatatatcca  360
agtagaaagg aagcttttca tgaaatgtcc acagagctca tgctctgtag tgactgtaat  420
gcaagattca aggctctatc tagaaaactc ctagccagtc ttgacggacc aagccctaca  480
ctgagcatgt acagagtctt rctgttccat gcagtacttg ctaacaaaac taatttaaat  540
gccttaccat gactcgatct cctttaaagt acctcattag tccttgatat ccctttgctg  600
tatctctggc ttgccttgcc actgctctgt gagtccccac aactcctcct ccacacatac  660
tcttccccca agagcttggc acagaataaa gatccatttt agatctggat ttaaatagtt  720
ttctttacta gctcatttcc ttatctacta atgagggaaa taccacctac gtcagagtgg  780
gaattaaatg aaataataaa cctaaagacc ccagctcaat ggttcaaaca taaataatgc  840
caaatattca ttcctctccc catgcccata tcctctcacc aagccccaat gttctatagc  900
ttatgaccca aaacgctaaa agtagaacat tctaatattg agcatattaa cagaagcttg  960
aagagatatg caagttataa atctgttttt gttcttcctc a                     1001

SEQ ID NO: 63          moltype = DNA  length = 1001
FEATURE                Location/Qualifiers
source                 1..1001
                       mol_type = genomic DNA
                       organism = Homo sapiens
SEQUENCE: 63
```

```
ctacattaga aacaggtttt ggaggagtag tgggaacatt gggtgatttc tagtggggtt  60
agagaaagca gtacctggtt ctttggccac atctaccaaa gcaaagacct agacttgtag  120
aggagagtat tgtttgcttg tttgaggatt gtatttccca ggtttgttca tttgcatgag  180
tggctgaata atgtaacaga gacttcagaa gtaaggaaaa tggttgtcac caaaatatct  240
tgttttacct ttatttggac taaatggaaa acacatgttt aatagctaag gctattgagt  300
gcttatcatt tgccaggaac tgtttctgag cctttcacat ataacacctc attttatcca  360
ccctctaccc ctaacaaatg gtgtggtttg agttggcctt ggtgaggtat gaaaaggaaa  420
caaagcagtg acctcttcct gcaggctggt cagatgtttg ggataacatt ccttagcatt  480
cttggtggaa gtggtgattt rgttgaaagc tgcttcccag ttgctctgga gtgcaggtgg  540
gaggggtgga ctttggcttt tccaaaggat cccaggaatg ggaaggacct taaagatcta  600
gaccaggggt atccaatctt ttggcttccc tgggccacat tgtaagaaga agaattatct  660
tgggctacac gtaaaatacg ctaacactaa tgatagctaa tgatcttaaa aattgccaa  720
aaaaatctca taatgtttaa gaaagtgtat gaatttttgt tgggctgcat ttaaagccat  780
cctggactgc atgtggccca tggccatga attggacaag ctttatctag actgttctga  840
actactcatc tgcctccccc agcccccacc cccaccccac acatccagaa ttctccaccc  900
attggttgtc tggcctctgc ctgaatagct gagtacctgt cttttccaaa actacccctt  960
gaggggagac ttacagcacc ctgtagcata gtatatgata t                     1001

SEQ ID NO: 64          moltype = DNA  length = 1402
FEATURE                Location/Qualifiers
source                 1..1402
                       mol_type = genomic DNA
                       organism = Homo sapiens
SEQUENCE: 64
aacttgatcc ttaacagaat ctcatgagag ctataagtct tattattatc ccctttattg  60
atgagaaaac tgaggcccaa ggaggttcag taacttgacc aaggttaaac ttccactagt  120
atgtggcaca tgtgtgattc taatcaaggg aggctggctg caaagcctct gcttctgtta  180
ttgctagaat ctaataagtt atttactaag tatgtaagga tacagtctca tttaattctc  240
acagtaacat tgtagatgag tgattagaaa atagctaaaa gacagacact tctcaaaaga  300
agacatttat gcagccaaaa aacacatgaa aaaatgctca ccatcactgg ccatcagaga  360
aatgcaaatc aaaaccacaa tgagatacca tctcacacca gttagaatgg caatcattaa  420
aaagtcagga aacaacaggt gctggagagg atgtggagaa ataggagcac ttttacactg  480
ttggtgggac tgtaaactag ttcaaccact gtggaagtca gtgtggtgat tcctcaggga  540
tctagaacta gaaataccat ttgacccagc catcgcatta ctgggtatat acccaaagga  600
ctataaatca tgctgctata aagacaaatg cacacgtatg tttattgcgg cactattcac  660
aatagcaaag acttggaacc aacccaaatg tccaacaatg atagactgga ttaagaaaat  720
gtggcacata tacaccatgg aatactacgc agccataaaa gtgagttcat gtcctttgta  780
gggacatgga tgaaattgga aatcatcatt ctcagtaaac tatcacaagg acaaaaaacc  840
aaacaccgca tgttctcact cataggtggg aattgaacaa tgagaacaga tggacacagg  900
aaggggaaca tcacactctg gggactgttg tggggtgggg ggagggggg agggatagca  960
ttaggagata tacctaatgt aaatgacgag ttaatgggtg cagcacacca acatggcaca  1020
tgtatacata tgtaactaac ctgcacattg tgcacatgta ccctaaaact taaagtataa  1080
taataataaa ataaaataat aaaaaagaaa atagctaaaa gatgtgaagt tggctagtct  1140
aaagattcaa aagtaatgaa tgggagaaag agaaattaga ctcaccatgt cctacttatt  1200
thgacttttt actgagctga actgcttccc ctacctgcat atccaggaaa atgggtaagg  1260
tctggtagat gctttcagcc ttatcgtgct atgatgtttg ggccgcagtg ttatttgctc  1320
attagtcctt tcttgtttct taaaatttaa catttagcca ctgttttgta aattctgact  1380
taggtgccaa gttatggcgc ta                                          1402

SEQ ID NO: 65          moltype = DNA  length = 2022
FEATURE                Location/Qualifiers
source                 1..2022
                       mol_type = genomic DNA
                       organism = Homo sapiens
SEQUENCE: 65
gctgggttga agtgaggctg gaggtggagg caggggccag tgtagtggtg cagagccact  60
gaagagctta agcagagaag ggacataata atgtttgggt tcttaaaaga tcacgttcag  120
atcctatatg agcaggtgat ttgagggggc aggagtggat ctgttagaag gctattgcaa  180
gtggtccagg agcaagaggg tggtggcttg gaatagtatc atagtagtag agatggagag  240
aagtgaatgg atgtaagagg tatttaggga ggtagactgc attgaacttg gagaatgact  300
aagataggaa gagaagggga caatgcttgg atttctggct ttggaaacca tatggatgac  360
catccttgtt cctgagccag acctattgtg ggaagggcag attttgaaag aaagatcatg  420
gtttagttgt tgacatgctg aatttaaggg ttggagtaca tacaagtgaa gttagatcaa  480
tagatctgat gatcggaggg gagatctggg ctgtgcataa agttgggagt catctgggat  540
ggactgaagt catgagagag aatgaatggt agcagggaat ggggattgga catgtgacta  600
ggaataacca cagaggccag ttgaaaatgt atggaaacga gaacatcaag catgaagggc  660
catgcccagt gctaaggaga aatctggtta ggaagtgcat ggatttagca gcrgtgaggt  720
tggatttagc aatcaagatt ggcacctcaa gcaggagaaa tttaagtgga gttgtgggga  780
cagaagccaa ttttgaacac tagatgagtg aattggaggc aggaatatga agacactgag  840
tatgggtacc ttttttgaga agttgggctc aaagggtaga gacagttaga ggggacctgc  900
aagaggtgtg taggatccag gcatatagct ctaggtctaa acatctctat gtttggatat  960
ttagagatgg aagagaaagg atatttagtt gcttaaggtt cctgcaaaga caggtgggat  1020
gtaacccaga gcccacacga agggacgggc atttatctcc agcacttcag aaggagagga  1080
agaggagggg gtgggtacag ctgcagatgc aggcaggtgt ggaggtttgg agtggaatgg  1140
taagtgatac cattctgata atttctgttt tctctgtgaa gtaggaggga aagtcatctt  1200
cccagatgaa gggaacggaa tcaggttgct gggtaagatc agttctccag ctgtgcttgg  1260
cagctaccac tgcaagcatg gaataggcgg ctaggtaagt tcagccaaga ttgaagtttt  1320
actctgtggg agtaataaaa ggacaaggaa cacgaaggct aaggacatta acacatggag  1380
gaatgatttc agtggaggtt cagttggatg aagataggtt agtgctgatg gagaatgacc  1440
```

```
tggcagtgtc aggggggcaat aaacagggta gtggtagtac ctgaataagg gaactagcta  1500
tgagtgcttc tccaactgta atgctaatgt gaatcacctg gggattttag taaaaacgca  1560
gattctgatt cagcaggtct gggctgaggc ctcagattct gcatttctaa caagttcctg  1620
tcacgccagc ctctctggcc cgtggatcac actgtgaggg ccaggtgtgg tggtgcatga  1680
ctataatcca aacactttgt gaggcccagg tgggaggatc acttgagctg aggagtttga  1740
gaccagcctg ggcaacatag acgtcatctc tacaaaaagt ttaaaaatta cctgggtgtg  1800
gtggcttgtg cctgtagtag ctacttgaaa agctgaggca ggaggatcac ctgagcctgg  1860
gaggtcaagg ctgcagtgag ccgagattgc accactgcac tccagcccgg gtgacagtaa  1920
aagcctgtct cttaaaataa aaaaaaaaaa aaaaaaaaaa gatttcgggc agagagtggg  1980
atgcctgaat tagaaatcgt ttgacatggt ataatctcaa gc                        2022

SEQ ID NO: 66          moltype = DNA  length = 1001
FEATURE                Location/Qualifiers
source                 1..1001
                       mol_type = genomic DNA
                       organism = Homo sapiens
SEQUENCE: 66
gtggcttctc tttggaaaca gttcactggt tttctcaagg gaccaatggg ctatgaagac  60
cagggactgt ccaagctggc cactcgggaa atgaaaaaaa atatgtgacg gaacatggga  120
aagaaccaca agtggaagaa gtttggacac acaggattct acctttttgc tcattctacc  180
caaaccatct gcacattgat aaattattag gatgagctgt gcatcctact ttacaatata  240
catgtccatg gggagaggt caatagaaac agttaccacg acagttggtg gagtcagaac  300
atctggcggc tacacagaca caccagctgc gtgacttggc aaactcagta tctctgtgcc  360
tcatattcct catccgtaaa atggagcagt gacgaggata ttgagagttc atcaaaaagc  420
acttactata gtgccaagga cacagctaag tgctcaaaga ttagccatga tgatgatctg  480
actatctatt tttatccctg rttgactaat ttttgtggga gaacaagggg aagaggtgaa  540
gaattgatgt aactttcata tattacctat cctacttttg tatatgtttg aaaattctta  600
taatggtaag ttaaattaaa aaaaaaaaac ctaatgtgtg tgtgtgtgtg gtgttttttt  660
gtgtgttttt ttgtttgttt ggttggtttt tttgagatag ggtgacgggg tcttgtcact  720
caggctggag tgcagtggtg tggtcacagt gtgatcacag cctaaattcc taggctcaag  780
ttatcctccc acctcagcct cccaagtagc agggactaca ggtgtgcact accacacctg  840
gccttatttt gtgcaggaga gaataaggtg aagaccaatc catttctaat atttttaagt  900
ttcttctatc attagatttt ctaaactaat agcaaacttt tttgtaaagg gcccaagagt  960
aaatatttta cactttgcag accatatggc cctgttgcaa g                         1001

SEQ ID NO: 67          moltype = DNA  length = 1001
FEATURE                Location/Qualifiers
source                 1..1001
                       mol_type = genomic DNA
                       organism = Homo sapiens
SEQUENCE: 67
tcgtcttgaa attcttaatc atatttgaac aatgtcccta cagattatgt agccagtctt  60
gctactaccg agctgcactt gacctccccg cactcatcct ggccatactt catccctgtc  120
cctctccttt ctactgcctg gtgctttgtc ccatttcctt gcccccaagg ccttaggagg  180
gtgtaaaaaa aaaaaaagat aaattcctca gggaaaagat gtgatttggc tcacagcata  240
tggaatattc aaagatagac atcatctgtt gcccacattt ttatgagact gacatgctgc  300
ctgtagcatt gagaaggcac tggttgccta cacttttaga agtcatttat taatggcttc  360
ctagggcatg ccaactctaa aatcaagcca caaaaatgat accaggtaaa aattgatcct  420
gtgaataact gtgacggtgg catttgggtg aaaggtcttg aaatgggctg tgtcttttcc  480
ctcaactttc ctcacccgct rttatcacac tctcccagcc agtgtcagat tacttctctt  540
ctcatctgtc tcataaatag ttctggcttg agttatcccc taccgtgatg acatatgatt  600
attcaaagaa agattttata gaaaatgcat tgtttctatt tggagttggg agactaggga  660
aaggtataaa gcacgccaca ggggcacagc cttgattgac tttctgtgct cagcttagcc  720
gttcaagccc ggggttgtgt ctgggtaaag ctgtttgact ttgggtaagt cctttaacaa  780
cctgaggtcc cagtgttctt aactttctac agttttgttc taatccagca ttcttgaact  840
agcacataag cataacttgc taaataagca ccacttgcta aatacaggct tagtgacaag  900
gaagttattt ggaaaatgaa aagagggcaa ttctcccatc aggacttgag aagccttgga  960
gttttctttc tttattgaaa agactcatga ggcctgtcca a                         1001

SEQ ID NO: 68          moltype = DNA  length = 1958
FEATURE                Location/Qualifiers
source                 1..1958
                       mol_type = genomic DNA
                       organism = Homo sapiens
SEQUENCE: 68
accccaaggt ggaagcttta catgactgag aaagcccatc cactcattgt catagaatca  60
actattaatt caacaaatac ttatggagcc tttgccatgc ctatgagcct tgtgctagaa  120
gccagggata agtaaaataa attctgcacc tgcctcctgc aacttagtcc aatttccagg  180
tctcccttag atttttctct gttttaattt ttattttgaa aatggagaca gggtctcact  240
atgttgccca ggctggtcat gaactcctgg gctcaagtga tcctcccgcc taggcctctt  300
aaagtgctga gattacaggc atgagccatc acacctagcc tctctcttaa aacaacttta  360
ttaaagatgt aattcaggct gggtgtggtg gctcacatct gtaatcccag cacttgaaaa  420
ttacttgaag ttgggaggtg gaggttgcaa tgagctcaga tcatgccact gcactccagc  480
ttgggtaaca gagcaagagt ccctctcaaa aaaaaaaaaa aaaaaaaaag taattcacat  540
accatacatt tcacctgttt aaagtgtaca attcagtggc tattagtata ttcacagagt  600
tgtgcatcta ttaccagaat caattttgag ccttttttttt tttttaaccc caaaaagaaa  660
cctcttccct ttaacactta tccccagtcc acctatcctt ctcagccctt ggcaacagct  720
agtctacttt ctgtctctat ggaccggcct agtctagata ttttatataa atggaattat  780
ataatatgtg gccttcatgt ctggcttatg tcatttagca taatattttc aaagttcttc  840
```

```
catgttgtag catgggttag aacttcattc ttcttttatt atggttgaat gatattccac  900
tgtatgaata taccacatct tttttttttt ttttttttg gagacagaat cttgctctgt  960
tgcccaggct agaatgcaat ggcacgatct cggctcactg caagctccgt ctcctgggtt  1020
caagggattc tcctgtctca gcttctcgag tagttgggat tacaggtgca cgccaccgca  1080
cccggctaat ttttgtattt ttagtagagg tggggcttca cctccttggc caggctggtc  1140
ttaaactcct gacctcatga tccacccgcc tctgcctccc aaagtgctgg gattacagga  1200
gtgagccacc ccgccgggcc acatcttttt ttaatctatt ccttcactaa tagattgtgg  1260
gttgtttcca ccttctcact atgtgagtaa tgctcttatg agcgtgcata caagtttttg  1320
tgtgggcata tgtgctcaag tctctgatcc cctagatgtc ttgcctatcc tacagatcca  1380
ggcctaccac aaaaaagtgt agaaggatca tataccatga gaacataaag gagggacatg  1440
tagacttaat tagggagtca gggaaggctg cccctgaggc caccatatcc aagctgcggc  1500
ttgagagatv ggttgaatag aaaagttttt caaactgcag ctgatcaccc attagtaggt  1560
tgtgaattca gtttagtgaa tcatggccag catttttag gaggtgaact aaaatagaat  1620
agtagatgtt agaggacatt ccatgtggta agggtaagta ttgttgcatg aaatttattt  1680
tcagtagcta tatgagcgca tctagcaaat tgtgacgtaa gaagtattct atattccggg  1740
ttgcaatcag aaaaatatga aagccactgc tctagggatt ttttaaaagg agattattta  1800
ttaatctgga gctttaaata tggttccact agaagattgg agagatacag gagagagaag  1860
aacctagaaa gctgaagatc ctttgaaagc ttaaagttct gtgatttcta cacttttaaa  1920
atgattcatt tattcaacaa atattaaaat atttacca                          1958

SEQ ID NO: 69          moltype = DNA  length = 1001
FEATURE                Location/Qualifiers
source                 1..1001
                       mol_type = genomic DNA
                       organism = Homo sapiens
SEQUENCE: 69
tcatatactg caacacaaca cacacacacc tcacttacat agacttttga tttaagctgt  60
gttcagattt ctcttagcac attcaagttt tccttccttc ttcccagaag cacctaaagg  120
ctgtaatgag aaacatattt tttactcctt tgttccctct ctttgtgtaa aggcatccca  180
agaaaatcag tgaaggattt tgtgctctat gtccctaagg ctccatgtcc cagttatttt  240
tctctctcaa ctggggcttg atttccactt tattcaagtc tacttcttat ttccttcggt  300
gatccgaagt actggcagat ttttctaaga cttcagacat gtggggagta actttcataa  360
ctccaaagaa tacactacca gaaatgtaac catctcagct gttctccgtc tactctgatg  420
ttgcctgtaa gaaataacaa gatgccactc tgttctttaa aagagatata taacattttt  480
cataagatgt ccttcattac wtggtgcaga attcgaactg atcgtttgtg gattaatcat  540
aataatgact tattttgttt atgttaacta aaaggagttt atcattttta tatgatattg  600
actgaatggt catagggaaat tgagatcttt ttcctaaaaa ggtgataaca tttactggag  660
tgttgtttta gtagataact tgatccttaa cagaatctca tgagagctat aagtcttatt  720
attatcccct ttattgatga gaaaactgag gcccaaggag gttcagtaac ttgaccaagg  780
ttaaacttcc actagtatgt ggcacatgtg tgattctaat caagggaggc tggctgcaaa  840
gcctctgctt ctgttattgc tagaatctaa taagttattt actaagtatg taaggataca  900
gtctcattta attctcacag taacattgta gatgagtgat tagaaaatag ctaaaagaca  960
gacacttctc aaaagaagac atttatgcag ccaaaaaaca c                      1001

SEQ ID NO: 70          moltype = DNA  length = 1001
FEATURE                Location/Qualifiers
source                 1..1001
                       mol_type = genomic DNA
                       organism = Homo sapiens
SEQUENCE: 70
cattgaattg ccttattaat ctcttgggtc atgcaattca gtgatataac tagggttagc  60
ctgagtgttt caaagcaaga ttaatggaag ctcattcgcc agctgtcggg ttaggagatt  120
attcacaaat gttgccctgt catttgaatc tggtagggtt tgctgatgaa taaatgaacc  180
ccattatact gacagccacc tcactaatcg atcctaacta aaccacctta tcctcttcac  240
cttccaattg tgtagccagc aacttgccag atctcaggga cgttgttggg acatgtggaa  300
ggtctgagac agagggccgg aaggacagac aatgccacca actctattaa tcagtccgca  360
tttctcagac ctggctctca gcctactgaa tttgacaacc aaggatttgc gtgtagtttt  420
tttttttttt cattttcaat taatttccct ttttatgcct tcctaatttc tcttcttttc  480
tgactaagct atatatttac rctgtgaaat tgactgtcat taatcttttt ctgccttgat  540
ttcctcaact aaaaaatggt taaactaata ccagcccttt cattcatggt gatcttggga  600
ggaaaaaaaa aagagataac tgatgtcaga gagtgctttg aacttaaagc aggaagattg  660
ttcaattata ataagactct tctatcttta tttttatgtg acatttagaa tgttagcgtt  720
gaatacgcgt caaggaagaa aatcccattt tgaatgacag tgttagaatg acggcctgta  780
agatattgga attgcatgca aaaaccaaga aaatgtgttt aaaaactgct aagaccaagc  840
cagctactgt ttcttttcaa agaatatatg tagggaatag gagaattagg taactctagg  900
gcataataaa aaagaagaac atgtgctttc tgattttgcc aatctatttt gtacttactt  960
tataattcaa ttttaagagt aaagtgtaat gtctgattca t                      1001

SEQ ID NO: 71          moltype = DNA  length = 1001
FEATURE                Location/Qualifiers
source                 1..1001
                       mol_type = genomic DNA
                       organism = Homo sapiens
SEQUENCE: 71
ctttgggatg gttggctgta cttttaacca ctactctgtc ttgtctctgc atgtgtgggc  60
atgaactttg ttaggttctg aggaggagga tggggggttg ggaggagctg catatgttct  120
ctgccccaga agaatcatgg cccaggggaa gaggtagcaa aaggaacaac tattccagta  180
tgacttgatc agtttcttga tggacatgtg tgcaaggcac tatagaagga cagaagagat  240
ttttacttta attaattgaa aattagtaat ttatatttgg tatatacgta atctaataat  300
```

```
tcattaagtg gagcaacttt tcaaactatt ctaacaaaat ctaacattat aaaactataa  360
catggagact gcattgctaa ataccttca tctacaaagg aaagttatag ggatttatta  420
tgttttctag atttctagct ctctagtgct caaaaaaatt gaaaattgaa aaattgaaga  480
aaaactgaaa ttgaagtgac mctcatcttt gttgaagaaa aaggaatgtg acaaaattta  540
tttctatgtg cagtcaaaaa gtgtggtttg tgaaatgtgt tgttgttgtt gatcttacag  600
gagaatcatg aaaaaagtct ccatggagcc atctgagcgc ctggctagtc tccaggcgct  660
gtgggacagc cagaccgtgg ctgagcaggg cccctgtggt gagcatgcat tttaaaactg  720
aaatgtgaat agctggatgg atatcccct gccaggaagt taagtctatt cctagtgtgc  780
tactgtaaag gtgcaattag tttcaaggtg taattagcag cgcacagact ttagattggt  840
ggacaaaagt cctatattta agctgtattg catcctgcta tgtacttact atagaacagg  900
gaggagaatc tttgctgttt tcccccctaa aaaggaaaag gataatcagc attgtcaaca  960
tcggccatat ttaagcttta aaattttaat ttaaacatca t                    1001
```

```
SEQ ID NO: 72          moltype = DNA  length = 1001
FEATURE                Location/Qualifiers
source                 1..1001
                       mol_type = genomic DNA
                       organism = Homo sapiens
SEQUENCE: 72
gatttggttt ctgtctctac tgagttctgg ttgttctttt gattacaaga actactcaat  60
ttcctttaag taaatttatt tattcttaaa attctgttgc ttgaaactaa gaataagccc  120
taataggcac agaggaataa tttaactctt cctgatctgt ttcctcatct gtaaaataaa  180
ggaaaagggc acacatatcc cctgacccct cttaactctc tcatctttag ctagaattgg  240
gttctagtga ttctcaaatg gatgtgttct aaaagaggct ggctggccct gtgttgggga  300
agcagaagtt ttagtaatta attaggttaa tatgaacttt atagttatat tttttctgta  360
ttccctgaat aactgtgact ctattacttg tgaatttatt taaaacataa atatgacagt  420
gatgactaga tgaggtctct tagcacacat gccctatgca gacctgtgag tcccctgctg  480
tctgctcacc caatagttga rggcctgggt aggagttctg ccacatgtga gttcttaaca  540
caaaatcctc atggaccctg tgggcctgga gctggatact tcactcatct tcacccttgg  600
cctcatgcta agaattacca tcctgccacc acttaaagat gcccattcat gttagtgtgt  660
cactgctaaa gtactgtcat taaagaagac ctatcattac tctgacttta aaatacattg  720
ttctaacaga atcactatgg gagattccag acttctgtat cagcgggtgc tttgaaaaga  780
ggatctgata tgtactggcc cctgtgttca cctgtgggcg aacattagac atgtttgttt  840
cttttatgct ttgataacac cttacaactt gcaatagtgt gactttggaa agaatgaagt  900
gattgtgtct ggcatgctgt atgtaaacat tccatttcta cataatgtga aaaggaatga  960
attaggtgaa aataaatgga tttgcacagg tgttagagta c                    1001
```

```
SEQ ID NO: 73          moltype = DNA  length = 1001
FEATURE                Location/Qualifiers
source                 1..1001
                       mol_type = genomic DNA
                       organism = Homo sapiens
SEQUENCE: 73
taagttttgt ttaacttatt taactaaaaa atgatgctaa tgaatgtgga ggggtgattt  60
ggatagaacc tgttctgtgt ggggccttca tgtaatccct agagaacgtg taaatcaaat  120
tatgcctgga ggaaatttta tttccaattt cagttgcttt actgatatgt taagggaatt  180
aaaaaatatt tagctcggcc tttcagagag ctgttattac tggttgaact atgactgtta  240
ttttaattct cattagataa ctagtatctt ttgagctgtt gttagctagg ctgtgtgcta  300
aaaagtttta tatacatcct cttatttaat cttcacgaca cttataggag gtagatacta  360
cattatgtgt ttttacagcc aagggtgagg tgtaggggat ctgataattc gctccaaatc  420
acacagctag taaatggtgg agctggtcca ggcgtgtctg tcttgagaag cgctgtacca  480
ttcaccttac aattatatct rtaggtattg tctgactcat agaatccatg cagtacatct  540
gtgcagcttc catttctgtc cttagcctca attcctttct gtctttagtt ctctatcttt  600
accttaaaat ctccatgtaa atcatgctaa cctagcacga tccatggtgc acccacttgg  660
cattttcagg gaaaagggat aaggcctata aagaaagtcc acacccagcg cctggttctg  720
cctgtgccca ttctgactgc tttatcttca gtgctttaga tgaatgtgca tcttcctgga  780
tgcttttcct tcctgcatga tttggaagaa ttagaatcag tcttccttcc atgagtttcc  840
cagggaatca gagggacttt ttaagcataa tgatggaatt tttattgtca ccttttgttg  900
taaaatgctc tatagatgag aaatagatta tatccatccc cccaccagct gtgcttcatg  960
gtaatggcca aaaaaatgtt cagaattaag actgggaatt t                    1001
```

```
SEQ ID NO: 74          moltype = DNA  length = 1001
FEATURE                Location/Qualifiers
source                 1..1001
                       mol_type = genomic DNA
                       organism = Homo sapiens
SEQUENCE: 74
tgtagtctgg actttcttag ggaagtcctt tacctgaaga atgagtaggc atgagccagg  60
tgaaggtaaa gcaagagggg gaagggatag ctcctaaagc agaggtgggg caggagccct  120
cctcttggga gagcaacaga aggccagtgt ggctgggttg aagtgaggct ggaggtggag  180
gcaggggcca gtgtagtggt gcagagccac tgaagagctt aagcagagaa gggacataat  240
aatgtttggg ttcttaaaag atcacgttca gatcctatat gagcaggtga tttgaggggg  300
caggagtgga tctgttagaa ggctattgca agtggtccag gagcaagagg gtggtggctt  360
ggaatagtat catagtagta gagatggaga gaagtgaatg gatgtaagag gtatttaggg  420
aggtagactg cattgaactt ggagaatgac taagatagga agagaagggg acaatgcttg  480
gatttctggc tttggaaacc rtatggatga ccatccttgt tcctgagcca gacctattgt  540
gggaagggca gattttgaaa gaaagatcat ggtttagttg ttgacatgct gaatttaagg  600
gttggagtac atacaagtga agttagatca atagatctga tgatcggagg ggagatctgg  660
gctgtgcata aagttgggag tcatctggga tggactgaag tcatgagaga gaatgaatgg  720
```

```
tagcagggaa tggggattgg acatgtgact aggaataacc acagaggcca gttgaaaatg  780
tatggaaacg agaacatcaa gcatgaaggg ccatgcccag tgctaaggag aaatctggtt  840
aggaagtgca tggatttagc agccgtgagg ttggatttag caatcaagat tggcacctca  900
agcaggagaa atttaagtgg agttgtgggg acagaagcca attttgaaca ctagatgagt  960
gaattggagg caggaatatg aagacactga gtatgggtac c                      1001

SEQ ID NO: 75          moltype = DNA  length = 1001
FEATURE                Location/Qualifiers
source                 1..1001
                       mol_type = genomic DNA
                       organism = Homo sapiens
SEQUENCE: 75
gaactcctag gctcaagtga tcctcccacc tacagcctcc caaagtgctg ggattataag  60
cataagctac cacacctggc tgagaattct catttttaac tttctacctg gtggccctat  120
gtatggcaga tgcacctgac agcaataatt taacttaagc atactctgta tggcagatgc  180
acctgacagc ataatttcac ttatgatatg agggttgcca tgtggaggtt gtgtggaagg  240
aggtggggtt gggggaagga gtgttaagga aaaatgctat ataaacagca cgcttttttta  300
aagtgatggt tgttcttctg accagcccac tgccactgga ctgccctgta agttcccaaa  360
taaattctat gtttcacctg ctggctccat gtctcttctt cagtcttgtg aacctggtgc  420
catccctatt gaagttaata agggtcatat aatccataag gcaggattct cagtcatttg  480
tgggtaatgc tctcctttga raatctatca ccccctaaca tgcatgtaac acaacatttt  540
gcttatagtt tcaggagatc tataggcccc tgaagcccat ttctggccct tctaagagaa  600
cgtgaactcc agattcaaca tttctgttcc aaatgttcct gagcaacaaa attttctagg  660
tctacctcat cccttggaac ctgatccaac tgtgttccca aaactaccag actctctctt  720
ccatgccaca ttcatctgtt tcttgttttt ctatcatgaa atttgtattt ttgctactgc  780
ttttttacca aaattccttt agataatctc acggctttgc cgaaatccaa ttcacaatgc  840
tctgtctaac ccacgaggat ggactataac tacttcctcc caatcctaga caatgtttct  900
gatgtgttcc tttaagctcc gggagctgcc agtgaatgtg tacctaaggc cctagggaaa  960
gaatccctgc tttaaagagc ttaagaaaga ccatgaggga a                      1001

SEQ ID NO: 76          moltype = DNA  length = 1001
FEATURE                Location/Qualifiers
source                 1..1001
                       mol_type = genomic DNA
                       organism = Homo sapiens
SEQUENCE: 76
cctccaggtg acaacacggg tggtgagagc cgccgcatga atccacactg cggctgaagg  60
tcaagaattg gcggtagccc atcggtagcc cagagaccca aactgtgtcc gatgtgagtg  120
aaggtcaccc cagatcagtg cgtcagttcc gttttggcgg ccaaatttct gacgatccca  180
tgtaagaaat gccacacctg tcaataggag cgactcacgc gctgggtctc tttctcggat  240
cgggtcgcca ccccagtgcc gggactatgc taaagactag agtctcagac ttggaatttc  300
gaggaaggtg ttccaaaacg ctgcgctccc tccggcgagg gacaagagca ggagcctggc  360
ttgcctgggt ccaaggacag tagctgggag gggtgtggca gccgcttagc ttgaaatctt  420
tcagataccc caccgaaata tcataaagag cacaaagaac ttttacgtag gaacaaaata  480
gtgaatctac aacaccttaa rcgcctgata acttcacaat gcatgcctag gaaaccaaat  540
agcagtcaaa tggagttagt ccccagagaa gaggaaacgc agaggaatct gatagggagc  600
aggcttcaga aatattgagc tgcctctctc ttctagaagg agagaaccaa ccctgagctg  660
aaatttctgc aaatagaact gagattatac cagacaatgt catggctgaa ggagggtagg  720
aaagtttata aagtgcttgt gttgctgggc acagtggctc acacctgtaa ccccagcact  780
ttgggaggct gaggcggatg gatcacctga ggtcaggagt tcgagaccac tctggctaac  840
atagtgaaac cccgtttcta ctaaaaacac aaaaattagc cggccgtggt ggtacgcgcc  900
tgtagtccca ggtattggga gcccgaggca ggggaattgc ttgaacccag gaggtggaga  960
ttgcagtaaa ctgagatcat gccactgcac tccagcttgg g                      1001

SEQ ID NO: 77          moltype = DNA  length = 1001
FEATURE                Location/Qualifiers
source                 1..1001
                       mol_type = genomic DNA
                       organism = Homo sapiens
SEQUENCE: 77
aagcctggcc aacatagtga aaccccgtcc ctactaaaag tacaaaaaat tagccgggct  60
ttgtggcggg tgcctgtaat cccagctact caggaggctg aggcaggaga atgtcttgaa  120
cccgggaggt ggaggttgca gtgagatgag attgtgccat tgcactccag cctgggcgac  180
agagcaagac tctgtctcaa aaacaaataa ataaataaca aaaaataaat tcatattgtc  240
ttaaaccacc aaatttgtgg taagcaatag gaagctaata aaaagccact aagatagtac  300
catgaatagg gctaaacagg cagaaagaag tctacagggc tttttctgg aacaattttt  360
agaggccaga ggagttcatg gagctcactt ttgttgtcat tgagagccct ggaggatatg  420
ttttgaactg tagagagagt caacagaagg aatttagagt cccaccaaca gttgggattt  480
ctgtatttgg agtccagagt rttaaccgtt ataccatggt atctttgtat aacaaaggtt  540
ctagggaaga cttgtatact attgcatctg gtcagttaac ctttaaaatg ggcatagatt  600
caatgtaagg aacactaata gcttctcata gggagaaaaa tgcaggttct cagatgactc  660
aatttgtggt ttgcacatat tcatgcccga gtccagagat agcatagaga gcattcggag  720
tgagctctga agaagaaaaa agtcataggt ggggcctctg acacatgaac ctttactcat  780
cccagcagat gattaactta cagtggtcta actgacttca ggctccagca aagcaaagca  840
aagctttcaa aagaagagct tctaggatac atgagggtga tgggcagtgg acaactttca  900
gtagccagag aaaagagcaa gaagcgggat gttgctccag aaaagaagtg caaatatgtg  960
agactatcta tacatgccca agtgtgcttc tccatttggg t                      1001

SEQ ID NO: 78          moltype = DNA  length = 1001
```

```
FEATURE                Location/Qualifiers
source                 1..1001
                       mol_type = genomic DNA
                       organism = Homo sapiens
SEQUENCE: 78
atacaaggga atactgcaca gtttgtaaaa ggaaaaagaa gcaattctct ctatactaat  60
atggaaagat ctccaagata cactttacac agaaaaagca agatgcagag ggacgtgtat  120
agaatgctat ttttagttta aacaagagga aaaataagaa tatattttaa tttacttttt  180
tttagttctc aattgggtta gtttacattt ttaaacttca acaagcaatt ttgtaacact  240
tactgtacat caggcacttt ataagtatta attcaattct tctaacctca ggaaataggt  300
attatcatta ccctcatttt acattagtag attaggccac tacaaacaga gaggttatgt  360
aagtagtcca acatcacact gctagtcaca tgggggagcc agcattgaaa cccatacoct  420
ctgactccac aggttatgtt cctaagcatc atattaagtg gactaagaag ttaatacatg  480
gagggaggga ggacagggtg ratgagagag ttgcgtgact ttatgtgtat gtagttttga  540
acgatgtaaa tgtgttacct attgaaaaaa tatttagaaa aaatgtgtat gactttgctc  600
aagttacttt ccatgtgaga ggcagacatc tcaagataag taatagtagt agcttgtagt  660
gagggtttac caaagtctta tctatagtcc tctgagactt tagggagaga atccttattt  720
aacctcatga gatagattcc ccacccccga cctgagctga gcagctaaag cttggggtgc  780
tgcaggctgg ggaggctgag cgcaccagcg cccatgacct acagctctcc ccttcgcaga  840
ccccttcttc aggagcgccc agccctggat cgcagccctg gcagggaccc tgcctatctt  900
gctgctgctt ctcgccggag ccagttactt cttgtggaga caacagaagg aaataactgc  960
tctgtccagt gagatagaaa gtgagcaaga gatgaaagaa a                      1001

SEQ ID NO: 79          moltype = DNA  length = 1001
FEATURE                Location/Qualifiers
source                 1..1001
                       mol_type = genomic DNA
                       organism = Homo sapiens
SEQUENCE: 79
atgaagagtg aaggaagaaa tgtaaatgag acacgtgcca ggcacacggg gacccagtga  60
ccagactcca agaaagcgca ggacagggct gggcgcggtg gctcacgcct gtaatcccag  120
cactttggga ggccgaggcg ggcggatcac gaggtcagga gatcgagacc atcccggcta  180
aaacggtgaa accccgtctc tactaaaaat acaaaaaatt agccgggcgt agtggcgggc  240
gcctgtagtc ccagctactt gggaggctga ggcaggagaa tggcgtgaac ccgggaggcg  300
gagcttgcag tgagccgaga ttgcgccact gcactccagc ctgggcgaca gagcgagact  360
ccgtctcaaa aaaaaaaaaa aaaaagaaaa agaaaaaaag aaaaaaaaaa agaaagcgca  420
ggacagaaag agcgaggtgc taagacttag agtggaccca gaggctctgg ccctcctgtc  480
tcccaccacg cactccattt rtgtcacatt tcaaacctat cgcttttacg atatatgttc  540
aaaaattgtt taatgaactg taaatggctt ggtaagggcc gcatcgtaaa tggcttggta  600
tgggccacat cgagaacagc tgtcaaatat aagcctaagg ctaaccacgg atctatttta  660
acactgagca gttgtggctg agtgtctgga gcttggcaga aagcaacgtc acaagtctgg  720
ctttttccca cgtagactga accctcgccc tcaaagctac aaacacaaca atttaaccaa  780
ctgagtgatc aactaggaga agaatcaata tgatctcttt caaaagctta aaatatgtca  840
aaatagtatt atctcagaaa gttttttttt cccaaaataa tacaagacat tatcgaattc  900
ttatttaacc cttttctaaa atcacccacc cacctcattg aatttccttt aaaaaatctt  960
catcctggcc gggcgcgatg gctcatgcct gtaatctcag c                      1001

SEQ ID NO: 80          moltype = DNA  length = 601
FEATURE                Location/Qualifiers
source                 1..601
                       mol_type = genomic DNA
                       organism = Homo sapiens
SEQUENCE: 80
actagagata atatgcatag cttaactaaa aattccaact gctaggaaag aaagtgcaca  60
aatgctaagg gaagaatgca gagaaaaagt gctcccacac atccaggctg acatgtcact  120
gatgtctgat gtcacctata cctctcttcc ttgtataaga aggggcagct ccaggcacag  180
tgcatcaaac actgctgtac aatggctctg gctcccttgt ggaccagaaa gaagcagatg  240
tttctggatg ggagttggga aatgatcagc caccttctcc ctgggccctg gaatcttcct  300
rttcccacaag tgacagaaga cctcagaatc ttctctttca ctgcctaccc ctgaccagct  360
ctgccctgga cagtcccctt ccaaagccaa aggcagcccc aatccacagt tgtcaggtac  420
actcacctgg ggagtctgtg cagcatgcct ctgggtggct gttctggcag agcagcacca  480
accagggcct gtttatattt ccccaagtcc cagtgctcat gggcaactcc cactggtgtc  540
acaatgtcaa tgtcataatt tctgactttg ccaaaggaaa aggggtcctt ctgtacaatg  600
t                                                                  601

SEQ ID NO: 81          moltype = DNA  length = 1001
FEATURE                Location/Qualifiers
source                 1..1001
                       mol_type = genomic DNA
                       organism = Homo sapiens
SEQUENCE: 81
agcattgtgt ccctgtgagc ccctctacgt tattttacct ctgactggaa cacacctcca  60
tcatttttcc ctcacttcct gcaagttgct gtctaaaggt gactgttcca catttttgtt  120
atgatagagg gtccttattg gtaccatgtg agaaattacc ttgatgccct ggtaggctcc  180
aagtatagtc ccatgcaagc tctcccagag gacacagcac aaataggttt gcagactatg  240
cagtgaaatg ctcaaatcac agcttcatta aaaaacatag caagcagcaa ggggaaaaag  300
aagagcaagt taatggttta gtgtgtaagt gaattggaag aaccacacta tctgactcaa  360
gtgtgagcag tttccgtata tctgatctct tttacatcgc tcaatcagcc tgtaggatag  420
acacagagat atatatgcct ggacccaacc aattagttgg ttgaatagcc atggatttta  480
```

```
tttttgttcc taaagtagag racttatggt gtctccaatt tgtggctgac tcaaggcctc  540
atgaataatg agtcagtgct tcgatgtctc atatatctgt gaattctgaa tgtgtggctc  600
cttttgtata ttttgtgcat caggaacatt aggtatcttt tgacccttcc atcccttata  660
tctatattta acaacatatg ctctttttac taactactta tgtctactta aaacatctta  720
agcatttttg cctacatttt actaactaaa agcatattta tcttttataa tagaattgct  780
catttacaaa agtaaatatg tgttacaatc catatcattt attggtgtat ccctgacata  840
tagtaggcac tcaatacata tatggaatga gagaattgtg ctttctctct cccttttcgc  900
cttcccctcc tcctgctttt tctcctactc tcacactgtc tctctctctc aaacacacac  960
acacacacac acacacacac acacacacac acattggaca g                        1001

SEQ ID NO: 82          moltype = DNA  length = 1001
FEATURE                Location/Qualifiers
source                 1..1001
                       mol_type = genomic DNA
                       organism = Homo sapiens
SEQUENCE: 82
tctcagcctc caggaccatg agccaaataa acttctattc tttataaatt atgtagtctg  60
tggtattctg ttatagcaaa aaaaaaaaga ctaaaacaga aaattggtaa aggctatttt  120
aatgaggtcc tagatggaaa tgaggagcaa ggtattggaa actagagtaa aggccatcct  180
tgtatacagt tgcaaagaac ttgggggatt gtgtctgcgt tctagggcct tataaagtgc  240
agaacttaac agtgacgaac tgggatatct ggtggaagaa atatctatgc agcaaagcat  300
tcagactgct gtgtggctgt ttttaactgc atacaatgag atgtgagagg aaagaaataa  360
agatggaatt tataattaaa agagaatcag ggtagaaata tttggaaaat gtatagcctg  420
gccatataaa taatagaaaa gtatgttcag gagagaaaac taagtgtgtg gctaagtgac  480
tttttactaa ggagataaac rtggacaaaa ggaaggtgct attcattaag acaatgggag  540
acagaccata aagcatttca aagatcttca agtctgcccc tacaatcaca ggcccagaac  600
tctaaaaggg taaaatgatt taggggaaag gcccaaggca ccctccatgg actcagctca  660
gagctgcctc aggtctgctc ctggggttcc agagcagcac tctgtggcca ccctagccat  720
ggctcattag gcccaggtat ggcttgatcc agaaaatgca agctgtagag cttggcagtg  780
tccatgtggt gctgatgcag caggcatgca caatgcaata gctgtgaaga cctggcttcc  840
tccacctaga tttcaaagga tgttgctgac agtctggggg cccaggcaga gaattgtgca  900
gggacacagc cactgcagag agcccctacg acaatgacaa gtggaaatgc ggggtcagag  960
ctgacacaga gtctccacta gggctgccta gtagagcatg g                        1001

SEQ ID NO: 83          moltype = DNA  length = 1001
FEATURE                Location/Qualifiers
source                 1..1001
                       mol_type = genomic DNA
                       organism = Homo sapiens
SEQUENCE: 83
gcgggagagc tgggccactg gttaaacatt tggaacgttt gttatgaaaa gataaagcat  60
ttttcatcta gagcttagga atgactttta ggaaaaacct tacaggattc aggtgacatg  120
tttaagtcag aatgtgaact agttatttaa tgtagggctt acaagaatgt tcgctgtgtt  180
tattcatctc gtgttatatg aactagaacc aataaaaaaa aatccagagc caggctcagt  240
ggctcacgcc tgtaatccca gcacttttgg aagctgaggc gggaagatcg ctggagctca  300
tgaattcgag atctgcctgg gcatcatagc ggatacaaaa attagccgac cggggtggtg  360
cacgccttta gtcctagcac ttcacagagg ctgaagtggg acgatccctt gagccgggga  420
ggctgaggct gtagtgagcc gagaccacgc cactgcacgc cagcctgggt gacagcgaga  480
acctgacttg aggaaaaaaa rataatccag tacagaatga cacggtcata tcaaattggc  540
atgtaataga gaccccatct tgaaacttgc tactatattg tcttgtgcgt tgatagcata  600
ttatattaat gccgaacaca ttagtgacgc cgaagtagct ggtgcctaaa tggcttaaac  660
gcggaaaaac cacatacaga tgatggaaca aaaactggcc aatcagatta tagagcgggc  720
tttttaaaat ataagaagct tctttgtagc taggcgtctg acaaaaagct tgacaccaac  780
ttaacaaaaa ccaacggctg gaattcatac tctaataaca gactgcatgg gtaaactacg  840
tggggagtcc aaccaacacc ctggactctt gcttgccttg cgttactcga ttagggttga  900
gggagaactg cccgagattt ttcgaatgca aggaatcttg ctgcctgatc taacatgttg  960
tgcacagcca ttttttagag gtctctgggt ggctctgaaa a                        1001

SEQ ID NO: 84          moltype = DNA  length = 1001
FEATURE                Location/Qualifiers
source                 1..1001
                       mol_type = genomic DNA
                       organism = Homo sapiens
SEQUENCE: 84
aagaaggcag tgacaaaggc ccagaagaag gacggcaaga agcgcaagcg cagccgcaag  60
gagagctact ccgtgtacgt gtacaaggtg ctgaagcagg tccaccccga caccggtatc  120
tcgtccaagg ccatgggcat catgaactcc ttcgtcaatg acatcttcga gcgcatcgcc  180
ggcgaggctt cccgcctggc gcattacaac aagcgctcga ccatcacctc cagggagatc  240
cagacggccg tgcgcctgct gctgccaggg gagctggcca agcacgcggt gtcggagggc  300
accaaggccg tcaccaagta caccagttcc aagtgagccc gcccaccgcg gaacgttcgg  360
tcagtctcgg cccacacccc aaaggctctt ttcagagcca ctcagtcttc ccaaagagaa  420
ctggcactca ctgttcttac agcaggtatt tcttacttgc tacaaagacg atttccaaga  480
ttcctttagc cttgttagaa rctaattttg gctcaagcct ctaatcccgg ttcgggaaac  540
cgaagcgggt ggctcacctg aggttagaag ttcgagacga gcctagccaa catggtgaaa  600
cccgtctcta ctaaaagtac aaaaaaatag ctgggcgtgg tggcggacgc ctgtaatccc  660
agctacccgg gaagctgagg caggagaatc gcttgaaccc ggcagatgga ggttgcagtg  720
agccgagatc gggccattgc accccagcct gggcagtaag agcgaaactc tgtctcaaaa  780
aagaaagaaa aagaaaagaa attaattagc actgcagtgt actgcatgtt gcagcaacgc  840
ttgagacaat tttatatctg aagaaggatg aggtttatca tcagacaaac ctagtaaagg  900
```

```
gaaaattcag ttcctgttga ccccaaagaa aatataatac ttaagtgtca ctggtaaaat  960
atccacagtg cttccggcgc tctgtcccta aacttcatgt g                      1001

SEQ ID NO: 85          moltype = DNA  length = 2052
FEATURE                Location/Qualifiers
source                 1..2052
                       mol_type = genomic DNA
                       organism = Homo sapiens
SEQUENCE: 85
tgaattcagt atatgttgta aagagggtaa ggtagcatag gttaattgaa tacgttaatc  60
taagggtaaa tacaaattaa aaatgagagg cttaattatc tgttgaaaac aaaagacttc  120
cctttccttt cccatcactt tcaaaatgtc tttctctgtc cttttaaaat gtatgtaaat  180
ccttttaatg gctaaatagg ccttataact cagaatattt tctcaatgcc tggagagcca  240
tcccttgaa atgttaatca ttaaaaaaga tagtggtctg tctcccagtt tccagcgaga  300
aaatgggctg aactttagct gtcacctgac ttcgaattgc aaaacctatc caatgtagcc  360
atacataata agcaagattt ctttctgctt ttgcaacctc ttcataaggt ttcctgtgat  420
aagcaactct ccctggttta atgcttattc aataataaaa ttatttcctt tgtcttcttt  480
gggagaagat tttaaaattg tatttcccca acattagtta acaagtatat ttctctactt  540
gagcttctca ctaatcagaa gcctttttct gtatctgatt tcatgagttt tcgcatagca  600
attagtgaca aggatagcaa tgaatggtaa aaggtggcag agcatgccat cccaaaatat  660
gccattttgg aataagaatt attctgagat acaggcaatt ttaaaaagag taggtacaag  720
aaaggcactt tgaccgttcc cttttacccc cttaaaagca ggaattaaaa ttcccmtgtg  780
gaagatgtcc tccctgtacc aaaaggaaaa gaacattttc atcaaggaca ggaagttgaa  840
accaagagaa ttctgtccaa gcagatctta aaataattct tgttttcctt tagccttcct  900
acatagttac atttccacaa tttactccat tcaacctact ataaaagcat ttaggttttg  960
ctacttcttt ggggtctatt attagagctc ccatgtccca tgccacataa aatttatatt  1020
aaatttatat ggtttctcc tcttaatctt atgtcagttt aattatcagg ccagccataa  1080
aaactcttaa gaggacagag gtaaaatttt gcctccccta caaggatatt tgagtttgtc  1140
agactcttta gtttctgaaa ttgacggtaa atttagttct gaaatagtaa acatacacgc  1200
agtataacat tttaaaaaaa tgttatgcta atcagtctgt tttctaacag gataactgac  1260
tatcaagata aacttagttc aaatagagta actctgagtt ctcacattct ttcacattac  1320
aaaacaaatc tggcagcaaa ctttgtcaga ggcgtttaaa ccagagaaac tccatcttga  1380
ataggggctg ggtaaaataa ggctgaggcc tactgggctg cattcccaga ggcttaaggc  1440
atttgtagtc acagaatagg tcagcacaaa gtacaggtca caaagacctt gctaataaaa  1500
gcatgcggta aagaagccag ccaaaaccta ccaaaatcaa gatggtgagg aaattgacct  1560
ctggttatcc tcactgctca ttatacacta cttataatgc attagcatgc taaaagacac  1620
tcctaccagt gccatgacca tttacagatg ccatggcaac gtcggaaagt taccctatag  1680
ggtctaaaag ggggaggaac tctcagttgg ggaattgccc accccgttcc cagaaaactc  1740
atgaagaatc cacccccttgt ttagcatgta gtcaagaaat aactataaat atccttagaa  1800
tagaacaaaa gaacaatttt ctttacttct ctaataaact tgctttcact gtactctatg  1860
gatttgcctt gaattctttc ttgagaaaga cccaagaact ctctcttggg gtctggattg  1920
ggaccccttt ccagtaacag ttacacttgc aaagtacatc ctgtgtccaa ccactgtata  1980
tttaattgtg aaatttatta aatattaatt taaataagtt gaaagacctt taaagacagg  2040
gcaattcaaa aa                                                      2052

SEQ ID NO: 86          moltype = DNA  length = 701
FEATURE                Location/Qualifiers
source                 1..701
                       mol_type = genomic DNA
                       organism = Homo sapiens
SEQUENCE: 86
ataagccaga aaatcggaag agggagaaaa atgaaaaatc agcaacaaaa ctgggtcgag  60
agtgaaaata gctttagtaa gaggaattaa gttcaattct atcgtggccc tgtagctcag  120
cggttggagc gctggtctcg taaacctagg ggtcgtgagt tcaaatctca ccagggccta  180
acagactgcc ctttgggttc rggtgtttac ctacacttct tgtgtcttat ttttatgttt  240
ttttgagaca aagtctcgct cacgtcaccc aggctggagt gcagtggcgc catctcggct  300
ctatacaacc tccgccttcc gggttcaagc gattttttcc cgcctcagcc tcccgagtag  360
atgggactac aggcctgcac caccaagccc ggctaatttt tgtgttttag ggtagagaca  420
aggtttcgcc atgttggcca gactggtttg gaactcctga tctcaagtga tctgcccgcc  480
tcgccctccc aaagtgctgg gactacaggc gtcaaccacc gcgccctgcc gaagggtgcg  540
tttattagat gccaaaacct aaaactggaa attattcaaa tcgataagca cccattttag  600
cccaccttct cagaatacag gaatgtactg gtagcaaaag taggaaatgc tagaaataca  660
ctctggttcc aaaatggcag aagcaagctg gcttcactgc t                      701

SEQ ID NO: 87          moltype = DNA  length = 1001
FEATURE                Location/Qualifiers
source                 1..1001
                       mol_type = genomic DNA
                       organism = Homo sapiens
SEQUENCE: 87
atttatccac tcttaaaagg gtatctttaa atagctgtgg tatccttttg tatttcagac  60
attttatgta atttaaattc tgattcatat ccctaatttt aggattaaag tgtttgttaa  120
caactaaaaa gcaaaacaaa acaaaactag gaagtcctta tctgcatctt taagattata  180
tcaaataggc tactgagtgc ttacctgtta acacctgctc caattgcttg caattgtggc  240
taatgtctta aaggtggtag atttctctgc tttccaataa aatcacattg ccagcatctc  300
cagatacaat tattctcatt ttgaatagcg aacattccat tgactagcaa aacaaaacat  360
ttgaattata tgagatatct agcagatcag aaagagacca tagcaattgg attaaaacag  420
aagttaatgg aagagaattt tagaaagctg ctgaggggat ctttatagtt tttatctgtg  480
atcactttag aatgttttaa rgcctagttt agaatactta cctagatgaa tacacatcct  540
```

```
tacctccttt cttacctgtg tattggttga ccttatgttt gtcatcttcc tcttgagttt  600
tctgattata tatatatttt taaatttttt agttattttt aattttatta ttattatact  660
ttaagtttta gggtacatgt gcacaacgtg caggtttgtt acatatgtat acatgtacca  720
tgttggtgtg ctgcacccac accaacatgg cacatgtata catatgtaac aaacctgcgc  780
gttgtgcaca tattttttaa tattaaaaaa ggtgaggttc aacagagtct tcaaagcatc  840
tttttaaatt gcactgtgga acaaaaatcg agacaagaga ggcaacaaga gttttagtcc  900
caaatctgcc atccaaagtc actgtataat tgggcgagtt agttaatagc tttggccgtc  960
agttttattt tctgtaacat tataaggttg ctgttttcct c                       1001

SEQ ID NO: 88          moltype = DNA  length = 1001
FEATURE                Location/Qualifiers
source                 1..1001
                       mol_type = genomic DNA
                       organism = Homo sapiens
SEQUENCE: 88
attctcctgc ctcagcctcc cgggtagctg ggattacagc agtatgccac cgcgctcggc  60
taatttctta tttatttatt tatttatttt tggtatattt agtagagatg gggtttcgcc  120
attttggcca ttatggtctc gaactcctga cctcaggtga tccgtccgcc tcggcctccc  180
aaagagctgg gattacaggc gtgagccgcc gcccaaccac tttttttagt attttaaatc  240
aagtatcttt ttgtttgttt gtttcttctg tgcctatgct tacccagaca gtttcttcat  300
ttattttccc ccgccttggg caggcttcca ctcttcagac cctttcctgc acaactttgt  360
ccctgagcat aggtcctgga cgtaaaagaa gggacatcgt ctggagaaat attgaattaa  420
gaaaggcgcg gctgtgaaga atagaaatca gtgtctccct tagtctctca gttcggcgat  480
cttggtaatg ccctgtccca rgcctgctaa cgcgattcag cctcgatatc cccgtccagt  540
cccacgatcg caccaagaag agcttgcgag ccttcctgct acatactgac attaagaaac  600
cggacttgaa agggatccca gacaaacgtt aaacatgcaa caagagggat agggtgtaag  660
gaagagaatc cttggggcgg tgtctgataa aacagatggc tctcctttcc aggtgtttct  720
gaatttgatc cccgacgcct ggggcatcgt ggaggaactt gcataggaaa tcaaggtgtc  780
gcaggaaaga gaacacgcac aagcaaaaga taccttaatt tgtagtatac tcaatattta  840
tcgtacagaa gtgtatcgac gatagacaat gtgcgatgtg atgggtgctg ggaacttaac  900
gaactctcca cgcgcctaga cctcattgga tccactttct cttgggctgt gagccggtaa  960
aaaaaaaagg ggtggatgtg gaggacggtc caaaggattc g                       1001

SEQ ID NO: 89          moltype = DNA  length = 501
FEATURE                Location/Qualifiers
source                 1..501
                       mol_type = genomic DNA
                       organism = Homo sapiens
SEQUENCE: 89
tgtggagctc cgccactccc agcccgggtg aaggaaaact gggaaacaga atgaatgtga  60
ttatctattc gaagataaat ttccacaaag catgccgttt gatagtagct tataatgtgg  120
aagtaaggca tcctgtcatc cggccggtta gctcagttgg ttagagcgtg gtgctaataa  180
cgccaaggtc gcgggttcga tccccgtact ggccaagtat tctctgtggc ttttatcacc  240
agaatggata rtaacccaga catcgatcta aacgtgtacc tgtgtgtttc tccaggctta  300
actttgcccc gagaaaacgg atctgtgaat ttggtgcgcc ctcgcttact cgacagcggt  360
taatttgaac ggggacgttt ctttccgctg cctccaaggc atacccacat cctacccgta  420
aaacaaaggg gctataggca ccttacagtg acagaggtac gttacggttg gaggcttttg  480
tgatttttgt cctcctctgc c                                             501

SEQ ID NO: 90          moltype = DNA  length = 501
FEATURE                Location/Qualifiers
source                 1..501
                       mol_type = genomic DNA
                       organism = Homo sapiens
SEQUENCE: 90
tttttgatgc ggatcgaaag ggactggccc cggagcctac aacctgacgc aggtgggact  60
tggggaaatg tcgagaaacc taggtctggg acttgagttg gcttccaggg cacacattct  120
tgttcagaag aaacacattg caaaaatcgg gaggtgacgg gcagatgaag tgtcggcgct  180
tcgcctcggg actccagtgc aacctatggg gcttttggaa atgaggaagt cgatgactct  240
gcagggactc mtctgaccca ggagcagatg gcgctcgtct gggcactccc caggagaaaa  300
ggtgcatcgg gaagcagcct ggcttgtgga tggtaataag tcactgttga tgggttgggt  360
gcagggaggg atttaagttc ttgagcgaca gatgctaggg agtttacctg ctctggataa  420
cagtatcttg tggaggatag tcacctggaa aacagaaatg gcgtgactgt gttgaataca  480
ctgtttgatg attctgggca t                                             501

SEQ ID NO: 91          moltype = DNA  length = 1001
FEATURE                Location/Qualifiers
source                 1..1001
                       mol_type = genomic DNA
                       organism = Homo sapiens
SEQUENCE: 91
tggggcctaa ggagattctg ttgtccagaa ttcagaaaat tctgcctcca gaaatacaaa  60
tatgctcttt tctaaacaag tgacaacaca atgtagccat aggctccctt aagcagccac  120
ctcatgtcaa ctaatagtct ttgctctcta gcctctctcc tccaaagtcc atttcgtctc  180
ctgaggcttc agctattact gtcagaccct cagttacttc tgatgaacag ggattaggct  240
tgagaaaatg gagatgcatt tagattggca gatatggggg acttcttaat gtgcttttat  300
tgctgcctta tctctgaaaa caggttctgg gagtttggga ataagtctga gggcatataa  360
aggattgaga ctgagtgact taggagtgtg agaggaaata tcttgatgtt gagaacaggg  420
ttgatgtgga ggggtattct ctgtgttatg catgtaaaaa gaaaaaaagg aaaaaaaaat  480
```

```
cattactggg aaagaaaaca rcccaagctg aagtccaaga aaggtacaca gaggaaacac  540
agaaacagtt gtgttagcag aagatgacat gaaacccagc tgacagtgaa attaggaagt  600
tgccttggaa tttcaagaac ttgcattctc aagtttatgg ttctgtgtcc aacagagcag  660
caaaatccag cacttcttct tttgagtctc catatcgtgc taacagaaag acaaggggtc  720
gggagatgca gagatgagga ggagctcaag agtgacagtg ttgaagagat tctgagcaga  780
actccacagt gatctgtgta actgatatcc aaccctgatc cctccatcgt ctgcctgtcc  840
aacccttgct tagatctcaa tgtaacttca cttcattgtg tccaagaagt tctctgatct  900
cttcccctgt ggatttagca accctccatt ttagaggcat tttcaggaat ctttttgcaa  960
tgcatcatct ctatgaaagc tcagcttcct gctccccagg c                     1001

SEQ ID NO: 92          moltype = DNA  length = 1001
FEATURE                Location/Qualifiers
source                 1..1001
                       mol_type = genomic DNA
                       organism = Homo sapiens
SEQUENCE: 92
ttgctgtaat gaaataaaca aaaaaaaaat aaaaataaaa ataaataaaa aaggagcatg  60
tccagtacta cgtcataact gaagaatggt agactgcatg aaatctagaa atgagtgaaa  120
aagaattagg ctttgtcagt atgtttcttg caatctccat ggaagggagt gctctgtttc  180
caatgaggaa aatataaatt tttctagtct ggccaaagac catttattca ggtaaatagt  240
tgttttttca agacatagct gtaaaaaaaa aaaaaaaaaa aagtccttta ggaccagatt  300
ctctcatata attctatgtt ccaatctgtt cctttttgcc ctacaaattg ttcttcagaa  360
aaaaaaatat atatatatat atagacatat atatatagac atatatatag acatatatat  420
atatacatac acaaaaagtt atttggggca aaacatgaat catgtgcttt cttgaagcta  480
ccatataaaa gttccagtgt raagcactaa catgacaacc tggtttggat tagctctaat  540
caattcccca aggctcatta gcaatgtcat aaattaatca agattgtttc agcaacagag  600
ggtaccatgc ttggctatca ggtgcaaata acttaaaaga tctatctttg agtccttatt  660
tctctttatc tctctgtttt agaaatttta acttcttaat aactgagagt aatgggcctg  720
atatgtgaac tttgtaaaga agtgttcaat ttttttctga atgcttctct ccattctcca  780
cacagatttt agccaccgca cacacaatat tcttctagac atcttcttcc ctgctgacaa  840
ttccaggtta ttcaagtagt ccctgatggc ccaaacttca tatagacata tagatgcaga  900
aatatagaca tctatctata ttctctgtat gtttaataag gagtcacttc actattcttt  960
attctggcct ggagaatgtg tttaggtatc ttaatccttc c                     1001

SEQ ID NO: 93          moltype = DNA  length = 1001
FEATURE                Location/Qualifiers
source                 1..1001
                       mol_type = genomic DNA
                       organism = Homo sapiens
SEQUENCE: 93
cgcttgtaat cccagcactt tgggaggccg aggccggtgg atcacctgag tcaggagttc  60
gagaccagtc tggccaacat ggtgaaaccg tgcctctact aaaaacacaa aaattagctg  120
ggcgtggtgg caggcacctg taatcccagg tatttgggag gctgaggcag gagaaacgct  180
tgaacccttg aggcggaggt tgcagtgagc caagaccaca ccaatgaact tccagcctgg  240
ctatcaagag cgaaactcca tctcaaaaaa taaataaata aaattaaaaa ataaaaaaag  300
aaaaagtaag gtattctacc catgaagctt gaaagatcat gctatacaaa taaaaaactc  360
tcatcttgga ttgacctaga tgagtttgta ggccaaggca aaaattacac ttctactgca  420
gagactgaac cctgcttcat acaaaacaaa agatacttga aactgtacta atgctaggaa  480
gaaagacatg atgacaagct vagagtgtca attggcagga caggcatagt tggggttctg  540
gggtttttct ggggacagaa ttactgggaa attcactgat cttccccaca tgcagaataa  600
tctgccatca gattctataa aacaagtttt tctactttac tttgaaactt tgaagaagat  660
agccccacaa aatattatca tattgcagaa aattttccta gatcattaaa gtaaaagaaa  720
tgttaattaa cagtaaataa cttgttaaac ttaaattttc cctctgctca aaataacttc  780
ccttcttctt caccacaagt ttactcaaat tttagatata cctcaagaat aatcttccct  840
tgggaggttt cctcagacca acgtgagtta catgtccttc ctctgtttcg atttgtcacg  900
acaaaaatat tatatgtatg aatttctaca tggaataaaa gtaggatttt attcttaaaa  960
aatatagttc ttagattttg ctctgcaggc attgagtttt t                     1001

SEQ ID NO: 94          moltype = DNA  length = 1001
FEATURE                Location/Qualifiers
source                 1..1001
                       mol_type = genomic DNA
                       organism = Homo sapiens
SEQUENCE: 94
ttataaaaac tgatacagga agtaatagaa aatttaaata gtgctattaa acaaatgaat  60
cagtaattta aaaaccttct tacagagaac actcccagct tatactgctt caaaggtgaa  120
ttcttccaaa tatttatgaa acaaataaca tgaatcttgc acaaactctc aagcaataga  180
gagaaaggaa cacttcctaa aatattttgt aagacaagca tactcttggg tatcagacat  240
atcttatgtg ccacctctga ttctcttgcc atcttacctt gcaacttgtt ttaccccaat  300
agtcatggca atcaatttcc tctgagtgca gaaaacaaca ggacttcact gttcacctct  360
gttgaacttc tcgtcttctg ctataaggct tctctgctgc tgttgaaaca tgagctgctg  420
agcgatcttt gatatctgca catgcccaac ttctatatgt agggctatta atgctctatg  480
gagcaaaact ttgatcagtt rgatatagta gctgaccaat aatttttttt tttttttgag  540
atgtgtcttg ctctgtcacc caggctggaa tgcagtggca tgatcttggc tcactgtaag  600
ctctgcctac ccagttcaag caattctcct gcctcagcct cccaagtagc taggattaca  660
ggtgtgcacc accatatcca gctaatcttt gtatttttag tagagatggg tatcactgtg  720
ttagccaggc tagtcctgaa ctcctgagct caactgatcc tcccgctttg gcctcctaaa  780
gtgctgggat tacaggtatg agccaccatg tccagccgtg accaataaat ttttcccact  840
ttcttcccct aaatagcctt ccctgagatt acactcctta atacattaat aatacattat  900
```

```
aatttgattc agtggatgct gtttacatga gtgtgttcag tttgtgaaac ttcatcaagg  960
tttacactta caggtggagt tttatgtgtg tatgttatgc c                       1001

SEQ ID NO: 95          moltype = DNA  length = 1001
FEATURE                Location/Qualifiers
source                 1..1001
                       mol_type = genomic DNA
                       organism = Homo sapiens
SEQUENCE: 95
aaaccacatc tctactaaac atacaagaat tagctggaca tggtggctca tgcctgtagc  60
cccagcttct cgggagggta aagcatgaga actgcttgaa cccaggaggc ggaggttgca  120
gtgagtggag atggcgccac tgccctccag cctgggtgac agagcaagat tctgtgttaa  180
aaaaaaaaaa aaaggatggc ctttttcaca gcctaatgcc cttgagatcc atccaatttg  240
ttgtatcaac agttcctgcc ttttaattgt tgagtagttg tttatagtat ggatgtacca  300
cagtttcttt aaccatctac ctattgaggt acattttagt agttttctag tgttttgcta  360
ttataaataa aggattacaa ataattgtga tagacttttg tgttgacata gttttcatgt  420
catttttatt atcgttatat attattgaat atatacaata tatattgaat gctacacatg  480
tagcattcac gtttctgttt rataaaatgt ctctgtttca tcactgtgaa atgcctcctt  540
ttctttttta ttatgtcacg tctctatggt aatactcctt gtcttaaaat ctacacttta  600
tgttaataca tacgttttat gttaattttt ttatggttcg cctttgtggg gttttttttt  660
tttttggttg ttgttgtttt taactttatt ttattttatt tattttattt attttttgag  720
actcactctg tcacccaggc tggagtgcaa tggcgtgatt ttgtctcact acaacctctg  780
cctcttgggt tcaaacgatt gtcatgcctc agcctcctga gtagctggga ctataggggt  840
gggccaccac acctggctaa tttttgtatt tttagtaaga gacagggttt caccattttg  900
gccaagccag tcttgaactc ctggcctcaa gtgatctacc tgcctcagcc ttgcaatgtt  960
ctggaattac aggtatgagc taccacaccc agcctaacct t                       1001

SEQ ID NO: 96          moltype = DNA  length = 1001
FEATURE                Location/Qualifiers
source                 1..1001
                       mol_type = genomic DNA
                       organism = Homo sapiens
SEQUENCE: 96
tgggtcaaaa tgacaccgga gaacggatac tggactatgg gcctgactga tgggaataag  60
tatcgggctc tcactgagcc cagaaccaac ctgaaacttc ctgagcctcc taggaaagtg  120
ggggtcatcc tggactatga gactggacat atctcgttct acaatggccac ggatggatct  180
catatctaca catttctgca cgcctcttcc tctgagcctc tgtatcctgt attcagaatt  240
ttgaccttgg agcccactgc cctgaccgtt tgcccaatac caaaagtaga gagttccccc  300
gatcccgacc tagtgcctga tcattccctg gagataccac tgaccccagg cttagctaat  360
gaaagtgggg agcctcaggc tgaagtaaca tctctgcttc tccctgccca gcctggagct  420
aagggtctca ccctccacaa cagccagtca gaaccataaa gctacaggca cacactgaag  480
cactttactg atattcattc rattattcca taggacagtt gtttgagttt ggtgccacct  540
tattggcccc tttatacaga taaggaaact ggggtgtaga aaagtgtatt gactttacaa  600
agcagacagg aatagtgaac aacagagctg ggatctgaac aacaatgact aacattaatg  660
gagaatttaa aacgttctga gtgctgtgtt atgagctttg gtgggtgtca ctcctttaat  720
cctcacaaca ccctgtcagg tagtctcatt tggcaagtat ggaagcagag gcagggcaac  780
attaagtagc ttacataact cacacggtaa tttgtgcagt tgggagatgt tcagcttcag  840
tccctggcca attgcccgtt cttttccagc ctgatttttc ctgcatggga agagcccaca  900
tgtagccctg aggttccctt cccaggacag ctccaggatc gagatcactg tgagtggttg  960
tggagttaag accoctatgg actccttccc agctgattat c                       1001

SEQ ID NO: 97          moltype = DNA  length = 2802
FEATURE                Location/Qualifiers
source                 1..2802
                       mol_type = genomic DNA
                       organism = Homo sapiens
SEQUENCE: 97
tctttctaca tttttgttgt ttccctcccc acattgattc tgcccactga tgctttatac  60
tcagaggtta attttctttt cttttctttt tttttttttt tttttttttc ttgagacaga  120
gtctcgctct gtctcccagg ctggagtgca gtggcgtgat ctcggctcac tgcaagctct  180
gccttccggg ttcatgccat tctcctgcct cagcctcccg agtagctggg actacaggtg  240
cccgtcacca tgcccggcta atttttttatt ttttgtattt ttagtagaga cggggtttca  300
ccgtgttagc caggatggtc ttgatctcct gaccttgtga tccgccctcc tcagccttcc  360
aaagtgctag gattacaggc atgagctgct ghgctggccc tcagaggtta attttcaatc  420
ttcactcgac cactcgtgag ctaaatgagt tccccttttc tgcagtctat ttttccatac  480
atccaattta tttaacaagg tggagcctca tctgaagcat ttcctcacct gaaaaatggg  540
gataaacata tgaatctcta gcgctgtaga aggcaatcat attatttact cagcccacag  600
caggccatga aggaagctcc tcatcttcct gatagctgca aggccgtctc tgtgctgggc  660
tctgtgtggg gccttatatg ccctagattc actctccagc cttcagcttt ctccaccctc  720
ttctggaccc caggaatctg tcctctatgg acagtgccac tgggctccct tgtcctctgg  780
tttgctgctg tgtttggcca atgggaggcc ctgatagaag attagaagga gaaagaaagg  840
agatacacac cgtttaattt cctgcttcct ccctgccagc agcagctggt ggtgctctaa  900
caaggcccga ggactcttct caggaagctc cctcgttaag ctacctcttt ctctgggttc  960
cagtaattgc ctccccttt tagccctccc aggctagggg tggagacagc tccccactgt  1020
tgggaaccat gggggcactg cacttttcct tgttgcttc ccttaaccct tctttctgga  1080
aaccttgtcc aactacccag tttgagctca ccatctattt cttgctaggt ttctgccaag  1140
catgttcatt attccttcag tcttcacctc aacccccatg aaaaacagat tgcaatcatc  1200
atctaaaaat gtggaggcca aagcttggaa gcattaaatc ctttgaggag atacaggcag  1260
taggtggcat gagaagcctg ggaaggacaa agttctttgg gcaggcatca cctcctctcc  1320
```

```
ttggcatttc catcctcact ctccctgcag tattactcag tgtgtgtctc cttcccttca  1380
cctccaccct ttatgcgtct tcctacccac gaaggaagtc aagggaactt ttctgctcca  1440
aatcacaaga gttggagaag aaaaaaggaa aaaggaatat agtccctcag gttgttggtc  1500
cagggaacat gcagtgattt actcaccagg cttgaagagg gccatttttc cattctgaaa  1560
ggaaggagac acagataaga aaaaggtcag tatttttgta cttttcccac tccattctcc  1620
tctcactaca tgtttctct  ccttttcttt agagtctctt ccagggtcca gcttccctcc  1680
tctacagctc tgatggatca gaggtggcac cttctcaaaa atgtcaggct tggctccctg  1740
tgtcatgggg ggtgcaggat gcatggccag gctttacaag gggggtgtgca ggatcaggag  1800
tttctcagag gctccagaaa agcggaggtg aaccccccacc acacagaaat tgagtcttta  1860
gattagatct aattaatcca gctgagaaca tccacgggtc acagtggaga aaaagttgaa  1920
atattcaggg catgtgaccc agcaaactta cagagcatca ggctgactta ttggtatcgg  1980
acgaagactc ctctccacct acaatgaaag aaaggtagag gtgtcaccag aactctgcct  2040
tttctgtgtt ggccccttcc ccttcttttt gcatccatct agtctttttt tttttttttt  2100
tttttttttt tttttttttt tttaccatcc cacccttccc catggtctcc atcttcaggt  2160
acaattcttt cttcacctct tcttaatatc aagtctggga acatcggttg aacgctagtg  2220
gcagggcagg cactgtgaga gttccttccc aatggggtcc agctcatctg ttttgaatgt  2280
gtacctgggc ataggtgtca ccatgtctat atgtgtatgc ctaggagtac aagattcatc  2340
cttctcaatc tgtatcattt cgtaccttgc tctaaaaaga atttgggaaa tttaatgagc  2400
aatttcaggg actagttttt gaaagcagtt atgatctatc tgtaccaact gagccactgt  2460
agctactcct ctttattaga cacacttttc tccctccctc tctcttttct gatttttcta  2520
tttcttaaat cttccattct tgttttcctt tcaacagcct ctagattatg ggaaacaaca  2580
agtaagtttc ctgccataga aaatgcacct catccttctc ttccctcttc cttttgaagt  2640
gtacccctgg atattcctca gtgcttttta gagcttaagg gtctgtagcc cctagtacaa  2700
agagattgaa gacctctttt tttttttttt ttttttctag agagaaaaag cactgggtgg  2760
tttctccaaa gagccacact tgttttcttt ttctgggtaa ag                     2802

SEQ ID NO: 98          moltype = DNA  length = 1001
FEATURE                Location/Qualifiers
source                 1..1001
                       mol_type = genomic DNA
                       organism = Homo sapiens
SEQUENCE: 98
tgggtgaaaa caagaaaaac ttttaaaaat ctactctggc atcttttgct agcaggcatt  60
gacaattagg agaaggcaag gtgttaactt ttactgatct cccacttttt tttttgagac  120
aaggcctggc tttatcaccc aggctggagt gcagtggtgc gatctcagct cactgtaaac  180
tccgcctacc aggctcaagc catcctccta catcagcccc ctaagtagct gggacaacag  240
gggcgcgcca ccactcctgg ctaattttttg tgctttttgc agagacgggg ttttgctatg  300
ttgcccaggc tggttgcgaa ctcctgggct caagggatcc gcccgcctcc acctcccaaa  360
gtgctgggat tacaggcatg agccaccgcg cccacccctc tagtttccag tttagtcgga  420
aagattaaaa acgccagcct tgttttccta gtgctgtttt tggtttttac ctcgggtctt  480
ttgtcgtgcc ttaaaatcat rtctggttgc gcaagtgagg gaaaggattg ggtaaagggg  540
gcgccaccgc aagttgctgt gcaacatcca gacatcacca gacccaccac ctggagcctg  600
gcctggcggt gtcaaacgca ttctggtctc atctttttag aaacccgtgg atgctcaagg  660
aatttccgga taacgtgatc ccggatgcgc ttgactgact tacacggaac gagcaaagcg  720
caaagcagtc cctgctaagg acttagttta tgccctcaag cgcaaaggtc ggaccctcta  780
tggtgttggt agctatatgc acgtacctca tgtacatttc accttaaatg gctttcaaag  840
agctagatta atttagtgga tagatcaaaa tgatttatga cccctcgccc cccagtgata  900
ggaagagcga accagctctt ctttagataa tagtgagtgg ctctgaaaag agcctttggg  960
ttggacaaga gcttgagaat ttacttggag ctggtgtact t                      1001

SEQ ID NO: 99          moltype = DNA  length = 1001
FEATURE                Location/Qualifiers
source                 1..1001
                       mol_type = genomic DNA
                       organism = Homo sapiens
SEQUENCE: 99
atttagtgga tagatcaaaa tgatttatga cccctcgccc cccagtgata ggaagagcga  60
accagctctt ctttagataa tagtgagtgg ctctgaaaag agcctttggg ttggacaaga  120
gcttgagaat ttacttggag ctggtgtact tggtgacggc cttggtgccc tccgacaccg  180
cgtgcttggc cagctccccc ggaagcagca ggcgcacggc ggtctggatc tccctggagg  240
tgatggtcga gcgcttgttg tagtgcgcca ggcgggaagc ctcgcttgcg atgcgctcga  300
agatgtcgtt gacgaaggag ttcatgattc ccatggcctt agaagagatg ccggtgtcgg  360
ggtggacctg cttcagcacc ttgtacacgt acacggagta gctctccttg cggctgcgct  420
tgcgcttctt gccatccttc ttctgggcct tggtcaccgc cttcttggag cccttcttcg  480
gggcgggagc agacttggcc rgctcgggca taatgaaaca atagtggcaa aaccaaaaca  540
agaagtcggt ctcctctttt tatataatag tttatgcggc cgaggtagtg ggaaggtctc  600
tgctgattgg taattatccg tggatgacga cagatgccag ttttgcccaa tcaaaatagg  660
tatcctgcat aatcgagtcc tattggtcta aataaaaata aaacgtaagc caatcgcaca  720
gcttcctttt cgcgcccagt agaggctata aaatgtacgt ttttctagtt tcacttcagt  780
ctttcttgac cgtatagata ataggccttt tgccatgtct gggcgtggca agcagggagg  840
caaagctcgc gccaaggcca agacccgctc ttctcgggcc gggcttcagt ttcccgtagg  900
ccgagtgcat cgcctgctcc gcaaaggcaa ctatgcggag cgggtcggtg ctggagcgcc  960
ggtgtacctg gcggcggtgc tggagtacct gaccgccgag a                      1001

SEQ ID NO: 100         moltype = DNA  length = 1366
FEATURE                Location/Qualifiers
source                 1..1366
                       mol_type = genomic DNA
                       organism = Homo sapiens
```

SEQUENCE: 100
ggtatttcct atgatttcat aatagacaaa ggtttaatta cacaactcct ggctgaatct 60
agagtactaa aatgtggctg ttagaaaagg ttgctctctg ggcccgatgc agtagctcat 120
gcctgtaatc ccagcacttt gggaggccaa ggctggcaga cagctttagg ccaggagttg 180
gagaccattc tggcctatgt gttgaaaccc cgtctctact aggaatacaa aaaattagcc 240
gggcgtggtg gcacacacct gtaatcccag ttacttgaga ggctgaggct gagaatcgct 300
taaacctggg acacagaggt tccagtaagc cgagatcaca cctctgccct ccagcctggg 360
tgacagagtg tcgccaaaca aaacaaaaca aaacaaaaaa acaaaaaaaa agattgctct 420
tacccaggga tgatggtcag atgcaattac aggttatgaa tttggcataa aagtaatgct 480
aagtgtttca cactgcactt actgttgtca gtgttctaag tgttttttat ttaccaattc 540
atttacactt gtttgtcttt tttttcaggt ctccaactcc tgggctcaag ctgtcctccc 600
acttctgcct ccccaaaagc tgagattaca ggcgtgagcc acccggccct actcatttaa 660
tccttacaac aacccttaga gctgggaact atttttatca tcatcacata attgtttaca 720
aaaataaath gaggcttaga gagcatatgc acctcaaccc aagatcccac aagtagaata 780
ttattgttac agatttggtt gcaaataatc tgcttcttat gattgtgctt taaatttttc 840
accgtgtcac atcactttgg tggtgtaaaa ttataaaaca acatttaagt cttaacttta 900
aaaatgtgtt tttggcctgg tgcgatggct catgcccata atcctagcac ttggggagga 960
tgaggcagtc agattgctta aggccaggac tttgagacca gcctggacaa catggtgagg 1020
caatttctct actaaaaata ctcaaaaatt agctgggcct ggtggcctgc gtatataatc 1080
tcagctactt gggaggctga ggcacgaaaa cccaggaggc agaggttgca gtgagccgag 1140
atcctgccac tgctctccag cctgggtgac agactaaggc tctgtctcaa aaaaaaaata 1200
tatatatata tatacatata tatatatatt tatatgtata gacatacata gttaaaatat 1260
atatattatt ttttacatct taaagagaaa cattatttat atgcaaaaaa ttttatttag 1320
gcccacttag caattccaga tctgacaact tttgaggatt taaaat 1366

SEQ ID NO: 101 moltype = DNA length = 528
FEATURE Location/Qualifiers
source 1..528
mol_type = genomic DNA
organism = Homo sapiens
SEQUENCE: 101
aacataaaac tctaagcatt tattcaaata tattagaaat ttaaatgaca taaaaattgt 60
taagtacttt atttggacta gtgcaaatag cataaatgtg aatttaaata tatacaaaaa 120
gttaagtaat tgaatatcaa taaaatatta ataaacagta aatataaatt ttctatatgt 180
gactagtgag atctactaag ctagtctagc catttttctc aattatctcc attatttcct 240
aaagtatcct gtggagtaac tctgattgcc tttactctca ttaaaaagat gaggaaatta 300
agacaaaaac agcaaaagta tctgcaarga agccacaatt tcagtctagg tttgtttgat 360
tgcagaggct gaactcacta ttctccaaag taaatattta catggaaaca ctaaaaaaca 420
aagaaattac attttaaatt gtgtcaagat tacactttct ttagagttaa aagaattcca 480
cagtgtatcc atgcatgtaa aaaatattaa atatatgaaa agacgact 528

SEQ ID NO: 102 moltype = DNA length = 801
FEATURE Location/Qualifiers
source 1..801
mol_type = genomic DNA
organism = Homo sapiens
SEQUENCE: 102
cagccttctt ggccttctta ggcgtggccc ccgcgggctt cttagcttta gcggcgcctg 60
ccttcttggc tttgggcttg gcttccccgg aggccgcctt cttgttgagt ttaaaggagc 120
cagaagcacc agtgcccttg gtctgcacca gggtgccctt gctcaccaag ctcttgaggc 180
ccagcttaat gcggctgtta ttcttctcca cgtcgtagcc accggccgct aaggccttct 240
taagggctgc caaagaaagg ccattgcgct ccttagaagc agccacagcc ttggtgatca 300
gctctgagac tgggggcccc gtcgctttgc gcttagcagc gccggcgccg gcagccttct 360
tagttgcctt cttcttagcc ggggatttct ccaccggcgc rggggtggct gtctcggcag 420
gagcggtttc cgacatggtg gcaagaaact gctagaagag aataagctcg aaatctaaag 480
agcaggtttt gcgttgctgc tatgctcggg ccccgggctt atataagccg gcgctgccct 540
gtgattggtg gagcgtccaa tccaccgccc tctggccgcc gccgctcgcg gttggactcc 600
caaattgtgt ttgttagtcc tcaaaatttg attaaatgct taaaacaatg gtacagaatt 660
tggcactttg aagctccaaa ggaggaaaac agcctccagg ttcacatact tgtttgtgtt 720
ttcaagaatc ttgtgcaatt gatgaaagat attttaaaaa atcccttcag cttttcataa 780
gaatccattg ggctgagggc a 801

SEQ ID NO: 103 moltype = DNA length = 1092
FEATURE Location/Qualifiers
source 1..1092
mol_type = genomic DNA
organism = Homo sapiens
SEQUENCE: 103
gatttggatt cctaatgaaa tcaacagtca cttatttctc attcttgaaa tgctgtgcaa 60
gaaaatttaa agtagccaat gcacttcatc ttctaagaac tcctggagaa gttggcagac 120
tatggccaaa tctggacaat ggctttttttc tgtatggccc tcaagctaag aagtgtcttt 180
atgttttaaa agtattgtta aaaaaaaaaa aaacaaaaac aaaggctggg cacggtggtt 240
catgtctgta atctcagcac ttggggacac tgggataggt gggttgcttg agctcaggag 300
ttggagacca gcttgggcaa cttggtaaaa ccccatcttt aataaaaata caaaacattt 360
tgctggatgt ggtggcacat gcctgtagtc tcagctactc gggaggctga ggtgggagga 420
tcacttgaat tcagggtgtc aaggctgcag tgagcaatga tagcagcact gcactccagc 480
cagggcaatg gagcaagatc ctgtctcgaa aaagcaaact aactaaaaac taaagagtgt 540
gtgacagaga ctatatatgg cctttaaacc ctaagctatt tattacctag ccctttttgct 600
gtgttataaa tttctccaca gagacacaga tattgtatag gcctcttacc gaacaatgca 660

```
aattgagaac taaagaaaag gagatcttca rgagcaaatg atctaaccaa gcactttcca  720
ctgttccaaa cacaaaactt agaaggtcca ggagaaaaaa accccaaaac tccatgtgta  780
atggagccag ggtataacaa taagagctga cactcattca gcatttacta cctgacagga  840
agtaatctta aatatgttct acaggtttct attaatttgc tacatttaca gctatacaag  900
atgaggccca gatagagaat taataacttg tcaaaggtta tacagctatg aagtggcagc  960
tctaaatttt aaacctagaa acatggcctc agctctatta tggagggaaa atccttgaag  1020
aggtgagaag agaactatct tcaaagcttg gaagaggcag tgtcaagttg ttcctacacc  1080
tagcaaacag cc                                                     1092

SEQ ID NO: 104         moltype = DNA  length = 1001
FEATURE                Location/Qualifiers
source                 1..1001
                       mol_type = genomic DNA
                       organism = Homo sapiens
SEQUENCE: 104
gatctcaggt gatccgcccg ccttggcctc ccaaagtgct gcgattacag gtgtgagcca  60
ctgtgtctag cctatattgc cttttaattc ttgtttttta caatgatggc aatccataat  120
gttattcaat tgttgtttaa tcctttcata agaatgttat tctagttttt ctggtaatta  180
aaaagacagc tctggaaact tccgtagact tacctataaa tctgttattg ttttgatttc  240
atatcacttt taaagattgt gtacattttg ttttgttttt ttaagtaatg tggtccagct  300
agtcacccag gctgaaatgc agtggggcca tcctagctta ctgcagcctt gaacttctgg  360
gctcaagcta tcttcctact ccagcctccc aagtagctgg gactatagac atgaggcacc  420
tctcctagct tcacttttaa aggttttaaa atctaatctt tctctggttt tagcttgctt  480
aatacaaaat tcaattatgt rctataggaa aaatttcctc tactttggga tcttggcagt  540
gatcctccta gaaatggtga tggcaaaaac aaaaggcttt tgattttgtt gaaatgtgtt  600
tgataggcta cattaaagcc acagcacaaa gaaaccttgt agagcaaagg aataaagaaa  660
ttattgatga aactctgaat cctggaagga aactcaaaga tcatcttact aaaccctacc  720
tttatttaca tttgaaggaa tggaaaccaa gaagtatttg tgaaaaacat gctgtcacgc  780
cagaacccag atctctggga ttcctgtcca atgtgtgtgt gtgtgtgtgt gtgtgtgtgt  840
gtgtgtgtgt gtttgagaga gagagacagt gtgagagtag gagaaaaagc aggaggaggg  900
gaaggcgaaa agggagagag aaagcacaat tctctcattc catatatgta ttgagtgcct  960
actatatgtc agggatacac caataaatga tatggattgt a                     1001

SEQ ID NO: 105         moltype = DNA  length = 1001
FEATURE                Location/Qualifiers
source                 1..1001
                       mol_type = genomic DNA
                       organism = Homo sapiens
SEQUENCE: 105
cacagcacaa agaaaccttg tagagcaaag gaataaagaa attattgatg aaactctgaa  60
tcctggaagg aaactcaaag atcatcttac taaaccctac ctttatttac atttgaagga  120
atggaaacca agaagtattt gtgaaaaaca tgctgtcacg ccagaaccca gatctctggg  180
attcctgtcc aatgtgtgtg tgtgtgtgtg tgtgtgtgtg tgtgtgtgtg tgtttgagag  240
agagagacag tgtgagagta ggagaaaaag caggaggagg ggaaggcgaa aagggagaga  300
gaaagcacaa ttctctcatt ccatatatgt attgagtgcc tactatatgt cagggataca  360
ccaataaatg atatggattg taacacatat ttacttttgt aaatgagcaa ttctattata  420
aaagataaat atgcttttag ttagtaaaat gtaggcaaaa atgcttaaga tgttttaagt  480
agacataagt agttagtaaa magagcatat gttgttaaat atagatataa gggatggaag  540
ggtcaaaaga tacctaatgt tcctgatgca caaaatatac aaaaggagcc acacattcag  600
aattcacaga tatatgagac atcgaagcac tgactcatta ttcatgaggc cttgagtcag  660
ccacaaattg gagacaccat aagttctcta ctttaggaac aaaaataaaa tccatggcta  720
ttcaaccaac taattggttg ggtccaggca tatatatctc tgtgtctatc ctacaggctg  780
attgagcgat gtaaaagaga tcagatatac ggaaactgct cacacttgag tcagatagtg  840
tggttcttcc aattcactta cacactaaac cattaacttg ctcttctttt tccccttgct  900
gcttgctatg tttttaatg aagctgtgat ttgagcattt cactgcatag tctgcaaacc  960
tatttgtgct gtgtcctctg ggagagcttg catgggacta t                     1001

SEQ ID NO: 106         moltype = DNA  length = 1001
FEATURE                Location/Qualifiers
source                 1..1001
                       mol_type = genomic DNA
                       organism = Homo sapiens
SEQUENCE: 106
tattgagtgc ctactatatg tcagggatac accaataaat gatatggatt gtaacacata  60
tttacttttg taaatgagca attctattat aaaagataaa tatgctttta gttagtaaaa  120
tgtaggcaaa aatgcttaag atgttttaag tagacataag tagttagtaa aaagagcata  180
tgttgttaaa tatagatata agggatggaa gggtcaaaag atacctaatg ttcctgatgc  240
acaaaatata caaaaggagc cacacattca gaattcacag atatatgaga catcgaagca  300
ctgactcatt attcatgagg ccttgagtca gccacaaatt ggagacacca taagttctct  360
actttaggaa caaaaataaa atccatggct attcaaccaa ctaattggtt gggtccaggc  420
atatatatct ctgtgtctat cctacaggct gattgagcga tgtaaaagag atcagatata  480
cggaaactgc tcacacttga mtcagatagt gtggttcttc caattcactt acacactaaa  540
ccattaactt gctcttcttt ttccccttgc tgcttgctat gttttttaat gaagctgtga  600
tttgagcatt tcactgcata gtctgcaaac ctatttgtgc tgtgtcctct gggagagctt  660
gcatgggact atacttggag cctaccaggg catcaaggta atttctcaca tggtaccaat  720
aaggaccctc tatcataaca aaaatgtgga acagtcacct ttagacagca acttgcagga  780
agtgagggaa aaatgatgga ggtgtgttcc agtcagaggt aaaataacgt agaggggctc  840
acagggacac aatgctcagc agtttgagga acatcaacgg ggccagggta gctagagtag  900
aggaaacaag taagacagcc ctaggagatg aggccaaata catcactggg gccagagtat  960
```

```
gcaaaacttc atagggcaag gtaagggctt tggaagtttc t                         1001

SEQ ID NO: 107          moltype = DNA  length = 1001
FEATURE                 Location/Qualifiers
source                  1..1001
                        mol_type = genomic DNA
                        organism = Homo sapiens
SEQUENCE: 107
agacttcttt agttgtcctt taggatgtat gtcctttagg acagtgacca tgttcttttg  60
tattgactgt ttctccaagg acacattcaa tgataatcaa tgtggaggac ttccgagata  120
atgacccttt gccatcacag gctgtctacc tcttctcagc attaagaccc tctgcttatt  180
cacatgccca cagctctcga gggaagaaaa gaagtctaga aatacccaac caggcgcatg  240
gacaaattgg cctacgtagg ccttcctcca tgcctcccct tcccccaaac ccacatttat  300
tttcattcct ttccttctag tctggcacaa catgtcagta aaaaggacac aagactagaa  360
agcaaattct gagatttgga gcatctgtct cagaataagc agttgcaata tgccttatct  420
ttcccagaat atgttcttgc tccacatcta acaataaagt tccaagaagg ggaattcgtc  480
aacatctctc tgactgattt racaaggtga agacatatct gtttaagagg tattgctggt  540
agccagacga gagaagctat tgagacatct gcagtgaggt acctgttgca aagcccccacc  600
gagaaggtgg ctgcggggaa ctcattcctt ctttgggatc agcatggttc tgtattacat  660
ttttagaaga gctgagtttc catgtgttct taaggtctag gatgtataca ggagctccag  720
tatcacagtg gaccccacag aagtggccaa ctacttacat ttcaatatcc ttctctgctt  780
ttttgtttat cagaccaaag ctgaatgtga atctgatggc tgctgcttta gttcaaagcc  840
aatggagtgc tatacctaca gaagcagaac tttaataaac tggcctgagc aatagcaaat  900
ggggaggact tctgaattaa cgaccctttg ccatcacagg ctgtccactt cttctcggta  960
ataagaccct ctgcttattc acatgtccac aggtaacctc t                         1001

SEQ ID NO: 108          moltype = DNA  length = 1001
FEATURE                 Location/Qualifiers
source                  1..1001
                        mol_type = genomic DNA
                        organism = Homo sapiens
SEQUENCE: 108
cagtgccagg tattttaaaa actctcttaa aagttttcat tatcacgcac ttgtgtatac  60
ttattctgta taagcgcttc tatatacact tcaacaatgt ataatttggt tttattttca  120
ttttatttat ttatttattt atttatttat ttatttattt atttatttat tttaagaggt  180
agggtctcac catactgccc aggctggtct tgaactcctg agcttaagca aacctcccat  240
ctcagcctcc caaagtgcta ggattacagg catgagccac catgcccagc catggtttta  300
cttctgagtt taaaaaaaat gttattatat atgaaccttc tgagacttac atttctaaaa  360
ttcaaccagg tactgtgtgt acctcaataa atgcattatt ttgaccatga acatgtagtt  420
gcctctagta tttttatcta ttaaaaatgg catttttttcc attctcatat gtctcctgtt  480
gcatgtgtgc aaaatattct rtcatgtaaa cagctaggaa tcgaatggtt gggtcactgg  540
agtacactta ctggataaaa aatattatca aaaaccttca gcaaatacaa tttgatgtgg  600
aagagttccc acactgattc ttggcaaaga ccaaaatact tttaaatatg ccactcctaa  660
gtgtttaaaa tgaagacact cattttgatt tcctgagttg ggggtggggg aaaacaatgg  720
agaacagccc ttctcctcct ctatttttttt ttcttttaac atttcttcca attactagag  780
atacagtaaa cgcaagtgac acagacaaga aaacatggag cagaccctaa cagaaaaagt  840
agggaataga aactatgttc ataaatagga attccacaca agagaattat gggaatgagt  900
aagacagcaa gattcctcca aaaaacctgc actgccaaga attttcccaa ctagaacact  960
caccagagaa aacggtggcc aagtttcaaa ctgccctcgc a                         1001

SEQ ID NO: 109          moltype = DNA  length = 1204
FEATURE                 Location/Qualifiers
source                  1..1204
                        mol_type = genomic DNA
                        organism = Homo sapiens
SEQUENCE: 109
tagagctgtg ttcagtttta tctgatagtc gagtcatttt gcaatggcac tggaatgctg  60
tatggagatg aagcaaaact aaacggcttt tacaccacat tgttttgaga tagaaagtag  120
acattgaaat gtttacggta catcaagaaa tttaggcgcg gcagctcgcg cctgcaatac  180
agctgaaaca ataagaaaag tgaggcaaga gaataacaaa gggagctgaa agttagaggg  240
cagaataagt aaaagcaaag ggcagaagta aggtagatgg gcgggtgaac aagaagcgag  300
ataacaagca gtgaaccttt tgcagccgaa acaaaagaga taatgtgagc aaggacctcg  360
tggccggcaa gatctggaac aaaccagttt aagaggcagc tcttcagaga tgggcatgcg  420
tattagagag gaaaagtatc cttaacaaaa gcccgtatga taatcagcta cttaaggttc  480
atgcatatgg gctacatatc atgcatatat ttaagattat aagatagagg cacaagccac  540
agaggacaaa gtaagcaaca aacctatcaa taaaagggca gatgctggct atagattagg  600
cagcactggg aacagaaaac atacacacac gcacgcacac acataaaatg actcaaacta  660
cagcaagctg acgctgatct cacctcgcag aggtcagtcc gctctctccc rcccccgaga  720
gtgtaatact ctgtttacta aacttttgct gctttgcttt gctatctgtg tgtgtgtcgt  780
ccaatttcta ccgggcacca agagcctgga actgtttggc accatccggt aaacagaacc  840
gctttgggaa gccgaggcgg aaggaccgct agagccttgg agttcgaagc cagcctgatc  900
tttacaaaag taaaataact aaccgtgcct ggcgtctcat agcctgtagt cctagctact  960
cgggaggctg agaccagaag gatcacttga gcccaggagt tcgaggctgc aatgagctat  1020
gattgcacca ctgcagtcca gcttgtgtga cagagcaaga gtgtttcaaa tgaacctagt  1080
gtcagatatt tactttctgt attacagagg actgaaagct agctaaataa tacttttcag  1140
tgtacctggg ttccagagat aaaattggta aactaacctt tgctccttac ttgggctttt  1200
agtt                                                                  1204

SEQ ID NO: 110          moltype = DNA  length = 1538
```

```
FEATURE               Location/Qualifiers
source                1..1538
                      mol_type = genomic DNA
                      organism = Homo sapiens
SEQUENCE: 110
agattttaaa catgtttctc aggtatccat ttatgaaact aaaccggtaa gcagtgtatg  60
ccaacagtaa gccttaaaag ggcgaggcaa ttgtcatcat ccaatatttg tcagtaagcc  120
aaactgtcat ttctctatgt accaggatgt tacctttttaa ggaggagtac tccacaaata  180
tgaaatatgc aactggggga aaattagctg atcctaacca ttttgtagta tctgaagcaa  240
gaatcaacct tattaattta cctagattta tcctgacatt tatgtgtttt catctttttg  300
catttttctg tgctggactc tccttaagat ttttggaaac ctgtgttctg aattcctccc  360
tttccctggg ctagagtggc tggaggcttt ggctcttggg aatggtctcg cgtccttcac  420
cagaacttac gggaatcatg tttggctgaa gagtcggaga cctctccaga gtcatctttt  480
ccagttagga tagaaacgag ccccccctcct cacctcgcaa gcccgcgcca gtccagtttt  540
agccgttctt ttggaagagc aagtcagttg aacgccatcg aagaggctcc tgatttagat  600
attaattgtg cttaaatgca gatgactccc cactctcatg cgttccctta tttcccgttg  660
cttctcccat tggcatttac agacttgagg ttgcttggac tctcaattca atactccttt  720
tctgcgggtt cgtgagaatt aggtgtgaac gtgatgtccg cggatatcag tggctagtgg  780
gcaagctcca gcgcccagga actttgagtc gcttgtctag gagtcctgta ttgaattgca  840
acactaagtg caatattctg gttcttgttg tgttctgaaa gagctctttc actcatgagg  900
agagacctgc acgagactgt gaagaccaac tgcttctcag cgctccacgc atccattatg  960
agttcaccgc aggattttac ctgmaaaaat tttgcgtaga ttaagtcacg cttattgcct  1020
cctactttttg tcagtgaaca ttatgtcaca agcattttcc cagaactatt acagtcttcc  1080
agcatgtcgt ttctagtggc ttggtaatga cctattaggc agatggagca ataataataa  1140
taaacaactc tcattttaat atctattttt cactatcaca attagaaata aaaataaaga  1200
ttcctgcata gtatatgtct tcctttggtt aagcttattt cctggctggg tgcagtggct  1260
cacacctgta atcccagaac tttgggaggc ggagatggaa gaatggcttg agaccagggg  1320
tttgaacaag gagtttaaga ccaggctggt caacacagtg aggcgccgca tttctattta  1380
taaaatataa aacaaacaaa caaataaaaa gattatttct ctaggagagc ggttctgaaa  1440
cttcagtggg catcagtacc agcaggatga cttgtttttt gtttgtttgt ttgtttttttg  1500
agatggagtc tcactctgtc tcccaggcta gagtgcag                          1538

SEQ ID NO: 111        moltype = DNA  length = 1001
FEATURE               Location/Qualifiers
source                1..1001
                      mol_type = genomic DNA
                      organism = Homo sapiens
SEQUENCE: 111
cacctgccac cacgaggcgt aggatggcct catcgtagga cctgccttct tggaagtaac  60
agcggtagat cccattctcc tgggctgtga cgttatgtat gaccagggcc acgctgcccc  120
tgttgatgtc tttgctcaca aaggtgattc ttccccggta ctcctccatc tgctcctctg  180
ttctctctct cccaccctta tacacaaaca ctgcggggga gaactgagac cggaaccacc  240
gcacctccat gtcctcagca tttttctcgg gtgacagatg gcagcgtaat gtagtgtttt  300
ctcccaccat ggccaggatg ggattagctg gccccacgac agtaaactgg gctgttcaac  360
aagggcagaa tcagacaagg atgccagtta tcacaactct aaggcaaaac aaaaaacaaa  420
aaacaaaaac aaacaaacaa aaaaaactcc agggatgaaa ggaagcagat attccaaggc  480
tacaggggtt cttgggctga saacccttct ggggaccagt agctgtggct ggtcggcagc  540
accaacccct gggagcagta actattgagg ctgctcctgc ttcacgaagg aaacattggg  600
gagcccgccc tgggcaccct gtgcccctga gattttcctc cattttgcaa tctagcactg  660
tgcctgagtg tagtgtaaac ttgaactgtc cattagggta tctatccact agctatttaa  720
cagttccaat aaaaatgaac tctaagtgta aaacacacac agattataaa gatttaaaat  780
ttcaaaatgt caaatatctc attggtaata gttctattaa ctaagcattt aaatattgat  840
atgtgattat ttatatgaaa caaaatacat tattaaaatt tatttcaagt atgtttttac  900
cttttaaaat aaaaagtaga ataggcacag ggtcttgcgc ctgtaattgc agatatttgg  960
gaggccaaag tgggaggatc cttaacagct aggagtttga g                      1001

SEQ ID NO: 112        moltype = DNA  length = 1001
FEATURE               Location/Qualifiers
source                1..1001
                      mol_type = genomic DNA
                      organism = Homo sapiens
SEQUENCE: 112
tggatgttct cagctggatt aattagatct aatctaaaga ctcaatttct gtgtggtggg  60
ggttcacctc cgcttttctg gagcctctga gaaactcctg atcctgcaca ccccccttgta  120
aagcctggcc atgcatcctg caccccccat gacacaggga gccaagcctg acatttttga  180
gaaggtgcca cctctgatcc atcagagctg tagaggaggg aagctggacc ctggaagaga  240
ctctaaagaa aaggagagaa aacatgtagt gagaggagaa tggagtggga aaagtacaaa  300
aatactgacc tttttcttat ctgtgtctcc ttcctttcag aatggaaaaa tggccctctt  360
caagcctggt gagtaaatca ctgcatgttc cctggaccaa caacctgagg gactatattc  420
ctttttcctt ttttcttctc caactcttgt gatttggagc agaaaagttc ccttgacttc  480
cttcgtgggt aggaagacgc rtaaagggtg gaggtgaagg gaaggagaca cacactgagt  540
aatactgcag ggagagtgag gatggaaatg ccaaggagag gaggtgatgc ctgcccaaag  600
aactttgtcc ttcccaggct tctcatgcca cctactgcct gtatctcctc aaaggattta  660
atgcttccaa gctttggcct ccacattttt agatgatgat tgcaatctgt ttttcatggg  720
ggttgaggtg aagactgaag gaataatgaa catgcttggc agaaacctag caagaaatag  780
atggtgagct caaactgggt agttggacaa ggtttccaga aagaagggtt aagggaaagc  840
aacaaggaaa agtgcagtgc cccatggtt cccaacagtg gggagctgtc tccacccccta  900
gcctgggagg gctaaaaagg ggaggcaatt actggaaccc agagaaagag gtagcttaac  960
gagggagctt cctgagaaga gtcctcgggc cttgttagag c                      1001
```

```
SEQ ID NO: 113          moltype = DNA  length = 1001
FEATURE                 Location/Qualifiers
source                  1..1001
                        mol_type = genomic DNA
                        organism = Homo sapiens
SEQUENCE: 113
ctttaactca aatgataatt tttttttca ttttctaaat acactcatca aagggcttga  60
aaaattctga gtttttaccc ctattgttcc acagacaaca aaccttttat aaacccctcc 120
gttactgcaa aatggaaaag agcacaattg tgtccaggtc agagagtctt cacttctcca 180
ggattctgag ctccttcctc ccaagggctc aaggcctcac gatatatgaa aatgaagaat 240
atttgagacc ctgtctctac caaaaaaagg aaagtagggt gaagtcagga caataatgaa 300
ttcataggct gctcctaaga tgtctaagtc ttgcattttc acatttatca tagcctgtcc 360
tcgcgcggga gaatgtacac ctgttttgga aggatctacc ccaccaggta acagtaagaa 420
agactaagat gaacagatat ggaagatagc tcagaggctg caatgggata aattctgggc 480
agaactcaaa cagtggtcca rgcaaccttg atcccttccc tgaactcttt ctctcttact 540
caatccaacc tcaatttatt ggctcccata agttccctgt ctacccctct tgttctagga 600
actctccatt tcaaaagtac ttccaagaat ataattcagg gacgtccaca ctctaccaga 660
tctcagcctt ttgcttcccc agggcaaacc cctgctaacc cctcttccac acagaagtcc 720
accatcttca tctccacacc atcttcactt cacttcccct ccaccttcac atatgcaagc 780
tgttgtgcat aaattacaca aattataatt ataacattat acaaactctg tatgtataat 840
tttaacacgg gcttggtaaa tagcggaatt atgtcactgt aataatgttg aagcaccatt 900
aggtcatatc tgattattac taccatatca atagtgtgtg cccccaagaa agagcagctg 960
accacaaagc tcactagtaa gccacagaag aatacagtat t                     1001

SEQ ID NO: 114          moltype = DNA  length = 1093
FEATURE                 Location/Qualifiers
source                  1..1093
                        mol_type = genomic DNA
                        organism = Homo sapiens
SEQUENCE: 114
tggccttgac taagtttatg gcgacagcag gtaagtctgg agagaaagct ttacaggaca  60
tgtgggtggc ttggacatgc ttctcctagc ccaatgctgt ccaatagaac tttatcctgt 120
atctgtgttg tccaacacag taatcgctat gtacatgtgg ctattaaact cttgaggctg 180
ggcatggtgg ctcacgcctg taatcccagc acttttggag gccgaggcag gcatatccct 240
tgacctcagg agtttgagac tagcctggac aaaatgatga aaccctgtct tcacaaaaaa 300
tacaaaaaaa attatcaggc atggtggcat gcccctgtag tcccagctac ttgggaggct 360
gaggtgggag gatcgcttga gcctgggagg tcgaggcatc agtaagctgt atttgcgcca 420
ctgcactcca gtctgggaga cagaaataga ccctgcctca aaaaaaaaaa aaaaaaaccac 480
ttgaaatgtg gctagtacta atgaattttt actgaatttt agtggctact ktattagaca 540
atacaactca actctaggca gtggtttctt aataggcagg tagtataacc agattatgtc 600
ttagattata gttataatat ggagaatgca ttgaacaggg acaagaccaa aaacagtaaa 660
atcagtcaaa agactctcgg aataatctag gtaggtgtgt gtaaactttg gccccccttt 720
agttatcagt ccttaattct actctgattt ttttcagtta ggatgtttat ttgattagta 780
ccataaagac caagtaacaa tgattaagca agatagaaaa ttttctttgt catataaatg 840
tgctgttgaa gggcaaacca gagacttcta gaagcccttc tccacaaagt tctccagggg 900
tctatgttct tctagctgct tttggacctc ctgaggattg ccttgttcac atgggtgaaa 960
cagaatcaca gcctgcagga aggggaaaga aaatattgtg acttagaagc ttcctttttaa 1020
gcaatgacag aatgaaagtt gcatataaca ctttggctca cattctatgt taagctaaaa 1080
cttgggagat tct                                                    1093

SEQ ID NO: 115          moltype = DNA  length = 1001
FEATURE                 Location/Qualifiers
source                  1..1001
                        mol_type = genomic DNA
                        organism = Homo sapiens
SEQUENCE: 115
acagcagcaa tataaaacta cttagaaata aataaaacat agccatgcca aataaagcat  60
aggaaaactt ctccctcctg agacccaaaa atagactcga ataaatggaa ggacagcctt 120
tgttcttgca tagaacaatt caacattatg aagatgttcc ctcctaagat ttataaacaa 180
tgcaatctca ataaaaataa caagcttctt tatgaaacta gactaagggg tggcaaacta 240
tggcccacag gccaattctg gcctgccacc tgtttttttc aaataaaatt ttactgaaat 300
agggtcatac ttattcatta atgtattgaa aggcagaatt gagtagtcac aatagagacc 360
agatagccac caaagcctaa atacaatact ttctggccct ttaaagaaaa atctccaatg 420
cctaagctgt acagttgcta ctcaagttca ctttgaaaag accaacaagg acagccatga 480
agcaatgaaa agacagacta rgaagggtaa ctaaacccat gagacattaa aataaacttt 540
aaagcttcta atattaaaac aacagagttc caaaacacaa ttagataaag ggacaaatag 600
aaaaggaaat ccagaaataa acacatatag aaatttagta tacaataaag atgacatctc 660
aaatcaccag ggcaaaaatg gactttttaa taaatgatgg taaaacatca aggtagccac 720
atgaaaatag gtacaatttg gtctacactt cataccacac accaatataa actcccaatt 780
ggttagggtt ctaaatgtat acatggaaat gataagatac tacaagaaaa ctaaagtaaa 840
ttctacatta atcttagggt accaaaaatt ttctatctgt aagactgatc atttgactaa 900
aaataaaaac tttttttaaa gttttctttt atatatacat acatatgtgt gtgtgtgtgt 960
gtgtgtgtgt gtgtgtgtgt gtgtatatat atatatatat a                     1001

SEQ ID NO: 116          moltype = DNA  length = 1072
FEATURE                 Location/Qualifiers
source                  1..1072
                        mol_type = genomic DNA
```

```
                         organism = Homo sapiens
SEQUENCE: 116
ccgagggcac caaggccgtc accaagtata ccagctccaa gtgagcctct cgctgcagta  60
acagttccgc cgtgacccac accccaaagg ctcttttcag agccgtccac gtttctcaag  120
aaagagccag ttcactgtta agtttgtctc ccattaggta ccctttggga ctcgcttcgt  180
acatataaat gtacttgtat rtgtgggttt ttttttgttt tttgttgttg tttttgaggt  240
gtagtctcac tttgttgccc accctggagt gcaatggcac gatctcggtt cactgcaatc  300
tccaccttcc gggttcaagc gattcttctg cctcagcctc tcgagtaggt gggaccacag  360
gcatgtggca ccaggccctg ctacttttg tatttttagt agatacgggg tttcaccacg  420
ttggccagac tggtatcgaa ctcctgacct taggtggtcc acttgcctcg gcctcccagt  480
gttgggatca caggtgtgag ccactgcgcc cggcccaaaa tattttaaag aggattatta  540
gcaactatga gtgaccgtgg cttagggaag acacaatccc ccgagaccat gagaaagtgg  600
ttctgaggca gtcagaatgc aactgttttg tacattttag ggaagcagaa gttataggta  660
aagtcataaa taaatatgtg gagggttagt ccaggcgtgg tggctcacgc ctgtaatccc  720
agcactctgg gagtcagagg cgggcggatc acttgagatc aggagtttga gactagcctg  780
gccaacgtgg tgaaaccccg tctgtactaa aaatacaaaa aattaaacgg gtgcagtggc  840
acgtgcctgt aacaccagct tctcgggagg ctgaggcagg agaatcgctt gaacccggga  900
ggcagaggtt gcagtgaacc gagtcgtgat cgcgccactg cactaacctg ggcaacagag  960
caagactctg tctcaaaaaa aatcaggtaa atcaaagaaa atgaactgga aaaaataatt  1020
gctcttaata tcactgtgaa tacctagtga gtgttctgta gatgtgttac ag          1072

SEQ ID NO: 117          moltype = DNA  length = 2784
FEATURE                 Location/Qualifiers
source                  1..2784
                        mol_type = genomic DNA
                        organism = Homo sapiens
SEQUENCE: 117
tgataaggta tatgacaaat aagtcctagg aattattgaa ttatttcctc tgaagaaata  60
attcaaaatt tatagtggaa aaatcatcaa agaaattaaa tgctacagta taaaatattt  120
gcttaatgca aaaatggaat ataggaggaa tggaagaacc aaaaaggcat gagacataca  180
gaaaataaaa agttaaatac cagacaaatc caaatatatc agtaataata atgttatatg  240
taaatatatt aagcaattga atcaaaaggc agagactgtc agggtggata aagaaacagt  300
attcagctat cttttgtcta gagaagacac catttacatt taaagataca agtaaattga  360
aagtaaaagg atggaaaaca tatgtcatgc aaacttcatc caaaaaaagc tgtaatgact  420
atacgagtag wcaaagtaga ctttaaaaca aataatgtta ctagggacaa ataaggacag  480
aaagggctaa tccatcagga agatatcaca attataaaca tctatgcaat taataagagc  540
accaaaatac ataacgacaa aagtgacaga aatgaagaga aaaatagaca atgcaaaaat  600
aatagttgga gtcctcagtg ccccactttc agtaatgaat agaacaacta agaaatagat  660
cagtagggaa atacaagact tgaagaatgc tataaaccaa ctagacctaa caaatattta  720
tagaatctcc attaaacagc agcagaatgt acattcttct caagagcata tggaacattc  780
tctgagatag atcctatgct aggtcataaa acaaatccaa ataaattgaa aaggatagaa  840
ataatgcaaa gtatgtttgt ctgatcacaa tggaatgaaa tcagaaatca aacacagaga  900
gaaatttaaa aatccacaaa taagtggaaa ttaaatttct aaatagccag tgggttaaag  960
aagaaatatt aagataaatt agaaaatatt tgagataaat gaaaataaag aaacgacata  1020
ccaaaactta tgggattcag gtaaattagt gtttagagga aaatttatag ctataaatgc  1080
ccatattaaa aaagaagaaa aatatcaaat gagtaaacta agtttttacc ttaagacact  1140
ggaaaaagac caaactaaac agaagcaaaa ttcaggataa cagtgaaatt aatgaagtta  1200
ataaatagaaa aatgtcaaga aaatcaatga aatgaaaaac tagctcttca aaaagatcaa  1260
taaaattaac aaacctttag atagagtgac caagaaaaaa agagaactga aattattgga  1320
atccaaaatg aaagagtgaa cattactact aaccatatag aaataaaaag actgtaaagg  1380
acagctgcga aaaactgtat gccaaaacat tagataactt agatggaata gacaaatccc  1440
tgtaatgatg ctaactactg aaactgactc aagaagaaat agacaatctg actagacctg  1500
taataagtaa agagataaat tagtaataaa aaaactatat acaaataaat gtccagactt  1560
agatggcttc agtgttgaat tctaccaaac acttaaaaga attaatacca actcttcaca  1620
aactcttcca aaaaacagaa gaggaggaaa cacttctcaa ctcattctac aaggccagta  1680
ccagtatcct tataccaaaa ccaggcaaag ccatcacaag aaaagaaaac tacagaccaa  1740
tatttcttat gaatacagac ataaaaatac tcaacaaaac accagcaaga tgaatccaac  1800
aacatataaa aagaactaga tatcattacc aagtgggatt tatcccagaa gtgcaagatt  1860
gttttaaatt ctgaaaatca gttaatatga tacaccatgt caacagaata aaaaacaaaa  1920
accacatgac catctcaaaa gatctctttc atgttaaaaa gtctcaacaa actagaaata  1980
gaagggaatt tcttcaaccc taaaaatgca cctacaattg catggaaccc ttgaaaaact  2040
agaacaaagt tgaaagactc acacttcctg atttcaaaat ttactataga gcaacagtaa  2100
ttaaaacaat gttgtactgc cataagcata aacatataga tgaatggaat ctacagttga  2160
gaggccagaa ataaacccat atgtctatgg ccaactgact ttttccaaga gtctgagact  2220
attcagtagg aaaagaatag tctttccaac aaatggtgcc gggacaaatt gacagacatg  2280
tgcaaatgaa taaagtttga cacttacctc acaccatata caaaaattga ctcaatggat  2340
taaagagcta aatataagag ctaaaactat aaaacccaat atttgggaaa ccactgcctt  2400
atagaaagct tatacatttg tactacaagg caaatacatg aatgtttata gcagtattat  2460
ttagaatata aaaaatctgg aaggtatctg aatgtgtatt cacaaaaacg aacaccagag  2520
aatttaattg tgatatacct gcgcagggga atacaatacc acaacgtaaa ctgaatggtc  2580
tccaggtaca ttcaataaca tggatgaata tcacaaacca aaagttgtgc aaaagaaggc  2640
aggcaaagaa taaaaagaca gtatatatat aaagttcaaa gactggaaaa tacattttgt  2700
cttttgattc atacacatga ggtgtattag tatcaagtaa ggaaaacaga gatcacactg  2760
attattttaa caggattact agat                                        2784

SEQ ID NO: 118          moltype = DNA  length = 1001
FEATURE                 Location/Qualifiers
source                  1..1001
                        mol_type = genomic DNA
```

```
                        organism = Homo sapiens
SEQUENCE: 118
gcttcgaact ccaaggctct agcggtcctt ccgcctcggc ttcccaaagc ggttctgttt  60
accggatggt gccaaacagt tccaggctct tggtgcccgg tagaaattgg acgacacaca  120
cacagatagc aaagcaaagc agcaaaagtt tagtaaacag agtattacac tctcgggggt  180
gggagagagc ggactgacct ctgcgaggtg agatcagcgt cagcttgctg tagtttgagt  240
cattttatgt gtgtgcgtgc gtgtgtgtat gttttctgtt cccagtgctg cctaatctat  300
agccagcatc tgccctttta ttgataggtt tgttgcttac tttgtcctct gtggcttgtg  360
cctctatctt ataatcttaa atatatgcat gatatgtagc ccatatgcat gaaccttaag  420
tagctgatta tcatacgggc ttttgttaag gatacttttc ctctctaata cgcatgccca  480
tctctgaaga gctgcctctt maactggttt gttccagatc ttgccggcca cgaggtcctt  540
gctcacatta tctcttttgt ttcggctgca aaaggttcac tgcttgttat ctcgcttctt  600
gttcacccgc ccatctacct tacttctgcc ctttgctttt acttattctg ccctctaact  660
ttcagctccc tttgttattc tcttgcctca cttttcttat tgtttcagct gtattgcagg  720
cgcgagctgc cgcgcctaaa tttcttgatg taccgtaaac atttcaatgt ctactttcta  780
tctcaaaaca atgtggtgta aaagccgttt agttttgctt catctccata cagcattcca  840
gtgccattgc aaaatgactc gactatcaga taaaactgaa cacagctcta cttggtgaaa  900
aagtaggtgg ctctgaaaag aaccttttg gtttggaccg aggtatgagt aatgaactgc  960
tccagccccg ctacttgccc ttggccttgt ggtggctctc a                     1001

SEQ ID NO: 119          moltype = DNA  length = 1001
FEATURE                 Location/Qualifiers
source                  1..1001
                        mol_type = genomic DNA
                        organism = Homo sapiens
SEQUENCE: 119
aatagggctg aggactctac cctcagtttt caatctagag actgtgaaac tgtagagaaa  60
cacactgtct agtagcaatc catatacttt ttctagtaag catattaaaa accgaatact  120
atactatatt ccttacagcc cagtgagttt cccagaatca taaataaaac ccaccagtac  180
ctactatgta actcccagta agaggctttg actttgtca aagttgtgtc ccagtaaaat  240
gccttcaaga taccacaaac tggcctggcg cagtggctca cgcctgtaat cccagcactt  300
tgggaggcct aggcgggtgg attacctgag gtcgagtcag agaccagcct ggccaccaag  360
gtaaaacccc tgaaaacacg tgttagcaaa cgtaccttgt tagtatctac attaagaaaa  420
aaaaaaaaaa aaaaaacctt gaaattcagg caatgtaaac aggttaaaga ttaacaccga  480
aacatcatga gtgtactgtg magtggtgaa gcagctgaaa acggactcgt gtcatctttt  540
tatgattgtt gaagtggctc tgaaaagagc ctttgttttt atgcgctttt caactcggtc  600
tttacttagt cttgtggtgg ctctcagttt tctttggcag cagcacggcc tggatgttgg  660
gcaggacgcc accctgtgcg atggtgactt tgcccagaag cttgttgagc tcctcatcgt  720
tgcggatggc cagctggagg tgacgcggga tgatgcgagt cttcttgttg tcgcgggccg  780
cgttgccagc cagctccagg atctcggcgg tcaggtactc cagcaccgcc gccaggtaca  840
ccggcgctcc agcaccgacc cgctccgcat agttgccttt gcggagcagg cgatgcactc  900
ggcctacggg aaactgaagc ccggcccgag aagagcgggt cttggccttg gcgcgagctt  960
tgcctccctg cttaccacgc ccagacatgg caaaaggtct a                     1001

SEQ ID NO: 120          moltype = DNA  length = 1001
FEATURE                 Location/Qualifiers
source                  1..1001
                        mol_type = genomic DNA
                        organism = Homo sapiens
SEQUENCE: 120
tcactaccaa agtatatgac tactactata gatattttat tttatttatt gattgatttg  60
tagagatggg gtttcattat gttgaccagg ctggtcttga attcctgggc tccagggatc  120
ctcccatctc aacttcccaa attgcaagga ttacaggcat gaaccactac ttaaacttgt  180
attcctttat gcttttttc atttgcaata ttgactataa tcaggaaaaa aaatatatcc  240
tttatgaaga agaaaaactt atgtctcatt ctaaggacag cagagaaatt gttaactcag  300
ggaaaatgat aataaaaatg atacccctc tatagcaaca taaagagcag tttcgaggag  360
caaaagatgt ggtgaaatgc attgtttact ctgggtgggt gcaagatcca ggcaggggtg  420
aagcatggcc ggctgcacag atctctgttc tcttgtttcc tttacatccc tccccacctc  480
cctctgcaga tcttgttctc rgaggccatt cccagaccca cagcaagagg gattatggct  540
gcaggcctca tgctcctttg ttttggaaga aactgttgag gagttagtat ttactgagca  600
gctaatatgt tcccgtcact attgtaactc ataataatta ttgttaagta atacacgaaa  660
agttttaaat ttaaagcatt ccaatatttt aaaagtaaag ggaacaaaag gccaagtgtc  720
ccttcactca ctaacctctg atcttcagat tagcatgcgt ctttttgag tttttcaggc  780
atttacataa atagttatgc agaaatggat agctttgctt ctgttcttca attgaatctt  840
tagtatagtt gtgcaaggtg ttttttgatc acttagtgtg tctccgttat ctaggttcat  900
gacaacaaat caactctttt tacctgctgc attgaattcc ctccgaggga tgagccgtca  960
ttcctctaag cagtctcctg atgggtggct ggttcagttg g                     1001

SEQ ID NO: 121          moltype = DNA  length = 1001
FEATURE                 Location/Qualifiers
source                  1..1001
                        mol_type = genomic DNA
                        organism = Homo sapiens
SEQUENCE: 121
ggggatggtg tagactgtgc caagttgaag acccatgtag ggaagaggcc aggagggtcc  60
ctagtaagcc tgacataagg gtgtaccaat aggtggccag aaatgccttt ctgctcttaa  120
gagaacacta atactttgtg tatagcctgc cgtgggaggg atttcaggtg ggtgggagag  180
cacagaaccc aattgcccac tcccagtgag cacttttcat cttatgattc agcccctctg  240
cccataagca ccacagaatc caagctttac cagataccat ggcacatgga cctttcctct  300
```

```
ttaggtgaat ttcaaaattg ccactgtcaa cttgggacaa aatagcaaat tgtcacagcc  360
agacatatta acttggggaa tggaggaaat cattttaaca caatagaaaa gtagactgaa  420
taagtaagaa taaatacaga tgggagaggt ctgcagaatg cccggagtct ggagcatttc  480
ttgtacctac agaagtgata rgtgaagaca tcagacccat gttgttgaag caaaactgga  540
tgggaatagt tactccctac atttgcccac agacccctca ggcaacaggt tttcttttgg  600
ggacatttat tctccttctt catttttga agggtgccct tgttagtcat ttaagtcagt  660
tgtgatctgg taaaaggaac acataggacc aatgaagaga ccctttatcc tccaggacag  720
tgtgaaggga aagactcacc ttagttgatc caccggggag aggaggagca ggacataaag  780
cctttgtgct ggtttaagcc aagttggaaa gtttctaagt aaagaaaatc ccagagatca  840
taggtcttca tttggggttt tgttttgttt tgttttgaga tgatgtcttg ctctgtcacc  900
caggctggag tgccatggca caatctgggc tcactgcaac ctctgcctcc cgggttcaag  960
caattctcgt gcctcagcct cctgagtagc tgggattaca g                      1001

SEQ ID NO: 122         moltype = DNA  length = 1001
FEATURE                Location/Qualifiers
source                 1..1001
                       mol_type = genomic DNA
                       organism = Homo sapiens
SEQUENCE: 122
aaagacattc ctagaagtca tccttcagtg atatcaccac ttgctcagtc accatctcaa  60
ccttatgtca cctcagccct catctcaatg cccaaacccc ttacacacac cttcagttag  120
cttcaactgc ctccgtttcc acactgtgca cctttcactt tccctaccca gctttcctac  180
atgctgcctc tcctcagggt cccctgaatg ctgcatcatt gtgttcagtg cagctggact  240
gattgcacct gtgtatttgc ccctgagcac tttcctttac acatgtggct tgtcttgcca  300
atagactcca ggcttatacc ttccatttcc atcgtattct ccagtttcca ggatagacgt  360
tgctcatcgt ctttacctaa taaataagtt tgtctgattg ctgaaagcaa cctcttaacc  420
tttcttttt aatatcaact gaaacaaaat aaaacatagg gcaagaaacc tgcatgggaa  480
tgcagctgtc taaagctttg rcattgtatg tggtctaaga cccatcccta ggcctgatgg  540
cagtgggctc accagggcag gtgcacatgg gggctgatgc ctcatgaggg aacaactgct  600
taccagggtc ttcaagcagg aatacagaat ctcaactcag gaacaatttt ttattagtcc  660
atcctcatat ttctgtaaag aaatacctga gactgggtaa tttataaaga taagaagttt  720
aggccgggca cggtggctca tgcctgtaat cccagcactt tggaaggccg aggcgggtgg  780
atcacgaggt caggagtttg aaaccagcct gacaaacatg gtgaaacccc gtctctacta  840
aaaacacaaa aattagccgg gtgtggtggc aggcacccgt aatcccagct gctcagaagg  900
ctgaggcagg agaatcactt gaacccggga ggcagaggtt gcagtgagct gagatcgcgc  960
cactgcactc cagcctgggt gacagagcaa gactccattt a                      1001

SEQ ID NO: 123         moltype = DNA  length = 1001
FEATURE                Location/Qualifiers
source                 1..1001
                       mol_type = genomic DNA
                       organism = Homo sapiens
SEQUENCE: 123
cattatggtc tcgaactcct gacctcaggt gatccgtccg cctcggcctc ccaaagagct  60
gggattacag gcgtgagccg ccgcccaacc actttttta gtattttaaa tcaagtatct  120
ttttgtttgt ttgtttcttc tgtgcctatg cttacccaga cagtttcttc atttattttc  180
ccccgccttg ggcaggcttc cactcttcag accctttcct gcacaacttt gtccctgagc  240
ataggtcctg gacgtaaaag aagggacatc gtctggagaa atattgaatt aagaaaggcg  300
cggctgtgaa gaatagaaat cagtgtctcc cttagtctct cagttcggcg atcttggtaa  360
tgccctgtcc catgcctgct aacgcgattc agcctcgata tccccgtcca gtcccacgat  420
cgcaccaaga agagcttgcg agccttcctg ctacatactg acattaagaa accggacttg  480
aaagggatcc cagacaaacg wtaaacatgc aacaagaggg atagggtgta aggaagagaa  540
tccttggggc ggtgtctgat aaaacagatg gctctccttt ccaggtgttt ctgaatttga  600
tccccgacgc ctggggcatc gtggaggaac ttgcatagga aatcaaggtg tcgcaggaaa  660
gagaacacgc acaagcaaaa gataccttaa tttgtagtat actcaatatt tatcgtacag  720
aagtgtatcg acgatagaca atgtgcgatg tgatgggtgc tgggaactta acgaactctc  780
cacgcgccta gacctcattg gatccacttt ctcttgggct gtgagccggt aaaaaaaaaa  840
ggggtggatg tggaggacgg tccaaaggat tcggagctcc ttaaaatgct actcaaactt  900
tatttagcgc gctggagaat ccctgagaag gagtattata cccagttttc cgggacttac  960
ctccagtgat tctacgtcga ttctttgatg aggcccatta a                      1001

SEQ ID NO: 124         moltype = DNA  length = 1001
FEATURE                Location/Qualifiers
source                 1..1001
                       mol_type = genomic DNA
                       organism = Homo sapiens
SEQUENCE: 124
gaaaaatttg aacaggcgct tcacaaagac ggccaaatgg caactgaaca atttgcaatc  60
agaaaaaaaa aaagaaagaa agaaagaggg aagagggtct aaacaagcaa ataaacgaaa  120
aacgagaggc gaggctacca ggtttcttcc atttctggca aacatttatt gttgttgttt  180
tttccttcac agaattattt tcagaaacct tccacaggag attcgtgcgt ggagggggtg  240
gggtggaaag aagtagggaa tggagaagat tactaagaaa agtttcctgt ctggaactgc  300
ggcagatctc tttggataga gatgactact taacctcact ctgctttcct tcgccgcggt  360
tgcggccgcg accctgttct taccaccagc aattcctcca gggacttggt cagcagccca  420
acttgatctg cgtctctctg ctaaggtgtt tccgcaacag ggtcaactcc aagtctcacc  480
tttctaggaa tcccgggcgc mgcgcggggg tcgggactcc gacctgtatt tccaggcgga  540
ggtttccctg ggtcaggcgg ccactctctg ccagagattg tcagttatcc aactgtcaat  600
agagccgccg ctccagcgag tttaatttag gcacagaaaa gtcctgcctg ggttgaggtg  660
ggcttaggat gagtttactt gagtgtgtga tttagaaata gatctatggg acagacagac  720
```

```
acgaaatcgg gcattggggc cctcgcaggc agggtatcta gactggcagc tgccggtgca  780
ggatattgcc aaggactcgg catccggctc agctcaaggt ggggacgaag acgtcctggt  840
tgcaaggagg agccctactc cccccggaat cagaactgtg catagcgggc tctggatttg  900
ccgggatgtt tgaggaattt gaaatgagaa aggagaggag gaaatggttt aatggtatat  960
tgagttactg gagtgtattt tagtcaccga ttttggtttt a                       1001

SEQ ID NO: 125          moltype = DNA  length = 1001
FEATURE                 Location/Qualifiers
source                  1..1001
                        mol_type = genomic DNA
                        organism = Homo sapiens
SEQUENCE: 125
tttgatcctc ttaccggcca catgaggaga attagttctt taccactttt gttgatcaca  60
tctcctgtga attctgcttc cagtttctcc gaaagtaagc tctatatcgc cactactgaa  120
ctggaaacac agtctttcaa aagaagaaat gtgggcgagg gcggtggctc acgcccgtaa  180
tcccagccct ttgggagacc gaggtgggcg gatcacttca gttcaggagt tcgagaccag  240
cctagctaac atggtaaaat ctccgtctct actagaaata caaaaattag ccgggcgtgg  300
ttgcgagcgc ctgtaatccc agctactcgg gaggctgaga caggagaatc gcttgaaccc  360
gcggggggga gtgggggggg ggcggcgcgc agaggttgca gaaagccaac atcgtgccac  420
tgcactccag cctagctgat aagagcgaaa aaaaaaaaaa aaaaaaaaaa gaagaggtaa  480
catgtgagag ctaagacgga rgccttcatt tttgttttta agtaaaattg agtaaggtaa  540
ggcgtgtgtg ctaagggaag gggaactagc gttaaacaat ttccagtttt gttttagaca  600
aaactttctg aaacatcgtt tcacattaaa cttgtgaaag acaaaaaaag attctatttg  660
ctgtggctgg ttagctcaac tggttagaat tcggtcatag attcccgttt gtccctgcct  720
aagaacactt tgtggtctcg caagtcctct ccaagattta acaacgtccc caataaatct  780
gtagaatccg atggctgttc cctcacagtt taggtctttg ctttttattc catcttcata  840
catagaaaat tggcctatgt gaattgtctc catctgagaa gaaattgtaa agccatctgc  900
acttccaatc acttccacac ttgggttttc accggatcac atgaaatagg atttttaaat  960
gacatatgtg aacaattttc attaacatca acacactagg a                       1001

SEQ ID NO: 126          moltype = DNA  length = 1001
FEATURE                 Location/Qualifiers
source                  1..1001
                        mol_type = genomic DNA
                        organism = Homo sapiens
SEQUENCE: 126
ggtgcaagca tgcatgtcct gttgcttcgc tgcgcgaggc tgaggcacga gttgctggat  60
tttgggggtg gggagtgcgg tgcttggctc ctggctggtg aatcagtctg tgaggatgct  120
ggggtgggcg ggcggagggg atatggggag agtgggtagc gcagtgtgtc tggtggttct  180
ttagttctcg gattgttact atttgtgttc ttatcccggc tctgttcacc tctctttccg  240
gacctgttta ctggtttgtt acatgaatac aacctgagta aaagtctcgt cagcttttct  300
acaaaactga acataactct ttagcattgc tgcctaggtc aagaaactat ttgatcaacc  360
gcccctcttc tttccaccct caattttaca ttgaggctga ggacttgtgc cggttttaag  420
cagcgttcag ggctggccag attaaggagt ggacaattaa ggaaagaatt gagttagcta  480
gaggaaaggg tgcgatttac rgttcccttc ctcctgggca aaaactcttc aggtgggact  540
cccactggca gatgtgaaga acgttgcggg cagtgggagg tgcttttgag tgagtgctgc  600
ataggcgtcc tggacgggtc tttgtctttg gcgcgcagac cggttcgtga gacgcaagaa  660
gaaggcagca gcagctgccg gaggaaaaaa gcggtcctac accaaggact acaccgaggg  720
atgggtggag ttccgtgaca agcgcatagc caagcgcgtg gcggccagtc tacacaacac  780
gcctatgggt gcccgcaggc gcagcccctt ccgttatgat ctttggaacc tcaaggtgag  840
aagatagatc tttctgccac acctctcacc ctcccttctc cccaactctg gcccaagtat  900
ccccatggcc tctcattggc cttgtcccct tgtctcatct ttctccctaa tctgcactat  960
cctgatcttt tcttcttttc tgcccacagt acttgcaccg t                       1001

SEQ ID NO: 127          moltype = DNA  length = 1399
FEATURE                 Location/Qualifiers
source                  1..1399
                        mol_type = genomic DNA
                        organism = Homo sapiens
SEQUENCE: 127
tccctcatga tctgtttcct ctgatttcaa caagcaggtg ttctttctcc tgtctcaggc  60
taattctgca cccacatcgg ggagccccca ccccagcttc cctcaggctt ctctatttgg  120
tcaattcatt aattcattca tttgacaagg atccatgaac gctaactatg tgccagtcac  180
tattctaggt ggtggagtca ragaagtgaa caaaacagaa agttctcatt caaaaacaac  240
ataacttgtg gtaggaggca gacaggaaat gaaataatta gtaatatata tggtgtgctg  300
gatgatgata agtgctcagg agagaaataa acctggaata gcagaacttg catttctttt  360
tgaaggggtc ttgctctgtt gttcaggcta gagtacattg gagtgatcat agctcactgc  420
agcctaattt tttttttttt tgaaagacag agatcttgct atgcatactg cccaggttct  480
tgaactcctg gcctcatgca attctcctcc ctcgatcttt caaggtcctg tgattacacc  540
tgtaagccct cgttcccggt tggaagttac agtttaaaat agggtggtta tgagcaaggg  600
gagcgaggca cagaatactt gggagaaaag cattccgagt tgagagaaca gcagtgccag  660
agcacagagg cagaagcact gtggtttgtg tgaagaaaag caatgaggct ggggtgcgca  720
gagcacacag ggtgatcagg agaagaggag gtgacaaggc cagagggggt tgagggccag  780
atcatgtatg gccttgaaag tcatcatgct gacctgggct ttacctctga gaggggagcc  840
actggaaggt tagagcagaa aaaggactgg actgacttat gttttaagaa gttacttcac  900
atgctagacc aagatgggct gtgggtaggg gtggtggatg gaggcctgaa gacccagctg  960
ggagctactg cagtgatcca ggggaaagat gcagatgact tgtaccaggg aggagccatg  1020
aaaatgttat gatgctggat ttattttcaa gatagaataa aaaggctttg ctgataaact  1080
tacaggtggg gtgtgaaaaa ggagggcatc aagggtgacc acaaggtttt ggtcctaaga  1140
```

```
aacggtacag atggagttgc cacttactga gatggggaaa atgagggaga aaccgcttgt  1200
ggaggccaga ggaggagcca gcacagaatc caaaggtcag ttttgaatat gttgggtttg  1260
aggagcttac tagagattcc cgtggagatg tagagtaggc aggtcaataa taagcttgca  1320
gtccaggcaa cgggtcaggg ctggaaacac aagttattct ctttgtcttc tttatattca  1380
tgtttgttgc cactgtgtg                                               1399

SEQ ID NO: 128         moltype = DNA  length = 1001
FEATURE                Location/Qualifiers
source                 1..1001
                       mol_type = genomic DNA
                       organism = Homo sapiens
SEQUENCE: 128
tgagaaacag cttaatggtg tcttgtgata aaattgttaa attttcacga agtcaaattt  60
atttcaattt tgtttactta tttttgtatc tccctatgaa atctttgttt ccccaaggtc  120
atggaaatag cctatgctcc acgacccccc cccccactta cataatcatt taccttttat  180
ttatttattt ttattttatt tattttttg agccatcttg gctcaccaca acctccatct  240
cccaggttca aacaattctc ctacctcagc ctcccgagta gctgggatta caggctcccg  300
ccacaacacc ccgctaattt tgtattttta ttagagaccg ggttactcca tgttggtcag  360
gctggtctcg aactcccgac ctcaggtgat ccccctgcct cggcctccca aaaccctggg  420
attacaggcg tgagccactg tgcctggcca catcatttac cttttatttt taggaatatg  480
atcaaaagac ctgaacaggc rcttccaaaa tagaatatgt caatggccag taagcacata  540
agcagatgtt gtgatatcaa taaaaagttt gcttatttat tttaaccagt ggtgaccaga  600
caaaagacct caactgtctc tggaaacttt attttatttc cagaaatctt ttcaaaactc  660
ttctgtgaag gttgtgtttg tctgggggag gggtgaagtt gtggtttggg atgagttgca  720
gatgaaggag ataagacaag gtttctgcct tcaggatctt caggaatatg tgtcctttaa  780
tcagactgct taacttgatt tggctgatcc ccctttcttt ttcagttccc tccatccctc  840
taatccccat cacctaaaaa gacctccaga gacttagttc atagctgggc ttgatctata  900
tctctttgct ccagacattt ctgctctgtg tcaatgccag cctgcatcta tctgggatgt  960
tgggtggggt agtagagtgg gatcggtctc tctagccata a                     1001

SEQ ID NO: 129         moltype = DNA  length = 1001
FEATURE                Location/Qualifiers
source                 1..1001
                       mol_type = genomic DNA
                       organism = Homo sapiens
SEQUENCE: 129
aagaagctcc tgaaattttt atgttagttt tgtcttttta ttttcctcct tcttcttctt  60
cctcttttc ttcttcctct tcttcttctt cacaccacta tacaaaggag gaagtttagt  120
tttgtctttt actttaaatt acacaagatt tttttttctt tctctctctg tctctttatt  180
attttaaatt gtttgtagag atggagtctc gctcgaactc cttagttggc tcaagtgatc  240
ttcctgcatt ggcctcccaa agtgctggga ttacaggtgt gagccaccgt acccagctga  300
ttttctcttt aacctggcaa tgactcttgt ttctgtttta ttatagaatg gaaactggct  360
cgatcttgtg caggttagtg gctgggcact gctctgggtg ctgagattta acctctgagg  420
tatccaaaga cctaaaataa gtggaaatga aaaatgctga taccctttta gtgatgaaca  480
cagagatttt aagttgtggg raaaaaaaaa agaaagaaag cctaatactt ccttggaaca  540
cagagagggg ctttggaaga tggccaagag tccagcttcc tgtgagatta tctcacgagg  600
cattacaagc ctgggcacag tcaactctta acatcaccct ctggctgctg gtgacagagg  660
gagcctgggg gaatggagac cccttagcag gccaaacagc cctccccctg aggagaccta  720
tcaactccta cagcagtgct ctgtttctta gaagcaaaaa tagtcctgta accataacac  780
tcaccaatgg tcagactttt tgtttctgtc tttctctcca gttgaagtga ctctggaccc  840
aaacatagcc ctccctcacc tctttcttta ttaggattca aatctgtttg actggaagat  900
tcatgtcaga aactgcctga aaaaccagag agatgtgact cctggccctg tgtgctaggc  960
ctggaagcct tcacctcgga gagacattac caggaagtgg a                     1001

SEQ ID NO: 130         moltype = DNA  length = 1001
FEATURE                Location/Qualifiers
source                 1..1001
                       mol_type = genomic DNA
                       organism = Homo sapiens
SEQUENCE: 130
caccccttcta tgcatcctca agcctaatct ttcctggtta tgtgacaaga acccggtttt  60
tagctgaact aaggagaaag tcctacaaca ctgccaccat gtggcaatta ctccaaatag  120
aaggagaggc tgaaggacac acaaccagga tgcagagaaa aagatggaga cagagtctgt  180
gcaagatggg attgatactg agactgggtt agccacctct cctagacagt gaaacagatc  240
gcaagagagg ctgacccaga aagacacatg caaaacaatg ggcaatagaa cacatgacct  300
gaattagatt atctgggttc aaatcctgat tttgctattc attatctgtg tatcactggg  360
caatttactc aatctctctg tgcctgaata tcctcattca aaatcaggga tgaaaagagt  420
acttatctca aagggctatt tgctcactta ttgcacaagt aatttggcat ctgatatgaa  480
ccaggtgcac ctctagatga rgatactgtc acattgaatg aagaccagtg accagaagcc  540
tgcctcacag cccagctcag tgagaaaaat aattccattc tcacctctaa tctcaaccct  600
gtgtcaccat ttatgtatag tcctttgcat tagtgtctgg aaaggtcatt ttttgagggc  660
agaatgaata acctatagaa ggatcattct tgggtataat gaattaaaga agtattatga  720
agctttataa ggcaggatta gctcataaaa atggagggtt cttttgcttt tccagtccca  780
tttgttgttt cacagacaaa gaataaaaca atcactgatg gcaaagactg caaactgcca  840
acgttcatcg gtagagcaag gtgacgctcg tcctgtccag gcctgtggtt gggataagct  900
cagaaagcag agtctccagg gctggtcatc atctatcata accctgcgta taaagaaagc  960
cttgagaaag aaaagaagtg acttattatg tgtcttctga c                     1001

SEQ ID NO: 131         moltype = DNA  length = 1001
```

```
FEATURE                 Location/Qualifiers
source                  1..1001
                        mol_type = genomic DNA
                        organism = Homo sapiens
SEQUENCE: 131
ctgtggacac tgctgaggaa gcactgttaa acgcccttct tcccactgcc atcatatcta  60
agtcagcgtc tcctaaagag cccgaacagc tgctgaagct tttcattgtc attggagggt  120
tgaattttgt ttttttcggt tttgtttttg tttttttga gacgagtctc tttctgtcgc  180
caagctggag gagtgcagtg gcgcaatctg ggatcgctgc aacctccgcc tcctgagttc  240
aagtgattct cctgcctcag cctcccaagt agctgggact acaggcgggc accaccacgc  300
ctggctaagt gtgtgtgtgt gtgtgtgtgt gtctgtgtgt gtgtagtaca gacgtggttt  360
cactatgttg tccaggttgg cctcccagag tgctaggatt acaggcatga gccactgcac  420
ctggccagga gggttgagct ttgaaacaac tgatgagagc ctgaggagcc attttgagca  480
atagggaacg ctcacggact rtgtagtaaa gaaagatcca aacaccaagc actccagggg  540
ctttgggttt gtcacatatg ccggtatgga aaaggtggat acagccatga atgcaaggcc  600
gcacaaggtg gatggaagat ttgtggaacc aaagacagct gtttcaagag aagattctca  660
aagaccaggt gcccacttaa ctgtgataaa gatgttaaag aagaactgaa gaacataaac  720
taagagatta tattgaacag tatggaaaaa ttgaagtgat tgagatcatg actgaccgag  780
gcagtggcaa gaacaggggc tttgccttgt aacttttgat gaccatgact ccatggaaag  840
gattgtcatt cagaaatacc acactgtgaa tggccacaac tgtgacttta ggagtgctct  900
gtcaaagcaa aagatgttta gtgcttcatc cagccaaaga gatcgaagtg gttctggaaa  960
ctttggtggt ggcgttggag gtggttttgg tgagaatgac a                       1001

SEQ ID NO: 132          moltype = DNA  length = 1001
FEATURE                 Location/Qualifiers
source                  1..1001
                        mol_type = genomic DNA
                        organism = Homo sapiens
SEQUENCE: 132
ctaccttgac agctataaaa agtcgctcta aagaaaaaga accagctctg gccaggcgca  60
gtggctcaca cctgtaattc cagcactttg ggacaccaag gcaggtggat cacttgaggt  120
caggagtttg agaccaagcc tggccaacat ggtgaaaccc tgtctctact aaaaatacaa  180
aaattagtgg agtgtggtgg tgctcgccta tagtcccagc tctcaggagg ctgaggcaga  240
attgcttgaa tcagggaggc ggaggttgtg gtgagtcaag attgcaccac tgcactccag  300
cctgggtgac agagtgagaa agaaaagaaa agaaggaaag aaaagacagg aaaaccagtt  360
atttccactg ttttcacaga acaaatcaac agactgaagt ttactcgtgt caacagtgtg  420
tgaggttaca atgtgatact tactattctt gagatggaaa tgttcagaaa agaagccaca  480
taaagcacat ggtggaagag maaaaatgca aaacaggctt aaagaactgt gagagtttag  540
aaaaaagcaa tagatcaaag ggatcaagaa tgggcattag aagatgaaac tgaagacaga  600
atagggagta gggggttcca ggcatggaaa taggatattc tgtatgagga aaagagaaga  660
acctctttag ttgggcatga aacatacatt ctaagtagaa ataatttttt ttttcttgag  720
atgacatcta gctctgtcac ccaggctgga gtgcaatggc acaatcttgg ttcactgcaa  780
cctccgcctc ccaggttcaa gcgattctcc tgcctcagcc tccaagtagc tgggattaca  840
ggtgcccgcc accacgccct gctaattttt gtatttttag tagagacggg gtttcactgt  900
gttggccagg ctggtctcta actcctgacc tcgtgatccg cctgccttgg cctcccaaag  960
tgctgggatt accggcatga gccaccgtgc ctggcccggt a                       1001

SEQ ID NO: 133          moltype = DNA  length = 2091
FEATURE                 Location/Qualifiers
source                  1..2091
                        mol_type = genomic DNA
                        organism = Homo sapiens
SEQUENCE: 133
gtaagtacca ttaacagctt ctcttgaact ggtttctcta aaaattcctc ctttaccttt  60
cttctaaagt gtcggatcct ttacctttca aaaacgagga ataggtctcg tggctcatgc  120
ctagcgagac ctcatctcca caaaaaataa taataaaaaa attagccagg tgtggtggtg  180
tgggcctgta gtcctagtta ctggggaggc tgaggtagga ggatcactta agcccaggag  240
gtcaaggtta tagtgagtta tgatcgtgcc actgcactgc agcctaggtg acagagcaag  300
accctgttcc ccaccctctg caaaaacaaa caaacaaaaa agcatcctga taaacataga  360
catgaaattg aaacatacag gtgaagggtc acagatttat gcctcagtct tctcatctgt  420
aagacaaaga cagcctcatc acttttaatg aggtgagrga atgagggagg agaccacccc  480
tcatattgtc ttatgcccga tttctgcctc caaagaaaga agaagtaaaa actaaaaagc  540
agaaatgaaa tccacaggca gacagcccgg cgccacgccc tgggcctggt agttaaagat  600
taacccctga cctaacactg gttatgttat ctatagtttc cagacattgt atggaaaagc  660
attgtaaaaa tccctgtcct gttctgttcc gttctgatta ctggtgcatg cagcccccaa  720
acatgcaccc cctgcttgct cagttgatca cgaccctctc atgtggaccc ccttagagtt  780
gtgagccctt aaaagggaca ggaattgctc actcagggag ctcggttctt gagacagaag  840
tcttgccgat gctccaggcc aaataaaccc cttccttctt taactcggtg tctgaggggt  900
tttgtctgcg gctcttcctg ctgcacatta agtgaggtac accactgcat attacatggc  960
aggtgctcag tctcctcctt ccacttcctc actggttttc tagtgaagag agaatgaagg  1020
ggtgggttgc ccctccacac ctgtgggtgt ttctcgtaag gtggaacgag agacttggaa  1080
aagaaaaaga cacagagaca aagtatagag aaagaaataa ggggacccgg gggaccagcg  1140
ttcagcatat ggaggatccc accagcctct gagttccctt agtatttatt gatcattcgt  1200
gggtgtttct ccgagagggg gatgtgtcag ggtcacaaga caattgtggg gagagggtca  1260
gcagacaaac acgtgaacaa aggtctttgc atcatagaca aggtaaagga ttaagtgctg  1320
tgcttttaga tatgcataca cataaacatc tcaatgcttt acaaagcagt attgctgccc  1380
gcatgtccca cctccagccc taacgcggtt tttccctatc tcagtagatg gaacgtacaa  1440
tcgggtttta taccgagaca ttccattgcc cagggacgga caggagacag atgccttgct  1500
cttgtctcaa ctgcaagagg catgccttcc tcttatacta atcctcctca gcacagaccc  1560
```

```
tttacaggtg tcgggctggg ggacggtcag gtctttccct tcccaagagg ccatatttca  1620
gactatcaca tggggagaaa ccttggacaa tacctggctt tcctaggcag aggtccctgc  1680
ggccttctgc agtgtttgtg tccctgggta cttgagatta gggagtggtg atgacgctta  1740
acgagcatgc tgccttcaag catctgttta acaaagcaca tcttgcaccg cccttaatcc  1800
atttaaccct gagtttgaca cagcacatgt ttcagagagc acggggtgg gagtaagttc  1860
atagattaac agaatctcaa ggcagaagaa tttgtcttag tacagaacaa aatggagtct  1920
cctatgtcta cttctttcta cacagacaca gtaacaatct gatctctctt gcttttcccc  1980
acagagaagg cccatgcaac acagacctaa accccttga gaggaaaata gggcatttgg  2040
tggaggggag gggaggagtc ctggcttgcg gctataaaaa tgtttttcca c           2091

SEQ ID NO: 134          moltype = DNA  length = 1001
FEATURE                 Location/Qualifiers
source                  1..1001
                        mol_type = genomic DNA
                        organism = Homo sapiens
SEQUENCE: 134
cctctttccc tgttttatta ttattttttct ccaatcgctt atcactatta ttttgtttat  60
ttaatgcttt attatccgct tccgccactg ccatgtaatc ttgagggcaa gggtctctca  120
tgttttcttc accgttatct gcagtgcctt gaacactaat actggttgaa tgaacgaacg  180
cattaatgga gcggtgatat tggggcagag aggatgcagg gcttgctttt caccgccatt  240
tttcagccgg cagagacaga ccgagaaagg aatgaaggcc acggggcgtg tgcagaagta  300
gctaccagag agtccatgcg ctgcgagcct ggaccagcgg gcaaacgcgg cttacaggcg  360
ttcacccaga tattacgggt acaacctagt ttcttatgaa atacctcgcc cctaaggtac  420
gcgcagggcc agtggcgcaa tggataacgc gtctgactac ggatcagaag attccaggtt  480
cgactcctgg ctggctcggt rtaagcaggg tcgttttaca actttctgac tccgcaggag  540
taaggaaatt cctgcaagat aaatttgcct ggaagactca gaagcaagag gggcagctcc  600
cgacaacata tggggttatc atttctttgc ggagcattct gccactgacc acgtggtaac  660
gccaactacg ccagagaaac gctcgcccta cccaagttgt gcccagcctt gcctggccat  720
tttggccgaa gaacgaagga ccgttcagag attaaattaa agtctctatt gtgttcttcc  780
ctattcagtc atttgtagaa taaattctat ggcttcagtt tgaacactgg aggggctggg  840
tctgagcttt tcattggttt ttctggtttg agaggtcggt acagagacgc acgcgcacat  900
cagcaaaaca cgcacttgga acgaagaaac acggaactag gcaggaagaa ctatttactc  960
tgaaaaataa gcccttagtg ggtttccgta gtgtagtggt t                      1001

SEQ ID NO: 135          moltype = DNA  length = 1001
FEATURE                 Location/Qualifiers
source                  1..1001
                        mol_type = genomic DNA
                        organism = Homo sapiens
SEQUENCE: 135
cgcggggaga ccccaatgga tttcaagtcc atcgccttaa ccactcggcc acgactacgt  60
acctccttca acaacctgga tatattccca tgaggaatat atgtttcttt tcacagacat  120
ctttaaattt gtttattttg acaaggtaac aactctggaa tgtctctcat cctggttaaa  180
aaacaaaatc aaaattttaa agatttagat attggctaaa agagatattg caaattgcaa  240
gacttgtctg atgtaggaag tacgaaagac tttacgaggg ggccacacgc caacccctaa  300
atggtctcca aacctacgaa actggctgaa agctctccac acctaattag taggattaca  360
gatattgaag cctacaaatg cgcatttcca ccaggatacc ttgtggattc ttacacgggt  420
caggtccgct gacgtttagc acgcctactt taaaacctct tttctgtagg gtcctagtct  480
tcaagtaaaa tatatgcggc ratatagcag aggatggttt cgatccatcg acctctgggt  540
tatgggccca gcacgcttcc gctgcgccac tctgctgtct cgacagtccg ctccgccact  600
ctgctgtttc aacattactc ttgtcaagta tgtattagag gctacaattt tcggcatctt  660
cctaatttta aatgatttgt tgtcgtttgc caaattatcc tggagaatga gaagtgcaca  720
ctggccatcc atatggggct gcacgccact tccaaacacc agcggtttag aattcttcct  780
cgataaattc gaatcagctg aggttgaagt tctctaaaac ggaagcatgt ttcgagttat  840
gggaaaacaa agtgcaggct aattggcata atttataaag gtgaaattat aaatgcttgg  900
gcaaatttca gccattcctg gataccggag ggagtcgtta ttacttccaa acatttttta  960
cttgagattt tcatcgaaaa tgttcacagg aaaaaaaaaa t                      1001

SEQ ID NO: 136          moltype = DNA  length = 1256
FEATURE                 Location/Qualifiers
source                  1..1256
                        mol_type = genomic DNA
                        organism = Homo sapiens
SEQUENCE: 136
ctgttaggct ttctccaaca gcagaaggct ctgtgatctc catctcttgg gaggcagaaa  60
attaccacaa gaaaatagcc gggaggcagc ggattgaacc ctggaaacgg cccgctcttt  120
gtgctgggcg gtgctcgaag ggaagaaact gagggcccgg gagtcgagtg tgtccagttg  180
tctgccaggc aggataagga ctgggaaaaa tgaaaaaaaa attcctagac atacacaacc  240
taccaagcct gaatcatgaa gacacagaaa atatgaacat accaatagta gataaggaaa  300
ttgaatcagc aataaaaaca tctcccatca aagaaaagcc caggacctgt agcgtctcta  360
gtgaattcta ccaactattt aaagaactaa taacatttat tatggaaaac agtattgtgg  420
ttcctcaaaa aattaaaaat agagatacca tatgatccag caaactctct agtgggtata  480
tagctaaagg aagtgaaatc agtatgtcca agagattatc tgcataccac caagatatgg  540
aattcttctt rttttttttt tttggtggca cagaatctct ctctgtcgcc cagggtgcga  600
ttttgactca ctgcaacctc tgtctcccgg gctcaaacga ttcttgtgcc tcagtctccc  660
gagtagctgg gattacaagc ctatgccaat ataccccgct gattttttt tttttttgta  720
tttttagtag ggcgcgttt tcaccatgtt gcccaggctg gtcttgaact tctgggctct  780
cctcggcctc ccaaagtgct gggattgcag gcgtgagcaa cggcgcccag ccaagatatg  840
gaattcttgt gttcaccaat ggatgaatgg atagagaaat gcgtttagct tccctgtgcc  900
```

```
ttggaagtat catttccaat ttatcatggg tgtgtacatt tttattggtg tacttgtgag  960
ctcatcacta atttttgcag tctgttaatc taccatagtt tcagtttcat tgtattttct  1020
tatatattta tattgtgtac tgatgtgtgc atggattagt aatgagtact ctattatttt  1080
taatgtcata attattcatt atttatttat tatttattaa aaataatatt taatattaaa  1140
tattatttat tacttatatt atttattatt ataataattt ataatatgtc acattataaa  1200
atattattta attaaaattt aatgtcactc tattatttta atatcataaa atacat      1256

SEQ ID NO: 137         moltype = DNA  length = 3934
FEATURE                Location/Qualifiers
source                 1..3934
                       mol_type = genomic DNA
                       organism = Homo sapiens
SEQUENCE: 137
ctaatagagt cctccctctg atcagtggca aagagtagcc attatcattt tttaatggta  60
ataatattta ttacttttta aacttatttt ttaatggtaa taacatttat attatactgg  120
gtgtctgtat attgagttgc cattccaaag gactatataa aaaatatata tctaaatgct  180
tgacaaaaaa aaaatgcaat ttttttggaa aggaatatat ttggtggctg cctcatgcag  240
cttaagtgtc caaaatctga tagattggtg tatcccagtg gtagttttct gttgccacaa  300
actccaatca gcaggaatgg gggttgtaac tcctgtacaa tagttctacc ttatccacag  360
ttctgttttc tgcagtttga gttgctcctg gtcaaccttg gtctgaaaat attaaatgaa  420
aaacttcaga aataaacatt tcatatgttt taagttgcaa ctgactctgg gtaggataat  480
gaaataccac cctgtccagg atatgaatca tccctttgtc ctgcttatcc aagctgtgta  540
tgctaactgc ccattagtca ttgacatcat ctgcccctga catccaacca cagacgttat  600
catggctcag tgatccagga tcacccaggc agatgatcct ccttctgatg tatcatgagg  660
tcaacagtag cctaacgttc catcacagtg cctacttcac tcatctcgct tcatctcacc  720
acttaggcat tttatcacct catcatcata agaagaaggg ggagtacagc acaagacgat  780
attttgagag agagacccca ttcacataac ttttattaca gtgtattgtt ataattgttc  840
tattttaagc tagtgttgtt aatctcttac tatgcttaat ttataaattc aactttacca  900
taggtatgtc tgtgataaac attgtatata tagtgtttga cacatccata gtttcaggca  960
tccactgagg gtcttggaac atgtccccca aggataagtg gggactactc tagtgccatc  1020
aggctagcag gctgtaaagg ttttaatggc agtccctgga ccatggctta tttaattgct  1080
tccaaggccc actgctacaa agggcctcat tcaaagctgg tggctttgtt ggtcaccctg  1140
acttagggga ccaaaagaac actcaggtgg ggtacatgtt gcctccaatg cccaagtacc  1200
caaagaggcc ttccagctgt tgggcctcct ttttattagt ggatgtctcc aaaattaaat  1260
ttttttgctt ggttgtatct agaatacttt tctggcttac tgcccatgtg gccttcgcat  1320
ttagcccagg gacagtccac tgttagtctc cacatccgaa agccttttttg actagccaaa  1380
ctgagctgtt acattatgac agggtagttt gtagcatttc catttgtaac aataattaac  1440
acaataatgt cctgttcttc agttagtatg cagtactgtt tttttgaata acccactggg  1500
acttgggtgg cttaggtggc agacaggcat ggatatgccc cgccgtaacg gctggaattc  1560
ttagctgtga gcgggcgcac ccctcaggca gtgatgatgt gctgagcccc aagcagccaa  1620
aatgtcaatg actataagac attcagccac aggaaccaaa gtcaccggca cctcaaatgg  1680
ccagaggcac ccccacagcag ataagcacca taggtcactg cttttgtccc caagcctctt  1740
aatgtcacca gtttaatttt tcccttaagg agacctggaa atattgtcac atgggttcca  1800
atatctaaga acaccagaaa aatatgaatt cctttttccc ccttttttatc ttttaaagga  1860
atattattaa ttttaaaagc agggaccatg ctaatcatct ctatatcatt ccaatttcag  1920
tatatgtgct gctgaagcaa gcatgtcttt ttttttttaa tttttaaatt ttaaatttta  1980
tgagcacata gtaagtggat atatttaata ggtacgtgag acattttggt acaggacgca  2040
atctgtaata atcacatcat ggaaaatggg gtatccatcc tttcaagcat ttatcctttg  2100
tgttaaaaac aatccaatta tactcttagt tattttaaaa tgtacaatta agatattatt  2160
gactatagtc ttcctgttgt gctgtcaaac attaggtctt tttcattctt ctgttttttt  2220
ttgttttttt ttttgttttt ttcttttttc agatggagtt ttgctcttgt tgccctggct  2280
ggagtgcaat ggcatggtct cggctcactg caacctgcgc ctcccgggtt caagtgattc  2340
tcctgtctca gcctcctgag tagctgggat tataggcaca caccaccatg cctggctaac  2400
ttttgtattt ttagaagaga cagggtttca ccatgttggc caggctgatc ttcaactact  2460
gacctcaggt gatccacccg cctcagcctc tcaaagtatt gggattacag gcacgagcca  2520
ccacatccgg cccttttttca ttaaccatcc ccacctcctc tcccgcttcc tcccacttcc  2580
actacccttc caagcctctg gtaaccatcc ttatattctc ttatctccat gagttcaatt  2640
gttttgattt ttagatcctg caaataactg agaacatcca aagtttgtct ttctgttcct  2700
ggcttattat aagaactcct gttttatctt gacaggaata tagagtgact gacctccagt  2760
ggggaggaaa ccagagaccg tggccccatt cccaactggg ccattcagcc tgagacattt  2820
ggatttgata gaacctcttt gatagaacca tggcttattg atgaagtgga aggagtgata  2880
cccgaagtac ccagcccacg gtgtagacat caacctacag gggtgcggaa gctggacaca  2940
ccacccagcc tgcacaagat ttagctggct attctccatt tttattcttt ggataatgag  3000
tttctgctct gtaaatgccc ttatgaactg tgtttggttc cctctcagat gcctcaggga  3060
ccaccagagg acctcttcct cttccctctc agggttctca gggatcaact gagtatccat  3120
ttcctgagtt ctctagctct cgggaatgaa caaccataca agtgtccaac aatcagaggg  3180
tggcttgcca ctgtcctatt ctatatttct ttctctctgc cccagtcagt gcagccagct  3240
cactcatatc cgcagggttg ggggtgacct atgtcctgtt tacaaaaaga gtcaaactgt  3300
aaaacatttg aagagattta ttctcagcca aatatgagtg accaatggcc tgtgacacag  3360
ccctcaggag atcctgaaaa catgtgccca aggtgatcgg ggcacagcca ggttttatag  3420
agtttaggga ggcatgagac atcaatcaaa cacatgtaaa aaattcattg gttgggtctg  3480
gaaaggcagg acaactcgaa gctgagaaag ggtggtgggg tgagggtgtg gcttcctggt  3540
tataggtaga tttaaaattt tgtgattggc aactggttga aagagttatt atcaatagga  3600
aggaatgtct gggttataat gataaggggt tgtggagaac aaagctttat tatgcagatg  3660
aagccttcag gtagcaggct tcagagagaa tagattgtaa atatttcttg tcagacttga  3720
ggtatgtgtt gatgttaatg ctggtcagct tttcctgaaa gccaaacttg agtggggtat  3780
aattggccct tctttcctgt catgacctga accagataat caggtaaact ttggaatgcc  3840
ctggccaaga ggaaaggtcc attcagatgg tgagaaggcc ttcaaatttt attgttggct  3900
tataatctca cctctcattc ttccttttat aaat                              3934
```

```
SEQ ID NO: 138         moltype = DNA  length = 2457
FEATURE                Location/Qualifiers
source                 1..2457
                       mol_type = genomic DNA
                       organism = Homo sapiens
SEQUENCE: 138
ttcacattat cctctaagcc atttccagat tgactgtaga tctgaatata aaagtaagca  60
aacaaagctt gtagaataca acatcgggga atatctttat gactttgacc caaggaaata  120
ttttctagac ttgatgctaa aagcgttagt cataaagggc aatccttccc gtctagatct  180
tcaagtcctt cagttctgag aatttttctt atatttcttg gtaaaattat cctccatttt  240
tcctttgtct tgctggaact cccagtaatg agatgatatt gaatctctgg aatgggttgt  300
tcaattttct ttccactact attttccatc tttgatgttt tcctactgtt tttgaagtag  360
ttctaaactg taacttccaa atttttcatt aaatgttttt cttttcccct gctactttat  420
tctttatttc taggagatct tgtttcatta tcataaaaag atagtacccc aagttactat  480
ttccaggtga gatgaagtgt gttttacatt ttttctccta tcaaacacaa ctataagtta  540
tgggcagaat gcatgaaata actatttgaa gactctgata ataaaagagt aaacaaaaga  600
gtgtaaggat ggaaaaagaa caccagaatt atcctatatg ttctccccaa attgagtata  660
gatgtaatgc aattgctatc aaaattccag tagaattttt tggagataga gaaaagctga  720
ttctaaactt tatatggata gatgaaagaa ttagaatagc taaatcaatt ttgaaaaaat  780
gcagtgaata atcacattac ctgattttca gatttaatac caacttcagt aatcaagata  840
gtaargtatt ggcagaaata taaacatgta gatcaattga tcagaacaga gattccagaa  900
ataaatttac acaaatatgg cgaattgatt tttgacaaag gtgcaaataa aataaatgaa  960
gaaattaaaa ttgttcaaca aataatattg ggacaatggg ctatccatat gcaaaggaaa  1020
gaaagaaagg agagaaaagg agagaaagaa aggaaggaaa aaaagtaagg aaggcgtgga  1080
agaaagaagt gaaggaaaag tggaaggaag aaagaaaaga tatcctaaca taaatctaac  1140
aatttataca aaaattaact aaaaaattga tcatatatgc aaatgtaaac ataaaactat  1200
aaaactgtta aaagaaaaca taacagaata tccacatgac cttgagttgg gtgatgagtt  1260
cttagatatg gcactttcca aaaaagaaaa aaaaatacat tggacttaat caacttttaa  1320
cacatttgct ctgcaaaaga aactgttaag acattgaaaa aaataaagac tggcagaaaa  1380
tatttgtaag tcatgtatct gatagagaaa ttttatctag aatatataaa gaatccttaa  1440
aactcagcaa taagaaaaca acccaataaa aattgggtaa aggcataaac actttaccaa  1500
acagagtata aggatggcaa ataagcacac aaaaaatgtt tgacatcatt agccattatg  1560
aaatgcaact tttttttca caattgcccc aaactggaaa caaatgtcac acaacacaaa  1620
tgtccttcaa tgagtggata aactgtggta catccgtgca atggaattct attcaagagc  1680
aaaaaggaat gaaattttga tatttgtaac aacttgggaa aatcttcatt tatttctttt  1740
ttttgagacg gtgtcttgct ctgtagccca ggttggagtg cagcagcgcg atttaggctc  1800
actgcaagct ccgcctcccg ggttcgcgcc attttcctgg ctcagccttc cgagtagctg  1860
ggactacagg cgcccgccac cacgcccggc taattttttg tatttttagt agagacaggg  1920
tttcatcgtg ttagccagga tggtctcgat ctcctgacct cgtgatccgt cctcctcggc  1980
ctcccaaggt gctgggatta caggcgtgag ccaccgctcc cagccaactt gggtaaatct  2040
taaggcatta tgctaagcaa aagaagctga tctcaaaaag ttacatactg tatgattcca  2100
tttctacatt ttccaaaagg ccaaaatata caaatggaaa gagtatttat gattgtcagc  2160
tgctatgtgt gggattagga tgagactata aaggaacagt gctagggagg cttatggact  2220
gatagaactg gtgtgtatcc tgatatggta atgggtatgt gtatatacat gtaagtgctt  2280
tttaaaagtc aattttactt aatacttttt aaaaatacag atagctccca tttgtggcat  2340
agactgtacc ttctccatgg tttctgtgag aaacactttc accgagctct tgaaagagtt  2400
tattttgagc agggtttgga ggagagaaaa cccggtgaga ccctggagca ctgcacg     2457

SEQ ID NO: 139         moltype = DNA  length = 3772
FEATURE                Location/Qualifiers
source                 1..3772
                       mol_type = genomic DNA
                       organism = Homo sapiens
SEQUENCE: 139
aatcgtacat gaatatgtat taatttagca aatatttact gatttctcca ctctttagaa  60
tgcaataatt agttgttatt ctatgtctgg tagttgctga tgagatattg ttatgtggaa  120
aaaacagaat ccaaaacagt tttgcaagat tatgattttt agtttaaaaa aaactgtatt  180
atgggatgat ttatatatga tarcgtgtac aatttgatgt tttggcatat ttatacatac  240
atgtaacaac taccacaatc aaagtagaga acatttccat gatcctaaaa agttcccttg  300
tggcctgtga tagtgaaacc tgtgaatatg ttatctttca cagcaaaagg aactttgcag  360
ctgtgattaa attaaggatt atgaaatgag gtgattatcc acaattacct ggattgggcg  420
ttgtaatcac aaggatcctt ttaagaggga tcattgtcag agaaggagat gtgacagtgg  480
aagcaaaagt tggaatgatg aggccgggcg cggtggctca tgcctataat cccagcactt  540
tgggaggctg aggtgggcag attgcctgag ctcaggagtt tgagaccagc accaccaaca  600
tggtgaaacc tcatctctac taaaaataca aaaattagcc agtaatcctg actaaatgct  660
cctgtaatcc tcgctactca ggaggctgag tcaggagaat tgcttgaacc cgggaggcgg  720
aggtcgcaat gagcagagat tgtgccactg cactccagct tgggcgacag agtgagacgc  780
cgtcttaaaa aaagaaaaaa agttggagtg ctgcagggcg atgagccaag taatgccagc  840
agcctcttct agctggcgaa ggcaaggaaa cagattctcc tctagagctt acagaaggaa  900
gatagccctg ctgactcact ctagacccct gacatccaga gctgtgagat aataaatttg  960
tgttgtttta agctattaag tttgtggtaa tttttcacag cagtaatagg aaactaatgc  1020
atgccctttc ccagtcagtc acactccgac cacacaattt ccagtcaact ataggccctt  1080
tccatcatga tggttttgcc ttttctggaa tttaatctaa atggattaaa ttatatgcta  1140
tgtactctag ttcctggttt ttgctcagaa catttttgag attcattcat gttgttgcac  1200
atatcagtaa tttattccat ttattagcac tttattggta aaatgtattc tatttgtaca  1260
gacatgccac aatttgtttt tccattcatg tgtgggtgaa cattttttatt attttcacat  1320
tctagctatt ataaataggg ctgctgtgca aatttgtgta acaagtcttt gtgtagacat  1380
atataagcca gagttcttca gaaacagaaa accaatagtg tgtgtgtgtg tgtgtgtgtg  1440
```

```
tgtgtgcgtg tgtgtgtgta gacagtgatt ttaaggaatg gacttacatg attgtagagt  1500
ctggccagtt cagattctgc acggtatgcc agcaggctgg aaacccagga aaaagttaat  1560
gtggcagcta aaactcaaag gctgtctgct ggcaaaagtc cctcttccta gggagagaag  1620
ttagtctttt ttctcttaag tatttttcaa ctgataggaa gcaatctgct ttactcaaag  1680
tgtactgaat taaatgttaa tctcatccag aagtaccttc acatcaacgt ctaaactagt  1740
gttcgatcaa atatctgaat actatgagct agccatgttg acacgaaaaa ttaaccattg  1800
catatgtttt cacttctttt ccaggaaata cctaggaatg gaattgctgg tcatttagta  1860
agtgggtgtt taactttata agaagctacc agtgtttttcc aaagtggtgg ttcactttac  1920
attccaaaaa gcattatatg agagttccag ttgtacaacc tcctcagcat ttgttattgt  1980
cagacttaat gtttatgcaa agatatccta tgacatcttt gcctatttca taatcatgat  2040
tttctcctat atttccttct cagagattta taaattagca cttttgttta ggcctatgat  2100
ctattttcag ttaatttttt tatgtattct aaaataagga tcaaagttaa ttttttttcca  2160
tatggctatc tccttgtttc tgcaccattt ttgaaaagac tatcctttcc tcataaagta  2220
cataggcact tttgttgaaa gtaaatttat tatacatgta catctatttt tggagtccct  2280
attttattcc attaatctat atgactttcc taattatact ttaatttgca ggccagttag  2340
gatggctatt atcaaaaacc agaaaataaa ttggtaagga tttattggta aggaacttta  2400
tgtattgctg gtggaaatga aaagcagagc agccactgtg gaaaacagta agattcctca  2460
aaattttctt ttcttttttt tttttgaca gagtcttgct ctgtccccca ggctggagtg  2520
caaggcgcga tctcagctca ctgcaacctc cgcctcctga gttgaagcaa ttctcctgcc  2580
tcagcctcct gagtagctgg gactacaggc gcacgccgcc atacctggct aatttttttc  2640
gtattttagt agagaccagg tttcattgtg ttgcccaggc tggtcgcaaa ctcctgagct  2700
caggcaatct gcccaccttg gcctcccaaa gtgctgggat tacaggcatg agccactgca  2760
ccctgccaat cctcaaacta ttaaatgtag aattaccata tgatccagca attccatttt  2820
tgcatatata tccaaaataa attaaaacac gggctcagat tcatagcagt gttattcaca  2880
atagccaaat atccatcaac agattaatgg ataaacaaaa tgtggtatac acacaatgga  2940
atattattca gccttgaaag gaaattctgg ctgggcacag tggctcatgc ctataatccc  3000
agcattgtgg gaggcccagg tgggtggatc acctgaggtc aggagttcaa gaccagcctc  3060
accaacatgg cgaaaccccg tctctactaa aaatacaaaa ttagcggggt gtggtggctc  3120
atgcctgtaa tcccagccgg aggctgaagc aggagaatcg cttggaccca ggaggcggag  3180
gttgcagtga gccaagataa caccattgca ttgcactcca gcctgggcaa caagagcaaa  3240
actcagtctc aagaaaaaaa aaaaaaggaa attctgacac atgctaaaac atgaatgaac  3300
cttgaagaca ttatgctaag tgaaataaac caatcacaaa aagatgaata ttttatattc  3360
catttatata acgtaccaaa gtagtacaat ttatagagag ataaagtgga atggtggttt  3420
ccaggggact agaaagaggc aaggatgtgg agttagtgtt taataagtac agtttcactt  3480
ggaaaagatg gaaaagttct ggagacaaat ggtgataatg gttgtacaac aatgtaaatg  3540
tacttaatgc cacagaactg agcacttaaa aatggctaag atggtaaatt ttatattatg  3600
gttgcttaca taataaaata attacacacc agagacctat gacatatgta ttagccacat  3660
ttttaaaaat gataaaagtg taacacctta ttagagactg actcaggtac ctacagcaag  3720
taataggtgg agttgtcagt agcctctcaa actcaggtgt ttgatggtcc ct          3772
```

```
SEQ ID NO: 140          moltype = DNA  length = 1001
FEATURE                 Location/Qualifiers
source                  1..1001
                        mol_type = genomic DNA
                        organism = Homo sapiens
SEQUENCE: 140
ttttggaagg tgacgagtgt attttgtgag agagactggg gtcataggtg gacagaggtc  60
ctatctggta ggcagcctct aagatgaccc ccaataatct ctacctcctg gtattcttgc  120
cctggtgtag ttccctatgt accaggggtg gtctttgtgt ctaatgtaag tgatagataa  180
gctctagagg gaagccagtt actatgtcac cagcagtcct gtttagtagc ctatttgggg  240
agggagtgag ccttcctgcc aacacccact agggagattg gaagaagatc ctccagacac  300
agtcaagcct tacgatgact agagccctag cctggcatct tgattgcaac cccaggagga  360
accctaagct ggaactaccc aaatacaaca ctttgatttt caagttacag acacagtaag  420
ataataaatg tgttgtttta aaccactaca tttggagtta tttgttacag caattgataa  480
gcaatacaaa tctcaaataa rttaagttta taacttaagg ctccctggac tattcaggaa  540
atgcacttcc aggatgccga tctactgtag gtcacctttg tggctttgat ttatcaagat  600
gaagatattt tctacttctt ttctttactt ggtgcattcc taagtgacaa gactactttt  660
cgggcagttc actagggatg atagttgagt tttctctcta gattattatt aatctgcatg  720
tatgacactg aggacgtgta gagtggttct ccattttcag caggtcctag tgacttcggt  780
tttcctcaat ttagaagctg ccaaagcata agcccaaatt tgcctccatg agcaagagct  840
ctaaaagcat aagcaactgg ttgttgtggt gctctgctta tctgtgttct catttccttt  900
tacatttgtt ttacatgtct cttaggtttc tttaatgttt tatcacttca ttgtctaaaa  960
caaaccttta aagaattgat ttagaacata ttttaataaa a                      1001
```

```
SEQ ID NO: 141          moltype = DNA  length = 1001
FEATURE                 Location/Qualifiers
source                  1..1001
                        mol_type = genomic DNA
                        organism = Homo sapiens
SEQUENCE: 141
caggtacttg ggaggctgag gtgggaggat cacttgagcc tgggaggcag agatttcagt  60
gagccaagaa tgcatcattg cactccagcc tgagcaacag agccagaccc tgcctcaaaa  120
agaaaatata tatgtatatt agtttgataa actccaatat aacttttttta cataaaattg  180
attttttaag tttataaata taaatattta aatatgatat ttaaatccaa ttttgctgga  240
aagcctaaac acaatgtgga agctattgac ttgtcccatt atcaatctta catactatta  300
taaaataaat gatataccat tatagcttct cccaactatc caaatgctta tgggttaggt  360
gtgaaaccta caagatgaag caaatgaggc tttatctagg ggtgacagtt ttatggaaag  420
aaatgagtat cagggaaggc tacacaatgc aaaaacaaaa ttctgtgagg acttgaaccc  480
aaggcatttt gcttaccaga raagtaagtt gaatgacaaa gcaacaattc cctgtcataa  540
```

```
aagttaattt atttgctatt acagtataga cattttaaaa cacaccagaa gaattttaga  600
gtttgaaaat gacaagttgc attttgtttt gagcaggaaa catatcaaga caaacttcct  660
tcatactaga cagtattgta atcccagcga ctcaggaggc ccaagcagga ggaccacttc  720
aggccaggaa tttgagatta gcctaggaaa catagcgaga cctcgtctct aagaaaataa  780
attagtcatt gtagtagcac acacctgtag ttctagctac ttggaaggct gaggtaggag  840
gatgacttga gcccaggagt ttgaggctgc agtgaaccat gatcacgcca ctgcactcca  900
gcctgggtga tagatcgaga ccccatttct gggagggtgg gaaaaccaga cattgacaag  960
gcctgagcag aggaggctgc caactgtaga aattgcaagt t                      1001

SEQ ID NO: 142         moltype = DNA  length = 1001
FEATURE                Location/Qualifiers
source                 1..1001
                       mol_type = genomic DNA
                       organism = Homo sapiens
SEQUENCE: 142
tatgtaatac tatacatatt tttaaaagaa tgaagaaaac ttgtctattc tgatatggaa  60
agtttgcaaa agtacattgt aagtaaaaat ttaaaaaggc aagggactta aaaagtgtat  120
aaaatgccac tattcatgaa gagaaaaaag aaaacacttg tgtaactttg tctatgtatt  180
caaaatctct ggaacgataa acaagacatt aaaaacaatg gtaaagcttt tgggaaacaa  240
tggctgagta gacaacgatt gggtttaacg gcccctggaa tggtgactag aaccacattt  300
ctagcatttt tcaataccaa ggtcttcgaa gcgacctttg atttgaggtc actttaggaa  360
tctgaaggaa cacataggaa gactcccaaa ttgaggatct agacataaga aacctgggac  420
gatctcgatc atgggaccat cgagaatcag actcgttggg aatatccttc aagtaccaat  480
ttgtatgttg tattagtgag rggcttttac gaagcaaaga ctcattaata tttcaccgaa  540
tctgattcat tgtctgcatg tattgactag acattcagaa ggcagcaaat atttccataa  600
attgctgggc cattagccac agtttgaaat gtttaagcgt cctctttcaa gtctacgaat  660
acagccattt tgctttgttt ttgcgttaag aggaaatttc tcgttatttc tattaagact  720
ctaaagcaac taagaaattg ttcctccctg taagacaaac aggaattacg ttgaagaatt  780
taatactttc acggagaagg ggcgaggatg cgggtgagat gaataacaaa agcacagatt  840
tgcggtcggc cggttagctc agttggttag agcgtgctgc tactaatgcc agggtcgagg  900
tttcgatccc cgtacgggcc tttggctttt tccccccctcg agaaatttgg ttttcatgct  960
ctaagatgat tcaaattaac cgtccccatt tcttaacgaa c                      1001

SEQ ID NO: 143         moltype = DNA  length = 1001
FEATURE                Location/Qualifiers
source                 1..1001
                       mol_type = genomic DNA
                       organism = Homo sapiens
SEQUENCE: 143
cgagaccggg tagatatact cccttgggtt ggtgtgagcc tagagactta gggacctcat  60
cagagcaaga aagtgcaagt aggcttttct gcatcatttt ctggccctcc agttcagaca  120
caaatcaaaa gttagtccct tcttgaaagc cattagcatt catcaaggag cctcaatgag  180
aggaagtttc aaacaaaaac taaatgtgtc aggcccagat ttacggtgag ggtctgattc  240
cacttccttg cggggtcagt ttgggtccag gtgagagagg tacagtggtc tctagttttc  300
tggaaacggt actgctgata gggcaaggac tccttgcggc tgccccagag aggttggctt  360
gtcttatcca acttgcactt cacgttagag tttctaatga actcgcagac tccagtttct  420
tgcccaggaa accattttta ccgtattttg ttcttttgac cgtttcttgt cagttagctg  480
gtgtaaattc tgtttaaaga hgtgaaggga gccttctcca ttcgtgtagt cgtggccgag  540
tggttaaggc gatggactag aaatccattg gggtctcccc gcgcaggttc gaatcctgcc  600
gactacggga tgttttactg agaacagttc agcgaggaaa taggatctca catttgcttt  660
cagtttggga gtaaagaaac tcgtgataga gcctctgcgt gtcacctaac atagcctgaa  720
cttttgccga cttcgggatg ttttactgag aacagttcag agaggaaata cgatgtcata  780
tttgctttca gtttgggagt aaaggaactc gtaatagagc ttctgcgtgc cacttaacgc  840
agcctgaact tttgccgact tcgggatgtt ttactgagaa cagagaggaa tcgtatttac  900
ttcagagagg aaatacgatg tcatatttgc tttcagtttg gggcgaggg aactcgtgat  960
aaagcttctg cgtgccactt gacgcatcct gaactttaaa a                      1001

SEQ ID NO: 144         moltype = DNA  length = 1001
FEATURE                Location/Qualifiers
source                 1..1001
                       mol_type = genomic DNA
                       organism = Homo sapiens
SEQUENCE: 144
cgaatccgag tcacggcagt accttgatgt cgcctcaatt tctcaacgta ctgagcagta  60
ccttgacgtc gcctcaattt ttcaacatac tggagtggag acagtctcgg aaaaaccctt  120
gcaaaattga attgacttac gatctaatct gtacacaaaa aacactagta ttcatcatgg  180
tgccccaacc agtcagccaa gcagagagtg tctacgcttg ttgccttgtc tttttttcc  240
cctctccaaa gattctcttc ccaaccctac ccaagcccta cagtcttgtt ggcattggct  300
gtatgtgaag aaactgaggt aattttttt taatggaaaa cttttacttt caaacactgg  360
taggcatgag gaaaggactg ttcaaaaggg gatccaggtt tgttgtggag atctttctta  420
aaacacaaaa gacaaattat taatcacgcg tttctaagta tcctagctgg accaatgctg  480
aaaaactgta acctttgatc rtctggagaa aattaaagaa atttgagtaa ttgaaggaat  540
ttgggtgggg gggaataatg gcccagaaga acagccccca tttctagccc gttcagtttc  600
tagaatgagt tctaaagagc caagtagact gggtgaggcg ggagtggagg agagctgatc  660
tgagatacgg aggtggctgg aaagaagtag ttggtgctac ctaggaccag taggaggtgg  720
ctggagacag gcagatcccc agaggcgctt ccatgagccc agttctagtt agtagcacag  780
cactctgaga acacattaat ggcacttcgt ccctcctggc cctggtggaa ggttagtatt  840
caaacaggtg tggtggctca tgcctataat cccagcactt tgggaggccg aggcgggcag  900
atcacctgag gtcgggagtt cgagaccagc atggccaaca tggtgaaacc ccgtctctac  960
```

```
taaaaataca aaaattagct tggcatagtg gcataggcct g                    1001

SEQ ID NO: 145         moltype = DNA  length = 2290
FEATURE                Location/Qualifiers
source                 1..2290
                       mol_type = genomic DNA
                       organism = Homo sapiens
SEQUENCE: 145
gagggagaga aataacgtga tttctctcac atgaactcag gggccaactt tggatagaac  60
tgaaagctgt acctgagaaa caaagagaaa tattccttcc tccttcattt tatactattt  120
ccagcaccaa aaccttttct tctctctgcc tgcccccttc cacacaaact gtccaactcc  180
attctcattt ccccactgag gtggatgctg tggtgccctg ccctggtcac tccgtgttgg  240
actgagacac acaatcaacc agctgcagag agtgttggtg gctcagggcc ctcagctgac  300
tccataccat gaattgttaa agagccaaag agagccctgt mgcccaaggt tattccacct  360
ctcagtgagt ggaccacatc caatgactgg aaaacatagg tgtaaaggtc ctggacccct  420
tgcacaaggt acacaactct gaagggtcac cccagttcca gagttcattg tgagactgca  480
ttatatttca acttttcctt ctgtctatcc tctttcctta acttcctcaa ggtattgatg  540
ctgcggggct ctccagtgga tgtcctatag tctatttctc tggaaccacc aaagacaggg  600
attcttaaaa gtgtggtctg accctaagat tctttcaggg gatccatgag gtgaagactt  660
tttttttttt ttttttttga gatggagtct cactctgtca cccaggctgg agtgcagtgg  720
tacgatctca gctcactgca acctctgcct cctgggttca agctattctc ctgtctcagc  780
ttcccgagta gccaccactc ctgcctaatt tttatatttt tagtagagat ggagtttcac  840
catattggtc aagctggtct caaactcctg acctcaggtg atccacccat ctctgcctcc  900
caaagtgctg agattacagg tgtgagccac cgcacctggc caagacaatg tttataatga  960
tactaaaatg ttatttgtgg ctgggcatgg tggctcatgc ctgtaatccc aacgctttgg  1020
gagaccaagg caggcagatc acttgatgcc agaagtttga gacctgcctg ggcaacatgg  1080
tgaaaccctg atctctacaa aaaatacata aaattatctg ggcatggtgg tgagttcctg  1140
tagtcccagc tactcaggag gctgatgtgg gaggatcacc tgagcctcgg aagtcgagga  1200
tgcagtgagc catgatcacg cctctacact ccagcttggg tgacagagtg agaactctgt  1260
ttcaaaaaaa aaagaagcga gaggatcact tgagcccagg aattcaagac cagcctggac  1320
aacatagtga gacccccatc tctattttta aaaataaata aataaatttt ttttaagtta  1380
tttgcctctt ttactcacat actctcacat gtgtgcattg gagttttcca gatgttgaag  1440
acatgatgac atcatccctc tgacacctat tggaatgtat gtcacaatgt gtattattgt  1500
gtttaaaatg ctgtgtttta agggccgggc atggtggctc acacctgtaa tcccagcact  1560
cagggaggcc gaggcaagcc gatcacttga gcccaggagt cagacctggc caacatggtg  1620
aaaccttgtc tctatgaaaa ataaaaaaat tagccagaca tggtggtgca tgcctgtaat  1680
cccagctact aggaaactga ggcaggagaa tcacttgaat ttgggaggcg gaggttgcag  1740
tgagccgaga ttgtaccact acactccagc cagggcaaca gagcgagact ctcatttaaa  1800
aaaaaaaaaa aaacctgttt tatttattta tttgagacag ggtctcaatc attcgcctag  1860
gctggagagt agtggtgcca tctagactca ctgcaacctt cacctcccag gctcaagtga  1920
tgttcctgcc tcagcctccc acgtagctga aattacaggt gcatgccacc acacatagct  1980
aatttttgta tttttttgta gagacaaggt ctcactatgt tgcccaggct tgtctcgaac  2040
tcctgagctc aagcgatcca cccaccttgg cctcccaacg tgctggagtt acagatgtgc  2100
accaccacac ccagcccagt tttaattttt aaatgctaag tgttgataga tataactcac  2160
ataaataaaa actctctggg attctcaatt attttcaaga gtataagaag gtcatgagac  2220
caaaacatct gagaattgct gctctaagat aaccaaatct accctgggag gaaaaggctg  2280
aggttttaaa                                                        2290

SEQ ID NO: 146         moltype = DNA  length = 1001
FEATURE                Location/Qualifiers
source                 1..1001
                       mol_type = genomic DNA
                       organism = Homo sapiens
SEQUENCE: 146
gaaacaaata cacatgaaaa tacagtatgg cacaaataag gagcaagagg tgaagaaagc  60
ttcagtcaca cccaaaataa ttttgtgaaa aatataaaat atgcagttat agacagcact  120
aactctggat accagaaaat tctataattc ggtaatggat ctgagacctg aattttggag  180
gtactaaaat agatgcaata gatctagttt tcattatgtt catactttca tttggctctg  240
tggtaaaaga tgataatatc caaaacaaaa gatgataata tcctccatgt aacaattaca  300
tgcaagggga tgtctgcaaa ctgccacagt atcattttaa ttaataccta tcttctcttc  360
ttaaaatctt ttcattttc cactcagttc tcctgatatt tctgttatga tataaaagac  420
agctgaatgt gaagaaacac tgattgtaca cgtaacacac acattaatga ttcaaatatg  480
taaacacaga gagctgcaaa ractttgaga ggtagggctg aaacttttcg tcaatgtgta  540
caattcaata tcgtttcagt tttcattcta accgtcccca gtggcttctg cccagcaact  600
gatgagaaat ggtacctctg agccaatcaa aacacgaatt cctacaaaga ggattctctt  660
agtgtttctc ggaccgagtg tacagcacat gctttctttt cctttattct ggatcagaga  720
atcttaacta aagcagaaat aattgtgtta aattaaacta aatttggtat gagatatgta  780
tacatttagc ctgagggatg gctcttgagc ccttaaataa tgaactgcaa cctaacttag  840
tatgtaaact aactgaaagc ttaaggcatg ggagtatact tttgtaacaa atagctgagt  900
ctcagccaat cccagtagcc gaacttcagt cggcggcagt caaccctgca gccaagtgat  960
cagactatgt tcaaataagg ccaactctga gctgtaacca a                    1001

SEQ ID NO: 147         moltype = DNA  length = 1001
FEATURE                Location/Qualifiers
source                 1..1001
                       mol_type = genomic DNA
                       organism = Homo sapiens
SEQUENCE: 147
gagtttctct tggtctgtgt gggagaagat ggagatcaca gctggagggg gaagacaagg  60
```

```
ggttagatgg aaaatgggtg cctcttggga ataggcagct tgctagcttg cttagctact  120
taatctgtga ggttatttcc cggctttcaa aagatgggtt attttggtgt cctgggacat  180
ggacaactgc aatctcttcc ggcagctgaa gattttctag cacttgcata attaattcct  240
tgtgggccaa atcttggccc ttactattga tgaggcctcg ttcagtccag atcttttccg  300
aaggcatact tggagtaagt gtaaatagtt ccttcctgat tctgcaggga ttttaaggct  360
tggtttaatg caaagagttc acatatttgg gcagaccact tatttggcag tctttctgac  420
tctaccactg tgagggtttc cctatcaact atggagtacc cgttgtgcct ttttccttca  480
atgacctggg aggagccgtc rataaagagg tgatgccctg tttggaaggg ggtttcatgc  540
ctggatgcgg tctgactcta gtttgaaaac tgattagatc taagcagtta tgctcacatt  600
cctcctggtt tggatttcct gttaggaaag cagcggggtt gagtgaattg tcagtggtta  660
gtgttaggtt atctccctct aataagatag cttcatattt taaaatcctt gagtcagtga  720
gccatctccc tgccttctga ttaagaatgg ttctgacttg atgaggggca cttacgaaga  780
ggtttccccc aaaggttatt ttcctgcttt cttctgttag caaggcagtt gctgctatgg  840
attgaacaca ttcgggccat ccacgggtta ctgggtcaag gatttttgac agaaagacta  900
caggctgccg gtggcctcca tgtttttggg tgagtacccc taaggccact cctttgctta  960
cattaatgaa aagatggaat ggctgttcta aggagggcaa a                       1001

SEQ ID NO: 148          moltype = DNA  length = 501
FEATURE                 Location/Qualifiers
source                  1..501
                        mol_type = genomic DNA
                        organism = Homo sapiens
SEQUENCE: 148
ctccagtgca acctatgggg cttttggaaa tgaggaagtc gatgactctg cagggactcc  60
tctgacccag gagcagatgg cgctcgtctg ggcactcccc aggagaaaag gtgcatcggg  120
aagcagcctg gcttgtggat ggtaataagt cactgttgat gggttgggtg cagggaggga  180
tttaagttct tgagcgacag atgctaggga gtttacctgc tctggataac agtatcttgt  240
ggaggatagt racctggaaa acagaaatgg cgtgactgtg ttgaatacac tgtttgatga  300
ttctgggcat caggtgaata ggaaatgtgt aacgttatgg atgagtgtgt gctcatcgga  360
cagtagcagt gcatcttaac agtcggcctc tcagtcctcc tcttccttag aatcacctat  420
agagctttaa aatttcctgg ataatgttaa tgtgcagcca gcgatgatga ccattgggct  480
acagtcaaat ccaagaggcg c                                             501

SEQ ID NO: 149          moltype = DNA  length = 1001
FEATURE                 Location/Qualifiers
source                  1..1001
                        mol_type = genomic DNA
                        organism = Homo sapiens
SEQUENCE: 149
cccacctcgg cctcccaaag tactgggatt acgggcatga gccaccatgc ctgtcctaca  60
tatatcttat tcattgtctt attcaatcat acaacttcct gataaaatga ggctgatttt  120
cacccctatt ttgctgttaa ggaaactggt ataatgagtg tcactgactt gtttgtgatc  180
acacagtgga caaaatggca tttgtttctt tgtggtgatc tcacaaaggt caagatgacc  240
ttagatcctc agttttggct gttttttttt tgttgttttt ttgtttgttt gtttgtttta  300
caccaaggaa ccaggttcta gctcctatgt ttgttcattg catggaaagg aacaggaaga  360
tctgggggcc actgaatgga aggttagatc cattttcttg gttaagcttg taggttttct  420
cgtctctttt ccttcctgca gcacaattct tatgaatggc aatatcttct attaaaattc  480
tcagtctgta gtcttcttgt rcatacagaa aatagatttc aggtcaacac atttgatagt  540
ctggactgtg ctaactgctc caatatttga gtacatcttt tggggatgtg ggaatttagt  600
gttgtaggcc tcaagtgggg ttcgttccca gaatttggag aggctataga aatataacct  660
ggttggccag gcacggtgac tcatgcctgt aaccccatca atgtgggagg ccgaggcagg  720
tggatcacct gaggtcagga gttcgggacc agcctggcca acatggagaa accctgtctc  780
tactaaaaac ttttaaaaaa ttaggcgggc gtggtggtac gtgcctgtaa tcccagctac  840
ttgggaggct gaagtaggag aatcccttga acccgggagg tggaggttgc agtgagctga  900
gatcacacca ttgcactcca gggcaacaga gtgagactcc atctcaaaaa aaaaaaaaaa  960
agaaaaagaa atataacctg gccataatat aagcataaat a                       1001

SEQ ID NO: 150          moltype = DNA  length = 1181
FEATURE                 Location/Qualifiers
source                  1..1181
                        mol_type = genomic DNA
                        organism = Homo sapiens
SEQUENCE: 150
gaggtcctgg ctgagccaag gagtaatgga ccagatctac ctcagtattc aagttcagtg  60
gggacaccag tggcttcaaa cttcctggtt tcatgatatc ttgagacgcc ttacaaatga  120
tggaggattc caaagagttt ttgtttattt gggttaatat ttgttggtat ttatggcatt  180
tgagattgaa actaagaaat gttttaattt attaccttta caacatttat ttacattaca  240
tacatacatt tacaacattt attaatttat attaaaatag catgaataag ccaattatag  300
gttaatataa gtagaatgtt tgtgaaaaat aagtatggta tccaaagcaa aataaatttt  360
attgtgaagt gtggcattga ttvacttttt ccagatctaa tgtgtggctt gaaagaatat  420
gactggattc tcatatctgc ctttatactc actctgttga gatatcatag actatatagg  480
ctcaagaaaa ctttatccta gtgacagaat gagattaaaa acaacaaact gtgttttatt  540
attaatatga aaatacgatt attaaccttg caggcccctt aaaacagttc tggttaactg  600
agaccttgtc tctaccaaaa acaaacaaaa aaaattaggt gtggtagcgc acgcctgtag  660
tccctgcttc aggagactaa aaagactaac tccaactcct tgcttgagcc aggagttgga  720
gtttgcaatg agctgtgatc ctgccattgc actccagcct aggcaacaga gtgagactct  780
gcctcaaaaa accaaaacac aggtcgggca cggtggctca cgcctgtaat cccagcactt  840
taggaagccg aggtgggtgg atcacctgag gtcaggagtt caagaccagc ctggtcaaca  900
tggcaaaacc ccatctcact aaaaatacaa aaattagcca ggcatggtgg cgggcaccta  960
```

```
taatcccagc tactcaggag gctgagacag ggaatccttg aaccccagtg gggtggaggt  1020
tgcagtgagc caagatcgtg ctgcttcact ccagcctggg tgaaagagtg aaactcccgt  1080
ctcaaacaaa gagggggagg gaacttatgt cagagacccc ccccacccca ccccaggaat  1140
cctgaaacca tatttgagag ttgggataga ggattcggga a                      1181

SEQ ID NO: 151          moltype = DNA  length = 1205
FEATURE                 Location/Qualifiers
source                  1..1205
                        mol_type = genomic DNA
                        organism = Homo sapiens
SEQUENCE: 151
ttatgggaag aatcaggaac atatatttaa atacctgatt tgttaaggca gaaaacaggg  60
ttgtttatgt gcatgtttta gtctgcccag acagctatga caaatatacc aagactgagt  120
cgtttataaa caaccaaaat tttttttctt gcactctggg ggctgggaaa tgtaagacca  180
aggcaccagc agtttggtaa ctggtaagag cctgcatcct tgttcacagc cttttaaatg  240
tgtcctcata tggcaaagga gaaaagtaga tctttggttt ttgtcccaag aaactggaaa  300
gatgggccgg gcacggtggc tcacgcccgt catcccagca ctttgggagg ccaaggcagg  360
tggatcactt aaggtgagga gttcgtgaac agcctggcca acatggtaaa accctgtctg  420
tactaaaacc cagaaggtgg aggttgcagt gcaccactgc actctagcct gagtggcaga  480
gtgagactct caaaaaagaa aagagagaga aggaaggaag gaaaggaagg aaggaaggaa  540
ggaaggaaaa gtaactggaa agatgaagtt gttaatttct gagatgggga aacggagaga  600
caaggagcaa gacgggagtg gtacagaacc aaaggttcag ttgtggatac attaaggttg  660
aggagtctat attagagatg cacatggaga tgcagagtag tccattgaat aaccaagagt  720
ccaggtgaga cctcaaggct ggagrtagag attccatact caactttcct atatgtttga  780
agagtttcat gatacactgt agtgggtaga gggaagaatt gtattttgtt attaataaca  840
gtcctgaata tcattggctt tgacaaaatg aggacttctt ttcatgtcaa taaatatgga  900
tggtggccat caagggctga tctgagagct tgaaatgtca tacatgcccc agcttagttc  960
tgtctttatt ttcttctgtc ttagcatgtg gcttgcatct tcaatgttgc ctcatggtca  1020
caaaagggct gcccagctcc aaagtccata ttctagataa gaggaagtag aaagtaaggg  1080
gagtgtaagg gtctaccagc tgttttagcc tcccottaaa taatctgtct gataaacttc  1140
caccctcaag caattggctc aaacttagtc ccttggcttc ccctgtctac aaatgagatg  1200
gacac                                                              1205

SEQ ID NO: 152          moltype = DNA  length = 1001
FEATURE                 Location/Qualifiers
source                  1..1001
                        mol_type = genomic DNA
                        organism = Homo sapiens
SEQUENCE: 152
cttgtcagat cccagccccc tggttgagat tttcctggac tatgaagcag gaggcatctc  60
cttctacaac atgagtgaca gaacccctta tctatgcttt ccccaaaggc tctttctctg  120
gctcccttca gcctttattc ttcttgtggt catgcgataa aaagcccctg accacctgcc  180
caattgttga tggactttca ggaggtcaca gtcttgtgaa gcctggggcc taaggagatt  240
ctgttgtcca gaattcagaa aattctgcct ccagaaatac aaatatgctc ttttctaaac  300
aagtgacaac acaatgtagc cataggctcc cttaagcagc cacctcatgt caactaatag  360
tctttgctct ctagcctctc tcctccaaag tccatttcgt ctcctgaggc ttcagctatt  420
actgtcagac cctcagttac ttctgatgaa cagggattag gcttgagaaa atggagatgc  480
atttagattg gcagatatgg rggacttctt aatgtgcttt tattgctgcc ttatctctga  540
aaacaggttc tgggagtttg ggaataagtc tgagggcata taaaggattg agactgagtg  600
acttaggagt gtgagaggaa atatcttgat gttgagaaca gggttgatgt ggaggggtat  660
tctctgtgtt atgcatgtaa aaagaaaaaa aggaaaaaaa aatcattact gggaaagaaa  720
acaccccaag ctgaagtcca agaaaggtac acagaggaaa cacagaaaca gttgtgttag  780
cagaagatga catgaaaccc agctgacagt gaaattagga agttgccttg gaatttcaag  840
aacttgcatt ctcaagttta tggttctgtg tccaacagag cagcaaaatc cagcacttct  900
tcttttgagt ctccatatcg tgctaacaga aagacaaggg gtcgggagat gcagagatga  960
ggaggagctc aagagtgaca gtgttgaaga gattctgagc a                      1001

SEQ ID NO: 153          moltype = DNA  length = 3934
FEATURE                 Location/Qualifiers
source                  1..3934
                        mol_type = genomic DNA
                        organism = Homo sapiens
SEQUENCE: 153
atatagtgtt tgacacatcc atagtttcag gcatccactg agggtcttgg aacatgtccc  60
ccaaggataa gtggggacta ctctagtgcc atcaggctag caggctgtaa aggttttaat  120
ggcagtccct ggaccatggc ttatttaatt gcttccaagg cccactgcta caaagggcct  180
cattcaaagc tggtggcttt gttggtcacc ctgacttagg ggaccaaaag aacactcagg  240
tggggtacat gttgcctcca atgcccaagt acccaaagag gccttccagc tgttgggcct  300
cctttttatt agtggatgtc tccaaaatta aattttttg cttggttgta tctagaatac  360
ttttctggct tactgcccat gtggccttcg catttagccc agggacagtc cactgttagt  420
ctccacatcc gaaagccttt ttgactagcc aaactgagct gttacattat gacagggtag  480
tttgtagcat ttccatttgt aacaataatt aacacaataa tgtcctgttc ttcagttagt  540
atgcagtact gttttttga ataacccact gggacttggg tggcttaggt ggcagacagg  600
catggatatg ccccgccgta acggctggaa ttcttagctg tgagcgggcg cacccctcag  660
gcagtgatga tgtgctgagc cccaagcagc caaaatgtca atgactataa gacattcagc  720
cacaggaacc aaagtcaccg gcacctcaaa tggccagagg caccccacag cagataagca  780
ccataggtca ctgcttttgt ccccaagcct cttaatgtca ccagtttaat ttttccctta  840
aggagacctg gaaatattgt cacatgggtt ccaatatcta agaacaccag aaaaatatga  900
attccttttt ccccctttt atcttttaaa ggaatattat taattttaaa agcagggacc  960
```

```
atgctaatca tctctatatc attccaattt cagtatatgt gctgctgaag caagcatgtc  1020
tttttttttt taatttttaa attttaaatt ttatgagcac atagtaagtg gatatattta  1080
ataggtacgt gagacatttt ggtacaggac gcaatctgta ataatcacat catggaaaat  1140
ggggtatcca tcctttcaag catttatcct ttgtgttaaa aacaatccaa ttatactctt  1200
agttatttta aaatgtacaa ttaagatatt attgactata gtcttcctgt tgtgctgtca  1260
aacattaggt ctttttcatt cttctgtttt tttttgtttt ttttttgtt tttttctttt  1320
ttcagatgga gttttgctct tgttgccctg gctggagtgc aatggcatgg tctcggctca  1380
ctgcaacctg cgcctcccgg gttcaagtga ttctcctgtc tcagcctcct gagtagctgg  1440
gattataggc acacaccacc atgcctggct aacttttgta tttttagaag agacagggtt  1500
tcaccatgtt ggccaggctg atcttcaact actgacctca ggtgatccac ccgcctcagc  1560
ctctcaaagt attgggatta caggcacgag ccaccacatc cggccctttt tcattaacca  1620
tccccacctc ctctcccgct tcctcccact tccactaccc ttccaagcct ctggtaacca  1680
tccttatatt ctcttatctc catgagttca attgttttga tttttagatc ctgcaaataa  1740
ctgagaacat ccaaagtttg tctttctgtt cctggcttat tataagaact cctgttttat  1800
cttgacagga atatagagtg actgacctcc agtggggagg aaaccagaga ccgtggcccc  1860
attcccaact gggccattca gcctgagaca tttggatttg atagaacctc tttgatagaa  1920
ccatggctta ttgatgaagt ggaaggagtg atacccgaag tacccagccc acggtgtaga  1980
catcaaccta caggggtgcr gaagctggac acaccaccca gcctgcacaa gatttagctg  2040
gctattctcc atttttattc tttggataat gagtttctgc tctgtaaatg cccttatgaa  2100
ctgtgtttgg ttccctctca gatgcctcag ggaccaccag aggacctctt cctcttccct  2160
ctcagggttc tcagggatca actgagtatc catttcctga gttctctagc tctcgggaat  2220
gaacaaccat acaagtgtcc aacaatcaga gggtggcttg ccactgtcct attctatatt  2280
tctttctctc tgccccagtc agtgcagcca gctcactcat atccgcaggg ttgggggtga  2340
cctatgtcct gtttacaaaa agagtcaaac tgtaaaacat ttgaagagat ttattctcag  2400
ccaaatatga gtgaccaatg gcctgtgaca cagccctcag gagatcctga aaacatgtgc  2460
ccaaggtgat cggggcacag ccaggtttta tagagtttag ggaggcatga gacatcaatc  2520
aaacacatgt aaaaaattca ttggttgggt ctggaaaggc aggacaactc gaagctgaga  2580
aagggtggtg gggtgagggt gtggcttcct ggttataggt agatttaaaa ttttgtgatt  2640
ggcaactggt tgaaagagtt attatcaata ggaaggaatg tctgggttat aatgataagg  2700
ggttgtggag aacaaagctt tattatgcag atgaagcctt caggtagcag gcttcagaga  2760
gaatagattg taaatatttc ttgtcagact tgaggtatgt gttgatgtta atgctggtca  2820
gcttttcctg aaagccaaac ttgagtgggg tataattggc ccttctttcc tgtcatgacc  2880
tgaaccagat aatcaggtaa actttggaat gccctggcca agaggaaagg tccattcaga  2940
tggtgagaag gccttcaaat tttattgttg gcttataatc tcacctctca ttcttccttt  3000
tataaatcat ctggctgctt gtccagctcc tgcacacctc taggttgatg tctacaccct  3060
gggctgggta cttcggggta tcattccttc cacttcatca ataagccatg gttctatcaa  3120
agagggccct gctcacttca ccaattttgt gaaccagatt caccatgcac tggtgaattt  3180
tgtgaacctg cctgagcctg gtgagacaga agacactcac atgcaacaag ttacatgaag  3240
caaatgtatt acttacagat aggaagcaag agacaacaga agactagaat tcattatgtg  3300
ccagtttccc aaggcttatg aaagctgcct tgggtggatg gagcttcaat tgcacatggc  3360
ctactgttgt tgcagctgag gggccccaaa agcagcttac cccaggctca gtacctcagg  3420
ggccacagga atcactgggt aaatctcatc ctactttcag ggagagagga acaaggctct  3480
ggttgtccta gcagttcctc cttaattcaa tatgttacat tctttaggag agccaggagc  3540
caggcccagg ctgtttcagg cagttcctcc ctgcctcagg atatgggcat tcccacacac  3600
tctacagttg ttcttcagac tacaagcaag aaatggagga gaactgggtc agtgcctggc  3660
cacttggaga acagttctgc agaaagaagt cacacctgtg aaaactgcct gccaagagga  3720
aacaactaca ttgacatgta tgtgagcaag aaatcaattg ctatttggtt aagccattga  3780
aactttctat ttttctttct tttttttttt cttttttttg agaaagggta tcactgtagc  3840
tcaggttgta gtacagtggc atgttaatgg cttactgcag ccttgacctc ccagatccaa  3900
gcaatccttt tgagtatcta gaaccacagg tgca                              3934

SEQ ID NO: 154          moltype = DNA  length = 1181
FEATURE                 Location/Qualifiers
source                  1..1181
                        mol_type = genomic DNA
                        organism = Homo sapiens
SEQUENCE: 154
gaggtcctgg ctgagccaag gagtaatgga ccagatctac ctcagtattc aagttcagtg  60
gggacaccag tggcttcaaa cttcctggtt tcatgatatc ttgagacgcc ttacaaatga  120
tggaggattc caaagagttt ttgtttattt gggttaatat ttgttggtat ttatggcatt  180
tgagattgaa actaagaaat gttttaattt attaccttta caacatttat ttacattaca  240
tacatacatt tacaacattt attaatttat attaaaatag catgaataag ccaattatag  300
gttaatataa gtagaatgtt tgtgaaaaat aagtatggta tccaaagcaa aataaatttt  360
attgtgaagt gtgrcattga ttaacttttt ccagatctaa tgtgtggctt gaaagaatat  420
gactggattc tcatatctgc ctttatactc actctgttga gatatcatag actatatagg  480
ctcaagaaaa ctttatccta gtgacagaat gagattaaaa acaacaaact gtgttttatt  540
attaatatga aaatacgatt attaaccttg caggcccctt aaaacagttc tggttaactg  600
agaccttgtc tctaccaaaa acaaacaaaa aaaattaggt gtggtagcgc acgcctgtag  660
tccctgcttc aggagactaa aaagactaac tccaactcct tgcttgagcc aggagttgga  720
gtttgcaatg agctgtgatc ctgccattgc actccagcct aggcaacaga gtgagactct  780
gcctcaaaaa accaaaacac aggtcgggca cggtggctca cgcctgtaat cccagcactt  840
taggaagccg aggtgggtgg atcacctgag gtcaggagtt caagaccagc ctggtcaaca  900
tggcaaaacc ccatctcact aaaaatacaa aaattagcca ggcatggtgg cgggcaccta  960
taatcccagc tactcaggag gctgagacag ggaatccttg aaccccagtg ggtggaggt  1020
tgcagtgagc caagatcgtg ctgcttcact ccagcctggg tgaaagagtg aaactcccgt  1080
ctcaaacaaa gagggggagg gaacttatgt cagagacccc ccccacccca ccccaggaat  1140
cctgaaacca tatttgagag ttgggataga ggattcggga a                      1181

SEQ ID NO: 155          moltype = DNA  length = 3934
```

```
FEATURE                 Location/Qualifiers
source                  1..3934
                        mol_type = genomic DNA
                        organism = Homo sapiens
SEQUENCE: 155
agacgtttac ctggagttgg tcctttttag ccgccagaaa gatacaggga ttaaaaacac  60
aaattgtaaa ttgagtgata atatttctta caaaggtaac attaaaactg tgttgagtcc  120
tattactatt attggatagt gtcctgaccc agatgctgcc attcataaat gggagtgcta  180
acttccatat cgactgctga attgggcccc tctttccttg atgacgccgc tgaggcaaag  240
gcggactaaa gcctgttccg tgccaagcca gttgcgtggc agattaggat tgaatcccaa  300
tgcgatatag cgaagaaatg ttaaatgttc accaccagtg gcagcgaagt ttgttccatg  360
aggtctgatt ctcatctctc ccaaatgacc acagggaccc cagtcaataa tgtctcccat  420
taacatagac ttgtctagct aaggggtcaa gacactggat ccaaggaggg gggtgagaat  480
tattgaaggg agcccattct gtataatcaa tacaatttgg acgatggggc tgggagagat  540
tagtaaatcc accagtaata ttattagagc taaggcctaa taggtacata atgtttccat  600
ggtgactcaa ccatgcctgg gattggactg caaggcaact gccattgagc gatgtatcct  660
tggtgatgca taaagggagt ccctccaatg gggcagtgta attgatacta ttgttctgac  720
agtctaatag ttctgtgtca gggggagtta ggggtcctgg ggtccatgct ccctgatcac  780
gatatacctc aggaggagtg tcactccaga gtacaggtcg cactactcag gggttaggaa  840
catatgcccg acatgttttt gcttctacac aggggaaaca taccacacag gacactacag  900
ctagtatggc caagaacatt gattcagggg tttttgcctg accctggcac tccagcattt  960
tctcagcttc ctgcatggtt ttcttgatct gtccccatgt tatgagggtg gatgtcaatg  1020
tgactccagt cggccccttgt tccatctttg cattcagatt caactggcct atggcttgta  1080
ctgggggaac cgggcccatg gttgcgatcc acggatccct ccagtctccc gttccatggt  1140
tgcacgtacc tggagggcac ctacacagtt tgtccatctc ctgtaaaaac acaagcatac  1200
cctcatcccc acatcagcaa atccactggg cctttccttt gtccttcttc tggggatttc  1260
cataacacct ttggataaac ttgcctcttt ccctctaaca cttgccaatg ttgttctgct  1320
agagtcttac catccatacc aggcatcaaa aaatttaaag taaacaagac taaatgtaat  1380
tttgtttaag gtggtagctg gtctcctatt ccccctttt ttctcaacat acgctgtagt  1440
gtttgatgtg cccgctctat aatgccttgt ccttggggat tgtaaggaat tcctgtttta  1500
tgaatgattg cccataactg taaaaaattt tgaaaagcat gactaacata agcaggtcca  1560
ttgtcagttt ttaattgttt agagaccccc atatgggcaa atgacgacaa acaatgccat  1620
tggacatggc cagcagtttc ccctgtttga catgtggcat gtaacatatt ggagtaggtg  1680
tctatagtca catgaacata gctaagtttg ccaaaggctg ctgtatgtgc aacatccatc  1740
tgccagattt catttggagc caagcctcgt gggtcgcatc cttccacggg tgcaacacca  1800
gggacatgct gacaagtgga gcaggcttgc acaatagctt gagcttgact gcaaggcaga  1860
tgaaacatat gagtaagggc agaggtgttt tgatgcagta atgcatggga agcttgggct  1920
tgttggaata cagaaccaat taatttatct gctttatcat taccttgaga tagtggtcca  1980
ggaagttgcg tatgagagcr aataggagca gcacaagaga gaatagcttg ctgaagtctt  2040
agaaacaaat taagcagctc tggttctagg gtgcccttaa tagtggcagt ctcaatgcaa  2100
ctagctgcat ttacaacata ggctgaatca caaacaatat taataggaga taaagccgtg  2160
agctctaaaa cctgaataac tgcgattaac tctgagcatt gagctgaaac tccagagatc  2220
tttattgttt gagtatgttt agttgcataa atagctgtgc ggcctttgta agagccattg  2280
gtaaaatatg tctttccacc tggaatgggc ttgtgatggg taattacagg gaggataaaa  2340
gggtgaactt tataaaattg caaaatcttg tctgatggat aatggttatc tattattccc  2400
acaaaatctg caaaagcaat ttgccatgca gtcgacattt cccatgctgc ggcctgttgt  2460
tgggaatcca agggaacaat aattttatca ggatcatatc ccgtaagcat tttttacctg  2520
tgcctaccta ttgttataag ttgagtaatt aaagaaagat aaacttgcaa agatttcact  2580
gtcagattga ataaaaaaaa aaaaagcctt tatattacca ttacagattt gtctatgaat  2640
tggcctaaaa atcctgatgg agaatggggg gtaggaagaa taaacaaaag caaaggcttt  2700
tgtggctgta gccgggaggc atgttgttgc tgaaggatct gttctacacg ctgtcactca  2760
gcttctgcct cgttagtaag ttgccgagga gaatctaatg aagaatctct ttggagggtt  2820
tgataaaggt gtgtgagttg gtagatggca atacctagca tcaggcacag ccaattgata  2880
tcccctaata attgttggaa gtcattcaga gtttgtaccc tctccctaca gagagttact  2940
ttctgaggcc gaacacttct tccagtaaca atagtaccta agtactggta tggggaggtt  3000
gtttgcacct tttcaggagc tattttgaga ttccatgcag tcaagactca ttttatttcc  3060
ctgaataact gatgtaacat ttgatctgta ggagcggcca aaagaatatc atccatataa  3120
tgaatgatgt aggcattggg aaatatattg cgaggctcct ttaaagcttt tcctacaaaa  3180
tgctgacata acataggact gttgagcatg ccttgggcta aaactttcca ctgagagcga  3240
gagacaggct ctctttgatt aatagaaggc acagagaagg caaattgagg cttatccttt  3300
ttgtgtaatg gtatattaaa aaaaaaactc tttaagacct attactacaa gagtccaatc  3360
tcttggaatg gctgctgagg atgacagacc ttgctgtaat gcacccactg gtttaatctg  3420
tgcatttaat agctctcaaa tcatgtagca gttgccattt tcctgacatt tttggatcac  3480
aaatacaggt gaattccagg ggctgactat tctgtatgtt ctgcttccag ttgctctctc  3540
actagctgat ggagttgcat cagtttctcc tgtgataggg gccattgatc cacccacaca  3600
ggtttgtcag tcagccactc tagcggcaaa gcagtgggtg gaggagaaat accaatgacc  3660
cccaccaaaa atcctgatga cctagccctt ttctgttttg tccagttatt gatattggat  3720
cagggtttcc ctgcaggggc tttcctaagc cttttccact ctgaatccca ttttctttaa  3780
cattttaaat cctggattat caatagtttc ctttttaagt ctcatgtccc atgctgtcag  3840
taaatctcgg ccccatagat taacagctat atttgcaaca taaggttgaa aagtacatga  3900
ctgtccatgt ggtctgagac aggataaaat ctca                              3934

SEQ ID NO: 156          moltype = DNA  length = 3639
FEATURE                 Location/Qualifiers
source                  1..3639
                        mol_type = genomic DNA
                        organism = Homo sapiens
SEQUENCE: 156
agttagtatg cagtactgtt tttttgaata acccactggg acttgggtgg cttaggtggc  60
```

```
agacaggcat ggatatgccc cgccgtaacg gctggaattc ttagctgtga gcgggcgcac  120
ccctcaggca gtgatgatgt gctgagcccc aagcagccaa aatgtcaatg actataagac  180
attcagccac aggaaccaaa gtcaccggca cctcaaatgg ccagaggcac ccccacagcag  240
ataagcacca taggtcactg cttttgtccc caagcctctt aatgtcacca gtttaatttt  300
tcccttaagg agacctggaa atattgtcac atgggttcca atatctaaga acaccagaaa  360
aatatgaatt cctttttccc ccttttttatc ttttaaagga atattattaa ttttaaaagc  420
agggaccatg ctaatcatct ctatatcatt ccaatttcag tatatgtgct gctgaagcaa  480
gcatgtcttt tttttttttaa tttttaaatt ttaaatttta tgagcacata gtaagtggat  540
atatttaata ggtacgtgag acattttggt acaggacgca atctgtaata atcacatcat  600
ggaaaatggg gtatccatcc tttcaagcat ttatcctttg tgttaaaaac aatccaatta  660
tactcttagt tattttaaaa tgtacaatta agatattatt gactatagtc ttcctgttgt  720
gctgtcaaac attaggtctt tttcattctt ctgtttttttt ttgtttttttt ttttgttttt  780
ttcttttttc agatggagtt ttgctcttgt tgccctggct ggagtgcaat ggcatggtct  840
cggctcactg caacctgcgc ctcccgggtt caagtgattc tcctgtctca gcctcctgag  900
tagctgggat tataggcaca caccaccatg cctggctaac ttttgtattt ttagaagaga  960
cagggtttca ccatgttggc caggctgatc ttcaactact gacctcaggt gatccacccg  1020
cctcagcctc tcaaagtatt gggattacag gcacgagcca ccacatccgg ccctttttca  1080
ttaaccatcc ccacctcctc tcccgcttcc tcccacttcc actacccttc caagcctctg  1140
gtaaccatcc ttatattctc ttatctccat gagttcaatt gttttgattt ttagatcctg  1200
caaataactg agaacatcca aagtttgtct ttctgttcct ggcttattat aagaactcct  1260
gttttatctt gacaggaata tagagtgact gacctccagt ggggaggaaa ccagagaccg  1320
tggccccatt cccaactggg ccattcagcc tgagacattt ggatttgata gaacctcttt  1380
gatagaacca tggcttattg atgaagtgga aggagtgata cccgaagtac ccagccccacg  1440
gtgtagacat caacctacag gggtgcggaa gctggacaca ccacccagcc tgcacaagat  1500
ttagctggct attctccatt tttattcttt ggataatgag tttctgctct gtaaatgccc  1560
ttatgaactg tgtttggttc cctctcagat gcctcaggga ccaccagagg acctcttcct  1620
cttccctctc agggttctca gggatcaact gagtatccat ttcctgagtt ctctagctct  1680
cgggaatgaa caaccataca agtgtccaac aatcagaggg tggcttgcca ctgtcctatt  1740
ctatatttct ttctctctgc cccagtcagt gcagccagct cactcatatc cgcagggttg  1800
ggggtgacct atgtcctgtt tacaaaaaga gtcaaactgt aaaacatttg aagagattta  1860
ttctcagcca aatatgagtg accaatggcc tgtgacacag ccctcaggag atcctgaaaa  1920
catgtgccca aggtgatcgg ggcacagcca ggttttatag agtttaggga ggcatgagac  1980
atcaatcaaa cacatgtaam aaattcattg gttgggtctg gaaaggcagg acaactcgaa  2040
gctgagaaag ggtggtgggg tgagggtgtg gcttcctggt tataggtaga tttaaaattt  2100
tgtgattggc aactggttga aagagttatt atcaatagga aggaatgtct gggttataat  2160
gataaggggt tgtggagaac aaagctttat tatgcagatg aagccttcag gtagcaggct  2220
tcagagagaa tagattgtaa atatttcttg tcagacttga ggtatgtgtt gatgttaatg  2280
ctggtcagct tttcctgaaa gccaaacttg agtggggtat aattggccct tctttcctgt  2340
catgacctga accagataat caggtaaact ttggaatgcc ctggccaaga ggaaaggtcc  2400
attcagatgg tgagaaggcc ttcaaatttt attgttggct tataatctca cctctcattc  2460
ttccttttat aaatcatctg gctgcttgtc cagctcctgc acacctctag gttgatgtct  2520
acaccctggg ctgggtactt cggggtatca ttccttccac ttcatcaata agccatggtt  2580
ctatcaaaga gggccctgct cacttcacca attttgtgaa ccagattcac catgcactgg  2640
tgaattttgt gaacctgcct gagcctggtg agacagaaga cactcacatg caacaagtta  2700
catgaagcaa atgtattact tacagatagg aagcaagaga caacagaaga ctagaattca  2760
ttatgtgcca gtttcccaag gcttatgaaa gctgccttgg gtggatggag cttcaattgc  2820
acatggccta ctgttgttgc agctgagggg ccccaaaagc agcttacccc aggctcagta  2880
cctcaggggc cacaggaatc actgggtaaa tctcatccta ctttcaggga gagaggaaca  2940
aggctctggt tgtcctagca gttcctcctt aattcaatat gttacattct ttaggagagc  3000
caggagccag gcccaggctg tttcaggcag ttcctccctg cctcaggata tgggcattcc  3060
cacacactct acagttgttc ttcagactac aagcaagaaa tggaggagaa ctgggtcagt  3120
gcctggccac ttggagaaca gttctgcaga aagaagtcac acctgtgaaa actgcctgcc  3180
aagaggaaac aactacattg acatgtatgt gagcaagaaa tcaattgcta tttggttaag  3240
ccattgaaac tttctatttt tctttctttt ttttttttctt tttttgaga aagggtatca  3300
ctgtagctca ggttgtagta cagtggcatg ttaatggctt actgcagcct tgacctccca  3360
gatccaagca atccttttga gtatctagaa ccacaggtgc acactaccat gcccagctaa  3420
attttaaact ctctaaagag acagggtctc cctatgtggc ccaggcttgt ctcaaacttt  3480
taggctcagg tgatccttcc acctctcgac atcccatagt gctgggatta caggagtgag  3540
ccgtcttccc tggcctgaaa cttttacata tatttgttac agcagttgac actactctaa  3600
gcaggatata taccttgcat gttcaataaa gaatatata                        3639
```

```
SEQ ID NO: 157         moltype = DNA  length = 1001
FEATURE                Location/Qualifiers
source                 1..1001
                       mol_type = genomic DNA
                       organism = Homo sapiens
SEQUENCE: 157
tatataatta ttgggagtct ctgtgagcct actctgactc agaaagccgc tcctaaagaa  60
gaaaaaagaa caaacaaaca aataaaaaac ccgaattatt tttaaaactc tttattttgg  120
atttttcagt ttctacattt tgttactgta gattttacta gattgaacag ccttatccat  180
aaatatttgc atcaatctct aaatttttttt cttcaacact aacttttata gttggaattt  240
tgggggcaaa taatacaaca ttttaaaggc acttgccatg tgtacatggc caaatgcttc  300
cagaaacatt tccacttcca ttagcaaagt atataactac agagtattta aggttttatt  360
cctttatatt tttttctttg gcaaaattgt ctatagtaga aagaatgaat aataaataac  420
ctaaaaaata aaagttctcc ctctgaggac agcagagaaa tttttagctt agcttaataa  480
tacctccttc tccttaggag mataaagagc agtttcgagg agcagaagat gtggtgaaat  540
ataatgttta gtctgatggt ggatgcaaga tccaggcagg ggtggagcat gaccagctgc  600
acagacctct gttcccttgc ttcctctaca tctctcccca cctccatctg cagaccttgt  660
tctcagaggc cattcccaga cccacagcag ctggtatgat ggctgcaggc ctcatgctcc  720
```

```
tttgttttgg gagaaactgt tgaggagtta gtatttactg agcagctaat atgttccagt  780
cactattatt cctcataata attagttatt aactaataca tgaaaatttt aaacttaaag  840
cattccaata attttaaaag taaaggaagc aaaaggccaa agcgtccttt cactcactta  900
acctccaatt ttcagtttag catccatcat tttagacttt ttcaggcatt tacatatata  960
gttatgcaga aatgtatagc tttgcttttg tttttcaatt g                     1001

SEQ ID NO: 158          moltype = DNA  length = 1001
FEATURE                 Location/Qualifiers
source                  1..1001
                        mol_type = genomic DNA
                        organism = Homo sapiens
SEQUENCE: 158
ttaaaagtaa aggaagcaaa aggccaaagc gtcctttcac tcacttaacc tccaattttc  60
agtttagcat ccatcatttt agactttttc aggcatttac atatatagtt atgcagaaat  120
gtatagcttt gcttttgttt ttcaattgaa tcattagtat agttctgcaa ggtgcttttt  180
aatcacttag tatatctcca ttatccaggc tagtgacatt aaatcactct ttttaactgc  240
tgcattgaat ttcctcctag ggatgagcca tcattcctct aaccagtctc ttgtgagtgg  300
ctggttcagt tggtaaccac ttttatactt taaaaatagt gctgcagtgt cattccccaca 360
gaggcttctc tctgcaccca tgcgagtact tcgctgaagt aaccatcagg aagtggaatt  420
gctgggccaa ttgtgaacat tctaagtctc atactcgata tttttgagta actaaagttg  480
aaatggtttt gtcccatgac rgagatcatc aagcttgtga cttgtagagc ctttacctat  540
tgtctaccct ctttgtgttc ctaactctac catagtgggt ccagcccatt gtgggtgctc  600
agtaaatatt tgttgaataa ctttatgaag ggaagaaaga aaagatgagt aaagcctggt  660
cttattcaaa gctctcctaa tcaatatctt tgtgattaaa cgtggtgggt tcagcccctg  720
actgacttca gagcctctgc caggcagtct gcctggatcc caccaggagc caccaggcca  780
taagttgact gtagtaatgg ccaagagttt gacgcttgag gagtccatag tgttggacac  840
ccacagagct gaacaagggt gggaccaggg aatccagtga agagggtcct tcatgaatca  900
gagggggatg atggaagctt ggacctggca agggaagtgt ggggaagtga taggattatg  960
aatattttaa tattttaatg cagtagagtc agagatgtcc t                     1001

SEQ ID NO: 159          moltype = DNA  length = 1263
FEATURE                 Location/Qualifiers
source                  1..1263
                        mol_type = genomic DNA
                        organism = Homo sapiens
SEQUENCE: 159
agaactcctt tcctctggcc accagagata taagcgaagt gaaggacgag ggataggaag  60
cataagaaac catctcttca gtgactggta cacagtcatt ttggtttagt tgtgtaacag  120
atggcttctg ttgtgtctcc aagtgcacac taccatgggt cctgggaggt ggaatagtga  180
ctgtatctgc tgccagtgtt rtccaactag ccatccccag gaatactcct gtagtagaac  240
tagctgtatt tcttacgtgt tgcagtgagg aagaacacac atcatgggga gctgtggcgg  300
ggtctcagta agaaggtgtt agagcagact tggtatacaa tttgggcttg tgttagggga  360
ttggggccgg gggagttcat agacttagcc ctctgctctg gatgagattc catcaggaag  420
gtgtgggcag gttaattctg agtgagagcc ttaatcaatc ttatgtagga agaaggagac  480
cagggtgaga caaaagctgt aattgatgaa ggggcagcaa tccctcattg ctgagggggg  540
atgtttggtc actgctgtgg tttggacaat gttcatgttt ttctctatgc tcacatatga  600
tgtggggtgg tattgttttt cccatgatcc atcatagtca caaagtgcca ttgtctgtgt  660
tctgtgaaat tgcttatgtt caacaggatg acacagagac ccggtgtcag tttccatatg  720
ttgggacagc ttttctcttt ctcagtgcaa tcccttgccc tgtggctgct ggttaggttt  780
ggtttaaggg gatctctagc agacaatcat aggaggaaga gaaaaggaag aagtctgggt  840
gcttattcac tggcttcctt actgcaagtt accctcaggc tggctgcatt gccttgctga  900
aggtaacagc tcctctaaag gaagtcctca atgcatgaat ctcttctttt ttgtgttcaa  960
aacagcttcc tctcctcctc cctctggtaa ttggggtggg tgggaatagc cccactgttt  1020
ctgaccctgg gatactgcac tagcaaattt agttttcccc tcatcatgac cacacttttg  1080
taaacagctc ctgaatgaaa tatctcttga attatcaaat ctgagcctga cattgattcc  1140
cattgagacc ctccctaata caggagctat ccagaattta ggccaaatta tccttccaca  1200
gcactgggtt ctaatcttca cgtcgaagtg aagggttatg aggatggagg gatccatctg  1260
gag                                                               1263

SEQ ID NO: 160          moltype = DNA  length = 1001
FEATURE                 Location/Qualifiers
source                  1..1001
                        mol_type = genomic DNA
                        organism = Homo sapiens
SEQUENCE: 160
tacacttcaa aaggaagagg gaagagaagg atgaggtgca ttttctatgg caggaaactt  60
acttgttgtt tcccataatc tagaggctgt tgaaaggaaa acaagaatgg aagatttaag  120
aaataagaaa atcagaaaag agagagggag ggagaaaagt gtgtctaata aagaggagta  180
gctacagtgg ctcagttggt acagatagat cataactgct ttcaaaaact agtccctgaa  240
attgctcatt aaatttccca aattcttttt agagcaaggt acgaaatgat acagattgag  300
aaggatgaat cttgtactcc taggcataca catatagaca tggtgacacc tatgcccagg  360
tacacattca aaacagatga gctggacccc attgggaagg aactctcaca gtgcctgccc  420
tgccactagc gttcaaccga tgttcccaga cttgatatta agaagaggtg aagaaagaat  480
tgtacctgaa gatggagacc rtggggaagg gtgggatggt aaaaaaaaaa aaaaaaaaaa  540
aaaaaaaaaa aaaaaaaaag actagatgga tgcaaaaaga aggggaaggg gccaacacag  600
aaaaggcaga gttctggtga cacctctacc tttctttcat tgtaggtgga gaggagtctt  660
cgtccgatac caataagtca gcctgatgct ctgtaagttt gctgggtcac atgccctgaa  720
tatttcaact ttttctccac tgtgacccgt ggatgttctc agctggatta attagatcta  780
atctaaagac tcaatttctg tgtggtgggg gttcacctcc gcttttctgg agcctctgag  840
```

```
aaactcctga tcctgcacac ccccttgtaa agcctggcca tgcatcctgc accccccatg  900
acacagggag ccaagcctga catttttgag aaggtgccac ctctgatcca tcagagctgt  960
agaggaggga agctggaccc tggaagagac tctaaagaaa a                      1001

SEQ ID NO: 161         moltype = DNA  length = 1001
FEATURE                Location/Qualifiers
source                 1..1001
                       mol_type = genomic DNA
                       organism = Homo sapiens
SEQUENCE: 161
agtgtgcata tggtgaatgc ttattacagg aaattcatga gaaatgcaca tgttatagac  60
tagagaatga agtgtacctg ccaatatgag tggatttatt ttatctagca ccaagagtag  120
caaactgagt aataattctc agtcatgatc ctgtggttgt agtgtatact ctgattcaac  180
ttagtttcac tcctgactga gaagctggga ctctgcattt gatggcaatg gagtgggctg  240
atttctttcc aaataagttg aggtgggact cctggtagag taagagggct ttaatagggt  300
atgtctgggt gcctaaaagc tttctctctc tttttttttt tcagagacag ggtctctcta  360
tgttgctcag gctggccttg agctcctggg ctcaagcgat cctcccgcct cagcctccca  420
aagtactggg attacaggca tgagccacca cgccctgccc taaaaatgtt caaaagtcgt  480
atttacagct actctcaaat rcctttttttt ttgtgattcc ttataaaacc tttctccctg  540
catttatctt gttatattac agtagaatta tgaggggaaa atcctttggt ggaagtctag  600
ggacatgctc agttcccagg aggcttaatg tgaattttag tgaattgctt aagatccagt  660
attagatctg ctggtccctg cccacccccc ttttattttt tgagacaggg tctcactttg  720
tcacccaggc tggagtgtag tggcatgatc ctgtctcact gtagcctcca tcttctgggc  780
tcaagcaatc ctcccacctc agtttcctga gtagctggga ccgcaggcat gcaccatcac  840
gcccagctaa tttttaaaat attttttgta gagatgaggt ctcactgtgt tgcccaggct  900
gctctcgaac tcccgttctc aagcgatcca cccaccttgg cctcccaaag tgctgagatt  960
acagccacgg tgctcggctc ccatcttgaa atcaatacct g                      1001

SEQ ID NO: 162         moltype = DNA  length = 1001
FEATURE                Location/Qualifiers
source                 1..1001
                       mol_type = genomic DNA
                       organism = Homo sapiens
SEQUENCE: 162
taaacgttac tgaacttgct tcttcccgac tacattaaag cacttacttg agatattaaa  60
cattttctca ttagtcctgt ttgcctagtc agtcacttgt atagacaggg caacagcacg  120
gcctgaatat tgggcaggac accgccctgc gcgatagtaa ctttgcccaa cagcttgttg  180
agcttctcgt cgtggatggc gagctgcagg cgtcgggggg tgacgcgggt cttcttgtct  240
cgggccgcgt tgcccgccaa ctccaggatc ttggcggtca ggtactccag caccgcctcc  300
aggtacaccg gcgcaccggc ccggacccgc ttggcgtagt tgcccttgcg gaggaggcgg  360
tgcactcggc ccacagaaaa ctggagacca gccctggaag agtgcgtttt agccttggcg  420
cgagctttgc tgccctgcat tccacatcca gacgcagtga agtatttaaa tacttgttta  480
gaagaaggaa agtgattgat rctagtaaaa cgcaagagct aaactcttat aatctatatt  540
cggcaaagta gactgtgcta tctcctgaac acagatttca gccaatcgaa aagcaggtgt  600
ttaaaaaaat ttaaaaaaaa aaaaaaaaaa aaaaccactt ctgacttaca tacttatagt  660
tgaaaggtca aattatgcaa ggttgagctt ctgggagagc cgatgagatt taggagttca  720
gaaatggcct atcatatatt cagacactaa aagaaccaat gagaaaccga aactcagcca  780
gcctcatttg catatacacg aggtaaataa tgagggcgtt tgggctcacc agcattttcc  840
tgtggtcatt tgacggtatc acttcggctg cgaacatgcc tgaaccagct aagtcagctc  900
ccgccccgaa gaagggctcc aagaaggcgg tgaccaaggc acagaagaag gatggcaaga  960
agcgcaagcg cagccgcaag gagagctatt ccgtgtacgt g                      1001

SEQ ID NO: 163         moltype = DNA  length = 1001
FEATURE                Location/Qualifiers
source                 1..1001
                       mol_type = genomic DNA
                       organism = Homo sapiens
SEQUENCE: 163
gacctcagct cactgcaacc tctccctcct gggttcaagc aattctcctg cctcagcctc  60
ccgagtagct ggagctacag gcacccacca ccacacctgg ctaatttttg tatttttagt  120
agagacgggg tttcaccata ttggccaggc tggtctcgaa ctcctgacct tgtgatccgc  180
ccaccttggc ctcccaaagt gctcggattg caggcgtggg ccaccgcgcc cggcctcctt  240
ggactttttta tctgcattgc aggcactcag tggtccaggc cacctacttc tgctctacct  300
ttggacatcc tggcaatgtg ctgctcctca gcctgaccac aacacctgca gtgtcccaaa  360
catatcatgc agtttcatgc ctctgcaccc atttcctctc cctggtcaac acacctgggt  420
gacccctatt ctactcactc agacaaacca ggacaggatc cttgaccttt ctgcaactct  480
atttttctca cctagaaata raattaatga catctacttc tttagcagat gtttaggaat  540
gagatacggt gtggagagca cctggtgcga acacagcgcg tatctgtgat agtgaccgtt  600
agccgttatc ctcatcacca catcctttcc ccacatctca gatggtgcca cagtctacca  660
cctcagagag aaaatagaaa agggaggtcc caaacttcct gctccaccac ctatacctgt  720
ccctcatgat ctgtttcctc tgatttcaac aagcaggtgt tctttctcct gtctcaggct  780
aattctgcac ccacatcggg gagcccccac cccagcttcc ctcaggcttc tctatttggt  840
caattcatta attcattcat ttgacaagga tccatgaacg ctaactatgt gccagtcact  900
attctaggtg gtggagtcac agaagtgaac aaaacagaaa gttctcattc aaaaacaaca  960
taacttgtgg taggaggcag acaggaaatg aaataattag t                      1001

SEQ ID NO: 164         moltype = DNA  length = 1637
FEATURE                Location/Qualifiers
source                 1..1637
```

```
                        mol_type = genomic DNA
                        organism = Homo sapiens
SEQUENCE: 164
catttctttt tgaaggggtc ttgctctgtt gttcaggcta gagtacattg gagtgatcat  60
agctcactgc agcctaattt tttttttttt tgaaagacag agatcttgct atgcatactg  120
cccaggttct tgaactcctg gcctcatgca attctcctcc ctcgatcttt caaggtcctg  180
tgattacacc tgtaagccct cgttcccggt tggaagttac agtttaaaat agggtggtta  240
tgagcaaggg gagcgaggca cagaatactt gggagaaaag cattccgagt tgagagaaca  300
gcagtgccag agcacagagg cagaagcact gtggtttgtg tgaagaaaag caatgaggct  360
ggggtgcgca gagcacacag ggtgatcagg agaagaggag gtgacaaggc cagagggggt  420
tgagggccag atcatgtatg gccttgaaag tcatcatgct gacctgggct ttacctctga  480
gaggggagcc actggaaggt tagagcagaa aaaggactgg actgacttat gttttaagaa  540
gttacttcac atgctagacc aagatgggct gtgggtaggg gtggtggatg gaggcctgaa  600
gacccagctg ggagctactg cagtgatcca ggggaaagat gcagatgact tgtaccaggg  660
aggagccatg aaaatgttat gatgctggat ttattttcaa gatagaataa aaaggctttg  720
ctgataaact tacaggtggg gtgtgaaaaa ggagggcatc aagggtgacc acaaggtttt  780
ggtcctaaga aacggtacag atggagttgc cacttactga gatggggaaa atgagggaga  840
aaccgcttgt ggaggccaga ggaggagcca gcacagaatc caaaggtcag ttttgaatat  900
gttgggtttg aggagcttac tagagattcc cgtggagatg tagagtaggc aggtcaataa  960
taagcttgca gtccaggcaa cgggtcaggg ctggaaacac aagttattct ctttgtcttc  1020
tttatattca tgtttgttgc cactgtgtgt ttcacttacc taargcattc gtgatttatt  1080
gctgcataac aaattaccac aaacttagtg gtttaaaaca gtacactttt ccagcctggg  1140
caacatgatg aaaccccatc tctactgaaa acgcaaaaaa taaaagataa aaaattagcc  1200
cagcgtggtg gcacacacct ataatccccg ctacttggta ggctgaggca caagaattgc  1260
tagaacccag gaagtggagg ttgcagtgag ccaagattgt gccactgcac tccagcctgg  1320
gcaacacagc gagactctgc ctcaaaaata aataaataaa taacagtaca cttttatcac  1380
ttcagtttct gtgggtcaga agtccaggca gagcttagtg ggcttctctg ctcagaactt  1440
cacaaagcaa aagtattatt catgcatgta aacctctaag cacaatacca acatcacggt  1500
aggttctatg tgagtataag ctattattaa gaataataat caatcctctt ccctctcctc  1560
catccctaag gcctcatcat ttcttgcctg gagtgtcaca gtagctttct tcctggtctc  1620
cttgtcttct accatct                                                 1637

SEQ ID NO: 165          moltype = DNA  length = 1001
FEATURE                 Location/Qualifiers
source                  1..1001
                        mol_type = genomic DNA
                        organism = Homo sapiens
SEQUENCE: 165
cctatcttgc tgctgcttct cgccggagcc agttacttct tgtggagaca acagaaggaa  60
ataactgctc tgtccagtga gatagaaagt gagcaagaga tgaaagaaat gggatatgct  120
gcaacagagc gggaaataag cctaagaggt atccaacgca agcagagaat ctaagctctt  180
ggcttgcatg ccccagcctg aaaacctcac ctctctcccc taccctggca ctgcatcatg  240
tttaaggttt atttcccgaa acaccaacct cacccataac agttcatctt tttttttttt  300
tttttttttt tttggttatt ttccagagag cctccaggag gaactcagta agttaccatt  360
cccccagaga tccagacatg tcttcctatc ctcgctttga gcaccttgat gactcttccc  420
tgttcattcc attgcagaga ggaaaaaaat ccagtacttg actcgtgagt ggctttgaca  480
ttttctctga attcaaatct rttactctct ctctgcttca ttattttcca gcccataagt  540
catagcccag ggttgaaaag tggtcttgga tccctttacc cagaaaaaga aaacaagtgt  600
ggctctttgg agaaaccacc cagtgctttt tctctctaga aaaaaaaaaa aaaaaaaaag  660
aggtcttcaa tctctttgta ctaggggcta cagaccctta agctctaaaa agcactgagg  720
aatatccagg ggtacacttc aaaaggaaga gggaagagaa ggatgaggtg cattttctat  780
ggcaggaaac ttacttgttg tttcccataa tctagaggct gttgaaagga aaacaagaat  840
ggaagattta agaaataaga aaatcagaaa agagagaggg agggagaaaa gtgtgtctaa  900
taaagaggag tagctacagt ggctcagttg gtacagatag atcataactg ctttcaaaaa  960
ctagtccctg aaattgctca ttaaatttcc caaattcttt t                      1001

SEQ ID NO: 166          moltype = DNA  length = 1001
FEATURE                 Location/Qualifiers
source                  1..1001
                        mol_type = genomic DNA
                        organism = Homo sapiens
SEQUENCE: 166
aactgctctg tccagtgaga tagaaagtga gcaagagatg aaagaaatgg gatatgctgc  60
aacagagcgg gaaataagcc taagaggtat ccaacgcaag cagagaatct aagctcttgg  120
cttgcatgcc ccagcctgaa aacctcacct ctctccccta ccctggcact gcatcatgtt  180
taaggtttat ttcccgaaac accaacctca cccataacag ttcatctttt tttttttttt  240
tttttttttt tggttatttt ccagagagcc tccaggagga actcagtaag ttaccattcc  300
cccagagatc cagacatgtc ttcctatcct cgctttgagc accttgatga ctcttccctg  360
ttcattccat tgcagagagg aaaaaaatcc agtacttgac tcgtgagtgg ctttgacatt  420
ttctctgaat tcaaatctgt tactctctct ctgcttcatt attttccagc ccataagtca  480
tagcccaggg ttgaaaagtg mtcttggatc cctttaccca gaaaaagaaa acaagtgtgg  540
ctctttggag aaaccaccca gtgctttttc tctctagaaa aaaaaaaaaa aaaaaaagag  600
gtcttcaatc tctttgtact aggggctaca gacccttaag ctctaaaaag cactgaggaa  660
tatccagggg tacacttcaa aaggaagagg gaagagaagg atgaggtgca ttttctatgg  720
caggaaactt acttgttgtt tcccataatc tagaggctgt tgaaaggaaa acaagaatgg  780
aagatttaag aaataagaaa atcagaaaag agagagggag ggagaaaagt gtgtctaata  840
aagaggagta gctacagtgg ctcagttggt acagatagat cataactgct ttcaaaaact  900
agtccctgaa attgctcatt aaatttccca aattcttttt agagcaaggt acgaaatgat  960
acagattgag aaggatgaat cttgtactcc taggcataca c                      1001
```

```
SEQ ID NO: 167          moltype = DNA  length = 1001
FEATURE                 Location/Qualifiers
source                  1..1001
                        mol_type = genomic DNA
                        organism = Homo sapiens
SEQUENCE: 167
gaaccaccta gtcttcaggt ttgcctggtg ctcaccagct gaagaaatcc tttaacgacc  60
tttattcagt caagtaaatt gttttctttt ggcaacttgc atgttatttt ttaggttttc  120
atttatttat ttttttatat ttaaagtcat attttcttcc ttttattcac tttgctggtc  180
tttctcactt tgattttttt ttgccttgtt ttgcatttgt ttactttaac atttttttgta  240
acttatctct tttattttgg aaattattca cattatcagt tttcttttgc taggcaattt  300
tgatattcta ataaacatta ttaacataaa atataaagtt tactaacacc aagcccaaac  360
aatacaaagt cttagggctc tttaattgca attatttaaa aatatttgct acaaattgtt  420
cattatttta tatttacgtt gtttttctta ttcccacaaa tcacatattg ttggtgtgtt  480
tgttaaataa aaatctttaa rtgcaattgt ttaaaaatat ttgctacaaa ttgtttgtta  540
ttttatattt acgttgtttt tcttattccc acaaatcaca tattgttggt gtgcttgtta  600
aataaaattg tgattgctta tatatatttt ttcacatcct ttcttcttgt aatattttgg  660
aatttacatc cagttaatta tcctttattc tatagtatat actgtaaaag ttactagtct  720
tgctagtaaa ccctcagttt ttggattgtc tgaagatgtc tctattttga tctgctcttg  780
aattctaaat ctaattgaca taaaattcta gatttgccat tatcatttat tagcctttca  840
aagatattcc acaattttct gactttcaat atttttgttg gtaaaaatgg ggattgttaa  900
tcggcttgca tattctgttt tggatattcc attgtttcct tataatttgt ttatttataa  960
ggaaacttat aaacaaatta taaggaaaca atagaatatc c                      1001

SEQ ID NO: 168          moltype = DNA  length = 1001
FEATURE                 Location/Qualifiers
source                  1..1001
                        mol_type = genomic DNA
                        organism = Homo sapiens
SEQUENCE: 168
agccgggggg tgcggagatt gcagtgagcc aagatcgcgc cactgtactg cagcctgggt  60
gatagagcga gaatccgtct caaaaaaaaa aaaaaaaaaa aaaaaaaaag tgggaagcaa  120
ccagtggaaa gcaatggtaa gagcctgaca aatctcataa aatctcccat tattttttttc  180
ttggtgcaag aaaaaagcaa gtcattaaaa aggaagagaa tgtcgtggtg actgtgatgg  240
gcctactttg tacttttcac tgctctgggg tgttcttgcc tgtctaaaag aattttgaca  300
aacgtgatac ctaccacaat tttttcagtg gacatctaac gtttttcatt aagtttaaat  360
ttttctgaag gatatagtga cttgtatcat aggaatctaa aaaccacagt aatttaatac  420
ttaccagcaa cctttttaaaa gagagaggtg aacattgcta cctctttaat tgtggaagat  480
tttacattga tcctttattt rtctgcattc atagtgccat tgcctgtctc ttatagaatt  540
tttatcccag tacaatgtca ttttgtagtt ttttcttgat ctttctatga tacttctttg  600
gaccaaatat aggtataaat attgaagtcc attgttattt cctgttaccc aaaatgtgtg  660
ttaaaaatag tttttctgga ttgtgttata tttgcatcta ctgctagtac ataatcaaaa  720
cataatagggt aaataacaat tttaaagccc ctttactgaa aggtgtaatg gaagtcaatg  780
tggaatttgt catccccttt cctccaagaa attgtacaca atatgcaagt ccacctcgat  840
ggatggaggc tctaacttag tattcccaat tgtttccatg ttgggagctc gagaggagag  900
aatttttagg cctggagcaa tgtgtcatag gcaaacaact accagaaatt tatcaagtga  960
tatctttcca tggagtgcca tcactgattt gattatcaga c                      1001

SEQ ID NO: 169          moltype = DNA  length = 1001
FEATURE                 Location/Qualifiers
source                  1..1001
                        mol_type = genomic DNA
                        organism = Homo sapiens
SEQUENCE: 169
agataagcaa aggaagagtc aggaagcaaa gagggcaggg catgagcatg gaaaaagcgc  60
caatgtttag gggtttatgt gtaggaaaag ttatctaatg ccaaaagaga gcgtttaatc  120
tccctttaaa gaggtggcca aagatagact gtccacgagg ggaattcttc attttagagt  180
cataacagca agccaagggc aaaagagaca gatctcactt atctgtgaat gcagaaaaca  240
aaacacgtcc tttaatgtca acgtcttgag ttctttttcc caggttgact gactaaatat  300
ctcagtacag atacttttgc ccccttccaa aacgcaacca cccatgaccc cgacgtgatt  360
tgaacacgca accttctgat ctggagtcag acgcgctacc gttgcgccac gaggtcacgg  420
agaccctcca ttttcctttt aagataagta tctaatctta tcctcctccc aaacaatttc  480
tttattattt gatttgatct rttttcacag ttttgctaag gctttttttga gaaaaataag  540
ggagtggctg gattaaatat taaccccaaa cccaaataaa tgctccatat atgaaaaaca  600
gtggtttctc aagttcaatc tttctatttc tcgaatttct ctgtttcgag aaaaagtgtc  660
tatgtgttgg gtttagatta gcagtgaaac agtaataaga acggttatga agtttgtact  720
actactttct gtaaatgcgc tagactactc cctcttcagg aagagaattc cagcattgca  780
ctgccccgca agacctggcc tagctagcac ttacttcact caaacccatc cgcacacccg  840
ccccatcctc aacctaatgg gattcgaaag cctaacataa ataatatctc tagcctaaac  900
gttcacttct cagtccaaat tcgcgggccc tctggtctct attgtgtaca caagccattc  960
agttcacaac aataacccca aagaatccgt taacatttac t                      1001

SEQ ID NO: 170          moltype = DNA  length = 1001
FEATURE                 Location/Qualifiers
source                  1..1001
                        mol_type = genomic DNA
                        organism = Homo sapiens
SEQUENCE: 170
```

```
gctgttggat gccaaatgta atagtctaat catgactctg aataaatgtg tctctttgaa  60
aaatgtgcta tgtaaagtta gtctactctg aagccatctt ggtaaatttc cccaacattg  120
tgaagggaat tccttcaggg tgatgccaca ttctatttgg aatttgtata tgacctgctt  180
gggtggagaa gccattatct tcagtaacct tggtgtagtt gaactgatag ttactgttgt  240
gacttgaagt tcaccattaa aagagttcac cgggccaggc gcggcggctc acatttgtaa  300
ttccagcact ttagaaggct gaggcaggag aattgcttga acccagaagg cagaggttac  360
agtgaggaga gatcttgtca ttgcgctcca gcctgggcga cagagtgaga ctccaactca  420
aaaaaaaaaa aaaaattagg ctcaaggatt ccagaaataa catggaagta gatatctggc  480
tatttgactt tcattctggg mtgggggtag ggggttcttt acagcctggg gcaatgaaag  540
tctcagctcc ctgttctgct ttcttcgaga agtgtgtgtg tgtgtgtgtg tgtgtgtgtg  600
tgtgtgtgtg tgtgtgtgtg ttggaggtag agggaatgca ccttgttaca gcttgatgga  660
agtctagatt ccccactttg cctttgctgt tgtgtgtgaa ggtttggacg acagttgttt  720
tttttttttt tttcctcttc cagcttccca agagcagaag tccgtagaaa tggagtttgt  780
aactccactg aacacacaaa attagctaaa aaaaaataac aagtcacaaa acaaaaattt  840
taaaaatgta aaactttttag aagtagagtc aggcttcggc cgggcgcggt ggctcacgcc  900
tgtaatccca gcactttggg aggccgaggt gggcggatca cgaggtcagg aaatagagac  960
catcctggct aactcggcta actcggtgaa accccgtctc t                      1001

SEQ ID NO: 171         moltype = DNA  length = 1001
FEATURE                Location/Qualifiers
source                 1..1001
                       mol_type = genomic DNA
                       organism = Homo sapiens
SEQUENCE: 171
cacttggttt aattttctga acaatgcaat ggttgatcaa accaatttaa ccaataaagc  60
acatgtccag ttctcctttt tacgtttgta actcgccagt tcctttagca gaatgtccag  120
atgctctata gaaatgaaat gaaatgaaaa aaacaaaaac aaaaaaccaa aaaacaaaga  180
actctaaatg tggatgccag atcccaagat gcatagatgt acagatccca ctttatggtc  240
agaaaaatgt taatcgacaa aatgaatttg atgcatcttg agaaagctaa ttgtttggtt  300
ttaatatatt atatttaacc ggaagtaaca aagtgccttt tacatagcat tctatttaat  360
tcatatatca cggagaaagt ttttttccag aaaactgaat ctttttcaaa atcaaataat  420
ttccttttat ctgtacctag agaaagttaa ttatgtcatg actgataaac agaataaatg  480
tggtcatgga aagtaagaat rcatcacact tactttctat atatagatgt ttatatcgaa  540
caagagcatt actaatgtgt tttttattgg ccatctttgg aaaacgtgca gtcatttgct  600
ttaaaagatt gtataatgta ttttaaatct ttattttcag ctgggcgcgg tggctcacac  660
ctgtaatccc agcactttgg gaggccgagg cggatagatc acctgaggtt aggagttcca  720
gaccagcctg accaatatga tgaaaccctg tctctactaa aaatacaaaa attagctggg  780
cgtggtggca tatgcctgta atcccagcta ctccggaggc tgagacagga ggattacttg  840
aactcgggag gcggagattg cagtgagccg agactgagcc attgcactcc agccacttca  900
gcctgggcaa ctagagtaaa attccttctc aaaaataaat acataaataa atatttattt  960
attttctgcc tgtcccttta ggactatttt tggagcaggc c                      1001

SEQ ID NO: 172         moltype = DNA  length = 626
FEATURE                Location/Qualifiers
source                 1..626
                       mol_type = genomic DNA
                       organism = Homo sapiens
SEQUENCE: 172
agactacttg tgattcatgt caaaacaaag tttaatcaag ccatatttaa agagacccta  60
caaatcataa gagaaagacc taacaactaa gtagaaaaat tagcacagaa tactatgcat  120
gtaacagaaa aggaaataca aatggctttt aaacatataa aaaggtgctc aaggacaata  180
taaccagtta aatgcaaaat aaaactccct gagggatcat tttcacattt caaactggaa  240
aaaacaagat aaactctgtt gagaaggact caaccatgct cttcagagtg tgtgagagac  300
agccctagct aagggttggg cttttcttgt acaatcattt ggaaactatg aaaatcctgg  360
ggagtggctc ttatttcctg ggaggtacct agaactagag tttcttacct gtggccttcc  420
ggtcaratag cctcagaggt tcagttcctg gtggaattga aaatcctgga gtaggccatg  480
gatgtgagcg gtggatatga gggatttttc cttctattgg caatctgata ggttgtggta  540
gagaatcatt cacacactac tgcctgttga ggcgatttct ttagatttga agacaaaaaa  600
acgtcagtgt taacgcaaag gggtag                                       626

SEQ ID NO: 173         moltype = DNA  length = 656
FEATURE                Location/Qualifiers
source                 1..656
                       mol_type = genomic DNA
                       organism = Homo sapiens
SEQUENCE: 173
ggctgtatct cacttttaga tatgtcttca gcatgttcct tctcctttct ccaaatgttt  60
gcgtaactcc tttcttactc atatcttatt tggaaaggca tatcttactt gggaagagga  120
ggtgacaatt ctcatgttta cttccaacaa attacctatc ttccagtgaa tagaaaatac  180
actgaggttg aatataattt tatattttct tgcactcgaa ggcaaaacac tgttactgac  240
ttttgcctga gaccattggt tattgtaaat cgttattgtc tttttgcttc tacgggagcc  300
tcctgcttct tttgctcttt tgttcatctc tatgcatgat ttattaaatt catttcgtgt  360
actgtgaatt cttctctaaa gctatctgtt acgatggcca aaagacatca tttataccct  420
cctccttcca tacttacaga aactagacac atggartgtt atgagaaaga gaagcaacaa  480
tgaagttaag tgtaaaatgg ttgattctac ttggatagat ttttttaaaa aatgtaaatg  540
gtagaaaaca taggggtaca tttaaagcat tttgtgaatc agaattccat gggcaaactc  600
agaagaccaa taatctttat tttgtctgct taccttctag aagcatttta actaac       656

SEQ ID NO: 174         moltype = DNA  length = 101
```

```
FEATURE                Location/Qualifiers
source                 1..101
                       mol_type = genomic DNA
                       organism = Homo sapiens
SEQUENCE: 174
actgcctggc ttggaaaagt taagaagccc ctcaggaaga gaatcgaggc raagttcctc  60
tgcgccgagg gccccgagca tatccgccaa ggctcagctg c                      101

SEQ ID NO: 175         moltype = DNA  length = 51
FEATURE                Location/Qualifiers
source                 1..51
                       mol_type = genomic DNA
                       organism = Homo sapiens
SEQUENCE: 175
ggttttttt tgttttttt ttgttntgtt tttttcctcc ttgcttggca a             51

SEQ ID NO: 176         moltype = DNA  length = 1168
FEATURE                Location/Qualifiers
source                 1..1168
                       mol_type = genomic DNA
                       organism = Homo sapiens
SEQUENCE: 176
cactttccag aaggaaggtc cctctggtgc aggctcacta ctaggtggca ctgtgcacta  60
ctgggctagt tctggtaaaa taccccctgcc ccagctaaag tctctccttc cctccctccc  120
tccttccctc cttctctcgc tccctccctc cttccttccc tccttctctc cctccctccc  180
tccttccttc ccctcctctt cttccttcct tcctcccttc ctttctctct ctctctttct  240
ctctcccttt cttcccttct ttcttttttt ttgagacgga gtttccctct tgttccccag  300
gctggagtgc aatagcgcaa tcttggctca ctgtaacctt cacctcccgc gttcaagcaa  360
ttctccttcc tcagcctcct gagtagctgg aattacaggt gcccaccacc atgcccagct  420
aatttttgta tttttagtag agacggagtt tcaccatgtt ggccaggctg gtctcgaact  480
cctgacctca ggtgatctgc ctgcttctgc ctcccaaagt gctgggatta caggcatgag  540
ccaccacgcc tggcctcttt cttttccttt catttccttt cctttctctt tctctctctt  600
tccttccttc cttccttctt tcttttctct tttccmcttt attttctttt aaattttaat  660
ttaatttaat ttaatttaca gagatggaga ctctctatgt tgcccaggct ggtttcaaac  720
tcctgggctc aagtgatcct cccacctcag cctcccaaag tgctaggata acagccatga  780
gccacggtgc ctggccagag cttcagtttc tatggacagg tgttttcggg cttgctaaat  840
caaaattctc cagaattcct aagatcagcc aattttaaga gcagtaattt ttttttaac   900
agtcttgctc tgtcacccag cttggagtgc agtgatgtga tctcagctca ctgcaacctc  960
tgcctcccgg gttcaagcaa ttctcgtgcc tcagcttccc aagtagctgg gattacagcc  1020
acgcaccacc acgcccagct aatttttgta tttttggtag agatgggtct caccatattg  1080
gccaggctgg tctcaaattc aagctgtctg cccatcttgg cccccagagt gctgggatta  1140
caggcgtgag ccaccatgcc cggcctga                                     1168

SEQ ID NO: 177         moltype = DNA  length = 701
FEATURE                Location/Qualifiers
source                 1..701
                       mol_type = genomic DNA
                       organism = Homo sapiens
SEQUENCE: 177
atgtggaaga aaggtggtcg aaaatgaaat ttacaggtga gttcctaaaa ggcctaccct  60
tccccatgtt gagttaagtg tcaaaacatt tctagggaga tgactgtggt aaacccgcgg  120
ggcggtcaga ggcatgcctg agagggggcc gtgagaactc agcagaaagc tgggggagtg  180
ctgtctgttt caggttgagc rccatgtgtt agcttggtgg gagaagaggg ggcatgagca  240
ttggttttaa tgtgtaaaac ctccggataa attttttttt tttttttgag atggactctt  300
gctctgtcgc caggccagag tgcagaggcg caatctcggc tcactgcaac ctctgcctcc  360
caggttcaag tgattctcct gcctcagcct cctgagtagc tgggactata ggcacgtgcc  420
agcacgcccg gctaattttt gtagttttag tagagagggg gtttcaccat attggccaga  480
atggtttcca tctcttgacc tcatgatctg cctgccttgg cctcccaaag tgctgggatt  540
acaggcatga gccaccacgt cctgccctct taggatgaat ttttacaaat taagttttta  600
ttttaccaaa ttgattttta aacattcccc tttattcatt ttatttttat ttcatttttt  660
tcattttatt tttatttatt ttttgtttgt ttgtttgagg t                      701

SEQ ID NO: 178         moltype = DNA  length = 1001
FEATURE                Location/Qualifiers
source                 1..1001
                       mol_type = genomic DNA
                       organism = Homo sapiens
SEQUENCE: 178
ataaagaatc aacaaggttt gtccagctgt cttgagcaat cccactgatc tgctcaggaa  60
ataccacatt tcactcatta gatgtggctc aatcgatcaa gccactcagg cctgatttga  120
ggctccagtt cacagtgaaa tggtccctgc actcttccat caccccttcaa taggtcaact 180
cacctccttc cctgtcagtc aacacaagag agtgagctcg gccgcaggag acctgcagca  240
cccgtgtctc ctgaggtctg tccagaggca gggagacggg tgagggctcc aacacatact  300
cgtagcccct cgctggaaaa gacacaggac actgattgag gcatgcattt ctaccactgg  360
aaatcatact gtccaactcc acgctactac actggaaaaa agagagtcgg aggtaggaaa  420
gactcatcaa gacaggtaag ttaggcgcag agcaaggacc agaagcccaa ctcccagccc  480
atggcatggg ctgtctctat racataatgc gggttccaga aaagcatact tggtcttctg  540
gctgggcgca gtggctcatg cctgtaatcc cagcactttg ggaggccgaa gcgggcagat  600
cacctgaggt caggagttcg agactagcct ggccaaaatg gtgaacccca tctctattta  660
```

```
aaatacaaaa attagccggg catggtggcg ggcgcctcta atcccagcta ctcgggaggc  720
tgaggcagaa gaactgcttg aacccggaag gcggaggttg cagtgagctg agattgcgcc  780
attgcacttc agcctggggg acaagagcga gacttcatct ggaaaaaaaa aaaaaatgca  840
tacttcgtct tcttattaaa gaaatcttgg ccgggcagtg gctcatgcct gtaatcccag  900
cgctttggga ggccaaggca ggcggatcac ttgaggtcag gagtttgata cccacctggc  960
caacaaggtg aaaccccccgt ctctactaaa aatacaaaat t                    1001

SEQ ID NO: 179         moltype = DNA  length = 1449
FEATURE                Location/Qualifiers
source                 1..1449
                       mol_type = genomic DNA
                       organism = Homo sapiens
SEQUENCE: 179
aaccccatct ctactaaaaa taccaaaaaa attagccagg tgtggtggca ggcgcctgtg  60
aacccagcta cttggaaggc tgaagcagga gaatcacttg aacctggaag gcggaggttg  120
cagtgagccg aggttgagcc actgcactct agtccgggca acagagtgag actccatctc  180
aaaaaaaaaa aaaaattaag aaaaaagaca agaggccagg tgcagtggct catgcctgtg  240
gtcccagcac tttgggaggt caaggtgggc ggatcacctg ggatcaggag ttcaagacca  300
gcctcaacat ggagaaaccc cgtctctact gaaaatacaa aaaaaaaaaa aattagctag  360
gcgtggtggt gcatacctgt ggtcccagct actcgggagg ctgaggcagg agaattgctt  420
caatctggga ggtggaggtt gcagtgggcc aagatcgtgc cattgcactc cagcctggac  480
aacaagagca aaactcagtc tcaaaaaaaa aaaaaaaaga caagagaaaa tatttagaca  540
ggtaacgaag ggttttatgc aaatatatca agtactccta caaagtaata agagacaaac  600
aatccagtat gggtgcggtg gtggctcacg cctgtaatcc cagcactttg ggaggctgag  660
acgggcggat cacctgaggt caggagttcg agaccagcct ggccaacatg gtgaaacccc  720
gtctctgcta aaaatactaa aattagccag gcatggtggt gcacgcctgc agtctcaggt  780
acttgggaga ctgggacatg agaatcactt gaacccatca ggcagaggtt gtggtgagcc  840
gagatcggac cactgcactt cagcctgggc gctgggccac agagtgagac tctgtctcaa  900
aaaaaaaaaa aaagagacaa cccaatagaa acgtcaccaa ggatatgagt agatttgcaa  960
ttctcagtag aggagacgtg aaactgtaag atgttcaact rttccagaga ttacagaaat  1020
ataaagtaaa taaaaaatga gatatgtttc aagtagcaga ttggcaaaca tttaaaaaac  1080
gtgggcgggg cacagtggct tatgcctata atcccagcac ttggggaagc tgaggcagga  1140
ggattgcttg agcccaggag ctggagtcca gcctgagcaa catagagaga cccccgtctc  1200
tgcaaaaaat tttagaaatg tccaggtgtg gtgaggtgtg cctgtagtcc tagctacttg  1260
ggaggctgag gtaggagtat cacgagagct ggcaagattg aatctgcaga ggctgcagtg  1320
agctacgatg gcaccactgt actccagcct ggttgataga gtgagacctt gtctgggaaa  1380
aaaaaaacca agtcgtgtag cagggggata tgtaaaagca aatcccactc ataatattga  1440
agcacaact                                                         1449

SEQ ID NO: 180         moltype = DNA  length = 501
FEATURE                Location/Qualifiers
source                 1..501
                       mol_type = genomic DNA
                       organism = Homo sapiens
SEQUENCE: 180
ggcctctcaa agtgctggga ttacaagcgt gagccactgc gcctggccaa ataattttta  60
aaatttgccg ggtgaggtga tgtgcgcctg tgatcccacc tactcgggag gctgacgtgg  120
gaggcttgct tgagtgcagg aggttgaggc tgcagtgagc tatgactgta ccactgcact  180
ccaacctggg tgacagagca agtccatctc ccctcaacac acatagcaaa aaaaaaaaaa  240
agagagagag wgaaagtggt agaatctggg caaagttaga gctgccggag gaatctgaag  300
gaatggtgtg gagcgtggga ggaataagat gcttccaagg cttctggctt gagtaagtgg  360
aggaatggag tttcattcat tgagctggag aagactgcag gagaagtgtg gggagcgtga  420
gacatgttct tcttgggatg cctattcatt ctccaagata aaaatttttt ttcttaagtc  480
gctgtacaag tggagatttc a                                           501

SEQ ID NO: 181         moltype = DNA  length = 601
FEATURE                Location/Qualifiers
source                 1..601
                       mol_type = genomic DNA
                       organism = Homo sapiens
SEQUENCE: 181
ttattattca ctgaacccct tctgtaatcc actctgatgt ctattttaga ctgagcttgg  60
gtgtatgatt gtcatttgta ttagggcctt tactaaattc ctataactgt atcaatcatt  120
cttctcaact actccccct caaaaaaaat ataggctagg gtatttttat ttaatgattt  180
tattctacta ttgtttgacc tacactatgg agacacagac acactgaaac acatgcatcc  240
atgcatacac acatttgttt taaattctct tccagtttat gtatcagtga ccttgaacaa  300
wgtcacctag attctgtgtt tcagttttct cttctccaaa taaaagaagt tactttacat  360
aaatttgttg ggattcaatg aaatattatt tagaaatgtg ctgtgtgtgg catatatgtc  420
taaaggacag aattaatgga tatatatata tatatatata tatatatata tatatatagg  480
aatgtattaa atactcacat gatcacaagg tcccacaata ggccatctgc aggctgagga  540
gcaaggagaa ccagtccgaa aaactgaagg atttggaatc caatgttcaa gggcaggaag  600
c                                                                 601

SEQ ID NO: 182         moltype = DNA  length = 549
FEATURE                Location/Qualifiers
source                 1..549
                       mol_type = genomic DNA
                       organism = Homo sapiens
SEQUENCE: 182
```

```
ggatcaagaa gttgcagtct gtgtcctaat ttccactccc tgccatgggt gcggaacctt  60
gagcagtaga ttgggcccta ttggggacat ctggatggta acacagactc caaaatgcaa  120
gggctaatga cccatcccct agtccgtggg agactgcaag tctctggggc attttgggct  180
ccccgaattg tctctatgtg cccagaccac ttacagcatg atgtctggac acaggattca  240
ggcatcacta tttggaaaaa aagccatctc agtggattcc aatatggcgc caaagtcaag  300
aaccactgct cagcggattc caatatggcr ccaaagtcaa gaaccactgc tctttgagaa  360
gtcagctcaa ggtcacatcc aaggtggcac aggagagaga gggacagagc acagcattgg  420
aggaggcagg tggctagaaa ggtgggctct gaggcagtac tctggccctt tccagaacgt  480
gtgtgtagaa tgcagaaatc ttgaggacca catgttccag gaggagagtg gtgaggaagt  540
ggaagaata                                                          549

SEQ ID NO: 183          moltype = DNA  length = 601
FEATURE                 Location/Qualifiers
source                  1..601
                        mol_type = genomic DNA
                        organism = Homo sapiens
SEQUENCE: 183
gtgccaaaag aagaactcaa aatccctgtc tctcacctga aaatgataca gaagactgga  60
cctaggggtg aggcctctgc aagcggggat tggagaagcc tgacctcaaa tctagaagat  120
cctataattt atattgcata atcacaggtc atagactcag ccacactgtt gggctgtagg  180
aaagcattgg tttacttcca agcaaagagg gatgcctgtg aagagccagc agtccttcca  240
ttcctgattt tcctccttct accaacccac aggaacattc ctaggctgcc ccactctgaa  300
rccagtgttc cttctgtaag aaaggccaga tatgactgtt tattttcagg atgcatgcta  360
acagggccgc caggaaggta tctcagcttt catgccagaa ccaatagagt attccccagc  420
tggaatttag agtgatccag gcctgaaatc tcactttcag caataattaa aattttatta  480
gtgcttcaga atttaagata tgtgtttctc attcaccatt tcatttaatt atcatgacat  540
tatattgtta tcccacttac acagaagata aaactggggt taagagaagt tatgtatcca  600
a                                                                  601

SEQ ID NO: 184          moltype = DNA  length = 401
FEATURE                 Location/Qualifiers
source                  1..401
                        mol_type = genomic DNA
                        organism = Homo sapiens
SEQUENCE: 184
cccctatcca caacccacag ggataaacag ggtaaagaaa ggaggaccag agcagaggtg  60
ggtgtggctt cagtagaact cagcttatcc agaaaccaag ctgaaatttc agccacactc  120
tgtgggtttc cccagaattt gtcttctgaa cactctataa atcccagaag actgaagggc  180
ttcctattga atttcagttg rcccattgga ctcaatattt ttattgagaa tttaatattt  240
ttattgggtc caatgggaca actgaaaatc agtatttttg ggatattttg ggaaactcat  300
cagccaaggt cctaaggcct ggccaggtca tgagtccctt ctgattagat gatcgttact  360
cacatcttag agaccattcc cactttagag aggagtaact a                      401

SEQ ID NO: 185          moltype = DNA  length = 1001
FEATURE                 Location/Qualifiers
source                  1..1001
                        mol_type = genomic DNA
                        organism = Homo sapiens
SEQUENCE: 185
agtcacccaa atgctttgtg aagatccatg tttcttcctc gtgggctgtt cacagttaat  60
ttgtgatccc atcttcatct cactcatccg cccattcact cattcaatgt gtgtgaatgc  120
cctccataaa tttgtactgt gctagtcact gaagtacaga gctgaataaa acaagactgc  180
ttctctcaag gagaggagag gataaaggat ataaacaaat aattattttg gaaaggatct  240
tagtctacct ctccagcttt tactaacacc atgatgaact ctgcccccca ctacagtttc  300
acgctgcgtt tcacactatg ttctgcaagc acctgatgac ttgaagcctc acaaaggcat  360
catcctttgc cttcaagatg tggcctctgt ttctcctttc actactggtg tgctaccctg  420
ccctctcttc ccagttaatt cttactcatc cttctaggct cagctcaggt gtcagtttat  480
ccaaaaggta acaatgatgt mtcctcccca taggttatgt gtccctccca tcagctccca  540
aagaatgtct cagattttcc caacacaccc ttcacacact taacattgta attatctgga  600
tatttttctt tctcgtttac tatattgaga aggctaagag ggaatggagt cacgttacaa  660
ttgttttgga gcctagctca atgcacaacg tacaagtgct caagaaatgt ggaaagaaga  720
aattaactgt ttttgtataa aggagggaga ggtcaattct ggagtaggga atcagagagg  780
gcttcacaga aactattgaa ttgaatcttg aagaattaac gtaaattcac cagatggaca  840
agtttcagaa aaaaactttc caggaaaaac aaacagtaca tacaaaacca aaaagaaaga  900
aaacaaacat tcaaagaaat gtaagtattt aacatgtctg ggtataaaat tgcgatgatt  960
aaaatttggc tatgattaag aagttcaccc tcaccaatgt g                      1001

SEQ ID NO: 186          moltype = DNA  length = 1001
FEATURE                 Location/Qualifiers
source                  1..1001
                        mol_type = genomic DNA
                        organism = Homo sapiens
SEQUENCE: 186
tcacccaaat gctttgtgaa gatccatgtt tcttcctcgt gggctgttca cagttaattt  60
gtgatcccat cttcatctca ctcatccgcc cattcactca ttcaatgtgt gtgaatgccc  120
tccataaatt tgtactgtgc tagtcactga agtacagagc tgaataaaac aagactgctt  180
ctctcaagga gaggagagga taaaggatat aaacaaataa ttattttgga aaggatctta  240
gtctacctct ccagctttta ctaacaccat gatgaactct gccccccact acagtttcac  300
gctgcgtttc acactatgtt ctgcaagcac ctgatgactt gaagcctcac aaaggcatca  360
```

```
tcctttgcct tcaagatgtg gcctctgttt ctcctttcac tactggtgtg ctaccctgcc  420
ctctcttccc agttaattct tactcatcct tctaggctca gctcaggtgt cagtttatcc  480
aaaaggtaac aatgatgtct rctccccata ggttatgtgt ccctcccatc agctcccaaa  540
gaatgtctca gattttccca acacaccctt cacacactta acattgtaat tatctggata  600
tttttctttc tcgtttacta tattgagaag gctaagaggg aatggagtca cgttacaatt  660
gttttggagc ctagctcaat gcacaacgta caagtgctca agaaatgtgg aaagaagaaa  720
ttaactgttt ttgtataaag gagggagagg tcaattctgg agtagggaat cagagagggc  780
ttcacagaaa ctattgaatt gaatcttgaa gaattaacgt aaattcacca gatggacaag  840
tttcagaaaa aaactttcca ggaaaaacaa acagtacata caaaaccaaa aagaaagaaa  900
acaaacattc aaagaaatgt aagtatttaa catgtctggg gtataaattg cgatgattaa  960
aatttggcta tgattaagaa gttcaccctc accaatgtga a                      1001

SEQ ID NO: 187          moltype = DNA  length = 1001
FEATURE                 Location/Qualifiers
source                  1..1001
                        mol_type = genomic DNA
                        organism = Homo sapiens
SEQUENCE: 187
gtatatgtgg aggtggggag acagaaacag agacagagag agagagagag agagaaatac  60
tgagacctag aaagcttgaa taactcattt caagtcaaga gcaacttaat ggtaaacttg  120
gatcaaaaca caaaacacta ttctttttag tcctgtattg tttccactat atcacaatac  180
agtgttcaat agttctcttt aaatcacata ccaggagcta aatttactga agtattacaa  240
aaccaccaaa tgagctttca caggagacct aaaagaggaa attaaagatg caaatagttt  300
aagaaaaatc tgtgtttgat tcagaaactt aaaaccagtt tcttcaaaaa cttgttaaaa  360
gagaaagaaa caggcatttt tacccaaaga aagaaatacc atattctaga gattcactaa  420
ataattttta tgattctcta tgctactttc aagaaactct gacttcagtt atgtagacta  480
aggtgacaag aaccatttat rtaatcaact gtaattacat gaaattctct ctttagcaca  540
tggtacccac tgaatgtggc acaaaagagg atatgatcag ttgattcagg atgatgtcat  600
ttccatgatt ctaaaccaag aatcttcaag aaagcctggg ctgcaagttc cagggtcaaa  660
ttgcagactg cttgcagaga gtggctctgc tattccaaga acctcagatg gctcactgga  720
gtgatctgct ttagatagtg tgatcatatg tcttgaaatt tccatgacag tcttgtttat  780
acatgttgct ccagaatatt tattatagtg ctctctttca caatcagagg tgttccgctt  840
tgaatggtga gttataaaat agttacccta gccatgtgga gtgtgctcgc tcacttaaca  900
ttcaacatgc agtaagccac tttcacacat ggccctgtgc tcacgactta atagaggtta  960
ttaggcaaac ccagcttcac tctgctaaag gtattttatt t                      1001

SEQ ID NO: 188          moltype = DNA  length = 1001
FEATURE                 Location/Qualifiers
source                  1..1001
                        mol_type = genomic DNA
                        organism = Homo sapiens
SEQUENCE: 188
caatcagagg tgttccgctt tgaatggtga gttataaaat agttacccta gccatgtgga  60
gtgtgctcgc tcacttaaca ttcaacatgc agtaagccac tttcacacat ggccctgtgc  120
tcacgactta atagaggtta ttaggcaaac ccagcttcac tctgctaaag gtattttatt  180
ttaaaattac tcaaagcctg tctgaattcc accctaactc cataacagac attgggtgcc  240
ttcaggaaat tacttagctt ccctctggtt tattcatgtt tactatgaaa tgggaataat  300
tgcatcagtc ttaccacacc aggtaataaa taatggtcga ggaagtaatt aggcttagaa  360
gctggataga aactaagatg cctaagtact aattaggaat acagctgagt agattgtggt  420
tgatggccgt ccaaatgaat atgtcacctc taatttctgc cttgtttctt gtcttatttt  480
aattgtatct atcttctaag rgtcttatct ttacaaagta ccaatcctga accaacgagg  540
ttagatgctt aatttttctc gtgttttgct gggcatttgc tggctctaac agcaaagggg  600
cattaaccta accaaaaata aaatggtttc atatcattat aaaaattatt ctgtcagtgt  660
gaaatgccat aacaaaaaag cttgtatatg ttgatgtcat atatatatat ttatatttat  720
gtattcattt attcttattt tacatatata gttatttgtg gataagcagt tttggtgaag  780
aatagctagt atgtttttga gtagtgtcaa ggcctatact tttgagctat tttctaactc  840
caaacagatc tagaatcaat taacctttac caagggcctg ctatatttca gggtctggac  900
tgaacagacg attatgtcat tgaatcttca ttgaattcct gcataatgga tattctgatt  960
ctcattttgc aggtgagtta cctaaaattt agaaagaaaa a                      1001

SEQ ID NO: 189          moltype = DNA  length = 401
FEATURE                 Location/Qualifiers
source                  1..401
                        mol_type = genomic DNA
                        organism = Homo sapiens
SEQUENCE: 189
agtcctggat tctgagtgca aagtatagcc ttctctgttc ttgatgctac cagactgtat  60
tcaggaacac ttaagagaaa tgatggaagt cagagctgaa agctgtgtcc tcgccagatc  120
agtggaaggg cacgacaatc attcagctaa cgaaggaaac tccttggcta gccatgagtt  180
cattataacc aaaagtggga rtgggcagga tggggtgttg agggatacat gaattgttga  240
gcaactgctt tggaagggca ccaaacttca tgtttgttcc cttgcacact tgtcctttcc  300
ataattcata gaataattct atctaaaggt taatatagac cttgaagttc tcctagccca  360
gcccccactt cacgtttgaa tgttttctat cacatctcac c                      401

SEQ ID NO: 190          moltype = DNA  length = 401
FEATURE                 Location/Qualifiers
source                  1..401
                        mol_type = genomic DNA
                        organism = Homo sapiens
```

SEQUENCE: 190
ctatcacatc tcaccaaaca tcatgcctgg gtaagtccag gaataaataa ctcattgctt 60
cctgagccat cccagctcat tttgaggcaa ctctaactat ttgaaaaacc atcattcatt 120
tattcaataa atatttatta aatgccaact aagtgcccaa gcctggtttt agatgataga 180
aaaaaaaagt aaacaaacaa rcaccccgca cgcccccacc aaaaaaatcc ctactttcat 240
gaagtttgct tttcttacac taagccaagc taaaagttga tcttacctaa ccttcttcct 300
cactgagcta cttacaaccc tctaggtcct ctcattaggc atgggaaaag tgcttagttc 360
ttctcccatg taaatattta aagacactgg tagtaccccg t 401

SEQ ID NO: 191 moltype = DNA length = 1001
FEATURE Location/Qualifiers
source 1..1001
mol_type = genomic DNA
organism = Homo sapiens
SEQUENCE: 191
cacatctcac caaacatcat gcctgggtaa gtccaggaat aaataactca ttgcttcctg 60
agccatccca gctcatttg aggcaactct aactatttga aaaaccatca ttcatttatt 120
caataaatat ttattaaatg ccaactaagt gcccaagcct ggttttagat gatagaaaaa 180
aaaagtaaac aaacaagcac cccgcacgcc cccaccaaaa aaatccctac tttcatgaag 240
tttgcttttc ttacactaag ccaagctaaa agttgatctt acctaacctt cttcctcact 300
gagctactta caaccctcta ggtcctctca ttaggcatgg gaaaagtgct tagttcttct 360
cccatgtaaa tatttaaaga cactggtagt accccgtttg gccttgtctt tttagttcct 420
acatttatcc atagttacat gttttcaagg ctcttcacta caccggctcc aaatttctgg 480
gcttgttctg cttcgttgtt sttccttttc aagtgcaatc ctcagaagtt aatcagctac 540
tccagatgag ttctgaccag cacagaatat agcagcggca tcattacctt gttctagttc 600
tcggatgtcc attaatacaa tctgagttta agttgccatt tttgatttca caaatcactg 660
ctgatgcaca tgaaactcag ctaatttttt caaccctgtt attatgtaag atacttactt 720
agattggaaa taggtccaca gcaaccagca acaaccacac tgctcatgag attctcctga 780
aaaacaagct cagcctccct caaagagagc tacgggacat tttcagccag cctgaagacc 840
acaagtgtgc ctggtgccag ccagaattgt cttccattga gagaatttgc agattctagt 900
aaatctcaag tctaaacctc agctaaatta tttagaaaca atgagcaagg gcagctctaa 960
cttggcccaa tatctgcaat aataaaagtt aatacatttt g 1001

SEQ ID NO: 192 moltype = DNA length = 1001
FEATURE Location/Qualifiers
source 1..1001
mol_type = genomic DNA
organism = Homo sapiens
SEQUENCE: 192
aatcccttgc ccaaacttag acagatttta agggcaagta ggactcaaat atagatgagt 60
ggactccaaa gcccatgtac ctaaccactc taatcaccag acttctcatt ttcattgcta 120
acctgtcaag caatgttgct tgagagggaa ggagatgcat tcccccaaca cattattctt 180
tctaaatttt ttaagaaatg ttaataatca agcttagaaa caagcaaaaa aaaatgactc 240
cacagacata ttagcttggg agggatcaag ttggtttctc ccacaggttc tgagaagcag 300
ggaggctatc tgggatcctc tcataaaaaa tccttctgat tctgattctg atgtccacct 360
cacaagtcaa atggggaact gagcttgaca acaaatagcc gctttcttat ttctactcct 420
ttcccataat tttcaacagg agatgactat gttttatcta atgatctgac tctgtggagt 480
ggtctctagg ttgcaccccc vcccccccg agtgtgagct aatggaaatg ttttggagac 540
cactgatcca acttgctcta gagttagggc tggccccctc catccaaaac actcaagggc 600
cctgatatct tagtctgctc agtacaaagc cacacaatct gactctaccc tgcccaggca 660
atagtgcagt cctaaacact gtcctctgac ttcaggtagc tcatgtacca gggagagacc 720
tttcaaagac cggtgagaat acccaactga ccagtgatta agaaagggaa atttcagatt 780
cttgcacagt gaatacacag ttgagccaag tacagaattt tgattttctc ctctctgctt 840
atggataatt cattctttta tttcttcatc tatatgtgaa aatttgtttt ccttatattt 900
tctgtgttgc ttctattcct atcaggcttt cctgtacaca ctgtgtaact ccaacagaaa 960
caacctgaac tcctaaggat acaattgaaa ctattagttt g 1001

SEQ ID NO: 193 moltype = DNA length = 1001
FEATURE Location/Qualifiers
source 1..1001
mol_type = genomic DNA
organism = Homo sapiens
SEQUENCE: 193
tcccttgccc aaacttagac agattttaag ggcaagtagg actcaaatat agatgagtgg 60
actccaaagc ccatgtacct aaccactcta atcaccagac ttctcatttt cattgctaac 120
ctgtcaagca atgttgcttg agagggaagg agatgcattc cccaacacaca ttattctttc 180
taaatttttt aagaaatgtt aataatcaag cttagaaaca agcaaaaaaa aatgactcca 240
cagacatatt agcttgggag ggatcaagtt ggtttctccc acaggttctg agaagcaggg 300
aggctatctg ggatcctctc ataaaaaatc cttctgattc tgattctgat gtccacctca 360
caagtcaaat ggggaactga gcttgacaac aaatagccgc tttcttattt ctactccttt 420
cccataattt tcaacaggag atgactatgt tttatctaat gatctgactc tgtggagtgg 480
tctctaggtt gcaccccccc bcccccgag tgtgagctaa tggaaatgtt ttggagacca 540
ctgatccaac ttgctctaga gttagggctg gccccctcca tccaaaacac tcaagggccc 600
tgatatctta gtctgctcag tacaaagcca cacaatctga ctctaccctg cccaggcaat 660
agtgcagtcc taaacactgt cctctgactt caggtagctc atgtaccagg gagagacctt 720
tcaaagaccg gtgagaatac ccaactgacc agtgattaag aaagggaaat ttcagattct 780
tgcacagtga atacacagtt gagccaagta cagaattttg attttctcct ctctgcttat 840
ggataattca ttcttttatt tcttcatcta tatgtgaaaa tttgttttcc ttatattttc 900
tgtgttgctt ctattcctat caggctttcc tgtacacact gtgtaactcc aacagaaaca 960

```
acctgaactc ctaaggatac aattgaaact attagtttgc t                    1001

SEQ ID NO: 194         moltype = DNA  length = 501
FEATURE                Location/Qualifiers
source                 1..501
                       mol_type = genomic DNA
                       organism = Homo sapiens
SEQUENCE: 194
acagaaacaa cctgaactcc taaggataca attgaaacta ttagtttgct ataacttttc  60
tatttgattt accaagatac tctccctata gccaaaataa ttatatagca atctatgttg  120
tagcaaaagg aaataaacaa cggtgtttct taaacactta catagagagt ttagatgtat  180
tttttaacct tcttttctct ttttcatcta atttaaggtg agattccagg atctttctca  240
tgaaagatcc rcagagaatg tgcctgctaa acttgataga gtcacaaagc taggttacaa  300
aagagagcaa attaaattta gacccaaaag tgttgatacc acatatactg acgcatttct  360
tcaacagttt tcctttgttt atttattcag ggcactagag aaggtgctct aatcttttaa  420
taacagactc aatctgccat tgtcaaaatt atcaacaaaa ataataaaat gggttaaata  480
caaccacaaa aattcactgt g                                          501

SEQ ID NO: 195         moltype = DNA  length = 401
FEATURE                Location/Qualifiers
source                 1..401
                       mol_type = genomic DNA
                       organism = Homo sapiens
SEQUENCE: 195
agtcagtaaa atccagcaag cacaggtacc aacattataa agatgattca tacatggttc  60
caggcttccc aactagtgga agaggcagag ctagaaacag atgagttcaa tgtcatcttt  120
taaaatgatg gttattcata ggatgcttgg aaatgcagag gggcactaaa tatttatgct  180
caataaatag ttgtggcctc vctgtgtggg agtgtttgga gatctaaagg tagcatgaga  240
tgtacaaatg tggagtttag ttttaaagag accaccaaga attgcttcat ttatgagtgg  300
ccctggccct gccactgatt agctccatga acttgagcaa gtaatccttc tcagaatgtt  360
tcttttgttg ataaagttag gagttgcatg ataatgatgt c                    401

SEQ ID NO: 196         moltype = DNA  length = 501
FEATURE                Location/Qualifiers
source                 1..501
                       mol_type = genomic DNA
                       organism = Homo sapiens
SEQUENCE: 196
ttttatgcca gatggcttta ttatttccct ggttccagat ccctttccct cttgcctttc  60
acgccctgtg ccctagggct gtatggtgtg tacccctata attctcccag cctgcagggc  120
aaaatgtaaa aacttcaagc ctctttttca gcagacagaa gggagggtca gggcaggatc  180
tcggtaggtt ttgtccaagc agtcggctca ctcttaagct ggcctgaggc agcagcacct  240
ccttacgctc vtgtgcagag atccagccct cccagtgccc cgctttgagt cccagggctt  300
ttctcagccc ttgcagccag ctgagccact tctaccactc ccaccagctt ataagagaaa  360
gagacttctt ctgtgctatg tctaatatta tcaggtccat tttgaaaatg agactaacat  420
agccacagct cctccctcca agggagactc tcatagcact attcaaattg catgatgaat  480
caagccctgc tgaactgcat t                                          501

SEQ ID NO: 197         moltype = DNA  length = 1001
FEATURE                Location/Qualifiers
source                 1..1001
                       mol_type = genomic DNA
                       organism = Homo sapiens
SEQUENCE: 197
aggtgttcct cagggcccag tccatgacac atgcttttcc atattaatgt atggaaaata  60
ctcctgtaga tttgagcagc taccattgct ttccctagcc ctttgctcag aagtaggcac  120
cagtccactg gctgttgggc aaaagcctgc tgagaaatcc aatgccttgg ccaaagatgc  180
tttgaagaaa tagtaagtga ggcagctctg acctcttctt atagaactcc ctgattcata  240
aaatcaaaca gcaaagactc ctagagacca ctgagtccaa gcctcttcat tttatagaag  300
agaaactgag gtccatagaa gcccattttt ttatagaatg agaaggaaag tgacttgccc  360
agggctcctg cttacagtag agttgggact ggcatttaca tctccttatc ctttacttag  420
tcctcttcgt aataaacagc gaaacactca ggggtccttc cttcctcttt ccaaaccctg  480
gaggagctga gggggagaca rgggggcttt actcctcgtg ttgtttcaga ctcagacttc  540
tcagcttcca cattgagaga ctatttgcaa ttgcttctcc ttgttgccca aattcctggc  600
tggcattcca gactgacacc agagacttcc ttcccaggga catccatcct gggcaggtca  660
gcagtttgca tcttccctgg ggcagaagtg gcagagtctc agaactcttg cttcttaaga  720
ctcagctcaa tctccacctg actcagcaga ggtttctgga atctcagatg ggtcctaacc  780
agaagcagct aggttgcttc tctgtttcta taatgagaaa acaaaaaaaa aagctgacta  840
tgaccattga gaaagaaaat gcacccatgt aaacacagca atctttaccc tataaataac  900
cctaattaaa atgaaaacac ccgagtgctc ccatcttttt tgattttttc tttctgctgg  960
acaccatggg aggtccttgc agcagagctc tggtgcttgc c                    1001

SEQ ID NO: 198         moltype = DNA  length = 1001
FEATURE                Location/Qualifiers
source                 1..1001
                       mol_type = genomic DNA
                       organism = Homo sapiens
SEQUENCE: 198
ctatatctcc aatctcctct tctatccgtc tccctctctt aatcagtttt tgataatggt  60
```

```
ggcctgatgt tctttcctac cacagtcccc agcaatcttc acacacacac tgtttcttca  120
gcctgggatt ctcttcacca tctctaaaat gtaagcagct cctacacatc cttcacttac  180
agagacaccg tatcttccac acagacactc ctcggtcatc tccagactaa ctcgctgcta  240
gtgagcaact gcaacttatg ttcccatgta tccattcaat cttctcttaa taagcatatt  300
ccctcatttc tgggggactc tctgtccctc gctcttgaac cacatctcat tttggtgagg  360
ctccacatgg cacaggctta tgccaaatgg tggttggtat gaagatgggt tcattacaca  420
atcatacttt ttctgaggat gttggaatca acatctcact ttttcctact gtcttggagc  480
tgggatgtga gctgtaatgc hgctgtagct ggaaccctct caaaatggca ttaacacagt  540
agacgcagag ctttgaaatg gagaaagaga aaccagatat aaatggctat ggaattactg  600
ttgccaggga agcctgaagg cttcaactta taaaattcct cttcttcttc ttcttctttg  660
tttttatttt cgattaaagc agcttgactt gagttttctc tcatttttaa aagaaaaatt  720
ctccgttgca cactttgagc accctgagtc ttctcacatt ttggcattca cgacaagggt  780
aagcatttgt tcaatttcta tctctttcat actagattgg aaattccatg gaagttggaa  840
tcctatgagt cttatatatc actatttctc tcgtttctag tacaatgtgg agcacataat  900
gaaatatcaa taaaatattt ctgaatttaa tgaatgaatg aatgggagat tctgagatcc  960
caacccctat caggcctttt gttccatgat cctgatctga a                       1001

SEQ ID NO: 199         moltype = DNA  length = 601
FEATURE                Location/Qualifiers
source                 1..601
                       mol_type = genomic DNA
                       organism = Homo sapiens
SEQUENCE: 199
tacttttttct gaggatgttg gaatcaacat ctcacttttt cctactgtct tggagctggg  60
atgtgagctg taatgccgct gtagctggaa ccctctcaaa atggcattaa cacagtagac  120
gcagagcttt gaaatggaga aagagaaacc agatataaat ggctatggaa ttactgttgc  180
cagggaagcc tgaaggcttc aacttataaa attcctcttc ttcttcttct tctttgtttt  240
tattttcgat taaagcagct tgacttgagt tttctctcat ttttaaaaga aaaattctcc  300
rttgcacact ttgagcaccc tgagtcttct cacattttgg cattcacgac aagggtaagc  360
atttgttcaa tttctatctc tttcatacta gattggaaat tccatggaag ttggaatcct  420
atgagtctta tatatcacta tttctctcgt ttctagtaca atgtggagca cataatgaaa  480
tatcaataaa atatttctga atttaatgaa tgaatgaatg ggagattctg agatcccaac  540
ccctatcagg ccttttgttc catgatcctg atctgaaaaa agtgaatcta gttcccagtg  600
c                                                                   601

SEQ ID NO: 200         moltype = DNA  length = 601
FEATURE                Location/Qualifiers
source                 1..601
                       mol_type = genomic DNA
                       organism = Homo sapiens
SEQUENCE: 200
tcttggagct gggatgtgag ctgtaatgcc gctgtagctg gaaccctctc aaaatggcat  60
taacacagta gacgcagagc tttgaaatgg agaaagagaa accagatata aatggctatg  120
gaattactgt tgccagggaa gcctgaaggc ttcaacttat aaaattcctc ttcttcttct  180
tcttctttgt ttttattttc gattaaagca gcttgacttg agttttctct catttttaaa  240
agaaaaattc tccgttgcac actttgagca ccctgagtct tctcacattt tggcattcac  300
racaagggta agcatttgtt caatttctat ctctttcata ctagattgga aattccatgg  360
aagttggaat cctatgagtc ttatatatca ctatttctct cgtttctagt acaatgtgga  420
gcacataatg aaatatcaat aaaatatttc tgaatttaat gaatgaatga atgggagatt  480
ctgagatccc aacccctatc aggccttttg ttccatgatc ctgatctgaa aaaagtgaat  540
ctagttccca gtgcctagac ttgctgttct gttatggaaa gatctctatt agggagcatt  600
c                                                                   601

SEQ ID NO: 201         moltype = DNA  length = 601
FEATURE                Location/Qualifiers
source                 1..601
                       mol_type = genomic DNA
                       organism = Homo sapiens
SEQUENCE: 201
ggcaataaag gcaatagttt aatcttcaac ctgtggaatc cattggctat cccttagctg  60
gttataaaca aaggtaggaa aaaaatggga tactacttat tttccttgtg aagcccaaca  120
tatggttgga aacatttaga aatagaaaag gattggaatt tggtaaatta aatggcattt  180
ttacctcaag gcttcctgtg gggccttgat tataggcatg aggctataga ttttagcaac  240
taggtattgt gggattttga ccctatgtca cggggttggt tcctatatct gtgtggctgg  300
rttttaacta gtgcacttgt aaaggcctta gcctttagaa gtaaatcata tggcattttg  360
acttttataa gtcactagag ttaacggcaa ctttgtttgc aaatgataac tttttgtaac  420
attcagaaat ctaagcaaat gccaactaaa tggggtgagg ggcttagtaa acctgtgcaa  480
gccatgttat ttctggcaag gatctgatca aaggaaaaga gtcttcctgt tacacacatt  540
taggcactgt ggcagaacag ggaggagccg agggatatcc aggaaggggt gccgcagaag  600
a                                                                   601

SEQ ID NO: 202         moltype = DNA  length = 601
FEATURE                Location/Qualifiers
source                 1..601
                       mol_type = genomic DNA
                       organism = Homo sapiens
SEQUENCE: 202
gtggctggtt tttaactagt gcacttgtaa aggccttagc ctttagaagt aaatcatatg  60
gcattttgac ttttataagt cactagagtt aacggcaact ttgtttgcaa atgataactt  120
```

```
tttgtaacat tcagaaatct aagcaaatgc caactaaatg gggtgagggg cttagtaaac  180
ctgtgcaagc catgttattt ctggcaagga tctgatcaaa ggaaaagagt cttcctgtta  240
cacacattta ggcactgtgg cagaacaggg aggagccgag ggatatccag gaaggggtgc  300
mgcagaagag tcgtttgctg tttgaactgt gtttctcagt caagaaagga gttctctatt  360
ttaaacttca aggtagcta ctttgcgttt gtgctacaga gcactgttat atgtgagatg  420
ctagctttac acttttaaac caagaatagt tagtccttga ttaagtaccc ataattttgt  480
tcattgttga tattatttg aacctctttt agagcctgga gaggaggtag ggaagaaata  540
actttgaatt caagtggttt atccacagat ccaagagtca ccacagagta aattgcttta  600
g                                                                  601
```

```
SEQ ID NO: 203          moltype = DNA  length = 1001
FEATURE                 Location/Qualifiers
source                  1..1001
                        mol_type = genomic DNA
                        organism = Homo sapiens
SEQUENCE: 203
ctggagtgat tcccaagtgg cacctacaac ttcacctgtc ttgacttttt ctggtctttt  60
tctcctgatt ttgtattttc acttttgttt ctttacttga ccaagtttgg ctctgggtat  120
gatttatctg tggctgatgt ggtattcccc atagacggca acaatgattg agaatctggt  180
tttgtcatct gtccatttgg tgatctcttg gataacaaga atctagtctc tctaaggtga  240
gaaacagtag ataatgtggt taattaattt ttgtttgtct ttttgtctac ccatgagctc  300
aaataaatat tgtatgtctt ccaaaaagga taacaaatct ttgagatcca gcccggtgag  360
tgtgtttttg tgtttacttt gactcatgtc tgaagttata gaactgaagc catgggctct  420
ctgtatatct gtaagtgaag aaagccttta cctctcagta cataaatgtg aaatattctt  480
ctacctctgg agtgtattaa maaattatgt cacaaagtat tttaaattat gttctatgtt  540
gtaattagct tagagagaat acgtgcttaa atgaatctat tattttccca gaattcagaa  600
tattttccta gaaaataaac taaaatttta atattttaaa tatattttaa agactatact  660
ttaagtattt tttaaaagta taaaaagccc tttttataaa aataattagc ccaaaagcat  720
ttttatgtaa aaatccaagt ttactgaatc aaggtgaaat ttttgttagg tcaaactggt  780
ttgtttggcc attttgtttc aaaatagcca tatatatagt tcccctgatc ttattagtgt  840
attaagcgta agtatatatt ttagttttat aagatttgag gtgtttcctg ataaagtgac  900
tagttattct gaacttccta aatttcttat attgacttac tgatcaaatt agctaatatg  960
acttctacat aatcatgatt gtgaaaattg taaaattatg t                     1001
```

```
SEQ ID NO: 204          moltype = DNA  length = 601
FEATURE                 Location/Qualifiers
source                  1..601
                        mol_type = genomic DNA
                        organism = Homo sapiens
SEQUENCE: 204
tataaaaagc ccttttata aaaataatta gcccaaaagc atttttatgt aaaaatccaa  60
gtttactgaa tcaaggtgaa atttttgtta ggtcaaactg gtttgtttgg ccattttgtt  120
tcaaaatagc catatatata gttcccctga tcttattagt gtattaagcg taagtatata  180
ttttagtttt ataagatttg aggtgtttcc tgataaagtg actagttatt ctgaacttcc  240
taaatttctt atattgactt actgatcaaa ttagctaata tgacttctac ataatcatga  300
rtgtgaaaat tgtaaaatta tgttttcaac caaattgaaa tacaatttta acaaagtttt  360
aacacattct ataatgtttc tgcttaaaaa taacttccaa gatccttagt taattttaag  420
atggactaac attacaccta gttaattaat ggctaattgt tggatgccta gataatttcc  480
aagtaagata gaatactcca aaattgatca ccatatacat agtatatata tatatatata  540
tagagagaga gagagagaga gagagagaga gagaaagaga gagagagaga aagagagaga  600
g                                                                  601
```

```
SEQ ID NO: 205          moltype = DNA  length = 601
FEATURE                 Location/Qualifiers
source                  1..601
                        mol_type = genomic DNA
                        organism = Homo sapiens
SEQUENCE: 205
atatagttcc cctgatctta ttagtgtatt aagcgtaagt atatatttta gttttataag  60
atttgaggtg tttcctgata aagtgactag ttattctgaa cttcctaaat ttcttatatt  120
gacttactga tcaaattagc taatatgact tctacataat catgattgtg aaaattgtaa  180
aattatgttt tcaaccaaat tgaaatacaa ttttaacaaa gttttaacac attctataat  240
gtttctgctt aaaaataact tccaagatcc ttagttaatt ttaagatgga ctaacattac  300
rcctagttaa ttaatggcta attgttggat gcctagataa tttccaagta agatagaata  360
ctccaaaatt gatcaccata tacatagtat atatatatat atatatagag agagagagag  420
agagagagag agagagagaa agagagagag agagaaagag agagagagag agagagagat  480
tgagagagag taagaaacta tatgtacata gttttttact tttatatgtc atggagtggc  540
tacacctttc agtcatgtta atgaatatgc tcttttttgc cactttagaa aggatttgtg  600
t                                                                  601
```

```
SEQ ID NO: 206          moltype = DNA  length = 601
FEATURE                 Location/Qualifiers
source                  1..601
                        mol_type = genomic DNA
                        organism = Homo sapiens
SEQUENCE: 206
tgatgggcct gatttgaccc agtgggccac agtttgtcaa catgtgatct aaagcatcct  60
aaaattttc tatttgctac cctgggacct tgattatttc agggccaacc taatttccaa  120
gtccaaggta tatgaagcat aagctttctt tggaggactt tttaatgggc ctttggattg  180
```

```
gtgaaaccat tttcttttac ctctgtctaa ttggatattt tatcttctat gtggtagagg  240
ctaacaggca ccagtcatct tctacccaag ttggaattaa gagagaaaca cctaagttag  300
rcaagtaggg attaaaatgt cagttttatt atagataaaa tccatttcag agaatccagc  360
tgaggtttac agctagtgac tatgcaagta atttattctg aattaaacag acctgctcac  420
ccaatcacaa gcacatctgg acacaggcct ctccacatgg acctatgtcg gtaaaagcta  480
gagtgcaaag caacaaggat gtgttcgctc tgcagcaata tctcaggaga tgaggaagga  540
aggtgctgaa ttatgcatcc ccaagtttat ctcccaaatt ctcaattgga aaatattatt  600
c                                                                  601

SEQ ID NO: 207         moltype = DNA  length = 714
FEATURE                Location/Qualifiers
source                 1..714
                       mol_type = genomic DNA
                       organism = Homo sapiens
SEQUENCE: 207
ataacttctt actcttttac tcccttgatt aaaatgttaa atgacccctc tttcctcaaa  60
agaaaaaaaa aatcagttct gatatcttat cctggtatta aacatgcttc actctctggc  120
actagactac tactacctag tatgactctc ctctctggcc aggtaagtct gtttataacc  180
tctgtaagat gacacttaaa ttttgcctcc ttgrctttgc caaggccatt gcttccacct  240
ggaatgcact ctttaattgt tttacttgat tcatatctat ctttcagcgc ccagctctag  300
cctctgtgaa gccttcctgg atcactctag ttctcaaagc cctctctgcc cttgaactac  360
taaagtcctt actgtctgta tcttaggcat ttgcagttgg tgttgttaat tttgcataat  420
tatatcctat ctccaaattg agatgttcag ttctttgagg atcagaaaca tttgttaggc  480
atctttatac cctcaaagca actagcacag tgatttcaca taatgtaagg gttcatatgt  540
ttgctcatgt gttatatacc ctttaaaata atttattaaa taattattta attacttatg  600
ttatgttata aatatataac aacaacgact tctcactaat ccagactagc tccattagta  660
aaagttaatg aggatgtgct ctattcagaa tacgtttcat gtgtttttgt gctg        714

SEQ ID NO: 208         moltype = DNA  length = 701
FEATURE                Location/Qualifiers
source                 1..701
                       mol_type = genomic DNA
                       organism = Homo sapiens
SEQUENCE: 208
cattgcttcc acctggaatg cactctttaa ttgttttact tgattcatat ctatctttca  60
gcgcccagct ctagcctctg tgaagccttc ctggatcact ctagttctca aagccctctc  120
tgcccttgaa ctactaaagt ccttactgtc tgtatcttag gcatttgcag ttggtgttgt  180
taattttgca taattatatc ctatctccaa attgagatgt tcagttcttt gaggatcaga  240
aacatttgtt aggcatcttt ataccctcaa agcaactagc acagtgattt cacataatgt  300
aagggttcat atgtttgctc atgtgttata taccctttaa aataatttat taaataatta  360
tttaattact tatgttatgt tataaatata taacaacaac gacttctcac taatccagac  420
tagctccatt agtaaaagtt aatgaggatg tgctctattc agaatacgtt tcatgtgttt  480
ttgtgctgct gttgcctaga wccatgaaac agatttgtag ttggttgttt ccagtcctga  540
ggaaatgtgg gcttgctgag cttctgaact acatccttct tgtgagcagc ttagatttca  600
aggttacgtg cttccagaaa tagaaaggga gtatttagat tctttccttc cctgtcaaga  660
aactctgttg aatcatcttt tggcaataat gccaaagtaa t                      701

SEQ ID NO: 209         moltype = DNA  length = 701
FEATURE                Location/Qualifiers
source                 1..701
                       mol_type = genomic DNA
                       organism = Homo sapiens
SEQUENCE: 209
cttctgaact acatccttct tgtgagcagc ttagatttca aggttacgtg cttccagaaa  60
tagaaaggga gtatttagat tctttccttc cctgtcaaga aactctgttg aatcatcttt  120
tggcaataat gccaaagtaa tttgtaagcg ttagaacatt tgtgcagaca gcataagttc  180
cttcaaataa tgcagttgca raaagcagta atgttaatta gtcaaagcaa ctttttttaaa  240
atcagtagtt ctatgcacat gtgacaccac cttggtaaaa agagctttag aaatttgaag  300
aaaatttga gttgtcccaa tatcgagagg ggatgccact gtcacttatt gtgaaatagc   360
tagggatgct agatgtcctg caacgtgtaa ggcattctca tgcagtgaaa aattgcccca  420
cattctaact ggtcttcaaa tgtccctcca tacatttatg tggatgaaaa ctatttaaac  480
ttatctgagc ctaacactta atgccattta catataaaca cctaggatct agtttttgta  540
cagtttaaat acatgatttt gtacagtttg aatttttgca actgttatgt aaatcaaaga  600
aagattacgt tttgtctcat atggaaattt aacaagcttc atttatcatt gtgaaaaatc  660
atgttaccag tggaagtacc acttttggta tttgaatacc c                      701

SEQ ID NO: 210         moltype = DNA  length = 1001
FEATURE                Location/Qualifiers
source                 1..1001
                       mol_type = genomic DNA
                       organism = Homo sapiens
SEQUENCE: 210
cctcaaagtg gcttaaaata acaacgattt aattatcatt tacaagtctg tggatcaatt  60
aagaggttct gctgatccaa ccccagctct aatctcagct gtgcttcctt atgagtttat  120
ggtcagctgg gagttggctg gtctgggaca gcctcagtca ggatcctcca gcagactagc  180
ctgggctttc tgggtaatgg tggggttcaa agagagtaag cccaggcctg caaagccttc  240
tgagactcag aattggcaca gtcaccactc tgcagcattt cattgaccaa ggcaagtcac  300
aaggccagcc cagattcaca gggtaggaaa agagacttca cccctcggcc atggaaggag  360
ctgcaaagtc acattttaaa gagggtaaga gtgtagacac aggaaggggt ggccattgtt  420
```

```
gtaatcagca gcaccaagtt aaggcgtaaa gaagggatag gagtcaacca aacagttagc  480
tgaagagaac tgtggtcagc rtgtcaaggc cctgaggcaa gaaatagcat gcagtcgtcc  540
agaaggctaa gaaagccaga gcggcagcat gctgagagtg aggggtgagt tgtacaaaat  600
gaggctggta agaaggaaag ggtcagatgt tgcagagcca tgtagtgtgg gccttgttgc  660
gattttcatc ctttatctga agaaatgttt taagcaggag agggagatga ttagttattt  720
aaattttctc cagtgatacc aatgtgcaac caaggttgaa actctctgtg taaaagaaag  780
gcacaactta ggaagttgtt attacttgtt atccaggtga aagacgacag tagcttgaat  840
gagtgtagtt acttagtgaa tgaatgaata aataaaatta aactccaagg gagagattta  900
ggatccacag gaagactgcc ttgtttcaaa tcacagctcc agcacccact agctgtactt  960
gctggggaaa cctcagtaca ttctttcatc cctttgtgcc a                        1001

SEQ ID NO: 211          moltype = DNA  length = 701
FEATURE                 Location/Qualifiers
source                  1..701
                        mol_type = genomic DNA
                        organism = Homo sapiens
SEQUENCE: 211
tgtaaaagaa aggcacaact taggaagttg ttattacttg ttatccaggt gaaagacgac  60
agtagcttga atgagtgtag ttacttagtg aatgaatgaa taaataaaat taaactccaa  120
gggagagatt taggatccac aggaagactg ccttgtttca aatcacagct ccagcaccca  180
ctagctgtac ttgctgggga aacctcagta cattctttca tccctttgtg ccacagagcc  240
ttctttccca aaacggagat agcaataata cctaccttag cagtgcatta taaaaactaa  300
tgcattaatg ctcatagagc agttatcatc atgccaggca aatgataggc actccataaa  360
cgttaactac tgtgattgtt gttaaaagga tgatgtctga ggcagtacag tatctcatgc  420
agaaaagctc tcatcccaaa atgaatctct attctaatcc caactatacc ctgtagctct  480
gactgtgctc atgtggttgc rattaagcca aagcccaagg tgggaccaga tactgtccat  540
ttcatctcgg cttgtcatcc atcctcctca ggtctgcctg gtgctctgac atctggcttc  600
cactcatctg gggggaggaca gggagaagcc agacagccat gaatcctgct gtctgctcac  660
aaattcgcag tctagggagg gctaggggga gttgctgtca g                        701

SEQ ID NO: 212          moltype = DNA  length = 401
FEATURE                 Location/Qualifiers
source                  1..401
                        mol_type = genomic DNA
                        organism = Homo sapiens
SEQUENCE: 212
gtcacctagg tgctattggt agatacaaag tgttttatga gcgatgctgg taagagctct  60
tttccaagtt atctccccag gcacctctgc ctgaaattgg tggtggttac aagcagagtt  120
ttgaagaaag acctgggtct ggaccctctc tcccctgctt acagttgtgg gattccaaaa  180
aagctactgt ctctgtttct ratctggcgc tggggcaatg actcctgcct tacacagcca  240
ttgtgtgaat actaatccat gatgtcatac cgcacatgcc caagagcagg caggaggccc  300
tctccctcac ttcttccagg ctctgatgga atggcagctt agtaacagcc ttgctgtagt  360
caccccgtat tcagcagagg ctctcctcca gcccaacaca t                        401

SEQ ID NO: 213          moltype = DNA  length = 701
FEATURE                 Location/Qualifiers
source                  1..701
                        mol_type = genomic DNA
                        organism = Homo sapiens
SEQUENCE: 213
aaaggctctc cccagcctcc tgccctgctt caccattccc cagtgtcttt atctccacct  60
gaagtttcac atgtacttgt ctgtctctcc gaagaattta agtgccacga gggcacggtg  120
gtttattcac ctctttaata gtagctggca tgcagtaggc actctgtagg catttggaat  180
taatgaataa gtaaataacct ggattaatta actagtattt caagggagag tgggatcctt  240
gggaaagaag gatagattac accacagttt gctatagaag gatgcctaag attggtcttt  300
gtcagttaat tactcactga tataacattg gctagtcagt tgctcttgag cctcagtttt  360
ccatatctaa aaaagagaca atgtcactta ccatacttac ctcaaacagc tagatggagg  420
ataaatctca aacatgggaa taagtctgct ttgaacactg taactcacca tgtaaaaatg  480
agaatttgga tttttttaag waacttagca gttaatttcc tgggtaatat cctaatagag  540
aaatgtccca cgtggtatgg gacaaaggag aatgcctcat ttggatccac atctgatttt  600
aaaccttgct gcatcaacct gacccaccca acacaacttc actcccttgg tcccagattg  660
gcaggcacac aagccctgag gacagtatgg cttcaggtct c                        701

SEQ ID NO: 214          moltype = DNA  length = 1001
FEATURE                 Location/Qualifiers
source                  1..1001
                        mol_type = genomic DNA
                        organism = Homo sapiens
SEQUENCE: 214
gccctgtcaa gcaagacgcg cagcttggca cagccagccc tgtagccagc ccaggcctcg  60
taatgggata cagagctcgt cgctaggtgc agcagagttt gcatcaggcg ttgtcactgt  120
ctggtggttg cctggtgacc ctaatggaaa atgagtggag gcagccccta ccacagaaac  180
cactccctca gctggcaggc ttgtcggaaa gcccagtgcc atgggagggg gaggggctgc  240
cacagaggag ctgtcaccca ggcgccctgt gtaggtggtg gcagggacgg ggagagaagg  300
gcgcagagcc acaggagggc tcagcagtgg tgtctgctct cccttctgca tgaattgttg  360
ctcataaaag atgggtgagc ccagcacagt aactaatgct tatccccagg cccaaattta  420
ggtaaaagca cacaaaaagt ctcatcagtg gtcaatgctc cacagctcca aacacaggaa  480
ggtgcattct caagctgtta rgagaagctc actcaagctg atggtattga cagccacagc  540
ccccatgcag ggaaggctgg acccgacacc tgcccacgag aagcagcata cctgggactg  600
```

```
gagggacttc ctggcctata agaagaacac taagagggga ggaggactcg ggctgattgg  660
gaaaacagat ggtgagctcc atccgtggga aaataaatga cagcgtgcat ttaagaggtt  720
gagccccaga gccaagcctg ctgaaatgcc agcttatcaa aagcacagga gcactgtgtg  780
ctagacgctc tatcatactc tcttccatcc tggtttctct taatcccaag ataatgtctg  840
taggcattgg aaagtcttgc ttgagagacg aagaaatgta ggctcagaga ggttgaacag  900
tttgtctgag gtcacacagc tactcaatca caggatttaa cacaggcttt tctgctttca  960
agtctaacat tccttctcct aacatcgtgg gagaaagtga t                      1001

SEQ ID NO: 215         moltype = DNA  length = 1001
FEATURE                Location/Qualifiers
source                 1..1001
                       mol_type = genomic DNA
                       organism = Homo sapiens
SEQUENCE: 215
gttaattgtg gctcaccaag gcttggagag agctggatga gaggggagca gagtccagcg  60
tgggtggggc tggactggca gtggcagagg agaggcagct gctgttcaca tcagggtctg  120
gatggccttg tcgccgcagg aggctgcgct gctccaccct cccaagcgtt tcccagctcc  180
gtcacagggt ctccgttccc accacagtgt gtcccagcag ttccatttgt atttgtaccc  240
agagagctcc actgaggcct gtggtcacag agtgactccc ttccatgttc tgccacaggt  300
tgcaagccat agggtgaagg tcacacagtt ttgtttggcc ataacagctg cctccatggc  360
aacagcgtgt gatatcactg gaaaagccat ttgtgggact ccaagctgga aggaaaaggc  420
agagttggag agagctgtag cgggagacag agaaagggca gggtctctcc ggatgctcca  480
aggtgctgga cgcacaggtc sctttctgta gtccttgtca tgtaagatct tttcatttag  540
gctaagcaaa tccagatgtt cttcaaataa ttcaggcata tttggcccaa gcataaactt  600
gtcttcattt ttcatccaat ctgacaaacg tttgcaatcg cctcactctg tgagttccag  660
gacaccttcg ggctggaagg ggttaatgag aacaagccct ccctggtggc ttcccttccc  720
cctggtgctg cccctcggcc cctcccaggc cagcaggatt tgctgtccaa aggccctcaa  780
aagacatcca agcagtcttt tcttagaaac aggaaactgt cttcggccaa gtacaaatga  840
agtgaagcac ccagaaacct gaggaccgct ccaaactgag gcctggaggc agacagggag  900
ggcccaactc ctggcagggc ctccaggact caggctctca tgaatgagac tgagctcagc  960
tgcagcctca gccattcttc gttgcactca acccattatg t                      1001

SEQ ID NO: 216         moltype = DNA  length = 1001
FEATURE                Location/Qualifiers
source                 1..1001
                       mol_type = genomic DNA
                       organism = Homo sapiens
SEQUENCE: 216
agggatagct gactatgagc ggccccactg ggctctcaag gtaccatgaa ggatccagtt  60
cccctctggc tgagctgttt gatcctaaga catccctgtt ggttggcagg gaccattttg  120
tcactgtttt ctgtcatgcc ttgttttctc attctttctg tcacatattt ctaagtgaga  180
gggaaagtta aagccacgga atcgcttatc atctcctccc tctgcctttg ggtttactca  240
gagaaagtca tatcttgaca ttcccaggag tattactatg cctttaccca ttttcagtag  300
taataataac caagttccct ttcccatttc cacctacatc cagccactga aatggaatta  360
acaagagtac cagaactaca tatattgcca gcagttattc ctgggaagat ggaagaagaa  420
aagtcctaaa catccaactc ctgggtacct gcttgcttga aactctaaac atcagtctta  480
ttcgctagtt atggaagtaa hgatatgtta ggtgatactc tgagaaagct gtgagctaaa  540
agttgcctta cattgcagaa ctctcagttt ccagagaagc agcagacaac acagattata  600
gactctgcag tcaaccaacc agtcctgtta agaacaaact cagccactta gttacgtgaa  660
tttggacacg ttgtttaatc actccccata cttgcctcag ttttctcata agcaaaatag  720
gcatattgag agtacattgc tcttaacatt gttgtgacaa tgaaatgata taatttatgc  780
agagtgaaca acactatgcc tgacacatag caagggctct acaaatgtta gatgttgttg  840
ttgttactat tattcggtat actggataat actgccagat tcaacatgtt tgtgcatttc  900
tctcaaattc gcggttgaaa gtatacaaaa aacaaaatca aaaaaatgtc tatttctctt  960
agccctgtgg tgtctctggc acaactcgtt ctaagaaaag t                      1001

SEQ ID NO: 217         moltype = DNA  length = 501
FEATURE                Location/Qualifiers
source                 1..501
                       mol_type = genomic DNA
                       organism = Homo sapiens
SEQUENCE: 217
tttctcataa gcaaaatagg catattgaga gtacattgct cttaacattg ttgtgacaat  60
gaaatgatat aatttatgca gagtgaacaa cactatgcct gacacatagc aagggctcta  120
caaatgttag atgttgttgt tgttactatt attcggtata ctggataata ctgccagatt  180
caacatgttt gtgcatttct ctcaaattcg cggttgaaag tatacaaaaa acaaaatcaa  240
aaaaatgtct mtttctctta gccctgtggt gtctctggca caactcgttc taagaaaagt  300
tagagctagg tatggtgaat tgtcccaaca acaaagcttt catcaaacaa agcagcaggg  360
agattctcaa gtctcctttt attattatta ttgtacttta agttttaggg tacatgtgca  420
caacgtgcag gttggttaca tatgtataca tgtgccatgt tggtgtgctg cacccattaa  480
ctcatcattt acattaggta t                                            501

SEQ ID NO: 218         moltype = DNA  length = 1001
FEATURE                Location/Qualifiers
source                 1..1001
                       mol_type = genomic DNA
                       organism = Homo sapiens
SEQUENCE: 218
ccccggtgtg tgatgttccc cactctgtac ccaagcattc tcattgttca attctcatgt  60
```

```
gagtgagaac atgcggtgtt ttttaatggg ctttccacct ttgtctgtag cgggggcaat  120
gttatctatt cagttcagtt cagacacaca agtgggctcc caacttccct caggctccaa  180
tattagccat tttcctctta gtgtgaattc caccagaata ttatcattcc cccactgtag  240
tagtgtggaa acacttatac tcagtgtcaa atggaaattt gggagcagat gtgcaagcac  300
gaagttcttc cagggaattc taaaagacaa acagggaagg cacttgtata tgggaacctc  360
aagtgctcgg ttgtcaagta gagcctcaat tcaaatcatc tcatttgtta ttttcataaa  420
ccctcaatgt tttctggaaa ctatattttc caggatgttt ctcacacttg gatgtagcaa  480
ggaaatcatt ttttatatca rgtgagtctc aaatttagtc catgaaattg agcaaattca  540
ttaatggaaa gacccttgga ctgagaattt attctactgt cactagagga ctttaatggg  600
ctaagaaaga gaagaaatta cagataatat ccaaagccca gcacgatacc ataaaggccc  660
ctcccagatg agtccaagac ctccagaaag aactaccaat gcctgaagtt ccagtaaaaa  720
cctccctcaa gaatgatcac attcataaca gaaagttatt actaccatca tccctggaga  780
atctcaaagc aaaatctatt atcctaatac agcatcactt gaattataaa gtctgatgaa  840
accagacttg gaggctaaat gatgtacaca gagttgcggc atctatcagg gagctcatcc  900
tagaacttga ttgtcataac aggttcattg caattttcgc tgcctgtgga actttgtgcc  960
ataacctgac tctccaacca aatgtgaatg tagcttaatt a                        1001

SEQ ID NO: 219          moltype = DNA  length = 401
FEATURE                 Location/Qualifiers
source                  1..401
                        mol_type = genomic DNA
                        organism = Homo sapiens
SEQUENCE: 219
tatattttcc aggatgtttc tcacacttgg atgtagcaag gaaatcattt tttatatcat  60
gtgagtctca aatttagtcc atgaaattga gcaaattcat taatggaaag acccttggac  120
tgagaattta ttctactgtc actagaggac tttaatgggc taagaaagag aagaaattac  180
agataatatc caaagcccag racgatacca taaaggcccc tcccagatga gtccaagacc  240
tccagaaaga actaccaatg cctgaagttc cagtaaaaac ctccctcaag aatgatcaca  300
ttcataacag aaagttatta ctaccatcat ccctggagaa tctcaaagca aaatctatta  360
tcctaataca gcatcacttg aattataaag tctgatgaaa c                        401

SEQ ID NO: 220          moltype = DNA  length = 1001
FEATURE                 Location/Qualifiers
source                  1..1001
                        mol_type = genomic DNA
                        organism = Homo sapiens
SEQUENCE: 220
gcagagcccc gaggcagata tggcatttac ggagacttta tcatggaagc acaacagctt  60
gtcctcagtg gaatacagca ggagatccct cgaagatctg tcaggcttgg ccatttagag  120
gcttggaccc ctgactcctg ccaagagcag taaggaagcg tgggggccaa cacctgtgca  180
catactctca tgccctcact ctccactcat tgtgcagagc agaaaccaga ctcagaagtg  240
ctccaggcca ggctttcttc accaaccttc accagcctct gctggatttg gccgtttgca  300
gtgaaaaatg agcctgaaag ccctggaggc ttcctggtga tttaccgaga attttacttc  360
cacatgggct ttccagctgc agccaacccc aagaggcaga ggtaggaaga ggaagaaaat  420
cataaatgga tagtaagatg agaaacagat gtttggaggc ttcactggaa gggaattctc  480
cacctctact ccctttcttc rtgagatgag aaggctcggg ccctaatgag cagtttctca  540
ctatacctgc aattcatctc cttcccccac caccagctct ctcaagtgtc acttttcaag  600
ggtcttcctg gtcctgccac atgggcatca actttgttgg gtgatttgtt tctggtttta  660
gccaaaataa atgaatgcta ggtgctctga ccatagacac atgttagaca atctcctgcc  720
ctcagggtgc tcaccagccg gaatgaataa gcaggtgcaa gcgtctgccc cctgacagag  780
gcaaggactg gaccctgaaa acccacagga ggggcagcaa acccagcctt ggctcaagga  840
ggcactggag ggtcaaagga aagctcagct gagttgtaaa gatgttaatc aattgaaaat  900
ggatagaagt cactttggag gtattaacct agcaggcttc aagagagttg tatatttatt  960
cagtgtaaca caagggttga gagcaacatc cccaaagcta g                        1001

SEQ ID NO: 221          moltype = DNA  length = 601
FEATURE                 Location/Qualifiers
source                  1..601
                        mol_type = genomic DNA
                        organism = Homo sapiens
SEQUENCE: 221
ccacatggac tggtgcacaa cccatctcta gcccccagct ctctctcacc cccgctgagt  60
caggttctca ctgctgttca catcatattt ttgacgccca aattttctca tagcattcct  120
caatttaaga ttcttttgtg gtccccccatt ggctattgaa aagtaacgga attccttaat  180
gtgacagatc cctttgtgaa tcgattctta ttttcctatc cagtcccagc tctggacacc  240
ctcagtgcct ccacccagtg gatgtattct tccgtgaaac cactgtgctc ctgctgtgga  300
racgttgtct cccataacag gaacagtgtc tctgtcctgt ccaccaaaca ctccgacttt  360
ttccctaaga attttcacat tgcttcgtct gtgacaacgt ctgtgattcc tttgggtccc  420
cctttctcaa gttccttgtg ctctgcacct gtctacatga atgatgggga gggttggaag  480
gagcagaaca tattaatagc actctccttt tctacccaag ctctgcaaaa attaagaaat  540
aaaaataaaa acaaaaaaca gcatatgaga caggatacca aaatatgacc cttattactg  600
a                                                                    601

SEQ ID NO: 222          moltype = DNA  length = 401
FEATURE                 Location/Qualifiers
source                  1..401
                        mol_type = genomic DNA
                        organism = Homo sapiens
SEQUENCE: 222
```

```
gggagcttcc taatgatatt tccagattag gctaacttac actcccaaat gcaggctcag  60
atgaacaggt cacctttccc cactcggggg cctataccag tatgagaatt atggcatggc  120
ctaacaaaaa caaatataaa tccctcacgg gcaggactaa tttcttcttt caaaacccac  180
ccattaaaca tagtattcct rggaggggag caagcaagga gcagagaaaa gctgggagtg  240
tcacactaat ggagctcctt ccacattaaa ggaaacacca ggagtaaaga agaaaagtgc  300
caacatgtta tatagtattt tcatttttgt gtctcttgat gaaactaaaa gctatttgta  360
ggcgagaata atgctttttc atctaatatt ttcatcctat a                      401

SEQ ID NO: 223          moltype = DNA  length = 701
FEATURE                 Location/Qualifiers
source                  1..701
                        mol_type = genomic DNA
                        organism = Homo sapiens
SEQUENCE: 223
aaccccgtct ctactaaaaa tacaaaaaaa aaaattaact ggatgtggtg gtgggcgcct  60
gtaatcccag ctactccaga ggctgaagca ggagaatcac ttgaacccag gaggtggagg  120
ttgcagtgag ccgagatcat gccactgcac tccagcctgg gcaacagagg gagagtctgt  180
ctcaaaaaaa aaaaaaagaa gaaagaaaga agaaagaaag aaagaaagaa agaaagaaag  240
aaagaaagaa agaaagaaag aaagaaagaa agagaaagaa agaagaaaga aagaaagaaa  300
gaaagaaaga aagaaagaaa gaaagaaaga aaagaaaaaa gaaaagaaaa gaaaagaaaa  360
aaaaagtatt atgtgcatgg actttgaccc agtagagtgg aaacagagtt gcttgccagg  420
cactctgttc tggaccctgt ctgcccaccc tcaagagaag cccccagtga tgggtgtctt  480
tccccacagc cacagctaca raggcaggag taagcactga gccccgtcct ctggattttt  540
aaattgtaac agagaaagag agagatttgg cctcttgtta tgtagctgga ccgatgatgc  600
ataaattctg gaattgctgc aaggtcatgc ttcctatcat gtggaacaag aaaaacagtg  660
gaaacttgcc taccaagaga gagaagaatg ccacagatgc a                      701

SEQ ID NO: 224          moltype = DNA  length = 1202
FEATURE                 Location/Qualifiers
source                  1..1202
                        mol_type = genomic DNA
                        organism = Homo sapiens
SEQUENCE: 224
tttagaaaca gctgctcaca tataccatta gtagaaatat aaagataaat cattttggag  60
agaaatctgg gaatatacat taaaagtgtg gctcatgcct gtaatcccag tactttggga  120
ggccgaggtg agtggatcat aaagtcagga gttcaagacc agcttggcca agatggtgaa  180
accccgtctc tactaaaaat acaaaaaaaa aaattaactg gatgtggtgg tgggcgcctg  240
taatcccagc tactccagag gctgaagcag gagaatcact tgaacccagg aggtggaggt  300
tgcagtgagc cgagatcatg ccactgcact ccagcctggg caacagaggg agagtctgtc  360
tcaaaaaaaa aaaaaagaag aaagaaagaa gaaagaaaga aagaaagaaa gaaagaaaga  420
aagaaagaaa gaaagaaaga aagaaagaaa gagaaagaaa gaagaaagaa agaaagaaag  480
aaagaaagaa agaaagaaag aaagaaagaa aagaaaaaag aaaagaaaag aaaagaaaaa  540
aaaagtatta tgtgcatgga ctttgaccca gtagagtgga aacagagttg cttgccaggc  600
actctgttct ggaccctgtc tgcccaccct caagagaagc ccccagtgat gggtgtcttt  660
ccccacagcc acagctacat aggcaggagt aagcactgag ccccgtcctc tggattttta  720
aattgtaaca gagaaagaga gagatttggc ctcttgttat gtagctggac hgatgatgca  780
taaattctgg aattgctgca aggtcatgct tcctatcatg tggaacaaga aaaacagtgg  840
aaacttgcct accaagagag agaagaatgc cacagatgca cagacaggag aaacaagaga  900
tggagaggaa gttctgacag tttttcagtt cctggctctg gaacctgcac agttccagct  960
gccttcctga caatcacaga ggcccatcac tcacctctga atctagaaat ttttttttt  1020
tcccaaggag agctcaagat gcttcctatt acttgcaact aaatgagtct caacagtaat  1080
tccattccta agagttttag ccttaagaaa cagtttcaga cacacagttg catatgtaaa  1140
gataaatacc atagtattgc atgtaatttt gataaaatga tcgatttgga tattaatgtg  1200
ac                                                                 1202

SEQ ID NO: 225          moltype = DNA  length = 1001
FEATURE                 Location/Qualifiers
source                  1..1001
                        mol_type = genomic DNA
                        organism = Homo sapiens
SEQUENCE: 225
gatgcacaga caggagaaac aagagatgga gaggaagttc tgacagtttt tcagttcctg  60
gctctggaac ctgcacagtt ccagctgcct tcctgacaat cacagaggcc catcactcac  120
ctctgaatct agaaattttt tttttttccc aaggagagct caagatgctt cctattactt  180
gcaactaaat gagtctcaac agtaattcca ttcctaagag ttttagcctt aagaaacagt  240
ttcagacaca cagttgcata tgtaaagata aataccatag tattgcatgt aattttgata  300
aaatgatcga tttggatatt aatgtgactc ttgtcaaaca aaccatctta atagtagaaa  360
catattaata tcattaatta atgcttaagc cttacttcat attcattttg tctcaggggt  420
tggattttgt gcttcacata catctatttt aatcctcaca gcagccctag aagatgggta  480
ctattacctt aagataaaca rgtaaagtgt ttagcatatt gttttgcata tagcaggact  540
tgcaaaatag ctaactacta ttattccaat ttctacagat gagaaaatta gaacttttttt  600
agctttatag ccagaaattc caaaggtgct cagataaatg tagtgggaaa atgtaatgat  660
gtgtgggaaa gtgagacagg cagagcacct aaaaggtacc ccctcctacc tattgatctt  720
gacagcaagt atcagatggc tgtacttaga ttgagtgtta gaggctaata cagtaattca  780
agatgtgtaa aagtcaacaa aaagaattag ttatcaaaca agttacattc aaggtatgga  840
atgaactata cacaaacggt caacagacat gcaaacacac atgcactttt ctaccaataa  900
cagcagatat agccacacgt tggcagtta ataccaagtt ttgcttgttg gctaagggaa  960
ctttcagtat cctaattctg attccatttt ttttttcact g                      1001
```

```
SEQ ID NO: 226          moltype = DNA  length = 3766
FEATURE                 Location/Qualifiers
source                  1..3766
                        mol_type = genomic DNA
                        organism = Homo sapiens
SEQUENCE: 226
ctaactgggc tatgaatgac ttgagcttgt ggtcttggcc tcattaacac tggacaacaa  60
ccaactgagc taatcagcca ctgctgacat tacagagaaa ctttattgag gtataattaa  120
agtacattaa accatacatg tataaaatgt acaatttgat cagcttttga atacgtatat  180
actcatgaaa ccatcaccac aatcaaaata acaaacattt aatcaactcc agaagtttct  240
ttgtgtccct ttataatcca ttattcctgc acctccatcc tcagcaactg ctgatctgtt  300
ttctctcagg acagaataat ttgctttttt ctagaatttt atataactgc aataatacag  360
tttgtactat ttggcttgtt atattttaat atctttagaa actagatatg ccccctctct  420
catttttgat attggtagtt tgtcttttct ctttttgtgc taataagtct agctagaaga  480
ttattgatct ttatgagttt tgcaaggaac catctcctga tttcattgat ttttttcaa  540
ttgtttttct gttttccagt gcatttattt tggctctgat catttcatgt cttttccttt  600
ctttgggttt tatttgcttt tattcttcta gtttcttaag gcagaagctg agttcattga  660
tttgaagatg tttttctttt ttaatatgaa accttttgt tctataaatg ttcccctaag  720
tgctgcctga gctacatctc acatattttt tgtattttgt tttcattttc atcgagttcc  780
aaatactttc cagtttctct tttgattttg tcaatgatcc atgagttatt ttaaatatta  840
tcttgagact acttgggata tcccagatat ctttctgata cactcatttc tgatttaatt  900
caattgtggt tactgtagga cagattttct attacttgac tcctttttaaa tttactggga  960
tttgttttct cattcaacat atggtctctc ttgggaaatg tttcattaat acttaaataa  1020
aaagtatatt cggtggttgt tgttgttggg tgcaatgttc cgtaattgtc agttaggtca  1080
atttagttaa tagtgttatt caaatcttct aaatacttat ggactttctg tctatatgtt  1140
ctatcaatta ctgaaatctc tgactataac tgtgaatatg tttgtttttc cttaagtttt  1200
gctccatgta ttttgatgct cagttattat atgtgtaaat atttaggatt gttatatcat  1260
cttgatgagg cgactacttt atcattatta aatggccctc tttatccctg gtaatctttg  1320
ctttaaaacc tactttttaa tatgaatata gcctcattag ctttattttg atgagtatta  1380
acattgtata taacttttca tctttttatt ttaatatgtt tgtatattta aagtgcattc  1440
cttataggta acatatagtt gagtctttct ttttatccaa tatgacacct ctgacttgac  1500
tttgaagtgt ttaaactttt tgtatttaat gtgaatatgt atatgatcgg ttttaaattt  1560
accagctggc tagtttttc tgtttattcc atctattatt ctttgttccc tttttcctct  1620
atgctttctt ttgggttaat tatactttta aaaatatttc gtatatcctt tgttgtatta  1680
ttttagtggt tgatatagtg tcattgatta cgtctttaac ttatcacagt tatctttcaa  1740
gtaacattat accactttgt acatgrgtat tagaaaacct tgcaacaatg tacttccatt  1800
ctctgtctcc tgaattttat actactgttg tcgtcataca tattattttt atttctacat  1860
atgtaataag acctatatta cattgtttct gtgtttgctt taaaaaacca agttttcaat  1920
gaaatgttta aaatgagaaa atatatttgt ctacataatt ttttttcaag gctcttaatt  1980
ctatccagta tatcagactt ctatctggta tcatttttct tctgcttgaa agatgtcttt  2040
tatcagggat gccctctctt accactccta ttcaacatag tgttggaagt tctggccagg  2100
gcaatcaggc aagagaaaga aataatgggt attcaattaa gaaaagagga agtcagattg  2160
gccctgtttg cagatggcat gattgtatat ttagaaaacc ccatcatctc agcccaaaat  2220
ctccataagc taatcagtaa cttcagcaaa gtctcaggat acaaaatcaa tgtgcaaaaa  2280
tcacaagcat tcctatacac caataacaga aaaacagaga tccaaatcat gagtgaactc  2340
ccatttacaa ttgctacaaa gagattaaaa tacctaggaa tccaacttac aagggatgtg  2400
aaggacatct tcaaggagaa ctacaaacca ctgcgcaacg aaataaaaaa ggacataaac  2460
aaatggaaga acaatccatg ctcatggata ggaagaatca atatcgtgaa aatggccata  2520
ctgcccaagg taaatttata gattcaatgc caccccacca agctaccaat gactttcttc  2580
acagaattgg aaaaaactac tttaaatttc atatggaaca aagaaaaacc tgcattgcca  2640
agtcaatcct aagcaaaaaa aaaaaaaaag ctggaggcat cacgctacct gacttcaaac  2700
tatactacaa ggctacagta accagaacag catggtactg gtacaaaaac agagatatag  2760
accaatggaa cagaacatag gtctcaggta taacaccaca catctacaac catctgatct  2820
ttgacaaacc tgacaaaaac aagaaatggg gaaaggattc cctttttaat aaatagttct  2880
gggaaaactg gctagccata tgtagaaaga tgaaactgga tcccttcctt acaccttata  2940
caaaaattaa ttcaagatgg attaaaggct taaatgttag acctaaaacc ataaaaaccc  3000
tagaagaaaa cctaggcaat accattcagg acataggcac gggcaaggac ttcatgacta  3060
aaacaccaaa agcaatggca acaaaagcca aaatagacaa atgggatcta attaaactaa  3120
agcacttctg cacagcaaaa gaaactacca tcagagtgaa caggcaacct accgaatggg  3180
aggaaaatgt ggcaatctac ccacctgaca aagggctaat atccagaatc tacaaagaac  3240
ttaaacaaat ttacaagaaa aaacaacccc atcaaaaagt gggcaaagga aatgaacaaa  3300
cacttctcaa aagaagacat ttatgcagcc aacagacaca tgaaaaaatg ctcatcatca  3360
ccggtcatca gagaaatgca aatcaaaacc acaatgagat accatctcac gccagttaga  3420
atggtgatca ttaaaaagtc aggaaacaac agatgctgga gaggatgtag agaaatagaa  3480
acacttttac actgttggtg ggagtttaaa ctagttcaac cattgtggaa gacagtgtgg  3540
caattcctca aggatctaga actagaaata ccatttgacc cagtgatccc attactgggt  3600
atatacccaa agatcataaa tcatgctact ataaagacac atgcacacgt atgtttattg  3660
caacactgtt cacaatagca aagacttgca tccaacccaa atgtccatca atgatagact  3720
gaattaagaa aatgtggcac atacacacca tggaatacta tgcagc                3766

SEQ ID NO: 227          moltype = DNA  length = 938
FEATURE                 Location/Qualifiers
source                  1..938
                        mol_type = genomic DNA
                        organism = Homo sapiens
SEQUENCE: 227
ctggcactct gctcattttt ctttgcaccc tttattttat atgtgcttta ttatgggtcg  60
tttctatgct gggacttcac agtgttgaat ctgccattaa tcccacccaa tgtatctttc  120
atgtcatatg ttatatagct ctcaactgca gaattttgac ttaggtcttt tgtatcgcat  180
```

```
ttggcatgtt tggtcttttc tctagcttct tcaacatgtg aaattgttac tctcttttaa  240
tgtccttggg tactaattct atcgtctgtg tcatttcttg gaaattttca actggctgat  300
tttttcttc attatgggtc atattttcct gcttcttagt atgcctggta attctttatt  360
ggatgccaga cattgtggac tgggtggata tttttgtatt cctaaaaata ctcttgagtt  420
aagttacttg gaaatagttt gaccctttcg agtcttgcct ttaagcttta tttggcagga  480
acagaacagc atttactctc rggctaattt tgctttacta ttgaggcaaa acctttcagt  540
actataccca atgcccataa attataaagt tcaagaacag gcaaaactat gccaatagaa  600
atcagaatag tgattgacgg tagggtgtgg atattggaat tttctggggt attgcttaca  660
caaatgtacc tattaaaatt catcaaactg ctcaaaatct gtgcatatca ctgtatatca  720
attttacctc tataaaaatc atgtttggta tcaaatatat gtgtacataa ttaaatgctg  780
aaaagattta tactaaaatt tcaatagtga agaatatcag gtagttttct aattggcttc  840
tgaatatttt catgttatct aaattttcaa tatatataac cttttaaaaa tacataaaac  900
taatatttaa tgaaacaatt taagggggac tctctacc                         938
```

```
SEQ ID NO: 228          moltype = DNA  length = 401
FEATURE                 Location/Qualifiers
source                  1..401
                        mol_type = genomic DNA
                        organism = Homo sapiens
SEQUENCE: 228
acaatataac aactctatca agtaggtatt atcccatttg caaaagagaa aacagtgatt  60
cagacttatg gttatgtgtc caaggaccct caacttgatc ttaggtctgc ctgcttctga  120
agtcggtatt ttgattctaa gagaattaag ccctcaagac ggatttctga aattcagaga  180
gtaaagaatg cttggtagga ragaagaatc ccagaaatac attactgtct acgagcatag  240
gaattggcac attggactct gggagttaac tattaaaatg ggaaagtgaa ttatccaaat  300
gtcagagtca caaatcaagc acagttaatc tgaaacccaa gaaagtctga cctgagacaa  360
ggaaagaggt gggtggctca gaggaaaaaa aaaaaaaaaa a                     401
```

```
SEQ ID NO: 229          moltype = DNA  length = 1001
FEATURE                 Location/Qualifiers
source                  1..1001
                        mol_type = genomic DNA
                        organism = Homo sapiens
SEQUENCE: 229
gggctgtggg agagcacacc catgaggttg ctcagggagc aatgggccac agcagttttc  60
cctgtgaatt gtgttcaggt aagaccctgc agtcagacca gctcactcct cctttgctat  120
ttctttatat atagtctctt tccattccga aaatgtactc tgagccctgg cctttaacag  180
cttcatttgt tttccttcat ctcccagttt acaactgtga aggaaacatt cattgatcaa  240
gttctttcag cttggaatgg agtctctgac tcccaaaaat ctctcccagg accaactgca  300
agggggtagt ggatctagga ttaaggctgg agcctgaagc actgctgaga atggggagtc  360
tgacacgtaa tgacctccat atatacaagc tggtcagtgc tctctcagag cctgcatgtg  420
gctttgtcca gagaatatga atcccagttt gagcagcaat atggatcaga gttggtagag  480
aggaagattg aggctctcac vctaggatgt cttcagcatc cttcttgtat ccttgtgtgc  540
aaaatgggag cctgggaaag gaactagaag aactgaaccc catccctctg atacatacac  600
attgcttttt tccttcttta tagcatagct tggctgtcca aatgttctgg cagagaccaa  660
gctccaggct cagtgggggg ttctaatttt ccatggctca ttcacttctg agaactttgg  720
ctcagttgca taatgggggg ctacttcctg ccagttgtgg ccctgttgtg tgataccttc  780
tgacacatac gttttttga aaaaagattg tctgctggga actggactga aaccaacata  840
taaccgtttg tttcatactg gttaggaagc caccaggaag gcctacccaa agtggtttta  900
aatacataca cacacagtcc tctcctctta gagccaagaa caggccatta gtgatgtgtt  960
agaaaatcca ggctgacctt ctcagtcatg agggaagctc c                     1001
```

```
SEQ ID NO: 230          moltype = DNA  length = 501
FEATURE                 Location/Qualifiers
source                  1..501
                        mol_type = genomic DNA
                        organism = Homo sapiens
SEQUENCE: 230
cacacagtcc tctcctctta gagccaagaa caggccatta gtgatgtgtt agaaaatcca  60
ggctgacctt ctcagtcatg agggaagctc cctgggccca ccagcaggct tttgccaaga  120
atgggctcca tcttgagccc acagctcttc cctagcttcc cagcagaagc aaggggagag  180
tggagaagtc aaacacttct tgagcattgc ttactatatg tcaagttcta ccctggaccc  240
tcaatagaaa statttcact gatcctcaca atagatctgt ggggtaagtg tcactattgt  300
tattttgagg aaactgaggc tcagaaaagt tacatgtatt cccaaagtca catagtaaac  360
tgagtgtgta aacttgagtg gtagagtcag aatttaaaca ctgattttta tctgttgcaa  420
atgttgggct tttcccacca ccagcagaaa tcttgctggc cctcagcaaa tattccttta  480
cagcagtcat ttcaaaactt t                                           501
```

```
SEQ ID NO: 231          moltype = DNA  length = 1001
FEATURE                 Location/Qualifiers
source                  1..1001
                        mol_type = genomic DNA
                        organism = Homo sapiens
SEQUENCE: 231
cttagagcca agaacaggcc attagtgatg tgttagaaaa tccaggctga ccttctcagt  60
catgagggaa gctccctggg cccaccagca ggcttttgcc aagaatgggc tccatcttga  120
gcccacagct cttccctagc ttcccagcag aagcaagggg agagtggaga agtcaaacac  180
ttcttgagca ttgcttacta tatgtcaagt tctaccctgg accctcaata gaaagtattt  240
cactgatcct cacaatagat ctgtggggta agtgtcacta ttgttatttt gaggaaactg  300
```

```
aggctcagaa aagttacatg tattcccaaa gtcacatagt aaactgagtg tgtaaacttg  360
agtggtagag tcagaattta aacactgatt tttatctgtt gcaaatgttg ggcttttccc  420
accaccagca gaaatcttgc tggccctcag caaatattcc tttacagcag tcatttcaaa  480
acttttctga ccctatactc rcatcagtaa acatttttaa gaaccacctt caatacagac  540
atatttattt atttataaac tccacgcact agctaatatc tgttagcatt gcctggtaat  600
ataataccc agagcactaa tcatcattaa tgacaataaa tatatatcca tgtttaatgt  660
agtcttcatg acttggaaaa ctttttggcc agatcttgtg aaatctaatt aaattgcttt  720
tgttttagct tcaatacatg gctggcaaat aatttgttcc aggagtagaa gaaatgatat  780
ggcattcttc ttaccttctt gggcatgagt tgctcctgct gtcaacaatc tccagtttcc  840
ttacagaaga atttttaaga cacttttcca ttttttaaaa gtgattcggt taaaatggga  900
taatatggtt tgtaaatcga ctcactgtgt ttatgcaaga ccatggaata ctatgcaccc  960
atataaaggg atgagttcat gtcctttgca gggacatgga t                      1001
```

SEQ ID NO: 232 moltype = DNA length = 1001
FEATURE Location/Qualifiers
source 1..1001
mol_type = genomic DNA
organism = Homo sapiens
SEQUENCE: 232

```
atttttatct gttgcaaatg ttgggctttt cccaccacca gcagaaatct tgctggccct  60
cagcaaatat tcctttacag cagtcatttc aaaacttttc tgaccctata ctcccatcag  120
taaacatttt taagaaccac cttcaataca gacatattta tttatttata aactccacgc  180
actagctaat atctgttagc attgcctggt aatataatac cccagagcac taatcatcat  240
taatgacaat aaatatatat ccatgtttaa tgtagtcttc atgacttgga aaactttttg  300
gccagatctt gtgaaatcta attaaattgc ttttgtttta gcttcaatac atggctggca  360
aataatttgt tccaggagta gaagaaatga tatggcattc ttcttacctt cttgggcatg  420
agttgctcct gctgtcaaca atctccagtt tccttacaga agaattttta agacactttt  480
ccatttttta aaagtgattc rgttaaaatg ggataatatg gtttgtaaat cgactcactg  540
tgtttatgca agaccatgga atactatgca cccatataaa gggatgagtt catgtccttt  600
gcagggacat ggatgaagct ggaaaccatc attctcagca aactaacaca agaacagaaa  660
accaaacacc acatgttctc actcataggt gggagttgaa caatgagaac acatggacac  720
aggaggggaa cgttacacac cggggcctac caggggggtgg tgggctaggg gagggctagc  780
attaggagaa acatctaatg tagatgatgg gctgatgggt gcagcaaacc accatggcac  840
ctgtatacct atgtaacaaa cctgcacgtt ctgcacatgt atcacagaac ttgaagtata  900
tatatatata tatatataaa acaccataat atgctaaaag agaaatcagg gcaccagtag  960
gacctccccc acccaccttg cagaatttca ctttcctcac a                      1001
```

SEQ ID NO: 233 moltype = DNA length = 1001
FEATURE Location/Qualifiers
source 1..1001
mol_type = genomic DNA
organism = Homo sapiens
SEQUENCE: 233

```
tgagttgctc ctgctgtcaa caatctccag tttccttaca gaagaatttt taagacactt  60
ttccattttt taaaagtgat tcggttaaaa tgggataata tggtttgtaa atcgactcac  120
tgtgtttatg caagaccatg gaatactatg cacccatata aagggatgag ttcatgtcct  180
ttgcagggac atggatgaag ctggaaacca tcattctcag caaactaaca caagaacaga  240
aaaccaaaca ccacatgttc tcactcatag gtgggagttg aacaatgaga acacatggac  300
acaggagggg aacgttacac accggggcct accaggggggt ggtgggctag gggagggcta  360
gcattaggag aaacatctaa tgtagatgat gggctgatgg gtgcagcaaa ccaccatggc  420
acctgtatac ctatgtaaca aacctgcacg ttctgcacat gtatcacaga acttgaagta  480
tatatatata tatatatata waacaccata atatgctaaa agagaaatca gggcaccagt  540
aggacctccc ccacccacct tgcagaattt cactttcctc acagtgcttc gcacggatgc  600
aaatgactcg tgggagtctg agggtaccgg ggtccatata tacattcaat attagtacat  660
agaaaagtag ttcccatttt tagattgaaa gtacctatga atagaagctc taatggtttc  720
ttcccttatc tcgtgttcta ttctgcgcaa ttcctggagc gggcagtccc cgccttggag  780
actcctgcct tacaggaagg ggtcacatat tcctgaattg gaccccactc agatgcagaa  840
ggctaagagt ttggatgaga aaagcgggcc agtgaacagg agagccggtg ggtggggtgg  900
atggaaggag gtgcccactc tggagggcaa gagaaaggca cgaaagcatg gggccacatg  960
agcgcggcgt tctgggccat ccccggtgga ctcctgccta g                      1001
```

SEQ ID NO: 234 moltype = DNA length = 1274
FEATURE Location/Qualifiers
source 1..1274
mol_type = genomic DNA
organism = Homo sapiens
SEQUENCE: 234

```
cagagcacta atcatcatta atgacaataa atatatatcc atgtttaatg tagtcttcat  60
gacttggaaa actttttggc cagatcttgt gaaatctaat taaattgctt ttgttttagc  120
ttcaatacat ggctggcaaa taatttgttc caggagtaga agaaatgata tggcattctt  180
cttaccttct tgggcatgag ttgctcctgc tgtcaacaat ctccagtttc cttacagaag  240
aatttttaag acacttttcc atttttttaaa agtgattcgg ttaaaatggg ataatatggt  300
ttgtaaatcg actcactgtg tttatgcaag accatggaat actatgcacc catataaagg  360
gatgagttca tgtcctttgc agggacatgg atgaagctgg aaaccatcat tctcagcaaa  420
ctaacacaag aacagaaaac caaacaccac atgttctcac tcataggtgg gagttgaaca  480
atgagaacac atggacacag gaggggaacg ttacacaccg gggcctacca gggggtggtg  540
ggctaggggga gggctagcat taggagaaac atctaatgta gatgatgggc tgatgggtgc  600
agcaaaccac catggcacct gtatacctat gtaacaaacc tgcacgttct gcacatgtat  660
cacagaactt gaagtatata tatatatata tatataaaac accataatat gctaaaagag  720
```

```
aaatcagggc accagtagga cctcccccac ccaccttgca gaatttcact ttcctcacag  780
tgcttcgcac ggatgcaaat gactcgtggg agtctgaggg taccggggtc catatataca  840
ttcaatatta gtacatagaa aagtagttcc catttttaga ttgaaagtac ctatgaatag  900
aagctctaat ggtttcttcc cttatctcgt gttctattct gcgcaattcc tggagcgggc  960
agtccccgcc ttggagactc ctgccttaca ggaaggggtc acatattcct gaattggacc  1020
ccactcagat gcagaaggct aagagtttgg atgagaaaag cgggccagtg aacrggagag  1080
ccggtgggtg gggtggatgg aaggaggtgc ccactctgga gggcaagaga aaggcacgaa  1140
agcatggggc cacatgagcg cggcgttctg ggccatcccc ggtggactcc tgcctagggg  1200
aggggtgcgt cggcggcggc agcccagttt tctggatttc tttatttctg agtccaggtc  1260
tttcagaagc ctct                                                    1274

SEQ ID NO: 235          moltype = DNA  length = 1001
FEATURE                 Location/Qualifiers
source                  1..1001
                        mol_type = genomic DNA
                        organism = Homo sapiens
SEQUENCE: 235
tgggagctcc agagtgggcg aggacttcgg gcagacccgg cgttgctgtt ggacatcatt  60
cagaagtccc cgctcagcgg gggcagcccg aagagcaaaa caaacagagc gaggagtagt  120
ggaaaatgct gagtcctgga gctggccgga acggccttcg cctttccacg cccaaagcca  180
gccgctctgc ccacctgcag ctgcaatagc aagcagggcc gcagcaggca gggaggcctt  240
ggcaccagag cccgtccagg gctgggaagg cggggaacag acactcctct ctcttcagac  300
aggccctcca gagtcctcac cctgaaggct gaggtctttt tcttgttcca ggagtccagt  360
gaaaaaatag ttctcaaaaa cggagaaaaa gactttcttg aactgcagtt tcagatttac  420
taatagagtc catttacata gcacttacta aatgtcaagc accaacacag atgaattggc  480
aatcaccatg tcagtcctgc raggttggta cttttatccc catttcacag atgaaaaaag  540
ccaggcacag agaagtcaaa taacttaacc caagttcaca atgctcaaca atggcagggc  600
caggatttac cacctggttt aaaatttaaa acgtaggatt taaaacctac tttacagtct  660
taaaggtgac tgccttttct cttcagctta ttagatttcc tctctaggaa tacaagatgt  720
gcaacacaaa gagaggaaac tcaagatgga gagtaaaggg aatgaatgag agacaggaga  780
atcaccaagg actagaataa tacaaaagat ttatttaaaa agcaggtggc catcggccca  840
ggagaaggag tgtgagacca aggtacagaa gtggcaagaa atgctgagct ggggctggaa  900
ggtatgacag tactagtcag acaggcacct gttctgtcca aaacaggatt ccagaagtaa  960
tgtgaagagg tcacttggca aagggggctc acacagctct a                      1001

SEQ ID NO: 236          moltype = DNA  length = 501
FEATURE                 Location/Qualifiers
source                  1..501
                        mol_type = genomic DNA
                        organism = Homo sapiens
SEQUENCE: 236
ccattcctct aagccaagag ctcttgtccc cagaggaaag aggagaagga agaaaggaac  60
aaacaaatga acagaggaag gaatgaagag agagagagag aaggagggag gaagggctgg  120
aaggaagaaa ggaaggggct gtttttttc ttgtgtttgg aagaacaagc tgccaaccct  180
cattaaatgc ataggattgg ctttagagtt actacaccta aattctaatt ctgtctctgt  240
caccggttag raatgtgatc tcatggaaat cactgaaact cccttaacct gaaaccccat  300
gtctatacaa tgaggacact ggaattcacc tctaaggttc tctctggatc taaaatctac  360
actctgatga tactgagacc aaggacaggg actttgattg ttgccttttc atgccaccca  420
aggtctacat cctagcacag tgcccaccac ccatccacac cgaccagaca cccagggcta  480
gtgattctgt gttctcaaca c                                            501

SEQ ID NO: 237          moltype = DNA  length = 401
FEATURE                 Location/Qualifiers
source                  1..401
                        mol_type = genomic DNA
                        organism = Homo sapiens
SEQUENCE: 237
ctggcctttg ttgattccct aggttgctgt gggcagatga tcatcgccat cattactttg  60
gatgtcagga cattgagata caccaggcaa tctgatgcaa ctggctttcc cagggcagaa  120
gcatttgcca ggaaagtgga aacagggaaa gggactggaa cattgagtaa atcaggaaat  180
agcactgacc aagggacaga raggccagag ccactttacc ccctcatttg gggttctaaa  240
ttcttatcaa attttttttc ctcaagttca aaccttgtgg cattttcacc aattgatcaa  300
caactgcctt tatcagactc cttgaatctc tgcctcactg caaaaagtgc caggggaatg  360
cttttctctt ctattattta ggtgaggatt ctcacggcat g                      401

SEQ ID NO: 238          moltype = DNA  length = 1001
FEATURE                 Location/Qualifiers
source                  1..1001
                        mol_type = genomic DNA
                        organism = Homo sapiens
SEQUENCE: 238
ggcagatgat catcgccatc attactttgg atgtcaggac attgagatac accaggcaat  60
ctgatgcaac tggctttccc agggcagaag catttgccag gaaagtggaa acagggaaag  120
ggactggaac attgagtaaa tcaggaaata gcactgacca agggacagag aggccagagc  180
cactttaccc cctcatttgg ggttctaaat tcttatcaaa ttttttttcc tcaagttcaa  240
accttgtggc attttcacca attgatcaac aactgccttt atcagactcc ttgaatctct  300
gcctcactgc aaaaagtgcc aggggaatgc ttttctcttc tattatttag gtgaggattc  360
tcacggcatg gagggatctc acagagtagt gagatgccag cagcatgccg agccaatatg  420
cccataaatg caagggccag gtccttaatc cagccatgag gatggtcaag gatccctgta  480
```

```
tacaagccag agaagggact rtgtacaact agaactgagt cgcaaaccat cttccagagc  540
agcccctggg gaaaagcaga ggccaaacag cagtatggaa gtgaaaaggc tcacgtactg  600
aaagaagact ttgtccttgt cccatatttg atgtgtgaaa cgtacccctt agtaaccagg  660
cctgtggctc ccagagctgg tgagccatca gccagcatca tcaaaagaga cttttcagcg  720
ttctatgcca gcaatacggc atcatggaaa gaacagggct tagaagtcag atggttctct  780
gatgaacctg atgacctctt gtactctctt ccaccgtagg ctctagaata aaatgagctt  840
catgccaagt aaacatggaa tgtggataga tatctacaca ggggtcacaa aattaaattc  900
tacagggaca aggcaggaat gtcaatgtgt gggcctgacc tatgagagtt aaaatagggg  960
actgatatgc acctaaagga ggcagcttca gttcagtgcc c                      1001

SEQ ID NO: 239         moltype = DNA  length = 1001
FEATURE                Location/Qualifiers
source                 1..1001
                       mol_type = genomic DNA
                       organism = Homo sapiens
SEQUENCE: 239
gatgcaactg gctttcccag ggcagaagca tttgccagga aagtggaaac agggaaaggg  60
actggaacat tgagtaaatc aggaaatagc actgaccaag ggacagagag gccagagcca  120
ctttaccccc tcatttgggg ttctaaattc ttatcaaatt ttttttcctc aagttcaaac  180
cttgtggcat tttcaccaat tgatcaacaa ctgcctttat cagactcctt gaatctctgc  240
ctcactgcaa aaagtgccag gggaatgctt ttctcttcta ttatttaggt gaggattctc  300
acggcatgga gggatctcac agagtagtga gatgccagca gcatgccgag ccaatatgcc  360
cataaatgca agggccaggt ccttaatcca gccatgagga tggtcaagga tccctgtata  420
caagccagag aagggacttt gtacaactag aactgagtcg caaaccatct tccagagcag  480
cccctgggga aaagcagagg rcaaacagca gtatggaagt gaaaaggctc acgtactgaa  540
agaagacttt gtccttgtcc catatttgat gtgtgaaacg taccccttag taaccaggcc  600
tgtggctccc agagctggtg agccatcagc cagcatcatc aaaagagact tttcagcgtt  660
ctatgccagc aatacggcat catggaaaga acagggctta gaagtcagat ggttctctga  720
tgaacctgat gacctcttgt actctcttcc accgtaggct ctagaataaa atgagcttca  780
tgccaagtaa acatggaatg tggatagata tctacacagg ggtcacaaaa ttaaattcta  840
cagggacaag gcaggaatgt caatgtgtgg gcctgaccta tgagagttaa aataggggac  900
tgatatgcac ctaaaggagg cagcttcagt tcagtgccca tggtggttgc tatgaaggaa  960
tatgctagaa tccaaagaca tcccattaac ctactacggt a                      1001

SEQ ID NO: 240         moltype = DNA  length = 1001
FEATURE                Location/Qualifiers
source                 1..1001
                       mol_type = genomic DNA
                       organism = Homo sapiens
SEQUENCE: 240
ggtctgacaa ggccagggac attccacaaa ggatgacaca atatattcaa agattgggat  60
gttcgatgac ttccctatat tcctgttata tttctcacct tattaggaaa tctttatctc  120
caatggtcct gagctagtga gatcagaaag actaaactgc atccctctgt gcttgcctct  180
ggttggttga tttgtcctgc tttaatacat gatccagaca agaaagaatc aagccaaagc  240
cacagcatta tgaatgaaat tctttgtttt taatttcaca cagtttaaaa tacaatatga  300
aatcaggcta cagtatataa aaaactctcc agcaaaatga tgtgccagca tcagctacta  360
aaataaacaa acaaaaaact ccgccataag aatttttttg catttttttt taaaaaaaca  420
tcgacactta catcgctaca tctctaagct acctcagttc tgatttttaa aaagcacctg  480
cttttccttt ttttcatctt rcttctaaat tttcagcttt taaaaaatat aaattatatg  540
aaaatacaag ttggaaaata gtcaaacaca atataacatc tttttcatcc ctatacttct  600
cagcttaaaa aaaaagtatt cttaaaaaaa aaagttcaat aactgaggca gtattcctga  660
taattttatt ttaatatata tattttatat atgtatatgt atacatatat ttatggttcc  720
ttgaaacttc tttggaatgt aggtaagagt tcaacaaatt tatatagacc ccaacagagt  780
aagcggcatg cacagcatga ctagaagaga gatggtgtat ttctcaccat gaaggttagg  840
caggttaatg ctgtaaaacc cagagtgttc atctccaaag tgaggaaaag cacatctgat  900
ctttgaatgc tacctccaat ccccacagcc acaaaaatca gggctctatg taggggaagt  960
ccctctccag aatggagaag ggaacaaaag tgactctgaa c                      1001

SEQ ID NO: 241         moltype = DNA  length = 401
FEATURE                Location/Qualifiers
source                 1..401
                       mol_type = genomic DNA
                       organism = Homo sapiens
SEQUENCE: 241
aattttattt taatatatat attttatata tgtatatgta tacatatatt tatggttcct  60
tgaaacttct ttggaatgta ggtaagagtt caacaaattt atatagaccc caacagagta  120
agcggcatgc acagcatgac tagaagagag atggtgtatt tctcaccatg aaggttaggc  180
aggttaatgc tgtaaaaccc rgagtgttca tctccaaagt gaggaaaagc acatctgatc  240
tttgaatgct acctccaatc cccacagcca caaaaatcag ggctctatgt aggggaagtc  300
cctctccaga atggagaagg gaacaaaagt gactctgaac cctaaagcca aaaccaacaa  360
aggttaaggc atctctggga aaataagggt ttcacccagc t                      401

SEQ ID NO: 242         moltype = DNA  length = 601
FEATURE                Location/Qualifiers
source                 1..601
                       mol_type = genomic DNA
                       organism = Homo sapiens
SEQUENCE: 242
acattagtct ctttctctgt taagccagag ccttcaagct tctgagaagg cccttctccc  60
```

```
tctcctgaaa atttgctcaa gaatttctgg tcccacccac cccacaagtc ctggctttcc  120
tttcccaact gcgcacaatt gattacagct gcaactgact tagctcccac ccctgaaggt  180
aaaaaatgag ttctggaaaa taaaaaatag aataacaatt caaaattcag agtccaacca  240
acacggctgt ccttggaagg tctcagcagg gtttccccag ccccttcagt gccatcactc  300
rtcggcatct ggcttgacgt ccagcatggc gtgcagctcc tcaggggtgt accccagcag  360
gctctgcagg tcacacacaa agcggtacac gtagcgtttc cccgctgtct tgtggatgat  420
gtttttgtcg taatagtagc gtaggccacg gctcagtttc tcataattca tcttaggttt  480
gtttttcctc tttccccatc tcctggccac ctgaaattta aaaagaaaaa taaaggagga  540
gtaggcaaaa atctacaaga caggccaaat atatatgttt ctatgcctat gctataccca  600
t                                                                  601

SEQ ID NO: 243          moltype = DNA  length = 1001
FEATURE                 Location/Qualifiers
source                  1..1001
                        mol_type = genomic DNA
                        organism = Homo sapiens
SEQUENCE: 243
atacccattc atggtgaccc atgatgctca agtaagatga tttgagattc atgtagatat  60
agaaaatatt tttcgggcct atctcctgaa ttccattttt catgggttgg gcaaggatgg  120
gagtcacaat gattctttaa gttgatgaaa acacagtgac cctgaactag gattaaatat  180
gtgactttaa aaaacaaaca aaaagccaca ctatacattc tcctctttcc gcatattatt  240
agtaaaatct ccttgctttg caagcatgaa atctaacagg gaagtgtgaa gcggaggagc  300
tgagctgcaa tcatacctgc ctttcatcaa caggaagtgt ttttttttcca taccagggca  360
caaatatttt ctcatgtctg ccagaacaaa gatgttgtct ctcctgttca ttgtttttta  420
tcctcagaat tgggcatggc acggaaccac tactccataa acatgtgtgt aatgaaataa  480
gaaactaatg agccaatctc rcaaggcctc ttgaactgtc tggccccttt cacactcaca  540
gagccaccgg gctaggaaga ggctaagtca caggaggcag ctctatgggt gataactgac  600
ctactgccag gcacgttaat gccttctatc agctaatcct gtaagacaaa tggggtaaca  660
tagatctttt ctctattttc caaataatga acctggagct cagacaggct acctagcttg  720
ctccgggtgg caagtggcag agctgggaat cccaatcctg gaacacgtca ttcaggccca  780
cgccacccct tccaggagtt ttctctcatc cttcctcaac acagtactcg caagcccctc  840
cttccttacc tcatctgggt cagaaagttt gaattcccag ccatctcctg tccagctgat  900
aaaagactga caggatttat cagtgagtaa ttccagaaga aactgccata gctggattgg  960
tccactgcct agaaacacaa gccattgtga atcattacac c                      1001

SEQ ID NO: 244          moltype = DNA  length = 1001
FEATURE                 Location/Qualifiers
source                  1..1001
                        mol_type = genomic DNA
                        organism = Homo sapiens
SEQUENCE: 244
cacaaatcag gggccacagg ctccctacta cagagcagtg cttatgagcc ataacttgtg  60
tttggaactg gcaaagacat tcattccttc gttaatatgt ttcttacttc tgaaggcaaa  120
aataatgact tagtttttgc aggtgtaaaa gattatgctg ccttagaata tcccagagga  180
taggcacagt gttctctttc tagaatttgt ttagcaataa aaatgaaccg atccttaagt  240
taatcaaaat aaagcacttg acacattttc ttccatgctt ttgttttata gggaggcctt  300
tgtcttttct atctgttcga gctcataaca cttcctccga catgtgcact gtctgttgcc  360
ttcattttct cctggctgga tgggctgaga gaagagggat gtgggagtgc cgtgtgtggg  420
gattagctgc gtagagtgct gaatatctgg tgtaatgatt cacaatggct tgtgtttcta  480
ggcagtggac caatccagct rtggcagttt cttctggaat tactcactga taaatcctgt  540
cagtctttta tcagctggac aggagatggc tgggaattca aactttctga cccagatgag  600
gtaaggaagg aggggcttgc gagtactgtg ttgaggaagg atgagagaaa actcctggaa  660
ggggtggcgt gggcctgaat gacgtgttcc aggattggga ttcccagctc tgccacttgc  720
caccccggagc aagctaggta gcctgtctga gctccaggtt cattatttgg aaaatagaga  780
aaagatctat gttaccccat ttgtcttaca ggattagctg atagaaggca ttaacgtgcc  840
tggcagtagg tcagttatca cccatagagc tgcctcctgt gacttagcct cttcctagcc  900
cggtggctct gtgagtgtga aaggggccag acagttcaag aggccttggg agattggctc  960
attagtttct tatttcatta cacacatgtt tatggagtag t                      1001

SEQ ID NO: 245          moltype = DNA  length = 401
FEATURE                 Location/Qualifiers
source                  1..401
                        mol_type = genomic DNA
                        organism = Homo sapiens
SEQUENCE: 245
tcaacactct gacagtcaat ttattctatg ctaaaaggtt tatatcacac cgatttcctt  60
tgaggatact tttctcatct gaaatgacaa tgccaccagt gattcttaat ttataggtgt  120
cggtggagag acaaataggg gttcaaaagt ccatgcttct tgttacactg ccccttataa  180
cataaacaaa ctgggcagag rgggactggg aaagacccag tccatgtctc tggatacagc  240
ccaggaagca ccagctccta caggaaagct ttgctcacta aggctctaat ttttcaccgg  300
agttgcaaat ttgtctgatc caaagtaaac tgagatttaa caggaaacaa actttaagtt  360
ccctctcaat ctaaaaaaga aattgccttc ataatccata a                      401

SEQ ID NO: 246          moltype = DNA  length = 601
FEATURE                 Location/Qualifiers
source                  1..601
                        mol_type = genomic DNA
                        organism = Homo sapiens
SEQUENCE: 246
```

```
ggcaacctcc aatgaagtaa agaaacagct actgacacga gctatcatcc cacagccaaa  60
ggaagtcctc ctccagtaac aacttcctaa tggtggtttc caaggctcct ctcagcactt  120
gccacgctaa atatgaaaac atgaaatagc tctacctcct ctttctgaga atggaccatt  180
agctctttaa aactatcttg caagaaatac cttacatgta ttccacaata aaatggctca  240
gtgaatgcct ataaaataaa gtaacattcg aacaacagcc cagagggccg cactggtaaa  300
dccgtagctt cctctgtttc tactttcatt caataaaaac cgtttcgtat tcaactcagg  360
gacatttgca ggtttcttgg gagttgccta aagtcatgag ctacttgttt tctgcctggg  420
ctcacaaaac taaccgtgac attctcagag gaatccactg agaagccatc ctaacaggca  480
caaagaagta aaacagcaaa tcgctctcaa gaaatgcagc tgccagagcc ctggtcacag  540
aataggtttc ttggagaaac tcacgataac tatagagact gaagagagac atgaagaaaa  600
c                                                                  601

SEQ ID NO: 247         moltype = DNA  length = 1001
FEATURE                Location/Qualifiers
source                 1..1001
                       mol_type = genomic DNA
                       organism = Homo sapiens
SEQUENCE: 247
accttacatg tattccacaa taaaatggct cagtgaatgc ctataaaata aagtaacatt  60
cgaacaacag cccagagggc cgcactggta aagccgtagc ttcctctgtt tctactttca  120
ttcaataaaa accgtttcgt attcaactca gggacatttg caggtttctt gggagttgcc  180
taaagtcatg agctacttgt tttctgcctg ggctcacaaa actaaccgtg acattctcag  240
aggaatccac tgagaagcca tcctaacagg cacaaagaag taaaacagca aatcgctctc  300
aagaaatgca gctgccagag ccctggtcac agaataggtt tcttggagaa actcacgata  360
actatagaga ctgaagagag acatgaagaa aaccattcta tcccaaagct atgtaaaaga  420
agcctcggag gagaggggt tgccttagac cctgacagag aaaaactaat gagtgctatg  480
cttgacggtg cacctactac rccgcagaca ctgtgagtga cgctctacac tcgtttcctt  540
cattcctccc aataattctg tggggtggat gcaactgttg tgctatttgt ttctaccact  600
tcacagcaga gaaaactgac acactgcaag gccatttaga tcagcagtgg agtagccggg  660
actggaaccc atgcagccca tccccaggtt cttcatctca atgctacgtt gcccctggac  720
aggaccaggc caaaggcctg gcatctaaac tgcctgactg agtgcaatgt tccaagggat  780
aaggggacct gacttgaaaa actctctccc ctacttctca cagcagttgc aggacacggg  840
atagccagtg gttctcccag tcatccgacc accagtggcc gtgccaggcc ccgccatggc  900
atccacctcc acaggagata tttccagcat cctcttgtgg tagccattat gttacattac  960
ttcattgttt ctccttccca atgttcacct ttgaacctct c                     1001

SEQ ID NO: 248         moltype = DNA  length = 1001
FEATURE                Location/Qualifiers
source                 1..1001
                       mol_type = genomic DNA
                       organism = Homo sapiens
SEQUENCE: 248
cagtcatccg accaccagtg gccgtgccag gccccgccat ggcatccacc tccacaggag  60
atatttccag catcctcttg tggtagccat tatgttacat tacttcattg tttctccttc  120
ccaatgttca cctttgaacc tctctcccac tatctgaaaa tctctttggg gcacggggtc  180
tcatgacacc aagccgagga aagggatggg aagatcgaga tccttccccc ggatgagtct  240
ttggcaggga gctgtcagca catctgctgg tgctggagaa cagggcccag gagcacactg  300
cagtctcctg cccttgggac ttggcagcca caatgcagag aagggacctt caattcccgt  360
ggtttgcacc agctcccaga ggacgaaccc tctgacggaa tggttagttt tccttttcta  420
ccagtgcatt ttccaaactg aaatgtcaag cagtcatagg ctgtagatgc cctgccctgc  480
cctttctctg tgatgtcagc rtacgggacc cggtgagtct gggacagggt gagtactcgt  540
cagaggactt ttgtcctcat tgtgactttt cctttgttca aaaggaatga aagaaaaaaa  600
aattaaattc aggccctaga agcccaagtc ctaggtgcag agctctctaa ctcttttttt  660
tttctgttta cacccaagga aagagggagg atagatagga aaagcagata cctaaagaaa  720
taatgggaat atgaatggga agaaatctct cccgttggct tcataatagg acagtcaaca  780
taacagagat gtcagttcct ggctccctcc cccgattcct gtagagaaac cccacaggcg  840
cactccagcc taactggtgc acacagggct cacccttcag aaagcccaca tttttgtacc  900
aagtgagagg agttcatgat ggccgctgaa gcgtcccctc tagcaccttt ttgctgactc  960
ctaaactgcc tttttgttgt ggggagcaag agaactagga a                     1001

SEQ ID NO: 249         moltype = DNA  length = 1001
FEATURE                Location/Qualifiers
source                 1..1001
                       mol_type = genomic DNA
                       organism = Homo sapiens
SEQUENCE: 249
tctctcccac tatctgaaaa tctctttggg gcacggggtc tcatgacacc aagccgagga  60
aagggatggg aagatcgaga tccttccccc ggatgagtct ttggcaggga gctgtcagca  120
catctgctgg tgctggagaa cagggcccag gagcacactg cagtctcctg cccttgggac  180
ttggcagcca caatgcagag aagggacctt caattcccgt ggtttgcacc agctcccaga  240
ggacgaaccc tctgacggaa tggttagttt tccttttcta ccagtgcatt ttccaaactg  300
aaatgtcaag cagtcatagg ctgtagatgc cctgccctgc cctttctctg tgatgtcagc  360
atacgggacc cggtgagtct gggacagggt gagtactcgt cagaggactt ttgtcctcat  420
tgtgactttt cctttgttca aaaggaatga aagaaaaaaa aattaaattc aggccctaga  480
agcccaagtc ctaggtgcag rgctctctaa ctcttttttt tttctgttta cacccaagga  540
aagagggagg atagatagga aaagcagata cctaaagaaa taatgggaat atgaatggga  600
agaaatctct cccgttggct tcataatagg acagtcaaca taacagagat gtcagttcct  660
ggctccctcc cccgattcct gtagagaaac cccacaggcg cactccagcc taactggtgc  720
acacagggct cacccttcag aaagcccaca tttttgtacc aagtgagagg agttcatgat  780
```

```
ggccgctgaa gcgtcccctc tagcaccttt ttgctgactc ctaaactgcc tttttgttgt  840
ggggagcaag agaactagga aagacatgga aatgttcttc cagccagaaa cactgggcca  900
gggtgggcgc agttcctggc tgggcccgtg gatggtctaa tacaggagcc tgtctccaca  960
gcaatgcatc accctcactt caggtctggg aggggacttc a                    1001

SEQ ID NO: 250         moltype = DNA  length = 1001
FEATURE                Location/Qualifiers
source                 1..1001
                       mol_type = genomic DNA
                       organism = Homo sapiens
SEQUENCE: 250
tcagtgacct ttgtccccta gagcagaaaa cggtactaat aatagcgcca gtcatgggaa  60
ggggagctca catgttcaat gtgactcata atggtgtccc tgtctgggat ctccaaggca  120
gtcaacagca cccttcacga tgctgcccgg gagtgtcaca catcaggaat ccagtggcat  180
cactgggaaa gtatgcttct caagtcgaag ctctgagcca caacaacaga ggggtccctg  240
ttagaaggag gtctctttcc agagccatgc gggcgggaga gcaccacaca cacactccac  300
acacccatct cccatggcac ggagcctcca cacccctgc tgtctgctcc ctctccaccc  360
tccctctcag gcggctgcag gggaatttcc ttctactgct ttgttcttct cagcctctgg  420
agaagaggac agttcttact acacactgac aggtctgatt tgaagaacgt gctacaagct  480
ctgaagaaga aataccaggt rggaacttgg agagctccca agcctacaaa gcaaatcaca  540
ccaaggatgt tcacccccta aggggacccc caaggctcct caaatctaag gcaacaatct  600
cactttttaa aaaaagtaaa gcttcaagta aattactgct catttgggtc atatttcctt  660
gtctgggagc tgcaaggccc actatctgtc tcaatgagga gctggttatt aaaaatcccc  720
tgctattctg gtcccttgcc ctgaggctga gaactgagca gcataaatac atatatagca  780
atgggctagg acaaggtgtt agtaacatgc tcttgatgga aatcccttcc atttcccgat  840
ttgtcagtat cattcttctc attttccaga tctgggagtt gcctgcctgt gacaaggaca  900
tcctcacagc aagtgaacag ggtcaggttg aacttcactt tttccttcta ctccttcctc  960
atttccattt caaccacaag ttctcactct tgtcacctgt g                    1001

SEQ ID NO: 251         moltype = DNA  length = 1001
FEATURE                Location/Qualifiers
source                 1..1001
                       mol_type = genomic DNA
                       organism = Homo sapiens
SEQUENCE: 251
tcacgatgct gcccgggagt gtcacacatc aggaatccag tggcatcact gggaaagtat  60
gcttctcaag tcgaagctct gagccacaac aacagagggg tccctgttag aaggaggtct  120
ctttccagag ccatgcgggc gggagagcac cacacacaca ctccacacac ccatctccca  180
tggcacggag cctccacacc ccctgctgtc tgctccctct ccaccctccc tctcaggcgg  240
ctgcagggga atttccttct actgctttgt tcttctcagc ctctggagaa gaggacagtt  300
cttactacac actgacaggt ctgatttgaa gaacgtgcta caagctctga agaagaaata  360
ccaggtagga acttggagag ctcccaagcc tacaaagcaa atcacaccaa ggatgttcac  420
cccctaaggg gacccccaag gctcctcaaa tctaaggcaa caatctcact tttaaaaaa  480
agtaaagctt caagtaaatt mctgctcatt tgggtcatat ttccttgtct gggagctgca  540
aggcccacta tctgtctcaa tgaggagctg gttattaaaa atcccctgct attctggtcc  600
cttgccctga ggctgagaac tgagcagcat aaatacatat atagcaatgg gctaggacaa  660
ggtgttagta acatgctctt gatggaaatc ccttccattt cccgatttgt cagtatcatt  720
cttctcattt tccagatctg ggagttgcct gcctgtgaca aggacatcct cacagcaagt  780
gaacagggtc aggttgaact tcactttttc cttctactcc ttcctcattt ccatttcaac  840
cacaagttct cactcttgtc acctgtgctc tgctgagagg agaacacagg agtttcttc  900
caaacagaag gaggtcaacg ctgggcaggc accttcccag gcagtctcct catatttcca  960
tagtacatgg cttacaccaa gaccacccca ttggtttggt c                    1001

SEQ ID NO: 252         moltype = DNA  length = 501
FEATURE                Location/Qualifiers
source                 1..501
                       mol_type = genomic DNA
                       organism = Homo sapiens
SEQUENCE: 252
ggattagaaa gtccgctcaa atggcttctc tctattaaac aatatttggg gccaaacaat  60
atgggtgacc ctcaggctgc atttcatcaa cgtgttccca aaaatgaaaa tgactacctg  120
tcctttggga gttaatttgc tactttaaga agctaatccc tttagctcta ttctaaaagt  180
caaatcaaat acctcggtgt gggcaggaca ccacatttat tttaacctat gaaactctca  240
tggttggtca mccttgcaat agggctgact ctgccctgat agcacacatc tggcaggtgg  300
ccctaaaaca gaggaacagg cctgctggcc cctcccttcc agccaggtgt ctctacccac  360
agccaaacga tgatggcaaa aacagaacat tcgaatccag aaatgaccca tctgttcaca  420
agtgtatcaa tctgcctttc atgctaccac aggaggacgc acctctgagg gtggggtggg  480
tgactcccca gtccaagcat c                                          501

SEQ ID NO: 253         moltype = DNA  length = 401
FEATURE                Location/Qualifiers
source                 1..401
                       mol_type = genomic DNA
                       organism = Homo sapiens
SEQUENCE: 253
atccagaaat gacccatctg ttcacaagtg tatcaatctg cctttcatgc taccacagga  60
ggacgcacct ctgagggtgg ggtgggtgac tccccagtcc aagcatcacc cctttctgtc  120
aaccctcttc taaatcacca ttcacaaagg cccctaaatc tcctgatttc cattaagttt  180
aaggacaaaa cagaaaacat rctgacagtt tcttggcctc tggaccaagc tcaacctgaa  240
```

```
gctgcacaaa gtcttgttgc ctgaggatga ataactcaag aaactgtatt gctggactga  300
ctggcaatca agaccctgag aaaattattt taagaagatt aagggccagg agtgcttgat  360
attttggctg agttctatgt ctctcatttc ttctgagttg t                      401

SEQ ID NO: 254         moltype = DNA  length = 1001
FEATURE                Location/Qualifiers
source                 1..1001
                       mol_type = genomic DNA
                       organism = Homo sapiens
SEQUENCE: 254
gtgttcctgt atcagtggct aataactcaa gggcagtgat tgggaatata acttccaata  60
attcaactca aacaacaaag aacattctga caggtgtttg gaaagcatac ttgctgaaca  120
cgatgatgaa caaacaacaa ctttataaac ttgtatttgt tgctgagata gccagtatct  180
aaccatgaaa aagagtgaga aaacagctct caaatcagtt aaaaccagtc tttgactgcc  240
gagttcatgt ctcttgcatg ttagatcaaa aacgaaagga ggaggagtgt caaaaaattt  300
aaaaataaaa gccattttac atgtcaggca gtggagtact gagtgatgac ggcatcctat  360
aaaattaaaa tatatgatgc ctgtgggaaa gccccgggta gggagttgag ggtacgaggc  420
tttgatatca gttcttacct gaatcaccat atgcaatctt atgcaactca tttaatctct  480
ctgggcttta ctttttcctt rcctaaaatg gaaatagtaa tctctgcttc tctttagttt  540
ataaaaatgt aaattaagtc cttattacaa aaatctgcat atatacatat atatagacag  600
agagagagaa agacacttaa agaggtgaac aatttaggag caactgaata tacaataatg  660
gaattacaaa gaagaatgaa acaacagaaa atatattttt aaaaacaatt ttcagtaaaa  720
aacaagaaaa aagatgcatt taaaaaaaat tgtaaaagca ctagaaaaaa tctaattaga  780
cttccaagga ttaaattggc cttcgtatgg caactttgaa aaagtagaaa gttggaggtt  840
aaggaaaaaa aagttacagt atacgaatgt aaaaattttt aatattttca atgagaataa  900
gcatttagga ctttttaag ttagggaaga ctctgaaatc cttgttccca tgttaaaagt  960
gcacacgcac caaaagagac agcagatgca aactgctttg c                      1001

SEQ ID NO: 255         moltype = DNA  length = 601
FEATURE                Location/Qualifiers
source                 1..601
                       mol_type = genomic DNA
                       organism = Homo sapiens
SEQUENCE: 255
ttatttggcc agtctgactt gggtctgaga acaagacagt tacacatttt tagggtatga  60
gggaaagacc tttgttttg ctctggctct gcacacctgc aagtgctcaa gtacacatgt  120
gtgggggcgg cagcaggaga aaggggactg ttcctctctt aaaggggcag tctctattca  180
aatgcaacca cctctttctt ctaaacccat cagtaactct gtctaacaca ttcaagctaa  240
cactcagaca caaacttgga cagtgagcca gtgaagctca agtcaggaag tgggtttctt  300
ratagctctt tcctcctgat gtcttctagg taaccggttc ttttaagaag tcaccagaga  360
tgggttaggt ttggatttgg gggaagggga taagaatttt gttataaacc aaagaaaagg  420
tttttccagc cactataaat gtacaaagaa aaatcttcct aagtgtgtag gtaatgagaa  480
gaaagaaaga tatgttcact gatcagggtt agaaaacagg actttagaag tctgaagatt  540
atagtctttt ctcagtagga ttctcaactt gctctctgga atttatttta tcctaggggt  600
t                                                                  601

SEQ ID NO: 256         moltype = DNA  length = 501
FEATURE                Location/Qualifiers
source                 1..501
                       mol_type = genomic DNA
                       organism = Homo sapiens
SEQUENCE: 256
atggtctgaa ggttccgctg ccttctcttc gctgcctttt tttccttcat agatgctcct  60
tccgtaaaca tcttgcacat ctaatcatgt cttggcacct gctttccggc acactcaaac  120
taacacagta ttttgaatat tttctgacat gtgaaaaccc tgaaagtcat cttatttgtt  180
gtttgctgtg taacattggg ctagacctcc tcctctaaaa agaaaaaaaa aagtctcgat  240
tccctcattt rtacaatggg cataacagaa acttcctcat gtgatatttg gtgaaggatt  300
taaaaagtca gtgtatatga aggagtctaa gcacacagta ggaacttaat acatctggga  360
ttgagctaaa taattgaaaa gacctaatta ttattaaatg cctgctacgc cccatgacac  420
tgccagcaat tactgcaatt ctataagtaa aatgcgttgt tccctggcct caaggaactt  480
agaattatac tggaaaaata a                                            501

SEQ ID NO: 257         moltype = DNA  length = 714
FEATURE                Location/Qualifiers
source                 1..714
                       mol_type = genomic DNA
                       organism = Homo sapiens
SEQUENCE: 257
tgaatatttt ctgacatgtg aaaaccctga aagtcatctt atttgttgtt tgctgtgtaa  60
cattgggcta gacctcctcc tctaaaaaga aaaaaaaaag tctcgattcc ctcatttata  120
caatgggcat aacagaaact tcctcatgtg atatttggtg aaggatttaa aaagtcagtg  180
tatatgaagg agtctaagca cacagtagga acttaataca tctgggattg agctaaataa  240
ttgaaaagac ctaattatta ttaaatgcct gctacgcccc atgacactgc cagcaattac  300
tgcaattcta taagtaaaat gcdttgttcc ctggcctcaa ggaacttaga attatactgg  360
aaaaataaaa ggtttggaga atactatgga atgtaggtga cagctagcac ttagagccta  420
gcttcctgta tacccagcac tgctccaagt gctctccata aactaattca ttagttctca  480
caacaagcct atggtataga aactattatt actgccattt gcagatgaga aaacagatac  540
agagatgtta gcttgccaaa ggttacacag ctgctcactg gcagggcctg actccatgct  600
ctcaattcta cagggatggc ccctgaatgt tgcccttggt aaaactgcat gggatgacca  660
```

```
ctctttcttg tgtttaactt ggacttctct acctgcaggc atccccaagt gact        714

SEQ ID NO: 258         moltype = DNA  length = 501
FEATURE                Location/Qualifiers
source                 1..501
                       mol_type = genomic DNA
                       organism = Homo sapiens
SEQUENCE: 258
ctccactgag atccccaggt ccacgccagg cacccctta ggatccactg ctaaacccag  60
caccgtgaat ggaatccctg ccagcatctc agctgctggc tgacaggaag gctctattta  120
agctgagggg gctgccagct tcctgcaact agttaatcac aacagcctct gagcaagaaa  180
gggaagacac tctgtttctg cccttctcat tcccaagctc ttttcctctt atccaatcag  240
gtactgccca rggatggtct acattgagac tgtgatggct tcagcaagcc tggaagccag  300
ccccagcttt gcctggcctg cagacctcag tgaaatgccc taacttctct gggcctgact  360
ttagccaatt cacactgtct tacacaacag catttacatg gagagacttt agattccaga  420
gcttcgctcc tgttatctcc ccaaattaaa aggctctacg ctgttcctaa tcacatgccc  480
acagcacaaa ttcacactgc a                                           501

SEQ ID NO: 259         moltype = DNA  length = 601
FEATURE                Location/Qualifiers
source                 1..601
                       mol_type = genomic DNA
                       organism = Homo sapiens
SEQUENCE: 259
tctgtggcta tgtctgacaa tctggaatga agttcaataa aggtgattta taggtcaata  60
attctggacg gaagccaagg ccagctctct tccctcccac atacccctaa cccacatgca  120
tatagtgttc attagtgaca agagggagat aaggtcctaa tcagtctagg caggcaactg  180
caataaccaa ggagtactct cattatctaa tatgaagaaa agattttcta ttcaggtgag  240
acatttggtg cttaagattc aattcagaag ctacctctgt gcagaatgca attacataca  300
rggccttgaa taagtcattt ttttgtgcct cagtttcatc atctatgaaa tgggactaga  360
ggggttgaga ggaagagaga ctactatgtg acaacccatt atattattct atacctactg  420
aaatggagaa gcaagaggaa gaagagatgc ctatgttttt caaggacttg gaaagcgttt  480
tgcttaggtc tataaaatgt atatagaaag cattgggcta cttctctagg actgtgttgt  540
aattagaagg ggttcataat gtatcttcga acaaaagaaa atggagcttt ctgatggtat  600
c                                                                 601

SEQ ID NO: 260         moltype = DNA  length = 1001
FEATURE                Location/Qualifiers
source                 1..1001
                       mol_type = genomic DNA
                       organism = Homo sapiens
SEQUENCE: 260
tatgtttttc aaggacttgg aaagcgtttt gcttaggtct ataaaatgta tatagaaagc  60
attgggctac ttctctagga ctgtgttgta attagaaggg gttcataatg tatcttcgaa  120
caaaagaaaa tggagctttc tgatggtatc agtttgataa ccgtaaacag ttcacagtaa  180
ggtaagaagg tacattttgg cggaagccaa cattgcattt gatgtattct taactcagct  240
aacaggcagg ctttcaagcc acgttatctg cccccgcatc ttgacctcat ttaacaagtt  300
gctatgggag cccagtgaag gttgatgcaa ttttcttatc tttggaggaa gaatgtaact  360
gtgcaggaga atgtgaaaat tcagtttcta actggcttcc gcacttacag tgcagtaaga  420
aagacatcct atcaagaagt aaaatgtatt cctttggacg tgatagggac aaagacccag  480
actcctggtg aaatggcagg dagatggatt ctcttcccag cttggagaat ctaagcatgc  540
accctttagt tcaggccaag taatagtgac atagagctat gtgtacccct actgtgtggc  600
caaacatact ctggagcaat caaattttaa gggaacagac agaaaagttg agcagaacct  660
gagaaggtga gtgtgacttt tacaagcaat aaaatgtatt gccaacaagt ctatacaatg  720
atttctgctt tccaaagtac ttttgcaaat ttcagctcat cttaacatgt ctgcataaag  780
ctagacagcc atttataggc actctagtga ctgcctcagg tggtgggtga ggctgtatgg  840
gcacatttca tccgcttccc tattccctag gacgcatctt aaatgaggtt ggcgggggca  900
ccatgagggt gtgagatcac cctcagaggg tgagtctgca gtacaggcag gaggtgttca  960
ccaggtatca attacaggga aaaaataaat actaaaatgt g                     1001

SEQ ID NO: 261         moltype = DNA  length = 1001
FEATURE                Location/Qualifiers
source                 1..1001
                       mol_type = genomic DNA
                       organism = Homo sapiens
SEQUENCE: 261
ggagaaagaa ttaaatggta agaggcttca aaaatgtttt ttcattaaaa tgattacttc  60
agactttgag acttttaaga gataatcacc accccttctc ttctactcac taaatgtttt  120
actcccttat cccatttctg aagaaagaga gagagaaaag aaggaaagga gggaggaagg  180
gaggaaggag ggagggagag agggagggaa ggagggaagg aaagaaggaa ggaaggaagg  240
aggaaggaag gaggaaggaa ggaggaagga agggagggag ggaggaaggg agggagggag  300
gaagggaggg aggggaagga aagaaggaaa ggaggtaggg agggagagag ggagggagga  360
aggaaggaag gaaggaagga aggaagggca gaagagaggg tgggcaggca actatcaatc  420
tatccaaaca taactcagac ctagagcata gttttctctg caccacaaaa acagaagcaa  480
gcactgccaa ttagagataa rgtctacctc ccaaggccac aaagtcattt tagagctacc  540
tctgcctttc ctttctcttc ccaattaagc agcacatctc ccttccttta tcactatatt  600
caactgcagt ctagttcttt aacccctaac aggtataact gcatgagctg gcactcttgt  660
acttcctgag agtgacttaa tacacttttc ctcatcccag acgtttttaa tggaaatgga  720
tatacttcct aataatctcc tttcaaagat gggaaaggac tcccttgaaa agtactaagt  780
```

```
tcctacatgc tagccatgtt caagcaaaga ccaccagggt attgtagaaa gaataaagta  840
aggaccttta agttccattc ctggccttga ccttgttgct actccaacat gtagacataa  900
ttcctgagca ctactcatgc aatgaactgc actaggagct acatggaatg caatataaga  960
gagatactcc tgatctttga aggaggagta agttttcaag c                      1001

SEQ ID NO: 262          moltype = DNA  length = 501
FEATURE                 Location/Qualifiers
source                  1..501
                        mol_type = genomic DNA
                        organism = Homo sapiens
SEQUENCE: 262
gaaaaacacc caaaatgtaa gtttcctacc attcttggaa atgatccctt tgaagagaat  60
gatactattt gcttccaaaa atcaatggct attcacaagc agagtggctg gagagagact  120
aaagaattct tagagagact tctcccccgt gccctgcaaa agggagtctc tcgtcgtctc  180
tggtcagagg tgcagagtgc cttccaggac cccacccaca gaaacgtgca gatggagttg  240
gcctaagcag rgggagggcg cctacctgtg tagccagcta gggcagcagc aggaatgaca  300
ggcttgtcct tattgaggtc agcacggtcc cgcacatagt ccttgaaggt gcccttgggc  360
ttgtggttgg gcagggcagc cggatagtcc tctgagtcga agctgtcata ggagggaaca  420
cgctgcaggc tgttgaaaga tgactggctg ctccaggact gggtgaggcg atcacaacta  480
tcgtagctct ctatgctttc a                                            501

SEQ ID NO: 263          moltype = DNA  length = 1001
FEATURE                 Location/Qualifiers
source                  1..1001
                        mol_type = genomic DNA
                        organism = Homo sapiens
SEQUENCE: 263
caggctgttg aaagatgact ggctgctcca ggactgggtg aggcgatcac aactatcgta  60
gctctctatg ctttcaaaag agtcctggcc cccgagttta cctggaggta aaggaggagg  120
taggaagagg acagggggag gagggagtgg gaaaaaaaaa aaactgtaaa aaccctctta  180
tggaggacag attgctaatc agatctgcag gaaggacgga agaagggaga ggcgagtggg  240
aacagaagct tcaggggtca tgggtttact ctgaggaaag gggctgcact aggccaccat  300
ccgagggtcc acggccactc tgctgcctgg tttgagaact ccaagtacag agattcagag  360
tcaaacgttg ctcacatctg tcggagtagc gtttgggtcc tcaagagttc taaagccaga  420
aatctagaag ctgaggatca cacatgttat gatatgattt ctggctgatg tcgtaggccc  480
aatgaataaa tgaagaaatc rgagcaatgt caggctgaat tccccactcc agctcaagcc  540
aatgagatga cttcaaaagg cccagtttgg aaaacatttt ggtcataaga aaaaagaatc  600
ccattagact aagagcagat tagcctgttt tgaccttgga actaagtgct atttttagc   660
atttttccca aatactattt taatatgaaa tacatgtact gaccctatgc cttttcaaat  720
agagtaagat ggtgtaagat gcttttccca agagattttt taaaatcaca cacactatca  780
ctcttctaaa cagaaaacca tattctttat cctctccaag taaaattatg tacttgaaat  840
ttaaacttca ttggaaaagt gtaggcaata tttaaaaggt ttattaaaga gttaaggtcc  900
acagcagtgt cagaaatcct ttactgtgtg agttgcttaa ggcattctta actgaccaca  960
agatcatgca agttcattaa tttcccaaac caggttataa a                      1001

SEQ ID NO: 264          moltype = DNA  length = 1001
FEATURE                 Location/Qualifiers
source                  1..1001
                        mol_type = genomic DNA
                        organism = Homo sapiens
SEQUENCE: 264
agcaaaaaaa aaaaaaaaat agttttggag gaaaacaaat gaatctaaga gcgaaaaagg  60
ctcgcaggaa tggtttttat atgcaacttt cagatacttt tcaagtaacc taagttaaat  120
cataggagac tagatggtca cctcaattca gcacaggcca aaaggcaaag ggatgtgaca  180
aatgtttacg gagaaatatc cgtaagtcaa ctcttaattg ttcaggggtg gttgatctat  240
aaatttcaaa tcccagaata aggctgactt atacaacttc atattagtgt gcctccagtg  300
tatttttccc tccatgacag cggagattgg ttaaaacaat aaacatcaaa catgaacaga  360
tgcccaaacc taaattaaat atataggaaa atatgttgct cccaacattg tttaaagatc  420
cggataaaat gtattcggtt gagtgtgtac tttttgtaaa atccactgct gtgggttttc  480
tctacatcct gaccccctct rgaactgctt taaacagaaa ggtggtgtca tccgtttcat  540
ctcattcctt cctccactca tccattcaga ggagggtaat ctctggaaag caaactgaag  600
agcttcatgg agttatcagc cctgcccacc cagtccacta gcaaaagggc acctcttcat  660
tcttactaaa aatgaatata tatttcttta taattcttaa aaattctttc ccatttaccc  720
accagaaaag tcatcttttt caccttttta gagatcattt aattttcttt caagaaattc  780
acactaaatg atttaagaaa acagcctaca accagaatgt caaagccttg ttttagcaga  840
acaggaaatt ctgtggcgtc tcataaaaag gtatttgttc ataccagcta ctgatcttca  900
tggtcactta ttttctcttt gagacaaaca taccaaaagc ctaagaagga gaatttatat  960
tttcatcaac accgcaccaa gtcgatagta tttatgctaa a                      1001

SEQ ID NO: 265          moltype = DNA  length = 1002
FEATURE                 Location/Qualifiers
source                  1..1002
                        mol_type = genomic DNA
                        organism = Homo sapiens
SEQUENCE: 265
caggcttact gcagggtcgt tcagagcttt ctgtccgcag gtgcacttcg tctcccttcc  60
tctccttttc ctaggggagt tggcatctgg gcaggagctt gactgggttg ctcttctctc  120
ccttgacaca agcgcagtcg catttcacca aatggagtca ccttaccagt gtcctgcttc  180
ttgtctgggc ctgaacttga aacctgaggg caatgggaaa aatacaaaac aaaaaccaga  240
```

```
catctgttag aggaaatgga gaacgtaaaa tctatggcct aaagactgca atatattttt  300
gagaaatttt gaaattgatt agtttggggg ttggggattg atcctgctaa cctgggatgt  360
actcaagcct ttggctatag tgtggtcgac atacacgcag cacgaatgca ttgagaatga  420
atgctgaatg ccttctgagc ccttagagat tactcatgga ttctctttcc aagatactaa  480
atcccatttt gcagctactg aaataataac cttagtcata tttttttgat ctcatcttta  540
gacaaggcca cagtcaggac agactcagat accaacccag ttaatgagta tgcagatttc  600
ttagaaaagg ggttgagatc attgtggtct ttgcatccaa gatcctttta ggccaagcat  660
gacttgaata ttgacctctt tgttccttcc ctatctgttc attacagagg atgtgaaacc  720
atatcaagtt aatggagtca acccagccta tccagaatcc cgctatacct cggattactt  780
cattagtaag ttcatttcta cccctcttct ctcatgataa tagcaaacta ggaaaagacc  840
cctatctcag tgaatctcag gctccttcat ggtaattcta tcaaaaatar tatcttctta  900
gatgtagact cttctttgtt actttatttt attattttcc acaaagcaca aagtttcaac  960
ctatatatat gtttcattaa cctaccaagt tcctacacac ta                    1002

SEQ ID NO: 266         moltype = DNA  length = 1001
FEATURE                Location/Qualifiers
source                 1..1001
                       mol_type = genomic DNA
                       organism = Homo sapiens
SEQUENCE: 266
actgcactcc agcctgggtg acagagcaag actctgtctc aaaaaataaa taaaataaaa  60
taaaataaaa atatactgaa agttgaaata aaatgaagaa aaggagatga gtgatactga  120
agaaatcgcc taccctgagc ttcattttac agacaaggac aataatagga cttgtcctta  180
ctatctcaca gttattttga taatccaaag agaaaatgta tttgaaagca ctttggaaac  240
agggagacat gatagagata ttaattgtaa ctacaatcag agatgggctt agatagccca  300
aaacacctag cagctccatt ttgataaatg gaggaaaaca gcctcttagt agaatatact  360
gggttacaca gtctgattga atctgctatt gtgtttagaa gtcaacagtc aaatcagatc  420
tgttaggagc ctgccgtatc gtttccctct ataaacaggt cgctcatgtc aacacctatg  480
agtgggtgtc tgtgcatgga daacatgccg gtgctttgca actgcctgcc atcctcggta  540
aaagcagcca cagaaagact cacctagttc tttcctgtat tcctttatgt cttatttttc  600
aacagaaagt gaaaagaagg aataaagata acatttttga gcacagagaa atctagtttg  660
ggtctctctt gagcactgca gaatggaata tattcttaac caaaggaagg tataatgcgg  720
ggtaaaagtg ctaatcctga gttttgctcc cctcccccag cgtctgtgcc aagggttaga  780
gctgatgacc acagggaaag gatgggcctg ggttagagag ggcaatgggc ttctaggctt  840
acagtcagct gaagggcact gctgactgct ggtaactgca atttatttta agaaaaaatt  900
caaaaaaata agcacaaaaa cacccaagtt tgccgcctgc tgctgtttct atactcagcc  960
aggactgtgg tacatgagtc acttggtcca aaaaggttgg a                     1001

SEQ ID NO: 267         moltype = DNA  length = 1001
FEATURE                Location/Qualifiers
source                 1..1001
                       mol_type = genomic DNA
                       organism = Homo sapiens
SEQUENCE: 267
ataaaatgaa gaaaaggaga tgagtgatac tgaagaaatc gcctaccctg agcttcattt  60
tacagacaag gacaataata ggacttgtcc ttactatctc acagttattt tgataatcca  120
aagagaaaat gtatttgaaa gcactttgga aacagggaga catgatagag atattaattg  180
taactacaat cagagatggg cttagatagc ccaaaacacc tagcagctcc attttgataa  240
atggaggaaa acagcctctt agtagaatat actgggttac acagtctgat tgaatctgct  300
attgtgttta gaagtcaaca gtcaaatcag atctgttagg agcctgccgt atcgtttccc  360
tctataaaca ggtcgctcat gtcaacacct atgagtgggt gtctgtgcat ggagaacatg  420
ccggtgcttt gcaactgcct gccatcctcg gtaaaagcag ccacagaaag actcacctag  480
ttctttcctg tattccttta rgtcttattt ttcaacagaa agtgaaaaga aggaataaag  540
ataacatttt tgagcacaga gaaatctagt ttgggtctct cttgagcact gcagaatgga  600
atatattctt aaccaaagga aggtataatg cggggtaaaa gtgctaatcc tgagttttgc  660
tcccctcccc cagcgtctgt gccaagggtt agagctgatg accacaggga aaggatgggc  720
ctgggttaga gagggcaatg ggcttctagg cttacagtca gctgaagggc actgctgact  780
gctggtaact gcaatttatt ttaagaaaaa attcaaaaaa ataagcacaa aaacacccaa  840
gtttgccgcc tgctgctgtt tctatactca gccaggactg tggtacatga gtcacttggt  900
ccaaaaaggt tggaagaggc tgttagggga ggccatgtca ttataaggtt gcaacatagc  960
gtcctgatat aaccccagtt cctgctccag atgtaaaagg t                     1001

SEQ ID NO: 268         moltype = DNA  length = 1001
FEATURE                Location/Qualifiers
source                 1..1001
                       mol_type = genomic DNA
                       organism = Homo sapiens
SEQUENCE: 268
agtggcgtga tctcagctca ctacaacctc tgcctcctgg gttcaagcga ttctcctgcc  60
tcagcctcct gagtagctag gattataggc atgtgccacc atgcccagct agttttttttt  120
atttttagga gagacagggt ttcaccatgt tggccaggct ggtctcgagc tcctgacctc  180
aagtgatcca cctgcctcgg cctcccaaag tgctgggatc ataggcatga gccactgtgc  240
cagcatgagc aggcaacatt taaggggctt tccacattgt gctaggtcta aaatgtcctg  300
catccctgac aaacaaatat gtttactctt cctgaacacc tctactagtt tatacacagt  360
ccctgcttat ctttcacatt taccgagaat attaatgtta ctacatactt tcagttacct  420
atgaaaatga aataacaata ttcattcatt caacaaatga ttatctagca cttgctttgt  480
gcaaggaatt aaagaaacaa magtgagcaa cacagaaata gtctccacag gagctagcta  540
tctgattctt gcagtagatt cagccactaa aaatctatct acacagttaa atgttcaaat  600
gcaatgtcaa taagggcttc aaaggagaag tacatgatgc aacgttaatg tgcaacagga  660
```

```
attcctggaa gtctgaagga aacaggaaag gcctccctta gaagatgaga gatgtttgac  720
ctgaattgtg aaggatgcat gagaatttag gaagaaaaga atactccaga tcagtggttc  780
tcaaagtgta gtcctcagag cagggacatc agcatcaact acaaaaagat cattttgttt  840
taagatcacc ttatccgttc tgtaaagagt gatttagggg tgagtatgaa tggatgagca  900
agacatttta gaaagttatt gcatcagtcc tggtgagaga ggatggtggc tttgactaca  960
aaagtggcaa ggcagataac ataagtgaac atgacttcaa g                      1001

SEQ ID NO: 269         moltype = DNA  length = 401
FEATURE                Location/Qualifiers
source                 1..401
                       mol_type = genomic DNA
                       organism = Homo sapiens
SEQUENCE: 269
ggaactgaag aatgagactg actaggaggc ccccagaatc ttctcaacat gaaagctggg  60
acagtgggat gccagtgtga ggtgacagcc aaggacgaca gcagaaagcc tgaaaaagaa  120
gttccttgag tctgcctccc ataactacac aagccctggc agtgtggtct ggacaggact  180
gctgagctga caattctcca rgtaggtttc tgcttcctgc cagggggcag gcacttctgg  240
gttctcactt gttctctccc aggaaagcag ctagaattac ttttgccttt ccacctcaat  300
gccatctcca caagcccagt ccacgtgctg ttggggcccc atcagaggtg cctggctctg  360
cccctctggc tgtgagactc aagtgctaga tctctttaaa a                      401

SEQ ID NO: 270         moltype = DNA  length = 1001
FEATURE                Location/Qualifiers
source                 1..1001
                       mol_type = genomic DNA
                       organism = Homo sapiens
SEQUENCE: 270
gctgagctga caattctcca cgtaggtttc tgcttcctgt cagggggcag gcacttctgg  60
gttctcactt gttctctccc aggaaagcag ctagaattac ttttgccttt ccacctcaat  120
gccatctcca caagcccagt ccacgtgctg ttggggcccc atcagaggtg cctggctctg  180
cccctctggc tgtgagactc aagtgctaga tctctttaaa aaaagggttc acatcccagc  240
tgggggaaac catccctgtc cacttaggac acttgcattt ggacttgatc agctccagag  300
aaggcacagc attgtctttg gagccaaagg attcagatgt aaaagtcaga actttatcct  360
ataaagtgtg gaattgtagt ttaaaaagaa aaaaaaagtc aaactccctt ctataactaa  420
gtgaacagtt ggcaaagatt gtctttttcg gttgtgtgag cattgctctt aagtgatgac  480
taatcatgct caaaaatgta rattaaatag aaaataaact caccatataa aatactaatt  540
caaaaattct cttcatgttg tttgcagatt gtagcagttc tgttcaatat actcatcaaa  600
aacaatgaca aaatcattac acgggtgaaa aatctgacat gacttagcct aagcagatat  660
cgctttactc ttaaaatact ttacttcatc acctattata atatttttac attaggtaca  720
aaatatttct aattttagaa tcagtgtctg aaagttaatc actacctcca tagacattaa  780
ctaattatat tttatggaaa aatactgaaa tctcctttgt gctaataatt acaatatctt  840
aaattcaaat aacgtatttg tttcaaaatg ctgagaatcc ggcctggaga aacactacgc  900
caacacagtg gagattctaa acacaacgca ctggaaaatg aggacataaa tatattgcaa  960
ttatattaga tttcctgccc actgattatt ccttgggacc c                      1001

SEQ ID NO: 271         moltype = DNA  length = 1001
FEATURE                Location/Qualifiers
source                 1..1001
                       mol_type = genomic DNA
                       organism = Homo sapiens
SEQUENCE: 271
catccctgtc cacttaggac acttgcattt ggacttgatc agctccagag aaggcacagc  60
attgtctttg gagccaaagg attcagatgt aaaagtcaga actttatcct ataaagtgtg  120
gaattgtagt ttaaaaagaa aaaaaaagtc aaactccctt ctataactaa gtgaacagtt  180
ggcaaagatt gtctttttcg gttgtgtgag cattgctctt aagtgatgac taatcatgct  240
caaaaatgta tattaaatag aaaataaact caccatataa aatactaatt caaaaattct  300
cttcatgttg tttgcagatt gtagcagttc tgttcaatat actcatcaaa aacaatgaca  360
aaatcattac acgggtgaaa aatctgacat gacttagcct aagcagatat cgctttactc  420
ttaaaatact ttacttcatc acctattata atatttttac attaggtaca aaatatttct  480
aattttagaa tcagtgtctg raagttaatc actacctcca tagacattaa ctaattatat  540
tttatggaaa aatactgaaa tctcctttgt gctaataatt acaatatctt aaattcaaat  600
aacgtatttg tttcaaaatg ctgagaatcc ggcctggaga aacactacgc caacacagtg  660
gagattctaa acacaacgca ctggaaaatg aggacataaa tatattgcaa ttatattaga  720
tttcctgccc actgattatt ccttgggacc ccaaatttca gttaatattt ataggaattc  780
ccctagacct ctgaaaggac agttgtgcag aagctggtga ttaaataacc attgcaggag  840
attgcacagt atttagacag aagtgagcag gtagctttct ctgaatctac agaagaataa  900
gctagtggca ttttgaatgc agggaaacat ctgctcattt ttcattgtgg cctaaccctg  960
aaccacctca tagatgtttc aagtgaaatg taaaacaagg g                      1001

SEQ ID NO: 272         moltype = DNA  length = 1001
FEATURE                Location/Qualifiers
source                 1..1001
                       mol_type = genomic DNA
                       organism = Homo sapiens
SEQUENCE: 272
caatcaatga tcatgtgaag actggagcgt ctgggatcct agggttagga gatgagggat  60
acagccaagg acaagaaatc caaggtgcat gtcccagttt tgcatgacca ttgaactggg  120
cccaacccca tcagattatg ataccagtca tgtgtgttgg gtatggtcac actcaatagc  180
agcatgaaag aaatactaag agtgagtaat atgccttata cctgagaaat gctttacagt  240
```

```
ttgccaagac tcttcacata cactattcca aaatatcctc taaacataaa actggagggg  300
cctggaaagg tatcacaagg tccccatttc acagatgagg aaatcaaggc cctgggagat  360
caagagcttg acctaaagtc acaaggccaa gagggaccag ctggggctag aagccagtct  420
tctaactctt aaagttcagg gtctttctct ctattccact gcaaacagaa atggatcaga  480
tatccaggaa aactaacatt mttcagagct gagaaaaaaa aaatgggact tttcctttct  540
tattttgaaa gattttagga gtgattaaaa acttaaaact attccaagaa acccagggtt  600
tcatacagct agccccgtaa gaacataatt aagagccatt tacagaatca actataatct  660
tttcttttcc tggcactcag gcaactgagg cttccttcca tatgaagcaa atgagttaag  720
tgaaaacctg gcttccttct ctgtccaacc ctgactcaac ctaatgggta actttgcata  780
taacagaagt ttaatttgtt acataaaggc ttactgaaat atatttttta aagtaaaagt  840
aaaccaagaa taaaccttct ggtccacatg gagaggataa aagaacagtt ctccaaactg  900
aaagatagga ttctaaagac aaagaaaaaa gagagagagg ggcgtgcatt gttgataact  960
tgttgatcaa aatccatagg ttctgatttc acatacgcca t                      1001

SEQ ID NO: 273          moltype = DNA  length = 1001
FEATURE                 Location/Qualifiers
source                  1..1001
                        mol_type = genomic DNA
                        organism = Homo sapiens
SEQUENCE: 273
ctaacatttt tcagagctga gaaaaaaaaa atgggacttt tcctttctta ttttgaaaga  60
ttttaggagt gattaaaaac ttaaaactat tccaagaaac ccagggtttc atacagctag  120
ccccgtaaga acataattaa gagccattta cagaatcaac tataatcttt tcttttcctg  180
gcactcaggc aactgaggct tccttccata tgaagcaaat gagttaagtg aaaacctggc  240
ttccttctct gtccaaccct gactcaacct aatgggtaac tttgcatata acagaagttt  300
aatttgttac ataaaggctt actgaaatat atttttttaaa gtaaaagtaa accaagaata  360
aaccttctgg tccacatgga gaggataaaa gaacagttct ccaaactgaa agataggatt  420
ctaaagacaa agaaaaaaga gagagagggg cgtgcattgt tgataacttg ttgatcaaaa  480
tccataggtt ctgatttcac wtacgccatt agtgtagaca cactggataa gtcacttact  540
caattcactt tgaaaagagg tctgttcata ggtggtgtct atatccctca tagagtttta  600
catttttttat ttggcaattt tcaaacatac ataaaagtag agagaaactc tactcaaaat  660
ttatcaatac tacccgtttt tatttcatct tccacacaca tgcacaccca tacacacacg  720
cagaagaatt atacacctaa tcccagaaaa caagtcattt cacccacaaa tatttcattg  780
tcacaaggat atttttttaga taaagggaga tcatagagtt aaagttcaat aagaggcaaa  840
taaactcaag gaaaaagaaa aaaagccttc aagttacttt ctctcatgct taaatctagg  900
tctatatttc atgcattggc ccacttgaac cacagaactt ctttcaaagc aacactgtca  960
tgatctggaa agtgccaatg ttggatcaca gagatgattt c                      1001

SEQ ID NO: 274          moltype = DNA  length = 1001
FEATURE                 Location/Qualifiers
source                  1..1001
                        mol_type = genomic DNA
                        organism = Homo sapiens
SEQUENCE: 274
tactcaattc actttgaaaa gaggtctgtt cataggtggt gtctatatcc ctcatagagt  60
tttacatttt ttatttggca attttcaaac atacataaaa gtagagagaa actctactca  120
aaatttatca atactacccg tttttatttc atcttccaca cacatgcaca cccatacaca  180
cacgcagaag aattatacac ctaatcccag aaaacaagtc atttcaccca caaatatttc  240
attgtcacaa ggatattttt tagataaagg gagatcatag agttaaagtt caataagagg  300
caaataaact caaggaaaaa gaaaaaaagc cttcaagtta ctttctctca tgcttaaatc  360
taggtctata tttcatgcat tggcccactt gaaccacaga acttctttca aagcaacact  420
gtcatgatct ggaaagtgcc aatgttggat cacagagatg atttcaaatc aagatggtaa  480
gccagttcca gggacttcca rttcctacaa gcagaaggct gcagtgatat ttcctcttaa  540
tggtcaacat cctcatgaac ttacaactgt aactaaagtg tacaaaacaa ataaaaaggc  600
tcggagttct ggccagcaca gaagggcagt gtgaaaggta atatcattgc caaactgccg  660
acaacaagtc ccagtttagg agataaggtg cctttacccc ttcagaccaa cacaaataga  720
gaaatggctg cagccacact gacggctctg cttctgaagt tgatgacccc tggagggtgg  780
tcactggtct acaagaggat tctcctgata aaaaagctaa tgatctcaga agaatgtgca  840
aaggaatctc aaagaaagac agtctctatt gccctctctc attcatataa aggcagggtt  900
gaagtagagt agaagggagt ggtaagtgat tcctgtgata ggcactagaa accgggcagg  960
caggacttcc agcttaggga ggtactataa tccacaaagc t                      1001

SEQ ID NO: 275          moltype = DNA  length = 1001
FEATURE                 Location/Qualifiers
source                  1..1001
                        mol_type = genomic DNA
                        organism = Homo sapiens
SEQUENCE: 275
ctgattttttg cgtttgtttt tcttattttc tcagtcgctt atttgtacct ggagaaattg  60
ccagattcct tcttgatgtt tctgtaagca ttgggaaata aaatcttttt ttttaagtct  120
ttatatttta taagatgctt ttcagtataa tcaagtagcc aatgatttgt tgagcaccta  180
ctatgtctta agctttggca ttgtcacaca tagtccactt aatcctcaca gcatggtggg  240
tagagcatcc tagagaatga aagcgagctt catctgaggg gctttgagac ctggtttatg  300
taccttcact tgccaggctg ctagagaaaa acacatattt aaaagccttt ccagcaggac  360
acattcattc atgtatttcc tattttaggc catttgccca atgtttaggg tgggagattt  420
gaactagtct aaggaatgag cgagaaaatt tagctacagg accaaggggg cagttctgct  480
ttctggctgg gatcctggaa rggaagagcc tctctgggtt tccctgaaca cctggaattg  540
atttgggttt tgctctgact tcgaaacatt tgctgaggtg gaggatggtg gaggaggtag  600
gaaagaaata aatccagtga ttaaaaatag cttgtgcatg tcaggtgcct gaacgaattt  660
```

```
gggaacatgc ctgcaatccc ttttgtctgg caggtctgaa ctccggcgct gccgaattac  720
aactgctttc atttgttttt cctgcttccc taccatgtaa tggtcaaggg ctcattggaa  780
ccatgtgtga gcctggtgag tcaccaaatc ctcaggactt cagtggtaat aatgtgttaa  840
aactcctttt gggggatggg gcaggaggtg gatgaaggga agagggagaa gtctgaggtc  900
acttcctaca gatgttcagt gtgctgagcc ctctctacag gcttctttct caggcctggc  960
tgcaggacct gaaaccagct tctccatgca atttggagct g                      1001

SEQ ID NO: 276          moltype = DNA  length = 1001
FEATURE                 Location/Qualifiers
source                  1..1001
                        mol_type = genomic DNA
                        organism = Homo sapiens
SEQUENCE: 276
tacacctgac tcccaccaca tgacatactt tatagttcct aaatgtccca gaacagtgtg  60
acttctttat ctgaaaaaca cagagccatg gtctctacat tactcaggag gaaagaatga  120
gttgggctct ttcgtctcca tggctttgca gagaaccaca ttgcatccta ttggttcttc  180
ccacatctta cacttctgaa tgaggaaaac tcctgccctg ccttcactaa aattctcatg  240
acaggatcat acggcttttg gtaccaacat gacataggat aaccccatcc aggaagacaa  300
tggagaatat ctgacaacta catcttgcta taatcccagc ttccactaat tctggtttac  360
ataatagcct ttgaggcctc atcctctgag atcttgcaga tgctgatgaa ttgggctaac  420
caatttattt taatttcact taactcccac ctataattat cattcctgct atttgactag  480
aactgtatct tttagaaagc rttttcttga atattctcat atgatttttc aaaacaagca  540
cttgtagtta ttatctttat catgtaggtg aggaaactga ggctcacaaa tgtttcttaa  600
gtgacttaac taagattatc aaaccagtaa agtgatataa caaggattca atcccacatc  660
ttcagacacg caagccacgt gttttctccc tgcacctatt cacagaatta aaagcaaatg  720
aggcaaaaat gatggggcat gataacattt ctttttcat tttctccaac attttcattc  780
tagaaaaagc tctttctgta gcagggaaga acctcaatcc ccgagactct ctaccgacag  840
caggctccat tgcacgtcct acccagaact ggcctggtca aacctcggct cggggcccac  900
ttggcacttg gtcggggggt aaaacaggca tcgggagagt ggtgctgaga atcaccaaga  960
aggccaggct gggcaaggtg tacgatgagg agtttctcc a                      1001

SEQ ID NO: 277          moltype = DNA  length = 1001
FEATURE                 Location/Qualifiers
source                  1..1001
                        mol_type = genomic DNA
                        organism = Homo sapiens
SEQUENCE: 277
atcttgctat aatcccagct tccactaatt ctggtttaca taatagcctt tgaggcctca  60
tcctctgaga tcttgcagat gctgatgaat tgggctaacc aatttatttt aatttcactt  120
aactcccacc tataattatc attcctgcta tttgactaga actgtatctt ttagaaagca  180
ttttcttgaa tattctcata tgatttttca aaacaagcac ttgtagttat tatctttatc  240
atgtaggtga ggaaactgag gctcacaaat gtttcttaag tgacttaact aagattatca  300
aaccagtaaa gtgatataac aaggattcaa tcccacatct tcagacacgc aagccacgtg  360
ttttctccct gcacctattc acagaattaa aagcaaatga ggcaaaaatg atggggcatg  420
ataacatttc tttttcatt ttctccaaca ttttcattct agaaaaagct ctttctgtag  480
cagggaagaa cctcaatccc rgagactctc taccgacagc aggctccatt gcacgtccta  540
cccagaactg gcctggtcaa acctcggctc ggggcccact tggcacttgg tcggggggta  600
aaacaggcat cgggagagtg gtgctgagaa tcaccaagaa ggccaggctg ggcaaggtgt  660
acgatgagga gtttctcca tggcaaatg aaaaatctgg gcaaacaaat ggagtagagc  720
ccgtttattt aggctggaag aggtaaagtt tttctgcact tttgaactgt tttctcaagg  780
cctgcctctc cctcccacgc aggaaacaaa cacagagaca ggcctcttcc agtgagggct  840
tcagttgttc aaagttagcc cgggaagggc agaaggaaga aaggcttaga gaaaggaagg  900
aggaacgggg gctaggaagg tggtgcagtg gccatggggg tagccgccaa gggagaaggc  960
tggagctggg atcagacaga ggaggagagc tggccaagaa g                      1001

SEQ ID NO: 278          moltype = DNA  length = 1001
FEATURE                 Location/Qualifiers
source                  1..1001
                        mol_type = genomic DNA
                        organism = Homo sapiens
SEQUENCE: 278
cacatatctt tgtcttgacc acaaatatat catggaaaga ctcagacaaa agcattactg  60
gaatcaaaat atgaggttac aatattcagt tggtctccca cttgtggagc cagttctccc  120
ctcgagtttc taagcatctg gcaagtgaaa ggtggctgat agtacaaatg gttgagctgg  180
aattcagacc cctgtacagt gaaataaaga aagacagaga aagggggtgg ggtggagaga  240
gagagagaga gagaaagaga gctgcagcca cagcattgct ttgcttctag aaacaatggg  300
cagttagaga acaatggcta cagacaaagt cttggtctat ttatatctgc cactgttagt  360
cccagacagg aggaactgga agtctgccct gtatgcacag ctccaactgg acccaagttg  420
ggaggaagat gaggtcacca agaaggctgc ctgcttagaa atgggcttct tttttcttcg  480
tatagttgct tcttagccta raggttctct taagcttgct tgccttctgc taaaatacag  540
ccactgctga gaagggagag atgagaaaag taactgctgc tctgcccagc ccaaagcaat  600
taaggcctct ctgtacagag gttgcaggaa ggtgggaacg ccaaggaaaa aataaccaat  660
cgatggaggt caactctatg gtttctgaaa caacagtctt attaggtctg ttaattatac  720
atgtttagga gcactataaa ggagcttttc cctgggaaag ttccctcctc atttctttgg  780
agacaaataa agaggccaag agctgaaatt cacagatatg tatgcattac atctcaggga  840
caatctcttc ttccctttat ttcagcccct ttttgatggt atctctattt tctggaattt  900
catcttttgc tctaacatgg ctttggagag atactcaatt ttaatccttc ccaaactgtg  960
ttacttgtat ccttaatcct cctacagcct tactaaaaag a                      1001
```

```
SEQ ID NO: 279          moltype = DNA  length = 1001
FEATURE                 Location/Qualifiers
source                  1..1001
                        mol_type = genomic DNA
                        organism = Homo sapiens
SEQUENCE: 279
atttccctgc ctctgtccct ctatcccgcc ctcactatag ctataggatg cataaagcct  60
tatccaggac caaaaagcag aaaagaggaa tttacagaat ttgctataaa actttaacaa  120
ctccttggag ggatgttctc tttccttgca accagacata gttataaaat ggatgaaaag  180
tggagagaag gaggagccaa gctctgccac tggtcagggg tcttacacta ttcctggaat  240
acagaattag aagacgcttt cgatgtcatc tagttcaaac cttttctttt actggtgggt  300
aaaatgaagc tcaaggtgac atcaacttgc cttaagtcac tggttactaa ttctagaact  360
ctggctccct ctcaggattt ttttttcctc tacatcattg ctgtttactt acaacagtgg  420
actgggaggg agaggctttc tcctatatct tcactactat caagtcctgg ttcatcattc  480
tggataaaca ctactcctcc rcaagttatt aagaatcaca gaggaatgag ccatccaaag  540
atctaataaa tatgatggga ttttacagat tcatgatgct atccactcct atttcaggtt  600
ataagtctgg aataccaatg gtcagactct aaggtggaaa agcttcctcc tagcaaagat  660
ccttgttgca taccagggat attaagcaac tttcaacagt caactccgat agcatgatac  720
catggtgtct gatggctctg aaatttgagg gtgctattcc tgtcaatcca gaaagagtga  780
agactgcagt taacttcagt gatctatgaa cctttatcta aaaagcactg aaaggcagag  840
tgcctcatat catttaaagg ttttacacca ctacccttct agtcctgctg gtattccaaa  900
tagggtcact gagccatggt gatagggttg agggaataca acaaacccca ctgacaaagc  960
cagaacttaa tatcaggggc actggccagt aagttgaatc t                     1001

SEQ ID NO: 280          moltype = DNA  length = 1001
FEATURE                 Location/Qualifiers
source                  1..1001
                        mol_type = genomic DNA
                        organism = Homo sapiens
SEQUENCE: 280
tacgagccct tctcctcaca tcccagctgg acagcattct ttttttcaga aagagctact  60
gactgctcat gagcatgggg cttcttttgg gagtgatgaa aacattctgg aattagacgt  120
tgatgatgat ggcacaactc tgtgaatgta ctggaatgca ctgacatgta cactttaaga  180
tggtaaattt tatgttatat caattatatc tcaatttaaa aaaaagtaaa tgttagagag  240
agaaagagct actggcccac tgctatgagc ccaacaatga ataccttggt gatagatccc  300
tcaggcagag tttccctcta gtgggagaag caaacaccgc ctaagtacag aagcaatagc  360
tatatgctca caacagacga tgagtgctgg gatcacggct gaagcggaag gttttgcaat  420
gcagagtgag tgaactagcg gggtccagaa gcactagggg agggggtagg aaggagtgca  480
cgtaagatgt cctgggtgta sggcgtgagg gacagaaggc gggcaaggtg tccaggatgg  540
cgcccctggc agttggtggc attactgaaa gggaagacga gaggatgaga tctcccacag  600
ccacctccgc cacctggaaa tccttgtgag atggaagccc cgcgatgctc actgggagac  660
cgaccgtggg agaggctggg cacgggccat ttccagaggc agacacctgg taactgcaat  720
ttctgggacc acttatgtga ggactaaaga ggaagggcca caggttctag gagacgaaca  780
aaatccctca agttccctac cctaaagatg ctcccagaaa aggctgccga gtgctctttt  840
aaagtgatat gtgcatcttt atacttacat acaaaagatt ctcaagggga agaagtctcc  900
atcagacagg gctctttcgc cctccagtcc ctggtggggg agacagagga aaagctgata  960
gggcggtggg gtgtgggggc ggtgaaggct cactgcacag g                     1001

SEQ ID NO: 281          moltype = DNA  length = 1001
FEATURE                 Location/Qualifiers
source                  1..1001
                        mol_type = genomic DNA
                        organism = Homo sapiens
SEQUENCE: 281
tgaggaaggt gcagtcacaa cactgtgatg ccagggatct ttttgggaaa ttcttttcca  60
aaagggatca tgaattttgg cccctggaat gccccagagc acctctgatt ggttccctgg  120
ccctgactca gatcgagccg ggctccaccc tccatgagta aataaaggca gggacggagg  180
gagggagagg gaaggagagg gagcggagtg ggcagacagg aaccagaagg ccagcgctgg  240
ttcagggaac acaccagatg agatttcagc gacgggtggt gtggcagaat tcaagacata  300
attctctgag ccttacacac cactccagtt gggattcagc cctgccttgg cagccggctc  360
agtgctgctt tataatatac tgaattagtc actggattag caagcacatt tacacacagt  420
ggcgcacagc tgtttaaaga cgcaggatcc ccttttctag gtgccagatt ctggctataa  480
atcaaccatt gcaatcagca rccagcaaac cccagaggtg catggttcct gcagacatct  540
tccttagggg aagcctgcta gaactgcgat ggccattttc tggggacagg agggacatct  600
gtggcaaaga aggaaaggtc ggtgggcttt ttctgtcttg aatcttatta tcttcagggg  660
gctgccaggt cttcactgac ctggaccttc ccggcagcag cctagctcag gaaatgacgc  720
ctgggagaac aggagttcta atcctgcctg gctgtattat caagtacaga gtttttctcc  780
taaaccttga atggctgggt cacctcccag aaaagaaaag actccagggc aaagaggaca  840
gtacttcagc aattaaaata attttaaatc ctgataacat caattccaaa aaactgcctt  900
gttgaagtgg caagggcaat gtctaaaaat aatgctttag agttggaatc ataactcaag  960
ccctaactca cgttcggtaa gaatgcgtga gaggcatttg a                     1001

SEQ ID NO: 282          moltype = DNA  length = 654
FEATURE                 Location/Qualifiers
source                  1..654
                        mol_type = genomic DNA
                        organism = Homo sapiens
SEQUENCE: 282
cttgtgcctc tgaacatccc ctccctggag aactctcaag ctggggtgga gctctcactt  60
```

```
cattcctcaa ttgtctaatc tggagagtgg gggccaaagc accaattctg tacacaagtt  120
tagtaaattt ggctagccac ctttcatgtg tctactttgg atttgaaaat gcaccatgga  180
aatcaggtga aaattttttt tttttttttt ttttttttta ctttccract actaacacat  240
cccaatggta gatatgtata agtgaaatga gtgcgttctt cctgcccccta taatgacaag  300
cctgacagag aacacatcac acagaagaat gtgccaagaa tcaagacctc ttagaagaat  360
gttagaaagt tttctctcca aatggattct gtctaagtag gaaggccttg gcaactagaa  420
aggtctaaga tcaaatttat gacttgaaaa ctctatggct ttgggcaaat tatctgaact  480
taattctgga ctcaatttct tatctacaaa atgggaatta aggcatcaac ctcaaagggt  540
tgtttaaaga atgtgattat gtatttctgt aaagcacatt gcaaagtatc tgacacatag  600
taggtactct ctgtaaatat tagcttcact tctctcactc ctccaactga actg        654
```

```
SEQ ID NO: 283         moltype = DNA  length = 1001
FEATURE                Location/Qualifiers
source                 1..1001
                       mol_type = genomic DNA
                       organism = Homo sapiens
SEQUENCE: 283
agacatgtgt ccatatctgg tggcttaagg taaagccaga cttgggtatc ctgattctca  60
catcaggcaa cagaaggtaa taagatgacc acctatgcca ccctgcccag ttaacagcag  120
agaaaatatt caaaccgggc aaagctaaga ccaaggaccc cttaggcctg acccaaaact  180
attggtacat ggagggcacc aagccatagt gctgaacccc aattggagga ggagacacac  240
ttcgtgacct cactaggatt tgctttacaa gataagattt tcctggcaag cattgaagtt  300
agtgcccaga ttcaaaacag caaacttaaa actattatct tcatgcttgc tataatcagg  360
tgtaccgccc aacttcccat ccctacctcc ccttccctag taatccagag gtactcaagg  420
tcactactgg ctacttaagg tttacatcca ctcccaagga aacaccagca accaaaagaa  480
tacttcccag atggaaaacc mgtcatttga ccttggaatg ctctgcctcc cataatgacc  540
aaaataaggt ccggccagag gggcttacgt tttttggtaa ggaacaacac attgttttag  600
agagataatc tgacataact ctgctaagct ctgagtgtct atgcatggta ccacagcaaa  660
caccctatgt cccaaatgga aactagcagg gtgaaaaaat tgttcatcta agatgacatt  720
aatctctgta tgcctccttg gtacagttct tttccacaac atgcagctta agattcaaca  780
attttttcat tgtgttttgt gtttcctgaa gcattcctcc agctacctga agctctcact  840
gattaaaata gacctccttt actaaaaggg gtaaactgag gcacagaaga acaaagcaat  900
gtgccttata gttcagaata ggtaaacaaa aattggacat ctattatttt caaatctctt  960
tagattaaaa gaaaaaaaaa tgtatttctc aaagtccaaa g                      1001
```

```
SEQ ID NO: 284         moltype = DNA  length = 1001
FEATURE                Location/Qualifiers
source                 1..1001
                       mol_type = genomic DNA
                       organism = Homo sapiens
SEQUENCE: 284
agacacactt cgtgacctca ctaggatttg ctttacaaga taagattttc ctggcaagca  60
ttgaagttag tgcccagatt caaaacagca aacttaaaac tattatcttc atgcttgcta  120
taatcaggtg taccgcccaa cttcccatcc ctacctcccc ttccctagta atccagaggt  180
actcaaggtc actactggct acttaaggtt tacatccact cccaaggaaa caccagcaac  240
caaaagaata cttcccagat ggaaaacccg tcatttgacc ttggaatgct ctgcctccca  300
taatgaccaa aataaggtcc ggccagaggg gcttacgttt tttggtaagg aacaacacat  360
tgttttagag agataatctg acataactct gctaagctct gagtgtctat gcatggtacc  420
acagcaaaca ccctatgtcc caaatggaaa ctagcagggt gaaaaaattg ttcatctaag  480
atgacattaa tctctgtatg rctccttggt acagttcttt tccacaacat gcagcttaag  540
attcaacaat tttttcattg tgttttgtgt ttcctgaagc attcctccag ctacctgaag  600
ctctcactga ttaaaataga cctcctttac taaaaggggt aaactgaggc acagaagaac  660
aaagcaatgt gccttatagt tcagaatagg taaacaaaaa ttggacatct attattttca  720
aatctcttta gattaaaaga aaaaaaaatg tatttctcaa agtccaaagt caaccttctc  780
caaagggaaa ctgcatgtct gtctagtaac ctataggatc attcacactt ttttttcctt  840
gagaaggaac taacttgcca gcctaccaac aattttgcca gtgccttggc atcaggcata  900
tctgcacaac ctttccagag cctatatcat agtgatctgt tcaagctgct caaagctcag  960
taatcatact aatctgtgca tagtgaccag tgctacctgc t                      1001
```

```
SEQ ID NO: 285         moltype = DNA  length = 1001
FEATURE                Location/Qualifiers
source                 1..1001
                       mol_type = genomic DNA
                       organism = Homo sapiens
SEQUENCE: 285
aggcatatct gcacaacctt tccagagcct atatcatagt gatctgttca agctgctcaa  60
agctcagtaa tcatactaat ctgtgcatag tgaccagtgc tacctgctca aagctcagta  120
atcagccagc tatgtgggac ttgttataga tgcataaaat atgtgggtga aatctacctc  180
caccaaaaga gaaaagaatg ccttgttgac actttgatct caagctaacg tttattaata  240
acatcattat tatatttaag tgaatgtact agatactcat cgaatcaaag aaatgtttaa  300
aatccatgtg gctgaactca aatgtcaggg gatttggaga aactgactgg agcttcatgt  360
tctaactctc cgcttatttg ccctggaacc ttgggagggt aacttggcat cggtgcactg  420
cactttcctt atttgtaaaa tattggtaac tctaaggatt accatgagct caaatgtggt  480
gaagtcacat ggcaaactgt maaatgctac cagatatagc caagtattaa gatgaactag  540
caaacaatat gcacaaacgg accttagtat ttccccccaaa ttccacaaac acccaaatat  600
ttctgagaat tctgaaaaca acagacatgg aattttcaag ttagctacag ctgggtttga  660
atctgaactc ctccactcag cagctttgca accttgggca agtcgtttaa tctcagtttc  720
ttcatctatg aaatggcaat aataatgctt cactattggg gcgaaataat gaggatactg  780
gcacaaagtt tgcgcccaat aactatcaga aaataaacag aacatgagga aaaaagaaaa  840
```

```
gatggatgga gatgagaagt gcttacacaa gcaccagtag ataaactcta cactgtcatc  900
aatgatcgtt ttccttgttt ttcccccaaa aactggcatg ctgaacttag gtccctgctt  960
tggaaagaga agggtaactg cgacagacct ttctcaaaat g                     1001

SEQ ID NO: 286          moltype = DNA  length = 1001
FEATURE                 Location/Qualifiers
source                  1..1001
                        mol_type = genomic DNA
                        organism = Homo sapiens
SEQUENCE: 286
aatacggtaa ggtcttcctt atcatctgtg attcttcatt gcattctgtg catttatttc  60
gtgtcttaat gatgtgagac aactgatgca taaggtatgg aattaactta aatttttggc  120
aaaagatatc aaataggaga aatgtgtagg tactagaagt acaaaagtcg gttacatgga  180
aactctttca ctgaaaattt cctgtgataa atttcttaaa gggtatttca aaatcagact  240
tgggcagggg cagtggctca tgcccgtaat cccaacattt taggaggcca aggtggaaag  300
attgtttgaa gccaagagtt taagaccagc ctgggcaaca tagcgagacc tcatttctac  360
aaaaaagaaa aagaaaatca gactcaacaa cacattttta ttctgaacat gaatgatact  420
aatgcatcac acaactctaa acgcatcaca caactctaat tgcacacaaa aaaagtaatt  480
aattgagaac aggtataaca sctggcacat agtgggagac cctagatact tcaaaaaacc  540
cgtatctaca aacactcacc aggcttagca gattcctgtg cctgaccgag gttattttcc  600
atttgtacct tgaaaatatg tacctgattg attttgtcat cttctctgag gtttaacgct  660
tattctgata aactgataca gaggttttaa caacagtatg agtaggagga aaagtaacca  720
aaaaaaaaaa gttacctatc tcataagctt actcaataac tctgctctac ccttaaatat  780
tcctactttc aaaggcaaaa ttcatcctga ggttcaaaac gctctttggg tcctggcctc  840
ctacttcctt ccttcatccc tttctacaag taagtttttt ttccttcatg tttatctaag  900
catctctttc attccaaact tgcagcattc ttcccacgct gctctctata tggaaaataa  960
tcctttccct gttcttacac ctccttcaaa tgcttcagaa g                     1001

SEQ ID NO: 287          moltype = DNA  length = 1001
FEATURE                 Location/Qualifiers
source                  1..1001
                        mol_type = genomic DNA
                        organism = Homo sapiens
SEQUENCE: 287
tagcttactt agatggtcta aaccctgaaa ttggcaattg agagaagata ttctagaaag  60
tacgattgac caaatttagt gtctaactcg ggtggccctc atctgtgggg agagccccag  120
ttaatgtctg tcattctgat gcaattatta atagtgcccc tttacactct caaaggtatc  180
ccagtttggg tggtaaatta tacgattttc tatctctaca ccattatgat ctgaagtcca  240
acagccttaa aatttctaat attactttgg gtctaaaagc actatctggg tcaatattcc  300
acaactctta gagacagtac taaatgctac aagaaagaac aattgagaaa agtggaaggg  360
gcagtaataa gccacatttg aagtgtcaag tgacaggctt gcacccaagc agtagacact  420
ggaaagcacc tgggaaatat gacagcgttg gccaagtgat caataaaata tttacggctt  480
gaatagcaat attttgagcg rgtctgttaa gcatggctct ctgccaatga aaccagacct  540
accacaatcc accctgcaga cctatgtctt tctgtatctg catggagatt atacattata  600
caatcagaag gaaaaggggg tgcagatagg cgaaggcttc agaaaagcag ccaagtagaa  660
atagcctgtt tatgcaattt ggaaaacatc cactgaagtt ttgaaaaaga tatcatcaac  720
ccgacagaaa aaataaagca gaaagtagct agagacacat gacaagtaaa aatgatagat  780
ttgggaatag ccttgacatt cctaaccctg agttaagaac agcttaacag ctgtgagcga  840
agggtagacc tagaatactg caaacataga ggcaaatgct atcagaggtt ccttgtgagc  900
aggaaaatgg agccaaggtt ttcattaagg agcagctaaa taaaaacacg gagatgatgt  960
tgttcatata caaattcctc tctgcggtga cagtgtgggc c                     1001

SEQ ID NO: 288          moltype = DNA  length = 1001
FEATURE                 Location/Qualifiers
source                  1..1001
                        mol_type = genomic DNA
                        organism = Homo sapiens
SEQUENCE: 288
acaagaatcc tggttctctg cctttcattc tgaggtaagc attgctggaa ctttcaaaca  60
tctttctaaa gcaacacatc tggactgcca ggcctgggga caacccacag gatggaccct  120
ttccccaagc cgtatgaagc actgagctaa caatgaggcc acctgattca gctcaggggg  180
ctcttgcaga gatagcaggg agccactgta cctcctgaac cccccaaagca ccgaccagca  240
ttgccttctc acctgcctgt gttctaattt ccagagtttt tgagaataac tcaaaatttt  300
aggtataaaa tgcctacaac atctcatcag tttctaaatt tctagagtgt ggccttaggc  360
caagtatgca tctctcagaa actcattttc ctcatctgaa aaatggagaa aataatactt  420
ccaccacacc tcagagtaag tgtgaagcat aaaagtgctc ttttatctgg ctgtgcccag  480
cacacaatgc aggctcgatg rgtgcttcag aaatatccca acaacttttg aatgacaaga  540
acctaccacc ttcaatgcaa gctcatggaa ttccaccaca gccatggatt attcattaca  600
caaaccagag agacatctgt aattacactg tcactgtaac cattgcagag ttatctgctg  660
tattctgaaa cagggagact ctcctgaaaa atcctgacct acactaacca gctctcagtt  720
tgcagagatt tgatggagcc cagagagacc tgggctccgg gaggttgacc acgagctggt  780
ttgtctcctg gagggaggcg atgctcctac agggtggtct ggcctcttta agagaaaaaa  840
aaagttacac agacaaaaaa acagcaacac aaaccaacca aaaatgccag gaatgcaagc  900
tctgccaacc aaataaataa ataaaatagg agatgcttta taataactgg acatgatgca  960
tttctcagcc ctgcataatt gaaaacttga cttttccatc a                     1001

SEQ ID NO: 289          moltype = DNA  length = 1001
FEATURE                 Location/Qualifiers
source                  1..1001
```

```
                         mol_type = genomic DNA
                         organism = Homo sapiens
SEQUENCE: 289
tggctttggc acctggcccc ttcacagcag gctccaccag gagagaacca ggagtgaacc  60
caatggctat atttgttttt aagctattta agatccttgc aatcacactg ttgcaatcaa  120
atagcatatc ccaccttact cttacacttg caaggaaaag tcaattctac tgttatttca  180
gagtatatgt taatttagca cttaacgctg tcaaactcct gtgaagtctc aaaatagaat  240
aaaagtgcat aaaggttctt ggtcaggtcc tagccaggaa aacaaataat ccaggtcttg  300
cggctcctgt ttggacaccc cactttctta ctgcctctct ttggcactca tgaatttggg  360
agggggtggg gagaaaattc tggtttaatc atttaagcca gataagatcc cacactagct  420
gtctccacac ataagaaact aagcaaccca aagaaatcat tctgacaaat atttaagtca  480
cagctgtgga taaaaagcta rgctgtgaga agttaaactt taaacacatg tcctatatgg  540
tctgatgggc aaggcaaatc cgcacttagc caatgtcttg tccttccact aacaaaagca  600
gacagccctg gccagaaaca ccgtttctcc catccttgct ttgcacctgc aagttaagtc  660
tcagctgagg tttctttgct gagcttttgg aaggtatctt gcaacattac tcaaagcaat  720
atacattgcg aagttagaaa caggaattga ttgtacttca gccactggct cactacatat  780
ttttatgtca attatttacc tttcctgtga ctctattttc ctctctgagg tatgggcata  840
atgttcgcat ataagcaact aaaggtccag aaaaaaaaaa gttgattata gtctatatat  900
tttttcaagt ttttgtcttt attttttcca agataataaa taatggtgct agaaatcaaa  960
cctctttaca atgaatggca gaagactgcc caatttcttt g                      1001

SEQ ID NO: 290           moltype = DNA  length = 401
FEATURE                  Location/Qualifiers
source                   1..401
                         mol_type = genomic DNA
                         organism = Homo sapiens
SEQUENCE: 290
tctttggcac tcatgaattt gggagggggt ggggagaaaa ttctggttta atcatttaag  60
ccagataaga tcccacacta gctgtctcca cacataagaa actaagcaac ccaaagaaat  120
cattctgaca aatatttaag tcacagctgt ggataaaaag ctacgctgtg agaagttaaa  180
ctttaaacac atgtcctata rggtctgatg ggcaaggcaa atccgcactt agccaatgtc  240
ttgtccttcc actaacaaaa gcagacagcc ctggccagaa acaccgtttc tcccatcctt  300
gctttgcacc tgcaagttaa gtctcagctg aggtttcttt gctgagcttt tggaaggtat  360
cttgcaacat tactcaaagc aatatacatt gcgaagttag a                      401

SEQ ID NO: 291           moltype = DNA  length = 1001
FEATURE                  Location/Qualifiers
source                   1..1001
                         mol_type = genomic DNA
                         organism = Homo sapiens
SEQUENCE: 291
ctgagctttt ggaaggtatc ttgcaacatt actcaaagca atatacattg cgaagttaga  60
aacaggaatt gattgtactt cagccactgg ctcactacat atttttatgt caattattta  120
cctttcctgt gactctattt tcctctctga ggtatgggca taatgttcgc atataagcaa  180
ctaaaggtcc agaaaaaaaa aagttgatta tagtctatat atttttttcaa gtttttgtct  240
ttattttttc caagataata aataatggtg ctagaaatca aacctcttta caatgaatgg  300
cagaagactg cccaatttct ttggccagtt gaaattttgt tgtatcgaag ttcacataca  360
aaagatgacc aatggcttgg aaatcttttt tgaaaaagaa agccattgca aatatgctta  420
ttataatgga cgctgactgt agcgttaggc cttattgttc ccattttaca gaatagaaag  480
ctaaagaaag ttacttgccc wgagcttatt tttaatcagt aactgaaatg acggcaccat  540
atacattgtc tctaatattt aatattaaat taccaaaaaa attgcctcag ctgttcactg  600
tgatctgaaa catgtgttgc cagggctctt tttcattccc aggatgaaag atcccttgta  660
ggtatgtgga ctgacatatc gacacgatat ttcccagatg accaaatctg tctcttcccc  720
cataaacacc cataacaaca catataaaca agctgttctt aaggaaagga cctattagtt  780
gagtttatat ctttgatgtg aactatcttt tcacttctat atatggtttc aatcaactga  840
caaacagaac tcattctagc ttcctcgaac ccccaaacac aaccatcata gaaacagcat  900
ttctgaattg taggcctaag tgccttaaat gtctccatgg ttccagctgc gctctcagca  960
ttgctcccac caccatcatc cttgcgagga gacaaaatct c                      1001

SEQ ID NO: 292           moltype = DNA  length = 1001
FEATURE                  Location/Qualifiers
source                   1..1001
                         mol_type = genomic DNA
                         organism = Homo sapiens
SEQUENCE: 292
tcctctgagg cagcgtccat ctccccttaa cattaaggaa taaggccaga gggttctcgc  60
tcatttggga aaataaaaaa agcaggaatg gggcgctgga aattctataa gcttttcccc  120
accactcaca aaaacacagc tgtgaaaata aataccaccc cccaaaccaa gggtctaggg  180
ccaccaacag tcctcctcct cctcctcctc ctccttctcc tcctcgtcct ccagatccag  240
ctgccaacag catccccgc tcctgaagaa atgcaccgcc cagaagggaa cggcgaaagg  300
gggaagaagt ccaggggacc cccggcctct ggccgagagc ttgggtgggg gcctcggccg  360
tcgccactca cccggggagg ggaaaagctc cagatcgact ttttccgtct tgatgatggt  420
gagagtcggc ttgagatcga cggccgcctt catggtgcca ggagtggggg acgtacggga  480
tggtagcaag tttgcagtta rtgttgtttt tctttttaat gaggattagt aacaggggga  540
aggggacggg ggaaatccga ctttcttccc aaaaatctca aattcccgct gcctttcttt  600
cccccgcgcc cggacggtgc gcgcccggca ctccagggga agttggcact ttgcggcgaa  660
gtgagcgcgc tcgggtccca gcctcgcccg cgccgcgccc gctcctcctg cccggccctc  720
gcccgctccc tcctctccgc cggcggctgc ctcgttcgct ctcgatctcc cggccgctct  780
ccctccctct cgccctcccg cgctctcccc tcctctttag ggcgtttctc gcggcgccgc  840
```

```
gtctcggccg ctgggtccgc gcgccctggg ccgggcgatg tccgcttggg ggagcgaggg  900
gcggggcgtc ggggcagggc ggggagccgg gggcggggcc gagcaccgcg gccaatctcc  960
gcccgcggcc caaagcgaaa ggaagggctg gcgagcgcgg g                      1001

SEQ ID NO: 293         moltype = DNA  length = 401
FEATURE                Location/Qualifiers
source                 1..401
                       mol_type = genomic DNA
                       organism = Homo sapiens
SEQUENCE: 293
agcatttgac tgtaactgta acctctgcct ctggtaagtt ttgacacaca ggcttacctt  60
catctaatcc cagttttgtg cccttgaagc cttagtaatt tgcagatttc ccacagcaaa  120
tcggggagga agccaggaac agaaaaatct gtggctcctg gtctaaactc cagattaaat  180
ccctccttag tgaccagagg raaatatttg tatgtgatag tcctaatttt tgaaagaaca  240
aagactgttg caatccagct gtgtttccac aaggtatgag aaaacaatgc tggcctccag  300
atgacaagaa cagacccttc tggtcctggg aaaagcctag agaaacagct gatgaatgaa  360
ttgtacattt acacgtccaa atgaaccaca aaaaaaaaaa g                      401

SEQ ID NO: 294         moltype = DNA  length = 1001
FEATURE                Location/Qualifiers
source                 1..1001
                       mol_type = genomic DNA
                       organism = Homo sapiens
SEQUENCE: 294
taacggctga tccagaacca gtttatgact cacagatgtt gatttactgg tataaatgta  60
agatttagaa aaaaaaaaaa aaaaaaaaaa gccctcaatt aacaacaacc tgtctgagct  120
gcatttgtgg tctcattttt ctctgagaaa aggcaacagt ctctgtcata cacagaaaca  180
agctttgaaa gcttacttct aaggcaagtg gtttctatgt gagaagttta gtcattaaaa  240
gtcacactag ggaagaaaaa tgcctggcac ttcaatatct acattatcaa gcagcaataa  300
aatggaaaat tagagatagg aaggaaaatt aaaataactc tcttaattaa acttggatgc  360
caaaaagcct tagggtcagt taagggaccc aagccagggg actcagatgg tactgttgct  420
gactgcaggc tggctctgtg acctcaccaa agccacttaa ccttttttgtg tcacaacctc  480
atctctgttt cagggaataa ratcagccct agctctccct agaatggaac acagactcat  540
tggctattgt ttagaaggca caataaacaa tgagggtagg aggagctgca gtcaggaggg  600
aagaagggag ggtggggtgg ggttggggga gaggggagga cttgggagcc tgtttgccct  660
ggaaagctca atataagaaa acaaagagga tagtagtgtg ggctttggaa taagactcag  720
gttcaaattc ttactctacc aactagccag ctgaattgcc acaggtaagt catttaaaca  780
atcccgaacc tcagttcctc catgtttcaa ctagggataa tagcagcaca caccttttaa  840
ggctatttga atgattaaat gagataatgt atgcaaagaa tttagcacag tgtctaggtg  900
agaattagta tttgattatt gttattaaga tctagtatac ggtagaatat gtgggaaatc  960
acattaaatg tctgtctaca gccatctctt tgcagaatag c                      1001

SEQ ID NO: 295         moltype = DNA  length = 1001
FEATURE                Location/Qualifiers
source                 1..1001
                       mol_type = genomic DNA
                       organism = Homo sapiens
SEQUENCE: 295
cagttcctcc atgtttcaac tagggataat agcagcacac accttttaag gctatttgaa  60
tgattaaatg agataatgta tgcaaagaat ttagcacagt gtctaggtga gaattagtat  120
ttgattattg ttattaagat ctagtatacg gtagaatatg tgggaaatca cattaaatgt  180
ctgtctacag ccatctcttt gcagaatagc ttggatgctc aattttcctg aacgatctcc  240
agcgagagat agaacaacta tcaccacatt tcatttaaaa atctcttcaa gacccttcct  300
cagttcttaa actggcaacc tgcccagcat cagcctcact tgagaaattc gagaactacc  360
tgattggaga agagaactag atttatattt gttttgagtc acagaaaagt gacagtttaa  420
attctgaaag aagatcacat ttgtagtgcc tctttggaga caaaacctta ggtcttggat  480
ttgtcacatg ttagagctca rtgggagttt atcagtgctc tccaagtcca gcactcctat  540
ttaccagagg tgaaaaatga gtgtgagtga ggaaattatt atttccaggg ccacacaatc  600
taaaaaagtc agtgtcagta ctagaaccag atgccctgat agcagttctc tccctggcat  660
ctccttgcat ttactttgca tttcactttg gcaggagaag taccagacac ccttgagaca  720
caagacagga tacaatggac atgggagtag atagatgagc agactcaatt tctagaaatc  780
caacttctct acactggatg tattgtcttt gggcaaatac attgcaggat aaccacacta  840
tggttccctg tgggagacag cttggcatgg gctgtcagga gagaaagggc ctgggttggc  900
tctattgctg tctgcagttt ctttagacta taattatgaa ccattcaact gcatctgcag  960
ccccaacaat gtggggtgga ttggcctaat ccacagacca a                      1001

SEQ ID NO: 296         moltype = DNA  length = 601
FEATURE                Location/Qualifiers
source                 1..601
                       mol_type = genomic DNA
                       organism = Homo sapiens
SEQUENCE: 296
tgtgaaacac tttcaagagt ccagggctgg cagtgagagg taatgacagg taacgtgcag  60
aatgaagaaa gcagaaagca tatagaagtt gcttcttaat ggaaacgtgt ttcatcagaa  120
tgatcagaaa catgtgttct ccccagattg ggaaaccatc ttgaaagact tcatcacaaa  180
aaggccttgg gtgggaagta ccacaaggga cccatccagg aggggtggga ggaggtgcag  240
ctgggtggga agctggcaat ggactgtgag aggaaaaaac aaagggcagt cagcgctctc  300
rtggcagatt cccaagagag aaccctttcc aggaatttaa aattctgaat aattgttgag  360
aatttctaaa aatcaagaag attataaact tttctttcag gggattccac agcattgaga  420
```

```
gagaccagat ggctggcaac aaaattccag atccaggaaa ggtccagcat ctacatatcc  480
atccactttt agtgagctaa tgctttctcc tacagagtgt atttgtctaa ttgaattgaa  540
ttgaattgaa ctgaggtgtg gaggtaaaaa ggctattgca aataagtgtt cctgtttcca  600
a                                                                   601

SEQ ID NO: 297         moltype = DNA  length = 1001
FEATURE                Location/Qualifiers
source                 1..1001
                       mol_type = genomic DNA
                       organism = Homo sapiens
SEQUENCE: 297
taattgaatt gaattgaatt gaactgaggt gtggaggtaa aaaggctatt gcaaataagt  60
gttcctgttt ccaaatagtc catacaaaaa cctgcagttt cttgccaagc agaaactacc  120
aggctttggt ttcctcacta tagaataaat ttaaactcta aaataaccag ggaggcaaca  180
tagtagagtg ggttaagagc acaagcttgg cagtaaatag acgagagttt gaattttagc  240
ttggctgctc tccagatgtc agtctttgac ctcagaaagc ctcagtttct tcatctacag  300
aatggagatg cggaaagtgc ctagttcaca gagttgaact gagatgagat gagatgaatg  360
ggtgccaagt gctttgcact gtgcatgatg cagaatgaag actcagtaac ccttcactgc  420
tattattgat tttaaaaatc agaattgtga cttcggattt agtgagcata aaattttcat  480
gaatgttaat ccaaactgta rtatatagta ttcttatgaa gaaatgagga cacagtgtcc  540
tatcttcatg tgcgctgtta aaatcatgac atagtgacaa agataagttt tggtctaggt  600
atgcaaatca tgcaaatcct tgacaccatc cctcttggat gaaaggggat taattcccac  660
tatatagatg tgagatacaa ttatgaaagt tctaatcata tactcacagc tacattacaa  720
attagcagca aagagaatat gtaccctctt gaatttcttc cagtattggg ttctccactc  780
tctggattgc acgtttgata gccaatgatt tttgcaacct aaacaaaata agaccttctt  840
aagcaactgg cctcagcatt tgactttcaa tctgggaaga atcccacatg ctattcaata  900
tgcccccata gcactctgcc taggtacttc ccaaactagc acccattagg cagcacctta  960
ctgcactcac ttcacagaag tctttttcta tgttattgca t                       1001

SEQ ID NO: 298         moltype = DNA  length = 1001
FEATURE                Location/Qualifiers
source                 1..1001
                       mol_type = genomic DNA
                       organism = Homo sapiens
SEQUENCE: 298
tgatggggac atactccaaa atgtacatgg ctgagtcctc ttgctctcct tttttttttt  60
ccccagtgac tttggggagg tttgggcagt gatcctgcat acacaatact gttcttgttc  120
ttcttttctc ttacagagca gccttgaata gctctgtcta aaattattag caggggcagc  180
cctaggctcc aagagatcac agccctcatg ctgggcctga acaaagaccc tgcttttttcc  240
caacaattag ccctgcaaaa aaggacatct atctccctct attaaaacca ccacgtgcct  300
tcaagtcagc ccattgtaaa gctaattaaa taacacgcct ctctccccat gcaggtctcc  360
tgattagctt tcctctgtca gaaacctctg caaagagcct agtgatagac aagccaatgt  420
tccacttctc cttagccccg ctcccatcgc caattagccg tcgcctttga aaagccatcc  480
ttatcaatgt tggtgagttt rttcacgctc catatccatc caaagcccag acgctagtca  540
cctccacctt aaaggaatgg ataaggttca tactgctttt aaaataaatt atttggaaag  600
gcaaaagttt tcatcacagt gtaaaatctt tggccagcat tccccacatc gcaatacaca  660
agggctgccg ccgccattgc aggagagtgt cagagaagga cttttctgaa agtcagagag  720
cctgggcaag atgcagccaa ggtggccatt tctaccagat ttctaaaaac aggatgcaga  780
agaccaccct ttaggttaaa ctcccttaga tactcctcac cgccaaacag ataaaatcca  840
agcacagtcc aaaaggccaa aattggtcct ctttaccttt tgaccacacc tcaccttctc  900
ccccacatag ggaccctgct ctctgacaat cctggacttg tggcaatccc ttgaacacac  960
tctagttctt cactctttta tgcattttta caggcttttt t                       1001

SEQ ID NO: 299         moltype = DNA  length = 1001
FEATURE                Location/Qualifiers
source                 1..1001
                       mol_type = genomic DNA
                       organism = Homo sapiens
SEQUENCE: 299
ggcagtaagt tctttattac tctcccttac cacagtgtgc ctccattctc agatgtttcc  60
ttaaagaaga gtaatctaag acctctaaat acataaaaaa taggataata agtaaagaca  120
aagagaccct catttttata tagatttgtc tcctccagat gcagcttggc atgtatacat  180
gtatacaaag cagccattga gaattaagca tgtgaaaatc acacctgtta atttgtcaag  240
gacagaccaa gtaaactata aggcagaaat aaaactgttt caacaaagat aaatggaaaa  300
catggttgaa aaagaagaat gatttggaat gaatgtcata gtattaatca aataaaaata  360
taagatgcat atagtcaata taatttattc aaatagtaag aagagaagaa atatgtatca  420
taaatgaaca ttatcatgag atattgggta caagaattca atacattggg taaacagact  480
gtagagatct taagagctta rgatttcaga gaatagcata cattctgtgg tctagaaaaa  540
gctgttttct gatccaattg agactgtgag caatgttaag aggcataaca gccaaatcaa  600
gacacacaag aagcctctca ttaggaggag aaagagcttg gaattggttg aagggagcag  660
ccgtgttgac agttcatgtc aatacattcc agttagcagg ttatttaagc aatgacttca  720
ggctaagctg gccttgtaat tctgcaaatc agatcccata gaagagcaat tagcagacat  780
tcatttcata ctctcttcat aaagtttggg tcattttaaa ttttttatgt gtcaaacttc  840
agaagtaaat atgaatacac atcacctctt tcctttgatt aaaacaatag ggatgcttta  900
ccttatttag catgaaagat cacaaaataa ttccaacatc acctcacagc acctctgaga  960
aatgcctaag aggtgggaaa ggatcccagc ctcactgtat g                       1001

SEQ ID NO: 300         moltype = DNA  length = 1001
FEATURE                Location/Qualifiers
```

```
source                  1..1001
                        mol_type = genomic DNA
                        organism = Homo sapiens
SEQUENCE: 300
atagtattaa tcaaataaaa atataagatg catatagtca atataattta ttcaaatagt  60
aagaagagaa gaaatatgta tcataaatga acattatcat gagatattgg gtacaagaat  120
tcaatacatt gggtaaacag actgtagaga tcttaagagc ttaagatttc agagaatagc  180
atacattctg tggtctagaa aaagctgttt tctgatccaa ttgagactgt gagcaatgtt  240
aagaggcata acagccaaat caagacacac aagaagcctc tcattaggag gagaaagagc  300
ttggaattgg ttgaagggag cagccgtgtt gacagttcat gtcaatacat tccagttagc  360
aggttattta agcaatgact tcaggctaag ctggccttgt aattctgcaa atcagatccc  420
atagaagagc aattagcaga cattcatttc atactctctt cataaagttt gggtcatttt  480
aaattttta tgtgtcaaac rtcagaagta aatatgaata cacatcacct ctttcctttg  540
attaaaacaa tagggatgct ttaccttatt tagcatgaaa gatcacaaaa taattccaac  600
atcacctcac agcacctctg agaaatgcct aagaggtggg aaaggatccc agcctcactg  660
tatgcagtat ctgtccaggg tacagagact ctctccaatg ttttgcacaa ctttgatcca  720
agtcagctgt gcaaaatact gaagatgcat attagctcaa ctctttcaaa tcattcatgt  780
gtccaaaatc actttcacct accaaagtcc ttaaaatgtg attttctcct gccaagtctt  840
tagtcgtcat ttgttggttt ttttaattag accttttatc actatgtacc ataatttacc  900
tgagacatta ttttcccact aacacagagt gtgtaggggg agagggaggg aaagcatggc  960
atggtgaata aagagactat taatccacta attcctactt g                     1001

SEQ ID NO: 301          moltype = DNA  length = 1718
FEATURE                 Location/Qualifiers
source                  1..1718
                        mol_type = genomic DNA
                        organism = Homo sapiens
SEQUENCE: 301
gaggaaccac ttaatacaaa taattatttt gccatagatt aaggaggtag ttcgtaggtg  60
acatatgtat ttaaaaatct ctatccacga cagtggacag acaatggaga aagaatactc  120
ttttaacaaa taatagggga gaaccagata cacatacgaa aaagaaagaa actagacctt  180
tgtgcataaa agttaactct aagtggatca gagacataaa tgtaagagct aaagctataa  240
agctcatata agaaaaaaca ggattaaatc ttcataacct tgtgttgggc aataatttct  300
taggtacaat gctaaaagca ctagaaaaac aaagaaaava tagataaatt gggctatatc  360
aaatctaaaa cctatggtgc tgcaaattct aaacatccag aaagtaaaaa gacaactcac  420
tttatgggag aaatatttgt aaattatatg cccgataagg gcttgtattc agaatatgta  480
aagaactctt acaactcaac aataaaaaga caacccaatt taaaaacggg ccaaggattt  540
taatagacat ttctccaaag aaggtataag aatgactggt aaacacgtga gaaaagctca  600
atatcattaa ttattaaaga aatgcaaatc aaaacgacaa tgaaatacta ctgctcattc  660
accatgagga taaattggaa ccctcttaca ttgctagtag gaatgtaaaa tgaagcagcc  720
actttcaaaa acagttgggc agttccacaa atagagttac catacgaccc agaaattcta  780
cccctggaga aatgaaaaca tattcacaca aaaaacttgt acattaatgt taatagcagc  840
cttatttata ataaccacaa agtgaaaagc acctaaatgg ccatcaaatt atggataaat  900
aaaatgtgcc atggccatat aatggaatat tattttgatg ataaaaggat atactgatgc  960
ctgctacaac atgggtgaaa cttgaaaaca ttatgcttag tggccagtca caaaggtcac  1020
atattatata actctactta tgagaattcc agaataggca aatttataaa gatagaaatt  1080
agaccagtag ctgttgaggt gtggagacag gaagaatgag aaagaatgaa gatcgactgc  1140
taatggatat aagatttctg ttaagaagaa taaaaatgtt gctgggcgca gtggatcatg  1200
cctgtaatcc cagcactttg ggaggccaag gcgggcggat cacctgaggt caggagttgg  1260
agaccagtct gaccaacatg gtgaaacctt gtctctatta aaaacacaaa acattagcca  1320
ggtgtggtgg caggcgcctg ttatcccagc tactcaggag tctgagactg gagaatcact  1380
tcaacccagg aggcggacgg aggatgcagt gagcggagat tgtgccattg tactactcca  1440
gcctgggcaa caagagagaa attccatctc aaaaaaaaaa aaaaaaaaga agaagaagaa  1500
aaatgttcta aaattaaatt gcaatgatag ctgcacaata ctgtaaatac actaaacaga  1560
actgtacact ttaaataggt gaattgtata gtatgtgaat tatatctcaa taaagctcac  1620
ctcaataaac cgtttaaaaa aaaaagttgg ttttctggag gtgaaggcaa gacaaaaaaa  1680
gagggagaat ttcctatcat ccaggaaagc ctgcccag                         1718

SEQ ID NO: 302          moltype = DNA  length = 1719
FEATURE                 Location/Qualifiers
source                  1..1719
                        mol_type = genomic DNA
                        organism = Homo sapiens
SEQUENCE: 302
gaggaaccac ttaatacaaa taattatttt gccatagatt aaggaggtag ttcgtaggtg  60
acatatgtat ttaaaaatct ctatccacga cagtggacag acaatggaga aagaatactc  120
ttttaacaaa taatagggga gaaccagata cacatacgaa aaagaaagaa actagacctt  180
tgtgcataaa agttaactct aagtggatca gagacataaa tgtaagagct aaagctataa  240
agctcatata agaaaaaaca ggattaaatc ttcataacct tgtgttgggc aataatttct  300
taggtacaat gctaaaagca ctagaaaaac aaagaaaaaa tagataaatt gggctatatc  360
aaatctaaaa cctatggtgc tgcaaattct aaacatccag aaagtaaaaa gacaactcac  420
tttatgggag aaatatttgt aaattatatg cccgataagg gcttgtattc agaatatgta  480
aagaactctt acaactcaac aataaaaaga caacccaatt taaaaacggg ccaaggattt  540
taatagacat ttctccaaag aaggtataag aatgactggt aaacacgtga gaaaagctca  600
atatcattaa ttattaaaga aatgcaaatc aaaacgacaa tgaaatacta ctgctcattc  660
accatgagga taaattggaa ccctcttaca ttgctagtag gaatgtaaaa tgaagcagcc  720
actttcaaaa acagttgggc agttccacaa atagagttac catacgaccc agaaattcta  780
cccctggaga aatgaaaaca tattcacaca aaaaacttgt acattaatgt taatagcagc  840
cttatttata ataaccacaa agtgaaaagc acctaaatgg ccatcaaatt atggataaat  900
```

```
aaaatgtgcc atggccatat aatggaatat tattttgatg ataaaaggat atactgatgc  960
ctgctacaac atgggtgaaa cttgaaaaca ttatgcttag tggccagtca caaaggtcac  1020
atattatata actctactta tgagaattcc agaataggca aatttataaa gatagaaatt  1080
agaccagtag ctgttgaggt gtggagacag gaagaatgag aaagaatgaa gatcgactgc  1140
taatggatat aagatttctg ttaagaagaa taaaaatgtt gctgggcgca gtggatcatg  1200
cctgtaatcc cagcactttg ggaggccaag gcgggcggat cacctgaggt caggagttgg  1260
agaccagtct gaccaacatg gtgaaacctt gtctctatta aaaacacaaa acattagcca  1320
ggtgtggtgg caggcgcctg ttatcccagc tactcaggag tctgagactg gagaatcact  1380
tcaacccagg aggcggacgg aggatgcagt gagcggagat tgtgccattg tactactcca  1440
gcctgggcaa caagagagaa attccatctc aaaaaaaaaa aaaaaaaaga agaagaagaa  1500
aaatgttcta aaattaaart gcaatgatag ctgcacaata ctgtaaatac actaaacaga  1560
actgtacact ttaaataggt gaattgtata gtatgtgaat tatatctcaa taaagctcac  1620
ctcaataaac cgtttaaaaa aaaaagttgg ttttctggag gtgaaggcaa gacaaaaaaa  1680
gagggagaat ttcctatcat ccaggaaagc ctgcccagt                        1719
```

```
SEQ ID NO: 303         moltype = DNA  length = 1799
FEATURE                Location/Qualifiers
source                 1..1799
                       mol_type = genomic DNA
                       organism = Homo sapiens
SEQUENCE: 303
gaggaaccac ttaatacaaa taattatttt gccatagatt aaggaggtag ttcgtaggtg  60
acatatgtat ttaaaaatct ctatccacga cagtggacag acaatggaga aagaatactc  120
ttttaacaaa taataggga gaaccagata cacatacgaa aaagaaagaa actagacctt  180
tgtgcataaa agttaactct aagtggatca gagacataaa tgtaagagct aaagctataa  240
agctcatata agaaaaaaca ggattaaatc ttcataacct tgtgttgggc aataatttct  300
taggtacaat gctaaaagca ctagaaaaac aaagaaaaaa tagataaatt gggctatatc  360
aaatctaaaa cctatggtgc tgcaaattct aaacatccag aaagtaaaaa gacaactcac  420
tttatgggag aaatatttgt aaattatatg cccgataagg gcttgtattc agaatatgta  480
aagaactctt acaactcaac aataaaaaga caacccaatt taaaaacggg ccaaggattt  540
taatagacat ttctccaaag aaggtataag aatgactggt aaacacgtga gaaaagctca  600
atatcattaa ttattaaaga aatgcaaatc aaaacgacaa tgaaatacta ctgctcattc  660
accatgagga taaattggaa ccctcttaca ttgctagtag gaatgtaaaa tgaagcagcc  720
actttcaaaa acagttgggc agttccacaa atagagttac catacgaccc agaaattcta  780
cccctggaga aatgaaaaca tattcacaca aaaaacttgt acattaatgt taatagcagc  840
cttatttata ataaccacaa agtgaaaagc acctaaatgg ccatcaaatt atggataaat  900
aaaatgtgcc atggccatat aatggaatat tattttgatg ataaaaggat atactgatgc  960
ctgctacaac atgggtgaaa cttgaaaaca ttatgcttag tggccagtca caaaggtcac  1020
atattatata actctactta tgagaattcc agaataggca aatttataaa gatagaaatt  1080
agaccagtag ctgttgaggt gtggagacag gaagaatgag aaagaatgaa gatcgactgc  1140
taatggatat aagatttctg ttaagaagaa taaaaatgtt gctgggcgca gtggatcatg  1200
cctgtaatcc cagcactttg ggaggccaag gcgggcggat cacctgaggt caggagttgg  1260
agaccagtct gaccaacatg gtgaaacctt gtctctatta aaaacacaaa acattagcca  1320
ggtgtggtgg caggcgcctg ttatcccagc tactcaggag tctgagactg gagaatcact  1380
tcaacccagg aggcggacgg aggatgcagt gagcggagat tgtgccattg tactactcca  1440
gcctgggcaa caagagagaa attccatctc aaaaaaaaaa aaaaaaaaga agaagaagaa  1500
aaatgttcta aaattaaatt gcaatgatag ctgcacaata ctgtaaatac actaaacaga  1560
actgtacact ttaaataggt gaattgtata gtatgtgart tatatctcaa taaagctcac  1620
ctcaataaac cgtttaaaaa aaaaagttgg ttttctggag gtgaaggcaa gacaaaaaaa  1680
gagggagaat ttcctatcat ccaggaaagc ctgcccagtg gggtctatga acatcatctt  1740
aagaccatat gcttcaccaa agttcagtgg aaaaatgtct aacatttcca tgaccttct   1799
```

```
SEQ ID NO: 304         moltype = DNA  length = 1001
FEATURE                Location/Qualifiers
source                 1..1001
                       mol_type = genomic DNA
                       organism = Homo sapiens
SEQUENCE: 304
taaatatttg tatcctggtt gtccaaactt gtcctagcta gtggagggat ggttggtgtc  60
ttggtcctca gttagatcat gggtaattcc aagttactga ctggtttagg gtgtcagtga  120
cattagagca tctttacttt gtcccctatt aatcaacaca tatttattaa gcccttgttc  180
ttcatgaggc gttggggcta tgaagtgtgg ttcagtctca tcctcaagga acatcacgca  240
acctggctgc cgtgctgaga cggacacagc caagctgcag agctggtgag caccagggga  300
ctgggaatga tgagagggat ggtcctgttg agactagaat tatggagaga ccctcctgag  360
gcctcccagt cacgtgaaac tgagggtgag ggggtttgcc ttgaggagca ctcattcatc  420
caaacttagt tggcagaatg aggacagagc tcgatttgga aaggggtgt tttactggtg  480
tttggaagag tggccactcc rgctctgctt tatgtatcct tgagcgttgt tattctttct  540
tctctctcct gtgttgattt tcacctccct caccctggtc tggcctctcc gtggccttcc  600
tgccgctttc agagatgagc ttagactcca cacggggctc ccaatctgaa tgaaatatcc  660
cattcctggg accgctgctc cctcacttca ttagtgctcc ttgctgttta taaagccagg  720
agataatatt tttaaattcc atttggagtt tcccgggcag cctctctcta agccacttag  780
gaagtttaga aaagaaggtc atggaaatgt tagacatttt tccactgaac tttggtgaag  840
catatggtct taagatgatg ttcatagacc ccactgggca ggctttcctg gatgatagga  900
aattctccct cttttttgt cttgccttca cctccagaaa accaactttt ttttttaaac  960
ggtttattga ggtgagcttt attgagatat aattcacata c                     1001
```

```
SEQ ID NO: 305         moltype = DNA  length = 401
FEATURE                Location/Qualifiers
source                 1..401
```

```
                         mol_type = genomic DNA
                         organism = Homo sapiens
SEQUENCE: 305
aacatcttta cctttgagaa acttgacaaa gagcagcatg aaaaatcatc tccacttggg  60
agtttatgta cttcagttta aggaaaagga aggccatgtc tctttgctat gaagaagaga  120
cattctgatc ttcaggctat gagcaaatgg agaaggcctc agatgttaat aagatgtaac  180
ttgtagcaag cagagaccat rgagagctgc aagtgttaaa gcaaggcagc tttaatctca  240
gttgcattgg gagatataag acttaagcct tgtggcatta ataggattca agaattatac  300
aaatataaat acagccattt tgaccttttg cttatacaaa caaaacctat tttgtttaga  360
attttaaagg atcacttttc tcatgtcctc aaatttttag t                        401

SEQ ID NO: 306           moltype = DNA  length = 401
FEATURE                  Location/Qualifiers
source                   1..401
                         mol_type = genomic DNA
                         organism = Homo sapiens
SEQUENCE: 306
ggcagcactg ccaccagcaa gtggaaggag agaagggaga gagagacaga ggaaaaagaa  60
ttgggatcca ggtgggcatg gacagagagg ccaggaacaa tggaaacaga tgatcatcga  120
aagaaagcat gttctctaag aaggccgagc aattcacaca cctctgttta tccagctcag  180
actctgtgac tgcaaaactt rtaggctctc tgacaacagc caaaacgggt gtcaggaaat  240
gcaggatagg caaaactatt tgcaaggtga agacctaaag caacctttct tgggcccatt  300
cctagagttt agacttcctg tcggggaata aagtaaccca aaatttatgg agaaggcccg  360
ggactttcca ttcaagaaca atagcatctg tacccgcata a                        401

SEQ ID NO: 307           moltype = DNA  length = 701
FEATURE                  Location/Qualifiers
source                   1..701
                         mol_type = genomic DNA
                         organism = Homo sapiens
SEQUENCE: 307
ttgtaaggag ttgttatgga tgtgttcccc caaatttaga agttgaaatg taaaacacca  60
atgtgataat attaacaggc ggaggcatta tgaggtgagt aagttgtcag ggcaaagccc  120
tcaaggatgg gactaggacc ctttaaaagg acctgaagga atgggtttgg cctcttccct  180
cccttccgcc actgaggaca cagcgttcat cccctctaga gaatgcagca ggaagggtcc  240
atcttggaag ctgagacggg actctcacca gacacagaga ctgccaatgc cttgatcttg  300
aacattccag catccagaac ggtgagcaat aaatttctat tctttttgaa ttacccagtc  360
tcaggtattt tgttatagca gcactaatgg accaagacag gagtgctata acaaaatacc  420
tgaggaaact ccagtaattc atttaacctc ttaggatctg aatttcctga tattgcaaga  480
tggtctttac attgtggtct sactctgaaa ttctctagct tgtgatgatt gaacctagta  540
gcttacagaa gccccacagt ccaagatgct ggaaaaatat aggttatttt cttctttcct  600
tcaatttctg tgacaaccac taagagttat gagcataaat aatttcccta aacattatgt  660
ttcagcagtc tcattcccac tttggtttta aatttctttt t                        701

SEQ ID NO: 308           moltype = DNA  length = 401
FEATURE                  Location/Qualifiers
source                   1..401
                         mol_type = genomic DNA
                         organism = Homo sapiens
SEQUENCE: 308
tgaggagttt ttaatacagt tacttcaccc tcaaattacc aggaatgtcc cttaagccca  60
gagtcttatc ataggaaatt ctggcacttg gggatatgta gttagcctct tgggcatagg  120
tgccttccct gaggtggagc acagtgggcc actcctgccc gagcatgttg ttctatctcc  180
caaagtctgt ggctctggga rgaggtgagt gggcagttcc tttcctctgt acagcccaag  240
gtgtttccta aagcccgcat ggccaaaggg gtcactagtc ccccaggaac tcctccgcac  300
atcctccttg ccggtgagac atcccaggct gggccatgtt tagtcaaaac tgagagcagc  360
ccagcccgct cattcccgcc actctcagct gggccagcac a                        401

SEQ ID NO: 309           moltype = DNA  length = 1001
FEATURE                  Location/Qualifiers
source                   1..1001
                         mol_type = genomic DNA
                         organism = Homo sapiens
SEQUENCE: 309
taggatgaca ttatattata tctgcaactt ttatacttat aataggcttt ttatctcagt  60
gtctaaacta agtacatatt tgtgtgacat ttctttcttt ctttcttttt cttttccttt  120
ttttttttt tttagatgga gtcttgctct gtcacccagg ctggagtgtg caatggcaca  180
atttcagctc actgcaacct ccacctcctg ggttcaagcg attctcatgc cacagcctcc  240
tgagtagctg ggattacaag gcatgtgcca ccacacctgg ctaatttttt ttgtattttt  300
agcagagact gggtttcatc atgttggcca ggctggtctc aaactcctga cctcaactga  360
tccgcccgcc tcagcctccc aaagtgccag gattacaggt gtgagccact gagcccagcc  420
atggcatttc attcttagcc aaaatattaa tctgttttaa tttgattata gtacctgtaa  480
atagaattaa catggactgg rttttaaatc ttatttttca agtcaatgac acattttgct  540
ctgaaatcac aatatcatta tttattttaa caaatttcta caatatcgtc tttaaggaaa  600
ttttaatgtc atttgtgtta actttaaata atgacctcta tgtgaggaaa aggaggagga  660
gcccttttct ggcaacttct tcagccctcg atatgatctt aaactgcaag tcctttggca  720
atcgctacta agcaaactcg agtgactcct tgcctggact tgtcgtgtag tggagtgttg  780
gggagtgggc agtttaaaca tatttctgat atatattatc gtctaaacct ttttctgatt  840
ctaatttttt gtaaaagtaa acggtgctta catgaacaca gaagccattt taaaaagaag  900
```

```
aaaaatgtgg taaaaacagc tactgaagag agatgtctca atcatcctta aaatgtgtct  960
tttcccttga acagaatagc tactgagagt tttggtttt t                       1001

SEQ ID NO: 310         moltype = DNA  length = 401
FEATURE                Location/Qualifiers
source                 1..401
                       mol_type = genomic DNA
                       organism = Homo sapiens
SEQUENCE: 310
tgacacattt tgctctgaaa tcacaatatc attatttatt ttaacaaatt tctacaatat  60
cgtctttaag gaaattttaa tgtcatttgt gttaacttta aataatgacc tctatgtgag  120
gaaaaggagg aggagccctt ttctggcaac ttcttcagcc ctcgatatga tcttaaactg  180
caagtccttt ggcaatcgct rctaagcaaa ctcgagtgac tccttgcctg gacttgtcgt  240
gtagtggagt gttggggagt gggcagttta aacatatttc tgatatatat tatcgtctaa  300
acctttttct gattctaatt ttttgtaaaa gtaaacggtg cttacatgaa cacagaagcc  360
attttaaaaa gaagaaaaat gtggtaaaaa cagctactga a                      401

SEQ ID NO: 311         moltype = DNA  length = 401
FEATURE                Location/Qualifiers
source                 1..401
                       mol_type = genomic DNA
                       organism = Homo sapiens
SEQUENCE: 311
aggtatgtca cccagtaacc caagaaacag ataaacagag agaaaccctg caaaagggat  60
tgagcattat tgatcttgaa aaaaggagaa gggctattaa ataacttgtt gagagctatt  120
ttctacattg gaagtctgag tgtctagaat gcttgagcaa ttttctggct gaagggattt  180
tccagttagc tactggtcat rattacatat cgaacatctc tgttgaccta aatactttcg  240
aaagttcatt acacactttc ataaacttaa tactatgcat ttaaaaagtc gttcttgaat  300
aatctcgaag attaaattcc taggcatacc aatcagaggc caaattctta ttgttaggaa  360
gtgacgcttt aacttcactg ctttccagtt tgtatttgtc t                      401

SEQ ID NO: 312         moltype = DNA  length = 1001
FEATURE                Location/Qualifiers
source                 1..1001
                       mol_type = genomic DNA
                       organism = Homo sapiens
SEQUENCE: 312
tcttaggtct aggaatctaa ctaagaaaat gccaattcta gtctctgaaa cctttgaaat  60
actaacaatc tacactttct agtcaatcat acttctgtca gaacatcttc ctgaagatca  120
aaggtaatat tcaatacact gccttaccat aaaagtggcc atagcctgtg tacaaatgct  180
atgcctcaaa tcctgtattt taccatgaaa ttcaacaaat gatcacactt ggccttagga  240
tgtactcctg agccagaagc atggtaagta ctcataaata actgaataaa taaataagga  300
ttgtgtttta cttcgaacct caaaacaaaa aaagaataag ctggaggaat aatgtagagt  360
actctttgct ttccaagaat ggtcgtaata gaggccatgg aataagagat tgttttccaa  420
gtcaaatgca aagaagggcc acgagattaa aaacgtcaac tctaatccaa tgaatgctgc  480
caatgaaacc tctgaagaga rtagcatttt aaagaattac attacagact cttagcctgt  540
gaagcatgtc agacataatc tagagtttag acttggctct ggctctaaag gaattctcaa  600
caaaactgag aggcaccata aatagaaaga gatattacaa gaacaatgag aggggactgg  660
atagttgcaa taatgcccct ttaaaattga actaaaagat accagctgcc ttagatctct  720
caaatccagc aagcaacttc ttggactatg tctgattgtg attttcatgg tggagtttca  780
tttgttttat tacccgaaat gtaaggttcc aatttctcag tataatgcta aacagcttgc  840
tagcattctt atataaagag ggattgtgca attccagtga attttggagt tggaaaaaat  900
tcatcaatct tctcatttat ttcaatgaac tgagtcctaa gaggttacgt gtttagcagt  960
gatcaagaac cctggagtta catactatgg gtgaacgtag a                      1001

SEQ ID NO: 313         moltype = DNA  length = 401
FEATURE                Location/Qualifiers
source                 1..401
                       mol_type = genomic DNA
                       organism = Homo sapiens
SEQUENCE: 313
actgcttgct gcgtgtatgg ccatgagcaa atttcttaac ctcacaatca gtttcctcaa  60
ctataaaatg caggtaataa tatcaacact ttcaggatta tagaggagga tcatacaaaa  120
cacaaatact tagcagcatg ctgtataaat agtaaaaatg gtcaataaat aataattgtt  180
attattgcta ttttatcagt mgtgcctggc aattagtaag cattagtaaa tgcttactaa  240
tgtcactaat tagtaacact actgttttat attaattact tttttctact gcccaacatg  300
gcagaggtta tttaagtgtt agagctagaa catggatagc taaatctctc atctcttttt  360
ctaaagactt gtattcaagt catgaaaaca ggattccctt t                      401

SEQ ID NO: 314         moltype = DNA  length = 401
FEATURE                Location/Qualifiers
source                 1..401
                       mol_type = genomic DNA
                       organism = Homo sapiens
SEQUENCE: 314
taaagacttg tattcaagtc atgaaaacag gattcccttt cataatcata ggttgagtag  60
cattagtcaa gaattttgca ggagaaaaga gccacaattt ctgtttaatg gtagtctgtt  120
tgtaccattg ttatgcataa aaccaagaag taagcatttt tcttacagtg gagaactaac  180
tcattgaaag attgcatagc mcaaatggtg aaatattgca gcttcctgag ttaaaccaac  240
```

```
atctttttga tataatgtcg atcttttgtg gacttacgct ttagcaacta gatacaaata  300
taaggaagta gtaaagcact gcggaaaata gtgcaagatt tcttgtttgt tcattttttt  360
cattttttgct ttttcatttg tttttgcttt ttctttagag c                      401

SEQ ID NO: 315         moltype = DNA  length = 713
FEATURE                Location/Qualifiers
source                 1..713
                       mol_type = genomic DNA
                       organism = Homo sapiens
SEQUENCE: 315
ctcttctcat tgagatggtg aaaaataaaa tgagaaaata gagagagaaa atgctttgaa  60
agaagaacac tttgcatatg aaagaaattg gagattttgt ttatgatagc tcagatgaat  120
cctgccttgt ctcattgcaa cagcctgtta taatatttca ttgttggaac tgaaattgcc  180
tcataataga caagtgtcat aggacttgga tcagtagata aacactacag ggaagcctat  240
ttcagatcaa aatggtgaag tgcttttgaa catttagaga gcttttgaat atttggagcc  300
attcaaaaac aaaatgagtg cctggaaagc actgaataag ttgaaacaga gctataagac  360
cagctagcag agatgctgta gaaaagtttc ttgcactgga mcagacaaca gctaacattc  420
tatcccagta agaatctggg aattcactac aatgattttt aatgctgctt ttaaataggt  480
gaagggctgt aatgtagaag aggaagtgtt ttctttcaga ttatcagact aagcccagtt  540
gatggaaagt ataagaagac gaactttggc acaatgcagc caatgcaaca atattcacaa  600
tattcatggc atttagaaat gccatataat taattttttc aaagtcgggt agatgtgaga  660
ataatctgac caaagctaat ccaccagtgt tagacctcaa actttagatt ctg         713

SEQ ID NO: 316         moltype = DNA  length = 610
FEATURE                Location/Qualifiers
source                 1..610
                       mol_type = genomic DNA
                       organism = Homo sapiens
SEQUENCE: 316
ctggctctgt tctatgccac ccacagcaat gggctagata cactctctga atgccaaact  60
tgtgcttccc aggcaccctg ctgccaaaat atagctggag aaagcagcca gagaacccca  120
tagtcaaggc aagcacaaga gcttaactgg agacaagact gtggggttga aagggaggga  180
gatgaatcct cttagatgtg tgttgactcc ttcctaagtt caaagcattt atgcttttaa  240
atcatctctc ctccaagtaa atttgtggga caagctgtat tttctccact taatagacga  300
tgaaattgag gctcagattt gatttggatc atagccagtt tgcatagata gcaccagatt  360
ctattccttg gccttctcac ttcagggact ttttcctara ccacattacc agtagatgtc  420
attctttgac cagcagacaa atgccagaga gtagaaattc tagccacttg gctgaaagtt  480
caggttcagg gagtatcttc aagagaggga gggactcgag accagtgtgc ccagctcctt  540
cgcctctgcc ccacccagag ctgagggcct ggacctcatg tgccctcccc acacggtgcc  600
tactttctct                                                          610

SEQ ID NO: 317         moltype = DNA  length = 401
FEATURE                Location/Qualifiers
source                 1..401
                       mol_type = genomic DNA
                       organism = Homo sapiens
SEQUENCE: 317
tagaccaggt gggttcaaat ttcccctatt ctaattttaa tttccacatg atcagaataa  60
acatggctgc cttgagatct cattttccag tgctgccaga aatgaaaatt ccacatagcc  120
tagtggacct tcccacctcc tttcactgga cagcttgctg tttagaggct cctgccattc  180
ttaacacggc agctgtcaca rcagttagcc atggaaagac ccattctctc atttgatccc  240
atctccctgc caggacagga tataggcctt aaaagtgctt cctggtgtaa ggactgagtc  300
ggggtttatt tatcctaggt tacagcaaac attacttcaa aaaacaggaa agagagtctc  360
atcttgttga ttatgatacc agttatagca atgaggtgga g                      401

SEQ ID NO: 318         moltype = DNA  length = 501
FEATURE                Location/Qualifiers
source                 1..501
                       mol_type = genomic DNA
                       organism = Homo sapiens
SEQUENCE: 318
agaagcatca tgaccaatga ccttggataa ctccactttc ttacagcccc tgcctcaaac  60
agggattaag gaagaaaata atctctggga tgctaccttc catgaatcag ggtctagcac  120
caacaaatat ttgggtatga ttcatccagc atcttcactc tcattgtcat atttgatgtg  180
tgggacaact atatgaatta ggccagtcag ataatactac tttacagata atacaactga  240
agctcagaaa scaggtgcag ttgagagttg agccagatcc ggtttcaaat cctatctgtt  300
ttctataaaa taatggcagc ctcttctgag aatgagaatc tgccccattc atgccaccct  360
aaagagatgg tttgctttac ctgggacttc gagctccacc cttgtggcac agatgtcatt  420
cgtggaggtt aagtgttctt ggcgggcaga ggtttccatg agagctcatt tatgttggct  480
acaagactgt tcttctccta g                                             501

SEQ ID NO: 319         moltype = DNA  length = 501
FEATURE                Location/Qualifiers
source                 1..501
                       mol_type = genomic DNA
                       organism = Homo sapiens
SEQUENCE: 319
cccatggttt ttaggatcct tagccctgcc aatggttatc tgagcagggg aagcatattt  60
gttttaagca actgggagtg tagaagacat gggtgcttcc ttcctgggat ggccaggcaa  120
```

```
caagaggcat gtaagaagat ttccaaggaa gagaaggcaa gccatggggc tgagtgggag  180
caagttggtc tgctgggaag gagcagaaat actgaccacc tcaagtcctg aacacccagt  240
ggaggtcatg rctttccatg ggtggtctcc aaattctggg catgcttttt cttcctgttt  300
ccaaatagct tagcaagctt aatccatcca cacaacatgt aataagctct tctgtgttcc  360
agatatttga taagaactga aaataaatga taaagcaaga ttctgttctt aaagagctta  420
tcagaggagt aagtaacaag aaatggtgtg aatttttagc agaagcttgt aaaacatcag  480
acgagaaaaa cacgatatgt g                                             501

SEQ ID NO: 320          moltype = DNA  length = 720
FEATURE                 Location/Qualifiers
source                  1..720
                        mol_type = genomic DNA
                        organism = Homo sapiens
SEQUENCE: 320
ttctgttctt aaagagctta tcagaggagt aagtaacaag aaatggtgtg aatttttagc  60
agaagcttgt aaaacatcag acgagaaaaa cacgatatgt gtgttctata tggattggca  120
gggtacatta ttttatacca actcatgacg ttccttaccc atttgatgtg tgttaaatcc  180
tagttcccca agtccataag gagctccttg agggcaggam caagactcat gtttatttgt  240
tcaacgatac ctcacccagc attaagcaca tcaaaagttg ttcactaatc tggacaagtt  300
cttcccctat ctggacatgt ggtagaatcc cactccctgc cctgttgaaa ttgggagtgg  360
tcctaggatg tgctttcact gatgaaattc gaacagggtc acttggcaga aaattagagg  420
accactgaag agtttcggcc tttctgtttg tctctctggc acgtgtcagg tgacagctgc  480
ttatcagcta gggcccggag taactctgat accatggaac aaaacccccct gccagcccag  540
tgttcatgca gcatgagtaa gatgtgttgc ttcaagccac tgaggtttgg ctcttgttac  600
cacagtgtaa cctagtccag tctgcctggt acagaagtgt tccacaaata tttgctgatc  660
tctgtactga tgcctcgatt atagcagata ggtaaggaag taaataaagt aagttggtag  720

SEQ ID NO: 321          moltype = DNA  length = 501
FEATURE                 Location/Qualifiers
source                  1..501
                        mol_type = genomic DNA
                        organism = Homo sapiens
SEQUENCE: 321
aggccattga cattccatct ctttcagcat ttcttccact ttgaggctgc tttgtggctg  60
ctcaaactca gatttaagtt tgctgtgaac cttagcagtg aatgcctcta tctttgcctc  120
aagacttttg tagtcagaat aggcaatgca ataagtagtc ctagatagag aatggtagac  180
aatttaggga agagttaaat gagagattgt ctgaaaaagt gtgcgaagat tggaaaggaa  240
aagttccacc ragacagagc ttcccaggga ttgcagtcaa aaaccactag gaaattgaga  300
tagatggtga tgcctttagg agcttggcct ctggcatcag gcaaacccga ccttgaatcc  360
cagctattca ctcacctact gagtgactga gcaatttact gaacctttct aaccaattca  420
gtttcctcat ctgtcaaaca agagtaagga ttgagctcag ctcttagggc cattgaccac  480
ataggaaagt aattttcctt a                                             501

SEQ ID NO: 322          moltype = DNA  length = 501
FEATURE                 Location/Qualifiers
source                  1..501
                        mol_type = genomic DNA
                        organism = Homo sapiens
SEQUENCE: 322
agtagtccta gatagagaat ggtagacaat ttagggaaga gttaaatgag agattgtctg  60
aaaaagtgtg cgaagattgg aaaggaaaag ttccaccgag acagagcttc ccagggattg  120
cagtcaaaaa ccactaggaa attgagatag atggtgatgc ctttaggagc ttggcctctg  180
gcatcaggca aacccgacct tgaatcccag ctattcactc acctactgag tgactgagca  240
atttactgaa mctttctaac caattcagtt tcctcatctg tcaaacaaga gtaaggattg  300
agctcagctc ttagggccat tgaccacata ggaaagtaat tttccttaat aataaggaca  360
catttttata ttatgtgctt ttaaaaggag ccttaaataa agagaagtga gatcattttc  420
cagtgcactt agcatagtaa cgacaacata gaaagcgtta aaaaaaatga cagcttaaga  480
aagcaaagga tgtggaaaca c                                             501

SEQ ID NO: 323          moltype = DNA  length = 501
FEATURE                 Location/Qualifiers
source                  1..501
                        mol_type = genomic DNA
                        organism = Homo sapiens
SEQUENCE: 323
tgaaagaggg ctctgcctgg gctcagcttc caggaaactc tcaaactctt gcccagagca  60
tcgtgatgta gccattggaa cctcacgcag gcgatgatga tccttttacc agatatcaga  120
acttacctaa ccttcagcca cttaaaaatg ctctctggaa agtattcaac aagggcttga  180
gaaaccaagg agaccctgat ggaggagatg tcaaataacg tgagagcctt gttctgtcta  240
agctaatttc rggcactttc cagagagtta gaagtgattg gtcttcggtc tgctcagctg  300
actttgaagc attggccaaa gggctcggga caagcaggga gaagctggaa gtcgtctatt  360
gcctccacct gggactgcct caatgtcctt ttgttccagc tggatgtagc cccagaaata  420
gcagtaaagg aaaaacatgt gatttgagtt tccccatctc ccttttctgt gccctctccc  480
ttaccagggg atttttcctg t                                             501

SEQ ID NO: 324          moltype = DNA  length = 601
FEATURE                 Location/Qualifiers
source                  1..601
                        mol_type = genomic DNA
```

```
                         organism = Homo sapiens
SEQUENCE: 324
tagccccaga aatagcagta aaggaaaaac atgtgatttg agtttcccca tctccctttt  60
ctgtgccctc tcccttacca ggggattttt cctgtgccca ggcaccccat gtttcttgaa  120
gttctgcccc agagacaatt attccctcca gtggagtgga gaaaacaaga gacttggaat  180
taaaagacac atatccaaat ctggatgctt tcacatgcca gttcttatct gattgcccct  240
gagcctcagt ttcctggaaa tagcagtaac caccccacag taggtaatta ttttattata  300
rtatagtact ttaacagatt tgggtttgat ttgaacagca gagataagaa gaattaattt  360
ctgctcttgt agatgaagcg aaatttttca accaggtaaa attccctaac ttgctcactc  420
cattaattcc tccaaccatc cattcactca ataaacatgt attctgagcc tactattgtg  480
ttaagtagca ctaattgacg agagctgaaa gagaattcag accttgggaa tgaggctgac  540
agagaaacag atggtaaagc aggagagtgg ctgcggtgtt taaagcagcc cagcagataa  600
g                                                                  601

SEQ ID NO: 325           moltype = DNA  length = 1001
FEATURE                  Location/Qualifiers
source                   1..1001
                         mol_type = genomic DNA
                         organism = Homo sapiens
SEQUENCE: 325
cacagaataa atgcccaaca aataatagcc ataattattc ccattcttgg tcgaccacct  60
taataaaagc taccatagag gcagggaatc agtaagaaga gatgactaag aggatgctta  120
ctgcatgtag gaaaatcagt taatgctcgt gtgactggct tatttccctt tgcatactgt  180
ccttcaggtc catccatgtt gtcacatatg gcacgatttt catttttttt taaggccgag  240
taatattcca ctgtctgtat ctacccattt tctttattcg cccattgatg aacatttagg  300
ttgtttccac atcttagctc atcttgacag tgctacaatg aacatgagca tgttaatatt  360
tctccaagat catgatttca attcttttgg ataaatacct aaaagtggaa tggctggatc  420
ctatattagt tctgttttcc tctttttgag gaacctccct actgttttcc atagcggcta  480
taccatttta cattcccacc rtctgcgcca gagttcgaat ttctccacat cctcaccaac  540
actttttatc ttttgttctt ttgataacag ccatcctcac tattgtaagg tgatatctca  600
ttatggggaa aaattatatg aaaaggaagc atcaaattaa taggcaagaa aaccagtaca  660
tagtatttgg acagttggca tattacttaa aaattatgta tgaatccaaa aaattaatta  720
actcttacta tattagtatt ctgattgttg acattaacct gtaacaatag gagaaaaagt  780
tagttcagga atcacttccc aattacatct gttacaaatg caaggagaaa caaatacaag  840
gagaaactcc tttgcataca atattttaaa gaaaaggaca ggtgagtttt gggatgcgag  900
gagaggggca agaaactgtc ttctgtgtgg agagggatct tgaaacatat cttccaatgg  960
gaggccaaat gcaggggggc attgctttca agaaactaaa g                      1001

SEQ ID NO: 326           moltype = DNA  length = 1701
FEATURE                  Location/Qualifiers
source                   1..1701
                         mol_type = genomic DNA
                         organism = Homo sapiens
SEQUENCE: 326
ggtcaaatga gcaaaggcac catcccaggc acagaatgtg catcctgtgg ttgttggggg  60
gagtctgtca gagtcttatt ctggactaga gtcaggactg ggtcccataa ggtcagggca  120
gggtgagtgt gaccttgggg ctacaggcaa ggccaggcat ccaaggggtc tcaactgccc  180
caaacaaccc catcctgcca ggccccactc cccctgtccc tccctcccat tgttcagtcc  240
cctcaccccc tcaccatggg cacctgcagt ctcattcaga gacaccctca tcttagagtc  300
cctgatagtg gggagtttgg cccctcagag gccttggttg ctttggtcaa tccataatgc  360
ctgggcctgg gacccccacc atttcttgtt catcagggac acagcagctg tgaaggcagc  420
tgccttcacc agagcagcga tgtagcccag caagggcagg gacagagacg caaggtctgg  480
gggatttttc cacaatgctg cagaaagaaa gtccctgtgg agctcagtct cagccatccc  540
tgccccagct gtgagctgaa ctgaatttca ggcatctcag agtcccttca cctttgcatg  600
acccatttcc aggacatgac aggtcaagcc catgggagag gggatcaccc aggtctccct  660
catctccatg gacctcctgg gaacattgcc agggtccact ccacccctgg acgctgtccc  720
caagcttcac cctctttttta taagttgtac atttttatta tgaagatctt tgaacacaaa  780
aatagggaga tgaaagaata ataatgtccc caaggttccc atcaccgagt ccccataatt  840
tttgattttc aaataatgtt gactcaccca caacagagta aacgattccc tcagacaata  900
gtctgaagca gatgcgaaag ccatcacaaa cttaaatgga gagaatcaat gatttcttga  960
cacgaaaaaa cagttaacga gggtctcacc aaatgtcttg tgaatttcat tgtgtatatt  1020
tttagttgac ttcgtggtgc attacgtatt tgtggattta actttagttt ctatgtggag  1080
taaatacttg atgttatcag tggtgaatgt gtttttagac ccattctatc tacagctgtc  1140
tcccaaatgg ctgtcaggct tttcctggca aggcaggagt ggcaggagca gagagctggt  1200
cctgagaccc tcccacagtc aggatgcagc cactgcctcc ctgagcagga acccagtgct  1260
tcctttagct tctcttttcc tgaaaaattg ttctagcatc aagaggctca gtggggttca  1320
ggctggacat tggcataact gcttcctagg acatgtggtt acttctagca aagccaccca  1380
tgttcatcat tcttttagtg acrttagctg tgtttgatga tcgataactt tgtgcttcag  1440
ataaaaagga agacagaggg ttgaggcttc cattcacctc ctcgtgagag ctgcagtgtg  1500
tcgctgaagg gagggcccag cagctgtgct atgaacctag gagtgtgctt cctgctttgg  1560
aaaaaaggaa gaaaagtagt ttcttccctt ttattcacca ctttgataat ggacgatctg  1620
gtgctcggcc atactcgagg gtgaacagaa caacatagag ccagagtgag ctccagcatg  1680
tgaggacatc tgacatgtgg g                                            1701

SEQ ID NO: 327           moltype = DNA  length = 2000
FEATURE                  Location/Qualifiers
source                   1..2000
                         mol_type = genomic DNA
                         organism = Homo sapiens
```

SEQUENCE: 327
ccgccacact tcagcacaaa caggaggagg tggccgtcta gagtctggag tccggggaga 60
ggaggaccgc tcctctcttg gagaccaccg ctgtcactga cgtgtccacc acccaccact 120
ggcagtgcag cccctgataa tgccccataa ctcatcccca tctaggatac tgcagcaccc 180
gatggtgccc acaacctgcc ccctgccatt ggcagtgcag cccaggttaa tgcccccaaa 240
ctgctccctg atgttggcag tgcagccacg gaaagtgccc ccaaccagcc tcccgccatg 300
ggaagtgact cccgggatag cgcccccaag cagaccctag ccttgggcag tgacgcccgg 360
gtaggtcgcc caaccgccac ccaccccgtt gccgagagtg cagcaccaga tagcgaccct 420
aacatgcccc ccatcactgg cggtgtagcc caggatagcg ccgccaaccc ctcacttgac 480
gcgacagtgt agcccctgat agtgcaccca atctgccacc cactgccggc actgcaaccc 540
cggatagtgc acccgacaca ctccctgctg ggcagtgcag ccccccaata gcacccaacc 600
cgtccctcca cccctgccac tggcagtcca ctcccgataa tgcccccaac acgttcctgg 660
ctgtgggcag tgtagtccat agatagcgcc ccaaaccagc ccccagccat gggcagtgac 720
acctcagata tcacacccaa ggagttcccc accatgggca ctgatgtccc agacagcacc 780
ccaactcgag cctcgtgtga ccaatgcagc cacagatagg cccccaacaa gcccccaccc 840
caccactgct gcaggaaatg atgcctggga taacacccaa ccattcccca ccgtgggcag 900
tgcaacaccc agtactgccc ctaacacacc ccccacacaa gatggcgccc ccaatccccc 960
cctcaccttg ggcagtgtag ttcacgatag tgcatccaar ccttggcccc tgagctcact 1020
gcccctctcc ccccgccaca agtccctgga tagctcacct actctgccac ctttctacca 1080
ctttggctgt gctgtactct acctcactgc caccagccac agtgaggcga gccatgctgc 1140
tgcaggctca agcctccagc atgccaccgg tgacaactcc ttctctaatc tggggtcgga 1200
acagatgggc gggcagacgt agaagaacct ggaatggcaa gactctcgct tacaaaggtt 1260
atgcaaatta ggttcctgga ctacatgttc tgattggatg agagaaaaat ctctaggtct 1320
actatgattg ggctttattt tcgtgttgtg actggatgag aggaagtctt aggataacca 1380
atcagaacat gataacaaag tccaatcaga ctaggcctag aggtttctct tgtccaatca 1440
gaacatgtag tccaggaact tcatttgcat caactccaca tataaaggat gccaagtgag 1500
gcggctcctc attctaggct cttcagtgtc cactggtgta gctgctccat tccaggctta 1560
caggagaagg aggaggaggc acttgccacg cacgctggag actcgagcct gccttggctc 1620
cccttgctgc tgtggttggt ggtggcaagg aagacgacag tgcagccagg atggtaaaaa 1680
ggtggtggga taggttcgct atcccaggag gtactgcctg aggcatgggg ggtgggttgg 1740
ggtccctatc cagggcgtca ctgcccgtgt tgaggggctg gttgggtgtg ctatctgggg 1800
catcactgcc tgtggagggg agtgggttgg ggccctatct ggggtgtgct gcccgtggct 1860
gggggtgggt tggggcacta tcccaatctg tactgctagc ggcagtgggt ggttttgggg 1920
ggcactatct ggggatgcac tgcctgcggc cagggggtga gttgggagaa ctatcgggtg 1980
ctgcaatgcc cttgttgggc 2000

SEQ ID NO: 328 moltype = DNA length = 1001
FEATURE Location/Qualifiers
source 1..1001
mol_type = genomic DNA
organism = Homo sapiens
SEQUENCE: 328
gttggaatca tttacttgca gagaggtgtg tgtgtgtgtg tgtgtattta tgtgtgtact 60
catgtgtata agaataggag aaacactttg tgggcatatc ctgctgaggt gagtaacgtg 120
ctgattagtg aactccagtc tcatcccatt taaacctgga ggagaaccac atcaagcaca 180
gaagcagcca aagcagcatt tcaacaggaa ggaaacatct attactgggg ctttgaagaa 240
acatgccatg aaggtgtact aatatcacaa agggaaggga aggactaaat tcagcatgat 300
aaacaaagtc cctttttttgt aacggaagtg tttgatgatg tttgatcaat ggtggatcta 360
tctcttgaaa ggaaaatgca tttaaacccc aaatggagga ttcttatata aggtgcctag 420
cttgtaatga tatattcatg tttataggta gagtgactgg tttttagaga agaggttttt 480
ttttttcctt catttttgaa ngaaaacttg tctgtctcta ggctttgaaa tgtagaatta 540
tttacctttc cccaaaatga aatgtttcac tgaatctcct acaagcttgt ggaggccatg 600
aagcatgttg aataagagca caggctctgg aggccctgcc acccacaaag ggtgtgctaa 660
ggtaaacaac tgatagtatt ttgaaaatta gatgacttag aatccattca ataaatttta 720
gctattttta ttgtcttttt tttctaaatc tatttggaaa atattgcaga taaagtagat 780
aataccttc taaaacacag tgagaccagg cgcagtggct catgcctgta atcccagcac 840
tttcggaggc cgaggtatgc ggatcacgag gtcaggagat cgagaccatc ctggctaaca 900
cggtgaaatc ccgtctctac taaaaataca aaaattagcc aggcgtgggg gcatgcgcct 960
gtaatcccag ctactcagga ggctgaggca ggagaatggc g 1001

SEQ ID NO: 329 moltype = DNA length = 1001
FEATURE Location/Qualifiers
source 1..1001
mol_type = genomic DNA
organism = Homo sapiens
SEQUENCE: 329
gatgggaaac aacaggccat gattttatgt ttttgttaaa ccagtataat tctttcaaag 60
cagtgtatat cacaactatt tctctgtgtt gaagagagta tcaagttctt aaagaaaaat 120
gtaatcccag cactttggga ggctgaggta ggaggagcac gaggtcagga gttggagagc 180
agacaggaga attgcttgaa tccgggaggt ggaggttgcg gtgagcagag atcgcgccac 240
tcactccgtc ctgggtgaca gagtgagact ccgtttcaaa aaaaaaaaaa aagaaagaaa 300
gaaagaacat tttctattct gcaggtggga ggaaatgaag aatgcaccta ttatttttgt 360
gttagtacaa cataaaaaaa atttgcattg taaagcaaac taccatcatc agctctttaa 420
tggacagcag cagacaggaa actgcctcca ccctgagact taaagactga gcaactgagt 480
tagatagcag gtgcgcaggc raatcaagtc aattttctaa cacagagtag catgttgtgg 540
aacttgttct attagtcttt tttctctgtt aaggaagcaa ggatctctct gtatggaagc 600
agtgctgcta tttctagttt gaggaaaaaa atggtaaaga atttgataat taattgttgt 660
taaaacagca aattatattt taaacacaga ttgtccacac ctgtaggagg aggaatctca 720
agaatgcaca caattaataa aagctggttc tgaattaccc atacaagtgc gcactgcgtt 780

```
cagtaaacaa ctgatttgca aactatatcc tttctttccc agaaatagca ggaggaagtt  840
tttcaaatca aaaaaaaaat ctaactaaaa tattttatac gtgaaggcct gcagaatttt  900
acttcctttt gctgttgaaa aatcacaata gccaagagga gtaatgtatt ttattttaac  960
ttttaaaaag tcatgatggt taagggtaga gtggaggtgc a                      1001

SEQ ID NO: 330         moltype = DNA  length = 1001
FEATURE                Location/Qualifiers
source                 1..1001
                       mol_type = genomic DNA
                       organism = Homo sapiens
SEQUENCE: 330
tgttgcccag gcttgtctcc aactcctgag ctcaagagac ccacccactt ccgcctcgca  60
aagtgctggg attacaggtg tgagccaccg cacccagtca cattcctttt aacacttggg  120
ttacatctcc tgaactgaat ggctaggtaa ctaaagacat ctgagaaagt ttcttgcacc  180
tatacattaa gccctcttta ccaagtcata taacctatca ctatctattg aatcttccca  240
tatgagctct aaaggctatt gttatcacaa aacacaatgc caacttttga gtgattaagt  300
atccttctca tctataagag gatgttgccc agactaatct caaacttctg gtctcccgcc  360
ttggcctccc aaagtgccag gattacaggc ataataaaac tccttgatgc catcttccta  420
gaaagatatg cttagcctca ttcaatccaa atagttcctg catttctttt gcatgagatg  480
taagacattt tctgacataa mataaaccaa ataactcaac tacattcatt tttataacaa  540
cagctttttg aaatataatt cacatacaat aaattcatcc ttttaaagca tataattcag  600
tgggtttcag catattcaaa gagttgggca atcattacta tctaattata gaacattttc  660
atcatcacca aaagaaatct catacttatt aggagtcacc tccctcccat ccctagcccc  720
tagtaataac tagccaactt tctgtctcct tagatttgcc tattctggac gttacttaaa  780
attgaaagca tatcatatgt ggcctttctt gtgcctctca gattcaccta tgtgacagca  840
tttatcaata atccattcct ttatactact taataatatt tcactgtatg gatataccac  900
aatttgttta ttcactcatg acatgataga catctgggtt gtttccattt tttaccatta  960
ttaataatgc tgtaatgaac atttggctac aagttttcat g                      1001

SEQ ID NO: 331         moltype = DNA  length = 1001
FEATURE                Location/Qualifiers
source                 1..1001
                       mol_type = genomic DNA
                       organism = Homo sapiens
SEQUENCE: 331
tacacaatat aactagtatt gacttaaggg tactgtgatc accatgcagt gatcccataa  60
aagatgtgac caaaataccc acttaaaatt tgaacgtcag tcatgtaaga acatgtaaaa  120
gatgaaggga atatttcaaa aacgactatc tgacgtaata tgatacttac tatgactcat  180
atgggctttg ttcttcatct catcttcaaa taaaaagttg atgattagaa aaaggagcat  240
tagaaggggg aagtaacact actcggcaat agagaaaaac tccggtcaaa ggaagagcat  300
agttacagag ctccgaatgt cagggaaaat caagcatccg tcattcggaa ttagctctgt  360
atcggtcggt ttcttcatta cttaattgta cggggggaaa ctacttcaaa gtaagggctc  420
ttacgagagg caacttaagc atttgaaagt gcaggtttat ttcctcctag cgagaagtag  480
ggggtcacta gtgagaaacc ratttcaatc tgtgagacgc ccccttctac tcagcccacg  540
tggctaaagt aaacagaagg tgggccgggg cggggagaaa cagaactcgg tcaatttccc  600
agtttgtcgg gtctttaaaa atacaggccc ctaaagcact aagggcatgc cctcggtgaa  660
acaggggagc gcttctgctg aatgagatta aagcgacaga aaagggaaag gagagcgcgg  720
gcaacgggat ctaaagggag atagagacgc gggcctctga gggtaaggtg ggcgcaagcg  780
gaggtgtggt gcggggagag gtgccagtgg gtggaggcgg gggccagagc gagggcacgt  840
gcgggtacac tccggaggag gtgggtgcgc gcgggggcgt gtgcgcggga cctcgaagtg  900
gtggtggagt gcagaccagc aaaaagtttc aaagggaaat cttagatgtc acgtctttgt  960
ccaggcaccc gtgccatccc aacctcccac ctcgccccca a                      1001

SEQ ID NO: 332         moltype = DNA  length = 1001
FEATURE                Location/Qualifiers
source                 1..1001
                       mol_type = genomic DNA
                       organism = Homo sapiens
SEQUENCE: 332
acaaagatga ctctttccag cgatttgaaa ttgctagata agactatgaa attctattaa  60
aacaataaca acaaaaacaa tttaacttgc attagaagca attaaagcat aaaaagtaga  120
tctaagattt tctaaatatt agatattcta aaatattgac attatacaat gtctagcatc  180
cgtaactttt gaagatattt tatttcaagg taatttcata agaattcata agaatttacc  240
tactcagact ttgggcagga tggaaaatag agtttctgtg aggtgtgcct atgaatcata  300
agaagggctt cttaatgagg tcagtaatta aggaaataca tttcaatagt gacatttgac  360
ttacaacatt gtttgggggt ggagtcttag aagaattgat agggaacttt taacttcaac  420
aagtgaaact aaaacattaa ctccagttgt tgttacctaa tacaagacca gtgcccaata  480
aggactttgg aattctttca raacaactcc ttggcaggtg cacttcactt gttctggaag  540
tgatattcac ttgccaatgt ctagtaggac catgtgccac tgcctcaaaa tcatatcaat  600
tcctccggct tctggcataa actggcacat cagacctaat taaagcctta agaagagttt  660
ggcaaatatg acaatttaaa caaagcaagg gatttctctc actgcaactt aatttctcat  720
tgatgattag ttcaataaga aaataagcaa aacaatgtca tagttaagaa aagctatcta  780
tcttgttatt gtccattatc atgttcctaa aattcaataa cccaagacag tcctatggaa  840
tttttggagc acctaggtag tatgatcaca tatatggtaa agaaagaact gaggttatgt  900
cttttattgt aaactacccc atacttatta aaataatttc tcttttccaa caaaggataa  960
agtgactaac atacacatct cttccttata atcactgaaa t                      1001

SEQ ID NO: 333         moltype = DNA  length = 1001
FEATURE                Location/Qualifiers
```

```
source                  1..1001
                        mol_type = genomic DNA
                        organism = Homo sapiens
SEQUENCE: 333
cagagagtaa agcctaaggg gaaagtttga caggctggtt gtatttatgt attcatcctg  60
ccacatcctc gaaaaaggta tttattgtta agtaggttca aaaacatctt caagaccaga  120
aaatgccttc ggacgccact gggctgttga attccttagt tattgattca ctaatgtcat  180
catgaaagaa tttatgattt tcccaatcca gtccaccagg agagggaagg ccttgataag  240
gatttagatg ataaggagaa gaattgccaa gattgaagac ccagagcaac agcaaagaat  300
tttggaaaag aaatttcacc aaagagtaaa gttagtgtta ttttggttat gtggaatatt  360
agagtgaatt aagtagagga ataaaatcac taataaaatt ggttagcaaa ggcgtcataa  420
aatcacacca atgagaaaca gagtgctaac ctagactttg tatatcttca gtttcctttc  480
aagcatttca aacctcccca rttagcttca agtttatcct taggtagatg tgtacaaaag  540
atttcttcaa ctactttcta gtattcaaga tattatttaa gggaaaaatc acatttattt  600
attcattaga tattttggta agtattctag gtgctggatt aaaagagaga aatggctcac  660
gcctgtaatc ctagcacttt gggaggccga gatgggcgga tcacttgaga tcagaagttt  720
gagaccagcc tggccaatgt gttgaaaccc tgtctctact aaaaatacaa aaattagccg  780
gaaatcacct gaacccggga ggtggaggtt gcagtgagcc gagattgtgt cactgcactc  840
tagcttgggc gacagagtga gactctttct taaaaaaaaa agttaaaaaa ataaaataga  900
taacatgtct tatttttcct caggctctgt ttaatggtgg tgatgatgac atgatggtca  960
tcactaccat ccattgagta catgcaccaa gtcatcatgt t                      1001

SEQ ID NO: 334          moltype = DNA  length = 3934
FEATURE                 Location/Qualifiers
source                  1..3934
                        mol_type = genomic DNA
                        organism = Homo sapiens
SEQUENCE: 334
tgactgtcat gtgctaattc taacaatatt tgaaagaccc ctatcaaaat aaatatacct  60
tttagtagcc actttattag aaaatcaact ttaagttatt cccccatgtt tttttctaat  120
tgagatataa ttcacatacc ataaaattta cccttttaaa gtatacaatt cagttgtttc  180
agtacattca caaagctatg caaatgtcac ctctacctag tttcagaacg ttttcatcat  240
tcccagaagg aaaccctgta tttattaggc agtcacttcc ccttctcccc ttcttccttc  300
ctctaagtgg caaccacaaa taaacattca gtttctctgg atttacctat tctgggcatt  360
ttgtattagt gaaatcatgt atttggcctt tctctctggc ttctttcatg tacctcaatg  420
ttttcaagtc tcattcattt tattaaaaaa aaaaagtacc tttttttcttt ttcttttttt  480
ttttttgtc cacgtatata ttcacaccac attttttgag acagagtctc gctctgttgc  540
ccaggctagg gtgcaatggt gcaacctcag ctcactgcaa cctctgtctc ccgggttcaa  600
gtgattctca tgcctcagcc cccaagtagt tgggattaca gttgtgcacc accacaccca  660
gctaattttt gtatttttag tagagacagg gtttcaccat gttggctagg ctggtctcaa  720
actcagcctc aagtgatcct tctaccttag cctcctaaag tgctgggatt acaagcatga  780
gccactgtgc ccagccacat tttctttttc catttattag ttaattgaca tttggatcgt  840
ttctactttt tggcgattat aaattatgct gcaatgaaca tcggtgtaca agtttttgtg  900
tgaacatgtt ttcagttacc ttgggatata cacctaggag tgacattgtt agtaatatgg  960
taactttatg tttaactttt tgaagaactg ccaaactgtt ttccaaagta gctttatgct  1020
tttacatttc tgccaacaat gtatgaaggt tccagtgtat ctccacatcc tcaagaaaat  1080
gttattgtct ttttaattgt aaccatccaa gtgggtatga agtttatctc gtgattttga  1140
tttgcatttt cctaatggct gatattgggc atcttttcac gtgtgtattg accatgtatt  1200
tttttgagaa aagtctactt atatgttttt aattgtatta tttttagagt tgtaagaata  1260
tgttatgttg atacttgaac tttgtcaaat gcctggtttg cagatatttt ctcctatccc  1320
acaggttgtc gcttcacttt gataatgtcc ttaaagtaca aaagttttaa attgattttg  1380
atgaaactca atttcttttt aattggcagc ttgtgcattt ggggtcatat ttaagaaatc  1440
attgcctcat tcaagatctg aaagatttac acctatgctt tcttctcaga gtattataac  1500
tttagttctt acatttagat ttttaattaa tgttgagtta atttgatggt gagagataag  1560
agtccaactt cattcctttg caagtagctg tccagttttc tcagcaccat ttgttaaaag  1620
actgtttttt ttcaattaac tgaccaagat gtatgggttt atttctggac tcttaattct  1680
gttaatctgc atgacttttc ttatgccagt accacactgt gctgattcct gtagttttgt  1740
agtaaatttt gaaatcaaga caggtaagtc ttccaacttt gtacttttgc ctaccatgtt  1800
tcttgggttt ccatatgcat tttaagatca gcttctccgt ttcctttctg gatttttttt  1860
ttttttttt ttttttttt tttggtggag ctggagtctt actatattac ccaagctggt  1920
tttgaactcc tggctaaaga gatcctccct cctaggcttc ccagagagct ggggttacag  1980
gcatgagcca ccacatccaa ccccccttctg ggactttgac tggggttctg ttgaatctgt  2040
tggtcaattt ggagagtatt gatatcttaa cattaaagct tccaatttat gaacacaggc  2100
tatttttcca tttattctta aatttctttc agtaatgttt tggatgaaac atgtacaaag  2160
tcctgcactt tttattttt ttaagacaga gtcttgctct gctgcccagt ccagagtgca  2220
gtgctgccat ctcagctcac tgcaacctcc acctccgggt tcaagtgatt ctcctgcctc  2280
agctggaact acaggtgcgc gccaccatgc ctggctaatt gttttgtgtt tttggtggag  2340
acagggtttc accatgttgg ccaggctggt ctcaaacacc tggcctcaag tgacctgact  2400
gccttggcct cccaaagtac tgggattaca ggcatgagcc accacgcctg gcctgtactt  2460
ctgttaaaat tttttctatg tattttttt atcctattgc aaaatcaaat tttttgttga  2520
taatatatgg tcataaattt catttttata tattggtctc atatcctacc aacttgctga  2580
actagcttat tagcactaac tttttttggt agattcctta ggatttgctg catacaagat  2640
tatgtcatct acaagtagag atagttttgt ttcttcactt ccaatctggg tggctttatg  2700
tttttttctt gcctgattac ccagttagaa cttccagaaa atgtcaggta caattaacaa  2760
ctgcaaacat ccttgtctta ttcattttag aaagaaattt ttagtttttc accattaagt  2820
atgatactag ttgtaggttt tgtttaaaaa aagactgtgt caagttcaga agttcccttc  2880
tgttgctagt ttgttgaata attttatcac gaaagggtgt tgaacttttc tcaaatgctg  2940
tggctacatc taatgaaatg atcatgcgtt cttctccttt attctattaa tatggtatat  3000
tatattgatt catttttata cattagatta acattatatt tctggaataa atcccacttg  3060
```

```
gcctcagtgt gtattacttt ttatatattg ctggagtctg tttgcaggta tttcattgag  3120
gactttcgca tctctgttga taaggtatac tgatctttag ttctcttgtg atatctttgg  3180
ttttggtgtc agagtaattc tgagttcaca aaatgcattg ggaaatgttc ccttctctat  3240
cttttggaag agtttacaaa ggattggttt aactcttttt taaatgtttg aggaaattct  3300
ctacccctgg gctttccttt gtgggaattt ttaaacattt ttaaaataga ttatttttaa  3360
agcaatttta gggtaaaagc acattgaatg aaaggcacag agcttcctta agtacatgct  3420
gcccctgtat gtgcatagcc tccctcatta tcaacatcct ttaccagaat ggtacatttg  3480
ttgcagtcaa tgaacctgca ttgacaattg tcgmtgaaag ttcatagttt agagttcacc  3540
tttggtgtta tgtattctgt gagtctggat ccatgtttaa tgatactcat tcaccattac  3600
agtatcattc agagtaattt cactgcctta aaagtcctct gtaccctacc tatttttctc  3660
tcctacccca ctaaccctta gcaaccaatg atctttttat ctcaataatt ttgcctattc  3720
cagaatgtca tatagttgga atgatacagt atatggagcc ttttcagact ggtttttgtc  3780
acttagtaat aagcttttaa attttccacc atgtcatgat cgttcatttc ttttcagcat  3840
tgaataatat tccattgtct ggtttatcac agttgattta tccattcaca tagtgaaaga  3900
catcttagtt gcttccaagt tttgacaatt atga                              3934
```

```
SEQ ID NO: 335         moltype = DNA  length = 3249
FEATURE                Location/Qualifiers
source                 1..3249
                       mol_type = genomic DNA
                       organism = Homo sapiens
SEQUENCE: 335
gcatgagcca ctgcgcctgg acttacaatt tcttaaaata agacaacagt gaggtttacc  60
acatcaattg accctttctt tcatgagtga tttctctgtg gcatgcaatg ctgtttgata  120
gcattttact cacagtagaa cttgttttaa aattggagtc aattgtcttc agccctccca  180
ctgctttatc aggtaagttt acgaaatatt ctaaatcatt tgttatgact caagggacat  240
taaaaaaaaa agaaaaacaa tcttttattg tcatttcaac caggttcaca gtgtcttttt  300
tttttaaatt atattttaag ttctagggta catgtgcaca acatgcaggt ttgatacaaa  360
ggtatacatg tgccatgctg gtttgctaca cccatcaact catcatttac attaggtatt  420
tctcctaata ctatccctcc cccagccccc accgcccgac aggccccggt ttgtgatgtt  480
ccctgccctg tgtccaagtg atctcattgt tcaattccca cctttgagtg agaagatgcg  540
gtgtttggtt ttctgtcctt gtgatagttt gctgagaatg atggtttcca gcctcatcca  600
tgtccctgca aaggacatga attcatcctt ttttatggca gcatagtatt ccatggagta  660
tatgcactac atttcttaa tccagtctat cattgatgga catctggtat ggttccaagt  720
ctttgctatt gtgaatagtg ctgcaataaa catacatgtg catgtgtctt tatagtagca  780
ggatttataa tcctttgggt atatacccag taatgggatt gctgggtcaa atggtaattc  840
tagttctaga tccttgagga atcgccacac tgtcttccac aatggttgaa ctactttaca  900
ctcccaccaa cagtgtaaaa gtgttcctat ttctccacat cctctccagc atctgttgtt  960
ccctgacttt ttaatgattg ccattctaac tggcgtgaga tggtatctca ttgtggtttt  1020
gccttgcatt tctctgatga ccagcatgtt cacagtatct ttatcagaag tagattccat  1080
ctcaagaaac ttctttcttt gctcatccat aagaagcaac ttctcatttg ttaaaagttt  1140
tttcgtggat tacaacaatt cattcacatt ttcaggctcc acttttaatt ctaattctat  1200
tgctgttttc accatatctg cagttacttc ctccactaaa ctcttatacc cttcaaggtc  1260
atccatgagg tttggaatca acttttttgg aactcctgtt gatgttgata ttttgacctc  1320
ttcccgtgag tcatgaatgt tctcaatggc atctatgatg gtgatttttt tctgaaggtt  1380
ttcaatttac tttgcccaga tgcatcagag gaatcactat ctatggctgc ttatattgcc  1440
ttacaaaata tatttctttt tttttttttt ttgagttgtt gtcttgctca gttacccagg  1500
ctggagtgca gtggcgtgat ctcggctcac tgcaagctcc gcctcccagg ttcatgccat  1560
tctcctgtct cagccttccg agtaactggg actacaggtg cccgccacca ggtccggcta  1620
attttttttt tgtattttta gtagagatgg ggtttcacca tgttagccgg gatggtctcg  1680
atctcctgac ctcgtgatcc acacgcctcg gctgggatta cagacacaaa atatatttct  1740
taataagact tgaaagtcaa acctattcct ggatccatgg gctgcagaat ggatattgaa  1800
ttagtaggca tgaaaacaac atggattttt ttgtacttct ccatcagaac tcttgtgtgg  1860
ccaggtgcat tgttaatgag cagtaacatt ttgacaggaa tctctttttc tgagcagtag  1920
gtctcaacag tgggcttaaa atattcagta aaccattctg taaatagatc tgctatcacc  1980
caggctttct tgttctattk tggagtgcaa gcagggagat ttagcatcat tcttaagggc  2040
cttgggtttt tggaatggaa catcagcact gattggcctc aacttagagt caccagctgc  2100
attagccact aacaagagag gcagcctgtc ctttgaagct ttgaagcctg ccattgactt  2160
ctccctagct aagaaagtgc tagatgacat cttcttccag taggaggctc tttcatctac  2220
attgaaaatc agttgtttag tgtagccatc ttcatcaatg atcttaacta tatcttctgg  2280
ataacttgct tcagcttctt catcagcact tgctccttca tcttgtactt ttacgttatg  2340
gagacaactt tccttaaacc tcatgaacca acgtttggta gcttccaact tcagcttcct  2400
cccctctctc agccttgata gaattgaaga gagttaaagc cttgttctgg attaggcttt  2460
ggcataggga atgtttcatt ccagaccact aaaactttct gcatctcagg gataaagttg  2520
tttcactttc tcatcattca catgttcatg gaagtagcgc ttttaacttc cttcaataac  2580
ttttcctttg catttgcaat tttgctaatt tttttgttgc aaaaggccta atttttagcc  2640
tgtcttggct ttccatgtgc ctttctcact aagcttgttt ctagcttttg atttaaaatg  2700
agagatgtgc gactattcct tttacttgaa cacttagagg ccattgcagg gttattaatt  2760
ggcctaattt caatattgtt gtgtctcaag taatgggctt ggtgaaaggg agagacagag  2820
aggaatggtt gtcagtggag cagtgagatc acacacactt ttaagtagct aagtttgctg  2880
tcttatatgg gtgtgattca tggtccccca aaatagttac aatagtaaca tcaaagatca  2940
ctgatcacgt caccaaaaca gatattataa taatgaggaa gtttgagata ttgtgagaat  3000
taccagaatg tggcacagag acaggaagtg agcacatgct gttggaaaaa tggcactgat  3060
agatttgctt aatgcaaggt tgccacaaag cttcaattgg caaaaaatgc aatacctgtg  3120
agtataatac aataaaatga ggtatgtcgg aacctgatta tgtcttagtc ataaaactta  3180
caaagaagta ggaggaatat tttccatgcc aacagaatgt atttaaatga tttgatatgt  3240
atttgaggt                                                          3249
```

```
SEQ ID NO: 336         moltype = DNA  length = 1001
```

```
FEATURE                Location/Qualifiers
source                 1..1001
                       mol_type = genomic DNA
                       organism = Homo sapiens
SEQUENCE: 336
aagtgtgttt ccaccatacc ttgttggtcc aaaacacctc tccccagctc cagcaactgc  60
tgcagctgtg cagggcagtc cctctccagg taggccctgt tctgcctggc ccgaatcttg  120
tgcctttccc actccagctt ggtgggccag gccctgggtt ctgctgctct ccaatccagt  180
gtgtcagggc agaattcaag gtggtcctgc ccatcatacc cgtacttcca gtagccctcg  240
gtactgttgt cttcttgcat ttcacagccc aggatgacct gcagggtgtg ggactctgga  300
aaaatcccca gccttgttaa ctgcaaccaa aggaataggt ccctatttcc accatcccca  360
aggaccaaat gatctcagga agcaaattcc ttccctcttc cctgctccca caagacctca  420
gacttccagc tgtttccttc aagatgcatg aaaagatgaa aagctctgac aacctcagga  480
aggtgaggcc ccctctccac rtacccttgc tgtggttgtg attttccata atagtccaga  540
agtcaacagt gaacatgtga tcccaccctt tcagactctg actcagctgc agccacatct  600
ggcttgaaat tctactggaa acccatggag ttcggggctc cacacggcga ctctcatgat  660
catagaacac gaacagctgg tcatccacgt agcccaaagc ttcaaacaag gaaagaccaa  720
ggtcctgctc tgaggcaccc atgaagaggt agtgcagaga gtgtgaacct ggagacagag  780
caacaggcct taaccatgtg tagtaggagg ggagcaggat gttgaggctc cacacacctg  840
catcaactca taccatcagc tgtgtctggt cctcattttg tgaagggtga gttgcagtcc  900
tgtctttctt ccatatgaca gtcctgggtg ctctttcctt gtgtgctttt ctctgccaca  960
cgtggctgcc accccctcac tgcccccaga tcctattcca a                       1001

SEQ ID NO: 337         moltype = DNA  length = 1001
FEATURE                Location/Qualifiers
source                 1..1001
                       mol_type = genomic DNA
                       organism = Homo sapiens
SEQUENCE: 337
cagagccacc ctagccattg gtataataga aataattatt attgccactc ttataaatta  60
ctgcaccagc cagtctacat caatcccaga tggagatatt actgaccctc ttcctccagg  120
tcacccagtt ggtaaatgaa agagatgata tttgttcaga agccagtttg acctgcaaaa  180
ttttgctttt aaacacctcg caagagtgcc tatttcttgg aattatcttc catagctgct  240
actgtctcca ctagctagtt tcaaagcata tggatgatca gatacaaagc ttcagcttcc  300
tgccacttct ccctcacttt tgtcagtctt gttaatatgg atttttacat ttttcatttt  360
tatttttatc atatgaggaa acttggggtt ggggagtata taaaaattgt ccattgctat  420
acagaaaaga gttttggagg tcttcatctc aataccaaga gaagtgactt accgacttaa  480
tgtctgtgga agggcttcaa rttgaaccca gcgtttcctc caagcttact cccttggact  540
ttttggagca gagagatgag gattctttgc caccctaggg cttaagttgc taatcattaa  600
taaaagtcat caaactacaa agttgactca gaagggcttc ttgccaaata ggctttgaag  660
aagcattcgg aaatccagcc caatcccctc tgcagttctt tctgcttttt ggctgatgta  720
agcttctcca ccttcccctt gtgagtgtct cctcaggacc tcataggtgt cctctggttc  780
agacacttgc atatagctat tttgctttgc tttgtggtgt cttcaatgtc tttagtcttt  840
tttgaaaagg ttaaaaagag ataaattata attaaagagt tcagtatttt tgtgtttttt  900
actttgctat ttttgatttt ccccccttaat tgaaattttg ttaatttttt tcttctttga  960
aatatgtgaa ttgtaatatt atgggtaaac ttgaacttca t                       1001

SEQ ID NO: 338         moltype = DNA  length = 2131
FEATURE                Location/Qualifiers
source                 1..2131
                       mol_type = genomic DNA
                       organism = Homo sapiens
SEQUENCE: 338
aaaaagtatc agcaagttat gtttggatgc caaattgctc tccacttccc ttccctgaca  60
ctggcatttc cagaacttag atgctcttac atgtaaaagc ctcctctagt gcaccatcga  120
gcttttcagg attggacatc agacttttta gttcctggac ctctagatat acggcagtct  180
ctgacaagaa gccctttttc tgttttaact tttttttttt ttaagttttg agacaacgtc  240
tgactcgctg tcacccaggc tggagtgagg tagcaccatc atagctcact gtatccttaa  300
acgcctgggt gcagggacta agggagcgtg ccaaccatgc ttgactaatt tactttttttg  360
taaaaccagt agtctccaac ctttttgaca caagagaccg ttttgtgtaa gacaattata  420
ccacggacca gggggtgcag gggctgggag caatgatttc cggactaaaa ctgctccaac  480
ctcagatcat caggcattag attgtcacaa ggagcctgaa acctagatcc cttgcatgtg  540
ccattcacaa tacagtttga gcttatgaga atctatctaa tgctgcagct aacctgacag  600
gcggtggagc tcagttggtt aatgttcgct cacccctcag ctgtgcggct caattcataa  660
cgtgccatgg acagggaccg gttaccggtc ggtggccggg graatgagga cccctggtat  720
agatggtagt ctggctatgt tgcccaggat ggtcttgaag cctggcctga attaattctc  780
caatctcaag ccttttcaac tcagctgcat cacaacttaa acctatagat aactgtcaca  840
gaaacttgtt tccagtgtta cgccatctta aaataatgtg ggtggctctt aaaagagcct  900
ttgggttctt tccaaattgg cctcccggaa agctctttac ttcttagatg tggcctttct  960
aacattaact tcatgatgtt gggtcaattt tgacttcgaa gcccttgcct tcactgggct  1020
cttctgctgt tgcttaccct tggctccttt agcctttctc ccgctcctaa cagttttagg  1080
agttgtcgct ctcggcttct tggctctctt attggtttta gcagtctttg gtgacttgga  1140
gtccctggat aaaaccagct tcttggtctt ggcagaaact gactttttag ccttgcttct  1200
ggtagattta ggaatcacct tcttactaag cttaaaggaa ccggaagcac cagtacccct  1260
ggtttgcacc aggattccct tgttcactaa gctcttgagg gacagtttga tgcggctgtt  1320
attcttctct acgtcgtagc cagcagcggc caatgccttc ttgagcgcaa ccaaagacat  1380
acctactcgt tcctgtgaca ctgaaagggc ctcggtgatc aacttggaca cagagaggtt  1440
cggcactttg cgacttgcac ttatcaagcc agccggcttc ctccctcgct tcttggttgg  1500
aagtttctcc atagcggcta caccagcact ggcagaagct gcaggcacgg tttcagacat  1560
```

```
aacaacagag aaacgcaaga tgtaataacc agcgaaaagc atgaaacacc cgggcggcct  1620
cggggcctta tatagggtag ggcgcgctgt gattggtgca tcacctaggc accgcccccg  1680
ccccttggag gaggagtatt tgtgtttgtt ttacccggaa aagttgagta taacaaaacc  1740
cctctttaca gaatctccca gggtctagtg ctgaataatc tgcggaaatt catatttgac  1800
atgacttttc tctttttaat gaaaaatgac cctggatgcc aaaactattc gagaaagccc  1860
tcgattttca atcaaattca cggagaggaa caaaacttcc ccttttcctt gtaaattaat  1920
aagtaatctt tggcagaaga cttatttcat ctcttcagag tggtcttcca aatggatagc  1980
ttcaaatcgg tagaggaaag aaattattca cgccatgatt tttatttaaa attatttata  2040
tatgtgaggg aagtaacaca gatctcttag ctgtctaatt gcggagtcag aagatgctta  2100
tagaattgtc aaaagactgc agaggatgtc t                                 2131

SEQ ID NO: 339          moltype = DNA  length = 1001
FEATURE                 Location/Qualifiers
source                  1..1001
                        mol_type = genomic DNA
                        organism = Homo sapiens
SEQUENCE: 339
tctctcagac ttttgcagaa aaatgagtca ttcaacaaat atttgaatcg agatagggaa  60
agtgacgagg aagaagtttg cacttatgag gttttaattt gcaattattt ggctaccttt  120
ttgccttccc aaaacatagg gtctttagga gtgaaacttc atagccaaac ttataccttg  180
tccagcacag agaaggccat caaaatgcct ggtttaaata aaaatattaa aatgattggg  240
agggtaaatc ccttgaccta taaatctgac ctcctttaaa cattatttgt atgttcccca  300
ataaactatt ccgtaattta ttagttagca agtggaaata aaaagaaatg tggaatgggg  360
ctatgcttag cgtcattaag ctgacaggaa tacagcgcat tcaacttgca aacacccttc  420
cactcccaca aagagcaagc tgtcactggc caatcaaaac aatgaaccat aatgaaacag  480
tttttcttgc tccacccact yggtgaccaa atttgaaaaa aaaaaaaaac cgcgccaact  540
catgttgttt tcaatcaggt ccgccaagtt tgtatttaag gaactgtttc agttcatacc  600
ttccactgcg ataggaatca tgtctggtcg cggcaaaggc ggaaaaggct tggggaaggg  660
tggtgctaag cgccatcgta aggtgctccg ggataacatc cagggcatta caaaaccggc  720
tattcgccgt ttggctcggc gcggtggcgt caagcgcatt tccggtctta tctatgagga  780
gactcgaggt gtgcttaagg ttttcttaga gaacgttatt cgagacgccg tcacctatac  840
ggagcacgcc aagcgcaaaa ctgtcacagc catggatgta gtatatgccc taaaacgtca  900
ggggcgcact ctgtatggct tcggcggctg aatctaagaa tacgcggtct cctgagaact  960
tcaaaaaaca aaaacaaaaa aacccaaagg cccttttcag g                      1001

SEQ ID NO: 340          moltype = DNA  length = 1001
FEATURE                 Location/Qualifiers
source                  1..1001
                        mol_type = genomic DNA
                        organism = Homo sapiens
SEQUENCE: 340
aatcattttt ttataacaac aaaggcattt gcactgagag tcaaggaagt accgaattat  60
tcctgttttt actgaattgt attaaaatat aaggaggata taataggaaa acacagcatg  120
tgttcatcaa tcacttctcc tgagtctcct cacttggtca aaaatttccg gagaaatttt  180
tgtttgtacc tgatttgaaa agaaaaacaa gggagcggtt ggaggggaag ggtggagaga  240
tgaggggagg gagtgcccta gtggaaacca cagcattaac accacctact acttctactt  300
cactaaaggc actgtcccga ttttttcttc agagatcact gttttgcctg ctgaattcaa  360
acctccaccc cagacacact gatgtcattg gaggcatcag gactgggggc ccaagtttta  420
ttatattaaa acgagttcat gctggggtaa attttaagat ctttagtgga cagaaaggca  480
gttcaaattc tttgatttta rtgacaaaat gctttaaact gacaatgcaa cctatcaaca  540
aaaggaccat attgagctgt gtgtgggctg cacagaaata cgccgcccca gaactctaag  600
tgctcccgga aaagctcgca attgttacaa cagagaatcc aattcttgtg gctaaagtat  660
ctcctggggg acttattaca aatgtggatt ctagaacccc tcgtgcaatg atcctgacta  720
aagcgattta ctatgggtcc caagaatctt aatcttacca agcaccctca agtaattcta  780
acttcaatag tctgctaaac ggcactcagt gaagggtgct aaagctgtca tggggaattt  840
aaaaactcat gaaataagct cgtagaaagg aagtttaggg tctggaggac acagagctga  900
aatgaaatcc tgaagtaggg ttggaatata attaatttat gtaacaatac tgaacaccta  960
gtgtgtggcg tgcccctttg tttttcaggt aatcagagga a                      1001

SEQ ID NO: 341          moltype = DNA  length = 520
FEATURE                 Location/Qualifiers
source                  1..520
                        mol_type = genomic DNA
                        organism = Homo sapiens
SEQUENCE: 341
ccttgaagct acggaattac aattctcctt cacaaagaca gtcaaaggat gtgatctgat  60
gtgttagatt ttctctctcc tgttcaatat ggagttttgc atcttagttt ctttgggccg  120
ctataagaaa atacactaaa ctaggtgact aacaaataac aggattttac ttcttacagt  180
tctaaaggct aggaagtcta agatcaagga gacaccatat tctatgtcta atgaggctca  240
ctctctgctt catagatagc atcttcttgc tgcaacttcg tayggtacag ggggtgaaca  300
agctccctct tttatagggg tactaatccc attcatgagg acgccatcct tatgacctat  360
tcacctccca aaggccccac ctcttaatac caccataatg gggattatgc ttcaacacaa  420
gtatttgttt cttgtttttg ttttcaacat aaatatttgg agggtaacca ttcagatcat  480
agtagtacca gtatccaaaa ctgccaccaa atagtttgtt                        520
```